United States Patent
Calabrese et al.

(10) Patent No.: US 12,129,274 B2
(45) Date of Patent: Oct. 29, 2024

(54) MODULAR SYNTHESIS OF AMINOGLYCOSIDES

(71) Applicant: REVAGENIX, INC., San Francisco, CA (US)

(72) Inventors: Andrew Antony Calabrese, Cockeysville, MD (US); Timothy Robert Kane, San Diego, CA (US); Darin Hildebrandt, San Diego, CA (US); Michael Lopez, Petaluma, CA (US); Nikolai Evdokimov, San Diego, CA (US); Frederick Cohen, San Diego, CA (US); Malken Bayrakdarian, Montreal (CA); Sanijia Xu, Montreal (CA); Samuel Desjardins, Montreal (CA); Olivier Soueidan, Montreal (CA)

(73) Assignee: Revagenix, Inc., San Francisco, CA (US)

( * ) Notice: Subject to any disclaimer, the term of this patent is extended or adjusted under 35 U.S.C. 154(b) by 44 days.

(21) Appl. No.: 18/085,645

(22) Filed: Dec. 21, 2022

(65) Prior Publication Data

US 2023/0167148 A1    Jun. 1, 2023

Related U.S. Application Data

(62) Division of application No. 17/044,960, filed as application No. PCT/US2018/047993 on Aug. 24, 2018, now Pat. No. 11,673,907.

(60) Provisional application No. 62/652,169, filed on Apr. 3, 2018.

(51) Int. Cl.
  *C07H 7/04* (2006.01)
  *C07H 5/06* (2006.01)
  *C07H 17/02* (2006.01)

(52) U.S. Cl.
  CPC .................. *C07H 7/04* (2013.01); *C07H 5/06* (2013.01); *C07H 17/02* (2013.01)

(58) Field of Classification Search
  None
  See application file for complete search history.

(56) References Cited

U.S. PATENT DOCUMENTS

| | | |
|---|---|---|
| 4,424,345 A | 1/1984 | Kirst et al. |
| 4,439,196 A | 3/1984 | Higuchi |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,596,556 A | 6/1986 | Morrow et al. |
| 4,790,824 A | 12/1988 | Morrow et al. |
| 4,941,880 A | 7/1990 | Burns |
| 5,064,413 A | 11/1991 | McKinnon et al. |
| 5,152,923 A | 10/1992 | Weder et al. |
| 5,312,335 A | 5/1994 | McKinnon et al. |
| 5,383,851 A | 1/1995 | McKinnon, Jr. et al. |
| 5,399,163 A | 3/1995 | Peterson et al. |
| 5,698,219 A | 12/1997 | Valdivia et al. |
| 5,753,241 A | 5/1998 | Ribier, deceased et al. |
| 5,925,341 A | 7/1999 | Cervantes et al. |
| 6,039,936 A | 3/2000 | Restle et al. |
| 6,120,778 A | 9/2000 | Simonnet |
| 6,274,150 B1 | 8/2001 | Simonnet et al. |
| 6,335,022 B1 | 1/2002 | Simonnet et al. |
| 6,375,960 B1 | 4/2002 | Simonnet et al. |
| 6,413,527 B1 | 7/2002 | Simonnet et al. |
| 6,419,946 B1 | 7/2002 | Sonneville et al. |
| 6,461,625 B1 | 10/2002 | Simonnet et al. |
| 6,464,990 B2 | 10/2002 | Simonnet et al. |
| 6,541,018 B1 | 4/2003 | Simonnet et al. |
| 6,689,371 B1 | 2/2004 | Simonnet et al. |
| 6,902,737 B2 | 6/2005 | Quemin |
| 6,998,426 B2 | 2/2006 | L'Alloret et al. |
| 7,314,624 B2 | 1/2008 | Baker et al. |
| 7,468,402 B2 | 12/2008 | Yang et al. |
| 7,476,393 B2 | 1/2009 | Dubief et al. |
| 8,318,685 B2 | 11/2012 | Goldblum et al. |
| 8,481,502 B2 | 7/2013 | Aggen et al. |
| 2004/0054164 A1 | 3/2004 | Buchanan et al. |
| 2004/0058880 A1 | 3/2004 | Liang et al. |
| 2004/0170661 A1 | 9/2004 | Brode, III et al. |
| 2006/0269485 A1 | 11/2006 | Friedman et al. |
| 2011/0218173 A1 | 9/2011 | Wu et al. |
| 2012/0208781 A1 | 8/2012 | Bruss et al. |

(Continued)

FOREIGN PATENT DOCUMENTS

| | | |
|---|---|---|
| DE | 2350169 A1 | 4/1974 |
| EP | 0048614 A1 | 3/1982 |
| WO | WO-0187263 A2 | 11/2001 |

(Continued)

OTHER PUBLICATIONS

Allen et al. Comparison of aminoglycoside antibiotics with respect to uptake and lethal activity in Escherichia coli. J Med Chem. Feb. 1987;30(2):333-40.

Alper et al. Probing the Specificity of Aminoglycoside—Ribosomal RNA Interactions with Designed Synthetic Analogs. J Am Chem Soc 120(9):1965-1978 (Feb. 24, 1998). DOI: https://doi.org/10.1021/ja972599h.

Anish et al. Chemical biology approaches to designing defined carbohydrate vaccines. Chem Biol. Jan. 16, 2014;21(1):38-50.doi: 10.1016/j.chembiol.2014.01.002.

Chandrika et al. Comprehensive review of chemical strategies for the preparation of new aminoglycosides and their biological activities. Chem Soc Rev. Feb. 19, 2018;47(4):1189-1249.doi: 10.1039/c7cs00407a.

(Continued)

*Primary Examiner* — Traviss C McIntosh, III
(74) *Attorney, Agent, or Firm* — Womble Bond Dickinson (US) LLP

(57) ABSTRACT

The present disclosure relates to novel methods for preparing antibacterial aminoglycoside compounds and the compounds used in such preparations.

5 Claims, No Drawings

(56) References Cited

U.S. PATENT DOCUMENTS

2014/0323422 A1     10/2014     Kett et al.

FOREIGN PATENT DOCUMENTS

| WO | WO-2017037719 A1 * | 3/2017 | ............ A61P 13/12 |
|---|---|---|---|
| WO | WO-2019046126 A1 | 3/2019 | |
| WO | WO-2019194858 A1 | 10/2019 | |

OTHER PUBLICATIONS

Co-pending U.S. Appl. No. 16/642,879, inventors Andrews; Logan et al., filed on Feb. 27, 2020.

Hamouda et al. A novel surfactant nanoemulsion with broad-spectrum sporicidal activity against Bacillus species. J Infect Dis. Dec. 1999; 180(6):1939-49.doi: 10.1086/315124.

Kim et al. Reaction Catalyzed by GenK, a Cobalamin-Dependent Radical S-Adenosyl-l-methionine Methyltransferase in the Biosynthetic Pathway of Gentamicin, Proceeds with Retention of Configuration. J Am Chem Soc. Nov. 15, 2017;139(45):16084-16087 and Supplementary Material, pp. S1-S52.doi: 10.1021/jacs. 7b09890. Epub Nov. 7, 2017.

Maianti et al. Toxicity modulation, resistance enzyme evasion, and A-site X-ray structure of broad-spectrum antibacterial neomycin analogs. ACS Chem Biol. Sep. 19, 2014;9(9):2067-73.doi: 10.1021/cb5003416. Epub Jul. 14, 2014.

Moazed et al. Interaction of antibiotics with functional sites in 16S ribosomal RNA. Nature. Jun. 4-10, 1987;327(6121):389-94.doi: 10.1038/327389a0.

PCT/US2018/047969 International Search Report and Written Opinion dated Dec. 4, 2018.

PCT/US2018/047993 International Search Report and Written Opinion dated Dec. 6, 2018.

Qin et al. Total Synthesis of a Densely Functionalized Plesiomonas shigelloides Serotype 51 Aminoglycoside Trisaccharide Antigen. J. Am. Chem. Soc. 140(8):3120-3127 (Jan. 29, 2018). DOI: https://doi.org/10.1021/jacs.8b00148.

Sati et al. N6', N6''', and O4' Modifications to Neomycin Affect Ribosomal Selectivity without Compromising Antibacterial Activity. ACS Infect. Dis. 2017, 3, 5, 368-377 with Supporting Information, pp. S1-S71 (Mar. 27, 2017). DOI: https://doi.org/10.1021/acsinfecdis.6b00214.

Silva et al. New insights into aminoglycoside antibiotics and derivatives. Curr Med Chem. 2007;14(10):1101-19.doi: 10.2174/092986707780362817.

* cited by examiner

MODULAR SYNTHESIS OF AMINOGLYCOSIDES

CROSS REFERENCE TO RELATED APPLICATIONS

This application is a divisional application of application Ser. No. 17/044,960, filed on Oct. 10, 2020, which is a 371 National Stage Application of International Application No. PCT/US2018/047993, filed Aug. 24, 2018, and which claims the benefit of U.S. Provisional Application No. 62/652,169, filed Apr. 3, 2018, the content of each of which is incorporated herein in its entirety.

FIELD OF THE DISCLOSURE

The present disclosure relates to novel synthetic methods for preparing aminoglycoside compounds, as well as to related intermediates.

BACKGROUND OF THE DISCLOSURE

Chemical synthesis, biosynthesis, and semi-synthesis on natural products are efficient means to procure amounts of oligosaccharide materials for assessment of therapeutic benefit in a wide variety of diseases [Anish, C.; Schumann, B.; Pereira, C. L.; Seeberger, P. H. Chem. Biol. 2014, 21, 38-50.].

Highly functionalized aminoglycoside di-, tri-, and tetra-saccharides have found utility in anti-bacterial therapeutics and are densely functionalized molecules on a carbohydrate backbone [Arya, D. P. Aminoglycoside Antibiotics: From Chemical Biology to Drug Discovery; Wiley: Hoboken, NJ, 2007]. These molecules are often prepared from natural and unnatural products formed from biosynthesis in combination with chemical synthesis and require judicious use of protecting groups and careful analysis of stereochemistry at newly created functional groups and/or glycosyl positions [Garneau-Tsodikova, S.; Chandrika, N. T.; Chemical Society Reviews (2018), 47(4), 1189-1249].

Given the complexity of performing synthetic chemistry on such densely functionalized and protected molecules, previous efforts in the field have led to modifications on the periphery [Cao, H.; Hwang, J.; Chen, X.; Opportunity, Challenge and Scope of Natural Products in Medicinal Chemistry (2011), 411-431] with only a few examples of modifications to the backbone [highlighted in bold, shown below] of the complex carbohydrate structure:

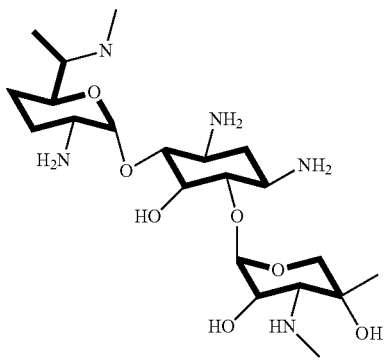

Gentamicin with backbone highlighted in bold for clarity

[Silva, J. G.; Carvalho, I.; Current Medicinal Chemistry (2007), 14(10), 1101-1119] and multiple reports on the lack of access to said molecules [Qin, C.; Schuumann, B.; Zou, X.; Periera, C. L.; Tian, G.; Hu, J.; Seeberger, P. H.; Yin, J.; J. Am. Chem. Soc. 2018, 140, 3120-3127 and references therein] which may represent novel therapeutics.

SUMMARY OF THE DISCLOSURE

In brief, the present disclosure relates to novel synthetic methods for preparing antibacterial aminoglycoside compounds and novel intermediates.

The present disclosure provides a process for preparing a compound of formula A-5,

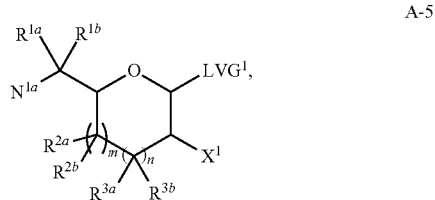

A-5 wherein
$R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and
wherein each $R^{12}$, $R^{13}$, $R^{14}$, $R^{15}$, and $R^{16}$ is independently H or alkyl; or
$R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and
wherein each $R^{22}$, $R^{21}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;
$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, —$OR^{30}$, —$NR^{31}R^{32}$, —$SR^{33}$, and —$SO_2R^{34}$;
wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or
$R^{2a}$ and $R^{2b}$ form an oxo or imino group substituted with $C_1$-$C_6$ alkyl;
$R^{3a}$ and $R^{3b}$ form an oxo or imino group substituted with $C_1$-$C_6$ alkyl;
$X^1$ is —F, —Cl, —Br, or —I;
$LVG^1$ is a leaving group;
$N^{1a}$ is —$NHPg^{1a}$, —$N(Pg^{1a})_2$, or $N_3$, wherein each $Pg^{1a}$ is independently an amino protecting group;

m is zero, 1, or 2;
n is zero, 1, or 2; and,
wherein m+n is 1, 2 or 3;
or a salt, solvate, enantiomer, or diastereomer thereof, comprising:
(a) contacting a compound of formula A-1:

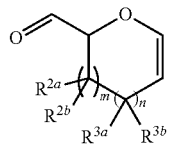

A-1 or a salt, solvate, enantiomer, or diastereomer thereof, with a chiral auxiliary reagent to yield a compound of formula A-2:

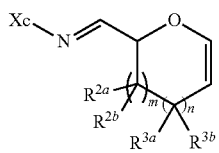

A-2 or a salt, solvate, enantiomer, or diastereomer thereof, wherein Xc is a chiral auxiliary group;
(b) contacting the compound of formula A-2 with a Grignard or organolithium reagent to yield a compound of formula A-3:

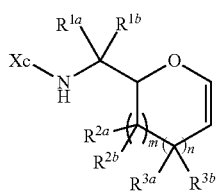

A-3 or a salt, solvate, enantiomer, or diastereomer thereof,
(c) contacting the compound of formula A-3 with a halogen reagent in presence of a nucleophile reagent (Nuc-1) to yield a compound of formula A-4:

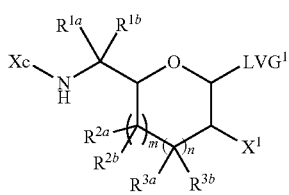

A-4 or a salt, solvate, enantiomer, or diastereomer thereof; wherein
$X^1$ is —F, —Cl, —Br, or —I;
Nuc-1 is $LVG^1$-M, wherein M is H, a metal cation, a non-metal cation, or a lone pair of electrons;
$LVG^1$ is a leaving group;
(d) exchanging the chiral auxiliary group for an amino protecting group in the compound of formula A-4 by reaction with an amino protecting group reagent to yield the compound of formula A-5:

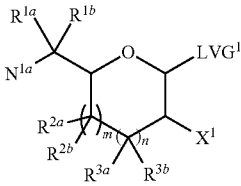

A-5 or a salt, solvate, enantiomer, or diastereomer thereof,
wherein $N^{1a}$ is —$NHPg^{1a}$, —$N(Pg^{1a})_2$, or $N_3$, wherein $Pg^{1a}$ is an amino protecting group.

The present disclosure provides a process for preparing a compound of formula A-5a,

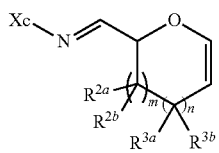

A-5a wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, and $R^{3a}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3b}$ is H;

$N^{1b}$ is —NHPg$^{1b}$, —N(Pg$^{1b}$)$_2$, or $N_3$, wherein each Pg$^{1a}$ is independently an amino protecting group;

$X^2$ is —F, —Cl, —Br, or —I;

$LVG^2$ is a leaving group.

m is zero, 1, or 2;

n is zero, 1, or 2;

wherein m+n is 1, 2 or 3;

or a salt, solvate, enantiomer, or diastereomer thereof, comprising:

(a) converting —OH in the compound of formula A-7

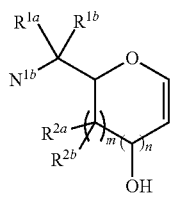

A-7 or a salt, solvate, enantiomer, or diastereomer thereof, to $R^{3a}$ to yield a compound of formula A-8:

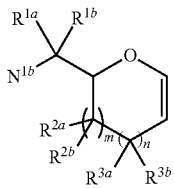

A-8 or a salt, solvate, enantiomer, or diastereomer thereof, wherein (b) contacting the compound of formula A-8 with a halogen reagent in presence of a nucleophile reagent (Nuc-2) to yield a compound of formula A-5a:

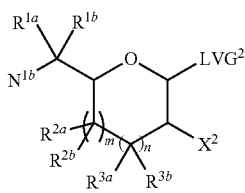

A-5a or a salt, solvate, enantiomer, or diastereomer thereof; wherein $X^2$ is —F, —Cl, —Br, or —I;

Nuc-2 is LVG$^2$-M, wherein M is H, a metal cation, a non-metal cation, or a lone pair of electrons;

$LVG^2$ is a leaving group.

The present disclosure provides a process for preparing a compound of formula B-6':

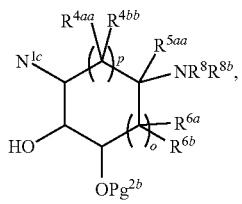

(B-6')

wherein $R^{4aa}$ and $R^{4bb}$ are, independently H, —OH, —OR$^{40}$, —NR$^{41}$R$^{42}$, or halogen;

wherein each $R^{40}$, $R^{41}$, and $R^{42}$ are independently H, alkyl, —CONH$_2$, or —COCH$_3$; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^{5aa}$ is H, —CN, —CONH$_2$ or $C_1$-$C_3$alkyl, wherein the alkyl is unsubstituted or substituted with one or more substituents selected from the group consisting of —OH, —OC(O)CH$_3$, —NH$_2$, —CN, —CONH$_2$, and halogen;

$R^{6a}$ and $R^{6b}$ are, independently H, halogen, NH$_2$, —OH, $C_1$-$C_3$alkoxy, —OC(O)CH$_3$, or —OPg$^{2o}$; wherein Pg$^{2o}$ is a hydroxyl protecting group;

$R^8$ is H, $C_1$-$C_6$ alkyl, an amino protecting group, or

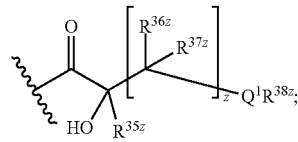

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{8b}$ is H or $C_1$-$C_3$alkyl;

$N^{1c}$ is —NHPg$^{1c}$ or $N_3$, wherein Pg$^{1c}$ is an amino protecting group Pg$^{2b}$ is a hydroxyl protecting group;

o is zero, 1, or 2;

p is zero, 1, or 2;

wherein o+p is 1, 2 or 3;

or a salt, solvate, enantiomer, or diastereomer thereof, comprising:

(a) contacting a compound of formula B-1':

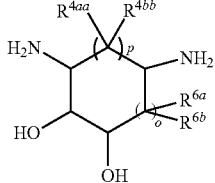

B-1' or a salt, solvate, enantiomer, or diastereomer thereof, with an amino protecting group reagent and a hydroxyl protecting group reagent to yield a compound of formula B-2':

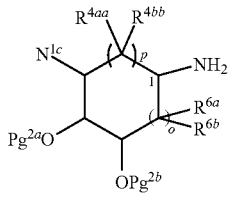

B-2' or a salt, solvate, enantiomer, or diastereomer thereof; wherein $Pg^{2a}$ is a hydroxyl protecting group;

(b) converting the amino group of the compound of formula B-2' at C1 to an azide group;

(c) converting the azide group of the compound of formula B-2' at C1 to a hydroxyl group;

(d) oxidizing the hydroxyl group of the compound of formula B-2' at C1 to an oxo group to yield a compound of formula B-3':

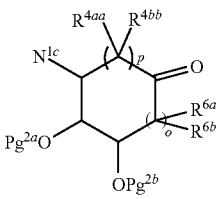

B-3' or a salt, solvate, enantiomer, or diastereomer thereof;

(e) converting the oxo group of the compound of formula B-3' to an imino group and contacting with an amino reactive reagent to yield a compound of formula B-4':

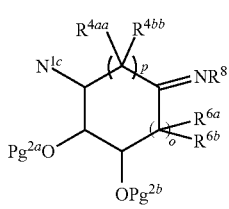

B-4' or a salt, solvate, enantiomer, or diastereomer thereof;

(f) contacting the compound of formula B-4' with a Grignard or organolithium reagent to yield a compound of formula B-5':

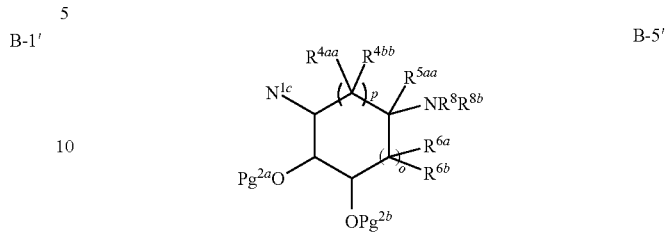

B-5' or a salt, solvate, enantiomer, or diastereomer thereof, (g) forming a hydroxyl group by selective removal of the $Pg^{2a}$ protecting group of the compound of formula B-5' to yield the compound of formula B-6':

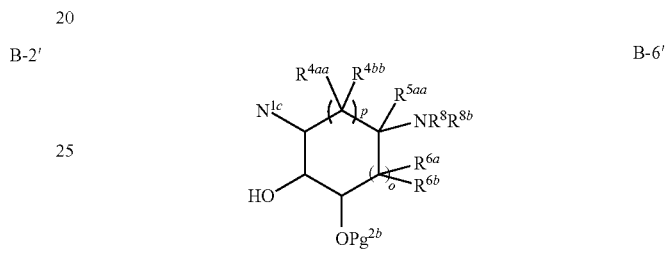

B-6' or a salt, solvate, enantiomer, or diastereomer thereof.

The present disclosure provides a process for preparing a compound of formula B-11':

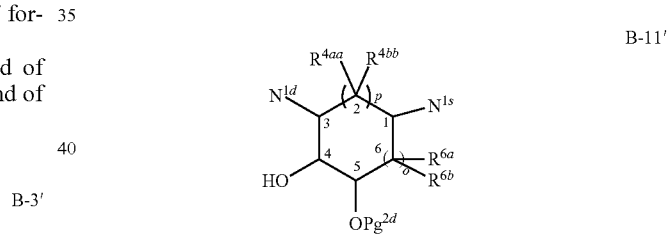

B-11' wherein
$R^{4aa}$ and $R^{4bb}$ are, independently H, —OH, —OR$^{40}$, —NR$^{41}$R$^{42}$, or halogen;
wherein each $R^{40}$, $R^{41}$, and $R^{42}$ are independently H, alkyl, —CONH$_2$, or —COCH$_3$; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;
$R^{6a}$ and $R^{6b}$ are, independently H, halogen, NH$_2$, —OH, $C_1$-$C_3$alkoxy, —OC(O)CH$_3$, or
—OPg$^{2o}$; wherein Pg$^{2o}$ is a hydroxyl protecting group;
$N^{1s}$ is $N_3$ or —NR$^8$R$^{8b}$;
$R^8$ is H, $C_1$-$C_6$ alkyl, an amino protecting group, or

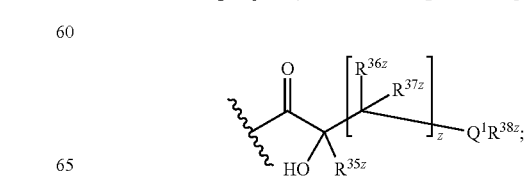

wherein

Q$^1$ is NH, O, or S;

z is an integer from 0 to 4,

R$^{35z}$ is H or C$_1$-C$_3$ alkyl;

each R$^{36z}$ and R$^{37z}$ is independently selected from the group consisting of H, alkyl, halogen, and —OH, and R$^{38z}$ is H, alkyl, or —C(=NH)NR$^{39z}$R$^{40z}$, wherein R$^{39z}$ and R$^{40z}$ are independently H or C$_1$-C$_3$ alkyl; or R$^{35z}$ and R$^{38z}$, together with the atoms to which they are attached, form a heterocycloalkyl group comprising at least one N;

R$^{8b}$ is H or C$_1$-C$_3$alkyl;

N$^{1d}$ is —NHPg$^{1d}$ or N$_3$, wherein Pg$^{1d}$ is an amino protecting group;

Pg$^{2d}$ is a hydroxyl protecting group;

o is zero, 1, or 2;

p is zero, 1, or 2;

wherein o+p is 1, 2 or 3;

or a salt, solvate, enantiomer, or diastereomer thereof, comprising:

(a) contacting a compound of formula B-8':

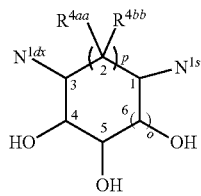

B-8' or a salt, solvate, enantiomer, or diastereomer thereof, wherein N$^{1dx}$ is —NH$_2$, —NHPg$^{1d}$ or N$_3$, wherein Pg$^{1d}$ is an amino protecting group, with a first selective hydroxyl protecting group reagent; a second selective hydroxyl protecting group reagent; an amino protecting group reagent, if N$^{1dx}$ is —NH$_2$; and an amino reactive reagent, if N$^{1s}$ is —NR$^8$R$^{8b}$, to yield a compound of formula B-9':

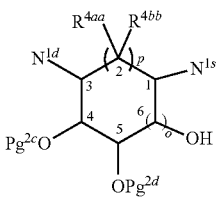

B-9' or a salt, solvate, enantiomer, or diastereomer thereof; wherein Pg$^{2c}$ is a hydroxyl protecting group;

(b) contacting the compound of formula B-9' with a electrophilic reagent or oxidizing the alcohol at C6 to an oxo group and contacting the oxo group with a nucleophilic reagent to yield a compound of formula B-10':

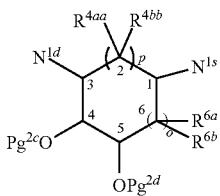

B-10' or a salt, solvate, enantiomer, or diastereomer thereof, c) forming a hydroxyl group by selective removal of the Pg$^{2c}$ protecting group of the compound of formula B-10' to yield the compound of formula B-11':

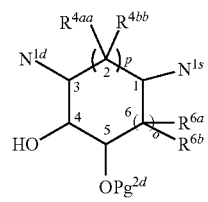

B-11' or a salt, solvate, enantiomer, or diastereomer thereof.

The present disclosure provides a process for preparing a compound of formula AB-1',

AB-1' wherein

R$^{1a}$ and R$^{1b}$ are independently selected from the group consisting of H, C$_1$-C$_{12}$ alkyl, C$_1$-C$_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —NR$^{14}$R$^{15}$, —N$_3$, and —OR$^{16}$, and wherein each R$^{12}$, R$^{13}$, R$^{14}$, R$^{15}$, and R$^{16}$ is independently H or alkyl; or R$^{1a}$ and R$^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each R$^{22}$, R$^{23}$, R$^{24}$, R$^{25}$, and R$^{26}$ is independently H or alkyl, wherein the alkyl is unsubstituted or substituted with one or more substituents independently selected from the group consisting of halogen, cyano, NR$^{14}$R$^{15}$, and —OR$^{16}$;

R$^{2a}$, R$^{2b}$, R$^{3a}$ and R$^{3b}$ are independently selected from the group consisting of H, —OR$^{27}$, —NR$^{28}$R$^{29}$, halogen, C$_1$-C$_4$ cycloalkyl, and $C_1$-$C_6$ alkyl, wherein each $R^{27}$, $R^2$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{14}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$R^{4aa}$ and $R^{4bb}$ are, independently H, —OH, —$OR^{40}$, —$NR^{41}R^{42}$, or halogen;

wherein each $R^{40}$, $R^{41}$, and $R^{42}$ are independently H, alkyl, —$CONH_2$, or —$COCH_3$; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5aa}$ is H, —CN, —$CONH_2$ or $C_1$-$C_3$alkyl, wherein the alkyl is unsubstituted or substituted with one or more substituents selected from the group consisting of —OH, —$OC(O)CH_3$, —$NH_2$, —CN, —$CONH_2$, and halogen;

$R^{6a}$ and $R^{6b}$ are, independently H, halogen, $NH_2$, —OH, $C_1$-$C_3$alkoxy, —$OC(O)CH_3$, or —$OPg^{2m}$; wherein $Pg^{2m}$ is a hydroxyl protecting group;

$R^{8a}$ is H, $C_1$-$C_6$ alkyl, an amino protecting group, or

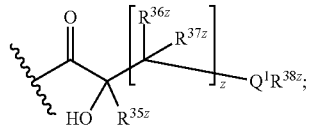

wherein
$Q^1$ is NH, O, or S;
z is an integer from 0 to 4,
$R^{35z}$ is H or $C_1$-$C_3$ alkyl;
each $R^{36z}$ and $R^{37z}$ is independently selected from the group consisting of H, alkyl, halogen, and —OH, and
$R^{38z}$ is H, alkyl, or —C(=NH)$NR^{39z}R^{40z}$, wherein $R^{39z}$ and $R^{40z}$ are independently H or $C_1$-$C_3$ alkyl; or
$R^{35z}$ and $R^{38z}$, together with the atoms to which they are attached, form a heterocycloalkyl group comprising at least one N;
$R^{8b}$ is H or $C_1$-$C_3$alkyl;
$N^{1e}$ is —OH, protected hydroxyl group, —$NHPg^{1e}$ or $N_3$, wherein $Pg^{1e}$ is an amino protecting group;
$N^{1f}$ is —$NHPg^{1f}$ or $N_3$, wherein $Pg^{1f}$ is an amino protecting group;
$Pg^{2e}$ is a hydroxyl protecting group;
$X^7$ is H, —$NH_2$, —$N_3$, protected amino group, —OH, protected hydroxyl group, or halogen;
m is zero, 1, or 2;
n is zero, 1, or 2;
wherein m+n is 1, 2 or 3;
o is zero, 1, or 2;
p is zero, 1, or 2;
wherein o+p is 1, 2 or 3;
or a salt, solvate, enantiomer, or diastereomer thereof, comprising:

(a) contacting a compound of formula A-9':

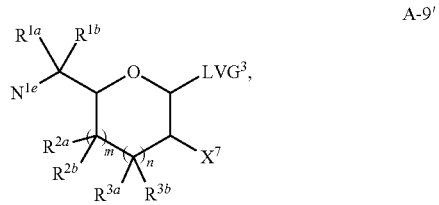

wherein $LVG^3$ is a leaving group,
with a compound of formula B-12:

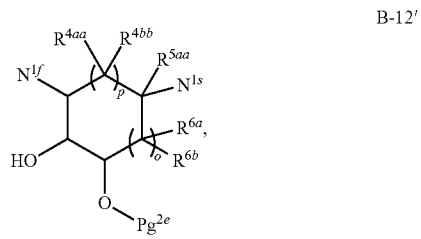

to yield the compound of formula (AB-1').

The present disclosure provides a process for preparing a compound of formula ABC-1',

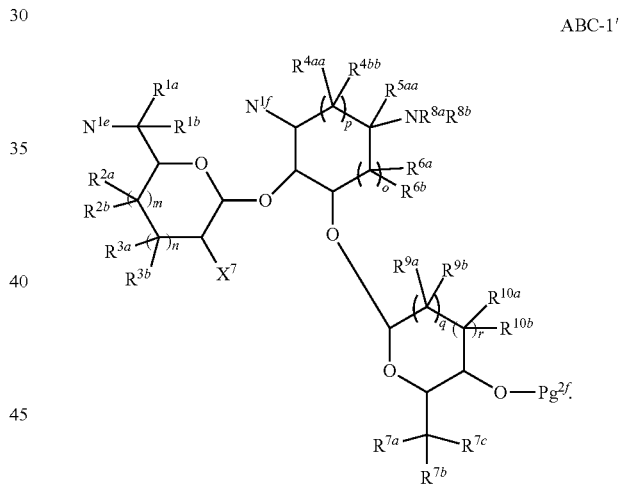

wherein the method comprises preparing a compound of formula AB-1, further comprising:

(b) selectively deprotecting the compound of formula AB-1' by removing the $Pg^{2e}$ moiety to yield a compound of formula AB-3:

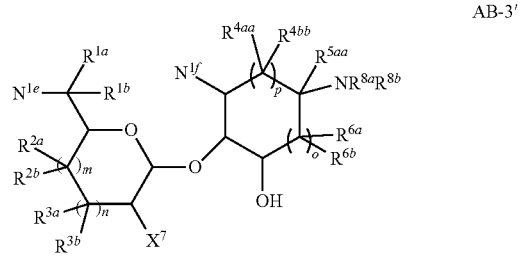

or a salt, solvate, enantiomer, or diastereomer thereof;

(c) contacting the compound of formula AB-3' with a compound of formula C-1, $$\text{C-1}$$

or a salt, solvate, enantiomer, or diastereomer thereof, wherein $R^{7a}$, $R^{7b}$, and $R^{7c}$ are, independently, H, $NH_2$, OH, —$OR^{71}$ or —$OPg^{2r}$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

wherein $Pg^{2r}$ is a hydroxyl protecting group;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$Pg^{2f}$ is a hydroxyl protecting group;

$LVG^4$ is a leaving group;

q is zero, 1, or 2;

r is zero, 1, or 2;

wherein q+r is 1, 2 or 3;

to yield a compound of formula ABC-1', or a salt, solvate, enantiomer, or diastereomer thereof.

The present disclosure provides a process for preparing a compound of formula ABCD-1', $$\text{ABCD-1'}$$

wherein the method comprises preparing a compound of formula AB-1', further comprising:

(b) selectively deprotecting the compound of formula AB-1' by removing the $Pg^{2e}$ moiety to yield a compound of formula AB-3':

$$\text{AB-3'}$$

or a salt, solvate, enantiomer, or diastereomer thereof;

(c) contacting the compound of formula AB-3' with a compound of formula CD-1, $$\text{CD-1}$$

or a salt, solvate, enantiomer, or diastereomer thereof, wherein $R^{7a}$, $R^{7b}$, and $R^{7c}$ are, independently, H, $NH_2$, OH, —$OR^{71}$ or —$OPg^{2r}$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

wherein $Pg^{2r}$ is a hydroxyl protecting group;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$LVG^5$ is a leaving group;

$N^{1g}$ is —$NHPg^{1g}$ or $N_3$, wherein $Pg^{1g}$ is an amino protecting group;

$N^{1h}$ is —$NHPg^{1h}$ or $N_3$, wherein $Pg^{1h}$ is an amino protecting group;

Pg²ᵍ is a hydroxyl protecting group;
Pg²ʰ is a hydroxyl protecting group;
q is zero, 1, or 2;
r is zero, 1, or 2;
wherein q+r is 1, 2 or 3;
to yield a compound of formula ABCD-1, or a salt, solvate, enantiomer, or diastereomer thereof.

The present disclosure provides a process for preparing a compound of formula B-6:

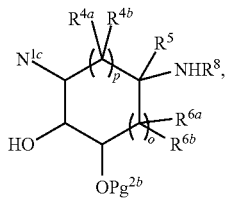

B-6 wherein
$R^{4a}$ and $R^{4b}$ are, independently H, —OH, —OR⁴⁰, —NR⁴¹R⁴², or halogen;
wherein each $R^{40}$, $R^{41}$, and $R^{42}$ are independently H or alkyl; wherein the alkyl is unsubstituted or substituted with one or more substituents selected from the group consisting of —CONH₂, —OH, —NH₂, —COCH₃, aryl, substituted aryl, heteroaryl, halogen, and substituted heteroaryl;
$R^5$ is H, —CN, —CONH₂ or $C_1$-$C_3$alkyl, wherein the alkyl is unsubstituted or substituted with one or more substituents selected from the group consisting of —OH, —NH₂, —CN, —CONH₂, and halogen;
$R^{6a}$ and $R^{6b}$ are, independently H, halogen, NH₂, —OH, $C_1$-$C_3$alkoxy, —OC(O)CH, or —OPg²ᵒ; wherein Pg²ᵒ is a hydroxyl protecting group;
$R^8$ is H, $C_1$-$C_6$ alkyl, an amino protecting group, or

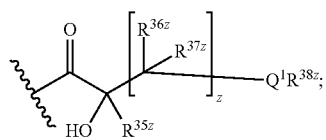

wherein
$Q^1$ is NH, O, or S;
z is an integer from 0 to 4,
$R^{35z}$ is H or $C_1$-$C_3$ alkyl;
each $R^{36z}$ and $R^{37z}$ is independently selected from the group consisting of H, alkyl, halogen, and —OH, and
$R^{38z}$ is H, alkyl, or —C(=NH)NR³⁹ᶻR⁴⁰ᶻ, wherein $R^{39z}$ and $R^{40z}$ are independently H or $C_1$-$C_3$ alkyl; or
$R^{35z}$ and $R^{38z}$, together with the atoms to which they are attached, form a heterocycloalkyl group comprising at least one N;
$N^{1c}$ is —NHPg¹ᵉ or N₃, wherein Pg¹ᶜ is an amino protecting group;
Pg²ᵇ is a hydroxyl protecting group;
o is zero, 1, or 2;
p is zero, 1, or 2;
wherein o+p is 1, 2 or 3;
or a salt, solvate, enantiomer, or diastereomer thereof, comprising:

(a) contacting a compound of formula B-1:

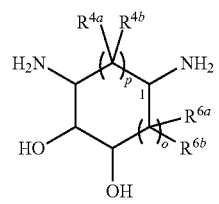

B-1 or a salt, solvate, enantiomer, or diastereomer thereof, with an amino protecting group reagent and a hydroxyl protecting group reagent to yield a compound of formula B-2:

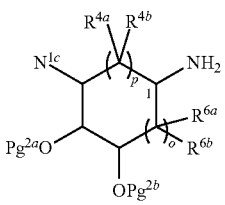

B-2 or a salt, solvate, enantiomer, or diastereomer thereof;
wherein Pg²ᵃ is a hydroxyl protecting group;
(b) converting the amino group of the compound of formula B-2 at C1 to an azide group;
(c) converting the azide group of the compound of formula B-2 at C1 to a hydroxyl group;
(d) oxidizing the hydroxyl group of the compound of formula B-2 at C1 to an oxo group to yield a compound of formula B-3:

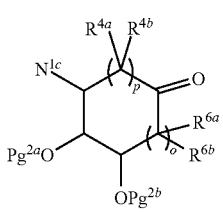

B-3 or a salt, solvate, enantiomer, or diastereomer thereof;
(e) converting the oxo group of the compound of formula B-3 to an imino group and contacting with an amino reactive reagent to yield a compound of formula B-4:

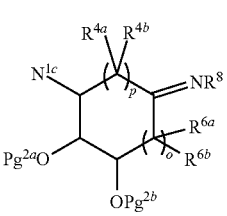

B-4 or a salt, solvate, enantiomer, or diastereomer thereof;

(f) contacting the compound of formula B-4 with a Grignard or organolithium reagent to yield a compound of formula B-5:

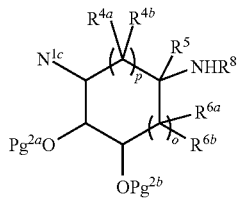

B-5 or a salt, solvate, enantiomer, or diastereomer thereof, (g) forming a hydroxyl group by selective removal of the $Pg^{2a}$ protecting group of the compound of formula B-6 to yield the compound of formula B-7:

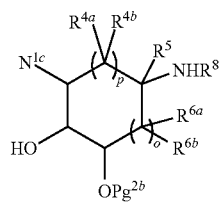

B-6 or a salt, solvate, enantiomer, or diastereomer thereof.

The present disclosure provides a process for preparing a compound of formula B-11:

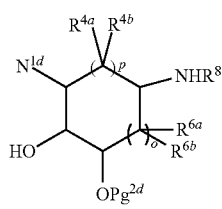

B-11 wherein $R^{4a}$ and $R^{4b}$ are, independently, H, —OH, —$OR^{40}$, —$NR^{41}R^{42}$, or halogen;

wherein each $R^{40}$, $R^{41}$, and $R^{42}$ are independently H or alkyl; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{6a}$ and $R^{6b}$ are, independently, H, halogen, $NH_2$, —OH, $C_1$-$C_3$alkoxy, —$OC(O)CH_3$, or —$OPg^{2o}$; wherein $Pg^{2o}$ is a hydroxyl protecting group;

$R^8$ is H, $C_1$-$C_6$ alkyl, an amino protecting group, or

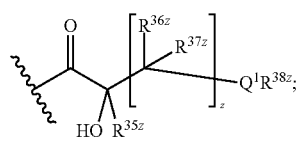

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —$C(=NH)NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$N^{1d}$ is —$NHPg^{1d}$ or $N_3$, wherein $Pg^{1d}$ is an amino protecting group;

$Pg^{2d}$ is a hydroxyl protecting group;

o is zero, 1, or 2;

p is zero, 1, or 2;

wherein o+p is 1, 2 or 3;

or a salt, solvate, enantiomer, or diastereomer thereof, comprising:

(a) contacting a compound of formula B-8:

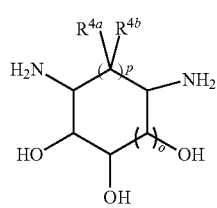

B-8 or a salt, solvate, enantiomer, or diastereomer thereof, with an amino protecting group reagent and a first selective hydroxyl protecting group reagent and a second selective hydroxyl protecting group reagent and an amino reactive reagent to yield a compound of formula B-9:

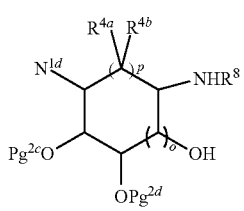

B-9 or a salt, solvate, enantiomer, or diastereomer thereof; wherein $Pg^{2e}$ is a hydroxyl protecting group;

(b) contacting the compound of formula B-9 with a electrophilic reagent to yield a compound of formula B-10:

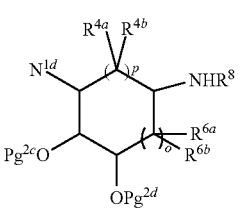

B-10 or a salt, solvate, enantiomer, or diastereomer thereof, c) forming a hydroxyl group by selective removal of the Pg$^{2c}$ protecting group of the compound of formula B-10 to yield the compound of formula B-11:

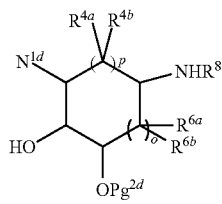

B-11 or a salt, solvate, enantiomer, or diastereomer thereof.

The present disclosure provides a process for preparing a compound of formula AB-1,

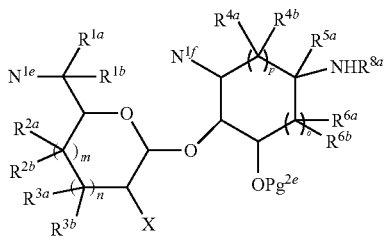

AB-1 wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^3$, —OSF$_2$NR$^{14}$R$^{15}$, —NR$^{14}$R$^{15}$, —N$_3$, and —OR$^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each $R^{22}$, $R^{23}$, $R^{24}$, $R^2$, and $R^{26}$ is independently H or alkyl, wherein the alkyl is unsubstituted or substituted with one or more substituents independently selected from the group consisting of halogen, cyano, NR$^{14}$R$^{15}$, and —OR$^{16}$;

$R^{2a}$, $R^{2b}$, $R^{3a}$ and $R^{3b}$ are independently selected from the group consisting of H, —OR$^{27}$, —NR$^{28}$R$^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —OR$^{30}$, —NR$^{31}$R$^{32}$, —SR$^{33}$, and —SO$_2$R$^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, NR$^{14}$R$^{15}$, and —OR$^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$R^{4a}$ and $R^{4b}$ are, independently, H, —OH, —OR$^{40}$, —NR$^{41}$R$^{42}$, or halogen;

wherein each $R^{40}$, $R^{41}$, and $R^{42}$ are independently H or alkyl;

wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^{5a}$ is H, —CN, —CONH$_2$ or $C_1$-$C_3$alkyl, wherein the alkyl is unsubstituted or substituted with one or more substituents selected from the group consisting of —OH, —NH$_2$, —CN, —CONH$_2$, and halogen;

$R^{6a}$ and $R^{6b}$ are, independently H, halogen, NH$_2$, —OH, $C_1$-$C_3$alkoxy, —OC(O)CH$_3$, or —OPg$^{2m}$; wherein Pg$^{2m}$ is a hydroxyl protecting group;

$R^{8a}$ is H, $C_1$-$C_6$ alkyl, an amino protecting group, or

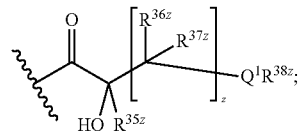

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$N^{1e}$ is —NHPg$^{1e}$ or N$_3$, wherein Pg$^{1e}$ is an amino protecting group;

$N^{1f}$ is —NHPg$^{1f}$ or N$_3$, wherein Pg$^{1f}$ is an amino protecting group;

Pg$^{2e}$ is a hydroxyl protecting group;

X is —NH$_2$, —N$_3$, protected amino group, —OH, or protected hydroxyl group;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3;

or a salt, solvate, enantiomer, or diastereomer thereof, comprising:

(a) contacting a compound of formula A-9:

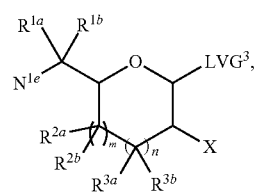

A-9 wherein LVG$^3$ is a leaving group, with a compound of formula B-12:

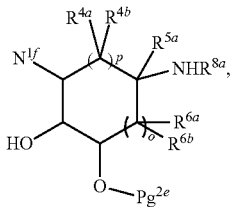

to yield the compound of formula (AB-1).

The present disclosure provides a process for preparing a compound of formula ABC-1,

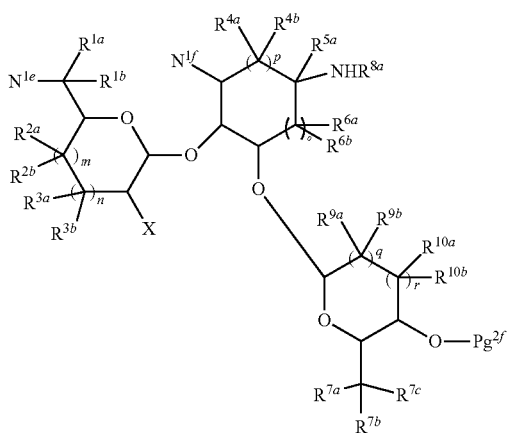

wherein the method comprises preparing a compound of formula AB-1, further comprising:

(b) selectively deprotecting the compound of formula AB-1 by removing the $Pg^{2e}$ moiety to yield a compound of formula AB-3:

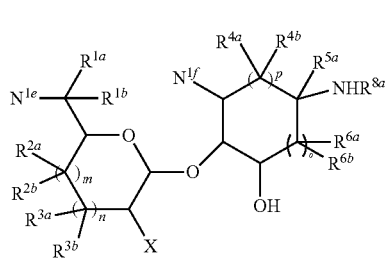

or a salt, solvate, enantiomer, or diastereomer thereof;

(c) contacting the compound of formula AB-3 with a compound of formula C-1,

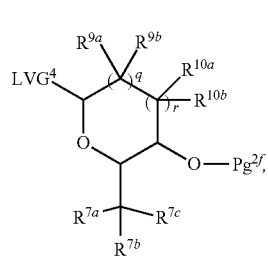

or a salt, solvate, enantiomer, or diastereomer thereof, wherein $R^{7a}$, $R^{7b}$, and $R^{7c}$ are, independently, H, $NH_2$, OH, —$OR^{71}$ or —$OPg^{2r}$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

wherein $Pg^{2r}$ is a hydroxyl protecting group;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$Pg^{2f}$ is a hydroxyl protecting group;

$LVG^4$ is a leaving group;

q is zero, 1, or 2;

r is zero, 1, or 2;

wherein q+r is 1, 2 or 3;

to yield a compound of formula ABC-1, or a salt, solvate, enantiomer, or diastereomer thereof.

The present disclosure provides a process for preparing a compound of formula ABCD-1, wherein the method comprises preparing a compound of formula AB-1, further comprising:

(b) selectively deprotecting the compound of formula AB-1 by removing the $Pg^{2e}$ moiety to yield a compound of formula AB-3:

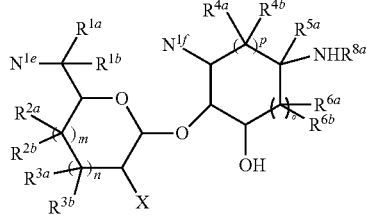

AB-3 or a salt, solvate, enantiomer, or diastereomer thereof;

(c) contacting the compound of formula AB-3 with a compound of formula CD-1,

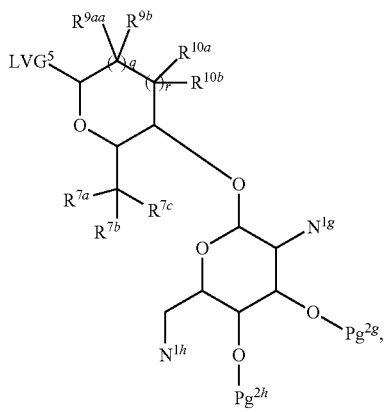

CD-1 or a salt, solvate, enantiomer, or diastereomer thereof, wherein $R^{7a}$, $R^{7b}$, and RC are, independently, H, $NH_2$, OH, $-OR^{71}$ or $-OPg^{2r}$;

wherein $R^{71}$ is alkyl; wherein the alkyl is unsubstituted or substituted with one or more substituents selected from the group consisting of $-CONH_2$, $-OH$, $-NH_2$, $-COCH_3$, aryl, substituted aryl, heteroaryl, halogen, and substituted heteroaryl;

wherein $Pg^{2r}$ is a hydroxyl protecting group;

$R^{9a}$ and $R^{9b}$ are independently H, OH, or $-OR^{91}$, wherein $R^{91}$ is alkyl, alkenyl, or alkynyl; wherein the alkyl, alkenyl, and alkynyl is unsubstituted or substituted with one or more substituents selected from the group consisting of $-CONH_2$, $-OH$, $-NH_2$, $-COCH_3$, aryl, substituted aryl, heteroaryl, and substituted heteroaryl;

$R^{10a}$ and $R^{10b}$ are independently H, OH, or $-OR^{101}$, wherein $R^{101}$ is alkyl, alkenyl, or alkynyl; wherein the alkyl, alkenyl, and alkynyl is unsubstituted or substituted with one or more substituents selected from the group consisting of $-CONH_2$, $-OH$, $-NH_2$, $-COCH_3$, aryl, substituted aryl, heteroaryl, and substituted heteroaryl;

$LVG^5$ is a leaving group;

$N^{1g}$ is $-NHPg^{1g}$ or $N_3$, wherein $Pg^{1g}$ is an amino protecting group;

$N^{1h}$ is $-NHPg^{1h}$ or $N_3$, wherein $Pg^{1h}$ is an amino protecting group;

$Pg^{2g}$ is a hydroxyl protecting group;

$Pg^{2h}$ is a hydroxyl protecting group;

q is zero, 1, or 2;

r is zero, 1, or 2;

wherein q+r is 1, 2 or 3;

to yield a compound of formula ABCD-1, or a salt, solvate, enantiomer, or diastereomer thereof.

The present disclosure provides a compound of formula A-10':

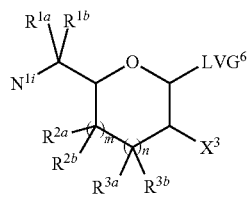

A-10' and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, $-SR^{12}$, $-SO_2R^{13}$, $-OSF_2NR^{14}R^{15}$, $-NR^{14}R^{15}$, $-N_3$, and $-OR^{16}$, and wherein each $R^{12}$, $R^{13}$, $R^4$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, $-SR^{22}$, $-SO_2R^{21}$, $-NR^{24}R^{25}$, and $-OR^{26}$, and wherein each $R^{22}$, $R^{21}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and $-OR^{16}$;

$R^{2a}$, $R^{2b}$, $R^{3a}$ and $R^{3b}$ are independently selected from the group consisting of H, $-OR^{27}$, $-NR^{28}R^{29}$, halogen, $C_1$-$C_4$ cycloalkyl, and $C_1$-$C_6$ alkyl, wherein each $R^{27}$, $R^{28}$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, $-OR^{30}$, $-NR^{31}R^{32}$, $-SR^3$, and $-SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and $-OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^3$ is selected from the group consisting of H, $NH_2$, $N_3$, protected amino group, OH, $-OPg^{2i}$, and halogen; wherein $Pg^{2i}$ is a hydroxyl protecting group;

$LVG^6$ is a leaving group;

$N^{1i}$ is $-OH$, protected hydroxyl group, $-NHPg^{1i}$, $N(Pg^{1i})_2$, $-NH_2$, or $N_3$, wherein each $Pg^{1i}$ is independently an amino protecting group;

m is zero, 1, or 2;
n is zero, 1, or 2;
wherein m+n is 1, 2 or 3.

The present disclosure provides a compound of formula B-13':

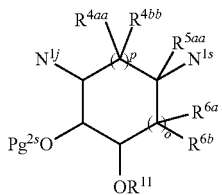

B-13' and salts, solvates, enantiomers, and diastereomers thereof, wherein $R^{4aa}$ and $R^{4bb}$ are, independently H, —OH, —OR$^{40}$, —NR$^{41}$R$^{42}$, or halogen;

wherein each $R^{40}$, $R^{41}$, and $R^{42}$ are independently H, alkyl, —CONH$_2$, or —COCH$_3$; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^{5aa}$ is H, —CN, —CONH$_2$ or C$_1$-C$_3$alkyl, wherein the alkyl is unsubstituted or substituted with one or more substituents selected from the group consisting of —OH, —OC(O)CH$_3$, —NH$_2$, —CN, —CONH$_2$, and halogen;

$R^{6a}$ and $R^{6b}$ are, independently H, halogen, NH$_2$, —OH, C$_1$-C$_3$alkoxy, —OC(O)CH$_3$, or —OPg$^{2j}$; wherein Pg$^{2j}$ is a hydroxyl protecting group;

$N^{1s}$ is N$_3$ or —NR$^{8a}$R$^{8b}$;

$R^{8a}$ is H, C$_1$-C$_6$ alkyl, an amino protecting group, or

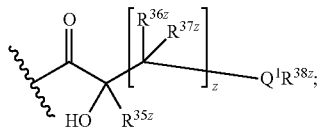

wherein

Q$^1$ is NH, O, or S;

z is an integer from 0 to 4, $R^{35z}$ is H or C$_1$-C$_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein $R^{39z}$ and $R^{40z}$ are independently H or C$_1$-C$_3$ alkyl; or $R^{35z}$ and $R^{38z}$, together with the atoms to which they are attached, form a heterocycloalkyl group comprising at least one N;

$R^{8b}$ is H or C$_1$-C$_3$alkyl;

$R^{11}$ is H, alkyl, —COCH$_3$, or a hydroxyl protecting group;

$N^{1j}$ is —NHPg$^{1j}$, —NH$_2$, or N$_3$, wherein Pg$^{1j}$ is an amino protecting group;

Pg$^{2s}$ is H or hydroxyl protecting group;

o is zero, 1, or 2;

p is zero, 1, or 2;

wherein o+p is 1, 2 or 3.

The present disclosure provides a compound of formula AB-4':

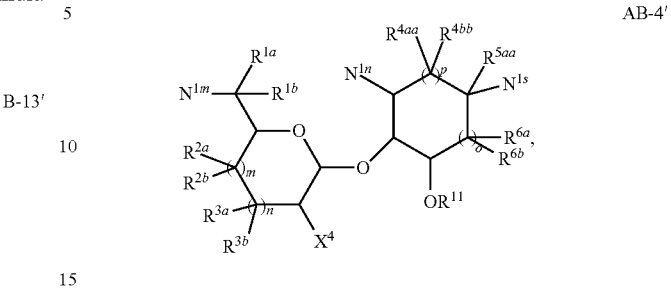

AB-4' and salts, solvates, enantiomers, and diastereomers thereof, wherein $R^{1a}$ and $R^{1b}$ are independently selected from the group consisting of H, C$_1$-C$_{12}$ alkyl, C$_1$-C$_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —N$_3$, and —OR$^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each $R^{22}$, $R^{21}$, $R^{24}$, $R^{25}$, and $R^{26}$ is independently H or alkyl, wherein the alkyl is unsubstituted or substituted with one or more substituents independently selected from the group consisting of halogen, cyano, NR$^{14}$R$^{15}$, and —OR$^{16}$;

$R^{2a}$, $R^{2b}$, $R^{3a}$ and $R^{3b}$ are independently selected from the group consisting of H, —OR$^{27}$, —NR$^{28}$R$^{29}$, halogen, C$_1$-C$_4$ cycloalkyl, and C$_1$-C$_6$ alkyl, wherein each $R^{27}$, $R^{28}$, and $R^{29}$ is independently H, alkyl, amino protecting group, or hydroxyl protecting group; wherein the C$_1$-C$_6$ alkyl or alkyl is unsubstituted or substituted with one or more substituents selected from the group consisting of aryl, halogen, —OR$^{30}$, —NR$^{31}$R$^{32}$, —SR$^{33}$, and —SO$_2$R$^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, NR$^{14}$R$^{15}$, and —OR$^{16}$; or $R^{2a}$ and $R^{2b}$ form an oxo or imino group substituted with C$_1$-C$_6$ alkyl;

$R^{3a}$ and $R^{3b}$ form an oxo or imino group substituted with C$_1$-C$_6$ alkyl;

$X^4$ is selected from the group consisting of H, NH$_2$, N$_3$, protected amino group, OH, —OPg$^{2k}$, and halogen; wherein Pg$^{2k}$ is a hydroxyl protecting group;

$R^{4aa}$ and $R^{4bb}$ are, independently, H, —OH, —OR$^{40}$, —NR$^{41}$R$^{42}$, or halogen;

wherein each $R^{40}$, $R^{41}$, and $R^{42}$ are independently H, alkyl, —CONH$_2$, or —COCH$_3$; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^{5aa}$ is H, —CN, —CONH$_2$ or C$_1$-C$_3$alkyl, wherein the alkyl is unsubstituted or substituted with one or more substituents selected from the group consisting of —OH, —OC(O)CH$_3$, —NH$_2$, —CN, —CONH$_2$, and halogen;

$R^{6a}$ and $R^{6b}$ are, independently H, halogen, $NH$, —OH, $C_1$-$C_3$alkoxy, —OC(O)CH$_3$, or —OPg$^{2j}$; wherein Pg$^{2j}$ is a hydroxyl protecting group;

$N^{1s}$ is $N_3$ or —NR$^{8a}$R$^{8b}$;

$R^{8a}$ is H, $C_1$-$C_6$ alkyl, an amino protecting group, or

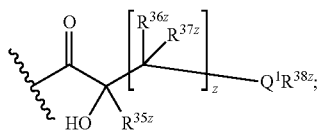

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{8b}$ is H or $C_1$-$C_3$alkyl;

$R^{11}$ is H, alkyl, —COCH$_3$, or a hydroxyl protecting group;

$N^{1m}$ is —OH, protected hydroxyl group, —NHPg$^{1m}$, N(Pg$^{1m}$)$_2$, —NH$_2$, or $N_3$, wherein each Pg$^{1m}$ is independently an amino protecting group;

$N^{1n}$ is —NHPg$^{1n}$, —NH$_2$, or $N_3$, wherein Pg$^{1n}$ is an amino protecting group;

m is zero, 1, or 2;

n is zero, 1, or 2;

wherein m+n is 1, 2 or 3;

o is zero, 1, or 2;

p is zero, 1, or 2;

wherein o+p is 1, 2 or 3.

The present disclosure provides a compound of formula ABC-3':

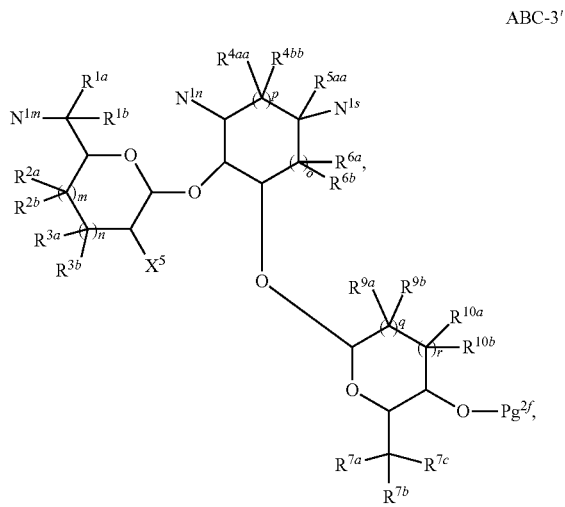

ABC-3' and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —N$_3$, and —OR$^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, NR$^{14}$R$^{15}$, and —OR$^{16}$;

$R^{2a}$, $R^{2b}$, $R^{3a}$ and $R^{3b}$ are independently selected from the group consisting of H, —OR$^{27}$, —NR$^{28}$R$^{29}$, halogen, $C_1$-$C_4$ cycloalkyl, and $C_1$-$C_6$ alkyl, wherein each $R^{27}$, $R^{28}$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, —OR$^{30}$, —NR$^{31}$R$^{32}$, —SR$^3$, and —SO$_2$R$^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, NR$^{14}$R$^{15}$, and —OR$^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^5$ is selected from the group consisting of H, NH$_2$, $N_3$, protected amino group, OH, —OPg$^{2l}$, and halogen; wherein Pg$^{2l}$ is a hydroxyl protecting group;

$R^{4aa}$ and $R^{4bb}$ are, independently H, —OH, —OR$^{40}$, —NR$^{41}$R$^{42}$, or halogen;

wherein each $R^{40}$, $R^{41}$, and $R^{42}$ are independently H, alkyl, —CONH$_2$, or —COCH$_3$; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^{5aa}$ is H, —CN, —CONH$_2$ or $C_1$-$C_3$alkyl, wherein the alkyl is unsubstituted or substituted with one or more substituents selected from the group consisting of —OH, —OC(O)CH$_3$, —NH$_2$, —CN, —CONH$_2$, and halogen;

$R^{6a}$ and $R^{6b}$ are, independently H, halogen, NH$_2$, —OH, $C_1$-$C_3$alkoxy, —OC(O)CH$_3$, or —OPg$^{2j}$;

wherein Pg$^{2j}$ is a hydroxyl protecting group;

$R^{7a}$, $R^{7b}$, and $R^{7c}$ are, independently, H, OH, —OR$^{71}$ or —OPg$^2$;

wherein $R^{71}$ is alkyl; wherein the alkyl is unsubstituted or substituted with one or more substituents selected from the group consisting of —CONH$_2$, —OH, —NH$_2$, —COCH$_3$, aryl, substituted aryl, heteroaryl, and substituted heteroaryl;

wherein Pg$^2$ is a hydroxyl protecting group;

N$^{1s}$ is N$_3$ or —NR$^{8a}$R$^{8b}$;

R$^{8a}$ is H, C$_1$-C$_6$ alkyl, an amino protecting group, or

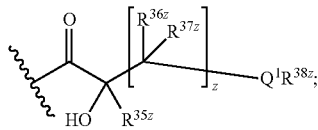

wherein

Q$^1$ is NH, O, or S;

z is an integer from 0 to 4,

R$^{35z}$ is H or C$_1$-C$_3$ alkyl;

each R$^{36z}$ and R$^{37z}$ is independently selected from the group consisting of H, alkyl, halogen, and —OH, and R$^{38z}$ is H, alkyl, or —C(=NH)NR$^{39z}$R$^{40z}$, wherein R$^{39z}$ and R$^{40z}$ are independently H or C$_1$-C$_3$ alkyl; or R$^{35z}$ and R$^{38z}$, together with the atoms to which they are attached, form a heterocycloalkyl group comprising at least one N;

R$^{8b}$ is H or C$_1$-C$_3$alkyl;

R$^{9a}$ and R$^{9b}$ are independently H, OH, or —OR$^{91}$, wherein R$^{91}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

R$^{10a}$ and R$^{10b}$ are independently H, OH, or —OR$^{101}$, wherein R$^{101}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

N$^{1o}$ is —OH, protected hydroxyl group, —NHPg$^{1o}$, N(Pg$^{1o}$)$_2$, —NH$_2$, or N$_3$, wherein each Pg$^{1o}$ is independently an amino protecting group;

N$^{1p}$ is —NHPg$^{1p}$, —NH$_2$, or N$_3$, wherein Pg$^{1p}$ is an amino protecting group;

Pg$^{2f}$ is a hydroxyl protecting group or H;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

The present disclosure provides a compound of formula ABCD-3':

ABCD-3'

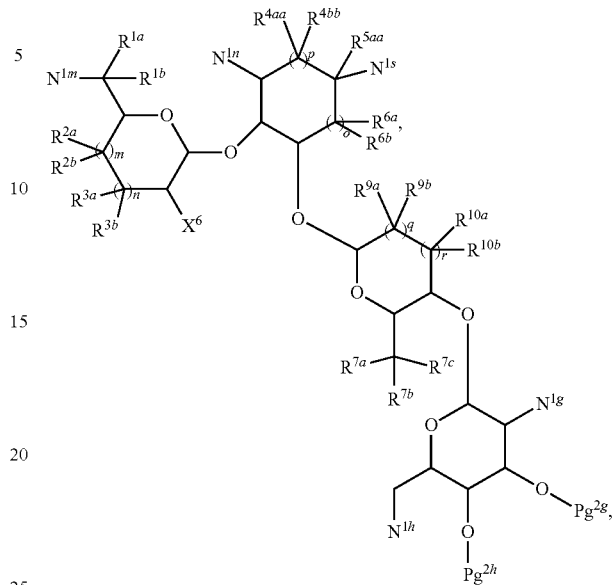

and salts, solvates, enantiomers, and diastereomers thereof, wherein

R$^{1a}$ and R$^{1b}$ are independently selected from the group consisting of H, C$_1$-C$_{12}$ alkyl, C$_1$-C$_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —N$_3$, and —OR$^{16}$, and wherein each R$^{12}$, R$^{13}$, R$^{14}$, R$^{15}$, and R$^{16}$ is independently H or alkyl; or R$^{1a}$ and R$^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each R$^{22}$, R$^{23}$, R$^{24}$, R$^{25}$, and R$^{26}$ is independently H or alkyl, wherein the alkyl is unsubstituted or substituted with one or more substituents independently selected from the group consisting of halogen, cyano, NR$^{14}$R$^{15}$, and —OR$^{16}$;

R$^{2a}$, R$^{2b}$, R$^{3a}$ and R$^{3b}$ are independently selected from the group consisting of H, —OR$^{27}$, —NR$^{28}$R$^{29}$, halogen, C$_1$-C$_4$ cycloalkyl, and C$_1$-C$_6$ alkyl, wherein each R$^{27}$, R$^{28}$, and R$^{29}$ is independently H, alkyl, amino protecting group, or hydroxyl protecting group; wherein the C$_1$-C$_6$ alkyl or alkyl is unsubstituted or substituted with one or more substituents selected from the group consisting of aryl, halogen, —OR$^{30}$, —NR$^{31}$R$^{32}$, —SR$^{33}$, and —SO$_2$R$^{34}$;

wherein each R$^{30}$, R$^{31}$, R$^{32}$, R$^{33}$, and R$^{34}$ is independently H or alkyl substituted with one or more substituents independently selected from the group consisting of halogen, cyano, NR$^{14}$R$^{15}$, and —OR$^{16}$; or R$^{2a}$ and R$^{2b}$ form an oxo or imino group substituted with C$_1$-C$_6$ alkyl;

R$^{3a}$ and R$^{3b}$ form an oxo or imino group substituted with C$_1$-C$_6$ alkyl;

X$^6$ is selected from the group consisting of H, NH$_2$, N$_3$, protected amino group, OH, —OPg$^{2m}$, and halogen; wherein Pg$^{2m}$ is a hydroxyl protecting group;

$R^{4aa}$ and $R^{4bb}$ are, independently H, —OH, —OR$^{40}$, —NR$^{41}$R$^{42}$, or halogen;

wherein each $R^{40}$, $R^{41}$, and $R^{42}$ are independently H, alkyl, —CONH$_2$, or —COCH$_3$; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^{5aa}$ is H, —CN, —CONH$_2$ or C$_1$-C$_3$alkyl, wherein the alkyl is unsubstituted or substituted with one or more substituents selected from the group consisting of —OH, —OC(O)CH$_3$, —NH$_2$, —CN, —CONH$_2$, and halogen;

$R^{6a}$ and $R^{6b}$ are, independently H, halogen, NH$_2$, —OH, C$_1$-C$_3$alkoxy, —OC(O)CH$_3$, or —OPg$^{2j}$; wherein Pg$^{2j}$ is a hydroxyl protecting group;

$R^{7a}$, $R^{7b}$, and $R^{7c}$ are, independently, H, OH, —OR$^{71}$ or —OPg$^2$;

wherein $R^{71}$ is alkyl; wherein the alkyl is unsubstituted or substituted with one or more substituents selected from the group consisting of —CONH$_2$, —OH, —NH$_2$, —COCH$_3$, aryl, substituted aryl, heteroaryl, and substituted heteroaryl;

wherein Pg$^2$ is a hydroxyl protecting group;

$N^{1s}$ is N$_3$ or —NR$^{8a}$R$^{8b}$;

$R^{8a}$ is H, C$_1$-C$_6$ alkyl, an amino protecting group, or

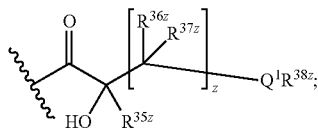

wherein
Q$^1$ is NH, O, or S;
z is an integer from 0 to 4,
$R^{35z}$ is H or C$_1$-C$_3$ alkyl;
each $R^{36z}$ and $R^{37z}$ is independently selected from the group consisting of H, alkyl, halogen, and —OH, and
$R^{38z}$ is H, alkyl, or —C(=NH)NR$^{39z}$R$^{40z}$, wherein $R^{39z}$ and $R^{40z}$ are independently H or C$_1$-C$_3$ alkyl; or
$R^{35z}$ and $R^{38z}$, together with the atoms to which they are attached, form a heterocycloalkyl group comprising at least one N;

$R^{8b}$ is H or C$_1$-C$_3$alkyl;

$R^{9a}$ and $R^{9b}$ are independently H, OH, or —OR$^{91}$, wherein $R^{91}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

$R^{10a}$ and $R^{10b}$ are independently H, OH, or —OR$^{101}$, wherein $R^{91}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

$N^{1q}$ is —OH, protected hydroxyl group, —NHPg$^{1q}$, N(Pg$^{1q}$)$_2$, —NH$_2$, or N$_3$, wherein each Pg$^{1i}$ is independently an amino protecting group;

$N^{1r}$ is —NHPg$^{1r}$ or N$_3$, wherein Pg$^{1r}$ is an amino protecting group;

$N^{1g}$ is —NHPg$^{1g}$ or N$_3$, wherein Pg$^{1g}$ is an amino protecting group;

$N^{1h}$ is —NHPg$^{1h}$ or N$_3$, wherein Pg$^{1h}$ is an amino protecting group;

Pg$^{2g}$ is a hydroxyl protecting group;
Pg$^{2h}$ is a hydroxyl protecting group;
wherein at least one of $N^{1q}$, $N^{1r}$, $N^{1g}$, $N^{1h}$ is not NH$_2$ or wherein at least one of PG$^{2g}$ or Pg$^{2h}$ is not H or wherein X$^6$ is not —OH or —NH$_2$;
m is zero, 1, or 2;
n is zero, 1, or 2;
wherein m+n is 1, 2 or 3;
o is zero, 1, or 2;
p is zero, 1, or 2;
wherein o+p is 1, 2 or 3;
q is zero, 1, or 2;
r is zero, 1, or 2;
wherein q+r is 1, 2 or 3.

The present disclosure provides a compound of formula A-10:

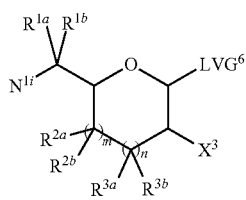

A-10 and salts, solvates, enantiomers, and diastereomers thereof, wherein $R^{1a}$ and $R^{1b}$ are independently selected from the group consisting of H, C$_1$-C$_{12}$ alkyl, C$_1$-C$_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —N$_3$, and —OR$^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each $R^{22}$, $R^{23}$, $R^{24}$, $R^{29}$, and $R^{26}$ is independently H or alkyl, wherein the alkyl is unsubstituted or substituted with one or more substituents independently selected from the group consisting of halogen, cyano, NR$^{14}$R$^{15}$, and —OR$^{16}$;

$R^{2a}$, $R^{2b}$, $R^{3a}$ and $R^{3b}$ are independently selected from the group consisting of H, —OR$^{27}$, —NR$^{28}$R$^{29}$, halogen, C$_1$-C$_4$ cycloalkyl, and C$_1$-C$_6$ alkyl, wherein each R$^{27}$, R$^{28}$, and R$^{29}$ is independently H or alkyl; wherein the C$_1$-C$_6$ alkyl or alkyl is unsubstituted or substituted with one or more substituents selected from the group consisting of halogen, —OR$^{30}$, —NR$^{31}$R$^{32}$, —SR$^{33}$, and —SO$_2$R$^{34}$;

wherein each R$^{30}$, R$^{31}$, R$^{32}$, R$^{33}$, and R$^{34}$ is independently H or alkyl substituted with one or more substituents independently selected from the group consisting of halogen, cyano, NR$^{14}$R$^{15}$, and —OR$^{16}$; or $R^{2a}$ and $R^{2b}$ form an oxo or imino group substituted with C$_1$-C$_6$ alkyl;

$R^{3a}$ and $R^{3b}$ form an oxo or imino group substituted with C$_1$-C$_6$ alkyl;

$X^3$ is selected from the group consisting of H, $NH_2$, $N_3$, protected amino group, OH, $—OPg^{2i}$, and halogen; wherein $Pg^{2i}$ is a hydroxyl protecting group;

$LVG^6$ is a leaving group;

$N^{1i}$ is $—NHPg^{1i}-NH_2$, or $N_3$, wherein $Pg^{1i}$ is an amino protecting group;

m is zero, 1, or 2;

n is zero, 1, or 2;

wherein m+n is 1, 2 or 3.

The present disclosure provides a compound of formula B-13:

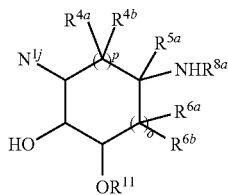

B-13 and salts, solvates, enantiomers, and diastereomers thereof, wherein $R^{4a}$ and $R^{4b}$ are, independently H, —OH, $—OR^{40}$, $—NR^{41}R^{42}$, or halogen;

wherein each $R^{40}$, $R^{41}$, and $R^{42}$ are independently H or alkyl; wherein the alkyl is unsubstituted or substituted with one or more substituents selected from the group consisting of $—CONH_2$, —OH, $—NH_2$, $—COCH_3$, aryl, substituted aryl, heteroaryl, halogen, and substituted heteroaryl;

$R^{5a}$ is H, —CN, $—CONH_2$ or $C_1$-$C_3$alkyl, wherein the alkyl is unsubstituted or substituted with one or more substituents selected from the group consisting of —OH, $—NH_2$, —CN, $—CONH_2$, and halogen;

$R^{6a}$ and $R^{6b}$ are, independently H, halogen, $NH_2$, —OH, $C_1$-$C_3$alkoxy, $—OC(O)CH_3$, or $—OPg^{2j}$; wherein $Pg^{2j}$ is a hydroxyl protecting group;

$R^{8a}$ is H, $C_1$-$C_6$ alkyl, an amino protecting group, or

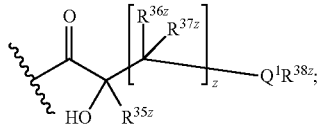

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or $—C(=NH)NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{11}$ is H, alkyl, $—COCH_3$, or a hydroxyl protecting group;

$N^{1j}$ is $—NHPg^{1j}$, $—NH_2$, or $N_3$, wherein $Pg^{1j}$ is an amino protecting group;

o is zero, 1, or 2;

p is zero, 1, or 2;

wherein o+p is 1, 2 or 3.

The present disclosure provides a compound of formula AB-4:

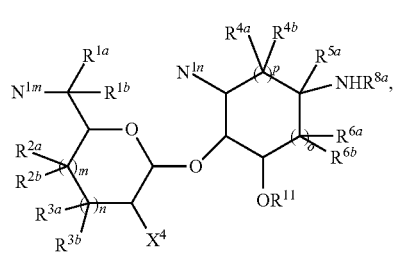

AB-4 and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, $—SR^{12}$, $—SO_2R^{13}$, $—OSF_2NR^{14}R^{15}$, $—NR^{14}R^{15}$, $—N_3$, and $—OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, $—SR^{22}$, $—SO_2R^{23}$, $—NR^{24}R^{25}$, and $—OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and $—OR^{16}$;

$R^{2a}$, $R^{2b}$, $R^{3a}$ and $R^{3b}$ are independently selected from the group consisting of H, $—OR^{27}$, $—NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, $—OR^{30}$, $—NR^{31}R^{32}$, $—SR^{33}$, and $—SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and $—OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^4$ is selected from the group consisting of H, $NH_2$, $N_3$, protected amino group, OH, $—OPg^{2k}$, and halogen; wherein $Pg^{2k}$ is a hydroxyl protecting group;

$R^{4a}$ and $R^{4b}$ are, independently H, —OH, $—OR^{40}$, $—NR^{41}R^{42}$, or halogen;

wherein each $R^{40}$, $R^{41}$, and $R^{42}$ are independently H or alkyl; wherein the alkyl is unsubstituted or substituted with one or more substituents selected from the group consisting of $—CONH_2$, —OH, $—NH_2$, $—COCH_3$, aryl, substituted aryl, heteroaryl, halogen, and substituted heteroaryl;

$R^{5a}$ is H, —CN, $—CONH_2$ or $C_1$-$C_3$alkyl, wherein the alkyl is unsubstituted or substituted with one or more substituents selected from the group consisting of —OH, —NH$_2$, —CN, —CONH$_2$, and halogen;

R$^{6a}$ and R$^{1b}$ are, independently H, halogen, NH$_2$, —OH, C$_1$-C$_3$alkoxy, —OC(O)CH$_3$, or —OPg$^{2j}$;

wherein Pg$^{2j}$ is a hydroxyl protecting group;

R$^{8a}$ is H, C$_1$-C$_6$ alkyl, an amino protecting group, or

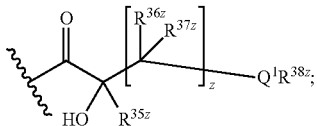

wherein

Q$^1$ is NH, O, or S;

z is an integer from 0 to 4,

R$^{35z}$ is H or C$_1$-C$_3$ alkyl;

each R$^{36z}$ and R$^{37z}$ is independently selected from the group consisting of H, alkyl, halogen, and —OH, and R$^{38z}$ is H, alkyl, or —C(=NH)NR$^{39z}$R$^{40z}$, wherein R$^{39z}$ and R$^{40z}$ are independently H or C$_1$-C$_3$ alkyl; or R$^{35z}$ and R$^{38z}$, together with the atoms to which they are attached, form a heterocycloalkyl group comprising at least one N;

R$^{11}$ is H, alkyl, —COCH$_3$, or a hydroxyl protecting group;

N$^{1m}$ is —NHPg$^{1m}$, —NH$_2$, or N$_3$, wherein Pg$^{1m}$ is an amino protecting group;

N$^{1n}$ is —NHPg$^{1n}$, —NH$_2$, or N$_3$, wherein Pg$^{1n}$ is an amino protecting group;

m is zero, 1, or 2;

n is zero, 1, or 2;

wherein m+n is 1, 2 or 3;

o is zero, 1, or 2;

p is zero, 1, or 2;

wherein o+p is 1, 2 or 3.

The present disclosure provides a compound of formula ABC-3:

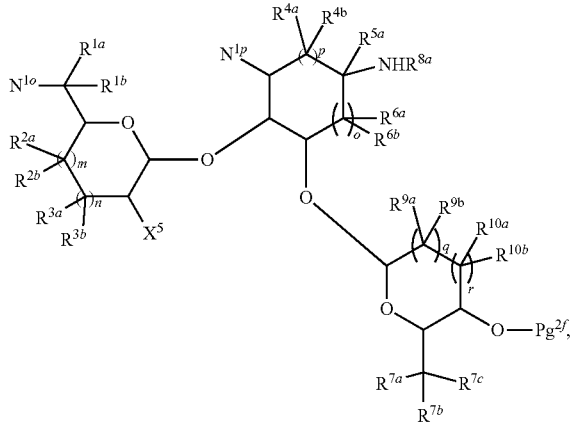

ABC-3 and salts, solvates, enantiomers, and diastereomers thereof, wherein

R$^{1a}$ and R$^{1b}$ are independently selected from the group consisting of H, C$_1$-C$_{12}$ alkyl, C$_1$-C$_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —N$_3$, and —OR$^{16}$, and wherein each R$^{12}$, R$^{13}$, R$^{14}$, R$^{15}$, and R$^{16}$ is independently H or alkyl; or R$^{1a}$ and R$^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each R$^{22}$, R$^{23}$, R$^{24}$, R$^{29}$, and R$^{26}$ is independently H or alkyl, wherein the alkyl is unsubstituted or substituted with one or more substituents independently selected from the group consisting of halogen, cyano, NR$^{14}$R$^{15}$, and —OR$^{16}$;

R$^{2a}$, R$^{2b}$, R$^{3a}$ and R$^{3b}$ are independently selected from the group consisting of H, —OR$^{27}$, —NR$^{28}$R$^{29}$, halogen, C$_1$-C$_4$ cycloalkyl, and C$_1$-C$_6$ alkyl, wherein each R$^{27}$, R$^{28}$, and R$^{29}$ is independently H or alkyl; wherein the C$_1$-C$_6$ alkyl or alkyl is unsubstituted or substituted with one or more substituents selected from the group consisting of halogen, —OR$^{30}$, —NR$^{31}$R$^{32}$, —SR$^{33}$, and —SO$_2$R$^{34}$;

wherein each R$^{30}$, R$^{31}$, R$^{32}$, R$^{33}$, and R$^{34}$ is independently H or alkyl substituted with one or more substituents independently selected from the group consisting of halogen, cyano, NR$^{14}$R$^{15}$, and —OR$^{16}$; or R$^{2a}$ and R$^{2b}$ form an oxo or imino group substituted with C$_1$-C$_6$ alkyl;

R$^{3a}$ and R$^{3b}$ form an oxo or imino group substituted with C$_1$-C$_6$ alkyl;

X$^5$ is selected from the group consisting of H, NH$_2$, N$_3$, protected amino group, OH, —OPg$^{2l}$, and halogen; wherein Pg$^{2l}$ is a hydroxyl protecting group;

R$^{4a}$ and R$^{4b}$ are, independently H, —OH, —OR$^{40}$, —NR$^{41}$R$^{42}$, or halogen;

wherein each R$^{40}$, R$^{41}$, and R$^{42}$ are independently H or alkyl; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

R$^{5a}$ is H, —CN, —CONH$_2$ or C$_1$-C$_3$alkyl, wherein the alkyl is unsubstituted or substituted with one or more substituents selected from the group consisting of —OH, —NH$_2$, —CN, —CONH$_2$, and halogen;

R$^{6a}$ and R$^{6b}$ are, independently H, halogen, NH$_2$, —OH, C$_1$-C$_3$alkoxy, —OC(O)CH$_3$, or —OPg$^{2j}$;

wherein Pg$^{2j}$ is a hydroxyl protecting group;

R$^{7a}$, R$^{7b}$, and R$^{7c}$ are, independently, H, OH, —OR$^{71}$ or —OPg$^2$;

wherein R$^{71}$ is alkyl; wherein the alkyl is unsubstituted or substituted with one or more substituents selected from the group consisting of —CONH$_2$, —OH, —NH$_2$, —COCH$_3$, aryl, substituted aryl, heteroaryl, and substituted heteroaryl;

wherein Pg$^2$ is a hydroxyl protecting group;

R$^{8a}$ is H, C$_1$-C$_6$ alkyl, an amino protecting group, or

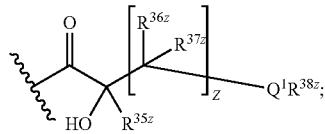

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$N^{1o}$ is —$NHPg^{1o}$, —$NH_2$, or $N_3$, wherein $Pg^{1o}$ is an amino protecting group;

$N^{1p}$ is —$NHPg^{1p}$, —$NH_2$, or $N_3$, wherein $Pg^{1p}$ is an amino protecting group;

$Pg^{2f}$ is a hydroxyl protecting group or H;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

The present disclosure provides a compound of formula ABCD-3:

ABCD-3

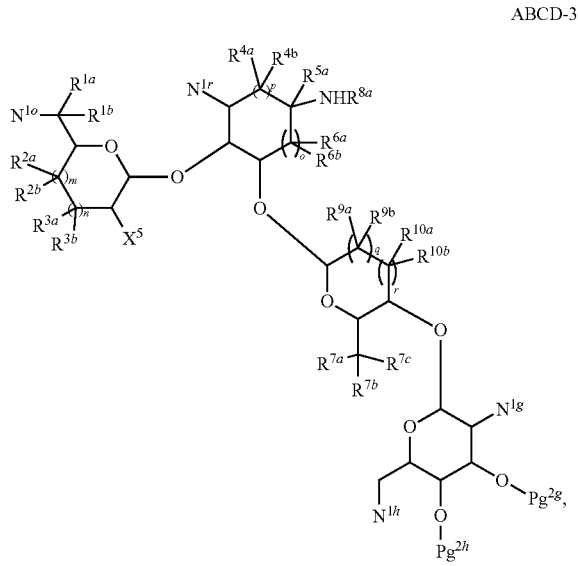

and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^3$, —$OSF_2NR^{14}R^{15}$, —$NR^{14}R^{15}$, —$N_3$, and —$OR^{16}$ and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl; $R^{3a}$ and $R^{3b}$ form an oxo or imino group substituted with $C_1$-$C_6$ alkyl;

$X^6$ is selected from the group consisting of H, $NH_2$, $N_3$, protected amino group, OH, —$OPg^{2m}$, and halogen; wherein $Pg^{2m}$ is a hydroxyl protecting group;

$R^{4a}$ and $R^{4b}$ are, independently, H, —OH, —$OR^{40}$, —$NR^{41}R^{42}$, or halogen;

wherein each $R^{40}$, $R^{41}$, and $R^{42}$ are independently H or alkyl;

wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5a}$ is H, —CN, —$CONH_2$ or $C_1$-$C_3$alkyl, wherein the alkyl is unsubstituted or substituted with one or more substituents selected from the group consisting of —OH, —$NH_2$, —CN, —$CONH_2$, and halogen;

$R^{6a}$ and $R^{6b}$ are, independently H, halogen, $NH_2$, —OH, $C_1$-$C_3$alkoxy, —OC(O)$CH_3$, or —$OPg^{2j}$; wherein $Pg^{2j}$ is a hydroxyl protecting group;

$R^{7a}$, $R^{7b}$, and $R^{7c}$ are, independently, H, OH, —$OR^{71}$ or —$OPg^2$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, and substituted heteroaryl;

wherein $Pg^2$ is a hydroxyl protecting group;

$R^{8a}$ is H, $C_1$-$C_6$ alkyl, an amino protecting group, or

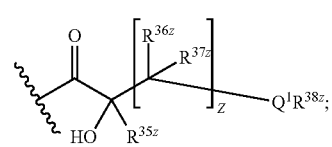

wherein

Q$^1$ is NH, O, or S;

z is an integer from 0 to 4,

R$^{35z}$ is H or C$_1$-C$_3$ alkyl;

each R$^{36z}$ and R$^{37z}$ is independently selected from the group consisting of H, alkyl, halogen, and —OH, and R$^{38z}$ is H, alkyl, or —C(=NH)NR$^{39z}$R$^{40z}$, wherein R$^{39z}$ and R$^{40z}$ are independently H or C$_1$-C$_3$ alkyl; or R$^{35z}$ and R$^{38z}$, together with the atoms to which they are attached, form a heterocycloalkyl group comprising at least one N;

R$^{9a}$ and R$^{9b}$ are independently H, OH, or —OR$^{91}$, wherein R$^{91}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

R$^{10a}$ and R$^{10b}$ are independently H, OH, or —OR$^{101}$, wherein R$^{101}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

N$^{1q}$ is —NHPg$^{1q}$ or N$_3$, wherein Pg$^{1q}$ is an amino protecting group;

N$^{1r}$ is —NHPg$^{1r}$ or N$_3$, wherein Pg$^{1r}$ is an amino protecting group;

N$^{1g}$ is —NHPg$^{1g}$ or N$_3$, wherein Pg$^{1g}$ is an amino protecting group;

N$^{1h}$ is —NHPg$^{1h}$ or N$_3$, wherein Pg$^{1h}$ is an amino protecting group;

Pg$^{2g}$ is a hydroxyl protecting group;

P$^{2h}$ is a hydroxyl protecting group;

wherein at least one of N$^{1q}$, N$^{1r}$, N$^{1g}$, N$^{1h}$ is not NH$_2$ or wherein at least one of PG$^{2g}$ or Pg$^{2h}$ is not H or wherein X$^6$ is not —OH or —NH$_2$;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

In certain aspects, provided herein is a method for treating a bacterial infection in a subject, comprising administering to a subject in need thereof a therapeutically effective amount of a compound of formulae AB-2, ABC-2, AB-2' or ABC-2', or a pharmaceutically acceptable salt, solvate, stereoisomer, or tautomer thereof.

In still another aspect, provided is a method for treating a bacterial infection in a subject, comprising administering to a subject in need thereof a therapeutically effective amount of a pharmaceutical composition comprising a compound AB-2, AB-2', AB-2", ABC-2, ABC-2', or ABC-2", or a pharmaceutically acceptable salt, solvate, stereoisomer, or tautomer thereof, and a pharmaceutically acceptable carrier.

In some variations of the provided methods, the bacterial infection is a gram-negative bacterial infection. In certain variations, the bacterial infection is infection of a *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Bacillus, Bacteroides, Peptococcus, Clostridium, Salmonella, Shigella, Serratia, Haemophilus, Brucella, Francisella, Anthracis, Yersinia, Corynebacterium, Moraxella*, or *Enterococcus* species.

In yet a further aspect, provided herein is the use of a compound AB-2, AB-2', AB-2", ABC-2, ABC-2', or ABC-2", or a pharmaceutically acceptable salt, solvate, stereoisomer, or tautomer thereof, in the manufacture of a medicament for treating a bacterial infection in a subject in need thereof.

In still a further aspect, provided herein is a compound AB-2, AB-2', AB-2", ABC-2, ABC-2', or ABC-2", or a pharmaceutically acceptable salt, solvate, stereoisomer, or tautomer thereof, for use in a method of treating a bacterial infection in a subject in need thereof.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Each embodiment described herein may be taken alone or in combination with any one or more other embodiments.

DETAILED DESCRIPTION OF THE DISCLOSURE

The present disclosure relates to novel methods for preparing antibacterial aminoglycoside compounds, as well as to related intermediates useful in such methods.

As discussed above, the present disclosure provides processes for preparing compounds AB, ABC, and ABCD. The processes comprise combinations of reactions and conditions that can provide certain novel intermediate compounds.

Scheme 1 shows a representation of preparation of compounds AB, ABC, and ABCD.

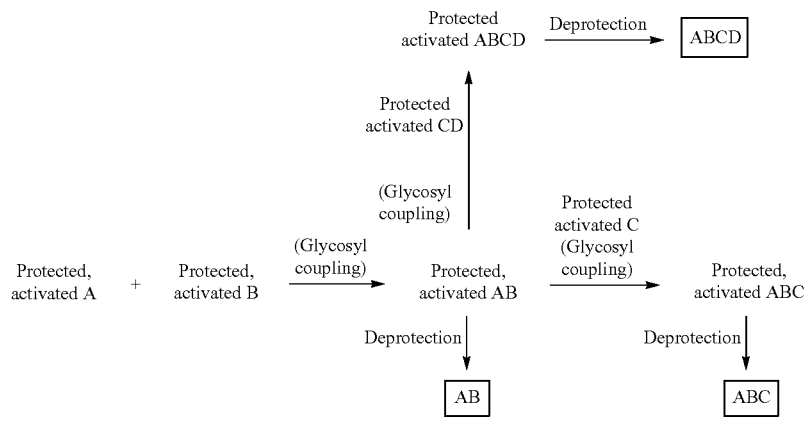

Scheme 1

The articles "a" and "an" as used in this disclosure may refer to one or more than one (i.e., to at least one) of the grammatical object of the article. By way of example, "an element" means one element or more than one element.

As used in this disclosure, "and/or" may mean either "and" or "or" unless indicated otherwise.

As used herein, ═══ may refer to a single bond or a double bond.

"Alkyl" may refer to a straight or branched chain saturated hydrocarbon. $C_1$-$C_3$ alkyl groups contain 1 to 3 carbon atoms. Examples of a $C_1$-$C_3$ alkyl group include, but are not limited to, methyl, ethyl, and propyl.

The term "protecting group," as used herein, may refer to a labile chemical moiety which is known in the art to protect reactive groups including without limitation, hydroxyl and amino groups, against undesired reactions during synthetic procedures. Hydroxyl and amino groups which protected with a protecting group are referred to herein as "protected hydroxyl groups" and "protected amino groups", respectively. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999). Groups may be selectively incorporated into aminoglycosides described herein as precursors. For example, an amino group can be placed into a compound described herein as an azido group that can be chemically converted to the amino group at a desired point in the synthesis. Generally, groups are protected or present as a precursor that will be inert to reactions that modify other areas of the parent molecule for conversion into their final groups at an appropriate time. Further, representative protecting or precursor groups are discussed in Agrawal, et al., Protocols for Oligonucleotide Conjugates, Eds, Humana Press; New Jersey, 1994; Vol. 26 pp. 1-72. Examples of "hydroxyl protecting groups" include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl (TBDPS), triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Examples of "amino protecting groups" include, but are not limited to, 2-trimethylsilylethoxycarbonyl (Teoc), 1-methyl-1-(4-biphenylyl)ethoxycarbonyl (Bpoc), t-butoxycarbonyl (Boc), allyloxycarbonyl (Alloc), 9-fluorenylmethyloxycarbonyl (Fmoc), benzyloxycarbonyl (Cbz), p-nitrobenzyloxycarbonyl (PNZ), formyl, acetyl, trihaloacetyl (e.g., trifluoroacetyl), benzoyl, nitrophenylacetyl, 2-nitrobenzenesulfonyl, phthalimido, and dithiasuccinoyl.

A salt may also include acid addition salts. An "acid addition salt" may refer to those salts which retain the biological effectiveness and properties of the freebases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

The compounds described herein and the process of making the compounds may include solvates of the compounds described herein. The term "solvate" may refer to a complex of variable stoichiometry formed by a solute and solvent. Such solvents for the purpose of the disclosure may not interfere with the biological activity of the solute. Examples of suitable solvents may include, but are not limited to, water, MeOH, EtOH, and AcOH. Solvates wherein water is the solvent molecule are typically referred to as hydrates. Hydrates may include compositions containing stoichiometric amounts of water, as well as compositions containing variable amounts of water.

Those skilled in the art will recognize if a stereocenter exists in any of the compounds described herein and the process of making the compounds. Accordingly, the present disclosure includes both possible stereoisomers (unless the stereochemistry is specified herein) and includes not only racemic compounds but the individual enantiomers and/or diastereomers as well. Additionally, those skilled in the art will recognize if a positional or geometric isomer exists for a compound described herein. Accordingly, the present disclosure includes all possible positional or geometric isomers (unless the isomer is specified herein). In the structures shown herein, where the stereochemistry of any particular chiral atom is not specified or the geometric or positional isomer is not specified, then all stereoisomers and geometric or positional isomers are contemplated and included in the compounds described herein and the process of making the compounds. Where stereochemistry or geometric or positional isomer is specified, then that stereochemistry or geometric or position isomer is so specified and defined.

The term "stereoisomers" may refer to the set of compounds which have the same number and type of atoms and share the same bond connectivity between those atoms, but differ in three dimensional structure. The term "stereoisomer" may refer to any member of this set of compounds. For instance, a stereoisomer may be an enantiomer or a diastereomer. The compounds described herein and the process of making the compounds may include stereoisomers.

The term "enantiomers" may refer to a pair of stereoisomers which are non-superimposable mirror images of one another. The term "enantiomer" may refer to a single member of this pair of stereoisomers. The term "racemic" may refer to a 1:1 mixture of a pair of enantiomers. The compounds described herein and the process of making the compounds may include enantiomers. Each compound herein disclosed may include all the enantiomers that conform to the general structure of the compound (unless the enantiomer is specified herein). The compounds may be in a racemic or enantiomerically pure form, or any other form in terms of stereochemistry (unless the stereochemistry is specified herein). In some embodiments the compounds are the (S)-enantiomer. In other embodiments the compounds are the (R)-enantiomer. In yet other embodiments, the compounds are the (+) or (−) enantiomers. In some embodiments, compounds described herein may be enriched to provide predominantly one enantiomer of a compound described herein. An enantiomerically enriched mixture may comprise, for example, at least 60 mol percent of one enantiomer, or more preferably at least 75, 80, 85, 90, 95, 96, 97, 98, 99, 99.5 or even 100 mol percent. In some embodiments, the compound described herein enriched in one enantiomer may be substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the compound mixture. For example, if a compound mixture contains 98 grams of a first enantiomer and 2 grams of a second enantiomer, it would be said to contain 98 mol percent of the first enantiomer and only 2 mol percent of the second enantiomer.

The term "diastereomers" may refer to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" may refer to any member of this set of compounds. In some examples presented, the synthetic route may produce a single diastereomer or a mixture of diastereomers. The compounds described herein and the process of making the compounds may include diastereomers. In some embodiments, the compounds described herein may be enriched to provide predominantly one diastereomer of a compound disclosed herein. A diastereomerically enriched mixture may comprise, for example, at least 60 mol percent of one diastereomer, or more preferably at least 75, 99, 95, 96, 97, 98, 99, or even 100 mol percent.

In addition, the compounds described herein and the process of making the compounds include all geometric and positional isomers. For example, if a compound described herein incorporates a double bond or a fused ring, both the cis- and trans-forms, as well as mixtures, may be embraced within the scope of the disclosure. If the compound contains a double bond, the substituent may be in the E or Z configuration (unless the configuration is specified herein). If the compound contains a disubstituted cycloalkyl, the cycloalkyl substituent may have a cis or trans configuration (unless the configuration is specified herein).

The compounds described herein may further include all isotopically labeled compounds. An "isotopically" or "radiolabeled" compound is a compound where one or more atoms are replaced or substituted by an atom having an atomic mass or mass number different from the atomic mass or mass number typically found in nature (i.e., naturally occurring). For example, in some embodiments, in the compounds described herein hydrogen atoms may be replaced or substituted by one or more deuterium or tritium. Certain isotopically labeled compounds of this disclosure, for example, those incorporating a radioactive isotope, may be useful in drug and/or substrate tissue distribution studies. The radioactive isotopes tritium, i.e., $^3H$, and carbon 14, i.e., $^{14}C$, are particularly useful for this purpose in view of their ease of incorporation and ready means of detection. Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances. Suitable isotopes that may be incorporated in compounds described herein may include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. Substitution with positron emitting isotopes, such as $^{11}C$, $^{18}F$, $^{15}O$, and $^{13}N$, may be useful in Positron Emission Topography (PET) studies.

As described herein, compounds of the present disclosure may optionally be substituted with one or more substituents, such as those illustrated generally herein, or as exemplified by particular classes, subclasses, and species of the present disclosure. In general, the term "substituted" refers to the replacement of a hydrogen atom in a given structure with a specified substituent. Combinations of substituents envisioned by the present disclosure are typically those that result in the formation of stable or chemically feasible compounds.

The compounds of any of the formulae described herein may be prepared by methods known in the art of organic synthesis as set forth in part by the following synthetic schemes and examples in conjunction with the guidance provided herein. In the schemes described below, it is understood that protecting groups for sensitive or reactive groups may be employed where necessary in accordance with general principles or chemistry in accordance with the guidance provided herein. Protecting groups may be manipulated according to standard methods of organic synthesis (T. W. Greene and P. G. M. Wuts, "Protective Groups in Organic Synthesis," Third edition, Wiley, New York 1999). These groups may be removed at a convenient stage of the compound synthesis using methods that are readily apparent to those skilled in the art based on the detailed teaching provided herein. The selection processes, as well as the reaction conditions and order of their execution, shall be consistent with the present disclosure.

Preparation of Compounds AB, ABC, and ABCD

As discussed above, the present disclosure provides processes for preparing compounds AB, ABC, and ABCD (described in greater detail below). The processes comprise combinations of reactions and conditions that can provide certain novel intermediate compounds. Scheme 1 shows a representation of preparation of compounds AB, ABC, and ABCD.

Conventional atom numbering for formulae AB, ABC, and ABCD is shown below. The A, B, C, and D rings are also identified below. The structures below are representative and are based on generic structures, such that the substituents are shown below for convenience. When a specific carbon is referenced in the disclosure, the carbon is referenced with the numbering shown below. For example, C-6' or C6' refers to the exocyclic carbon on the A ring, labeled as 6', as shown below.

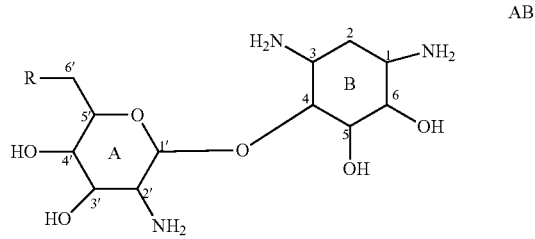

AB

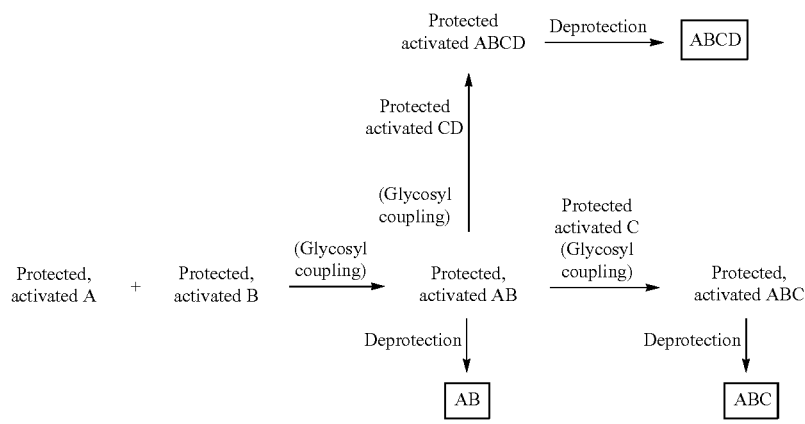

Scheme 1

Discussion of the preparation of protected activated A and protected activated B is provided below. Then, discussion of the preparation of compound AB is provided. Thereafter, discussion of the preparation of compounds ABC and ABCD is provided.

The processes comprise reactions that can yield novel intermediate compounds through a combination of reaction conditions and steps. Also, Scheme 1 provides a modular synthesis of aminosaccharides and provides a synthetic scheme that allows for ease of functionalizing the rings and a diversity of substituents. Compounds with modifications on the core carbon backbone of the aminoglycosides can be prepared, which were previously unobtainable by methods of synthesis in the art. Compounds with two, three, or four rings can be prepared and tested or screened for activity expeditiously.

The reactions in the Scheme 1 can be performed through chemical reactions using standard synthetic chemistry procedures and practices optionally using reagents such as catalysts including, but not limited to, Pd reagents, chiral ligands, and enzymes.

-continued

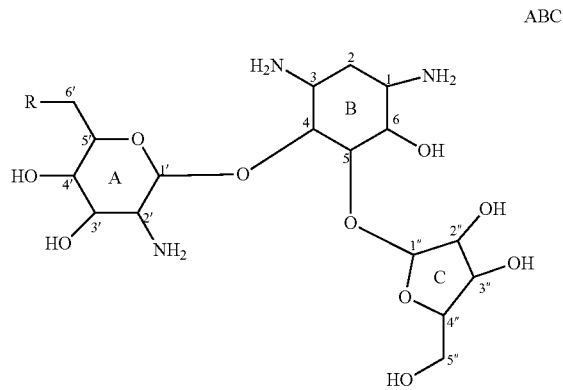

ABC

-continued

ABCD

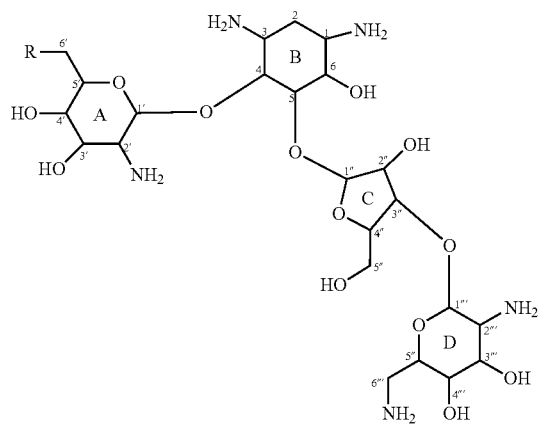

In certain embodiments, conventional atom numbering for formulae AB, ABC, and ABCD is shown below in another format.

AB$^s$

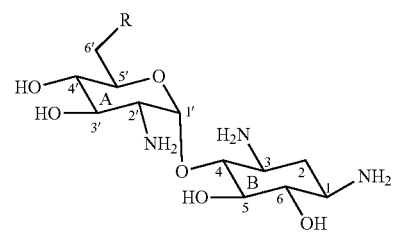

ABC$^s$

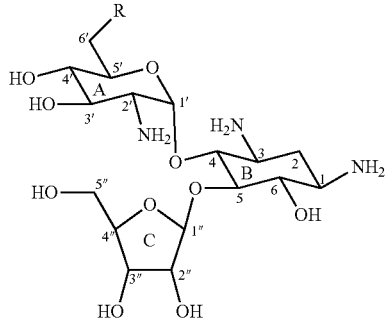

ABCD$^s$

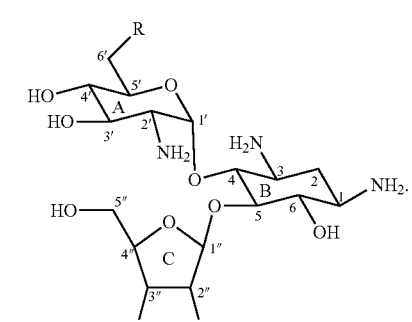

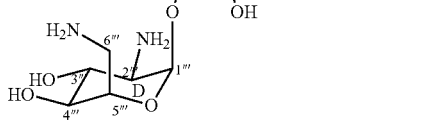

Preparation of Ring A

The present disclosure includes processes, methods, reagents, and intermediates for the synthesis of Ring A:

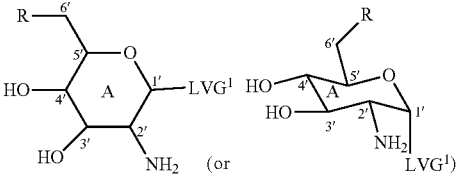

In Ring A, $LVG^1$ is a leaving group suitable of reacting with a reactant or a glycosyl acceptor, to form an interglycosidic linkage. The structure shown above for Ring A is representative and is based on a generic structure, such that the substituents are shown above for convenience. That is, the substituents shown above for Ring A are not limited to the certain substituents recited above. Suitable substituents for Ring A are described herein.

A process for the preparation of a Ring A is illustrated in Scheme 2 below and is discussed in greater detail herein.

Scheme 2

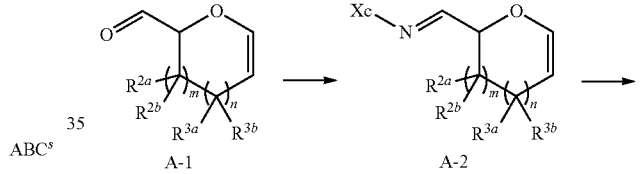

As noted above and with reference to Scheme 2, the present disclosure provides processes for preparing Ring A. The present disclosure provides a process for preparing a compound of formula A-5,

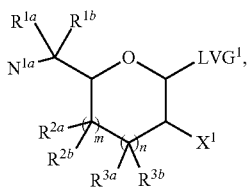

A-5 wherein
$R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and
wherein each $R^{12}$, $R^{13}$, $R^{14}$, $R^5$, and $R^{16}$ is independently H or alkyl; or
$R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and
wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;
$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, —$OR^{30}$, —$NR^{31}R^{32}$, —$SR^{33}$, and —$SO_2R^{34}$;
wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or
$R^{2a}$ and $R^{2b}$ form an oxo or imino group substituted with $C_1$-$C_6$ alkyl;
$R^{3a}$ and $R^{3b}$ form an oxo or imino group substituted with $C_1$-$C_6$ alkyl;
$N^{1a}$ is —$NHPg^{1a}$, $N(Pg^{1a})_2$, or $N_3$, wherein each $Pg^{1a}$ is independently an amino protecting group;
$X^1$ is —F, —Cl, —Br, or —I;
$LVG^1$ is a leaving group;
m is zero, 1, or 2;
n is zero, 1, or 2; and,
wherein m+n is 1, 2 or 3;
or a salt, solvate, enantiomer, or diastereomer thereof, comprising:
(a) contacting a compound of formula A-1:

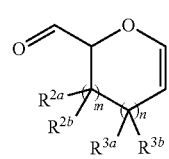

A-1 or a salt, solvate, enantiomer, or diastereomer thereof, with a chiral auxiliary reagent to yield a compound of formula A-2:

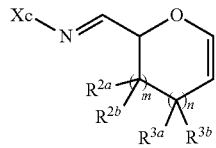

A-2 or a salt, solvate, enantiomer, or diastereomer thereof, wherein Xc is a chiral auxiliary group;
(b) contacting the compound of formula A-2 with a Grignard or organolithium reagent to yield a compound of formula A-3:

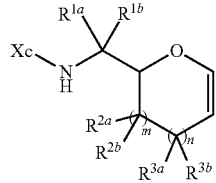

A-3 or a salt, solvate, enantiomer, or diastereomer thereof,
(c) contacting the compound of formula A-3 with a halogen reagent in presence of a nucleophile reagent (Nuc-1) to yield a compound of formula A-4:

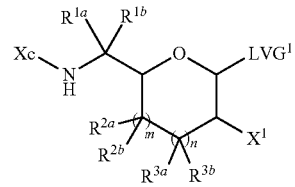

A-4 or a salt, solvate, enantiomer, or diastereomer thereof; wherein
$X^1$ is —F, —Cl, —Br, or —I;
Nuc-1 is $LVG^1$-M, wherein M is H, a metal cation, a non-metal cation, or a lone pair of electrons;
$LVG^1$ is a leaving group;
(d) exchanging the chiral auxiliary group for an amino protecting group $Pg^{1a}$ in the compound of formula A-4 by reaction with an amino protecting group reagent to yield the compound of formula A-5:

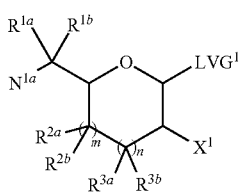

A-5 or a salt, solvate, enantiomer, or diastereomer thereof, wherein $N^{1a}$ is —$NHPg^{1a}$ $N(Pg^{1a})_2$, or $N_3$, wherein each $Pg^{1a}$ is independently an amino protecting group.

Synthesis of Compound A-2

With continued reference to Scheme 2, compound A-1 is contacted with a chiral auxiliary reagent to yield compound A-2, which has a chiral auxiliary group. The chiral auxiliary reagent provides a chiral auxiliary group for compound A-2.

A chiral auxiliary reagent means any chiral compound or optically active catalyst, e.g. a compound comprising asymmetrically substituted carbon atoms or axially chiral compounds, or mixtures of chiral compounds and/or optically active catalysts, which will improve the yield of a compound of A-2 with respect to its epimer. Said chiral auxiliary reagent will thus be any compound which is capable of increasing the stereoselectivity in comparison to the yield or stereoselectivity without the chiral auxiliary reagent present or involved. Suitable chiral auxiliary reagents that contain a free amino group such as tert-butanesulfinamide or (S)-1-amino-2-methoxymethylpyrrolidine (SAMP) and (R)-1-amino-2-methoxymethylpyrrolidine (RAMP) hydrazones or imines formed using pseudoephedrine.

Synthesis of Compound A-3

With continued reference to Scheme 2, compound A-2 is contacted with a Grignard or organolithium reagent to yield compound A-3. The Grignard or organolithium reagent provides $R^{1a}$ and/or $R^{1b}$ substituents on compound A-3. Thus, the Grignard or organolithium reagent corresponds to $R^{1a}$ and/or $R^{1b}$ moieties. In certain embodiments, $R^{1b}$ is hydrogen.

In certain embodiments, the addition reaction in Scheme 3 can be carried out using a Grignard reagent of formula: $R^{1a}MgX$, where $R^{1a}$ is as defined herein for general formula A-5 and X is a halide. In certain embodiments, the addition reaction in Scheme 3 can be carried out using an organolithium reagent of formula: $R^{1a}$—Li, where $R^{1a}$ is as defined herein for general formula A-5.

A Grignard reagent of formula: $R^{1a}MgX$ or an organolithium reagent of formula: $R^{1a}$—Li can be prepared from the corresponding halide of $R^{1a}$. A Grignard reagent is prepared by reaction of an organic halide with magnesium An organolithium reagent is prepared by reaction of an organic halide with lithium. For example, Grignard reagent or organolithium reagent such as MeMgBr, EtMgBr, MeLi, or EtLi would provide substituents, such as methyl or ethyl.

Synthesis of Compound A-4

With continued reference to Scheme 2, compound A-3 is contacted with a halogen reagent in the presence of a nucleophile reagent (Nuc-1) to yield compound A-4. A halonium ion formation can occur from the reaction of the alkene of compound A-3 with the halogen reagent. Subsequently, a nucleophilic reaction can open up the halonium ion to provide $X^1$ and $LVG^1$ substituents on compound A-4.

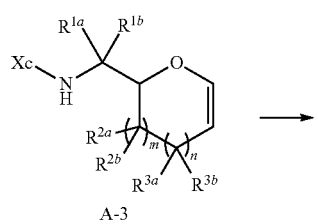

A-3

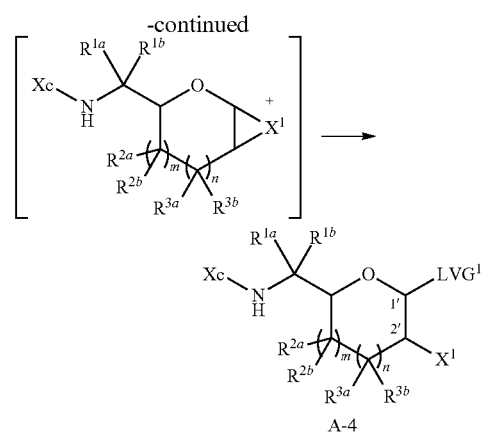

A-4

A halogen reagent can provide the halo group (e.g., $X^1$) on compound A-4 at C2', e.g., —F, —Cl, —Br, and —I. Examples of halogen reagents for reaction with compound A-3 include $Cl_2$, $Br_2$, NBS, NIS, HOCl, DAST, or $I_2$.

A nucleophilic reaction can open up the halonium ion to provide $X^1$ and $LVG^1$ substituents on compound A-4. A nucleophile reagent provides the $LVG^1$ substituent on compound A-4 at C1'. The $LVG^1$ substituent is a leaving group, such that Ring A becomes a glycosyl donor. In certain embodiments, $LVG^1$ is halo, OMs, OTs, OH, a thioalkyl, a thioaryl, an imidate, an acetate, a phosphate, or an O-pentenyl group. A nucleophilic reagent can be prepared from the corresponding protonated or salt version of $LVG^1$. For example, in certain embodiments, $LVG^1$ is —OH and the corresponding nucleophilic reagent (Nuc-1) is water. Reaction with water provides —OH as the substituent for $LVG^1$.

Synthesis of Compound A-5

With continued reference to Scheme 2, the chiral auxiliary group in compound A-4 is exchanged for an amino protecting group $Pg^{1a}$ to yield compound A-5.

Removal of the chiral auxiliary group is conventional and depends on the identity of the chiral auxiliary group. Examples include hydrolysis under conditions such as base (for example, NaOH, KOH, $Et_3N$) or acid mediated (for example, HCl, TfOH, p-TSA) in aqueous media optionally including organic solvents (for example, MeOH, $Et_2O$, DMF) at temperatures between 0° C. and the reflux point of the solvent; or hydrogenolysis under conditions such as an H2 atmosphere at pressures ranging from 1-10 ATM, in a solvent such as MeOH, DMF, EtOH atr room temperature.

Addition of amino protecting group $Pg^{1a}$ to yield compound A-5 is provided by an amino protecting group reagent. Examples of amino protecting group $Pg^{1a}$ include Bn, CBZ, and tert-butanesulfinamide. Suitable protecting group reagents to provide amino protecting group $Pg^{1a}$ can be found in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski). In certain embodiments, $N^{1a}$ is $N_3$.

In certain embodiments, the chiral auxiliary can act as a protecting group. Thus, in certain embodiments, $Pg^{1a}$ can include tert-butanesulfinamide or (S)-1-amino-2-methoxymethylpyrrolidine (SAMP) and (R)-1-amino-2-methoxymethylpyrrolidine (RAMP) hydrazones or imines formed using pseudoephedrine.

In certain embodiments, compound A-5 can be used in the glycosylation reaction with a B ring.

In certain embodiments, compound A-5 can be hydrodehalogenated and then used in the glycosylation reaction with a B ring. In such instances, X is converted to hydrogen. Examples of hydrodehalogenation reactions include use of metal catalysts, such as transition metal catalyst, alkali and alkaline-earth metals.

In certain embodiments, in compound A-5, $R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H, alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$.

In certain embodiments, in compound A-5, $N^{1a}$ is —$NHPg^{1a}$ or $N_3$, wherein $Pg^{1a}$ is an amino protecting group.

Synthesis of Compound A-6

In some embodiments, compound A-5 is converted to a compound A-6, as described in Scheme 3.

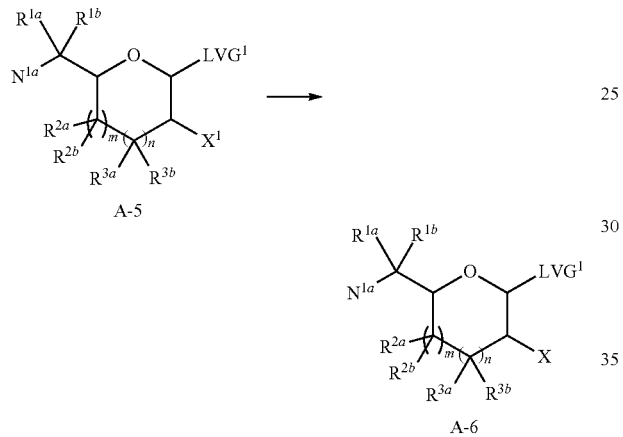

With reference to Scheme 3a, when $X^1$ is not —$NH_2$, —$N_3$, a protected amino group, —OH, or protected hydroxyl group, the process further comprises after step (d):

(e) converting $X^1$ in the compound of formula A-5 to X to yield a compound of formula A-6:

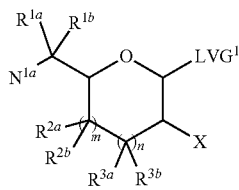

or a salt, solvate, enantiomer, or diastereomer thereof;
wherein X is —$NH_2$, —$N_3$, a protected amino group, —OH, or protected hydroxyl group.

For example, in certain embodiments, $X^1$ is halo. For this example, the halo of $X^1$ is displaced with an azide (—$N_3$), which is then left alone or converted to an amine through a reduction reaction. If $X^1$ becomes an amino group, the amino group can be further protected.

For example, in certain embodiments, the halo of $X^1$ is displaced with a source of —OH. In certain embodiments, a source of —OH is NaOH or KOH in a solvent such as DMF or MeOH at temperatures between 0° C. and the reflux point of the solvent. If $X^1$ becomes an hydroxyl group, the hydroxyl group can be further protected.

Additional Synthesis of Compound A-6

In some embodiments, compound A-5 is converted to a compound A-6, as described in Scheme 3b. Scheme 3b also shows a transformation of compound A-5 to compound A-6 and details intermediate steps of oxidation and reduction.

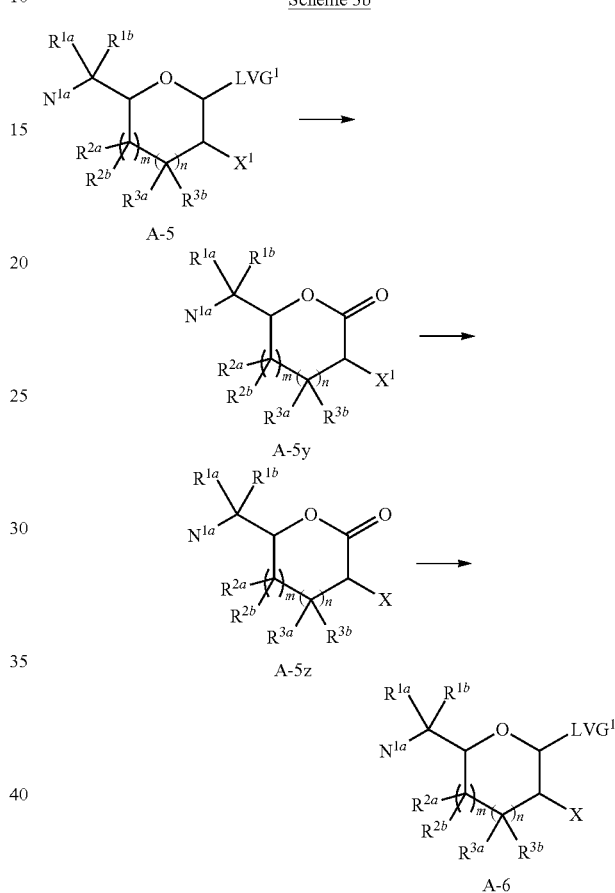

With reference to Scheme 3b, when $X^1$ is not —$NH_2$, —$N_3$, a protected amino group, —OH, or protected hydroxyl group, the process further comprises after step (d):

(e2) oxidizing the $LVG^1$ of formula A-5 to yield a compound of formula A-5y, wherein the compound of formula A-5y comprises an oxo group;

(e3) converting $X^1$ in a compound of formula A-5y to X to yield a compound of formula A-5z; and (e4) reducing the oxo group in the compound of formula A-5z to $LVG^1$ to yield a compound of formula A-6;

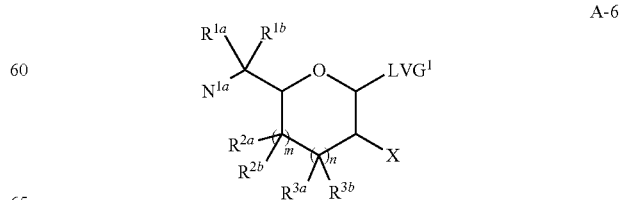

or a salt, solvate, enantiomer, or diastereomer thereof;

wherein X is —NH$_2$, —N$_3$, a protected amino group, —OH, or protected hydroxyl group.

In Scheme 3b, step (e2) is an oxidation step to convert the LVG$^1$ to an oxo group. For example, in certain embodiments for step (e2), an oxidation can be performed in the presence of pyridinium chlorochromate (PCC), pyridinium dichromate (PDC), Dess-martin periodinane (DMP) or Swern oxidation conditions in the solvents such as dichloromethane (DCM) or the like. In certain embodiments, LVG$^1$ is hydroxyl and the oxidation is performed in the presence of PDC in dichloromethane.

In Scheme 3b, for example, in certain embodiments for step (e3), X$^1$ is halo. For this example, the halo of X$^1$ is displaced with an azide (—N$_3$), which is then left alone or converted to an amine through a reduction reaction. If X$^1$ becomes an amino group, the amino group can be further protected.

In Scheme 3b, for example, in certain embodiments for step (e3), the halo of X$^1$ is displaced with a source of —OH. In certain embodiments, a source of —OH is NaOH or KOH in a solvent such as DMF or MeOH at temperatures between 0° C. and the reflux point of the solvent. If X$^1$ becomes an hydroxyl group, the hydroxyl group can be further protected.

In Scheme 3b, step (e4) is a reduction step to convert the oxo group to LVG$^1$. For example, in certain embodiments for step (e4), a reduction can be performed in the presence of a reducing agent. Examples of reducing agents include hydrogen gas (H$_2$) and hydride reagents such as borohydrides, lithium aluminium hydride, diisobutylaluminium hydride (DIBAL-H) and lithium triethylborohydride.

Additional Preparation of Ring A

An additional process for the preparation of a Ring A is illustrated in Scheme 4 below and is discussed in greater detail herein.

Scheme 4

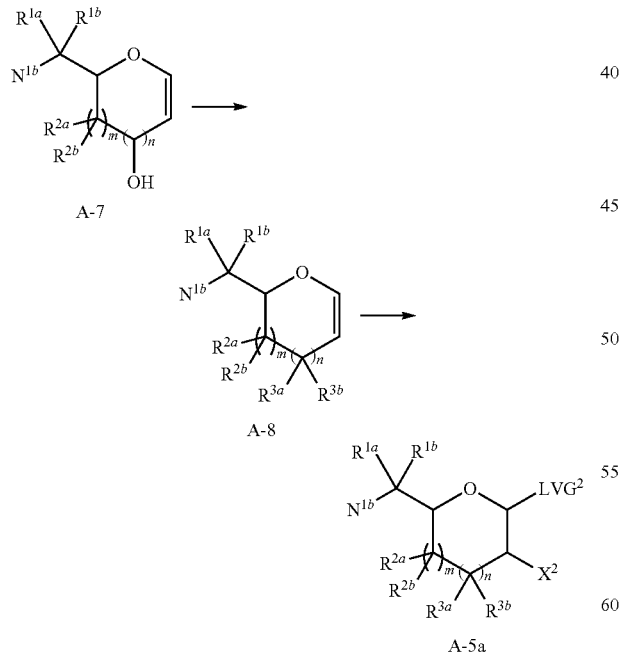

As noted above, the present disclosure provides processes for preparing Ring A. The present disclosure provides a process for preparing a process for preparing a compound of formula A-5a,

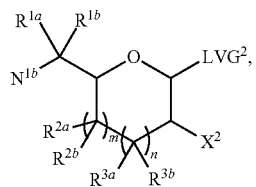

A-5a wherein

R$^{1a}$ and R$^{1b}$ are independently selected from the group consisting of H, C$_1$-C$_{12}$ alkyl, C$_1$-C$_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —N$_3$, and —OR$^{16}$, and wherein each R$^{12}$, R$^{13}$, R$^{14}$, R$^{15}$, and R$^{16}$ is independently H or alkyl; or R$^{1a}$ and R$^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each R$^{22}$, R$^{23}$, R$^{24}$, R$^{25}$, and R$^{26}$ is independently H or alkyl, wherein the alkyl is unsubstituted or substituted with one or more substituents independently selected from the group consisting of halogen, cyano, NR$^{14}$R$^{15}$, and —OR$^{16}$;

R$^{2a}$, R$^{2b}$, and R$^{3a}$ are independently selected from the group consisting of H, —OR$^{27}$, —NR$^{28}$R$^{29}$, halogen, C$_1$-C$_4$ cycloalkyl, and C$_1$-C$_6$ alkyl, wherein each R$^{27}$, R$^{28}$, and R$^{29}$ is independently H, alkyl, amino protecting group, or hydroxyl protecting group; wherein the C$_1$-C$_6$ alkyl or alkyl is unsubstituted or substituted with one or more substituents selected from the group consisting of aryl, halogen, —OR$^{30}$, —NR$^{31}$R$^{32}$, —SR$^{33}$, and —SO$_2$R$^{34}$;

wherein each R$^{30}$, R$^{31}$, R$^{32}$, R$^{33}$, and R$^{34}$ is independently H or alkyl substituted with one or more substituents independently selected from the group consisting of halogen, cyano, NR$^{14}$R$^{15}$, and —OR$^{16}$; or R$^{2a}$ and R$^{2b}$ form an oxo or imino group substituted with C$_1$-C$_6$ alkyl;

R$^{3b}$ is H;

N$^{1b}$ is —NHPg$^{1b}$ N(Pg$^{1b}$)$_2$, or N$_3$, wherein each Pg$^{1b}$ is independently an amino protecting group;

X$^2$ is —F, —Cl, —Br, or —I;

LVG$^2$ is a leaving group.

m is zero, 1, or 2;

n is zero, 1, or 2;

wherein m+n is 1, 2 or 3;

or a salt, solvate, enantiomer, or diastereomer thereof, comprising:

(a) converting —OH in the compound of formula A-7

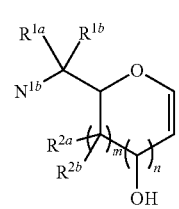

A-7 or a salt, solvate, enantiomer, or diastereomer thereof, to yield a compound of formula A-8:

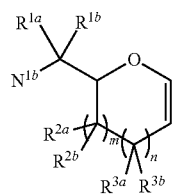

or a salt, solvate, enantiomer, or diastereomer thereof, wherein (b) contacting the compound of formula A-8 with a halogen reagent in presence of a nucleophile reagent (Nuc-2) to yield a compound of formula A-5a:

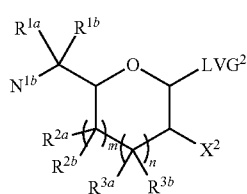

or a salt, solvate, enantiomer, or diastereomer thereof; wherein $X^2$ is —F, —Cl, —Br, or —I;

Nuc-2 is $LVG^2$-M, wherein M is H, a metal cation, a non-metal cation, or a lone pair of electrons;

$LVG^2$ is a leaving group.

Synthesis of Compound A-8

With continued reference to Scheme 4, the hydroxyl group of compound A-7 is converted to $R^{3a}$ to yield a compound of formula (A-8). As shown above, $R^{3b}$ is hydrogen.

In certain embodiments, the hydroxyl group of compound A-7 is converted to a halo group for $R^{3a}$. For example, compound A-7 is contacted with a halogenating reagent. For example, DAST or Dexa-Fluor can be used to convert a hydroxyl group to a fluoro group. For example, thionyl chloride or the Appel reaction ($PPh_3$ and $CCl_4$) can be used to convert a hydroxyl group to a chloro group. For example, $PBr_3$, $SOBr_2$, or the Appel reaction ($PPh_3$ and $CBr_4$) can be used to convert a hydroxyl group to a bromo group. For example, the Appel reaction ($PPh_3$, iodine and imidazole) can be used to convert a hydroxyl group to a iodo group.

In certain embodiments, the hydroxyl group of compound A-7 is converted to an amino group for $R^{3a}$. Suitable reactions that can convert a hydroxyl group to an amino group include the Gabriel synthesis and Mitsonobu reaction (using an amine nucleophile).

In certain embodiments, the hydroxyl group of compound A-7 is converted to an alkyl group for $R^{3a}$. Suitable reactions that can convert a hydroxyl group to an alkyl group include transformation of the above produced halogen containing derivatives under metalating condition such as treatment of the halogen containing derivative with n-Bu-Li or Mg followed by treatment with an alkylating reagent RX such as MeI or EtCl in solvents such as DCM or $Et_2O$ at temperatures ranging from −78° C. to room temperature.

Synthesis of Compound A-5a

With continued reference to Scheme 4, compound A-8 is contacted with a halogen reagent in the presence of a nucleophile reagent (Nuc-2) to yield compound A-5a. A halonium ion formation can occur from the reaction of the alkene of compound A-8 with the halogen reagent. Subsequently, a nucleophilic reaction can open up the halonium ion to provide $X^2$ and $LVG^2$ substituents on compound A-5a.

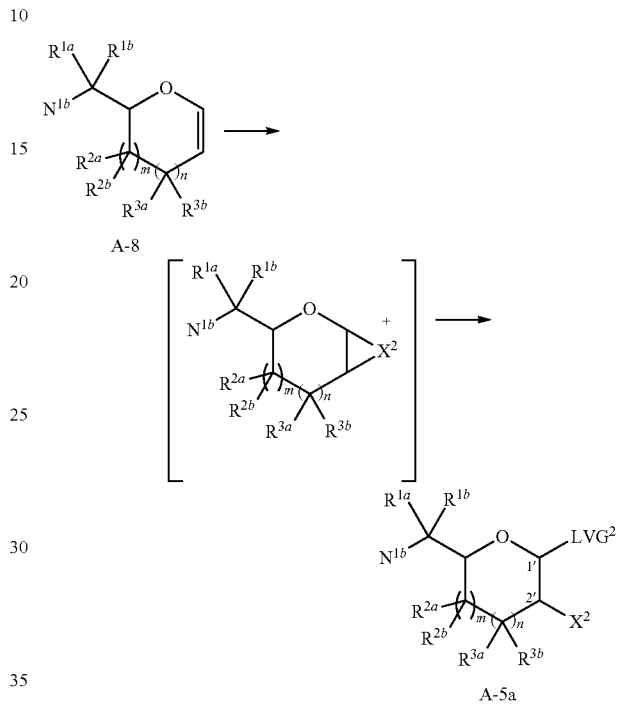

A halogen reagent can provide the halo group (e.g., $X^2$) on compound A-5a at C2', e.g., —F, —Cl, —Br, and —I. Examples of halogen reagents for reaction with compound A-8 include $Cl_2$, $Br_2$, NBS, NIS, HOCl, DAST, or $I_2$ A nucleophilic reaction can open up the halonium ion to provide $X^2$ and $LVG^2$ substituents on compound A-8. A nucleophile reagent provides the $LVG^2$ substituent on compound A-8 at C1'. The $LVG^2$ substituent is a leaving group, such that Ring A becomes a glycosyl donor. In certain embodiments, $LVG^2$ is halo, OMs, OTs, OH, a thioalkyl, a thioaryl, an imidate, an acetate, a phosphate, or an O-pentenyl group. A nucleophilic reagent can be prepared from the corresponding protonated or salt version of $LVG^2$. For example, in certain embodiments, $LVG^2$ is —OH and the corresponding nucleophilic reagent (Nuc-2) is water. Reaction with water provides —OH as the substituent for $LVG^2$.

In certain embodiments, compound A-5a can be used in the glycosylation reaction with a B ring.

In certain embodiments, compound A-5a can be hydrodehalogenated and then used in the glycosylation reaction with a B ring. In such instances, $X^2$ is converted to hydrogen. Examples of hydrodehalogenation reactions include use of metal catalysts, such as transition metal catalyst, alkali and alkaline-earth metals.

In certain embodiments, in compound A-5a, $R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H, alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$.

In certain embodiments, in compound A-5a, $N^{1b}$ is —$NHPg^{1b}$ or $N_3$, wherein $Pg^{1b}$ is an amino protecting group.

Synthesis of Compound A-6a

In some embodiments, compound A-5a is converted to a compound A-6a, as described in Scheme 5.

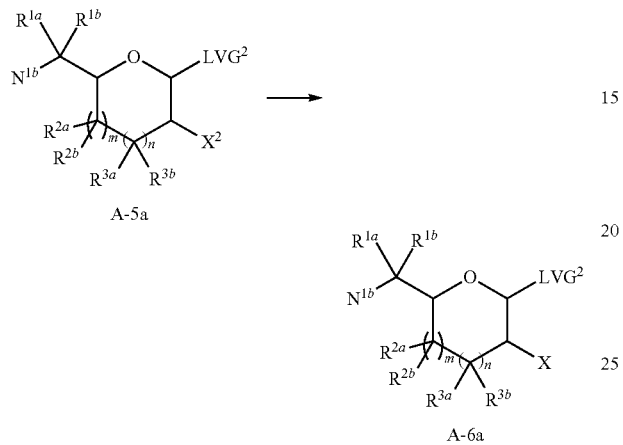

Scheme 5a

A-5a

A-6a

With reference to Scheme 5, wherein when $X^1$ is not —$NH_2$, —$N_3$, a protected amino group, —OH, or protected hydroxyl group, further comprising after step (b):

(c) converting $X^2$ in the compound of formula A-5a to X to yield a compound of formula A-6a:

A-6a or a salt, solvate, enantiomer, or diastereomer thereof;
wherein X is —$NH_2$, —$N_3$, a protected amino group, —OH, or protected hydroxyl group.

For example, in certain embodiments, $X^2$ is halo. For this example, the halo of $X^2$ is displaced with an azide (—$N_3$), which is then left alone or converted to an amine through a reduction reaction. If $X^2$ becomes an amino group, the amino group can be further protected.

For example, in certain embodiments, the halo of $X^2$ is displaced with a source of —OH. In certain embodiments, a source of —OH is NaOH or KOH in a solvent such as DMF or MeOH at temperatures between 0° C. and the reflux point of the solvent. If $X^2$ becomes an hydroxyl group, the hydroxyl group can be further protected.

Additional Synthesis of Compound A-6a

In some embodiments, compound A-5a is converted to a compound A-6a, as described in Scheme 5b. Scheme 5b also shows a transformation of compound A-5a to compound A-6a and details intermediate steps of oxidation and reduction.

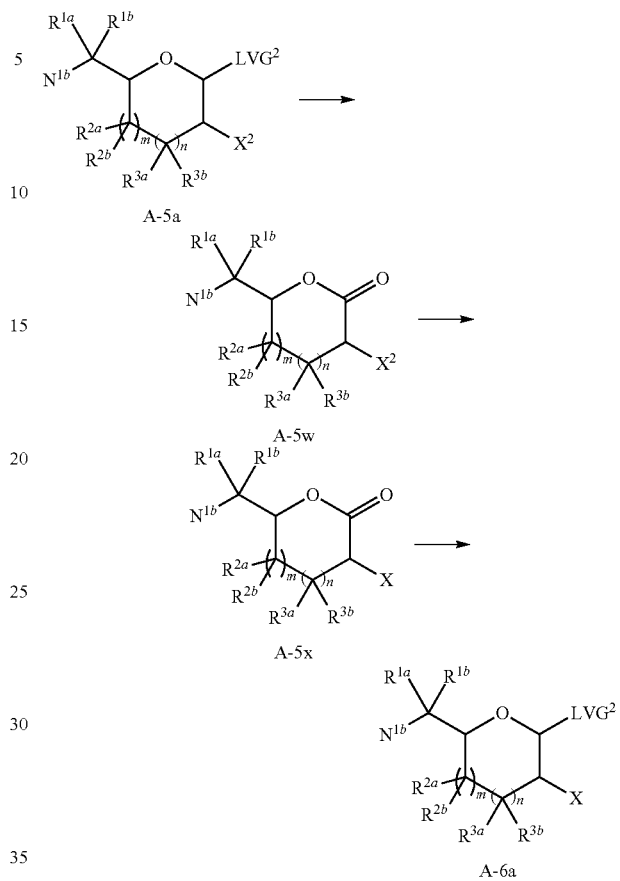

Scheme 5b

A-5a

A-5w

A-5x

A-6a

With reference to Scheme 5b, when $X^2$ is not —$NH_2$, —$N_3$, a protected amino group, —OH, or protected hydroxyl group, the process further comprises after step (b):

(c2) oxidizing the $LVG^2$ of formula A-5a to yield a compound of formula A-5w, wherein the compound of formula A-5w comprises an oxo group;

(c3) converting $X^2$ in a compound of formula A-5w to X to yield a compound of formula A-5x; and (c4) reducing the oxo group in the compound of formula A-5x to $LVG^2$ to yield a compound of formula A-6a;

A-6a or a salt, solvate, enantiomer, or diastereomer thereof;
wherein X is —$NH_2$, —$N_3$, a protected amino group, —OH, or protected hydroxyl group.

In Scheme 5b, step (c2) is an oxidation step to convert the $LVG^2$ to an oxo group. For example, in certain embodiments for step (c2), an oxidation can be performed in the presence of pyridinium chlorochromate (PCC), pyridinium dichromate (PDC), Dess-martin periodinane (DMP) or Swern oxidation conditions in the solvents such as dichloromethane (DCM) or the like. In certain embodiments, LVG² is hydroxyl and the oxidation is performed in the presence of PDC in dichloromethane.

In Scheme 5b, for example, in certain embodiments for step (c3), X² is halo. For this example, the halo of X² is displaced with an azide (—N₃), which is then left alone or converted to an amine through a reduction reaction. If X² becomes an amino group, the amino group can be further protected.

In Scheme 5b, for example, in certain embodiments for step (c3), the halo of X² is displaced with a source of —OH. In certain embodiments, a source of —OH is NaOH or KOH in a solvent such as DMF or MeOH at temperatures between 0° C. and the reflux point of the solvent. If X² becomes an hydroxyl group, the hydroxyl group can be further protected.

In Scheme 5b, step (c4) is a reduction step to convert the oxo group to LVG². For example, in certain embodiments for step (c4), a reduction can be performed in the presence of a reducing agent. Examples of reducing agents include hydrogen gas (H₂) and hydride reagents such as borohydrides, lithium aluminium hydride, diisobutylaluminium hydride (DIBAL-H) and lithium triethylborohydride.

Additional Embodiments of Ring A

In certain embodiments, Ring A at the 6'-position can be —OH. In such instances, the A ring with a hydroxyl group at the 6'-position can be commercially available or prepared with techniques known in the art. For example, compounds A-5 and A-5a herein are shown below as A-5″ and A-5a″, wherein $N^{1a}$ is —OH, protected hydroxyl group, —NHPg$^{1a}$, —N(Pg$^{1a}$)₂, or N₃, wherein each Pg$^{1a}$ is independently an amino protecting group and wherein $N^{1b}$ is —OH, protected hydroxyl group, —NHPg$^{1b}$, —N(Pg$^{1b}$)₂, or N₃, wherein each Pg$^{1a}$ is independently an amino protecting group.

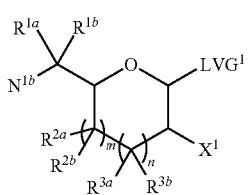

A-5″

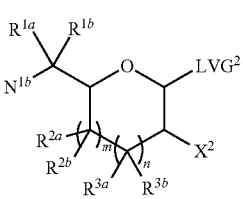

A-5a″

Embodiments of Ring A

In certain embodiments, the stereochemistry in the ring of formulae A-1, A-2, A-3, A-4, ≡ A-5, A-5a, A-6, A-6a, A-7, and A-8 is as indicated in formula (A'), wherein === is a single bond or a double bond and wherein ⁓ indicates a point of attachment to a hydrogen or a moiety:

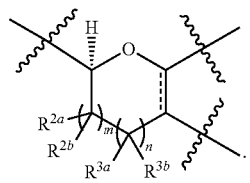

(A')

In certain embodiments, m is one. In certain embodiments, n is one. In certain embodiments, m is one and n is one.

Preparation of Ring B

The present disclosure includes processes, methods, reagents, and intermediates for the synthesis of Ring B:

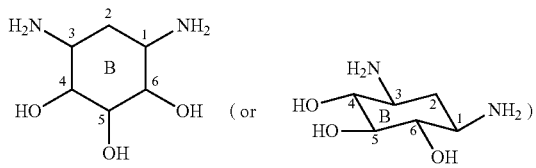

In Ring B, the hydroxyl group at C5 is group suitable of reacting with a reactant or a glycosyl donor, to form an interglycosidic linkage. The structure shown above for Ring B is representative and is based on a generic structure, such that the substituents are shown above for convenience. That is, the substituents shown above for Ring B are not limited to the certain substituents and suitable substituents for Ring B are described herein.

A process for the preparation of a Ring B is illustrated in Schemes 6 and 6a below and is discussed in greater detail herein.

Scheme 6

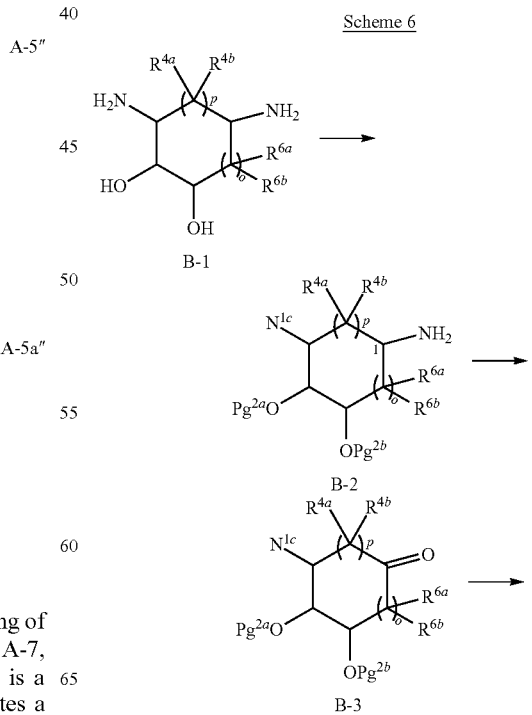

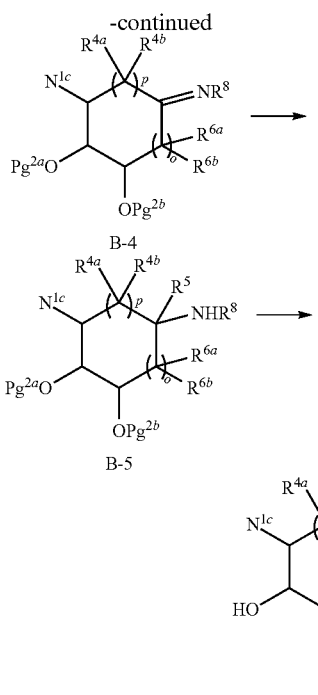

B-4

B-5

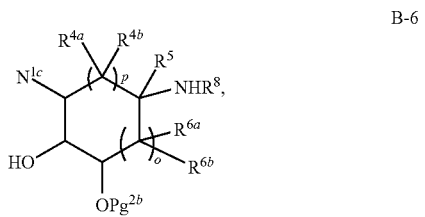

B-6

As noted above, the present disclosure provides processes for preparing Ring B. With reference to Scheme 6, the present disclosure provides a process for preparing a compound of formula B-6,

B-6

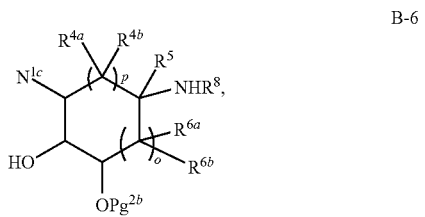

wherein $R^{4a}$ and $R^{4b}$ are, independently H, —OH, —OR$^{40}$, —NR$^{41}$R$^{42}$, or halogen;

wherein each $R^{40}$, $R^{41}$, and $R^{42}$ are independently H or alkyl; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^5$ is H, —CN, —CONH$_2$ or C$_1$-C$_3$alkyl, wherein the alkyl is unsubstituted or substituted with one or more substituents selected from the group consisting of —OH, —NH$_2$, —CN, —CONH$_2$, and halogen;

$R^{6a}$ and $R^{6b}$ are, independently H, halogen, NH$_2$, —OH, C$_1$-C$_3$alkoxy, —OC(O)CH$_3$, or —OPg$^{2o}$; wherein Pg$^{2o}$ is a hydroxyl protecting group;

$R^8$ is H, C$_1$-C$_6$ alkyl, an amino protecting group, or

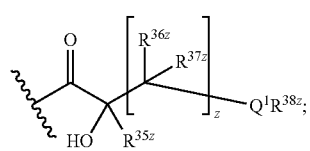

wherein $Q^1$ is NH, O, or S;

z is an integer from 0 to 4, $R^{35z}$ is H or C$_1$-C$_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein $R^{39z}$ and $R^{40z}$ are independently H or C$_1$-C$_3$ alkyl; or $R^{35z}$ and $R^{38z}$, together with the atoms to which they are attached, form a heterocycloalkyl group comprising at least one N;

$N^{1c}$ is —NHPg$^{1c}$ or N$_3$, wherein Pg$^{1c}$ is an amino protecting group;

Pg$^{2b}$ is a hydroxyl protecting group;

o is zero, 1, or 2;

p is zero, 1, or 2;

wherein o+p is 1, 2 or 3;

or a salt, solvate, enantiomer, or diastereomer thereof, comprising:

(a) contacting a compound of formula B-1:

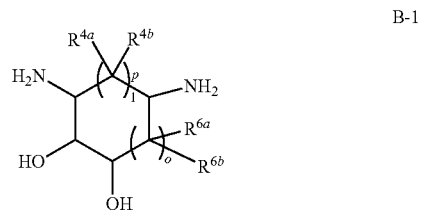

B-1 or a salt, solvate, enantiomer, or diastereomer thereof, with an amino protecting group reagent and a hydroxyl protecting group reagent to yield a compound of formula B-2:

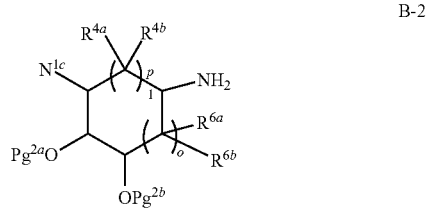

B-2 or a salt, solvate, enantiomer, or diastereomer thereof;

wherein Pg$^{2a}$ is a hydroxyl protecting group;

(b) converting the amino group of the compound of formula B-2 at C1 to an azide group;

(c) converting the azide group of the compound of formula B-2 at C1 to a hydroxyl group;

(d) oxidizing the hydroxyl group of the compound of formula B-2 at C1 to an oxo group to yield a compound of formula B-3:

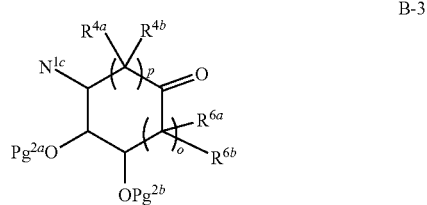

B-3 or a salt, solvate, enantiomer, or diastereomer thereof;

(e) converting the oxo group of the compound of formula B-3 to an imino group and contacting with an amino reactive reagent to yield a compound of formula B-4:

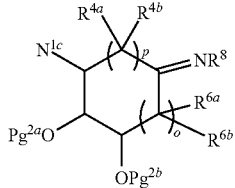

B-4 or a salt, solvate, enantiomer, or diastereomer thereof;

(f) contacting the compound of formula B-4 with a Grignard or organolithium reagent to yield a compound of formula B-5:

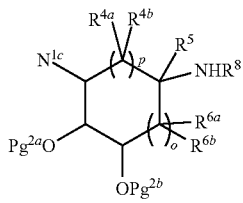

B-5 or a salt, solvate, enantiomer, or diastereomer thereof, (g) forming a hydroxyl group by selective removal of the $Pg^{2a}$ protecting group of the compound of formula B-5 to yield the compound of formula B-6:

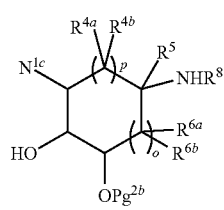

B-6 or a salt, solvate, enantiomer, or diastereomer thereof.

A process for the preparation of a Ring B is illustrated in Scheme 6a below and is discussed in greater detail herein.

Scheme 6a

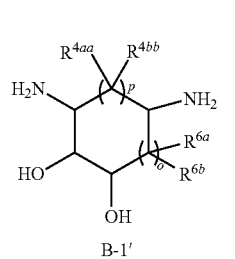

B-1'

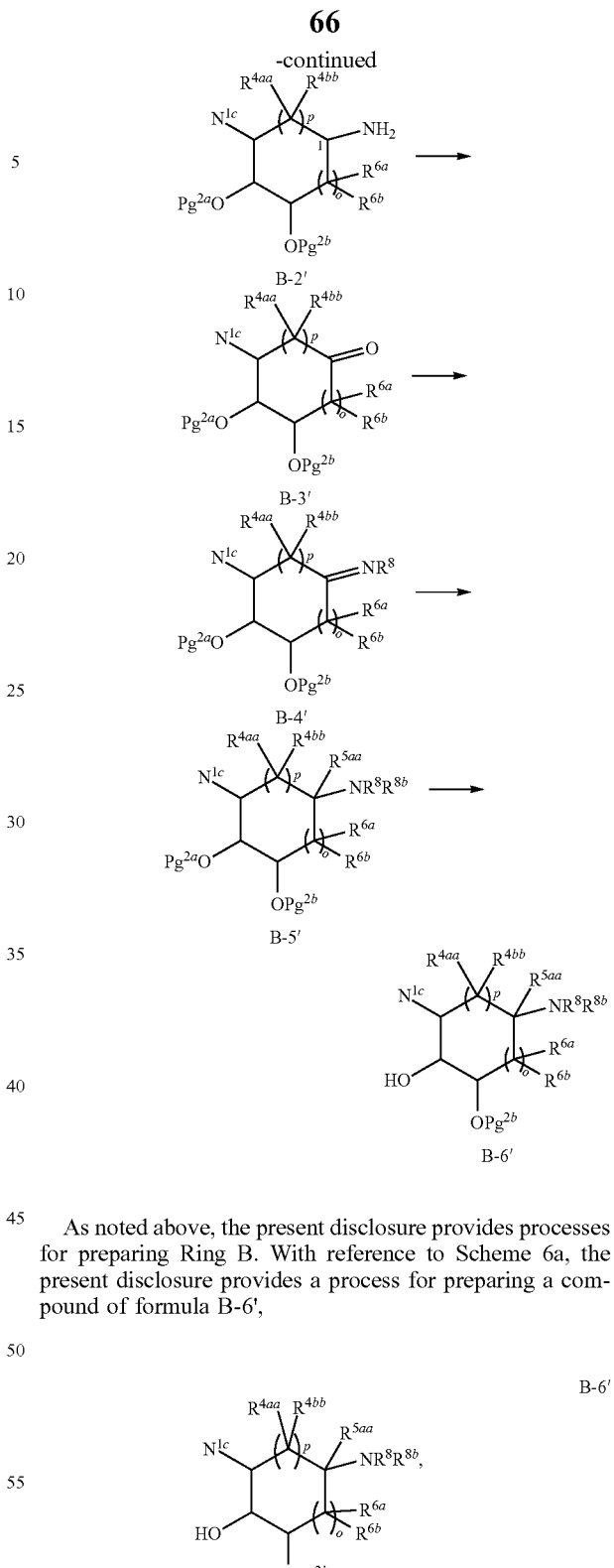

As noted above, the present disclosure provides processes for preparing Ring B. With reference to Scheme 6a, the present disclosure provides a process for preparing a compound of formula B-6', wherein $R^{4aa}$ and $R^{4bb}$ are, independently H, —OH, —$OR^{40}$, —$NR^{41}R^{42}$, or halogen;

wherein each $R^{40}$, $R^{41}$, and $R^{42}$ are independently H, alkyl, —$CONH_2$, or —$COCH_3$; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

R$^{5aa}$ is H, —CN, —CONH$_2$ or C$_1$-C$_3$alkyl, wherein the alkyl is unsubstituted or substituted with one or more substituents selected from the group consisting of —OH, —OC(O)CH$_3$, —NH$_2$, —CN, —CONH$_2$, and halogen;

R$^{6a}$ and R$^{6b}$ are, independently H, halogen, NH$_2$, —OH, C$_1$-C$_3$alkoxy, —OC(O)CH$_3$, or —OPg$^{2o}$; wherein Pg$^{2o}$ is a hydroxyl protecting group;

R$^8$ is H, C$_1$-C$_6$ alkyl, an amino protecting group, or

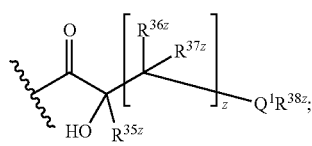

wherein

Q$^1$ is NH, O, or S;

z is an integer from 0 to 4,

R$^{35z}$ is H or C$_1$-C$_3$ alkyl;

each R$^{36z}$ and R$^{37z}$ is independently selected from the group consisting of H, alkyl, halogen, and —OH, and R$^{38z}$ is H, alkyl, or —C(=NH)NR$^{39z}$R$^{40z}$, wherein R$^{39z}$ and R$^{40z}$ are independently H or C$_1$-C$_3$ alkyl; or R$^{35z}$ and R$^{38z}$, together with the atoms to which they are attached, form a heterocycloalkyl group comprising at least one N;

R$^{8b}$ is H or C$_1$-C$_3$alkyl;

N$^{1c}$ is —NHPg$^{1c}$ or N$_3$, wherein Pg$^{1c}$ is an amino protecting group;

Pg$^{2b}$ is a hydroxyl protecting group;

o is zero, 1, or 2;

p is zero, 1, or 2;

wherein o+p is 1, 2 or 3;

or a salt, solvate, enantiomer, or diastereomer thereof, comprising:

(a) contacting a compound of formula B-1':

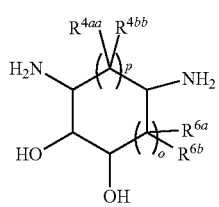

or a salt, solvate, enantiomer, or diastereomer thereof, with an amino protecting group reagent and a hydroxyl protecting group reagent to yield a compound of formula B-2':

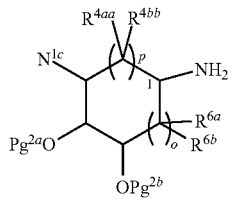

or a salt, solvate, enantiomer, or diastereomer thereof;

wherein Pg$^{2a}$ is a hydroxyl protecting group;

(b) converting the amino group of the compound of formula B-2' at C1 to an azide group;

(c) converting the azide group of the compound of formula B-2' at C1 to a hydroxyl group;

(d) oxidizing the hydroxyl group of the compound of formula B-2' at C1 to an oxo group to yield a compound of formula B-3':

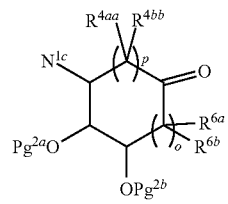

or a salt, solvate, enantiomer, or diastereomer thereof;

(e) converting the oxo group of the compound of formula B-3' to an imino group and contacting with an amino reactive reagent to yield a compound of formula B-4':

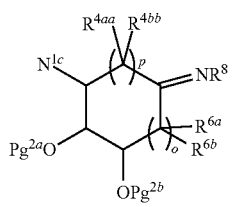

or a salt, solvate, enantiomer, or diastereomer thereof;

(f) contacting the compound of formula B-4' with a Grignard or organolithium reagent to yield a compound of formula B-5':

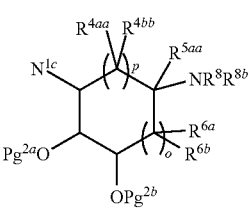

or a salt, solvate, enantiomer, or diastereomer thereof, (g) forming a hydroxyl group by selective removal of the Pg$^{2a}$ protecting group of the compound of formula B-5' to yield the compound of formula B-6':

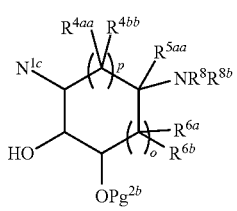

B-6' or a salt, solvate, enantiomer, or diastereomer thereof.

Synthesis of Compound B-2

Reference to compounds B-1 to B-6 are meant to encompass compounds B-1' to B-6'. With reference to Schemes 6 and 6a, compound B-1 is contacted with an amino protecting group reagent and a hydroxyl protecting group reagent to yield a compound B-2.

Addition of amino protecting group $Pg^{1c}$ to yield compound B-2 is provided by an amino protecting group reagent. Examples of amino protecting group $Pg^{2a}$ include, but are not limited to, 2-trimethylsilylethoxycarbonyl (Teoc), 1-methyl-1-(4-biphenylyl)ethoxycarbonyl (Bpoc), t-butoxycarbonyl (Boc), allyloxycarbonyl (Alloc), 9-fluorenylmethyloxycarbonyl (Fmoc), benzyloxycarbonyl (Cbz), p-nitrobenzyloxycarbonyl (PNZ), formyl, acetyl, trihaloacetyl (e.g., trifluoroacetyl), benzoyl, nitrophenylacetyl, 2-nitrobenzenesulfonyl, phthalimido, and dithiasuccinoyl. Suitable protecting group reagents to provide amino protecting group $Pg^{2a}$ can be found in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski).

Addition of hydroxyl protecting groups $Pg^{2a}$ and $Pg^{2b}$ to yield compound B-2 is provided by hydroxyl protecting group reagents. Examples of hydroxyl protecting group $Pg^{2a}$ and $Pg^{2b}$ include t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl (TBDPS), triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Suitable protecting group reagents to provide hydroxyl protecting groups $Pg^{2a}$ and $Pg^{2b}$ can be found in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski).

Synthesis of Compound B-3

With continued reference to Schemes 6 and 6a, the amino group of compound B-2 is converted to an azide, then displaced with a hydroxyl group, and then the hydroxyl group is oxidized to an oxo group to yield compound B-3.

The amino group of the compound B-2 at C1 to an azide group. Suitable reactions that convert an amino group to an azide group include the use of an azide donor such as $TfN_3$ or $NaN_3$ in solvents such as MeOH or DMF at temperatures below 0° C.

The azide group of the compound B-2 at C1 is converted to a hydroxyl group. Suitable reactions that convert an azide group to a hydroxyl group include displacement of the azide by an OH— source such as NaOH or KOH is a solvent such as DMF or MeOH at temperatures between 0° C. and the reflux point of the solvent.

The hydroxyl group of the compound B-2 at C1 is converted to an oxo group by oxidizing the hydroxyl group of the compound B-2 at C1 to yield a compound B-3. Suitable reactions that convert an hydroxyl group to a oxo group include Swern oxidation, Jones oxidation, Dess-Martin oxidation, and use of PCC (pyridinium chlorochromate).

Synthesis of Compound B-4

With continued reference to Schemes 6 and 6a, the oxo group of compound B-3 is converted to an imino group. A suitable reaction that converts an oxo group to a imino group includes treatment with an amine in a solvent such at PhMe or MeOH optionally under dehydrating conditions such as Dean-Stark at temperatures between room temperature and the reflux point of the solvent.

After conversion to an imino group, compound B-3 is contacted with an amino reactive reagent to yield compound B-4. The reaction provides functionalization of =NH of B ring with $R^8$ moiety. The amino reactive reagent provides Rx substituent on compound B-4. Thus, the amino reactive reagent corresponds to $R^8$ moiety.

In certain embodiments, $R^8$ is an amino protecting group. Examples of amino protecting groups include, but are not limited to, 2-trimethylsilylethoxycarbonyl (Teoc), 1-methyl-1-(4-biphenylyl)ethoxycarbonyl (Bpoc), t-butoxycarbonyl (Boc), allyloxycarbonyl (Alloc), 9-fluorenylmethyloxycarbonyl (Fmoc), benzyloxycarbonyl (Cbz), p-nitrobenzyloxycarbonyl (PNZ), formyl, acetyl, trihaloacetyl (e.g., trifluoroacetyl), benzoyl, nitrophenylacetyl, 2-nitrobenzenesulfonyl, phthalimido, and dithiasuccinoyl. Suitable protecting group reagents to provide amino protecting group $Pg^{2a}$ can be found in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski).

In certain embodiments, $R^8$ is H. In certain embodiments, $R^8$ is $C_1$-$C_6$alkyl, In certain embodiments, $R^8$ is methyl. In certain embodiments, $R^8$ is ethyl.

In certain embodiments, $R^8$ forms an amide with the imino group. Carboxylic acids corresponding to the $R^8$ moiety can react with imino group on C1 of the B ring to provide the $R^8$ substituent. In certain instances, a catalyst or activating agent can assist with amide formation reaction.

In certain embodiments, $R^8$ is

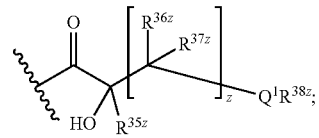

wherein $Q^1$ is NH, O, or S. In certain embodiments, $Q^1$ is NH. In certain embodiments, $Q^1$ is O. In certain embodiments, $Q^1$ is S. In certain embodiments, wherein when z is one, then $R^{36z}$ and $R^{37z}$ are not halo.

In certain embodiments, $R^8$ is

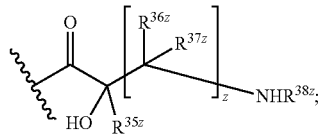

wherein z is an integer from 0 to 4, $R^{35z}$ is H or $C_1$-$C_3$alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$alkyl; or $R^{35z}$ and $R^{38z}$, together with the atoms to which they are attached, form a heterocycloalkyl group comprising at least one N.

In other embodiments, $R^8$ is

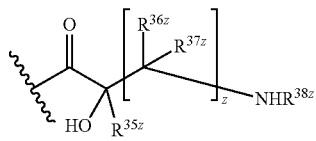

for example

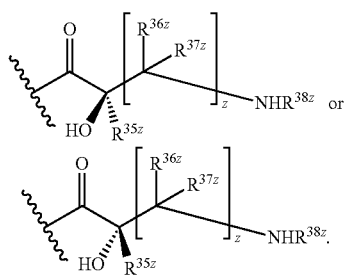

In some embodiments, $R^{35z}$ is H. In certain embodiments, each $R^{36z}$ and $R^{37z}$ are H. In certain embodiments, $R^{38z}$ is H. In other embodiments, $R^{38z}$ is alkyl, for example $C_1$alkyl, $C_2$alkyl, or $C_3$alkyl. In other embodiments, $R^{38z}$ is —C(=NH)$NR^{39}R^{40}$, for example —C(=NH)$NH_2$. In certain embodiments, $R^{35z}$ and $R^{38z}$, together with the atoms to which they are attached, form a heterocycloalkyl group comprising at least one N.

In some embodiments, z is an integer from 0 to 4, from 0 to 3, from 0 to 2, from 1 to 4, from 2 to 4, or from 1 to 3. In certain embodiments, z is 0, or z is 1, or z is 2, or z is 3, or z is 4.

In some embodiments, $R^8$ is:

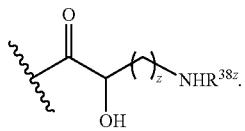

For example, $R^8$ may be:

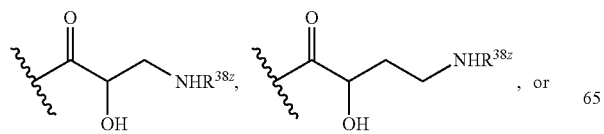

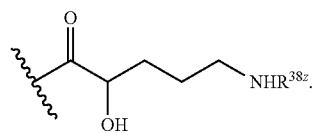

In some embodiments, $R^{38z}$ is H. For example, $R^8$ may be:

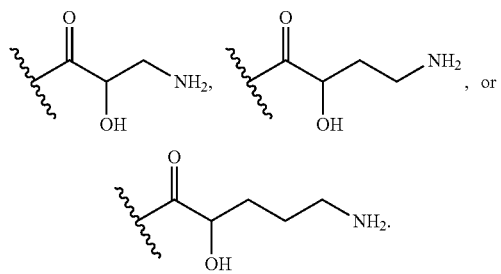

In some embodiments, $R^8$ may be:

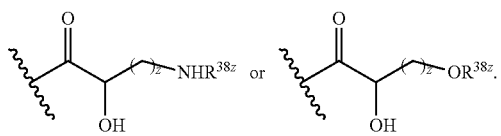

In some embodiments, $R^8$ may be:

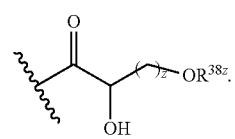

In certain embodiments, $R^8$ is:

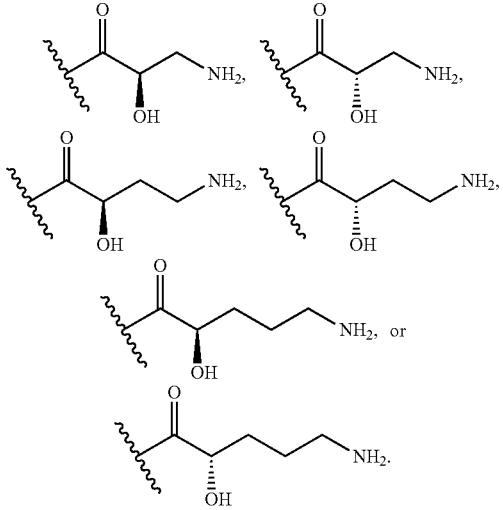

In certain embodiments, $R^8$ is:

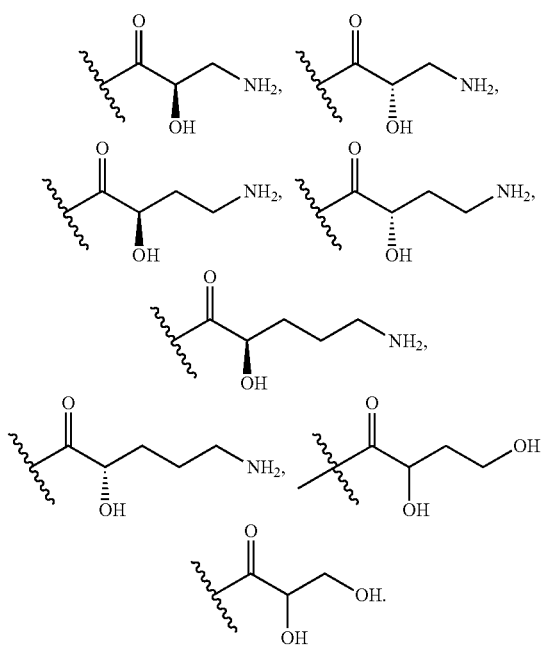

In certain embodiments, $R^8$ is:

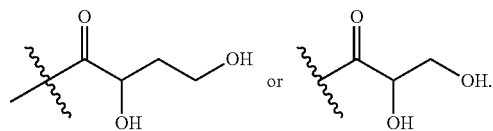 [SMILES: *C(=O)C(O)CCO ; *C(=O)C(O)CO]

In other embodiments, at least one $R^{36z}$ or $R^{37z}$ is halogen. For example, in certain embodiments, $R^8$ is:

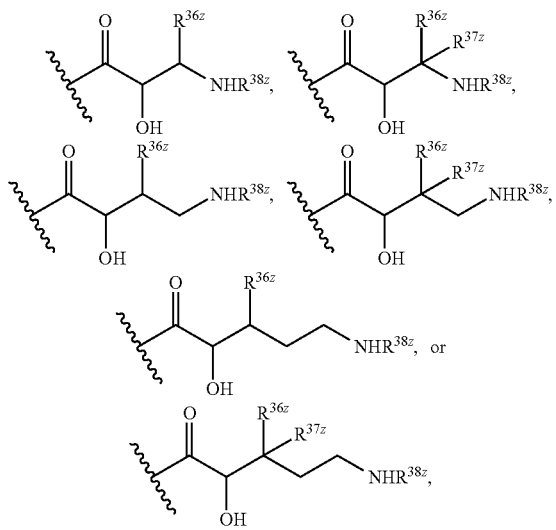

wherein each $R^{36z}$ and $R^{37z}$ is independently halogen, for example fluoro.

In certain embodiments, at least one $R^{36z}$ or $R^{37z}$ is halogen, and $R^{38z}$ is H. For example, $R^8$ may be:

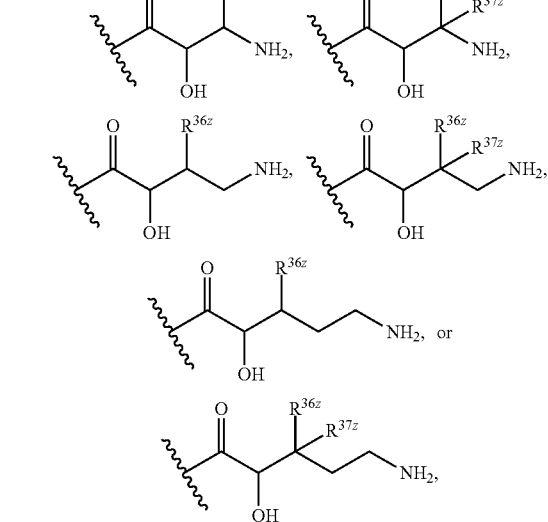

wherein each $R^{36z}$ and $R^{37z}$ are independently halogen, for example fluoro.

In other embodiments, at least one $R^{36z}$ or $R^{37z}$ is halogen. For example, in certain embodiments, $R^8$ is:

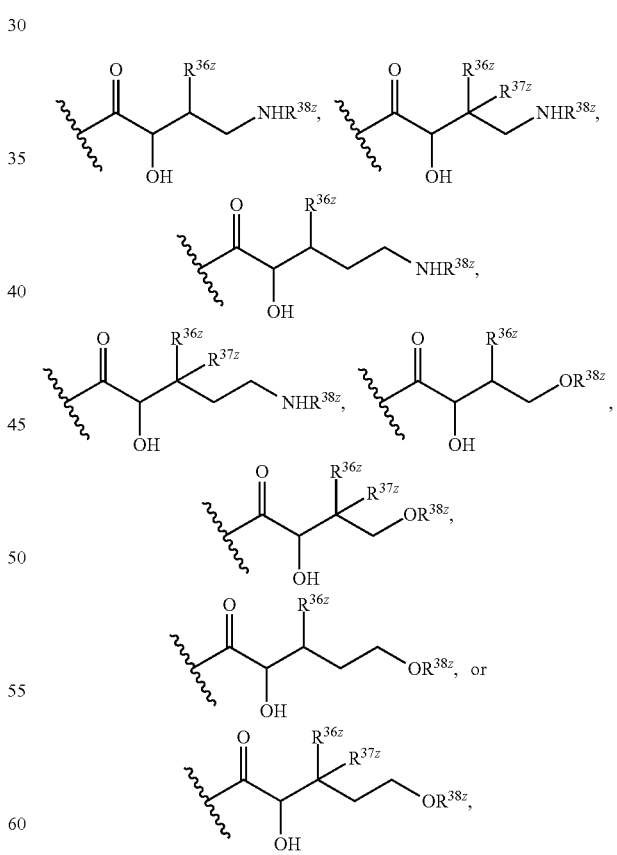

wherein each $R^{36z}$ and $R^{37z}$ is independently halogen, for example fluoro.

In certain embodiments, at least one $R^{36z}$ or $R^{37z}$ is halogen, and $R^{38z}$ is H. For example, $R^8$ may be:

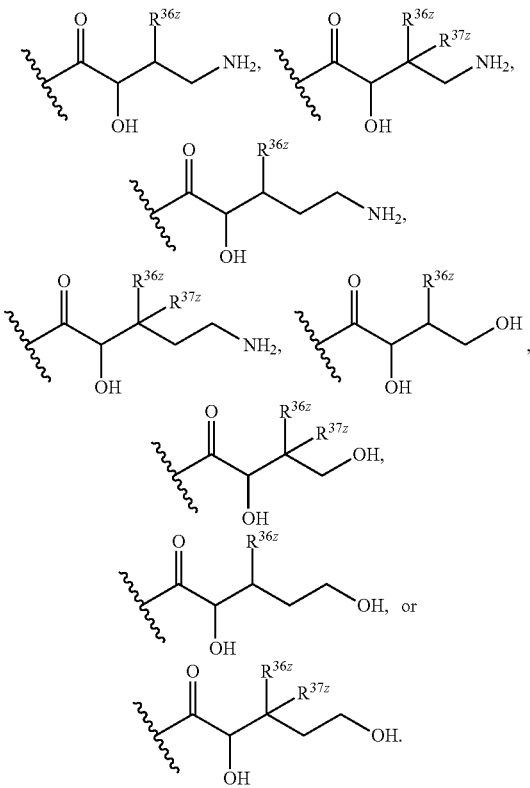

wherein each $R^{36z}$ and $R^{37z}$ are independently halogen, for example fluoro.

In other embodiments, $R^8$ is

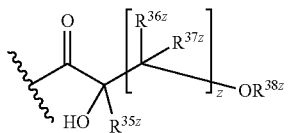

wherein at least one $R^{36z}$ or $R^{37z}$ is hydroxyl.

In other embodiments, $R^8$ is

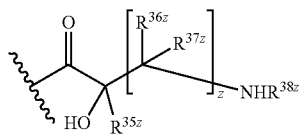

wherein at least one $R^{36z}$ or $R^{37z}$ is hydroxyl.

In some embodiments, $R^{38z}$ is —C(=NH)NR$^{39z}$R$^{40z}$, and $R^8$ is:

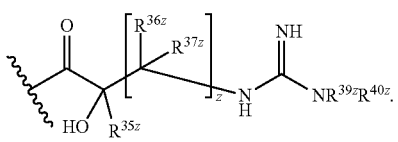

In some embodiments, $R^{39z}$ and $R^{40z}$ are both H. In other embodiments, $R^{39z}$ and $R^{40z}$ are both $C_1$-$C_3$alkyl. In still other embodiments, one of $R^{39z}$ and $R^{40z}$ is H and the other is $C_1$-$C_3$alkyl.

$R^{38z}$ may be —C(=NH)NH$_2$. Thus, in certain embodiments, $R^8$ is:

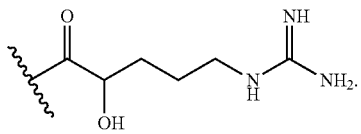 [SMILES: *C(=O)C(O)CCCNC(=N)N]

In certain embodiments, $R^{36z}$ and one $R^{37z}$, together with the atoms to which they are attached, form a carbocylic ring having from 3 to 6 ring atoms.

In certain embodiments, $R^{8b}$ is H. In certain embodiments, $R^{8b}$ is $C_1$-$C_3$alkyl.

Synthesis of Compound B-5

With continued reference to Schemes 6 and 6a, compound B-4 is contacted with a Grignard or organolithium reagent to yield a compound B-5. The reaction provides functionalization of C1 of B ring with $R^5$ moiety. The Grignard or organolithium reagent provides $R^5$ substituent on compound B-5. Thus, the Grignard or organolithium reagent corresponds to $R^5$ moiety.

In certain embodiments, the addition reaction in Schemes 6 and 6a can be carried out using a Grignard reagent of formula: $R^5$MgX, where $R^5$ is as defined herein for general formula B-5 and X is a halide. In certain embodiments, the addition reaction in Schemes 6 and 6a can be carried out using an organolithium reagent of formula: $R^5$—Li, where $R^5$ is as defined herein for general formula B-5.

A Grignard reagent of formula: $R^5$MgX or an organolithium reagent of formula: $R^5$—Li can be prepared from the corresponding halide of $R^5$. Depending on the functional groups on $R^5$, various modifications for the reaction with a Grignard reagent or organolithium reagent can be used, including use of protecting groups.

A Grignard reagent is prepared by reaction of an organic halide with magnesium An organolithium reagent is prepared by reaction of an organic halide with lithium. For example, Grignard reagent or organolithium reagent such as MeMgBr, EtMgBr, MeLi, or EtLi would provide substituents, such as methyl or ethyl.

Synthesis of Compound B-6

With continued reference to Schemes 6 and 6a, a selective removal of the Pg$^{2a}$ protecting group of the compound B-5 yields compound B-6, which has a hydroxyl group from the removal of the Pg$^{2a}$ protecting group. Selective removal of Pg$^{2a}$ protecting group can be performed by hydrolysis. For example, selective removal of Pg$^{2a}$ protecting group can be performed by hydrolysis under conditions such as base (for example, NaOH, KOH, Et$_3$N) or acid mediated (for example, HCl, TfOH, p-TSA) in aqueous media optionally including organic solvents (for example, MeOH, Et$_2$O, DMF) at temperatures between 0° C. and the reflux point of the solvent.

Additional Preparation of Ring B

An additional process for the preparation of a Ring B is illustrated in Schemes 7, 7a, and 7b below and is discussed in greater detail herein. The atom numbering below is for a compound, where o and p are each one.

Scheme 7

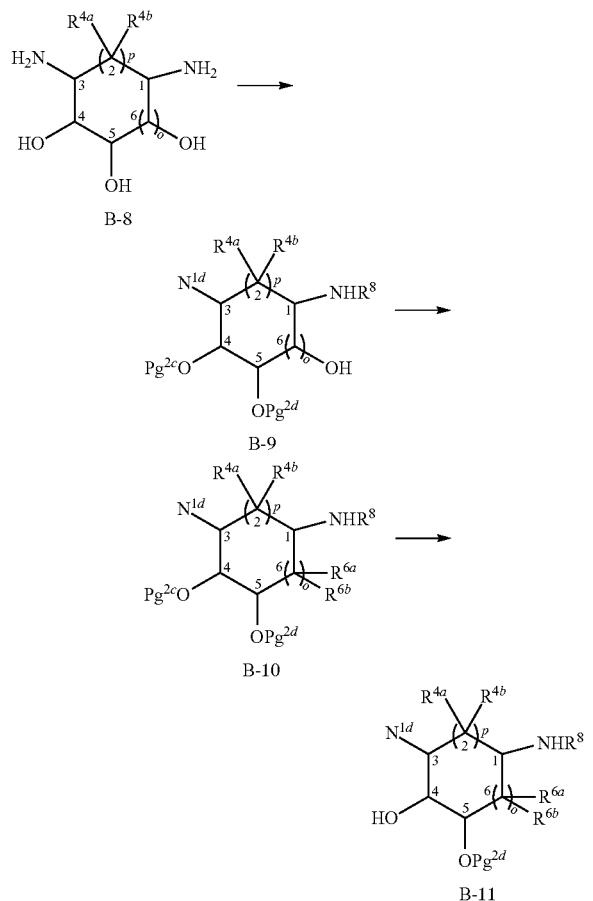

As noted above, the present disclosure provides processes for preparing Ring B. With reference to Scheme 7, the present disclosure provides a process for preparing a process for preparing a compound of formula B-11,

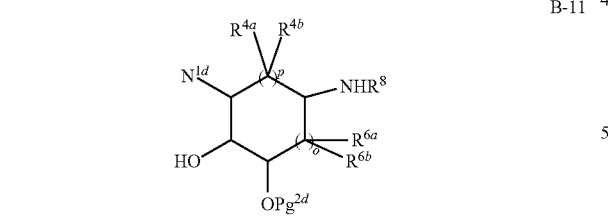

wherein $R^{4a}$ and $R^{4b}$ are, independently, H, —OH, —OR$^{40}$, —NR$^{41}$R$^{42}$, or halogen;

wherein each $R^{40}$, $R^{41}$, and $R^{42}$ are independently H or alkyl; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^{6a}$ and $R^{6b}$ are, independently H, halogen, NH$_2$, —OH, $C_1$-$C_3$ alkoxy, —OC(O)CH$_3$, or —OPg$^{2o}$; wherein Pg$^{2o}$ is a hydroxyl protecting group;

$R^8$ is H, $C_1$-$C_6$ alkyl, an amino protecting group, or

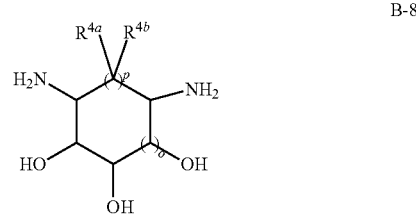

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$N^{1d}$ is —NHPg$^{1d}$ or N$_3$, wherein Pg$^{1d}$ is an amino protecting group;

Pg$^{2d}$ is a hydroxyl protecting group;

o is zero, 1, or 2;

p is zero, 1, or 2;

wherein o+p is 1, 2 or 3;

or a salt, solvate, enantiomer, or diastereomer thereof, comprising:

(a) contacting a compound of formula B-8:

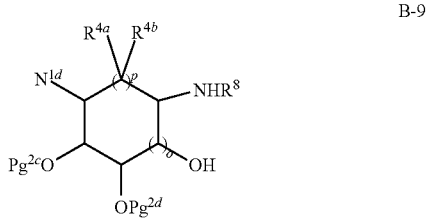

or a salt, solvate, enantiomer, or diastereomer thereof, with an amino protecting group reagent and a first selective hydroxyl protecting group reagent and a second selective hydroxyl protecting group reagent and an amino reactive reagent to yield a compound of formula B-9:

B-9

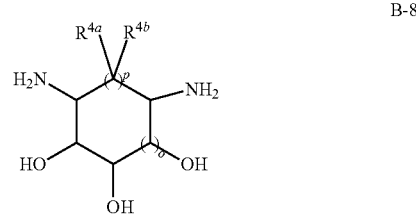

or a salt, solvate, enantiomer, or diastereomer thereof; wherein Pg$^{2c}$ is a hydroxyl protecting group;

(b) contacting the compound of formula B-9 with a electrophilic reagent to yield a compound of formula B-10:

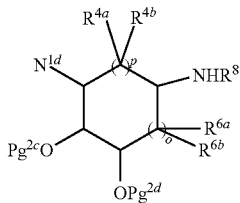

or a salt, solvate, enantiomer, or diastereomer thereof, c) forming a hydroxyl group by selective removal of the Pg$^{2c}$ protecting group of the compound of formula B-10 to yield the compound of formula B-11:

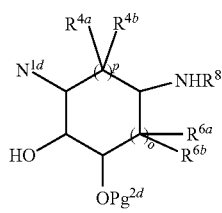

or a salt, solvate, enantiomer, or diastereomer thereof.

A process for the preparation of a Ring B is illustrated in Schemes 7a and 7b below and is discussed in greater detail herein. Scheme 7b is Scheme 7a, wherein N$^{1s}$ is —NR$^8$R$^{8b}$. Also, for Scheme 7b, compound B-8″ comprises —NH$_2$ for N$^{1dx}$, in compound B-8' in Scheme 7a.

Scheme 7a

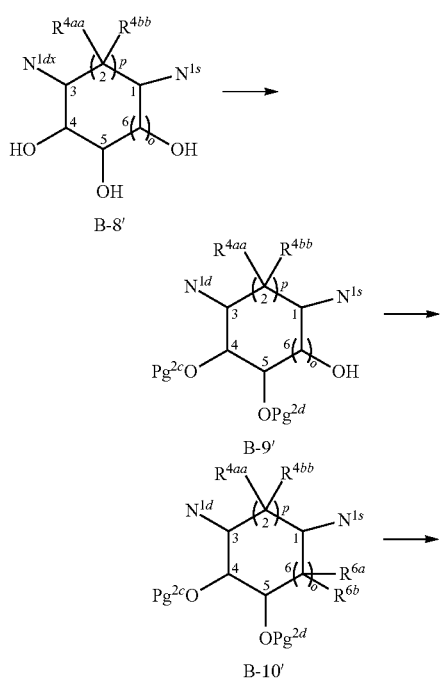

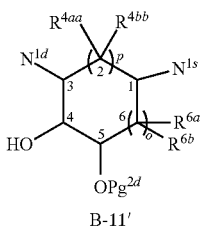

Scheme 7b

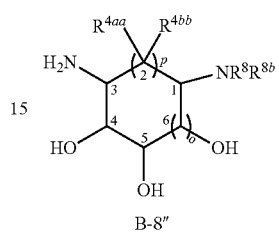

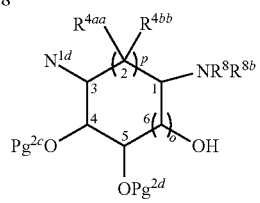

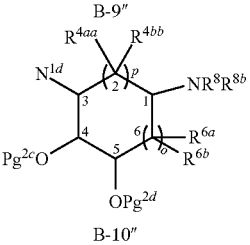

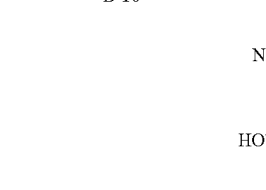

As noted above, the present disclosure provides processes for preparing Ring B. With reference to Schemes 7a and 7b, the present disclosure provides a process for preparing a process for preparing a compound of formula B-11',

B-11' wherein
R$^{4aa}$ and R$^{4bb}$ are, independently H, —OH, —OR$^{40}$, —NR$^{41}$R$^{42}$, or halogen;
wherein each R$^{40}$, R$^{41}$, and R$^{42}$ are independently H, alkyl, —CONH$_2$, or —COCH$_3$; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

R$^{6a}$ and R$^{6b}$ are, independently H, halogen, NH$_2$, —OH, C$_1$-C$_3$alkoxy, —OC(O)CH$_3$, or —OPg$^{2o}$; wherein Pg$^{2o}$ is a hydroxyl protecting group;

N$^{1s}$ is N$_3$ or —NR$^8$R$^{8b}$;

R$^8$ is H, C$_1$-C$_6$ alkyl, an amino protecting group, or

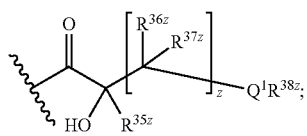

wherein

Q$^1$ is NH, O, or S;

z is an integer from 0 to 4,

R$^{35z}$ is H or C$_1$-C$_3$ alkyl;

each R$^{36z}$ and R$^{37z}$ is independently selected from the group consisting of H, alkyl, halogen, and —OH, and R$^{38z}$ is H, alkyl, or —C(=NH)NR$^{39z}$R$^{40z}$, wherein R$^{39z}$ and R$^{40z}$ are independently H or C$_1$-C$_3$ alkyl; or R$^{35z}$ and R$^{38z}$, together with the atoms to which they are attached, form a heterocycloalkyl group comprising at least one N;

R$^{8b}$ is H or C$_1$-C$_3$alkyl;

N$^{1d}$ is —NHPg$^{1d}$ or N$_3$, wherein Pg$^{1d}$ is an amino protecting group;

Pg$^{2d}$ is a hydroxyl protecting group;

o is zero, 1, or 2;

p is zero, 1, or 2;

wherein o+p is 1, 2 or 3;

or a salt, solvate, enantiomer, or diastereomer thereof, comprising:

(a) contacting a compound of formula B-8':

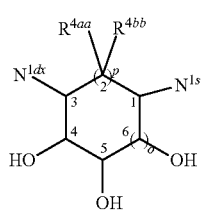

or a salt, solvate, enantiomer, or diastereomer thereof, wherein N$^{1dx}$ is —NH$_2$, —NHPg$^{1d}$ or N$_3$, wherein Pg$^{1d}$ is an amino protecting group, with a first selective hydroxyl protecting group reagent; a second selective hydroxyl protecting group reagent; an amino protecting group reagent, if N$^{1dx}$ is —NH$_2$; and an amino reactive reagent, if N$^{1s}$ is —NR$^8$R$^{8b}$, to yield a compound of formula B-9':

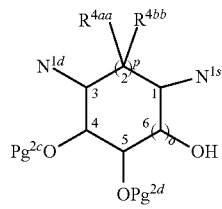

or a salt, solvate, enantiomer, or diastereomer thereof; wherein Pg$^{2c}$ is a hydroxyl protecting group;

(b) contacting the compound of formula B-9' with a electrophilic reagent or oxidizing the alcohol at C6 to an oxo group and contacting the oxo group with a nucleophilic reagent to yield a compound of formula B-10':

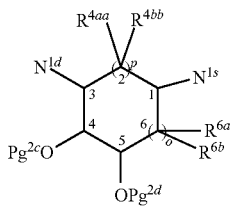

or a salt, solvate, enantiomer, or diastereomer thereof, c) forming a hydroxyl group by selective removal of the Pg$^{2c}$ protecting group of the compound of formula B-10' to yield the compound of formula B-11':

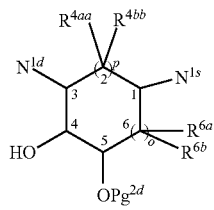

or a salt, solvate, enantiomer, or diastereomer thereof.

Synthesis of Compound B-9

Reference to compounds B-8 to B-11 are meant to encompass compounds B-8' to B-11' and compounds B-8" to B-11". With continued reference to Schemes 7, 7a, and 7b, compound B-8 is contact with an amino protecting group reagent and a first selective hydroxyl protecting group reagent and a second selective hydroxyl protecting group reagent and an amino reactive reagent to yield a compound B-9.

Addition of amino protecting group Pg$^{1d}$ to yield compound B-9 is provided by an amino protecting group reagent. Examples of amino protecting group Pg$^{1d}$ include Bn, CBZ, and tert-butanesulfinamide. Suitable protecting group reagents to provide amino protecting group Pg$^{1d}$ can be found in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski). In certain embodiments, N$^{1d}$ is N$_3$. In certain embodiments, N$^{1dx}$ is N$_3$.

In certain embodiments, N$^{1s}$ is N$_3$. In such instances, the B ring with an azido group at the 1-position can be commercially available or prepared with techniques known in the art. In certain embodiments, $N^{1s}$ is $-NR^8R^{8b}$.

Addition of hydroxyl protecting groups $Pg^{2c}$ and $Pg^{2d}$ to yield compound B-9 is provided by a hydroxyl protecting group reagent. Examples of hydroxyl protecting groups $Pg^{2c}$ and $Pg^{2d}$ include t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl (TBDPS), triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Suitable protecting group reagents to provide hydroxyl protecting groups $Pg^{2c}$ and $Pg^{2d}$ can be found in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski).

The reaction also provides functionalization of $-NH_2$ of B ring with $R^8$ moiety. The amino reactive reagent provides $R^8$ substituent on compound B-9. Thus, the amino reactive reagent corresponds to $R^8$ moiety.

In certain embodiments, $R^8$ is an amino protecting group. Examples of amino protecting groups include, but are not limited to, 2-trimethylsilylethoxycarbonyl (Teoc), 1-methyl-1-(4-biphenylyl)ethoxycarbonyl (Bpoc), t-butoxycarbonyl (Boc), allyloxycarbonyl (Alloc), 9-fluorenylmethyloxycarbonyl (Fmoc), benzyloxycarbonyl (Cbz), p-nitrobenzyloxycarbonyl (PNZ), formyl, acetyl, trihaloacetyl (e.g., trifluoroacetyl), benzoyl, nitrophenylacetyl, 2-nitrobenzenesulfonyl, phthalimido, and dithiasuccinoyl. Suitable protecting group reagents to provide amino protecting group $Pg^{2a}$ can be found in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski).

In certain embodiments, $R^8$ is H. In certain embodiments, $R^8$ is $C_1$-$C_6$alkyl, In certain embodiments, $R^8$ is methyl. In certain embodiments, $R^8$ is ethyl.

In certain embodiments, $R^8$ forms an amide with the imino group. Carboxylic acids corresponding to the $R^8$ moiety can react with imino group on C1 of the B ring to provide the $R^8$ substituent. In certain instances, a catalyst or activating agent can assist with amide formation reaction.

In certain embodiments, $R^8$ is

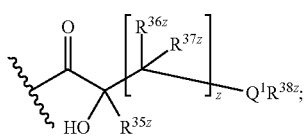

wherein $Q^1$ is NH, O, or S. In certain embodiments, $Q^1$ is NH. In certain embodiments, $Q^1$ is O. In certain embodiments, $Q^1$ is S. In certain embodiments, wherein when z is one, then $R^{36z}$ and $R^{37z}$ are not halo.

In certain embodiments, $R^8$ is

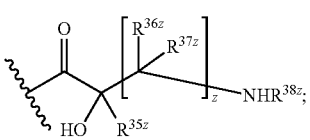

wherein z is an integer from 0 to 4, $R^{35z}$ is H or $C_1$-$C_3$alkyl;

each $R^{36z}$ and $R^{37z}$ is independently selected from the group consisting of H, alkyl, halogen, and —OH, and $R^{38z}$ is H, alkyl, or $-C(=NH)NR^{39z}R^{40z}$, wherein $R^{39z}$ and $R^{40z}$ are independently H or $C_1$-$C_3$alkyl; or $R^{35z}$ and $R^{38z}$, together with the atoms to which they are attached, form a heterocycloalkyl group comprising at least one N.

In other embodiments, $R^8$ is

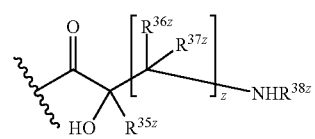

for example

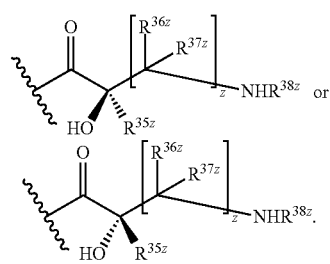

In some embodiments, $R^{35z}$ is H. In certain embodiments, each $R^{36z}$ and $R^{37z}$ are H. In certain embodiments, $R^{38z}$ is H. In other embodiments, $R^{38z}$ is alkyl, for example $C_1$alkyl, $C_2$alkyl, or $C_3$alkyl. In other embodiments, $R^{38z}$ is $-C(=NH)NR^{39z}R^{40}$, for example $-C(=NH)NH_2$. In certain embodiments, $R^{35z}$ and $R^{38z}$, together with the atoms to which they are attached, form a heterocycloalkyl group comprising at least one N.

In some embodiments, z is an integer from 0 to 4, from 0 to 3, from 0 to 2, from 1 to 4, from 2 to 4, or from 1 to 3. In certain embodiments, z is 0, or z is 1, or z is 2, or z is 3, or z is 4.

In some embodiments, $R^8$ is:

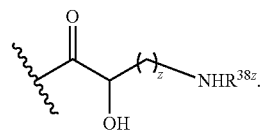

For example, $R^8$ may be:

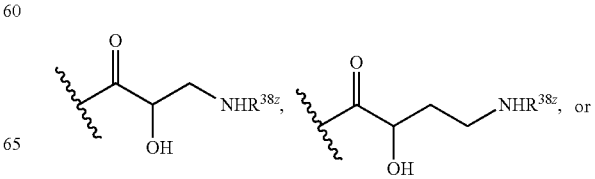

-continued

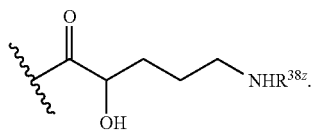

In some embodiments, $R^{38z}$ is H. For example, $R^8$ may be:

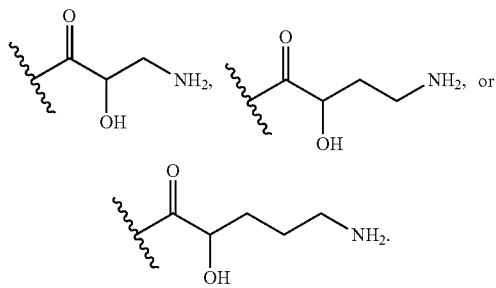

In some embodiments, $R^8$ may be:

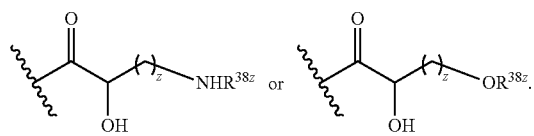

In some embodiments, $R^8$ may be:

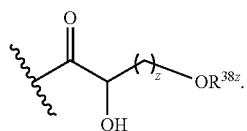

In certain embodiments, $R^8$ is:

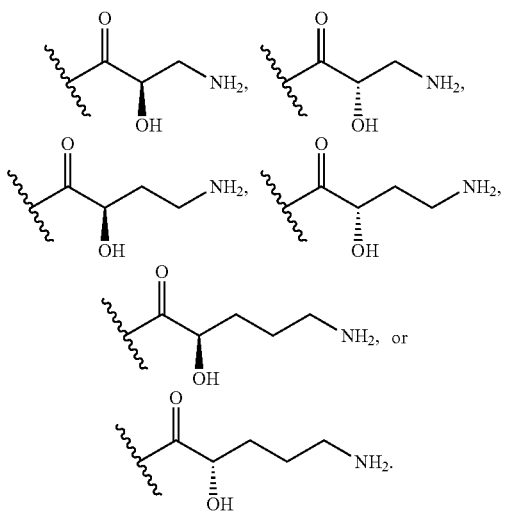

In certain embodiments, $R^8$ is:

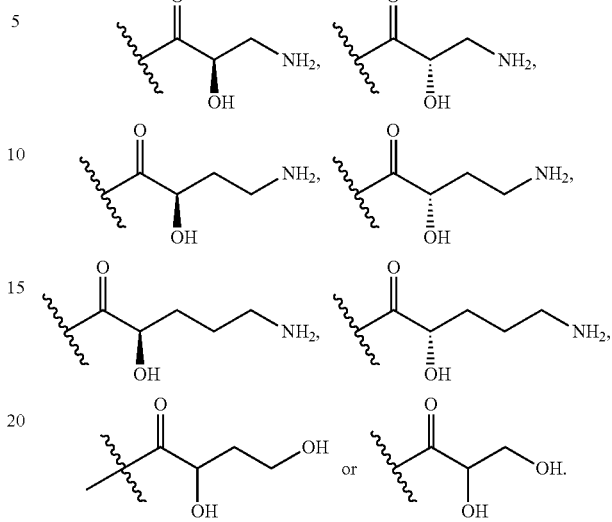

In certain embodiments, $R^8$ is.

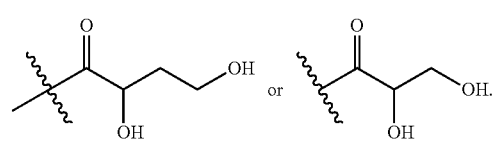 [SMILES: *C(=O)C(O)CCO ; *C(=O)C(O)CO]

In other embodiments, at least one $R^{36z}$ or $R^{37z}$ is halogen. For example, in certain embodiments, $R^8$ is:

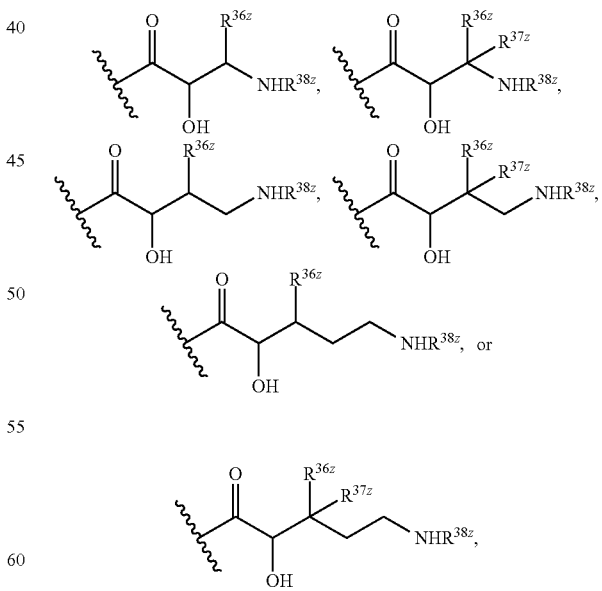

wherein each $R^{36z}$ and $R^{37z}$ is independently halogen, for example fluoro.

In certain embodiments, at least one $R^{36z}$ or $R^{37z}$ is halogen, and $R^{38z}$ is H. For example, $R^8$ may be:

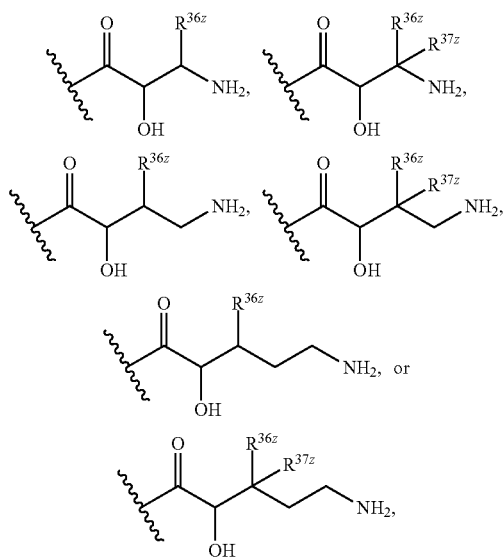

wherein each $R^{36z}$ and $R^{37z}$ are independently halogen, for example fluoro.

In other embodiments, at least one $R^{36z}$ or $R^{37z}$ is halogen. For example, in certain embodiments, $R^8$ is:

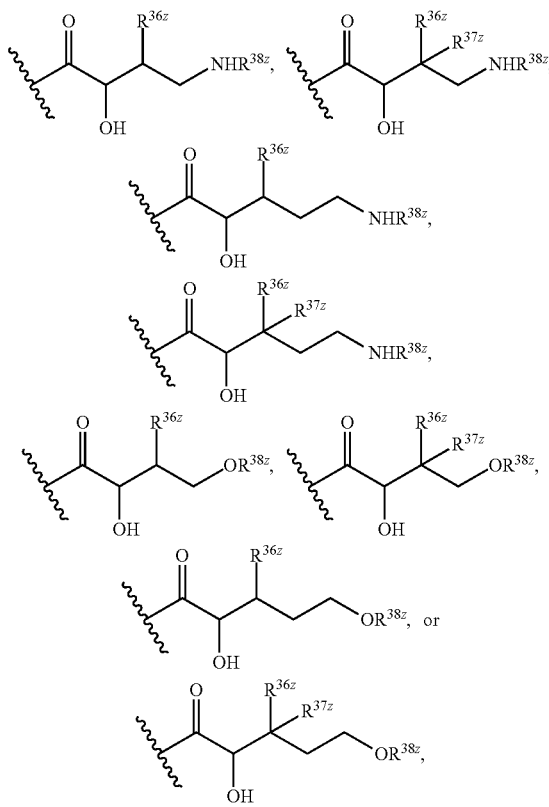

wherein each $R^{36z}$ and $R^{37z}$ is independently halogen, for example fluoro.

In certain embodiments, at least one $R^{36z}$ or $R^{37z}$ is halogen, and $R^{38z}$ is H. For example, $R^8$ may be:

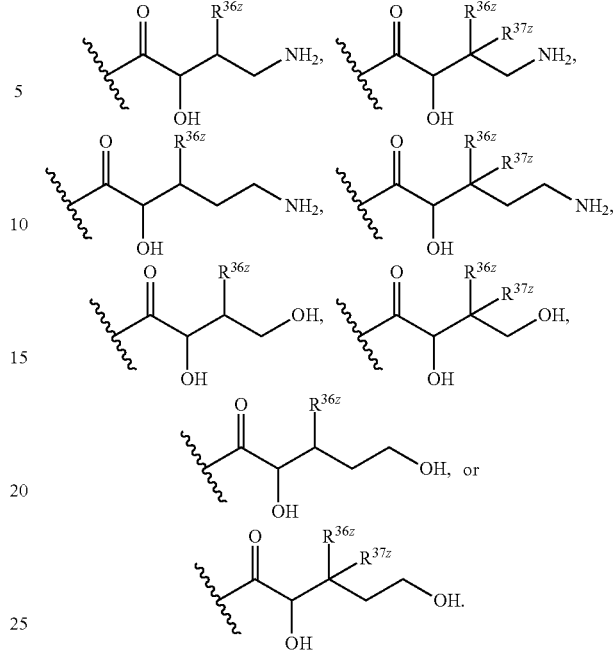

wherein each $R^{36z}$ and $R^{37z}$ are independently halogen, for example fluoro.

In other embodiments, $R^8$ is

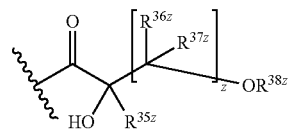

wherein at least one $R^{36z}$ or $R^{37z}$ is hydroxyl.

In other embodiments, $R^8$ is

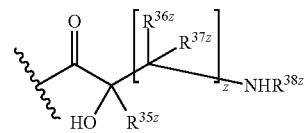

wherein at least one $R^{36z}$ or $R^{37z}$ is hydroxyl.

In some embodiments, $R^{38z}$ is —C(=NH)NR$^{39z}$R$^{40z}$, and $R^8$ is:

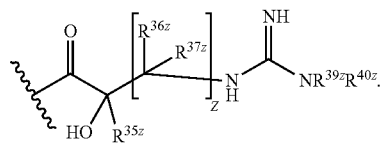

In some embodiments, $R^{39z}$ and $R^{40z}$ are both H. In other embodiments, $R^{39z}$ and $R^{40z}$ are both $C_1$-$C_3$alkyl. In still other embodiments, one of $R^{39z}$ and $R^{40z}$ is H and the other is $C_1$-$C_3$alkyl.

$R^{38z}$ may be —C(=NH)NH$_2$. Thus, in certain embodiments, $R^8$ is:

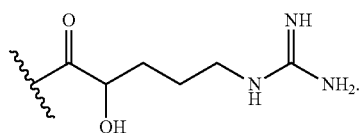 [SMILES: *C(=O)C(O)CCCNC(=N)N]

In certain embodiments, $R^{36z}$ and one $R^{37z}$, together with the atoms to which they are attached, form a carbocyclic ring having from 3 to 6 ring atoms.

In certain embodiments, $R^{8b}$ is H. In certain embodiments, $R^{8b}$ is $C_1$-$C_3$alkyl.

Synthesis of Compound B-10

With continued reference to Schemes 7, 7a, and 7b, compound B-9 is contacted with an electrophilic reagent to yield compound B-10. The reaction provides functionalization of C6 of B ring with $R^{6a}$ and/or $R^{6b}$ moieties, as shown below.

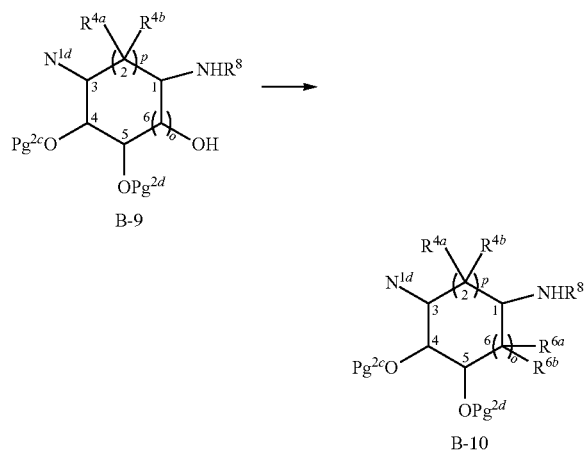

In certain embodiments, the hydroxyl group is nucleophilic and can react with an electrophilic reagent. For example, an electrophilic reagent that can provide an optionally substituted alkoxy for $R^{6a}$ can be the corresponding optionally substituted alkyl bearing a halide group. In this instance, the substituted alkyl attaches with the oxygen of the hydroxyl, while the halide serves as a leaving group for the nucleophilic reaction.

In certain embodiments, the alcohol at C6 of compound B-9 is oxidized to an oxo group and then the oxo group is contacted with a nucleophilic reagent.

In certain embodiments, $R^{6b}$ is hydrogen. In certain embodiments, $R^{6a}$ is an optionally substituted alkoxy. For example, in certain embodiments, $R^{6a}$ is —$OCH_3$, —$OCH_2CH_3$, or —$OCH_2CH_2NRR'$, wherein R and R' are independently alkyl.

Synthesis of Compound B-11

With continued reference to Schemes 7, 7a, and 7b, a selective removal of the $Pg^{2e}$ protecting group of compound B-10 to yield compound B-11, which has a hydroxyl group resulting from the selective removal of the $Pg^{2e}$ protecting group. Selective removal of $Pg^{2e}$ protecting group can be performed by hydrolysis. For example, selective removal of $Pg^{2e}$ protecting group can be performed by hydrolysis under conditions such as base (for example, NaOH, KOH, $Et_3N$) or acid mediated (for example, HCl, TfOH, p-TSA) in aqueous media optionally including organic solvents (for example, MeOH, $Et_2O$, DMF) at temperatures between 0° C. and the reflux point of the solvent.

Additional Embodiments of Ring B

In certain embodiments, Ring B at the 1-position can be —$N_3$. In such instances, the B ring with an azido group at the 1-position can be commercially available or prepared with techniques known in the art. For example, compounds B-6 and B-11 herein are shown below as B-6″ and B-11″, wherein $N^{1s}$ is $N_3$ or —$NR^{8a}R^{8b}$.

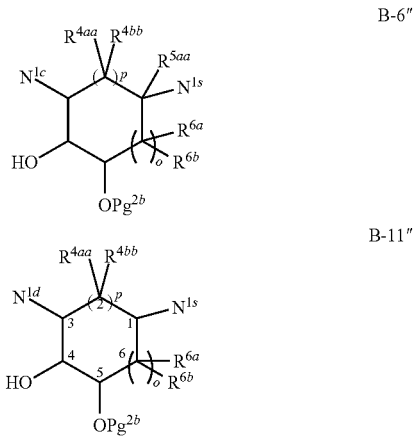

In certain embodiments, Ring B is protected at the 1 and 3 positions as a heterocyclic ring. In such instances, the B ring with 1 and 3 positions protected as a heterocyclic ring can be commercially available or prepared with techniques known in the art. For example, compounds B-6 and B-11 herein are shown below as B-6′ᵉ and B-11′ᵉ, wherein E is a 4-8 membered heterocyclic ring, that is unsubstituted or substituted with an oxo group.

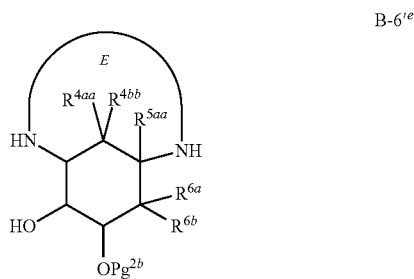

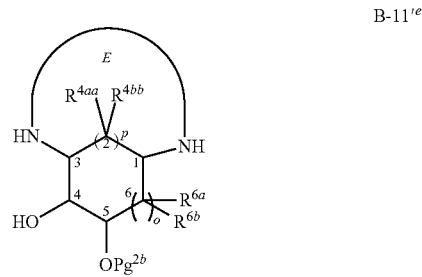

For example, a B ring from B-6'ᵉ and B-11'ᵉ can be

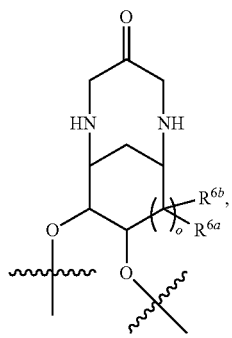

wherein ⁓ indicates a point of attachment to a hydrogen or a moiety.

In certain embodiments, Ring B is protected at the 1 and 6 positions as a heterocyclic ring. In such instances, the B ring with 1 and 6 positions protected as a heterocyclic ring can be commercially available or prepared with techniques known in the art. For example, compounds B-6 and B-11 herein are shown below as B-6¹ᶠ and B-11¹ᶠ, wherein F is a 4-8 membered heterocyclic ring, that is unsubstituted or substituted with an oxo group.

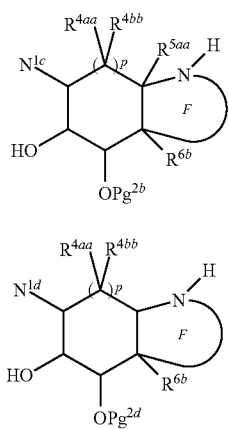

For example, a B ring from B-6¹ᶠ and B-11¹ᶠ can be

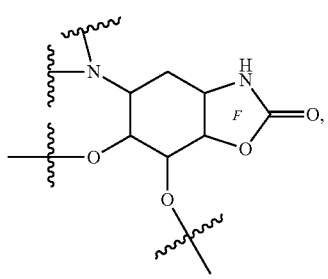

wherein ⁓ indicates a point of attachment to a hydrogen or a moiety. In such instances, the F ring can be opened up and reacted to form the moieties at the 1 and 6 positions in the B ring.

Embodiments of Ring B

In certain embodiments, the stereochemistry in the ring of formulae B-1, B-2, B-3, B-4, B-5, B-6, B-8, B-9, B-10, and B-11, is as indicated in formula (B'), wherein ⁓ indicates a point of attachment to a hydrogen or a moiety:

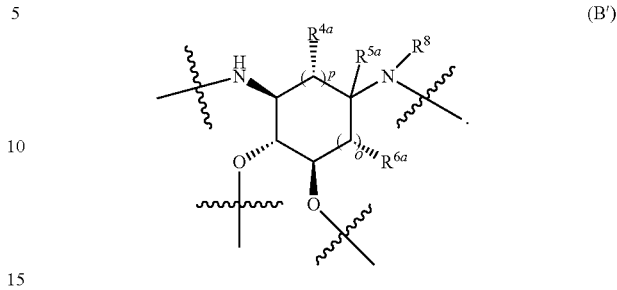

In certain embodiments, the stereochemistry in the ring of formulae B-1', B-2', B-3', B-4', B-5', B-6', B-8', B-9', B-10', and B-11', is as indicated in formula (B''), wherein ⁓ indicates a point of attachment to a hydrogen or a moiety:

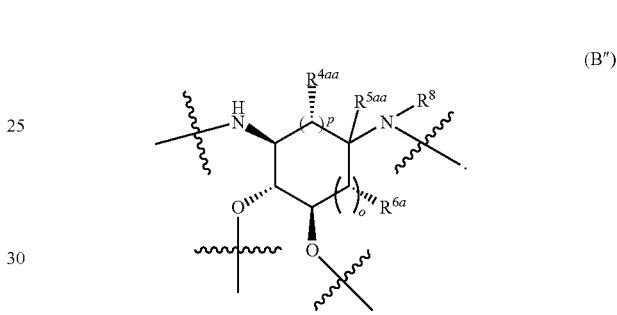

In certain embodiments, o is one. In certain embodiments, p is one. In certain embodiments, o is one and p is one.

Preparation of AB

The present disclosure includes processes, methods, reagents, and intermediates for the synthesis of Compound AB, as shown in Scheme 1.

In Ring A, LVG¹ is a leaving group suitable of reacting with a reactant or a glycosyl acceptor, to form an interglycosidic linkage. In Ring B, the hydroxyl group at C5 is group suitable of reacting with a reactant or a glycosyl donor, to form an interglycosidic linkage.

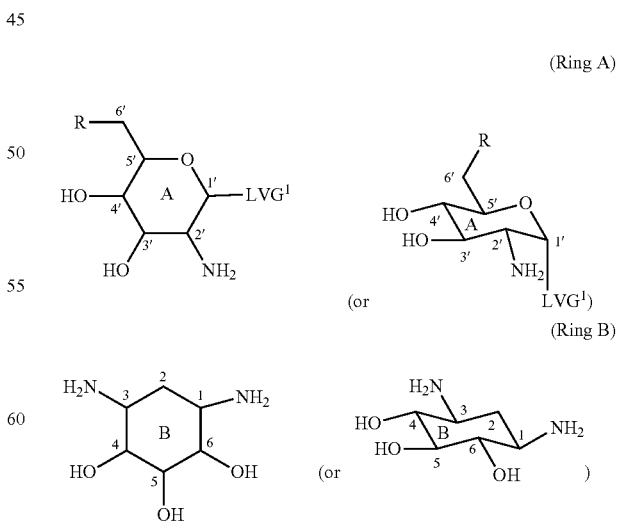

The structures shown above for Rings A and B are representative and are based on a generic structure, such that the substituents are shown above for convenience. That is, the substituents shown above for Rings A and B are not limited to the certain substituents and suitable substituents for Rings A and B are described herein.

A process for the preparation of compound AB-1 is illustrated in Schemes 8, 8a, and 8b below and is discussed in greater detail herein.

Scheme 8

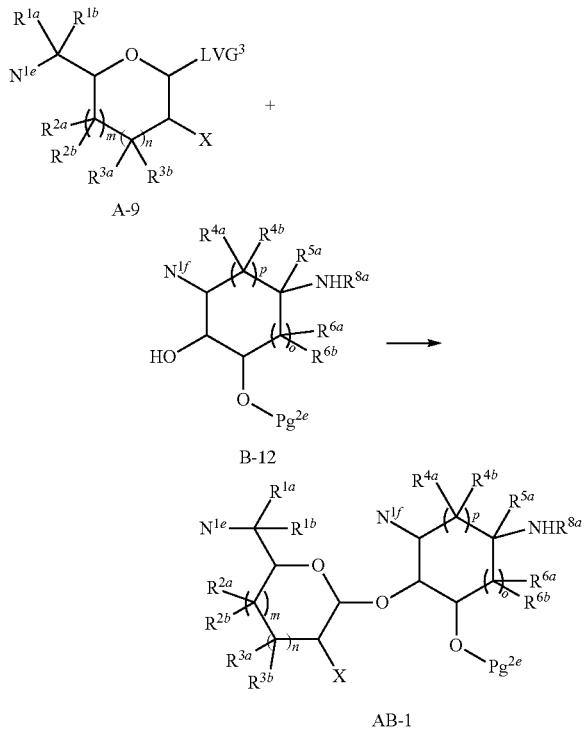

With reference to Scheme 8, the present disclosure provides a process for preparing a process for preparing a compound of formula AB-1,

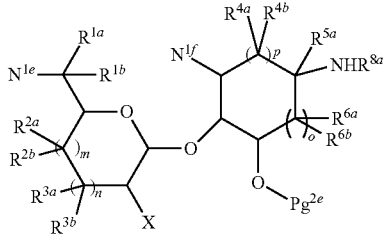

AB-1 wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl; $R^{3a}$ and $R^{3b}$ form an oxo or imino group substituted with $C_1$-$C_6$ alkyl; $R^{4a}$ and $R^{4b}$ are, independently, H, —OH, —$OR^{40}$, —$NR^{41}R^{42}$, or halogen;

wherein each $R^{40}$, $R^{41}$, and $R^{42}$ are independently H or alkyl;

wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5a}$ is H, —CN, —$CONH_2$ or $C_1$-$C_3$alkyl, wherein the alkyl is unsubstituted or substituted with one or more substituents selected from the group consisting of —OH, —$NH_2$, —CN, —$CONH_2$, and halogen;

$R^{6a}$ and $R^{6b}$ are, independently H, halogen, $NH_2$, —OH, $C_1$-$C_3$alkoxy, —$OC(O)CH_3$, or —$OPg^{2m}$; wherein $Pg^{2m}$ is a hydroxyl protecting group;

$R^{8a}$ is H, $C_1$-$C_6$ alkyl, an amino protecting group, or

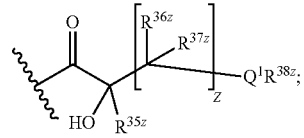

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$N^{1e}$ is —$NHPg^{1e}$ or $N_3$, wherein $Pg^{1e}$ is an amino protecting group;

$N^{1f}$ is —$NHPg^{1f}$ or $N_3$, wherein $Pg^{1f}$ is an amino protecting group;

$Pg^{2e}$ is a hydroxyl protecting group;

X is —$NH_2$, —$N_3$, protected amino group, —OH, or protected hydroxyl group;

m is zero, 1, or 2;
n is zero, 1, or 2;
wherein m+n is 1, 2 or 3;
o is zero, 1, or 2;
p is zero, 1, or 2;
wherein o+p is 1, 2 or 3;
q is zero, 1, or 2;
r is zero, 1, or 2;
wherein q+r is 1, 2 or 3;
or a salt, solvate, enantiomer, or diastereomer thereof, comprising:

(a) contacting a compound of formula A-9:

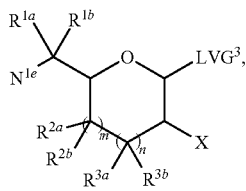

wherein LVG$^3$ is a leaving group,
with a compound of formula B-12:

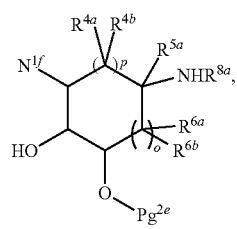

to yield the compound of formula (AB-1).

A process for the preparation of compound AB-1' is illustrated in Schemes 8a and 8b below and is discussed in greater detail herein. Scheme 8b is Scheme 8a, wherein N$^{1s}$ is —NR$^{8a}$R$^{8b}$.

Scheme 8a

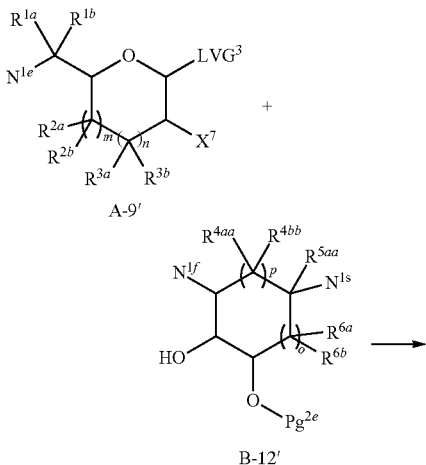

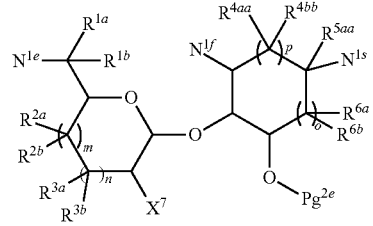

Scheme 8b

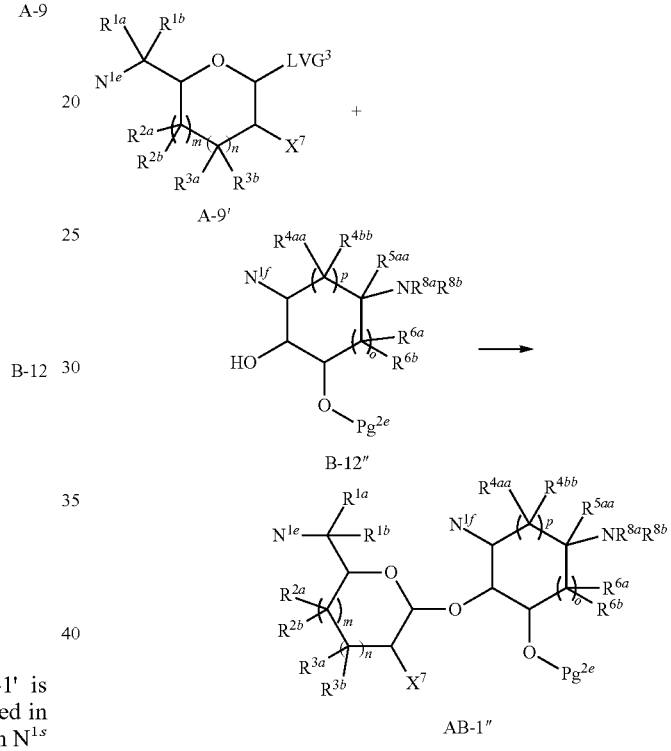

With reference to Scheme 8a, the present disclosure provides a process for preparing a process for preparing a compound of formula AB-1',

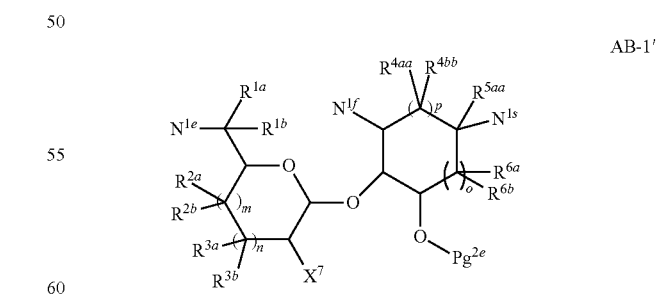

wherein
R$^{1a}$ and R$^{1b}$ are independently selected from the group consisting of H, C$_1$-C$_{12}$ alkyl, C$_1$-C$_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —N$_3$, and —OR$^{16}$, and wherein each R$^{12}$, R$^{13}$, R$^{14}$, R$^{15}$, and R$^{16}$ is independently H or alkyl; or R$^{1a}$ and R$^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each R$^{22}$, R$^{23}$, R$^{24}$, R$^{25}$, and R$^{26}$ is independently H or alkyl, wherein the alkyl is unsubstituted or substituted with one or more substituents independently selected from the group consisting of halogen, cyano, NR$^{14}$R$^{15}$, and —OR$^{16}$;

R$^{2a}$, R$^{2b}$, R$^{3a}$ and R$^{3b}$ are independently selected from the group consisting of H, —OR$^{27}$, —NR$^{28}$R$^{29}$, halogen, C$_1$-C$_4$ cycloalkyl, and C$_1$-C$_6$ alkyl, wherein each R$^{27}$, R$^{28}$, and R$^{29}$ is independently H, alkyl, amino protecting group, or hydroxyl protecting group; wherein the C$_1$-C$_6$ alkyl or alkyl is unsubstituted or substituted with one or more substituents selected from the group consisting of aryl, halogen, —OR$^{30}$, —NR$^{31}$R$^{32}$, —SR$^{33}$, and —SO$_2$R$^{34}$;

wherein each R$^{30}$, R$^{31}$, R$^{32}$, R$^{33}$, and R$^{34}$ is independently H or alkyl substituted with one or more substituents independently selected from the group consisting of halogen, cyano, NR$^{14}$R$^{15}$, and —OR$^{16}$; or R$^{2a}$ and R$^{2b}$ form an oxo or imino group substituted with C$_1$-C$_6$ alkyl;

R$^{3a}$ and R$^{3b}$ form an oxo or imino group substituted with C$_1$-C$_6$ alkyl;

R$^{4aa}$ and R$^{4bb}$ are, independently H, —OH, —OR$^{40}$, —NR$^{41}$R$^{42}$, or halogen;

wherein each R$^{40}$, R$^{41}$, and R$^{42}$ are independently H, alkyl, —CONH$_2$, or —COCH$_3$; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

R$^{5aa}$ is H, —CN, —CONH$_2$ or C$_1$-C$_3$alkyl, wherein the alkyl is unsubstituted or substituted with one or more substituents selected from the group consisting of —OH, —OC(O)CH$_3$, —NH$_2$, —CN, —CONH$_2$, and halogen;

R$^{6a}$ and R$^{6b}$ are, independently H, halogen, NH$_2$, —OH, C$_1$-C$_3$alkoxy, —OC(O)CH$_3$, or —OPg$^{2m}$; wherein Pg$^{2m}$ is a hydroxyl protecting group;

N$^{1s}$ is N$_3$ or —NR$^{8a}$R$^{8b}$;

R$^{8a}$ is H, C$_1$-C$_6$ alkyl, an amino protecting group, or

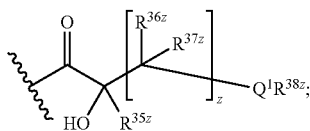

wherein

Q$^1$ is NH, O, or S;

z is an integer from 0 to 4,

R$^{38z}$ is H or C$_1$-C$_3$ alkyl;

each R$^{36z}$ and R$^{37z}$ is independently selected from the group consisting of H, alkyl, halogen, and —OH, and R$^{38z}$ is H, alkyl, or —C(=NH)NR$^{39z}$R$^{40z}$, wherein R$^{39z}$ and R$^{40z}$ are independently H or C$_1$-C$_3$ alkyl; or R$^{35z}$ and R$^{38z}$, together with the atoms to which they are attached, form a heterocycloalkyl group comprising at least one N;

R$^{8b}$ is H or C$_1$-C$_3$alkyl;

N$^{1e}$ is —OH, protected hydroxyl group, —NHPg$^{1e}$, N(Pg$^{1e}$)$_2$, or N$_3$, wherein each Pg$^{1e}$ is independently an amino protecting group;

N$^{1f}$ is —NHPg$^{1f}$ or N$_3$, wherein Pg$^{1f}$ is an amino protecting group;

Pg$^{2e}$ is a hydroxyl protecting group;

X$^7$ is H, —NH$_2$, —N$_3$, protected amino group, —OH, protected hydroxyl group, or halogen;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3;

or a salt, solvate, enantiomer, or diastereomer thereof, comprising:

(a) contacting a compound of formula A-9':

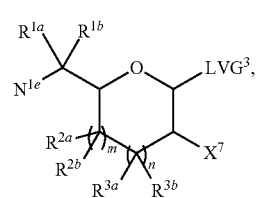

wherein LVG$^3$ is a leaving group, with a compound of formula B-12':

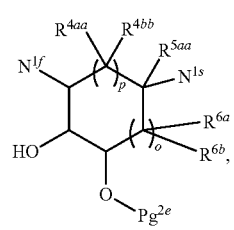

to yield the compound of formula (AB-1').

Synthesis of Compound AB-1

With reference to Scheme 8, compound A-9 is contacted with compound B-12 to yield compound AB-1. In certain embodiments, compound A-9 is compound A-5. In certain embodiments, compound A-9 is compound A-5a. In certain embodiments, compound B-12 is compound B-6. In certain embodiments, compound B-12 is compound B-11.

With reference to Scheme 8a, compound A-9' is contacted with compound B-12' to yield compound AB-1'. Scheme 8b is Scheme 8a, wherein N$^{1s}$ is —NR$^{8a}$R$^{8b}$. Reference to compounds A-9, B-12, and AB-1 herein are meant to encompass compounds A-9', A-9'', B-12', B-12'', AB-1', and AB-1''

The reaction is performed under to conditions to allow for chemical glycosylation with coupling of a glycosyl donor and a glycosyl acceptor. In Scheme 8, a glycosyl donor (LVG$^3$ on compound A-9) and a glycosyl acceptor (—OH on compound B-12) are coupled. In certain embodiments, LVG³ is selected from the group consisting of OH, halides, thioalkyl groups, thioaryl groups, imidates, acetate, phosphate, and O-pentenyl groups. In certain embodiments, LVG³ is halo, OMs, OTs, OH, a thioalkyl, a thioaryl, an imidate, an acetate, a phosphate, or an O-pentenyl group.

In certain embodiments, a suitable activating reagent is provided to assist the chemical glycosylation reaction. In certain embodiments, $BF_3$ is used as an activating agent. In certain embodiments, standard glycosyl formation conditions include use of an activating agent, such as $BF_3 \cdot Et_2O$ or $AlMe_3$ in solvents such as MeOH or THF at temperatures between 0° C. and room temperature.

In certain embodiments, $R^{8a}$ is an amino protecting group. Examples of amino protecting groups include, but are not limited to, 2-trimethylsilylethoxycarbonyl (Teoc), 1-methyl-1-(4-biphenylyl)ethoxycarbonyl (Bpoc), t-butoxycarbonyl (Boc), allyloxycarbonyl (Alloc), 9-fluorenylmethyloxycarbonyl (Fmoc), benzyloxycarbonyl (Cbz), p-nitrobenzyloxycarbonyl (PNZ), formyl, acetyl, trihaloacetyl (e.g., trifluoroacetyl), benzoyl, nitrophenylacetyl, 2-nitrobenzenesulfonyl, phthalimido, and dithiasuccinoyl. Suitable protecting group reagents to provide amino protecting group $Pg^{2a}$ can be found in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski).

In certain embodiments, $R^{8a}$ is H. In certain embodiments, $R^{8a}$ is $C_1$-$C_6$alkyl, In certain embodiments, $R^{8a}$ is methyl. In certain embodiments, $R^{8a}$ is ethyl.

In certain embodiments, $R^{8a}$ forms an amide with the imino group. Carboxylic acids corresponding to the $R^{8a}$ moiety can react with imino group on C1 of the B ring to provide the $R^{8a}$ substituent. In certain instances, a catalyst or activating agent can assist with amide formation reaction.

In certain embodiments, $R^{8a}$ is

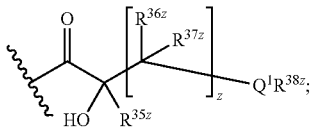

wherein $Q^1$ is NH, O, or S. In certain embodiments, $Q^1$ is NH. In certain embodiments, $Q^1$ is O. In certain embodiments, $Q^1$ is S. In certain embodiments, wherein when z is one, then $R^{36z}$ and $R^{37z}$ are not halo.

In certain embodiments, $R^{8a}$ is

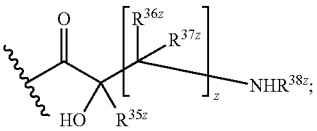

wherein z is an integer from 0 to 4,
$R^{35z}$ is H or $C_1$-$C_3$alkyl;
each $R^{36z}$ and $R^{37z}$ is independently selected from the group consisting of H, alkyl, halogen, and —OH, and
$R^{38z}$ is H, alkyl, or —C(=NH)NR$^{39z}$R$^{40z}$, wherein $R^{39z}$ and $R^{40z}$ are independently H or $C_1$-$C_3$alkyl; or
$R^{35z}$ and $R^{38z}$, together with the atoms to which they are attached, form a heterocycloalkyl group comprising at least one N.

In other embodiments, $R^{8a}$ is

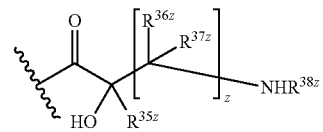

for example

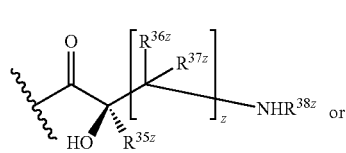

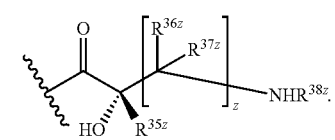

In some embodiments, $R^{35z}$ is H. In certain embodiments, each $R^{36z}$ and $R^{37z}$ are H. In certain embodiments, $R^{38z}$ is H. In other embodiments, $R^{38z}$ is alkyl, for example $C_1$alkyl, $C_2$alkyl, or $C_3$alkyl. In other embodiments, $R^{38z}$ is —C(=NH)NR$^{39}$R$^{40}$, for example —C(=NH)NH$_2$. In certain embodiments, $R^{35z}$ and $R^{38z}$, together with the atoms to which they are attached, form a heterocycloalkyl group comprising at least one N.

In some embodiments, z is an integer from 0 to 4, from 0 to 3, from 0 to 2, from 1 to 4, from 2 to 4, or from 1 to 3. In certain embodiments, z is 0, or z is 1, or z is 2, or z is 3, or z is 4.

In some embodiments, $R^{8a}$ is:

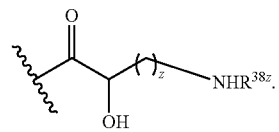

For example, $R^{8a}$ may be:

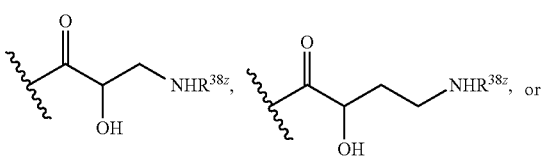

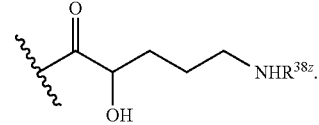

In some embodiments, $R^{38z}$ is H. For example, $R^8$ may be:

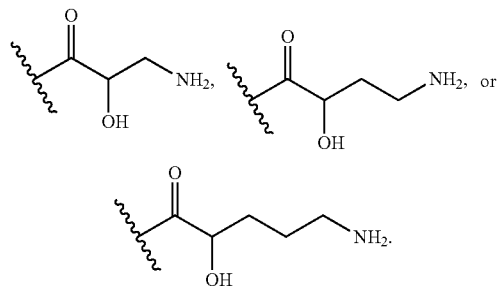

In some embodiments, $R^{8a}$ may be:

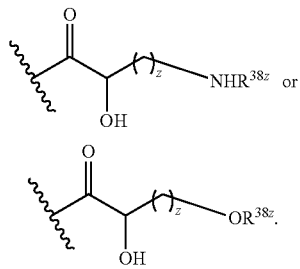

In some embodiments, $R^{8a}$ may be:

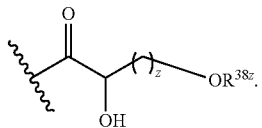

In certain embodiments, $R^{8a}$ is:

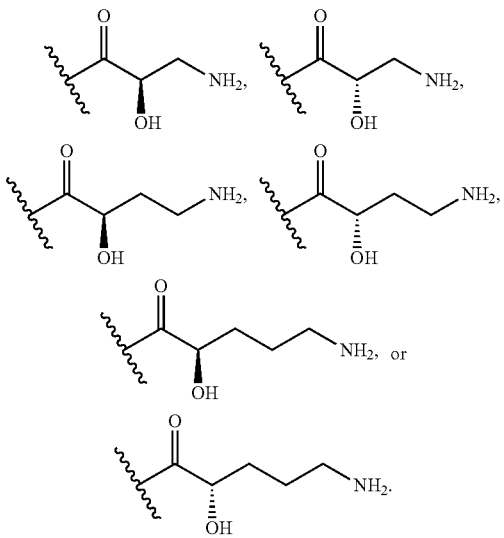

In certain embodiments, $R^{8a}$ is:

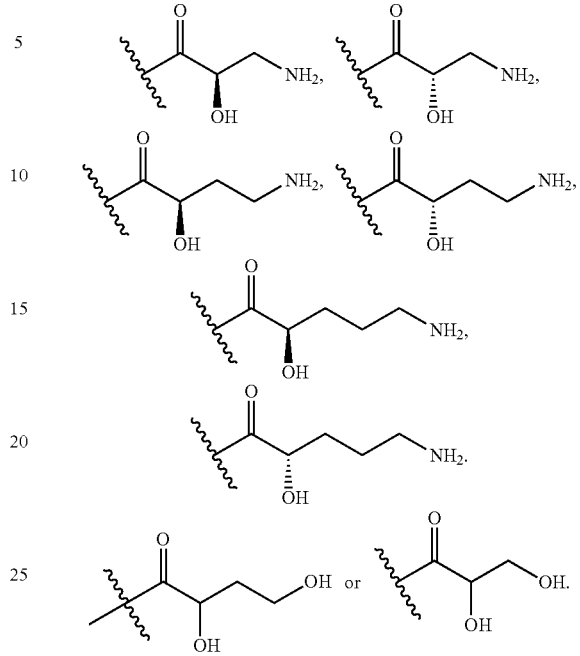

In certain embodiments, $R^{8a}$ is:

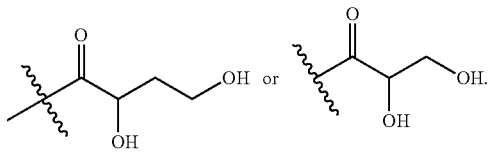 [SMILES: *C(=O)C(O)CCO ; *C(=O)C(O)CO]

In other embodiments, at least one $R^{36z}$ or $R^{37z}$ is halogen. For example, in certain embodiments, $R^{8a}$ is:

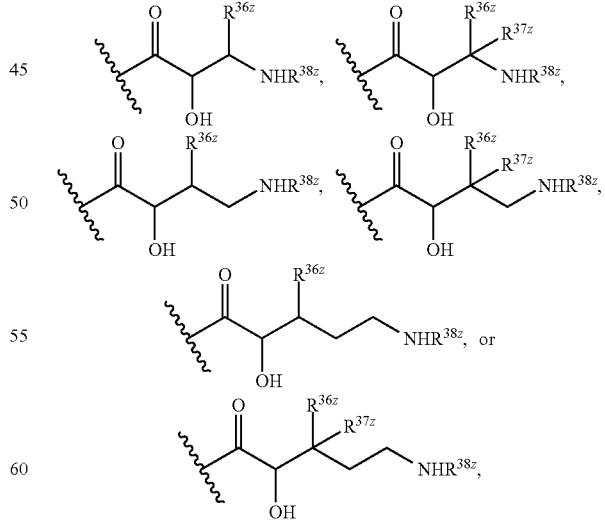

wherein each $R^{36z}$ and $R^{37z}$ is independently halogen, for example fluoro.

In certain embodiments, at least one $R^{36z}$ or $R^{37z}$ is halogen, and $R^{38z}$ is H. For example, $R^{8a}$ may be:

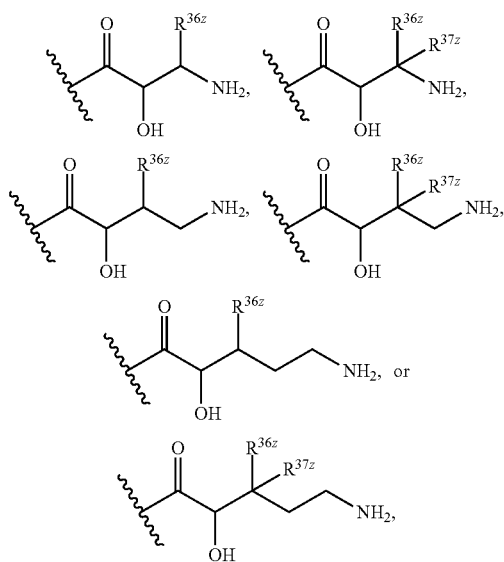

wherein each $R^{36z}$ and $R^{37z}$ are independently halogen, for example fluoro.

In other embodiments, at least one $R^{36z}$ or $R^{37z}$ is halogen. For example, in certain embodiments, $R^{8a}$ is:

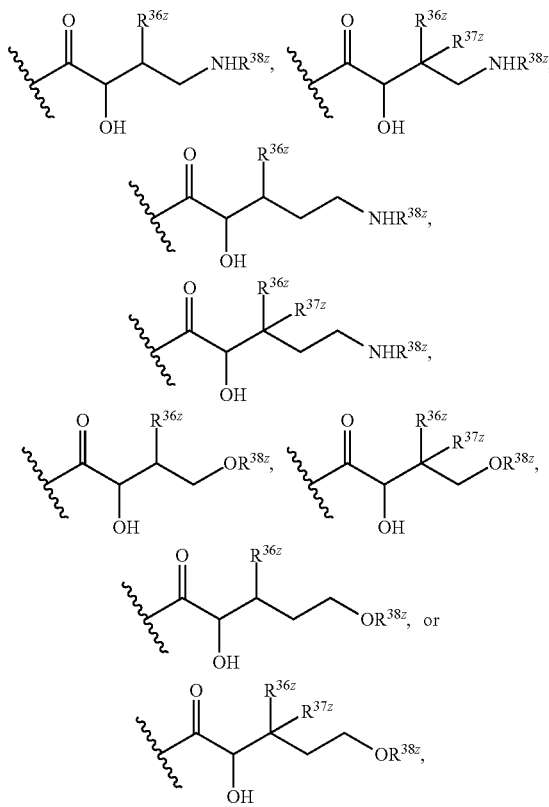

wherein each $R^{36z}$ and $R^{37z}$ is independently halogen, for example fluoro.

In certain embodiments, at least one $R^{36z}$ or $R^{37z}$ is halogen, and $R^{38z}$ is H. For example, $R^8$ may be:

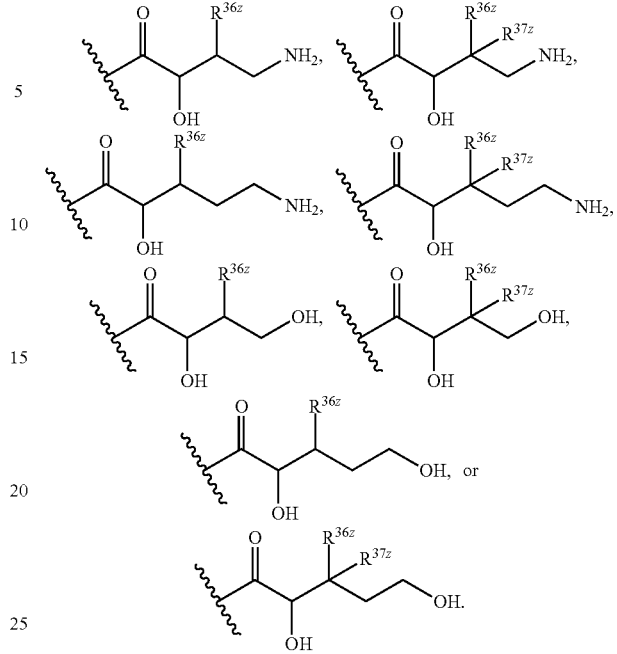

wherein each $R^{36z}$ and $R^{37z}$ are independently halogen, for example fluoro.

In other embodiments, $R^{8a}$ is

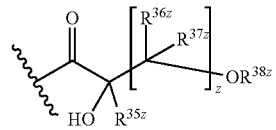

wherein at least one $R^{36z}$ or $R^{37z}$ is hydroxyl.

In other embodiments, $R^{8a}$ is

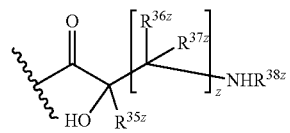

wherein at least one $R^{36z}$ or $R^{37z}$ is hydroxyl.

In some embodiments, $R^{38z}$ is —C(=NH)NR$^{39z}$R$^{40z}$, and $R^8$ is:

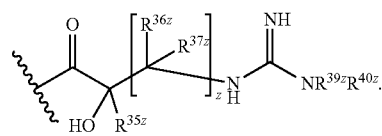

In some embodiments, $R^{39z}$ and $R^{40z}$ are both H. In other embodiments, $R^{39Z}$ and $R^{40z}$ are both $C_1$-$C_3$alkyl. In still other embodiments, one of $R^{39z}$ and $R^{40z}$ is H and the other is $C_1$-$C_3$alkyl.

$R^{38z}$ may be —C(=NH)NH$_2$. Thus, in certain embodiments, $R^{8a}$ is:

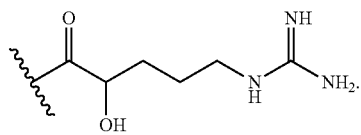 [SMILES: *C(=O)C(O)CCCNC(=N)N]

In certain embodiments, $R^{36z}$ and one $R^{37z}$, together with the atoms to which they are attached, form a carbocyclic ring having from 3 to 6 ring atoms.

In certain embodiments, $R^{8b}$ is H. In certain embodiments, $R^{8b}$ is $C_1$-$C_3$alkyl.

Synthesis of Compound AB-2

In some embodiments, the protecting groups of compound AB-1 are removed to yield compound AB-2, as described in Scheme 9. In some embodiments, the protecting groups of compound AB-1' are removed to yield compound AB-2', as described in Scheme 9a. Scheme 9b is Scheme 9a, wherein $N^{1s}$ is —$NR^{8a}R^{8b}$.

Scheme 9

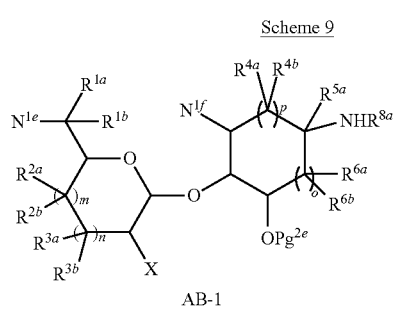

AB-1

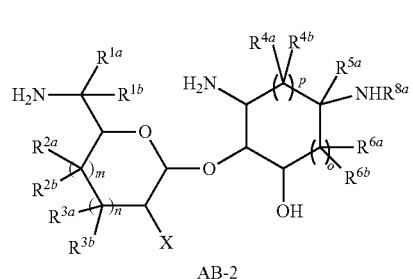

AB-2

Scheme 9a

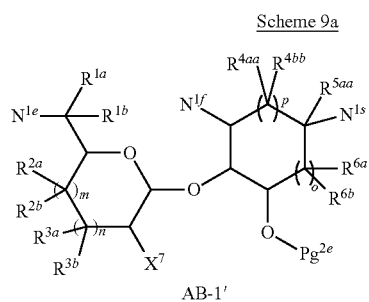

AB-1'

-continued

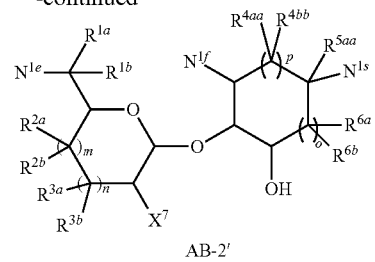

AB-2'

Scheme 9b

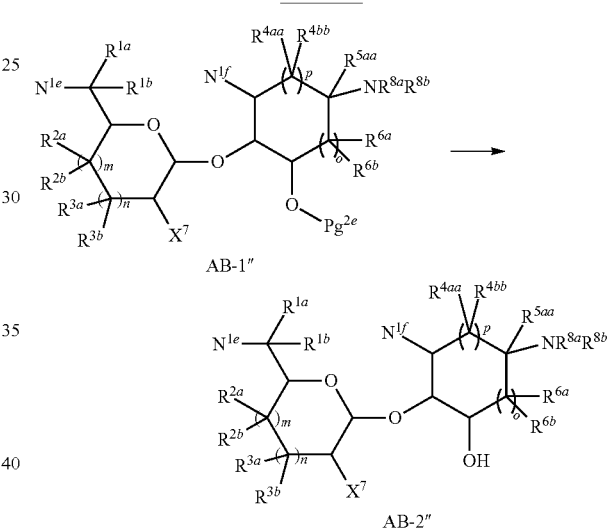

AB-1″

AB-2″

With reference to Schemes 9, 9a, and 9b, the process further comprises after step (a):

(b) if amino protecting groups and hydroxyl protecting groups are present, remove the amino protecting groups and hydroxyl protecting groups to yield a compound of formula AB-2, or a salt, solvate, enantiomer, or diastereomer thereof.

Reference to compounds AB-1 and AB-2 herein are meant to encompass compounds AB-1', AB-1″, AB-2' and AB-2″. In certain embodiments, the process comprises removing the amino protecting groups $Pg^{1e}$ and $Pg^{1f}$ or converting $N_3$ to $NH_2$ and removing the hydroxyl protecting group $Pg^{2c}$ to yield a compound of formula AB-2, or a salt, solvate, enantiomer, or diastereomer thereof.

Conditions for removing protecting group can be found in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski). In certain embodiments, hydrolysis or hydrogenation can be used to remove the protecting groups.

Embodiments of Compound AB

In certain embodiments, the stereochemistry of compound AB-1, AB-2, and AB-3, or a salt, solvate, enantiomer, or diastereomer thereof, is as indicated in formula (AB'):

(AB')

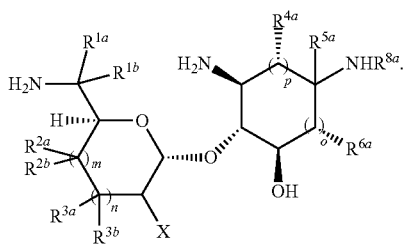

In certain embodiments, the stereochemistry of compound AB-1, AB-2, and AB-3, or a salt, solvate, enantiomer, or diastereomer thereof, is as indicated in formula (AB$^{S2}$), wherein ⌇ indicates a point of attachment to a hydrogen or a moiety:

(AB$^{S2}$)

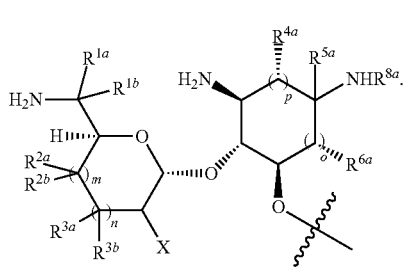

In certain embodiments, the stereochemistry of compound AB-1', AB-2', and AB-3', or a salt, solvate, enantiomer, or diastereomer thereof, is as indicated in formula (AB''):

(AB'')

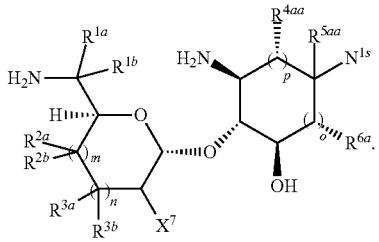

In certain embodiments, the stereochemistry of compound AB-1', AB-2', and AB-3', or a salt, solvate, enantiomer, or diastereomer thereof, is as indicated in formula (AB$^{S4}$), wherein ⌇ indicates a point of attachment to a hydrogen or a moiety:

(AB$^{S4}$)

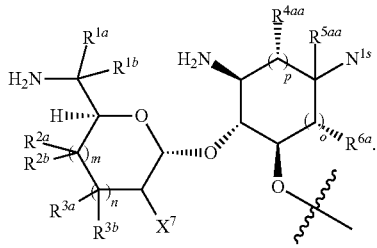

In certain embodiments, m is one. In certain embodiments, n is one. In certain embodiments, m is one and n is one.

In certain embodiments, o is one. In certain embodiments, p is one. In certain embodiments, o is one and p is one.

Preparation of ABC

The present disclosure includes processes, methods, reagents, and intermediates for the synthesis of compound ABC, as shown in Schemes 10, 10a, and 10b. In compound AB-1 and AB-1', the hydroxyl protecting group is selectively removed to form a hydroxyl group, which is suitable of reacting with a reactant or a glycosyl donor, to form an interglycosidic linkage. In compound C-1, LVG$^4$ is a leaving group suitable of reacting with a reactant or a glycosyl acceptor, to form an interglycosidic linkage.

Scheme 10

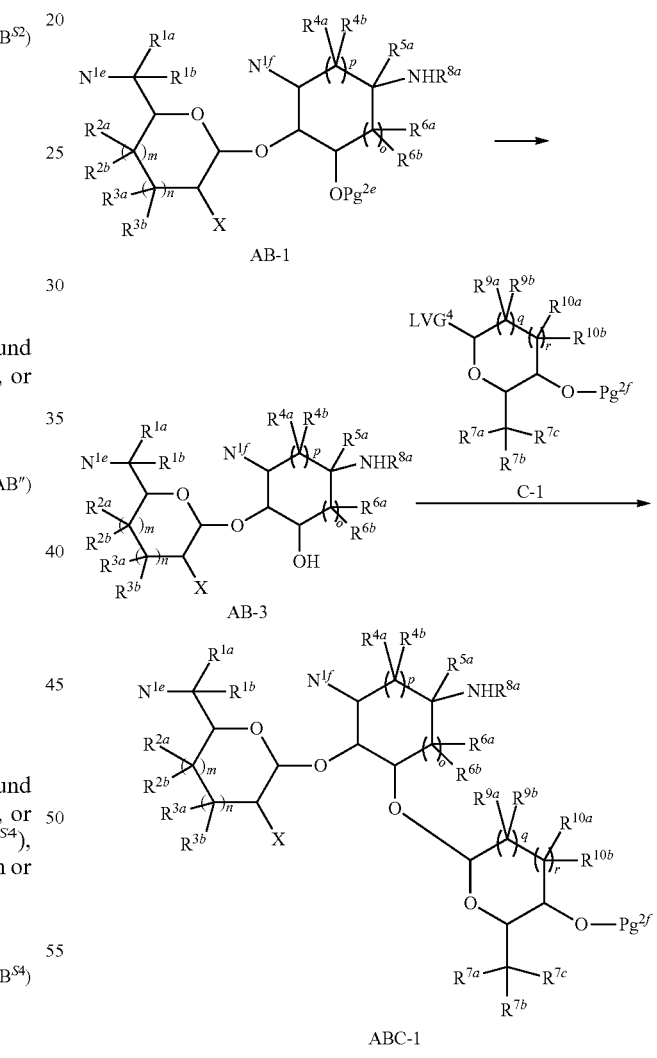

The present disclosure provides a process for preparing a process for preparing a compound of formula ABC-1, comprising the following steps after the preparation of compound AB-1, shown above:

(b) selectively deprotecting the compound of formula AB-1 by removing the Pg$^{2e}$ moiety to yield a compound of formula AB-3:

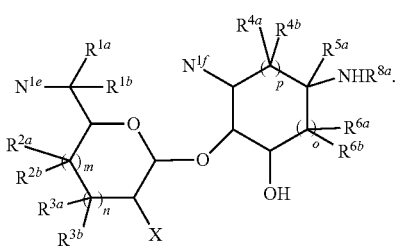

AB-3 or a salt, solvate, enantiomer, or diastereomer thereof;

(c) contacting the compound of formula AB-3 with a compound of formula C-1,

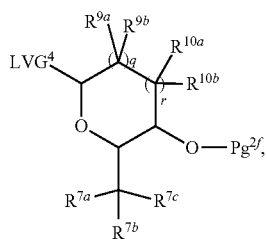

C-1 or a salt, solvate, enantiomer, or diastereomer thereof, wherein $R^{7a}$, $R^{7b}$, and $R^{7c}$ are, independently, H, $NH_2$, OH, —$OR^{71}$ or —$OPg^{2r}$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

wherein $Pg^{2r}$ is a protecting group for hydroxyl group;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$Pg^{2f}$ is a hydroxyl protecting group;

$LVG^4$ is a leaving group;

q is zero, 1, or 2;

r is zero, 1, or 2;

wherein q+r is 1, 2 or 3;

to yield a compound of formula ABC-1, or a salt, solvate, enantiomer, or diastereomer thereof,

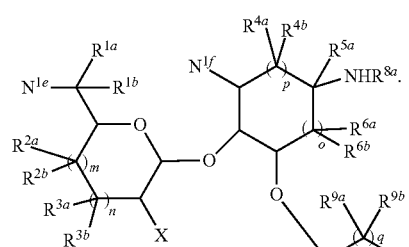

ABC-1

A process for the preparation of compound ABC-1' is illustrated in Schemes 10a and 10b below and is discussed in greater detail herein. Scheme 10b is Scheme 10a, wherein $N^{1i}$ is —$NR^{8a}R^{8b}$.

Scheme 10a

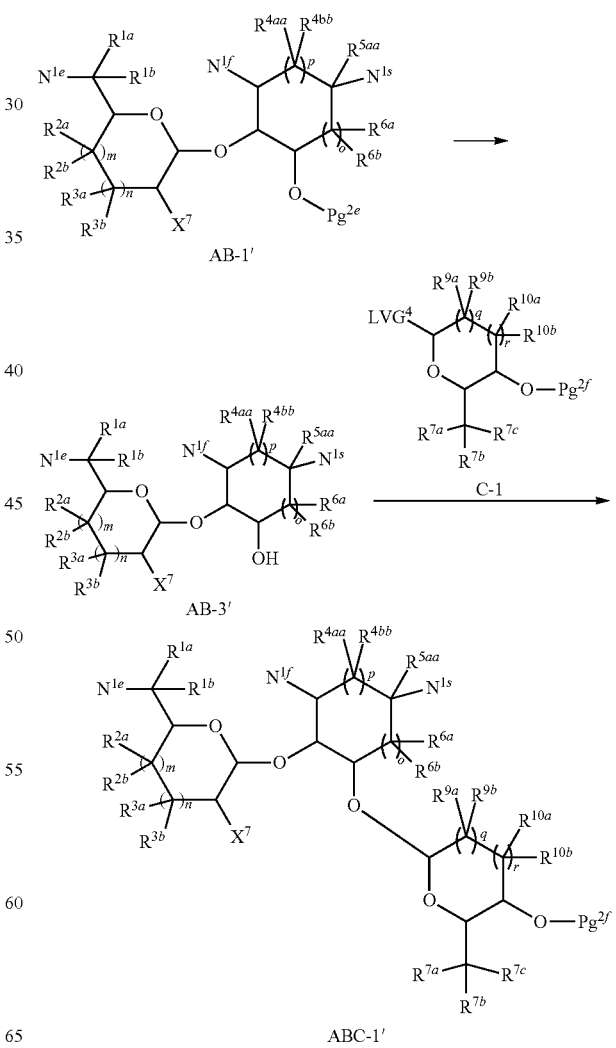

Scheme 10b

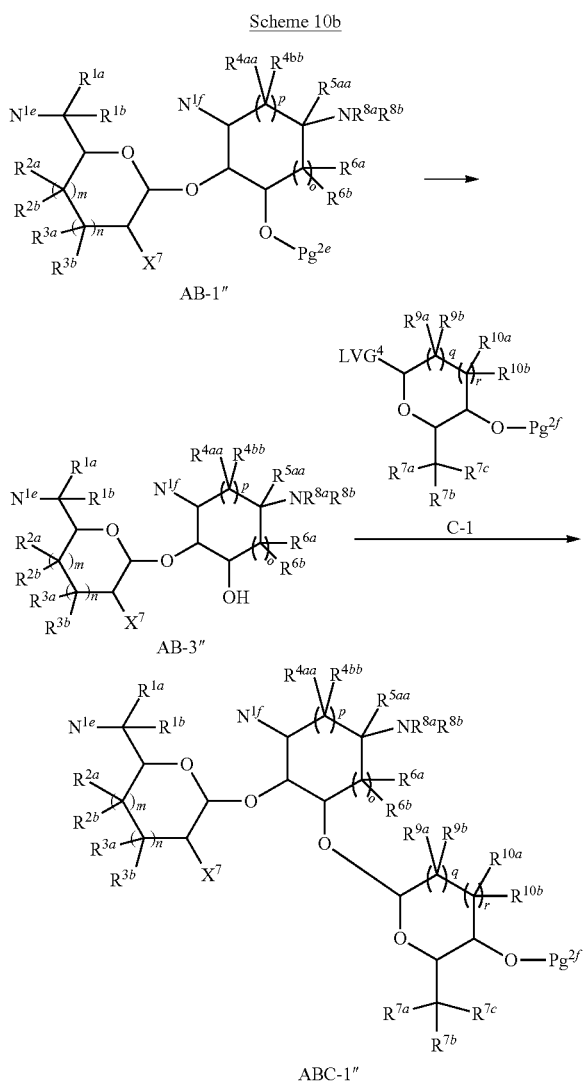

AB-1″

C-1

ABC-1″

With reference to Schemes 10a, the present disclosure provides a process for preparing a process for preparing a compound of formula ABC-1'. The present disclosure provides a process for preparing a process for preparing a compound of formula ABC-1', comprising the following steps after the preparation of compound AB-1', shown above:

(b) selectively deprotecting the compound of formula AB-1' by removing the Pg$^{2e}$ moiety to yield a compound of formula AB-3':

AB-3'

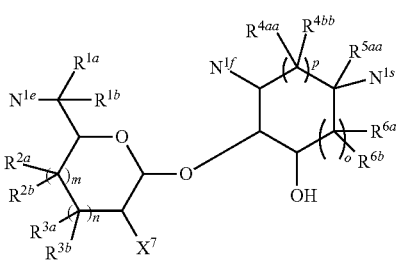

or a salt, solvate, enantiomer, or diastereomer thereof;

(c) contacting the compound of formula AB-3 with a compound of formula C-1,

C-1

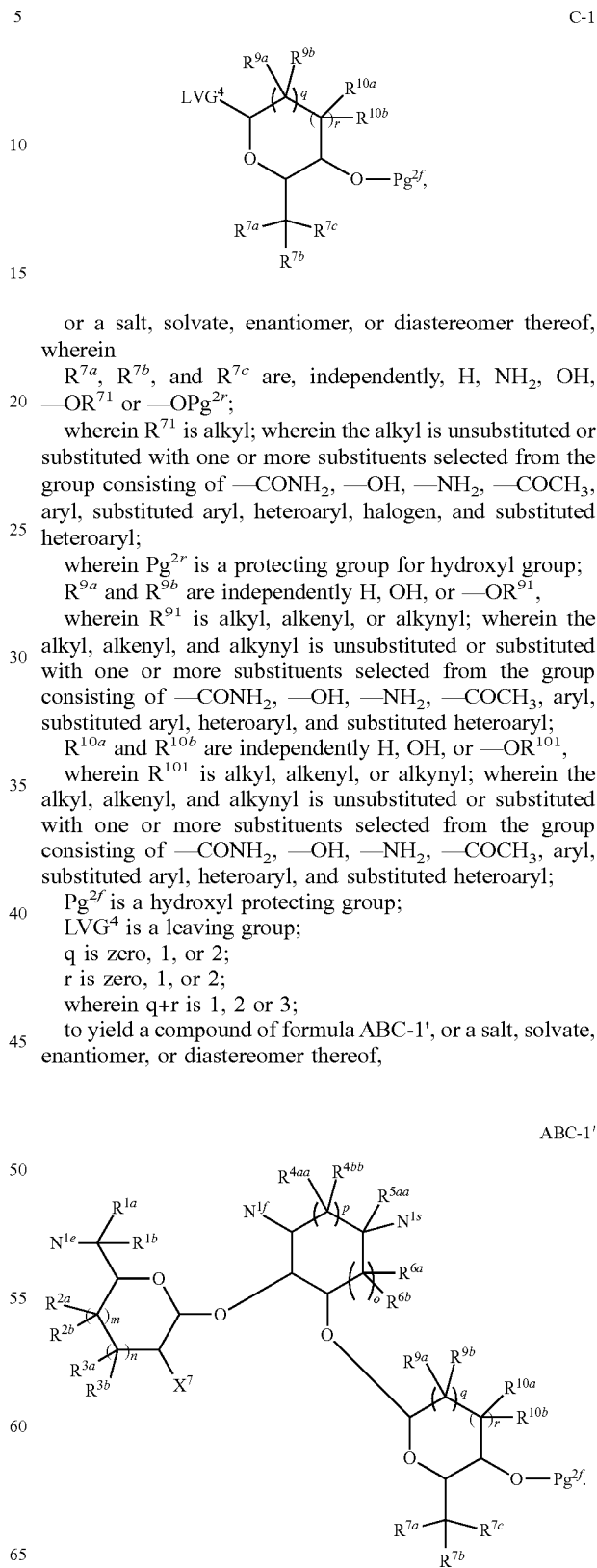

or a salt, solvate, enantiomer, or diastereomer thereof, wherein

R$^{7a}$, R$^{7b}$, and R$^{7c}$ are, independently, H, NH$_2$, OH, —OR$^{71}$ or —OPg$^{2r}$;

wherein R$^{71}$ is alkyl; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

wherein Pg$^{2r}$ is a protecting group for hydroxyl group;

R$^{9a}$ and R$^{9b}$ are independently H, OH, or —OR$^{91}$, wherein R$^{91}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

R$^{10a}$ and R$^{10b}$ are independently H, OH, or —OR$^{101}$, wherein R$^{101}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

Pg$^{2f}$ is a hydroxyl protecting group;

LVG$^4$ is a leaving group;

q is zero, 1, or 2;

r is zero, 1, or 2;

wherein q+r is 1, 2 or 3;

to yield a compound of formula ABC-1', or a salt, solvate, enantiomer, or diastereomer thereof,

ABC-1'

Synthesis of Compound ABC-1

Reference to compounds AB-1 to AB-3 are meant to encompass compounds AB-1' to AB-3' and AB-1" to AB-3". With reference to Schemes 10, 10a, and 10b, a selective removal of the $Pg^{2e}$ protecting group of compound AB-1 to yield compound AB-3, which has a hydroxyl group resulting from the selective removal of the $Pg^{2e}$ protecting group. Selective removal of $Pg^{2c}$ protecting group can be performed by hydrolysis. For example, removal of protecting group can be performed by hydrolysis under conditions such as base (for example, NaOH, KOH, $Et_3N$) or acid mediated (for example, HCl, TfOH, p-TSA) in aqueous media optionally including organic solvents (for example, MeOH, $Et_2O$, DMF) at temperatures between 0° C. and the reflux point of the solvent.

With continued reference to Schemes 10, 10a, and 10b, compound AB-3 is contacted with compound C-1 to yield compound ABC-1. The reaction is performed under to conditions to allow for chemical glycosylation with coupling of a glycosyl donor and a glycosyl acceptor. In Scheme 10, 10a, and 10b, a glycosyl donor ($LVG^4$ on compound C-1) and a glycosyl acceptor (—OH on compound AB-3) are coupled. In certain embodiments, $LVG^4$ is selected from the group consisting of OH, halides, thioalkyl groups, thioaryl groups, imidates, acetate, phosphate, and O-pentenyl groups. In certain embodiments, $LVG^4$ is halo, OMs, OTs, OH, a thioalkyl, a thioaryl, an imidate, an acetate, a phosphate, or an O-pentenyl group.

In certain embodiments, a suitable activating reagent is provided to assist the chemical glycosylation reaction. In certain embodiments, $BF_3$ is used as an activating agent. In certain embodiments, standard glycosyl formation conditions include use of an activating agent, such as $BF_3 \cdot Et_2O$ or $AlMe_3$ in solvents such as MeOH or THF at temperatures between 0° C. and room temperature.

Synthesis of Compound ABC-2

In some embodiments, the protecting groups of compound ABC-1 are removed to yield a compound ABC-2, as described in Scheme 11. In some embodiments, the protecting groups of compound ABC-1' are removed to yield a compound ABC-2', as described in Scheme 11a. Scheme 11b is Scheme 11a, wherein $N^{1s}$ is —$NR^{8a}R^{8b}$.

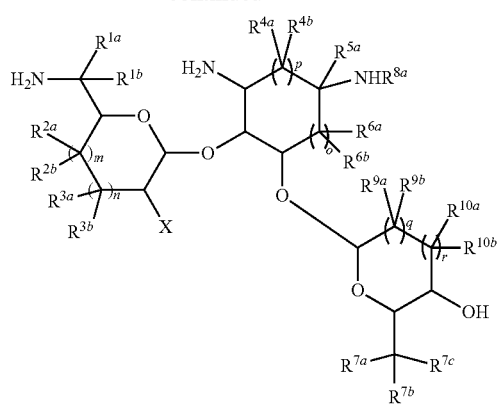

ABC-2

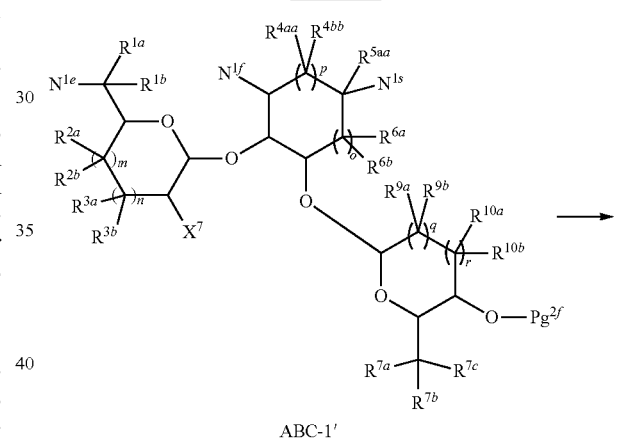

Scheme 11a

ABC-1'

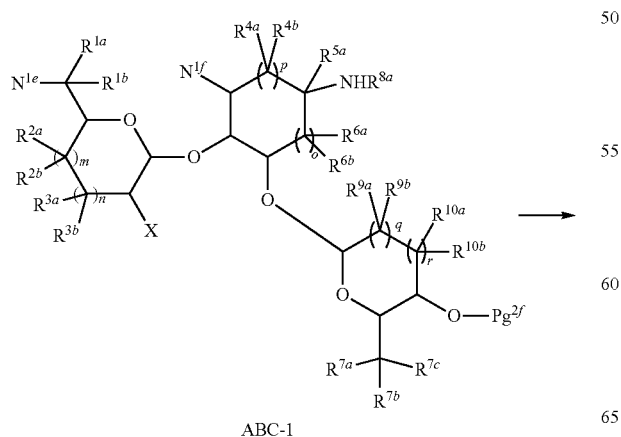

Scheme 11

ABC-1

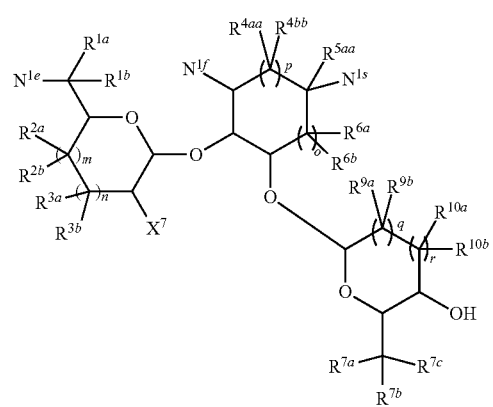

ABC-2'

Scheme 11b

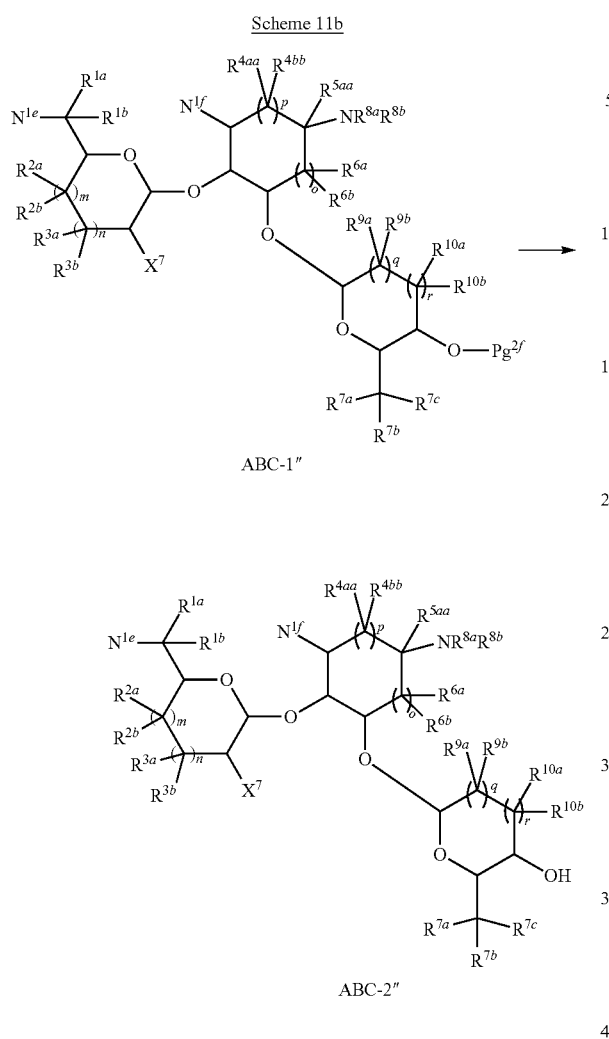

ABC-1″

ABC-2″

With reference to Schemes 11, 11a, and 11b, the process further comprises after step (c):

(d) if amino protecting groups and hydroxyl protecting groups are present, remove the amino protecting groups and hydroxyl protecting groups to yield a compound of formula ABC-2, or a salt, solvate, enantiomer, or diastereomer thereof.

Reference to compounds ABC-1 and ABC-2 herein are meant to encompass compounds ABC-1', ABC-1″, ABC-2' and ABC-2″. In certain embodiments, the process comprises removing the amino protecting groups $Pg^{1e}$ and $Pg^{1f}$ or converting $N_3$ to —$NH_2$ and removing hydroxyl protecting group $Pg^{2f}$ to yield a compound of formula ABC-2, or a salt, solvate, enantiomer, or diastereomer thereof.

Conditions for removing protecting group can be found in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski). In certain embodiments, hydrolysis or hydrogenation can be used to remove the protecting groups.

Additional Preparation of Compound ABC

Compound ABC can also be prepared with the use of a catalyst, such as an enzyme, for example, as described in Examples 43 and 44.

Embodiments of Compound ABC

In certain embodiments, the stereochemistry in the ring of formulae ABC-1 and ABC-2, is as indicated in formula (ABC'), (ABC')

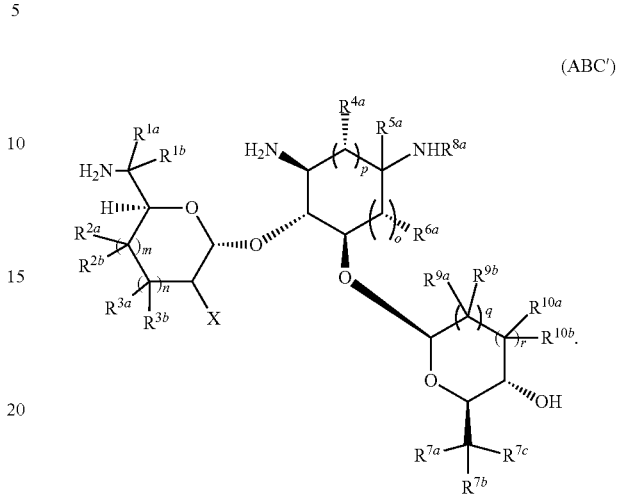

In certain embodiments, the stereochemistry of compound ABC-1', ABC-2', and ABC-3', or a salt, solvate, enantiomer, or diastereomer thereof, is as indicated in formula (ABC″):

(ABC″)

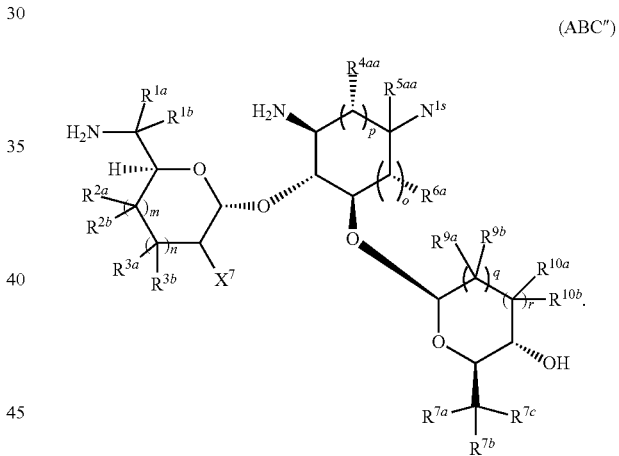

In certain embodiments, m is one. In certain embodiments, n is one. In certain embodiments, m is one and n is one.

In certain embodiments, o is one. In certain embodiments, p is one. In certain embodiments, o is one and p is one.

In certain embodiments, q is one. In certain embodiments, q is zero. In certain embodiments, r is one. In certain embodiments, r is zero. In certain embodiments, q is one and r is zero. In certain embodiments, q is zero and r is one.

Preparation of ABCD

The present disclosure includes processes, methods, reagents, and intermediates for the synthesis of compound ABCD-1, as shown in Schemes 12, 12a, and 12b In compound AB-1, the hydroxyl protecting group is selectively removed to expose a hydroxyl group, which is suitable of reacting with a reactant or a glycosyl donor, to form an interglycosidic linkage. In compound CD-1, $LVG^5$ is a leaving group suitable of reacting with a reactant or a glycosyl acceptor, to form an interglycosidic linkage.

Scheme 12
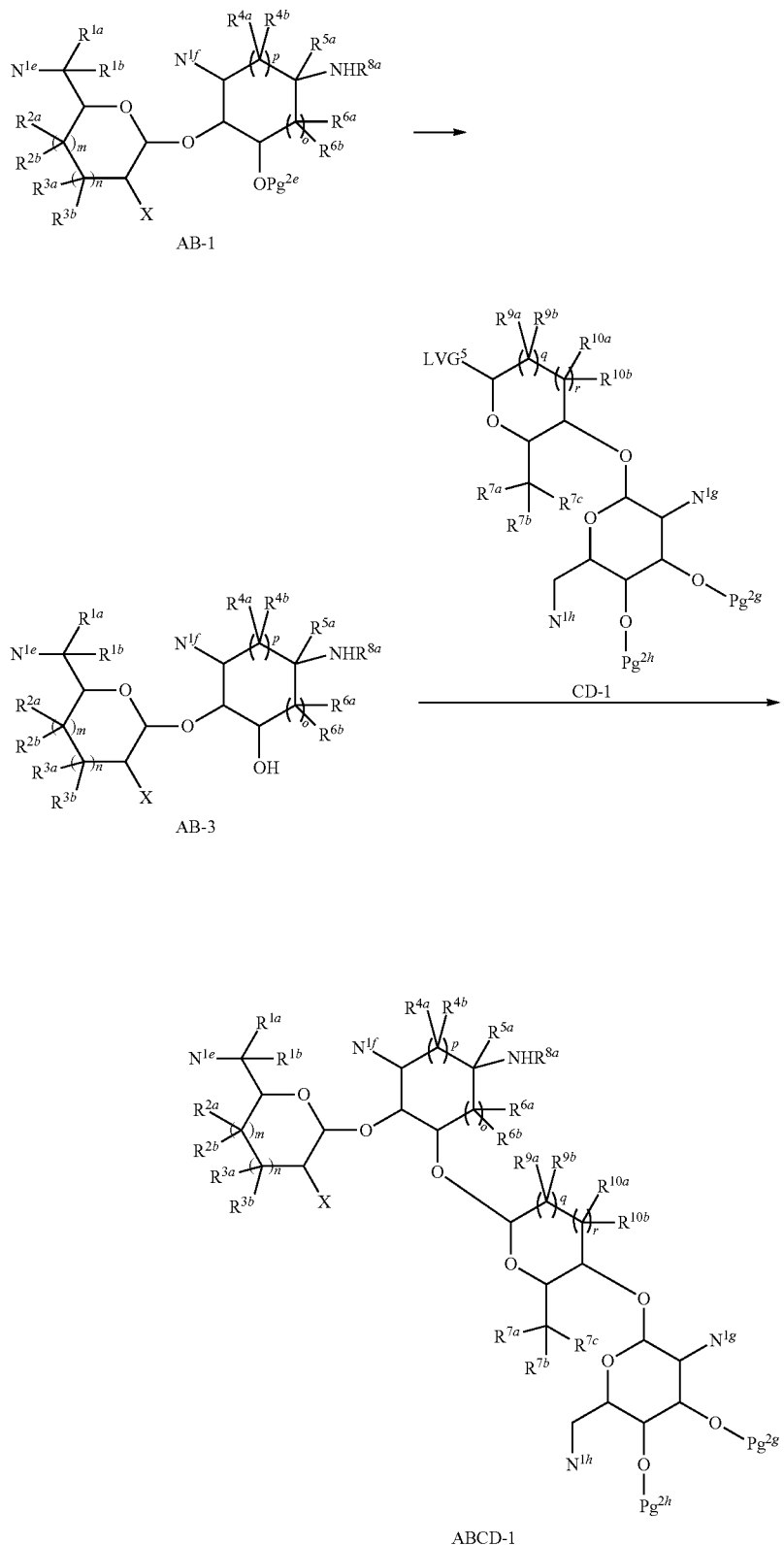
The present disclosure provides a process for preparing a process for preparing a compound of formula ABCD-1, comprising the following steps after the preparation of compound AB-1, shown above:

(b) selectively deprotecting the compound of formula AB-1 by removing the Pg$^{2e}$ moiety to yield a compound of formula AB-3:

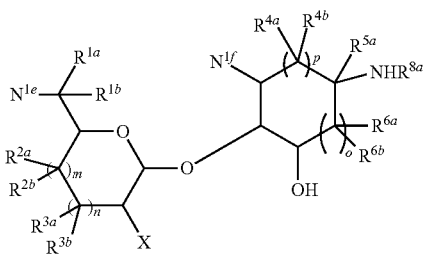

AB-3 or a salt, solvate, enantiomer, or diastereomer thereof;

(c) contacting the compound of formula AB-3 with a compound of formula CD-1,

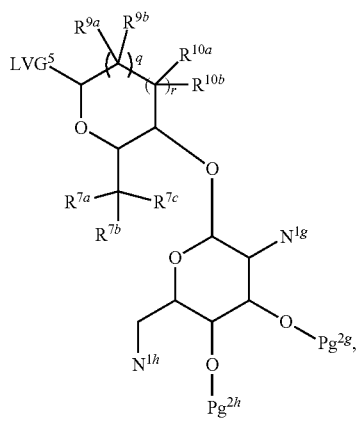

CD-1 or a salt, solvate, enantiomer, or diastereomer thereof, wherein

R$^{7a}$, R$^{7b}$, and R$^{7c}$ are, independently, H, NH$_2$, OH, —OR$^{71}$ or —OPg$^{2r}$;

wherein R$^{71}$ is alkyl; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

wherein Pg$^{2r}$ is a protecting group for hydroxyl group;

R$^{9a}$ and R$^{9b}$ are independently H, OH, or —OR$^{91}$, wherein R$^{91}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

R$^{10a}$ and R$^{10b}$ are independently H, OH, or —OR$^{101}$, wherein R$^{10}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, or substituted heteroaryl;

LVG$^5$ is a leaving group;

N$^{1g}$ is —NHPg$^{1g}$ or N$_3$, wherein Pg$^{1g}$ is an amino protecting group;

N$^{1h}$ is —NHPg$^{1h}$ or N$_3$, wherein Pg$^{1h}$ is an amino protecting group;

Pg$^{2g}$ is a hydroxyl protecting group;

Pg$^{2h}$ is a hydroxyl protecting group;

q is zero, 1, or 2;

r is zero, 1, or 2;

wherein q+r is 1, 2 or 3;

to yield a compound of formula ABCD-1, or a salt, solvate, enantiomer, or diastereomer thereof,

ABCD-1

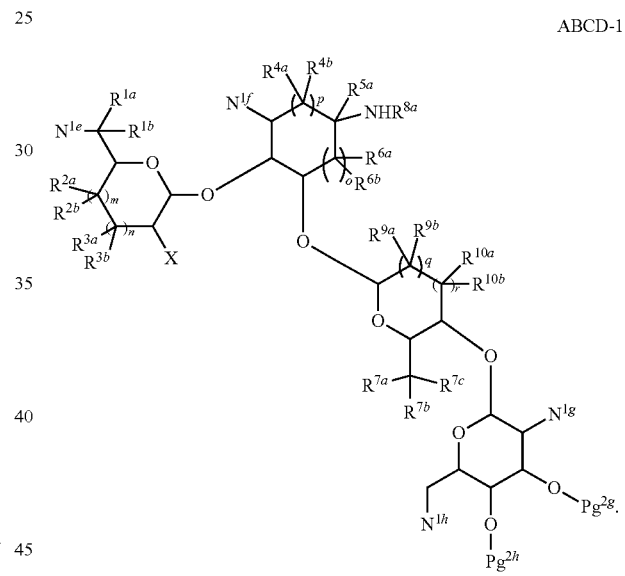

A process for the preparation of compound ABCD-1' is illustrated in Scheme 12a below and is discussed in greater detail herein. Scheme 12b is Scheme 12a, wherein N$^{1i}$ is —NR$^{8a}$R$^{8b}$.

Scheme 12a

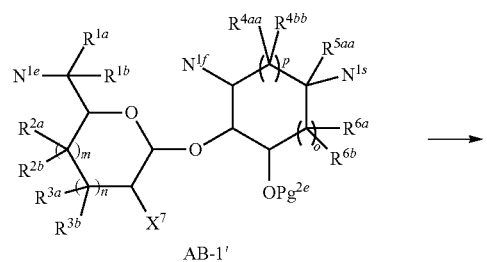

AB-1'

-continued
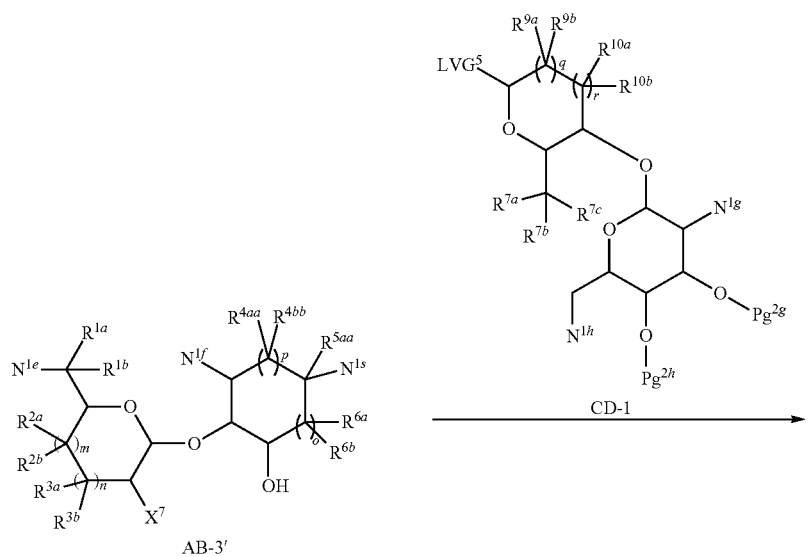
AB-3'  →(CD-1)→  ABCD-1'
Scheme 12b
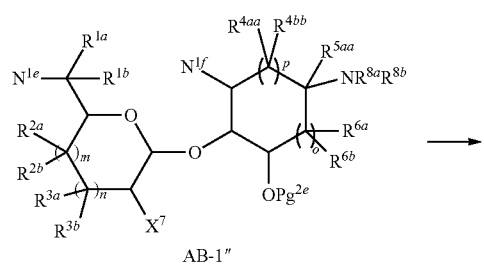
AB-1″  →

-continued

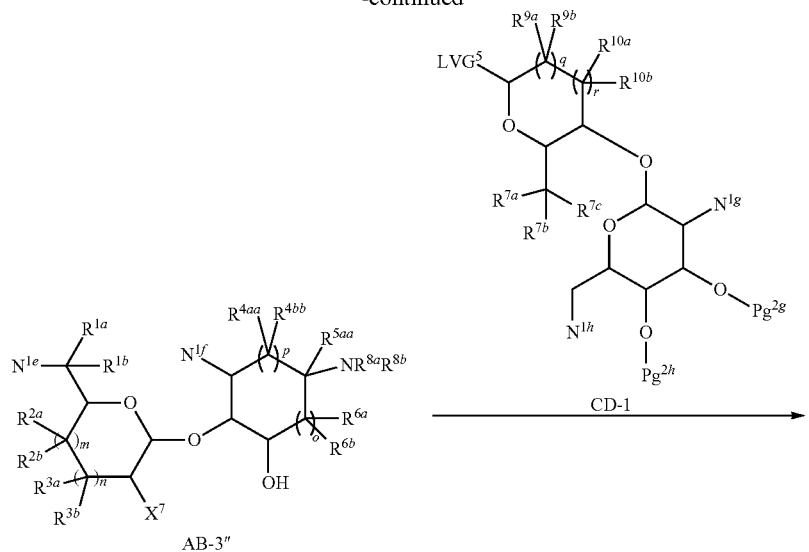

AB-3″

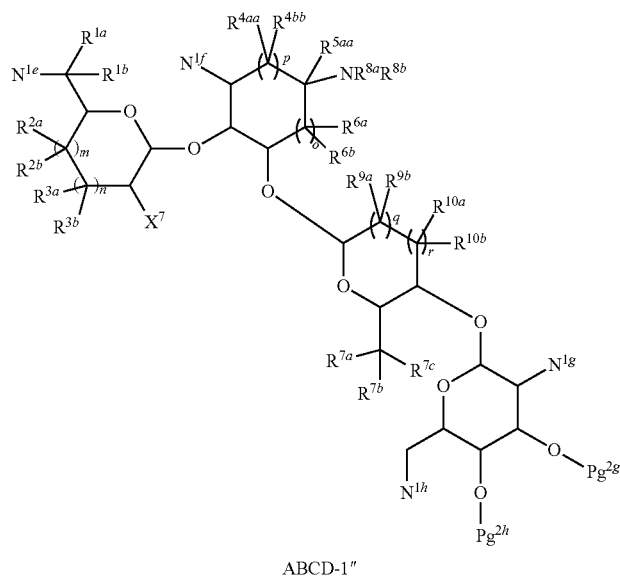

ABCD-1″

With reference to Scheme 12a, in compound AB-1', the hydroxyl protecting group is selectively removed to expose a hydroxyl group, which is suitable of reacting with a reactant or a glycosyl donor, to form an interglycosidic linkage. In compound CD-1, $LVG^5$ is a leaving group suitable of reacting with a reactant or a glycosyl acceptor, to form an interglycosidic linkage.

The present disclosure provides a process for preparing a process for preparing a compound of formula ABCD-1', comprising the following steps after the preparation of compound AB-1', shown above:

(b) selectively deprotecting the compound of formula AB-1' by removing the $Pg^{2e}$ moiety to yield a compound of formula AB-3':

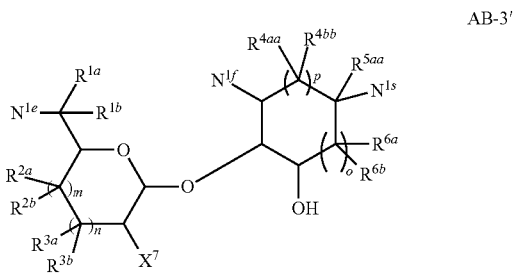

AB-3' or a salt, solvate, enantiomer, or diastereomer thereof;

(c) contacting the compound of formula AB-3 with a compound of formula CD-1,

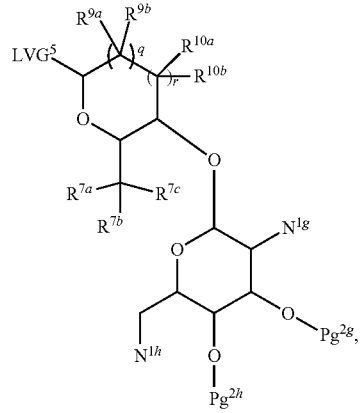

or a salt, solvate, enantiomer, or diastereomer thereof, wherein $R^{7a}$, $R^{7b}$, and $R^{7c}$ are, independently, H, $NH_2$, OH, $-OR^{71}$ or $-OPg^{2r}$;

wherein $R^{71}$ is alkyl; wherein the alkyl is unsubstituted or substituted with one or more substituents selected from the group consisting of $-CONH_2$, $-OH$, $-NH_2$, $-COCH_3$, aryl, substituted aryl, heteroaryl, halogen, and substituted heteroaryl;

wherein $Pg^{2r}$ is a protecting group for hydroxyl group;

$R^{9a}$ and $R^{9b}$ are independently H, OH, or $-OR^{91}$, wherein $R^{91}$ is alkyl, alkenyl, or alkynyl; wherein the alkyl, alkenyl, and alkynyl is unsubstituted or substituted with one or more substituents selected from the group consisting of $-CONH_2$, $-OH$, $-NH_2$, $-COCH_3$, aryl, substituted aryl, heteroaryl, and substituted heteroaryl;

$R^{10a}$ and $R^{10b}$ are independently H, OH, or $-OR^{101}$, wherein $R^{101}$ is alkyl, alkenyl, or alkynyl; wherein the alkyl, alkenyl, and alkynyl is unsubstituted or substituted with one or more substituents selected from the group consisting of $-CONH_2$, $-OH$, $-NH_2$, $-COCH_3$, aryl, substituted aryl, heteroaryl, or substituted heteroaryl;

$LVG^5$ is a leaving group;

$N^{1g}$ is $-NHPg^{1g}$ or $N_3$, wherein $Pg^{1g}$ is an amino protecting group;

$N^{1h}$ is $-NHPg^{1h}$ or $N_3$, wherein $Pg^{1h}$ is an amino protecting group;

$Pg^{2g}$ is a hydroxyl protecting group;

$Pg^{2h}$ is a hydroxyl protecting group;

q is zero, 1, or 2;

r is zero, 1, or 2;

wherein q+r is 1, 2 or 3;

to yield a compound of formula ABCD-1', or a salt, solvate, enantiomer, or diastereomer thereof,

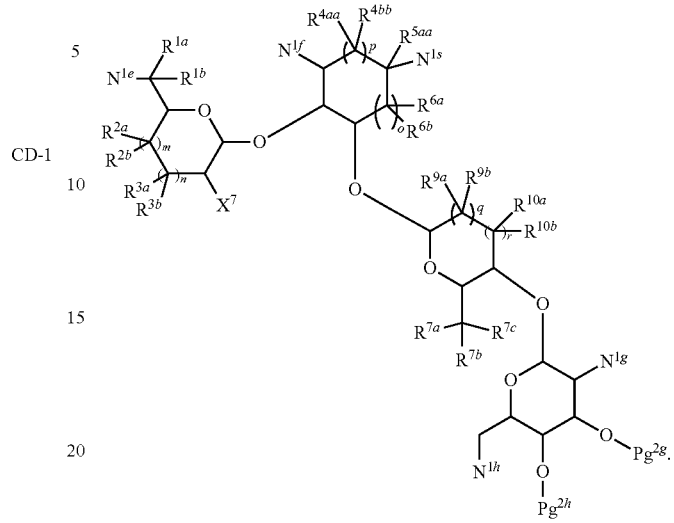

Synthesis of Compound ABCD-1

Reference to compounds AB-1 to AB-3 are meant to encompass compounds AB-1' to AB-3' and AB-1" to AB-3". With reference to Schemes 12, 12a, and 12b, a selective removal of the $Pg^{2e}$ protecting group of compound AB-1 to yield compound AB-3, which has a hydroxyl group resulting from the selective removal of the $Pg^{2e}$ protecting group. Selective removal of $Pg^{2e}$ protecting group can be performed by hydrolysis. For example, removal of protecting group can be performed by hydrolysis under conditions such as base (for example, NaOH, KOH, $Et_3N$) or acid mediated (for example, HCl, TfOH, p-TSA) in aqueous media optionally including organic solvents (for example, MeOH, $Et_2O$, DMF) at temperatures between 0° C. and the reflux point of the solvent.

With continued reference to Schemes 12, 12a, and 12b, compound AB-3 is contacted with compound CD-1 to yield compound ABCD-1. The reaction is performed under to conditions to allow for chemical glycosylation with coupling of a glycosyl donor and a glycosyl acceptor. In Scheme 12, 12a, and 12b, a glycosyl donor ($LVG^5$ on compound CD-1) and a glycosyl acceptor (—OH on compound AB-3) are coupled. In certain embodiments, $LVG^5$ is selected from the group consisting of OH, halides, thioalkyl groups, thioaryl groups, imidates, acetate, phosphate, and 0-pentenyl groups. In certain embodiments, $LVG^5$ is halo, OMs, OTs, OH, a thioalkyl, a thioaryl, an imidate, an acetate, a phosphate, or an O-pentenyl group.

In certain embodiments, a suitable activating reagent is provided to assist the chemical glycosylation reaction. In certain embodiments, $BF_3$ is used as an activating agent. In certain embodiments, standard glycosyl formation conditions include use of an activating agent, such as $BF_3 \cdot Et_2O$ or $AlMe_3$ in solvents such as MeOH or THF at temperatures between 0° C. and room temperature.

Synthesis of Compound ABCD-2

In some embodiments, the protecting groups of compound ABCD-1 are removed to yield a compound ABCD-2, as described in Scheme 13. In some embodiments, the protecting groups of compound ABCD-1' are removed to yield a compound ABCD-2', as described in Scheme 13a. Scheme 13b is Scheme 13a, wherein $N^{1s}$ is $-NR^{8a}R^{8b}$.

Scheme 13
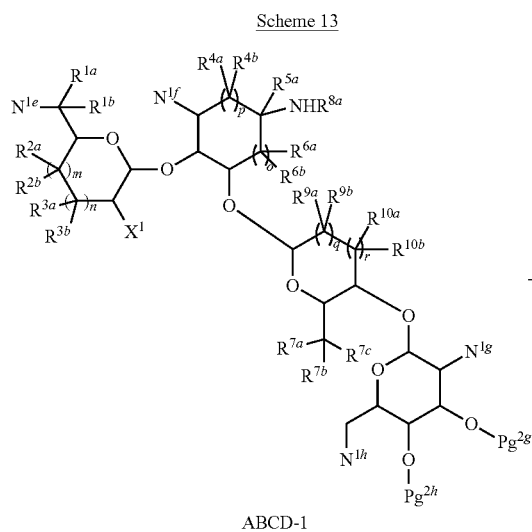
ABCD-1
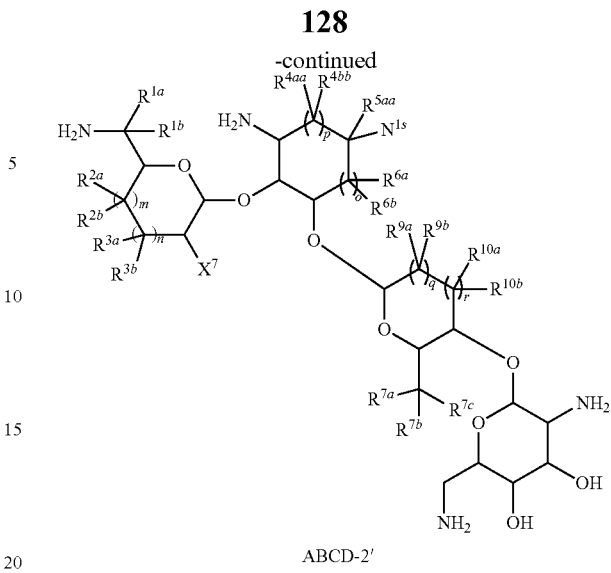
ABCD-2'
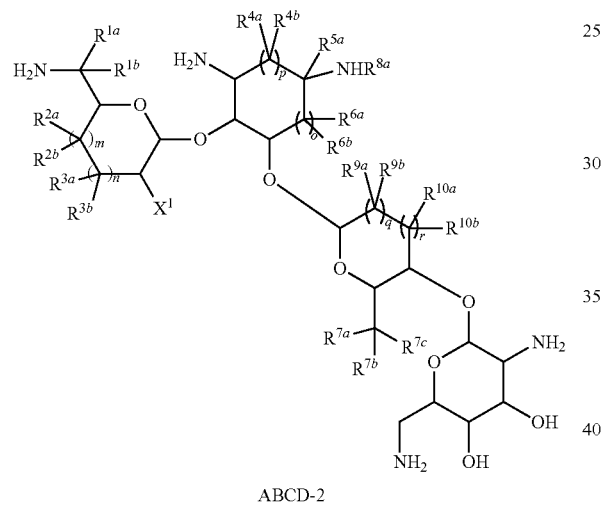
ABCD-2
Scheme 13b
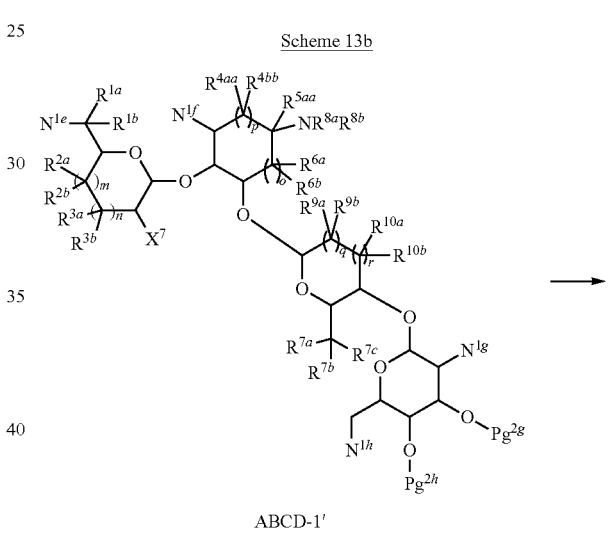
ABCD-1'
Scheme 13a
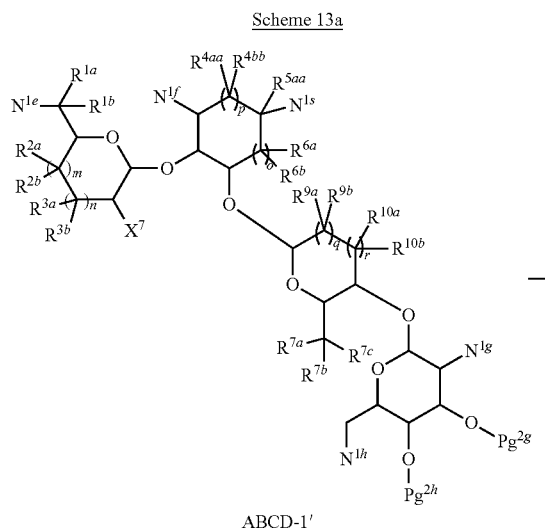
ABCD-1'
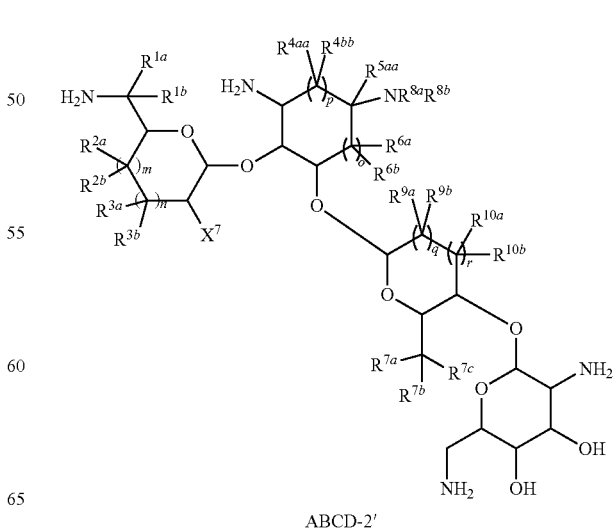
ABCD-2'

With reference to Schemes 13, 13a, and 13b, the process further comprises after step (c):

(d) if amino protecting groups and hydroxyl protecting groups are present, remove the amino protecting groups and hydroxyl protecting groups to yield a compound of formula ABCD-2, or a salt, solvate, enantiomer, or diastereomer thereof.

Reference to compounds ABCD-1 and ABCD-2 herein are meant to encompass compounds ABCD-1', ABCD-1", ABCD-2' and ABCD-2". In certain embodiments, the process comprises removing the amino protecting groups $Pg^{1e}$ $Pg^{1f}$, $Pg^{1g}$, and $Pg^{1h}$ or converting $N_3$ to —$NH_2$ and removing and hydroxyl protecting groups $Pg^{2g}$ and $Pg^{2h}$ to yield a compound of formula ABCD-2, or a salt, solvate, enantiomer, or diastereomer thereof.

Conditions for removing protecting group can be found in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski). In certain embodiments, hydrolysis or hydrogenation can be used to remove the protecting groups.

Additional Preparation of Compound ABCD

Compound ABCD can also be prepared with the use of a catalyst, such as an enzyme, for example, as described in Examples 43 and 44

Embodiments of Compound ABCD

In certain embodiments, the stereochemistry in the ABCD ring are indicated as in formula (ABCD'):

(ABCD')

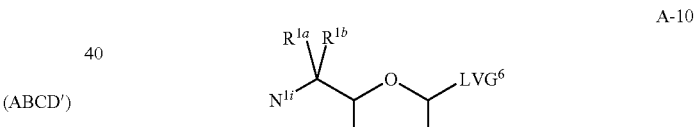

In certain embodiments, the stereochemistry in the ABCD ring are indicated as in formula (ABCD"):

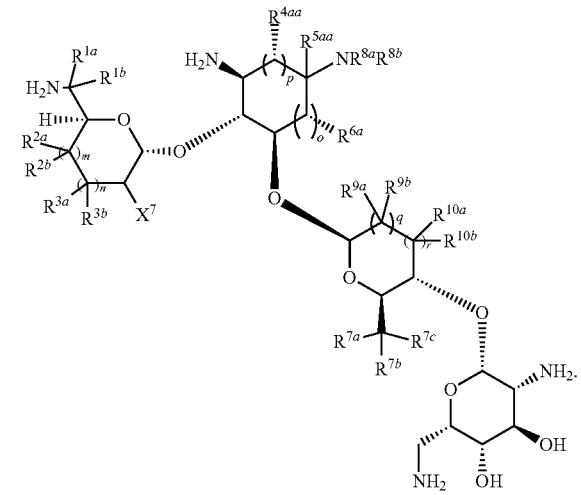

(ABCD")

In certain embodiments, m is one. In certain embodiments, n is one. In certain embodiments, m is one and n is one.

In certain embodiments, o is one. In certain embodiments, p is one. In certain embodiments, o is one and p is one.

In certain embodiments, q is one. In certain embodiments, q is zero. In certain embodiments, r is one. In certain embodiments, r is zero. In certain embodiments, q is one and r is zero. In certain embodiments, q is zero and r is one.

Compounds of Formulae A, B, AB, ABC, ABCD

Compounds of Formula A

The present disclosure provides a compound of formula A-10:

A-10 and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{29}$, and $R^{26}$ is independently H or alkyl, wherein the alkyl is unsubstituted or substituted with one or more substituents independently selected from the group consisting of halogen, cyano, NR$^{14}$R$^{15}$, and —OR$^{16}$;

R$^{2a}$, R$^{2b}$, R$^{3a}$ and R$^{3b}$ are independently selected from the group consisting of H, —OR$^{27}$, —NR$^{28}$R$^{29}$, halogen, C$_1$-C$_4$ cycloalkyl, and C$_1$-C$_6$ alkyl, wherein each R$^{27}$, R$^{28}$, and R$^{29}$ is independently H or alkyl; wherein the C$_1$-C$_6$ alkyl or alkyl is unsubstituted or substituted with one or more substituents selected from the group consisting of halogen, —OR$^{30}$, —NR$^{31}$R$^{32}$, —SR$^{33}$, and —SO$_2$R$^{34}$;

wherein each R$^{30}$, R$^{31}$, R$^{32}$, R$^{33}$, and R$^{34}$ is independently H or alkyl substituted with one or more substituents independently selected from the group consisting of halogen, cyano, NR$^{14}$R$^{15}$, and —OR$^{16}$; or R$^{2a}$ and R$^{2b}$ form an oxo or imino group substituted with C$_1$-C$_6$ alkyl;

R$^{3a}$ and R$^{3b}$ form an oxo or imino group substituted with C$_1$-C$_6$ alkyl;

X$^3$ is selected from the group consisting of H, NH$_2$, N$_3$, protected amino group, OH, —OPg$^{2i}$, and halogen; wherein Pg$^{2i}$ is a hydroxyl protecting group;

LVG$^6$ is a leaving group;

N$^{1i}$ is —NHPg$^{1i}$, —NH$_2$, or N$_3$, wherein each Pg$^{1i}$ is independently an amino protecting group;

m is zero, 1, or 2;

n is zero, 1, or 2;

wherein m+n is 1, 2 or 3.

The present disclosure provides a compound of formula A-10':

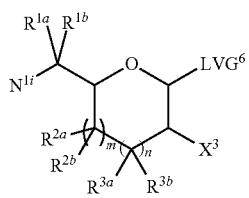

A-10' and salts, solvates, enantiomers, and diastereomers thereof, wherein

R$^{1a}$ and R$^{1b}$ are independently selected from the group consisting of H, C$_1$-C$_{12}$ alkyl, C$_1$-C$_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —N$_3$, and —OR$^{16}$, and wherein each R$^{12}$, R$^{13}$, R$^{14}$, R$^{15}$, and R$^{16}$ is independently H or alkyl; or R$^{1a}$ and R$^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each R$^{22}$, R$^{23}$, R$^{24}$, R$^{25}$, and R$^{26}$ is independently H or alkyl, wherein the alkyl is unsubstituted or substituted with one or more substituents independently selected from the group consisting of halogen, cyano, NR$^{14}$R$^{15}$, and —OR$^{16}$;

R$^{2a}$, R$^{2b}$, R$^{3a}$ and R$^{3b}$ are independently selected from the group consisting of H, —OR$^{27}$, —NR$^{28}$R$^{29}$, halogen, C$_1$-C$_4$ cycloalkyl, and C$_1$-C$_6$ alkyl, wherein each R$^{27}$, R$^{28}$, and R$^{29}$ is independently H, alkyl, amino protecting group, or hydroxyl protecting group; wherein the C$_1$-C$_6$ alkyl or alkyl is unsubstituted or substituted with one or more substituents selected from the group consisting of aryl, halogen, —OR$^{30}$, —NR$^{31}$R$^{32}$, —SR$^{33}$, and —SO$_2$R$^{34}$;

wherein each R$^{30}$, R$^{31}$, R$^{32}$, R$^{33}$, and R$^{34}$ is independently H or alkyl substituted with one or more substituents independently selected from the group consisting of halogen, cyano, NR$^{14}$R$^{15}$, and —OR$^{16}$; or R$^{2a}$ and R$^{2b}$ form an oxo or imino group substituted with C$_1$-C$_6$ alkyl;

R$^{3a}$ and R$^{3b}$ form an oxo or imino group substituted with C$_1$-C$_6$ alkyl; X$^3$ is selected from the group consisting of H, NH$_2$, N$_3$, protected amino group, OH, —OPg$^{2i}$, and halogen; wherein Pg$^{2i}$ is a hydroxyl protecting group;

LVG$^6$ is a leaving group;

N$^{1i}$ is —OH, protected hydroxyl group, —NHPg$^{1i}$, N(Pg$^{1i}$)$_2$, —NH$_2$, or N$_3$, wherein each Pg$^{1i}$ is independently an amino protecting group;

m is zero, 1, or 2;

n is zero, 1, or 2;

wherein m+n is 1, 2 or 3.

Compounds of Formula B

The present disclosure provides a compound of formula B-13:

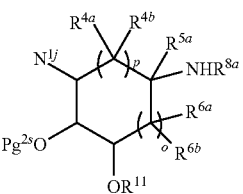

B-13 and salts, solvates, enantiomers, and diastereomers thereof, wherein

R$^{4a}$ and R$^{4b}$ are, independently H, —OH, —OR$^{40}$, —NR$^{41}$R$^{42}$, or halogen;

wherein each R$^{40}$, R$^{41}$, and R$^{42}$ are independently H or alkyl; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

R$^{5a}$ is H, —CN, —CONH$_2$ or C$_1$-C$_3$alkyl, wherein the alkyl is unsubstituted or substituted with one or more substituents selected from the group consisting of —OH, —NH$_2$, —CN, —CONH$_2$, and halogen;

R$^{6a}$ and R$^{6b}$ are, independently H, halogen, NH$_2$, —OH, C$_1$-C$_3$alkoxy, —OC(O)CH$_3$, or —OPg$^{2j}$; wherein Pg$^{2j}$ is a hydroxyl protecting group;

R$^{8a}$ is H, C$_1$-C$_6$ alkyl, an amino protecting group, or

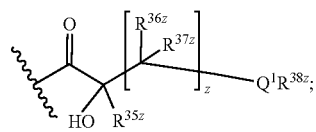

wherein

Q$^1$ is NH, O, or S;

z is an integer from 0 to 4,

R$^{35z}$ is H or C$_1$-C$_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{11}$ is H, alkyl, —COCH$_3$, or a hydroxyl protecting group;

$N^{1j}$ is —NHPg$^{1j}$, —NH$_2$, or N$_3$, wherein Pg$^{1j}$ is an amino protecting group;

Pg$^{2s}$ is H or hydroxyl protecting group;

o is zero, 1, or 2;

p is zero, 1, or 2;

wherein o+p is 1, 2 or 3.

The present disclosure provides a compound of formula (B-13')

B-13

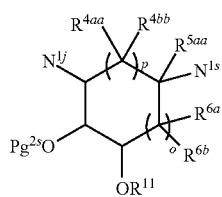

and salts, solvates, enantiomers, and diastereomers thereof, wherein $R^{4aa}$ and $R^{4bb}$ are, independently H, —OH, —OR$^{40}$, —NR$^{41}$R$^{42}$, or halogen;

wherein each $R^{40}$, $R^{41}$, and $R^{42}$ are independently H, alkyl, —CONH$_2$, or —COCH$_3$; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^{5aa}$ is H, —CN, —CONH$_2$ or $C_1$-$C_3$alkyl, wherein the alkyl is unsubstituted or substituted with one or more substituents selected from the group consisting of —OH, —OC(O)CH$_3$, —NH$_2$, —CN, —CONH$_2$, and halogen;

$R^{6a}$ and $R^{6b}$ are, independently H, halogen, NH$_2$, —OH, $C_1$-$C_3$alkoxy, —OC(O)CH$_3$, or —OPg$^{2j}$; wherein Pg$^{2j}$ is a hydroxyl protecting group;

$N^{1s}$ is N$_3$ or —NR$^{8a}$R$^{8b}$;

$R^{8a}$ is H, $C_1$-$C_6$ alkyl, an amino protecting group, or

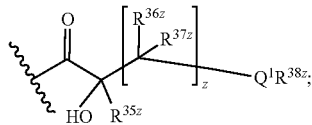

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{8b}$ is H or $C_1$-$C_3$alkyl;

$R^{11}$ is H, alkyl, —COCH$_3$, or a hydroxyl protecting group;

$N^{1j}$ is —NHPg$^{1j}$, —NH$_2$, or N$_3$, wherein Pg$^{1j}$ is an amino protecting group;

Pg$^{2s}$ is H or hydroxyl protecting group;

o is zero, 1, or 2;

p is zero, 1, or 2;

wherein o+p is 1, 2 or 3.

Compounds of Formula AB

The present disclosure provides a compound of formula AB-4:

AB-4

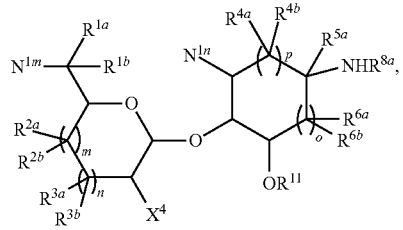

and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —N$_3$, and —OR$^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, NR$^{14}$R$^{15}$, and —OR$^{16}$;

$R^{2a}$, $R^{2b}$, $R^{3a}$ and $R^{3b}$ are independently selected from the group consisting of H, —OR$^{27}$, —NR$^{28}$R$^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —OR$^{30}$, —NR$^{31}$R$^{32}$, —SR$^{33}$, and —SO$_2$R$^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, NR$^{14}$R$^{15}$, and —OR$^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^4$ is selected from the group consisting of H, NH$_2$, N$_3$, protected amino group, OH, —OPg$^{2k}$, and halogen; wherein Pg$^{2k}$ is a hydroxyl protecting group;

$R^{4a}$ and $R^{4b}$ are, independently H, —OH, —OR$^{40}$, —NR$^{41}$R$^{42}$, or halogen;

wherein each $R^{40}$, $R^{41}$, and $R^{42}$ are independently H or alkyl; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^{5a}$ is H, —CN, —CONH$_2$ or C$_1$-C$_3$alkyl, wherein the alkyl is unsubstituted or substituted with one or more substituents selected from the group consisting of —OH, —NH$_2$, —CN, —CONH$_2$, and halogen;

$R^{6a}$ and $R^{6b}$ are, independently H, halogen, NH$_2$, —OH, C$_1$-C$_3$alkoxy, —OC(O)CH$_3$, or —OPg$^{2j}$;

wherein Pg$^{2j}$ is a hydroxyl protecting group;

$R^{8a}$ is H, C$_1$-C$_6$ alkyl, an amino protecting group, or wherein

Q$^1$ is NH, O, or S;

z is an integer from 0 to 4, $R^{35z}$ is H or C$_1$-C$_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39}$R$^{40z}$, wherein R$^{39z}$ and R$^{40z}$ are independently H or C$_1$-C$_3$ alkyl; or $R^{35z}$ and $R^{38z}$, together with the atoms to which they are attached, form a heterocycloalkyl group comprising at least one N;

$R^{11}$ is H, alkyl, —COCH$_3$, or a hydroxyl protecting group;

N$^{1m}$ is —NHPg$^{1m}$, —NH$_2$, or N$_3$, wherein Pg$^{1m}$ is an amino protecting group;

N$^{1n}$ is —NHPg$^{1n}$, —NH$_2$, or N$_3$, wherein Pg$^{1n}$ is an amino protecting group;

m is zero, 1, or 2;

n is zero, 1, or 2;

wherein m+n is 1, 2 or 3;

o is zero, 1, or 2;

p is zero, 1, or 2;

wherein o+p is 1, 2 or 3.

The present disclosure provides a compound of formula AB-4':

AB-4' and salts, solvates, enantiomers, and diastereomers thereof, wherein $R^{1a}$ and $R^{1b}$ are independently selected from the group consisting of H, C$_1$-C$_{12}$ alkyl, C$_1$-C$_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —N$_3$, and —OR$^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, NR$^{14}$R$^{15}$, and —OR$^{16}$;

$R^{2a}$, $R^{2b}$, $R^{3a}$ and $R^{3b}$ are independently selected from the group consisting of H, —OR$^{27}$, —NR$^{28}$R$^{29}$, halogen, C$_1$-C$_4$ cycloalkyl, and C$_1$-C$_6$ alkyl, wherein each $R^{27}$, $R^{28}$, and $R^{29}$ is independently H, alkyl, amino protecting group, or hydroxyl protecting group; wherein the C$_1$-C$_6$ alkyl or alkyl is unsubstituted or substituted with one or more substituents selected from the group consisting of aryl, halogen, —OR$^{30}$, —NR$^{31}$R$^{32}$, —SR$^{33}$, and —SO$_2$R$^{34}$;

wherein each $R^{30}$, $R^{31}$, $R^{32}$, $R^{33}$, and $R^{34}$ is H or alkyl substituted with one or more substituents independently selected from the group consisting of halogen, cyano, NR$^{14}$R$^{15}$, and —OR$^{16}$; or $R^{2a}$ and $R^{2b}$ form an oxo or imino group substituted with C$_1$-C$_6$ alkyl;

$R^{3a}$ and $R^{3b}$ form an oxo or imino group substituted with C$_1$-C$_6$ alkyl;

$X^4$ is selected from the group consisting of H, NH$_2$, N$_3$, protected amino group, OH, —OPg$^{2k}$, and halogen; wherein Pg$^{2k}$ is a hydroxyl protecting group;

$R^{4aa}$ and $R^{4bb}$ are, independently H, —OH, —OR$^{40}$, —NR$^{41}$R$^{42}$, or halogen;

wherein each $R^{40}$, $R^{41}$, and $R^{42}$ are independently H, alkyl, —CONH$_2$, or —COCH$_3$; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^{5aa}$ is H, —CN, —CONH$_2$ or C$_1$-C$_3$alkyl, wherein the alkyl is unsubstituted or substituted with one or more substituents selected from the group consisting of —OH, —OC(O)CH$_3$, —NH$_2$, —CN, —CONH$_2$, and halogen;

$R^{6a}$ and $R^{6b}$ are, independently H, halogen, NH$_2$, —OH, C$_1$-C$_3$alkoxy, —OC(O)CH$_3$, or —OPg$^{2j}$; wherein Pg$^{2j}$ is a hydroxyl protecting group;

N$^{1s}$ is N$_3$ or —NR$^{8a}$R$^{8b}$;

$R^{8a}$ is H, C$_1$-C$_6$ alkyl, an amino protecting group, or wherein

Q$^1$ is NH, O, or S;

z is an integer from 0 to 4, $R^{35z}$ is H or C$_1$-C$_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{8b}$ is H or $C_1$-$C_3$alkyl;

$R^{11}$ is H, alkyl, —COCH$_3$, or a hydroxyl protecting group;

$N^{1m}$ is —OH, protected hydroxyl group, —NHPg$^{1m}$, N(Pg$^{1m}$)$_2$, —NH$_2$, or N$_3$, wherein each Pg$^{1m}$ is independently an amino protecting group;

$N^{1n}$ is —NHPg$^{1n}$, —NH$_2$, or N$_3$, wherein Pg$^{1n}$ is an amino protecting group;

m is zero, 1, or 2;

n is zero, 1, or 2;

wherein m+n is 1, 2 or 3;

o is zero, 1, or 2;

p is zero, 1, or 2;

wherein o+p is 1, 2 or 3.

The present disclosure provides a compound of formula AB-5:

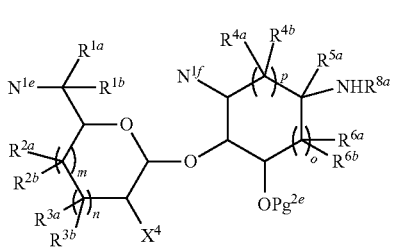

AB-5 and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^3$, —OSF$_2$NR$^{14}$R$^{15}$, —NR$^{14}$R$^{15}$, —N$_3$, and —OR$^{16}$, and wherein each $R^1$, $R^{13}$, $R^{14}$, $R^1$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, NR$^{14}$R$^{15}$, and —OR$^{16}$;

$R^{2a}$, $R^{2b}$, $R^{3a}$ and $R^{3b}$ are independently selected from the group consisting of H, —OR$^{27}$, —NR$^{28}$R$^{29}$, halogen, $C_1$-$C_4$ cycloalkyl, and $C_1$-$C_6$ alkyl, wherein each R$^{27}$, R$^{28}$, and R$^{29}$ is independently H or alkyl; wherein the $C_1$-$C_6$ alkyl or alkyl is unsubstituted or substituted with one or more substituents selected from the group consisting of halogen, —OR$^{30}$, —NR$^{31}$R$^{32}$, —SR$^{33}$, and —SO$_2$R$^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, NR$^{14}$R$^{15}$, and —OR$^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$R^{4a}$ and $R^{4b}$ are, independently H, —OH, —OR$^{40}$, —NR$^{41}$R$^{42}$, or halogen;

wherein each $R^{40}$, $R^{41}$, and $R^{42}$ are independently H or alkyl;

wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^{5a}$ is H, —CN, —CONH$_2$ or $C_1$-$C_3$alkyl, wherein the alkyl is unsubstituted or substituted with one or more substituents selected from the group consisting of —OH, —NH$_2$, —CN, —CONH$_2$, and halogen;

$R^{6a}$ and $R^{6b}$ are, independently H, halogen, NH$_2$, —OH, $C_1$-$C_3$alkoxy, —OC(O)CH$_3$, or —OPg$^{2m}$; wherein Pg$^{2m}$ is a hydroxyl protecting group;

$R^{8a}$ is H, $C_1$-$C_6$ alkyl, an amino protecting group, or

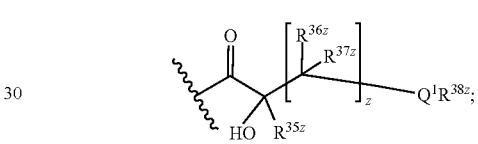

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$N^{1e}$ is —NHPg$^{1e}$ or N$_3$, wherein Pg$^{1e}$ is an amino protecting group;

$N^{1f}$ is —NHPg$^{1f}$ or N$_3$, wherein Pg$^{1f}$ is an amino protecting group;

Pg$^{2e}$ is a hydroxyl protecting group;

X is —NH$_2$, —N$_3$, protected amino group, —OH, or protected hydroxyl group;

wherein at least one of $N^{1e}$ and $N^{1f}$ is not NH$_2$ or wherein PG$^{2e}$ is not H or wherein X is not —OH or —NH$_2$;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

The present disclosure provides a compound of formula AB-5':

139

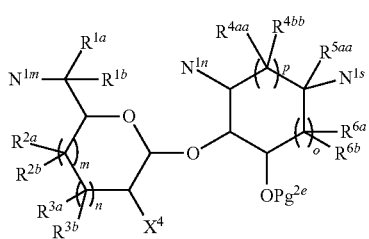

AB-5' and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$R^{4aa}$ and $R^{4bb}$ are, independently H, —OH, —$OR^{40}$, —$NR^{41}R^{42}$, or halogen;

wherein each $R^{40}$, $R^{41}$, and $R^{42}$ are independently H, alkyl, —$CONH_2$, or —$COCH_3$; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5aa}$ is H, —CN, —$CONH_2$ or $C_1$-$C_3$alkyl, wherein the alkyl is unsubstituted or substituted with one or more substituents selected from the group consisting of —OH, —$OC(O)CH_3$, —$NH_2$, —CN, —$CONH_2$, and halogen;

$R^{6a}$ and $R^{6b}$ are, independently H, halogen, $NH_2$, —OH, $C_1$-$C_3$alkoxy, —$OC(O)CH_3$, or —$OPg^{2m}$; wherein $Pg^{2m}$ is a hydroxyl protecting group;

140

$N^{1s}$ is $N_3$ or —$NR^{8a}R^{8b}$;

$R^{8a}$ is H, $C_1$-$C_6$ alkyl, an amino protecting group, or

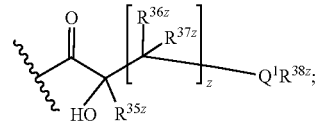

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{8b}$ is H or $C_1$-$C_3$alkyl;

$N^{1m}$ is —OH, protected hydroxyl group, —$NHPg^{1m}$, $N(Pg^{1m})_2$, —$NH_2$, or $N_3$, wherein each $Pg^{1m}$ is independently an amino protecting group;

$N^{1n}$ is —$NHPg^{1n}$, —$NH_2$, or $N_3$, wherein $Pg^{1n}$ is an amino protecting group;

$Pg^{2e}$ is H or a hydroxyl protecting group;

$X^4$ is selected from the group consisting of H, $NH_2$, $N_3$, protected amino group, OH, —$OPg^{2k}$, and halogen; wherein $Pg^{2k}$ is a hydroxyl protecting group;

wherein at least one of $N^{1m}$ and $N^{1n}$ is not $NH_2$ or wherein $PG^{2e}$ is not H or wherein $X^4$ is not —OH or —$NH_2$;

m is zero, 1, or 2;

n is zero, 1, or 2;

wherein m+n is 1, 2 or 3;

o is zero, 1, or 2;

p is zero, 1, or 2;

wherein o+p is 1, 2 or 3.

The present disclosure provides a compound of formula AB-1:

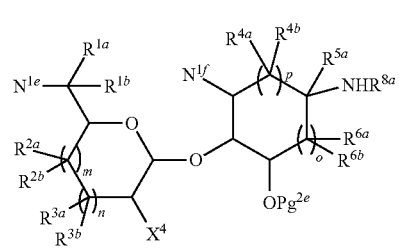

AB-1 and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$R^{4a}$ and $R^{4b}$ are, independently H, —OH, —$OR^{40}$, —$NR^{41}R^{42}$, or halogen;

wherein each $R^{40}$, $R^{41}$, and $R^{42}$ are independently H or alkyl;

wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5a}$ is H, —CN, —$CONH_2$ or $C_1$-$C_3$alkyl, wherein the alkyl is unsubstituted or substituted with one or more substituents selected from the group consisting of —OH, —$NH_2$, —CN, —$CONH_2$, and halogen;

$R^{6a}$ and $R^{6b}$ are, independently H, halogen, $NH_2$, —OH, $C_1$-$C_3$alkoxy, —$OC(O)CH_3$, or —$OPg^{2m}$; wherein $Pg^{2m}$ is a hydroxyl protecting group;

$R^{8a}$ is H, $C_1$-$C_6$ alkyl, an amino protecting group, or

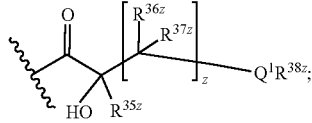

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$N^{1e}$ is —$NHPg^{1e}$ or $N_3$, wherein $Pg^{1e}$ is an amino protecting group;

$N^{1f}$ is —$NHPg^{1f}$ or $N_3$, wherein $Pg^{1f}$ is an amino protecting group;

$Pg^{2e}$ is a hydroxyl protecting group;

X is —$NH_2$, —$N_3$, protected amino group, —OH, or protected hydroxyl group;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

The present disclosure provides a compound of formula AB-1':

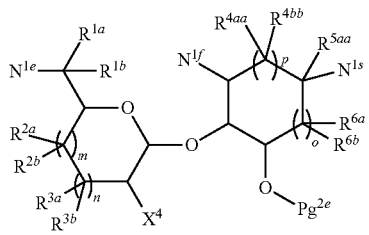

AB-1' and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$R^{4aa}$ and $R^{4bb}$ are, independently H, —OH, —$OR^{40}$, —$NR^{41}R^{42}$, or halogen;

wherein each $R^{40}$, $R^{41}$, and $R^{42}$ are independently H, alkyl, —$CONH_2$, or —$COCH_3$; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

R$^{5aa}$ is H, —CN, —CONH$_2$ or C$_1$-C$_3$alkyl, wherein the alkyl is unsubstituted or substituted with one or more substituents selected from the group consisting of —OH, —OC(O)CH$_3$, —NH$_2$, —CN, —CONH$_2$, and halogen;

R$^{6a}$ and R$^{6b}$ are, independently H, halogen, NH$_2$, —OH, C$_1$-C$_3$alkoxy, —OC(O)CH$_3$, or —OPg$^{2m}$; wherein Pg$^{2m}$ is a hydroxyl protecting group;

N$^{1s}$ is N$_3$ or —NR$^{8a}$R$^{8b}$;

R$^{8a}$ is H, C$_1$-C$_6$ alkyl, an amino protecting group, or wherein
Q$^1$ is NH, O, or S;
z is an integer from 0 to 4,
R$^{35z}$ is H or C$_1$-C$_3$ alkyl;
each R$^{36z}$ and R$^{37z}$ is independently selected from the group consisting of H, alkyl, halogen, and —OH, and
R$^{38z}$ is H, alkyl, or —C(=NH)NR$^{39z}$R$^{40z}$, wherein R$^{39z}$ and R$^{40z}$ are independently H or C$_1$-C$_3$ alkyl; or
R$^{35z}$ and R$^{38z}$, together with the atoms to which they are attached, form a heterocycloalkyl group comprising at least one N;

R$^{8b}$ is H or C$_1$-C$_3$alkyl;

N$^{1e}$ is —OH, protected hydroxyl group, —NHPg$^{1e}$, N(Pg$^{1e}$)$_2$, —NH$_2$, or N$_3$, wherein each Pg$^{1e}$ is independently an amino protecting group;

N$^{1f}$ is —NHPg$^{1f}$ or N$_3$, wherein Pg$^{1f}$ is an amino protecting group;

Pg$^{2e}$ is a hydroxyl protecting group;

X$^4$ is selected from the group consisting of H, NH$_2$, N$_3$, protected amino group, OH, —OPg$^{2k}$, and halogen; wherein Pg$^{2k}$ is a hydroxyl protecting group;

m is zero, 1, or 2;
n is zero, 1, or 2;
wherein m+n is 1, 2 or 3;
o is zero, 1, or 2;
p is zero, 1, or 2;
wherein o+p is 1, 2 or 3.

The present disclosure provides a compound of formula AB-2:

AB-2 and salts, solvates, enantiomers, and diastereomers thereof, wherein

R$^{1a}$ and R$^{1b}$ are independently selected from the group consisting of H, C$_1$-C$_{12}$ alkyl, C$_1$-C$_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —N$_3$, and —OR$^{16}$ and wherein each R$^{12}$, R$^{13}$, R$^{14}$, R$^{15}$, and R$^{16}$ is independently H or alkyl; or R$^{1a}$ and R$^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each R$^{22}$, R$^{23}$, R$^{24}$, R$^{29}$, and R$^{26}$ is independently H or alkyl, wherein the alkyl is unsubstituted or substituted with one or more substituents independently selected from the group consisting of halogen, cyano, NR$^{14}$R$^{15}$, and —OR$^{16}$;

R$^{2a}$, R$^{2b}$, R$^{3a}$ and R$^{3b}$ are independently selected from the group consisting of H, —OR$^{27}$, —NR$^{28}$R$^{29}$, halogen, C$_1$-C$_4$ cycloalkyl, and C$_1$-C$_6$ alkyl, wherein each R$^{27}$, R$^{28}$, and R$^{29}$ is independently H or alkyl; wherein the C$_1$-C$_6$ alkyl or alkyl is unsubstituted or substituted with one or more substituents selected from the group consisting of halogen, —OR$^{30}$, —NR$^{31}$R$^{32}$, —SR$^{33}$, and —SO$_2$R$^{34}$;

wherein each R$^{30}$, R$^{31}$, R$^{32}$, R$^{33}$, and R$^{34}$ is H or alkyl substituted with one or more substituents independently selected from the group consisting of halogen, cyano, NR$^{14}$R$^{15}$, and —OR$^{16}$; or R$^{2a}$ and R$^{2b}$ form an oxo or imino group substituted with C$_1$-C$_6$ alkyl;

R$^{3a}$ and R$^{3b}$ form an oxo or imino group substituted with C$_1$-C$_6$ alkyl;

R$^{4a}$ and R$^{4b}$ are, independently H, —OH, —OR$^{40}$, —NR$^{41}$R$^{42}$, or halogen;

wherein each R$^{40}$, R$^{41}$, and R$^{42}$ are independently H or alkyl;

wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

R$^{5a}$ is H, —CN, —CONH$_2$ or C$_1$-C$_3$alkyl, wherein the alkyl is unsubstituted or substituted with one or more substituents selected from the group consisting of —OH, —NH$_2$, —CN, —CONH$_2$, and halogen;

R$^{6a}$ and R$^{6b}$ are, independently H, halogen, NH$_2$, —OH, C$_1$-C$_3$alkoxy, —OC(O)CH$_3$, or —OPg$^{2m}$; wherein Pg$^{2m}$ is a hydroxyl protecting group;

R$^{8a}$ is H, C$_1$-C$_6$ alkyl, an amino protecting group, or wherein
Q$^1$ is NH, O, or S;
z is an integer from 0 to 4,
R$^{35z}$ is H or C$_1$-C$_3$ alkyl;
each R$^{36z}$ and R$^{37z}$ is independently selected from the group consisting of H, alkyl, halogen, and —OH, and
R$^{38z}$ is H, alkyl, or —C(=NH)NR$^{39z}$R$^{40z}$, wherein R$^{39z}$ and R$^{40z}$ are independently H or C$_1$-C$_3$ alkyl; or $R^{35z}$ and $R^{38z}$, together with the atoms to which they are attached, form a heterocycloalkyl group comprising at least one N;

X is —NH$_2$ or —OH;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

The present disclosure provides a compound of formula AB-2":

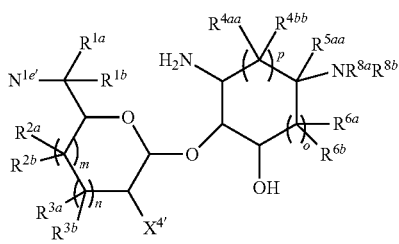

AB-2"

and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —N$_3$, and —OR$^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, NR$^{14}$R$^{15}$, and —OR$^{16}$;

$R^{2a}$, $R^{2b}$, $R^{3a}$ and $R^{3b}$ are independently selected from the group consisting of H, —OR$^{27}$, —NR$^{28}$R$^{29}$, halogen, $C_1$-$C_4$ cycloalkyl, and $C_1$-$C_6$ alkyl, wherein each $R^{27}$, $R^{28}$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, —OR$^{30}$, —NR$^{31}$R$^{32}$, —SR$^{33}$, and —SO$_2$R$^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, NR$^{14}$R$^{15}$, and —OR$^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$R^{4aa}$ and $R^{4bb}$ are, independently H, —OH, —OR$^{40}$, —NR$^{41}$R$^{42}$, or halogen;

wherein each $R^{40}$, $R^{41}$, and $R^{42}$ are independently H, alkyl, —CONH$_2$, or —COCH$_3$; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^{5aa}$ is H, —CN, —CONH$_2$ or $C_1$-$C_3$alkyl, wherein the alkyl is unsubstituted or substituted with one or more substituents selected from the group consisting of —OH, —OC(O)CH$_3$, —NH$_2$, —CN, —CONH$_2$, and halogen;

$R^{6a}$ and $R^{6b}$ are, independently H, halogen, NH$_2$, —OH, $C_1$-$C_3$alkoxy, —OC(O)CH$_3$, or —OPg$^{2m}$; wherein Pg$^{2m}$ is a hydroxyl protecting group;

$R^{8a}$ is H, $C_1$-$C_6$ alkyl, an amino protecting group, or

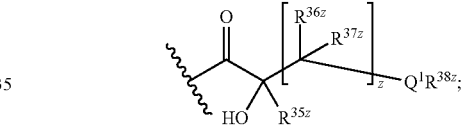

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$N^{1e}$ is —OH or —NH$_2$;

$R^{8b}$ is H or $C_1$-$C_3$alkyl;

$X^{4'}$ is selected from the group consisting of H, NH$_2$, OH, and halogen;

m is zero, 1, or 2;

n is zero, 1, or 2;

wherein m+n is 1, 2 or 3;

o is zero, 1, or 2;

p is zero, 1, or 2;

wherein o+p is 1, 2 or 3.

Compounds of Formula ABC

The present disclosure provides a compound of formula ABC-3:

ABC-3

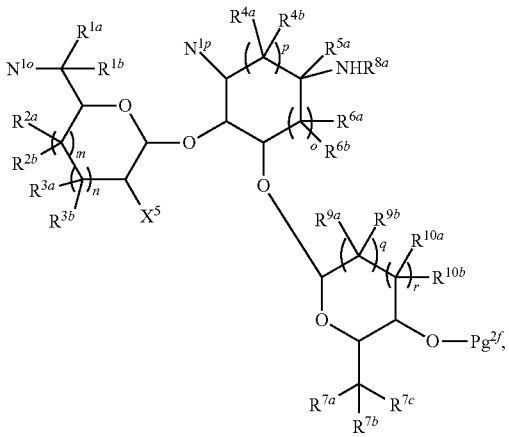

and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^5$ is selected from the group consisting of H, $NH_2$, $N_3$, protected amino group, OH, —$OPg^{2l}$, and halogen; wherein $Pg^{2l}$ is a hydroxyl protecting group;

$R^{4a}$ and $R^{4b}$ are, independently H, —OH, —$OR^{40}$, —$NR^{41}R^{42}$, or halogen;

wherein each $R^{40}$, $R^{41}$, and $R^{42}$ are independently H or alkyl; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5a}$ is H, —CN, —$CONH_2$ or $C_1$-$C_3$alkyl, wherein the alkyl is unsubstituted or substituted with one or more substituents selected from the group consisting of —OH, —$NH_2$, —CN, —$CONH_2$, and halogen;

$R^{6a}$ and $R^{6b}$ are, independently H, halogen, $NH_2$, —OH, $C_1$-$C_3$alkoxy, —$OC(O)CH_3$, or —$OPg^{2j}$;

wherein $Pg^{2j}$ is a hydroxyl protecting group;

$R^{7a}$, $R^{7b}$, and $R^{7c}$ are, independently, H, OH, —$OR^{71}$ or —$OPg^2$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, and substituted heteroaryl;

wherein $Pg^2$ is a hydroxyl protecting group;

$R^{8a}$ is H, $C_1$-$C_6$ alkyl, an amino protecting group, or

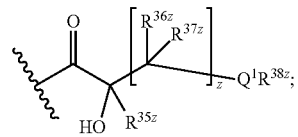

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —$C(=NH)NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$N^{1o}$ is —$NHPg^{1o}$, —$NH_2$, or $N_3$, wherein $Pg^{1o}$ is an amino protecting group;

$N^{1p}$ is —$NHPg^{1p}$, —$NH_2$, or $N_3$, wherein $Pg^{1p}$ is an amino protecting group;

$Pg^{2f}$ is a hydroxyl protecting group or H;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

The present disclosure provides a compound of formula ABC-3':

ABC-3

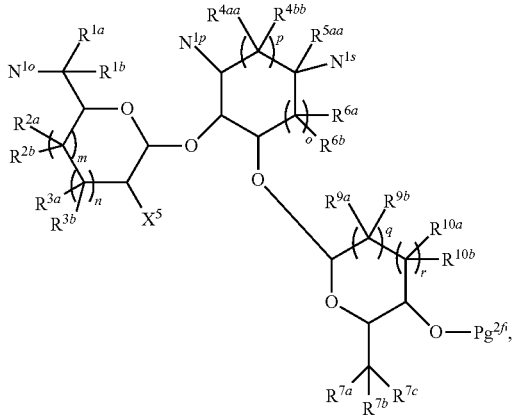

and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^5$ is selected from the group consisting of H, $NH_2$, $N_3$, protected amino group, OH, —$OPg^{2l}$, and halogen; wherein $Pg^{2l}$ is a hydroxyl protecting group;

$R^{4aa}$ and $R^{4bb}$ are, independently, H, —OH, —$OR^{40}$, —$NR^{41}R^{42}$, or halogen;

wherein each $R^{40}$, $R^{41}$, and $R^{42}$ are independently H, alkyl, —$CONH_2$, or —$COCH_3$; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5aa}$ is H, —CN, —$CONH_2$ or $C_1$-$C_3$alkyl, wherein the alkyl is unsubstituted or substituted with one or more substituents selected from the group consisting of —OH, —OC(O)$CH_3$, —$NH_2$, —CN, —$CONH_2$, and halogen;

$R^{6a}$ and $R^{6b}$ are, independently H, halogen, $NH_2$, —OH, $C_1$-$C_3$alkoxy, —OC(O)$CH_3$, or —$OPg^{2j}$;

wherein $Pg^{2j}$ is a hydroxyl protecting group;

$R^{7a}$, $R^{7b}$, and $R^{7c}$ are, independently, H, OH, —$OR^{71}$ or —$OPg^2$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, and substituted heteroaryl; wherein $Pg^2$ is a hydroxyl protecting group;

$N^{1s}$ is $N_3$ or —$NR^{8a}R^{8b}$;

$R^{8a}$ is H, $C_1$-$C_6$ alkyl, an amino protecting group, or

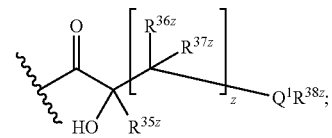

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{8b}$ is H or $C_1$-$C_3$alkyl;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$N^{1o}$ is —OH, protected hydroxyl group, —$NHPg^{1o}$, $N(Pg^{1o})_2$, —$NH_2$, or $N_3$, wherein each $Pg^{1o}$ is independently an amino protecting group;

$N^{1p}$ is —$NHPg^{1p}$, —$NH_2$, or $N_3$, wherein $Pg^{1p}$ is an amino protecting group;

$Pg^{2f}$ is a hydroxyl protecting group or H;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

The present disclosure provides a compound of formula ABC-4:

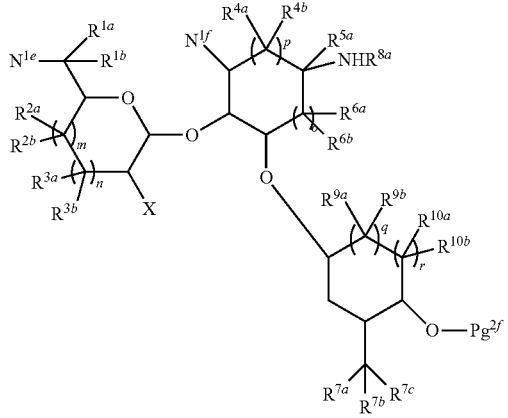

and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$N^2R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$ and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

X is —$NH_2$, —$N_3$, protected amino group, —OH, or protected hydroxyl group;

$R^{4a}$ and $R^{4b}$ are, independently H, —OH, —$OR^{40}$, —$NR^{41}R^{42}$, or halogen;

wherein each $R^{40}$, $R^{41}$, and $R^{42}$ are independently H or alkyl; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5a}$ is H, —CN, —$CONH_2$ or $C_1$-$C_3$alkyl, wherein the alkyl is unsubstituted or substituted with one or more substituents selected from the group consisting of —OH, —$NH_2$, —CN, —$CONH_2$, and halogen;

$R^{6a}$ and $R^{6b}$ are, independently H, halogen, $NH_2$, —OH, $C_1$-$C_3$alkoxy, —$OC(O)CH_3$, or —$OPg^{2j}$;

wherein $Pg^{2j}$ is a hydroxyl protecting group;

$R^{7a}$, $R^{7b}$, and $R^{7c}$ are, independently, H, OH, —$OR^{71}$ or —$OPg^2$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, and substituted heteroaryl;

wherein $Pg^2$ is a hydroxyl protecting group;

$R^{8a}$ is H, $C_1$-$C_6$ alkyl, an amino protecting group, or

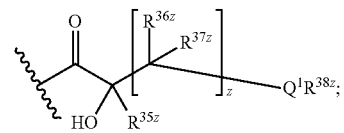

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$N^{1o}$ is —$NHPg^{1o}$, —$NH_2$, or $N_3$, wherein $Pg^{1o}$ is an amino protecting group;

$N^{1p}$ is —$NHPg^{1p}$, —$NH_2$, or $N_3$, wherein $Pg^{1p}$ is an amino protecting group;

$Pg^{2f}$ is a hydroxyl protecting group or H;

wherein at least one of $N^{1e}$ and $N^{1f}$ is not $NH_2$ or wherein $Pg^{2f}$ is not H or wherein X is not —OH or —$NH_2$;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

The present disclosure provides a compound of formula ABC-4':

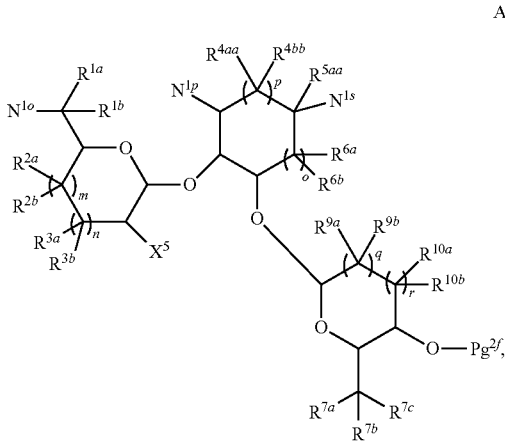

and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^5$ is selected from the group consisting of H, $NH_2$, $N_3$, protected amino group, OH, —$OPg^{2l}$, and halogen; wherein $Pg^{2l}$ is a hydroxyl protecting group;

$R^{4aa}$ and $R^{4bb}$ are, independently, H, —OH, —$OR^{40}$, —$NR^{41}R^{42}$, or halogen;

wherein each $R^{40}$, $R^{41}$, and $R^{42}$ are independently H, alkyl, —$CONH_2$, or —$COCH_3$; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5aa}$ is H, —CN, —$CONH_2$ or $C_1$-$C_3$alkyl, wherein the alkyl is unsubstituted or substituted with one or more substituents selected from the group consisting of —OH, —$OC(O)CH_3$, —$NH_2$, —CN, —$CONH_2$, and halogen;

$R^{6a}$ and $R^{6b}$ are, independently H, halogen, $NH_2$, —OH, $C_1$-$C_3$alkoxy, —$OC(O)CH_3$, or —$OPg^{2j}$;

wherein $Pg^{2j}$ is a hydroxyl protecting group;

$R^{7a}$, $R^{7b}$, and $R^{7c}$ are, independently, H, OH, —$OR^{71}$ or —$OPg^2$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, and substituted heteroaryl;

wherein $Pg^2$ is a hydroxyl protecting group;

$N^{1s}$ is $N_3$ or —$NR^{8a}R^{8b}$;

$R^{8a}$ is H, $C_1$-$C_6$ alkyl, an amino protecting group, or

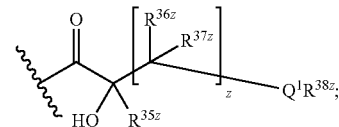

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{8b}$ is H or $C_1$-$C_3$alkyl;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$N^{1o}$ is —OH, protected hydroxyl group, —$NHPg^{1o}$, $N(Pg^{1o})_2$, —$NH_2$, or $N_3$, wherein each $Pg^{1o}$ is independently an amino protecting group;

$N^{1p}$ is —$NHPg^{1p}$, —$NH_2$, or $N_3$, wherein $Pg^{1p}$ is an amino protecting group;

$Pg^{2f}$ is a hydroxyl protecting group or H;

wherein at least one of $N^{1o}$ and $N^{1p}$ is not $NH_2$ or wherein $Pg^{2f}$ is not H or wherein $X^5$ is not —OH or —$NH_2$;

m is zero, 1, or 2;

n is zero, 1, or 2;

wherein m+n is 1, 2 or 3;

o is zero, 1, or 2;

p is zero, 1, or 2;
wherein o+p is 1, 2 or 3;
q is zero, 1, or 2;
r is zero, 1, or 2;
wherein q+r is 1, 2 or 3.

The present disclosure provides a compound of formula ABC-1:

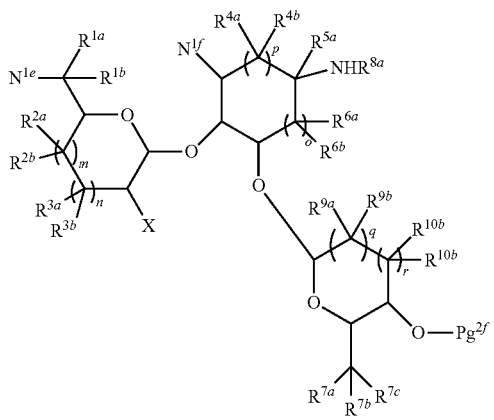

and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, $-SR^{12}$, $-SO_2R^{13}$, $-OSF_2NR^{14}R^{15}$, $-NR^{14}R^{15}$, $-N_3$, and $-OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, $-SR^{22}$, $-SO_2R^{23}$, $-NR^{24}R^{25}$, and $-OR^{26}$, and wherein each $R^{22}$, $R^{23}$, $R^{24}$, $R^{29}$, and $R^{26}$ is independently H or alkyl, wherein the alkyl is unsubstituted or substituted with one or more substituents independently selected from the group consisting of halogen, cyano, $NR^{14}R^{15}$, and $-OR^{16}$;

$R^{2a}$, $R^{2b}$, $R^{3a}$ and $R^{3b}$ are independently selected from the group consisting of H, $-OR^{27}$, $-NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, $-OR^{30}$, $-NR^{31}R^{32}$, $-SR^{33}$, and $-SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and $-OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

X is $-NH_2$, $-N_3$, protected amino group, $-OH$, or protected hydroxyl group;

$R^{4a}$ and $R^{4b}$ are, independently H, $-OH$, $-OR^{40}$, $-NR^{41}R^{42}$, or halogen;

wherein each $R^{40}$, $R^{41}$, and $R^{42}$ are independently H or alkyl; wherein the alkyl is unsubstituted or substituted with one or more substituents selected from the group consisting of $-CONH_2$, $-OH$, $-NH_2$, $-COCH_3$, aryl, substituted aryl, heteroaryl, halogen, and substituted heteroaryl;

$R^{5a}$ is H, $-CN$, $-CONH_2$ or $C_1$-$C_3$alkyl, wherein the alkyl is unsubstituted or substituted with one or more substituents selected from the group consisting of $-OH$, $-NH_2$, $-CN$, $-CONH_2$, and halogen;

$R^{6a}$ and $R^{6b}$ are, independently H, halogen, $NH_2$, $-OH$, $C_1$-$C_3$alkoxy, $-OC(O)CH_3$, or $-OPg^{2j}$;

wherein $Pg^{2j}$ is a hydroxyl protecting group;

$R^{7a}$, $R^{7b}$, and $R^{7c}$ are, independently, H, OH, $-OR^{71}$ or $-OPg^2$;

wherein $R^{71}$ is alkyl; wherein the alkyl is unsubstituted or substituted with one or more substituents selected from the group consisting of $-CONH_2$, $-OH$, $-NH_2$, $-COCH_3$, aryl, substituted aryl, heteroaryl, and substituted heteroaryl;

wherein $Pg^2$ is a hydroxyl protecting group;

$R^{8a}$ is H, $C_1$-$C_6$ alkyl, an amino protecting group, or

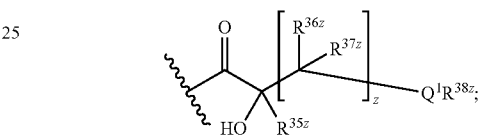

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and $-OH$, and $R^{38z}$ is H, alkyl, or $-C(=NH)NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{9a}$ and $R^{9b}$ are independently H, OH, or $-OR^{91}$, wherein $R^{91}$ is alkyl, alkenyl, or alkynyl; wherein the alkyl, alkenyl, and alkynyl is unsubstituted or substituted with one or more substituents selected from the group consisting of $-CONH_2$, $-OH$, $-NH_2$, $-COCH_3$, aryl, substituted aryl, heteroaryl, and substituted heteroaryl;

$R^{10a}$ and $R^{10b}$ are independently H, OH, or $-OR^{101}$, wherein $R^{101}$ is alkyl, alkenyl, or alkynyl; wherein the alkyl, alkenyl, and alkynyl is unsubstituted or substituted with one or more substituents selected from the group consisting of $-CONH_2$, $-OH$, $-NH_2$, $-COCH_3$, aryl, substituted aryl, heteroaryl, and substituted heteroaryl;

$N^{1e}$ is $-NHPg^{1e}$ or $N_3$, wherein $Pg^{1e}$ is an amino protecting group;

$N^{1f}$ is $-NHPg^{1f}$ or $N_3$, wherein $Pg^{1f}$ is an amino protecting group;

$Pg^{2f}$ is a hydroxyl protecting group;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

The present disclosure provides a compound of formula ABC-1':

ABC-1' and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$ and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^5$ is selected from the group consisting of H, $NH_2$, $N_3$, protected amino group, OH, —$OPg^{2l}$, and halogen; wherein $Pg^{2l}$ is a hydroxyl protecting group;

$R^{4aa}$ and $R^{4bb}$ are, independently H, —OH, —$OR^{40}$, —$NR^{41}R^{42}$, or halogen;

wherein each $R^{40}$, $R^{41}$, and $R^{42}$ are independently H, alkyl, —$CONH_2$, or —$COCH_3$; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5aa}$ is H, —CN, —$CONH_2$ or $C_1$-$C_3$alkyl, wherein the alkyl is unsubstituted or substituted with one or more substituents selected from the group consisting of —OH, —$OC(O)CH_3$, —$NH_2$, —CN, —$CONH_2$, and halogen;

$R^{6a}$ and $R^{6b}$ are, independently H, halogen, $NH_2$, —OH, $C_1$-$C_3$alkoxy, —$OC(O)CH_3$, or —$OPg^{2j}$;

wherein $Pg^{2j}$ is a hydroxyl protecting group;

$R^{7a}$, $R^{7b}$, and $R^{7c}$ are, independently, H, OH, —$OR^{71}$ or —$OPg^2$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, and substituted heteroaryl;

wherein $Pg^2$ is a hydroxyl protecting group;

$N^{1s}$ is $N_3$ or —$NR^{8a}R^{8b}$;

$R^{8a}$ is H, $C_1$-$C_6$ alkyl, an amino protecting group, or wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{8b}$ is H or $C_1$-$C_3$alkyl;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$N^{1e}$ is —OH, protected hydroxyl group, —$NHPg^{1e}$ $N(Pg^{1e})_2$, —$NH_2$, or $N_3$, wherein each $Pg^{1e}$ is independently an amino protecting group;

$N^{1f}$ is —$NHPg^{1f}$ or $N_3$, wherein $Pg^{1f}$ is an amino protecting group;

$Pg^{2f}$ is a hydroxyl protecting group;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;
r is zero, 1, or 2;
wherein q+r is 1, 2 or 3.

The present disclosure provides a compound of formula ABC-2:

ABC-2 and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{29}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

X is —$NH_2$ or —OH;

$R^{4a}$ and $R^{4b}$ are, independently H, —OH, —$OR^{40}$, —$NR^{41}R^{42}$, or halogen;

wherein each $R^{40}$, $R^{41}$, and $R^{42}$ are independently H or alkyl; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5a}$ is H, —CN, —$CONH_2$ or $C_1$-$C_3$alkyl, wherein the alkyl is unsubstituted or substituted with one or more substituents selected from the group consisting of —OH, —$NH_2$, —CN, —$CONH_2$, and halogen;

$R^{6a}$ and $R^{6b}$ are, independently H, halogen, $NH_2$, —OH, $C_1$-$C_3$alkoxy, —OC(O)$CH_3$, or —$OPg^{2j}$; wherein $Pg^{2j}$ is a hydroxyl protecting group;

$R^{7a}$, $R^{7b}$, and $R^{7c}$ are, independently, H, OH, —$OR^{71}$ or —$OPg^2$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, and substituted heteroaryl;

wherein $Pg^2$ is a hydroxyl protecting group;

$R^{8a}$ is H, $C_1$-$C_6$ alkyl, an amino protecting group, or wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

The present disclosure provides a compound of formula ABC-2":

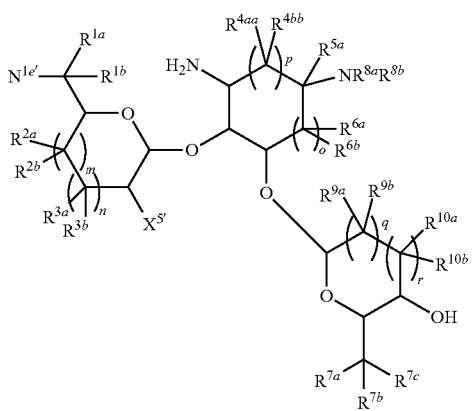

ABC-2'' and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^1$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^{5'}$ is selected from the group consisting of H, $NH_2$, OH, and halogen;

$R^{4aa}$ and $R^{4bb}$ are, independently, H, —OH, —$OR^{40}$, —$NR^{41}R^{42}$, or halogen;

wherein each $R^{40}$, $R^{41}$, and $R^{42}$ are independently H, alkyl, —$CONH_2$, or —$COCH_3$; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5aa}$ is H, —CN, —$CONH_2$ or $C_1$-$C_3$alkyl, wherein the alkyl is unsubstituted or substituted with one or more substituents selected from the group consisting of —OH, —$OC(O)CH_3$, —$NH_2$, —CN, —$CONH_2$, and halogen;

$R^{6a}$ and $R^{6b}$ are, independently H, halogen, $NH_2$, —OH, $C_1$-$C_3$alkoxy, —$OC(O)CH_3$, or —$OPg^{2j}$; wherein $Pg^{2j}$ is a hydroxyl protecting group;

$R^{7a}$, $R^{7b}$, and $R^{7c}$ are, independently, H, OH, —$OR^{71}$ or —$OPg^2$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, and substituted heteroaryl;

wherein $Pg^2$ is a hydroxyl protecting group;

$R^{8a}$ is H, $C_1$-$C_6$ alkyl, an amino protecting group, or

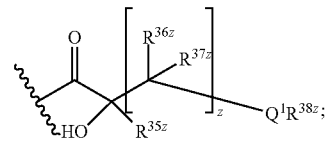

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38Z}$, together with the atoms to which they are attached, form a heterocycloalkyl group comprising at least one N;

$N^{1e'}$ is —OH or —$NH_2$;

$R^{8b}$ is H or $C_1$-$C_3$alkyl;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of—$CONH_2$, —OH, —$NH_2$, —$COCH_3$, aryl, substituted aryl, heteroaryl, and substituted heteroaryl;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

Compounds of Formula ABCD

The present disclosure provides a compound of formula ABCD-3:

ABCD-3 and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^3$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^6$ is selected from the group consisting of H, $NH_2$, $N_3$, protected amino group, OH, —$OPg^{2m}$, and halogen; wherein $Pg^{2m}$ is a hydroxyl protecting group;

$R^{4a}$ and $R^{4b}$ are, independently, H, —OH, —$OR^{40}$, —$NR^{41}R^{42}$, or halogen;

wherein each $R^{40}$, $R^{41}$, and $R^{42}$ are independently H or alkyl;

wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5a}$ is H, —CN, —$CONH_2$ or $C_1$-$C_3$alkyl, wherein the alkyl is unsubstituted or substituted with one or more substituents selected from the group consisting of —OH, —$NH_2$, —CN, —$CONH_2$, and halogen;

$R^{6a}$ and $R^{6b}$ are, independently H, halogen, $NH_2$, —OH, $C_1$-$C_3$alkoxy, —$OC(O)CH_3$, or —$OPg^{2j}$; wherein $Pg^{2j}$ is a hydroxyl protecting group;

$R^{7a}$, $R^{7b}$, and $R^{7c}$ are, independently, H, OH, —$OR^{71}$ or —$OPg^2$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, and substituted heteroaryl;

wherein $Pg^2$ is a hydroxyl protecting group;

$R^{8a}$ is H, $C_1$-$C_6$ alkyl, an amino protecting group, or wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$N^{1q}$ is —$NHPg^{1q}$ or $N_3$, wherein $Pg^{1q}$ is an amino protecting group;

$N^{1r}$ is —$NHPg^{1r}$ or $N_3$, wherein $Pg^{1r}$ is an amino protecting group;

$N^{1g}$ is —$NHPg^{1g}$ or $N_3$, wherein $Pg^{1g}$ is an amino protecting group;

$N^{1h}$ is —$NHPg^{1h}$ or $N_3$, wherein $Pg^{1h}$ is an amino protecting group;

$Pg^{2g}$ is a hydroxyl protecting group;

$Pg^{2h}$ is a hydroxyl protecting group;

wherein at least one of $N^{1q}$, $N^{1r}$, $N^{1g}$, $N^{1h}$ is not $NH_2$ or wherein at least one of $PG^{2g}$ or $Pg^{2h}$ is not H or wherein $X^6$ is not —OH or —$NH_2$;

m is zero, 1, or 2;

n is zero, 1, or 2;

wherein m+n is 1, 2 or 3;

o is zero, 1, or 2;

p is zero, 1, or 2;

wherein o+p is 1, 2 or 3;
q is zero, 1, or 2;
r is zero, 1, or 2;
wherein q+r is 1, 2 or 3.

The present disclosure provides a compound of formula ABCD-3':

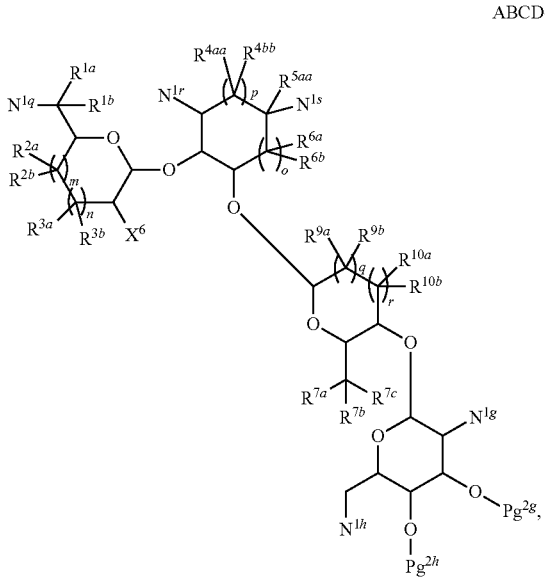

ABCD-3' and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{29}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^6$ is selected from the group consisting of H, $NH_2$, $N_3$, protected amino group, OH, —$OPg^{2m}$, and halogen; wherein $Pg^{2m}$ is a hydroxyl protecting group;

$R^{4aa}$ and $R^{4bb}$ are, independently H, —OH, —$OR^{40}$, —$NR^{41}R^{42}$, or halogen;

wherein each $R^{40}$, $R^{41}$, and $R^{42}$ are independently H, alkyl, —$CONH_2$, or —$COCH_3$; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5aa}$ is H, —CN, —$CONH_2$ or $C_1$-$C_3$alkyl, wherein the alkyl is unsubstituted or substituted with one or more substituents selected from the group consisting of —OH, —OC(O)$CH_3$, —$NH_2$, —CN, —$CONH_2$, and halogen;

$R^{6a}$ and $R^{6b}$ are, independently H, halogen, $NH_2$, —OH, $C_1$-$C_3$alkoxy, —OC(O)$CH_3$, or —$OPg^{2j}$; wherein $Pg^{2j}$ is a hydroxyl protecting group;

$R^{7a}$, $R^{7b}$, and $R^{7c}$ are, independently, H, OH, —$OR^{71}$ or —$OPg^2$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, and substituted heteroaryl;

wherein $Pg^2$ is a hydroxyl protecting group;

$N^{1s}$ is $N_3$ or —$NR^{8a}R^{8b}$;

$R^{8a}$ is H, $C_1$-$C_6$ alkyl, an amino protecting group, or

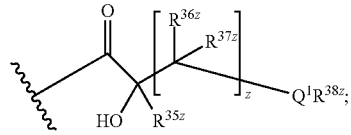

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{8b}$ is H or $C_1$-$C_3$alkyl;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$N^{1q}$ is —OH, protected hydroxyl group, —$NHPg^{1q}$, $N(Pg^{1q})_2$, —$NH_2$, or $N_3$, wherein each $Pg^{1i}$ is independently an amino protecting group;

$N^{1r}$ is —NHPg$^{1r}$ or $N_3$, wherein Pg$^{1r}$ is an amino protecting group;
$N^{1g}$ is —NHPg$^{1g}$ or $N_3$, wherein Pg$^{1g}$ is an amino protecting group;
$N^{1h}$ is —NHPg$^{1h}$ or $N_3$, wherein Pg$^{1h}$ is an amino protecting group;
Pg$^{2g}$ is a hydroxyl protecting group;
Pg$^{2h}$ is a hydroxyl protecting group;
wherein at least one of $N^{1q}$, $N^{1r}$, $N^{1g}$, $N^{1h}$ is not $NH_2$ or wherein at least one of PG$^{2g}$ or Pg$^{2h}$ is not H or wherein $X^6$ is not —OH or —$NH_2$;
m is zero, 1, or 2;
n is zero, 1, or 2;
wherein m+n is 1, 2 or 3;
o is zero, 1, or 2;
p is zero, 1, or 2;
wherein o+p is 1, 2 or 3;
q is zero, 1, or 2;
r is zero, 1, or 2;
wherein q+r is 1, 2 or 3.

The present disclosure provides a compound of formula ABCD-4:

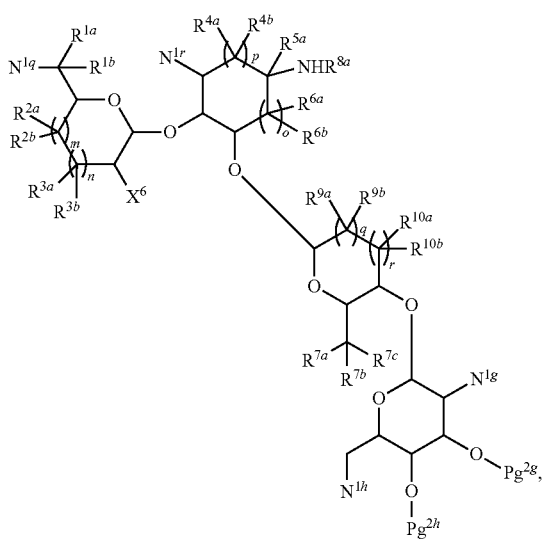

ABCD-4 and salts, solvates, enantiomers, and diastereomers thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —N$_3$, and —OR$^{16}$, and wherein each R$^{12}$, R$^{13}$, R$^{14}$, R$^{15}$, and R$^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each R$^{22}$, R$^{23}$, R$^{24}$, R$^{25}$, and R$^{26}$ is independently H or alkyl, wherein the alkyl is unsubstituted or substituted with one or more substituents independently selected from the group consisting of halogen, cyano, NR$^{14}$R$^{15}$, and —OR$^{16}$;

$R^{2a}$, $R^{2b}$, $R^{3a}$ and $R^{3b}$ are independently selected from the group consisting of H, —OR$^{27}$, —NR$^{28}$R$^{29}$, halogen, $C_1$-$C_4$ cycloalkyl, and $C_1$-$C_6$ alkyl, wherein each R$^{27}$, R$^{28}$, and R$^{29}$ is independently H or alkyl; wherein the $C_1$-$C_6$ alkyl or alkyl is unsubstituted or substituted with one or more substituents selected from the group consisting of halogen, —OR$^{30}$, —NR$^{31}$R$^{32}$, —SR$^{33}$, and —SO$_2$R$^{34}$;

wherein each R$^{30}$, R$^{31}$, R$^{32}$, R$^{33}$, and R$^{34}$ is independently H or alkyl substituted with one or more substituents independently selected from the group consisting of halogen, cyano, NR$^{14}$R$^{15}$, and —OR$^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^6$ is selected from the group consisting of H, $NH_2$, $N_3$, protected amino group, OH, —OPg$^{2m}$, and halogen; wherein Pg$^{2m}$ is a hydroxyl protecting group;

$R^{4a}$ and $R^{4b}$ are, independently H, —OH, —OR$^{40}$, —NR$^{41}$R$^{42}$, or halogen;

wherein each R$^{40}$, R$^{41}$, and R$^{42}$ are independently H or alkyl;

wherein the alkyl is unsubstituted or substituted with one or more substituents selected from the group consisting of —CONH$_2$, —OH, —NH$_2$, —COCH$_3$, aryl, substituted aryl, heteroaryl, halogen, or substituted heteroaryl;

$R^{5a}$ is H, —CN, —CONH$_2$ or $C_1$-$C_3$alkyl, wherein the alkyl is unsubstituted or substituted with one or more substituents selected from the group consisting of —OH, —NH$_2$, —CN, —CONH$_2$, and halogen;

$R^{6a}$ and $R^{6b}$ are, independently H, halogen, $NH_2$, —OH, $C_1$-$C_3$alkoxy, —OC(O)CH$_3$, or —OPg$^{2j}$; wherein Pg$^{2j}$ is a hydroxyl protecting group;

$R^{7a}$, $R^{7b}$, and $R^{7c}$ are, independently, H, OH, —OR$^{71}$ or —OPg$^2$;

wherein $R^{71}$ is alkyl; wherein the alkyl is unsubstituted or substituted with one or more substituents selected from the group consisting of —CONH$_2$, —OH, —NH$_2$, —COCH$_3$, aryl, substituted aryl, heteroaryl, and substituted heteroaryl;

wherein Pg$^2$ is a hydroxyl protecting group;

$R^{8a}$ is H, $C_1$-$C_6$ alkyl, an amino protecting group, or

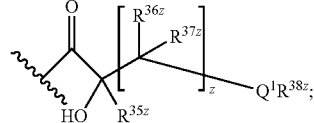

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein R$^{39z}$ and R$^{40z}$ are independently H or $C_1$-$C_3$ alkyl; or $R^{35z}$ and $R^{38z}$, together with the atoms to which they are attached, form a heterocycloalkyl group comprising at least one N;

$R^{9a}$ and $R^{9b}$ are independently H, OH, or —OR$^{91}$, wherein $R^{91}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

$R^{100a}$ and $R^{100b}$ are independently H, OH, or —OR$^{101}$, wherein $R^{101}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

$N^{1q}$ is —NHPg$^{1q}$, —NH$_2$, or N$_3$, wherein Pg$^{1q}$ is an amino protecting group;

$N^{1r}$ is —NHPg$^{1r}$, —NH$_2$, or N$_3$, wherein Pg$^{1r}$ is an amino protecting group;

$N^{1g}$ is —NHPg$^{1g}$, —NH$_2$, or N$_3$, wherein Pg$^{1g}$ is an amino protecting group;

$N^{1h}$ is —NHPg$^{1h}$, —NH$_2$, or N$_3$, wherein Pg$^{1h}$ is an amino protecting group;

Pg$^{2g}$ is H or a hydroxyl protecting group;

Pg$^{2h}$ is H or a hydroxyl protecting group;

$N^{1p}$ is —NHPg$^{1p}$, —NH$_2$, or N$_3$, wherein Pg$^{1p}$ is an amino protecting group;

wherein at least one of $N^{1q}$, $N^{1r}$, $N^{1g}$, $N^{1h}$ is not NH$_2$ or wherein at least one of PG$^{2g}$ or Pg$^{2h}$ is not H or wherein $X^6$ is not —OH or —NH$_2$;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2.

The present disclosure provides a compound of formula ABCD-4':

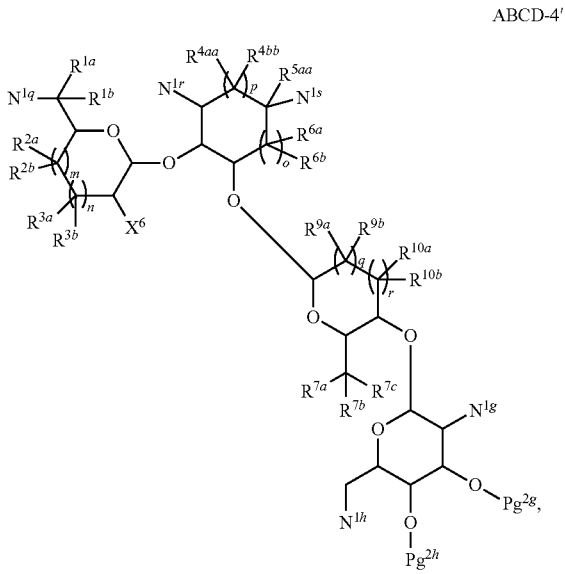

ABCD-4' and salts, solvates, enantiomers, and diastereomers thereof, wherein $R^{1a}$ and $R^{1b}$ are independently selected from the group consisting of H, C$_1$-C$_{12}$ alkyl, C$_1$-C$_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^1$, —SO$_2$R$^{13}$, —OSF$_2$NR$^{14}$R$^{15}$, —NR$^{14}$R$^{15}$, —N$_3$, and —OR$^{16}$ and wherein each R$^{12}$, R$^{13}$, R$^{14}$, R$^{15}$, and R$^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{12}$, —SO$_2$R$^{23}$, —NR$^{24}$R$^{25}$, and —OR$^{26}$, and wherein each R$^{22}$, R$^{23}$, R$^{24}$, R$^{25}$, and R$^{26}$ is independently H or alkyl, wherein the alkyl is unsubstituted or substituted with one or more substituents independently selected from the group consisting of halogen, cyano, NR$^{14}$R$^{15}$, and —OR$^{16}$;

$R^{2a}$, $R^{2b}$, $R^{3a}$ and $R^{3b}$ are independently selected from the group consisting of H, —OR$^{27}$, —NR$^{28}$R$^{29}$, halogen, C$_1$-C$_4$ cycloalkyl, and C$_1$-C$_6$ alkyl, wherein each R$^{27}$, R$^{28}$, and R$^{29}$ is independently H, alkyl, amino protecting group, or hydroxyl protecting group; wherein the C$_1$-C$_6$ alkyl or alkyl is unsubstituted or substituted with one or more substituents selected from the group consisting of aryl, halogen, —OR$^{30}$, —NR$^{31}$R$^{32}$, —SR$^{33}$, and —SO$_2$R$^{34}$;

wherein each R$^{30}$, R$^{31}$, R$^{32}$, R$^{33}$, and R$^{34}$ is independently H or alkyl substituted with one or more substituents independently selected from the group consisting of halogen, cyano, NR$^{14}$R$^{15}$, and —OR$^{16}$; or $R^{2a}$ and $R^{2b}$ form an oxo or imino group substituted with C$_1$-C$_6$ alkyl;

$R^{3a}$ and $R^{3b}$ form an oxo or imino group substituted with C$_1$-C$_6$ alkyl;

$X^6$ is selected from the group consisting of H, NH$_2$, N$_3$, protected amino group, OH, —OPg$^{2m}$, and halogen; wherein Pg$^{2m}$ is a hydroxyl protecting group;

$R^{4aa}$ and $R^{4bb}$ are, independently H, —OH, —OR$^{40}$, —NR$^{41}$R$^{42}$, or halogen;

wherein each R$^{40}$, R$^{41}$, and R$^{42}$ are independently H, alkyl, —CONH$_2$, or —COCH$_3$; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^{5aa}$ is H, —CN, —CONH$_2$ or C$_1$-C$_3$alkyl, wherein the alkyl is unsubstituted or substituted with one or more substituents selected from the group consisting of —OH, —OC(O)CH$_3$, —NH$_2$, —CN, —CONH$_2$, and halogen;

$R^{6a}$ and $R^{6b}$ are, independently H, halogen, NH$_2$, —OH, C$_1$-C$_3$alkoxy, —OC(O)CH$_3$, or —OPg$^{2j}$; wherein Pg$^{2j}$ is a hydroxyl protecting group;

$R^{7a}$, $R^{7b}$, and $R^{7c}$ are, independently, H, OH, —OR$^{71}$ or —OPg$^2$;

wherein $R^{71}$ is alkyl; wherein the alkyl is unsubstituted or substituted with one or more substituents selected from the group consisting of —CONH$_2$, —OH, —NH$_2$, —COCH$_3$, aryl, substituted aryl, heteroaryl, and substituted heteroaryl;

wherein Pg$^2$ is a hydroxyl protecting group;

$N^{1s}$ is N$_3$ or —NR$^{8a}$R$^{8b}$;

$R^{8a}$ is H, C$_1$-C$_6$ alkyl, an amino protecting group, or

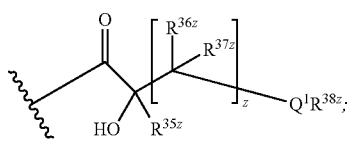

wherein

Q$^1$ is NH, O, or S;

z is an integer from 0 to 4,

R$^{35z}$ is H or C$_1$-C$_3$ alkyl;

each R$^{36z}$ and R$^{37z}$ is independently selected from the group consisting of H, alkyl, halogen, and —OH, and R$^{38z}$ is H, alkyl, or —C(=NH)NR$^{39z}$R$^{40z}$, wherein R$^{39z}$ and R$^{40z}$ are independently H or C$_1$-C$_3$ alkyl; or R$^{35z}$ and R$^{38z}$, together with the atoms to which they are attached, form a heterocycloalkyl group comprising at least one N;

R$^{8b}$ is H or C$_1$-C$_3$alkyl;

R$^{9a}$ and R$^{9b}$ are independently H, OH, or —OR$^{91}$, wherein R$^{91}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

R$^{10a}$ and R$^{10b}$ are independently H, OH, or —OR$^{101}$, wherein R$^{101}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

N$^{1q}$ is —OH, protected hydroxyl group, —NHPg$^{1q}$, N(Pg$^{1q}$)$_2$, —NH$_2$, or N$_3$, wherein each Pg$^{1q}$ is independently an amino protecting group;

N$^{1r}$ is —NHPg$^{1r}$, —NH$_2$, or N$_3$, wherein Pg$^{1r}$ is an amino protecting group;

N$^{1g}$ is —NHPg$^{1g}$, —NH$_2$, or N$_3$, wherein Pg$^{1g}$ is an amino protecting group;

N$^{1h}$ is —NHPg$^{1h}$, —NH$_2$, or N$_3$, wherein Pg$^{1h}$ is an amino protecting group;

Pg$^{2g}$ is H or a hydroxyl protecting group;

Pg$^{2h}$ is H or a hydroxyl protecting group;

wherein at least one of N$^{1q}$, N$^{1r}$, N$^{1g}$, N$^{1h}$ is not NH$_2$ or wherein at least one of PG$^{2g}$ or Pg$^{2h}$ is not H or wherein X$^6$ is not —OH or —NH$_2$;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2.

In some embodiments, the compound of the present disclosure is selected from the group consisting of:

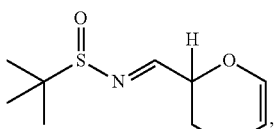

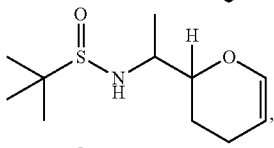

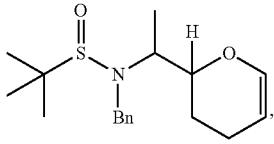

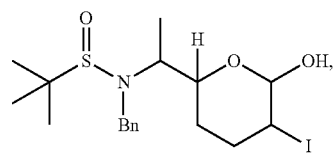

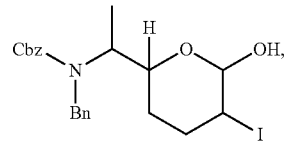

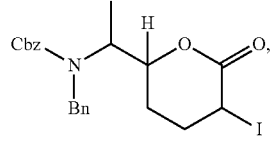

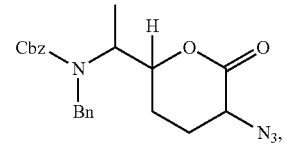

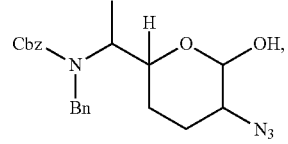

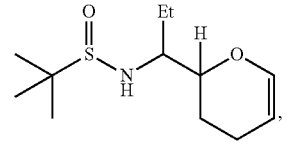

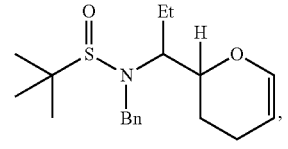

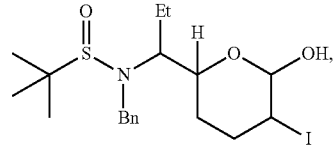

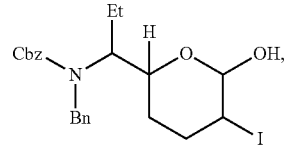

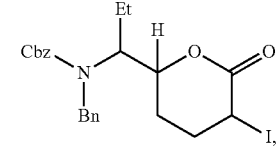

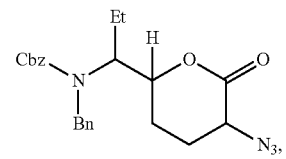

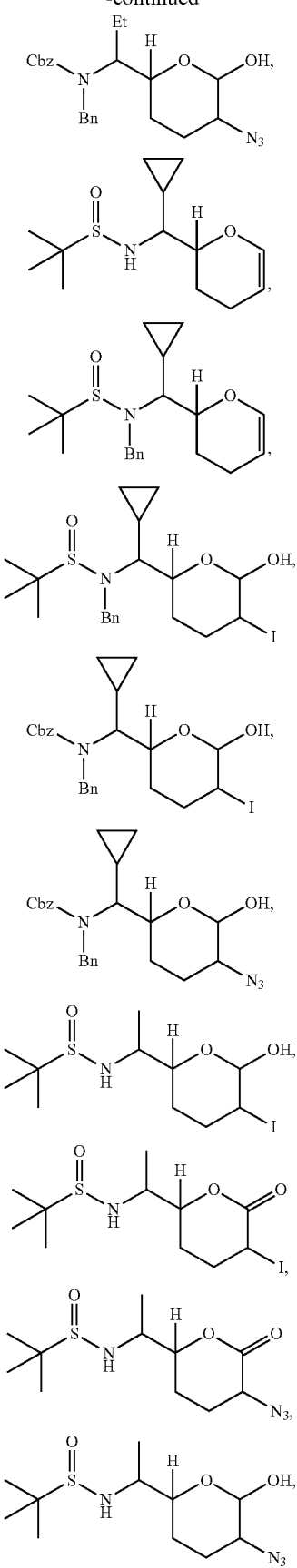
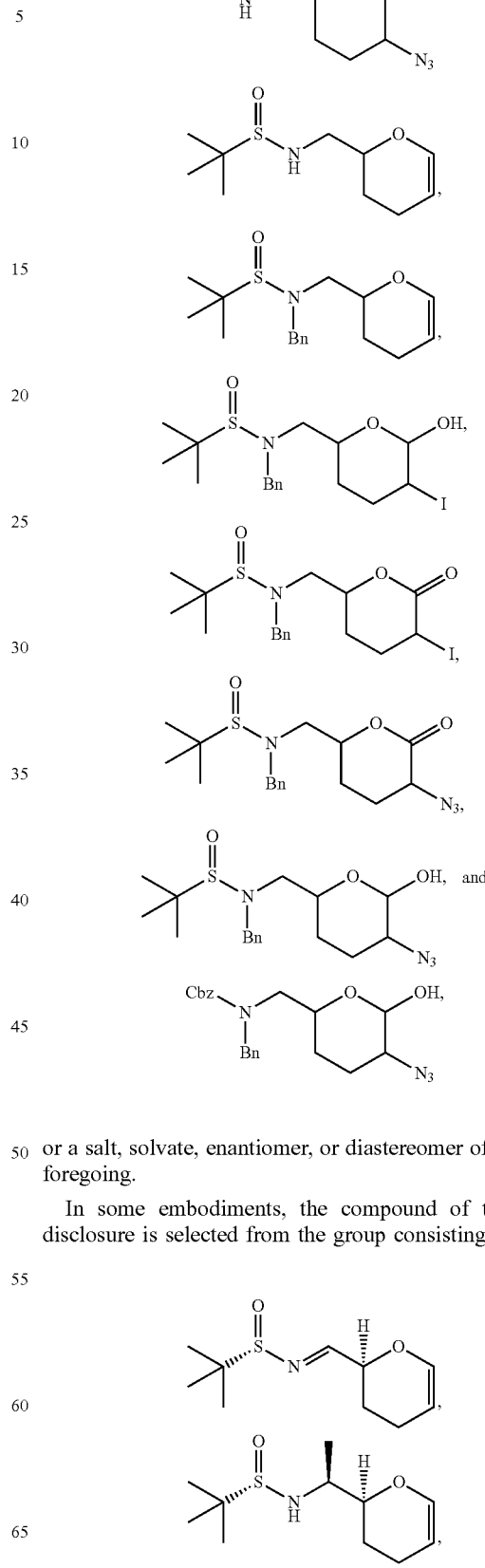
or a salt, solvate, enantiomer, or diastereomer of any of the foregoing.
In some embodiments, the compound of the present disclosure is selected from the group consisting of:

175
-continued
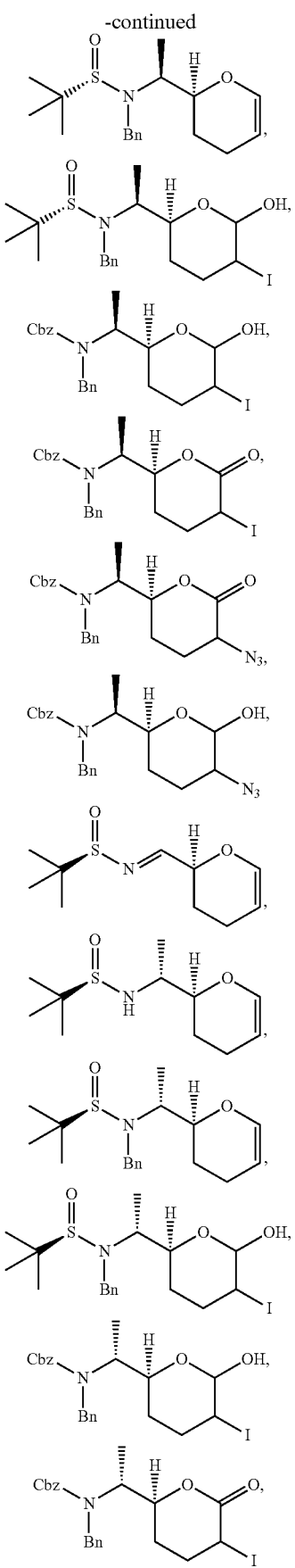
176
-continued
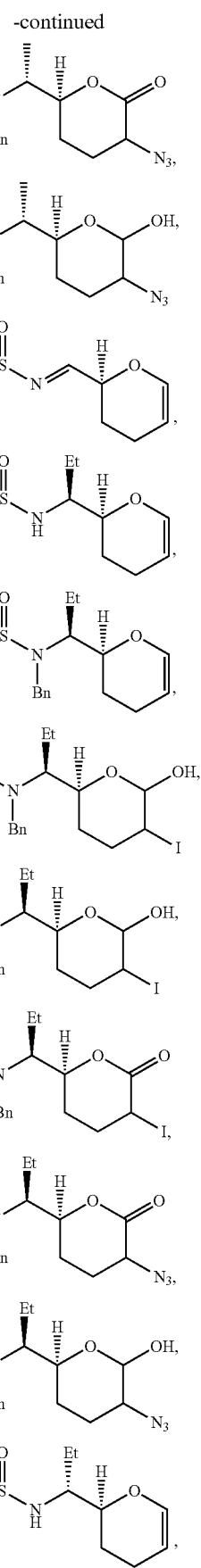

177
-continued
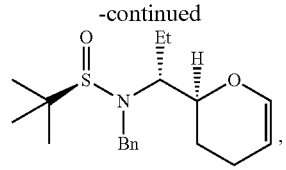
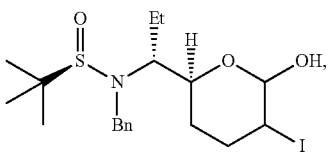
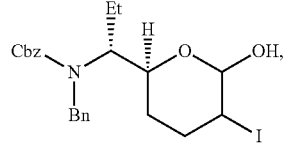
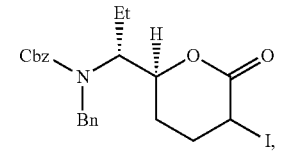
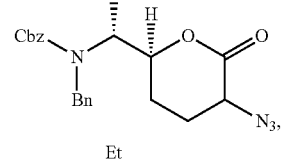
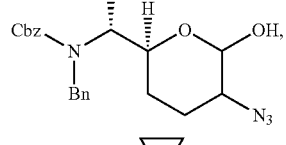
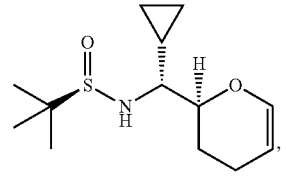
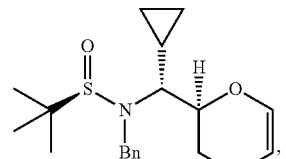
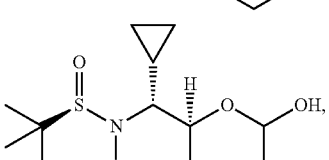
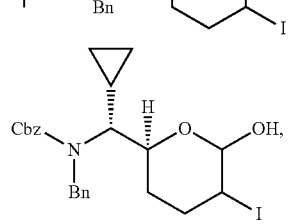
178
-continued
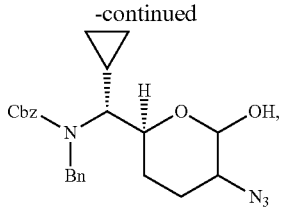
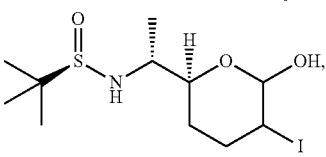
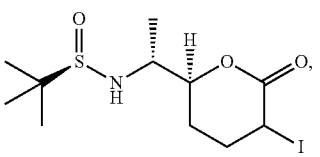
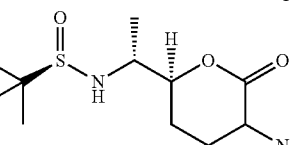
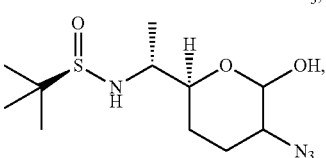
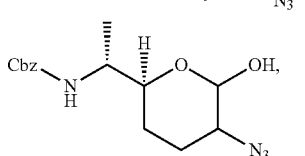
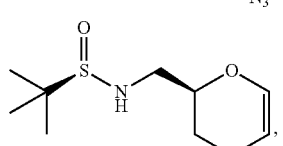
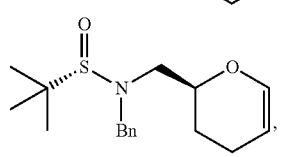
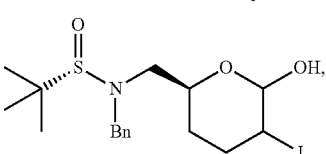
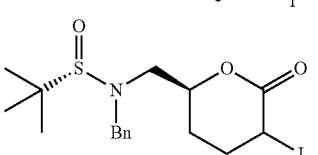
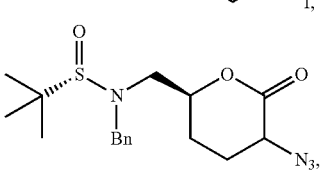

-continued

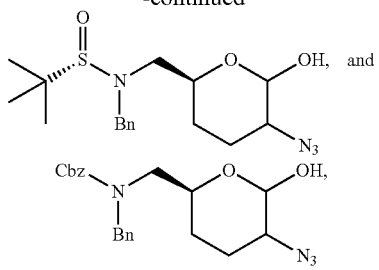

or a salt, solvate, enantiomer, or diastereomer of any of the foregoing.

In some embodiments, the compound of the present disclosure is selected from the group consisting of:

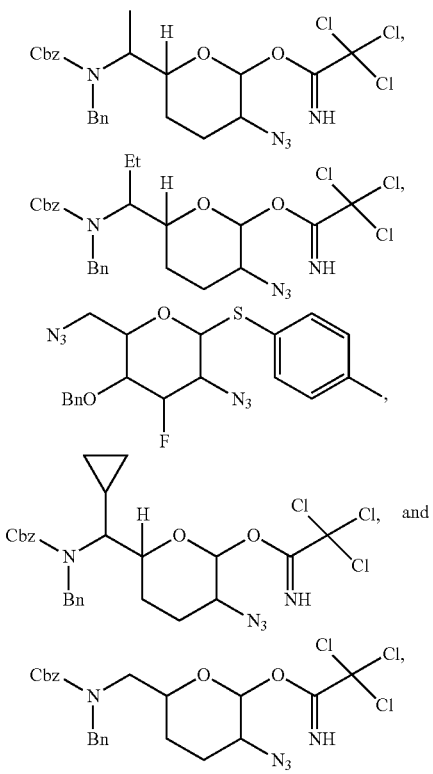

or a salt, solvate, enantiomer, or diastereomer of any of the foregoing.

In some embodiments, the compound of the present disclosure is selected from the group consisting of:

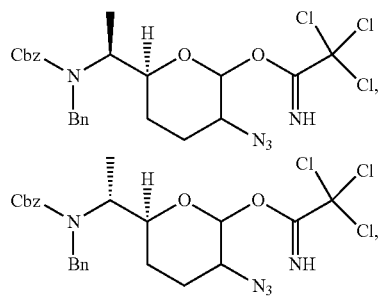

-continued

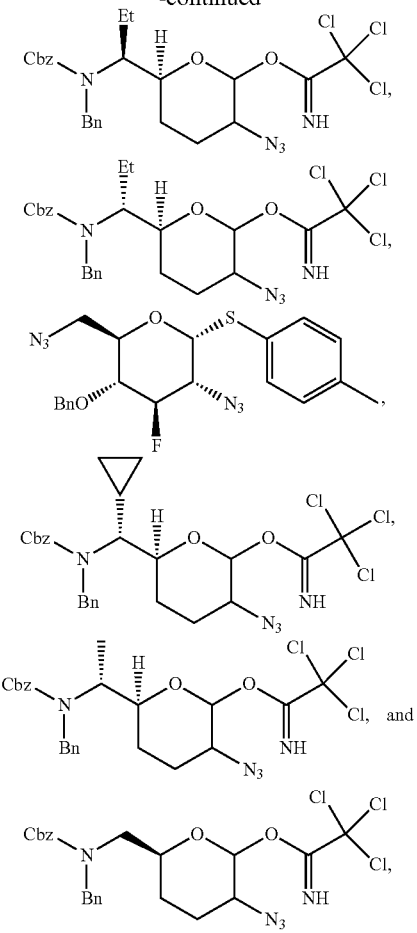

or a salt, solvate, enantiomer, or diastereomer of any of the foregoing.

In some embodiments, the compound of the present disclosure is

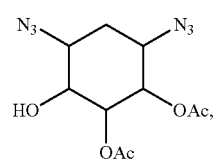

or a salt, solvate, enantiomer, or diastereomer of any of the foregoing.

In some embodiments, the compound of the present disclosure is

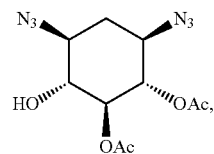

or a salt, solvate, enantiomer, or diastereomer of any of the foregoing.

In some embodiments, the compound of the present disclosure is selected from the group consisting of:

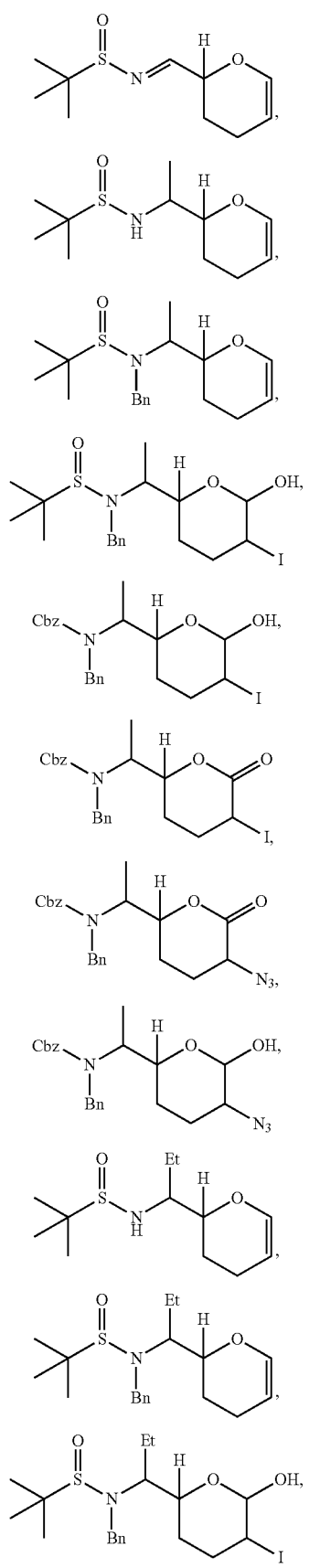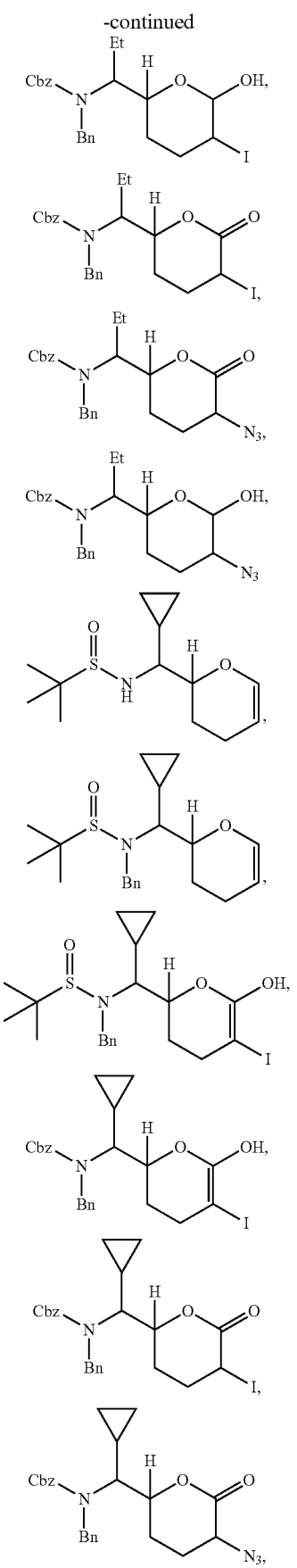

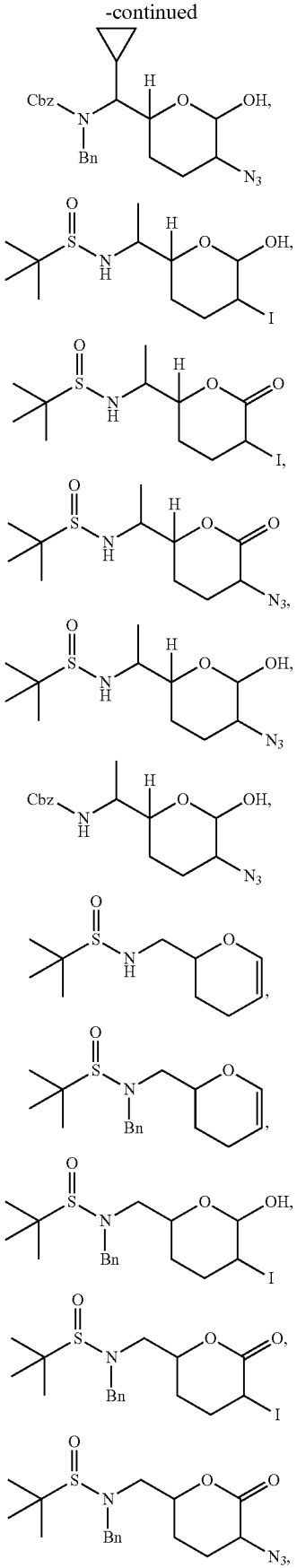
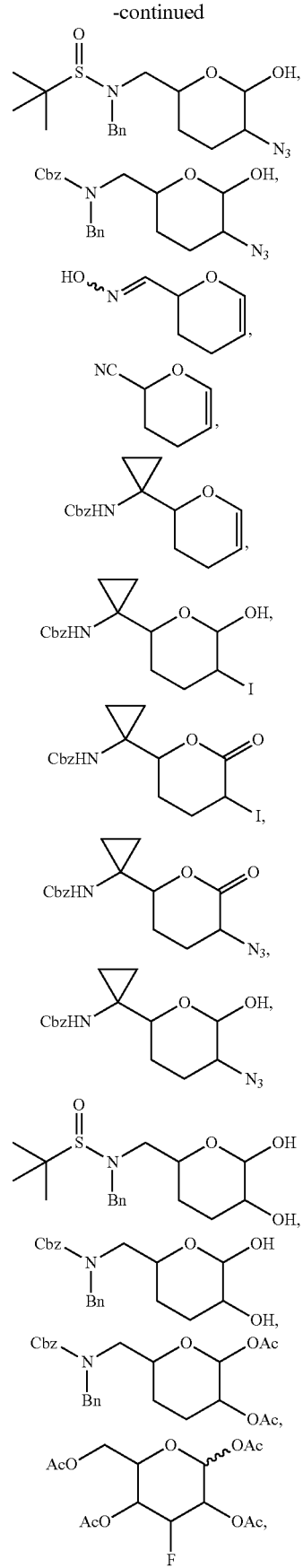

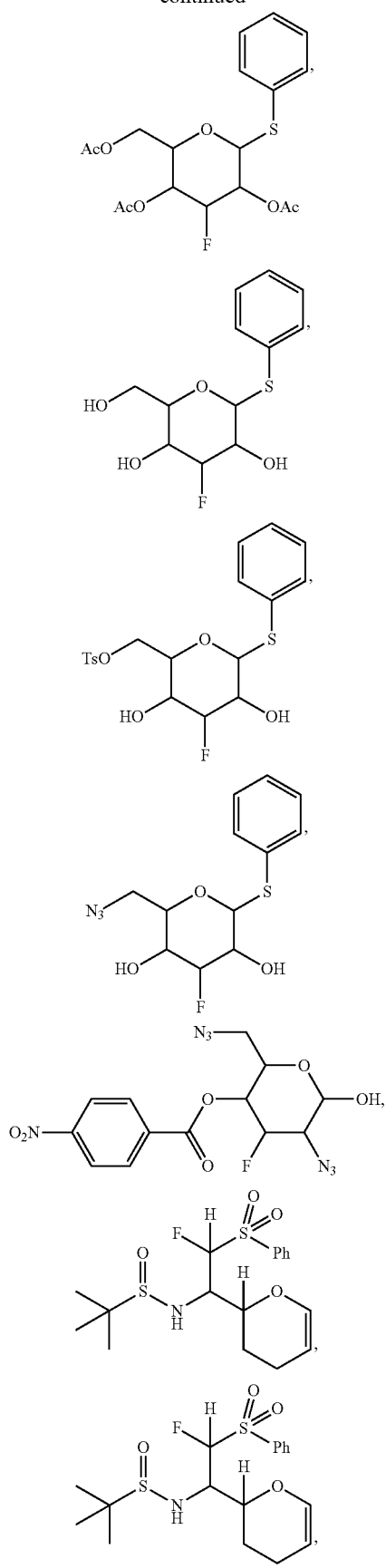
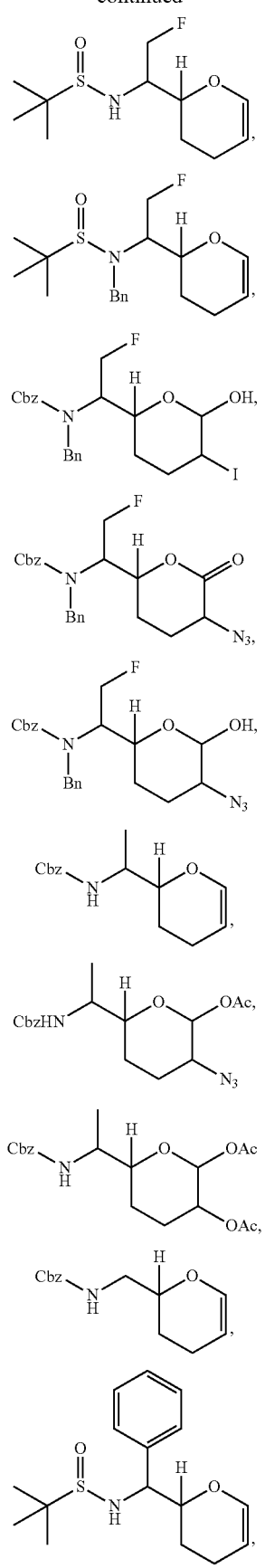

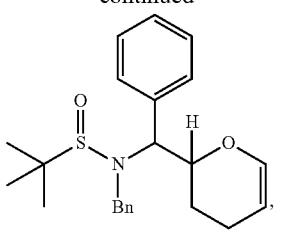
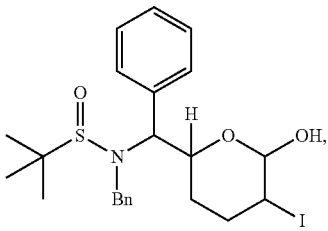
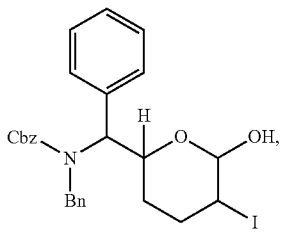
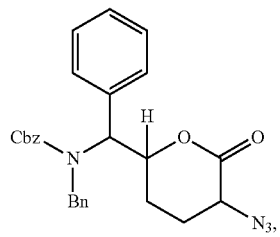
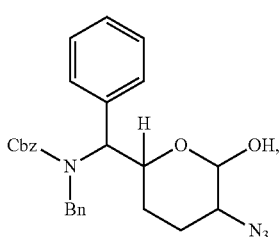
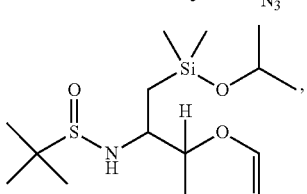
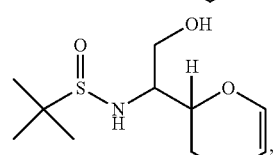
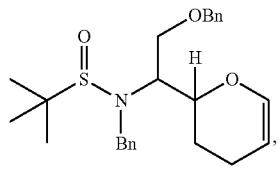
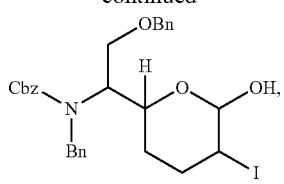
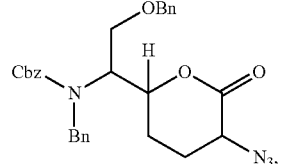
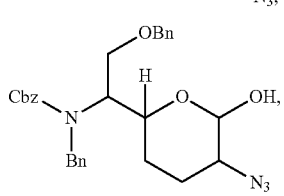
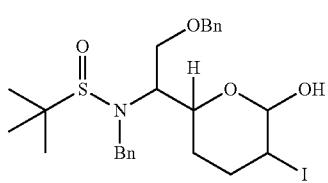 [SMILES: CC(C)(C)S(=O)N(Cc1ccccc1)C(COCc1ccccc1)C1CCC(I)C(O)O1]
or a salt, solvate, enantiomer, or diastereomer of any of the foregoing.
In some embodiments, the compound of the present disclosure is selected from the group consisting of:
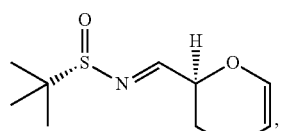
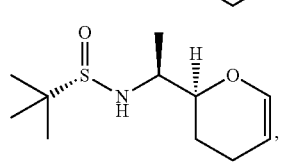
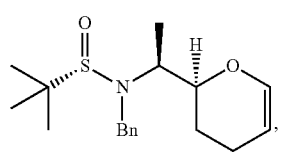
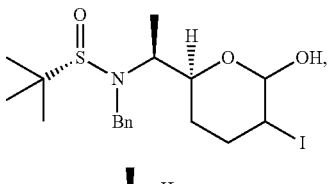
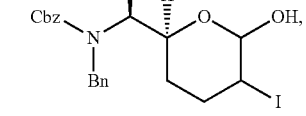

-continued

191
-continued
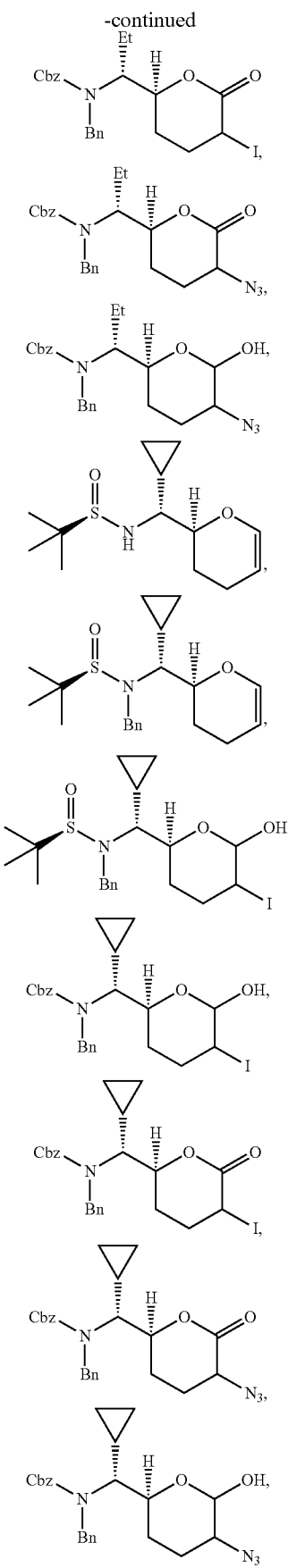
192
-continued
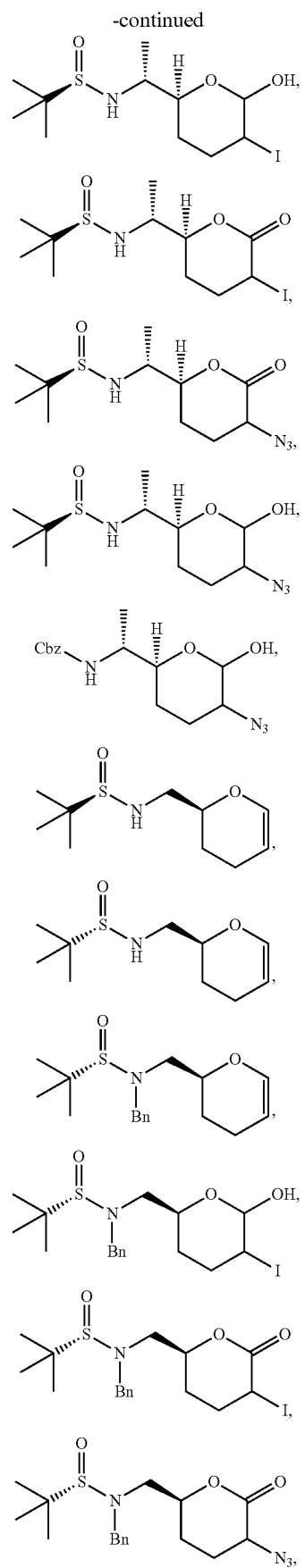

-continued
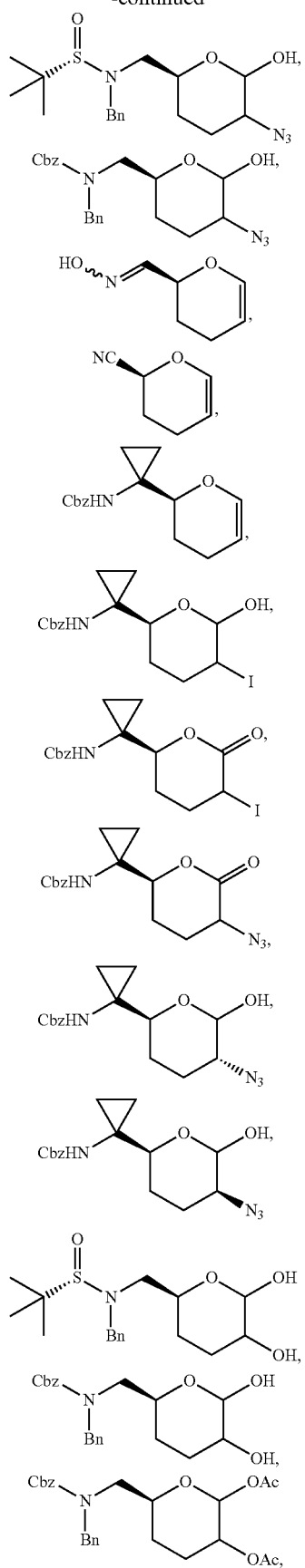
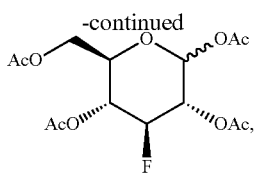
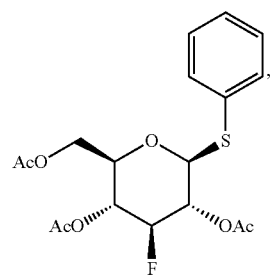
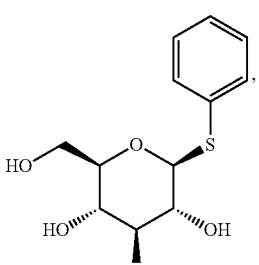
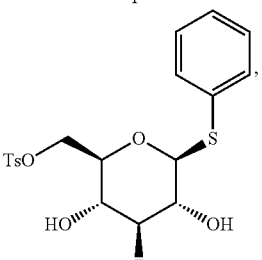
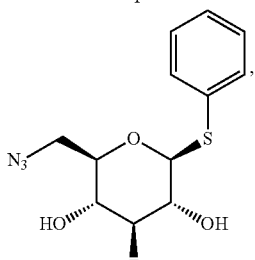
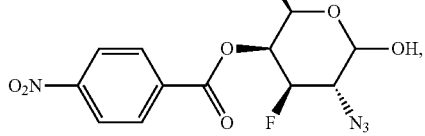
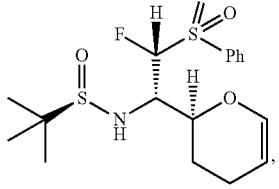

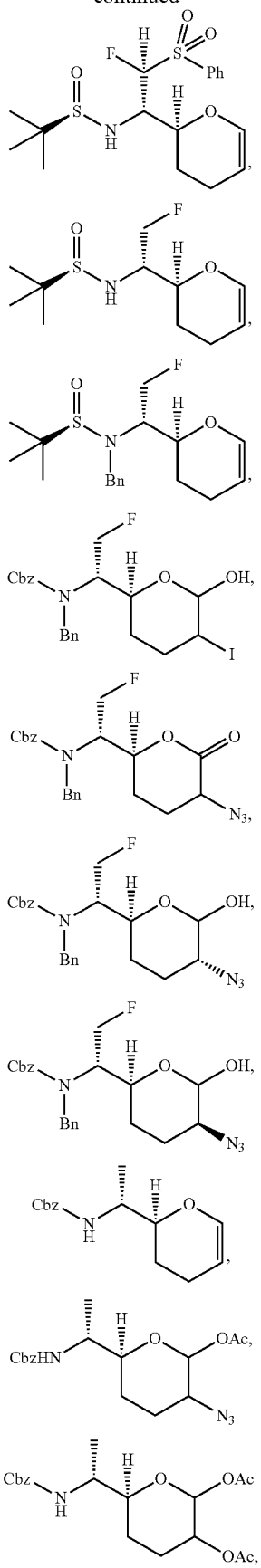
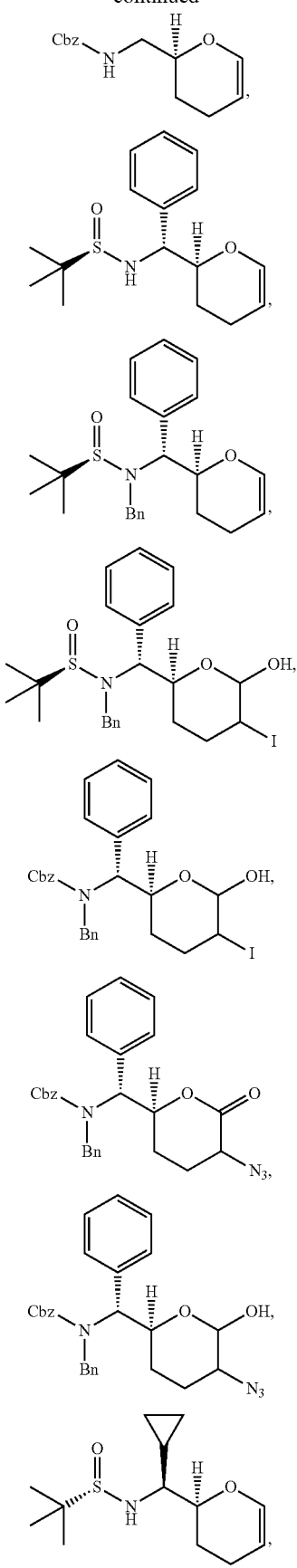

-continued
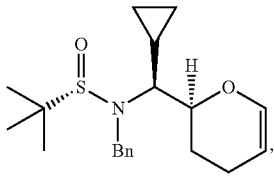
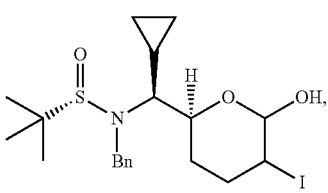
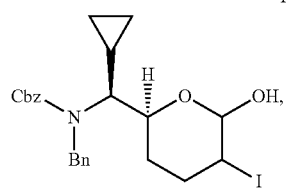
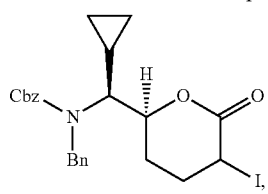
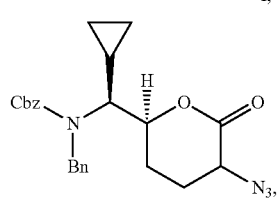
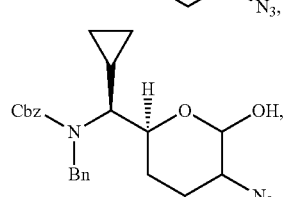
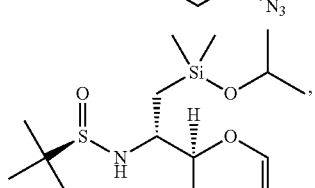
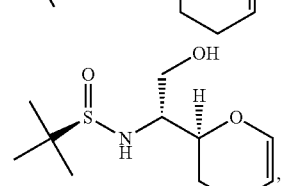
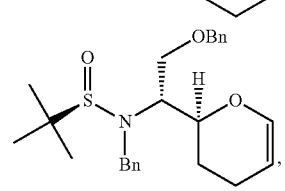
-continued
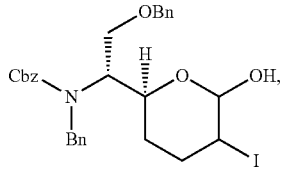
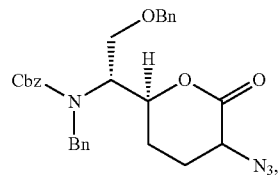
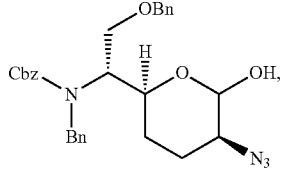
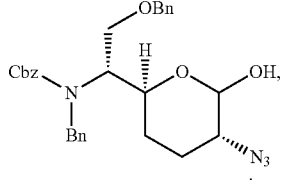
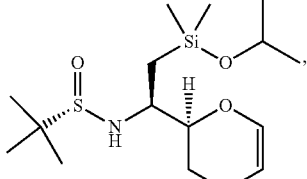
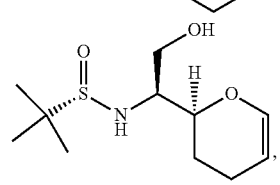
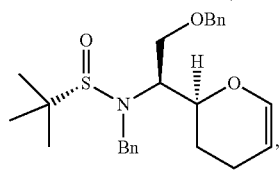
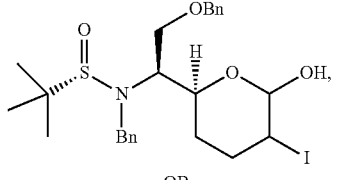
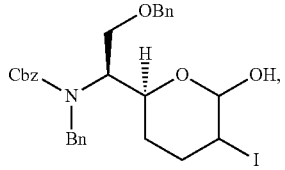

-continued

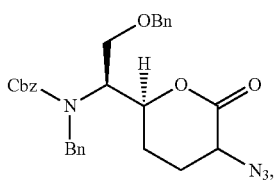

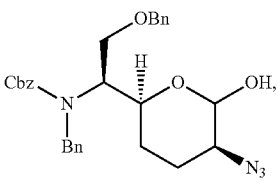

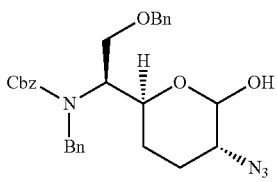

or a salt, solvate, enantiomer, or diastereomer of any of the foregoing.

In some embodiments, the compound of the present disclosure is selected from the group consisting of:

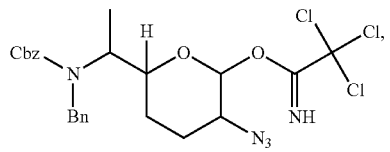

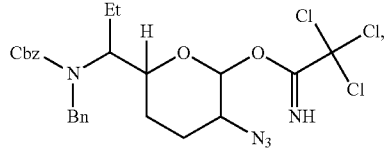

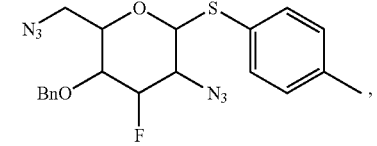

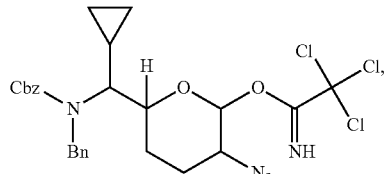

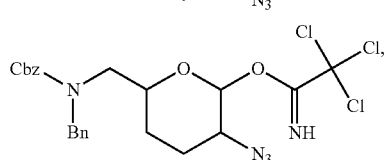

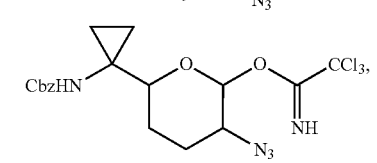

-continued

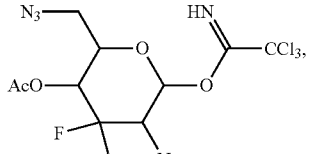

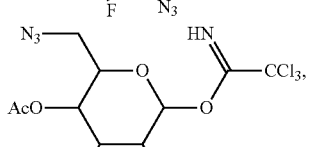

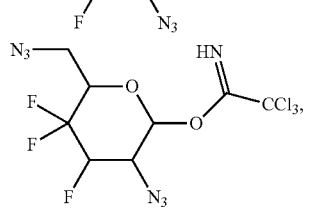

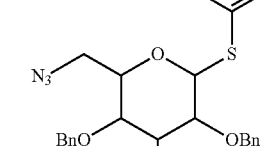

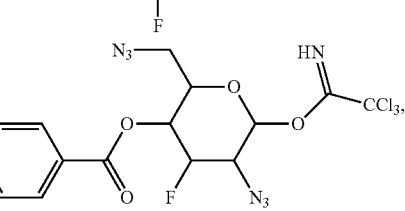

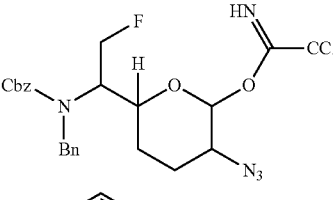

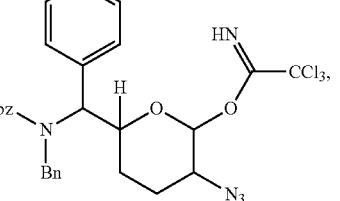

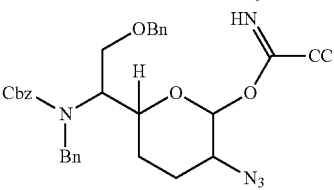

or a salt, solvate, enantiomer, or diastereomer of any of the foregoing.

In some embodiments, the compound of the present disclosure is selected from the group consisting of:

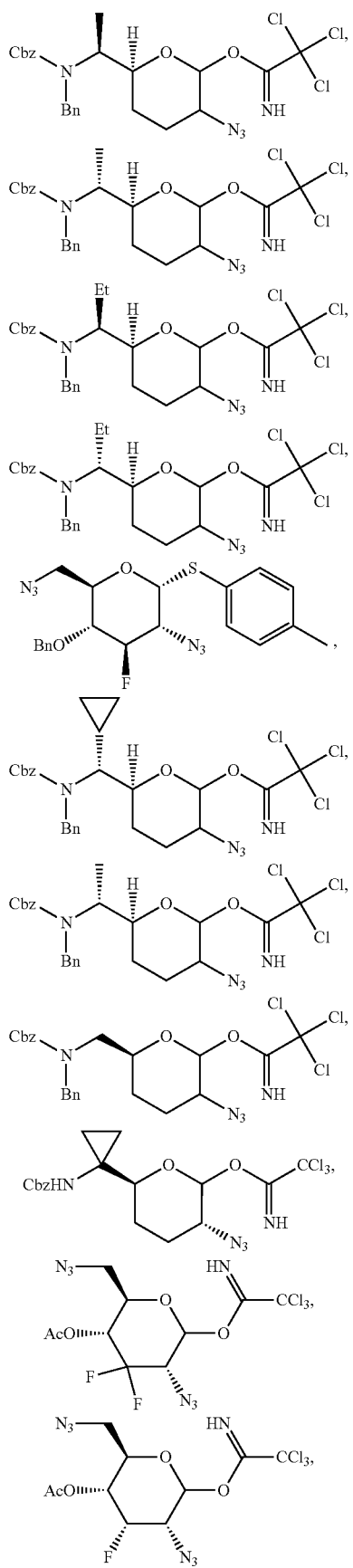
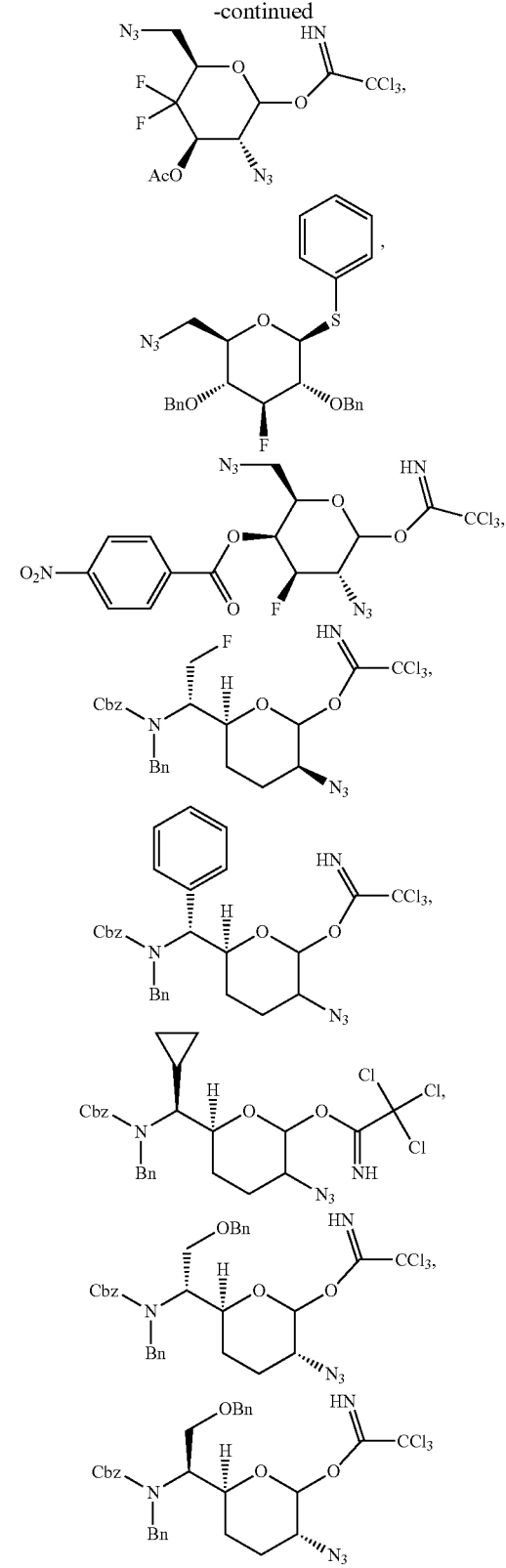
or a salt, solvate, enantiomer, or diastereomer of any of the foregoing.
In some embodiments, the compound of the present disclosure is selected from the group consisting of:

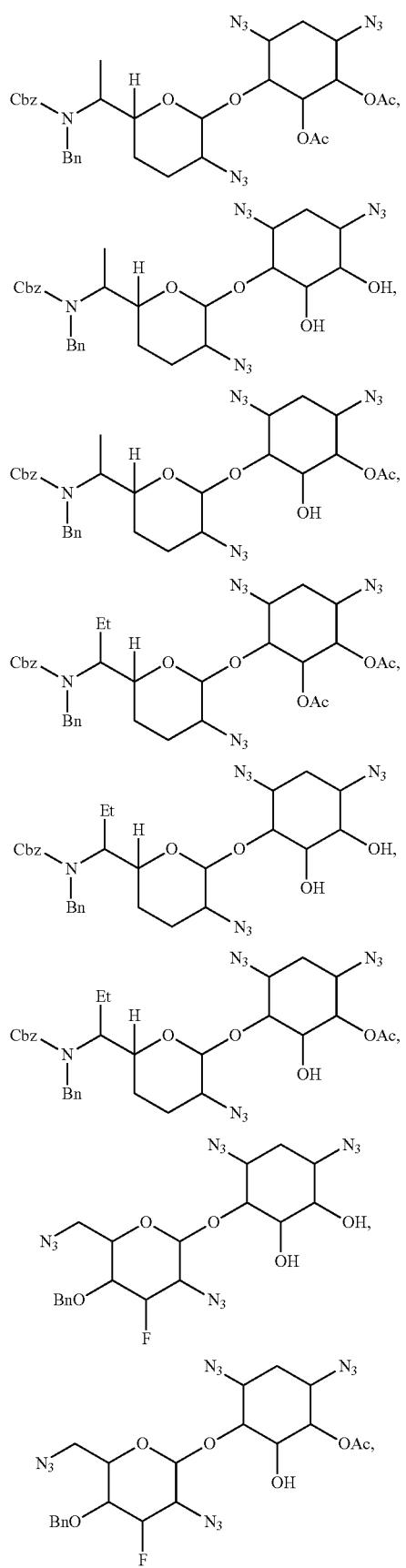
or a salt, solvate, enantiomer, or diastereomer of any of the foregoing.
In some embodiments, the compound of the present disclosure is selected from the group consisting of:

205 206
-continued

-continued
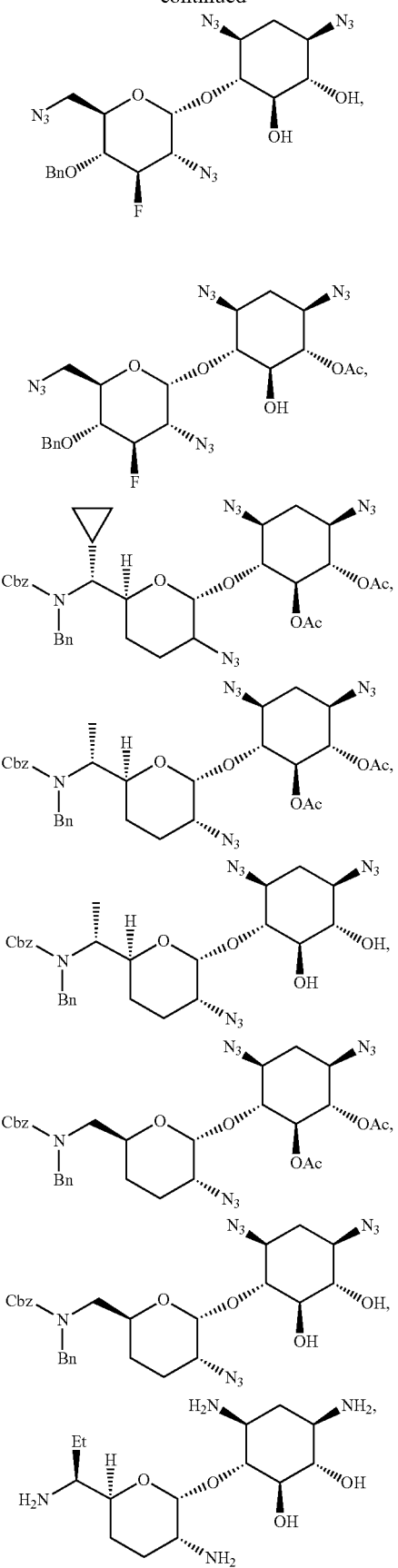
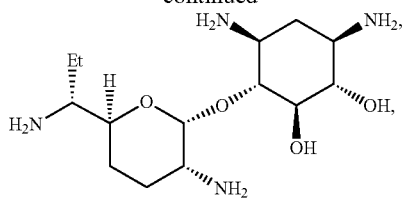
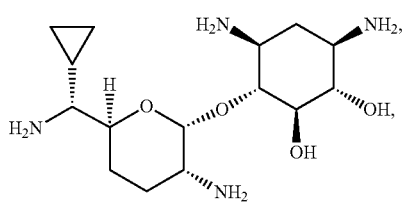
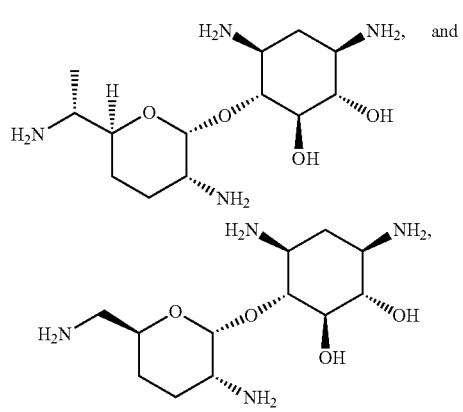
or a salt, solvate, enantiomer, or diastereomer of any of the foregoing.
In some embodiments, the compound of the present disclosure is selected from the group consisting of:
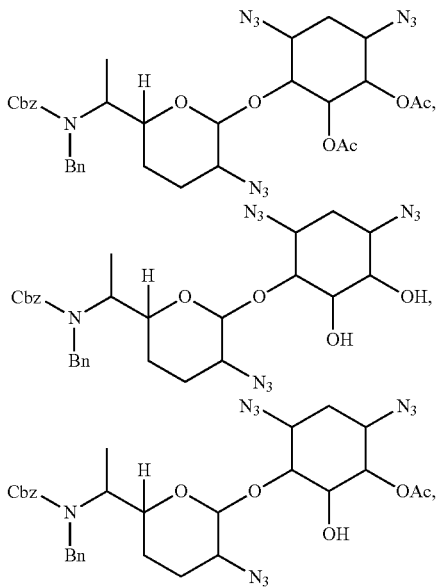

In some embodiments, the compound of the present disclosure is selected from the group consisting of:
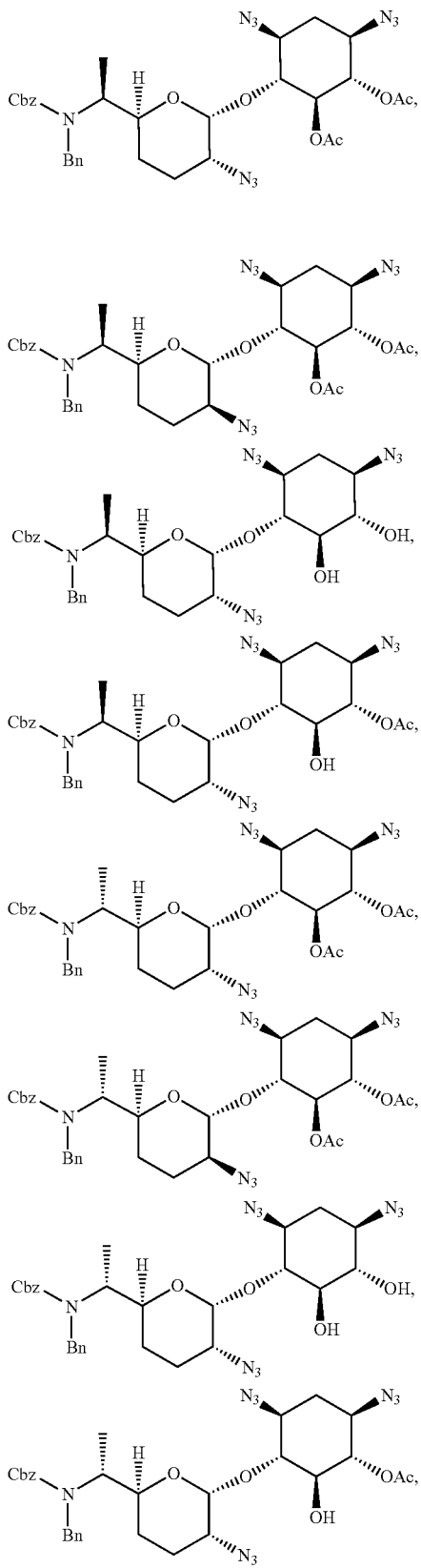
or a salt, solvate, enantiomer, or diastereomer of any of the foregoing.

-continued
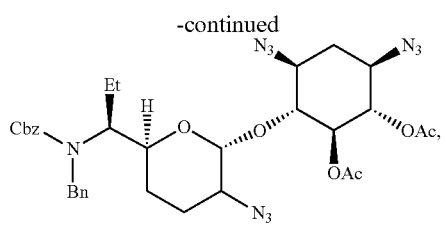
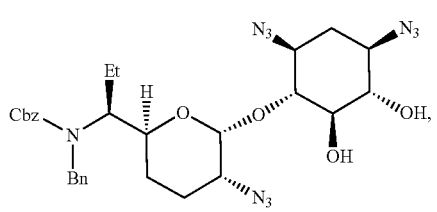
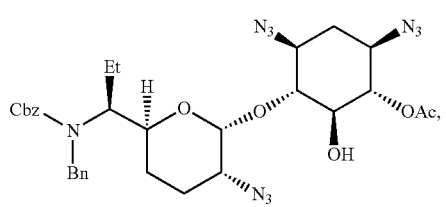
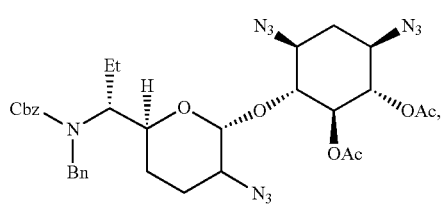
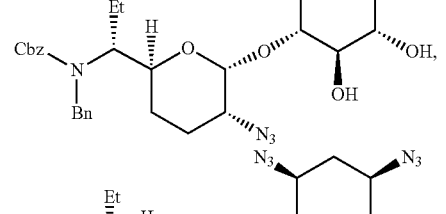
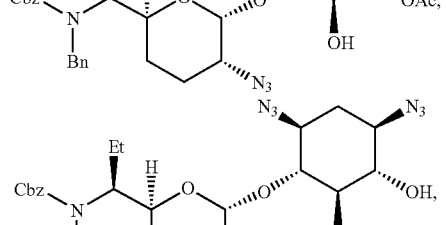
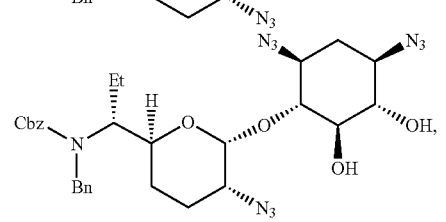
-continued
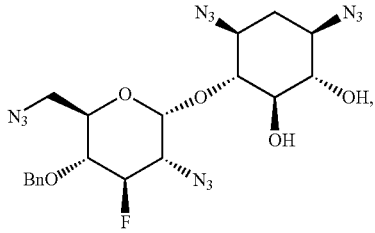
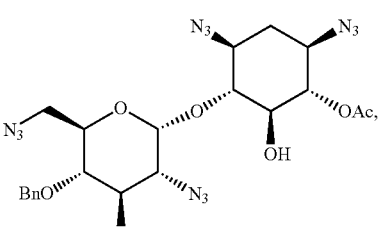
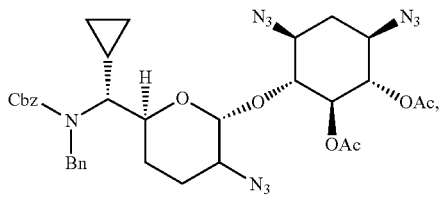
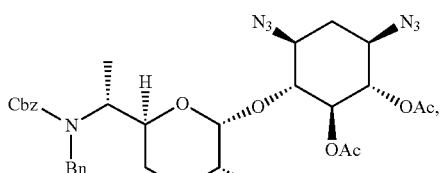
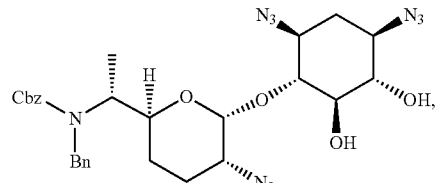
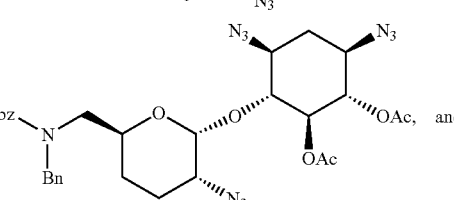
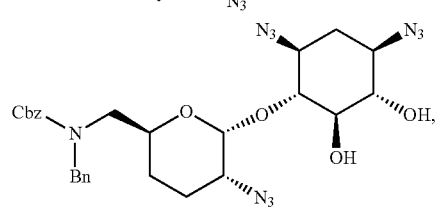
or a salt, solvate, enantiomer, or diastereomer of any of the foregoing.
In some embodiments, the compound of the present disclosure is selected from the group consisting of:

213
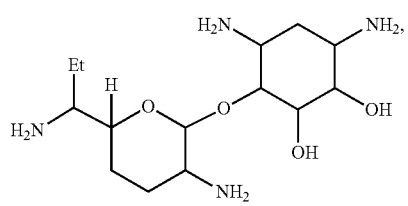
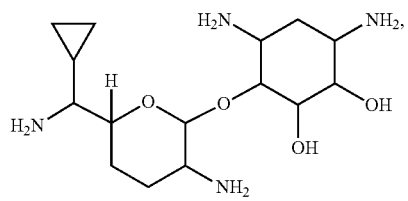
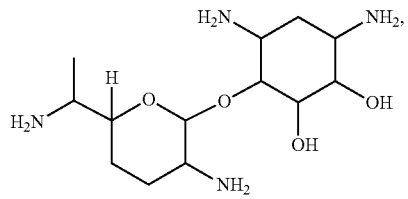
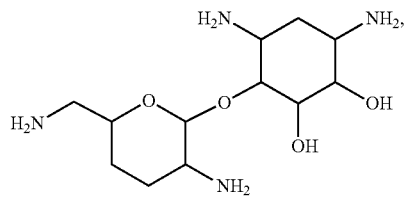
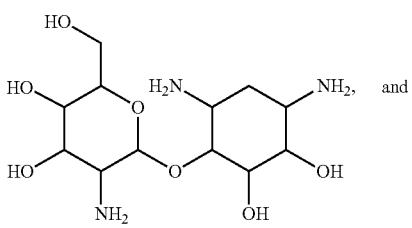
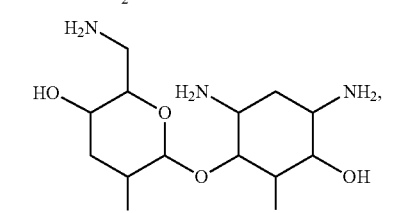
or a salt, solvate, enantiomer, or diastereomer of any of the foregoing.
In some embodiments, the compound of the present disclosure is selected from the group consisting of:
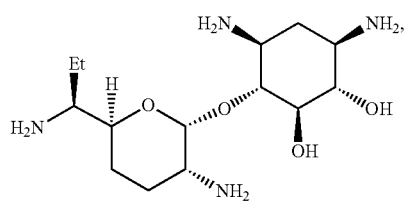
214
-continued
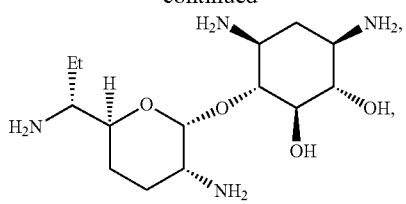
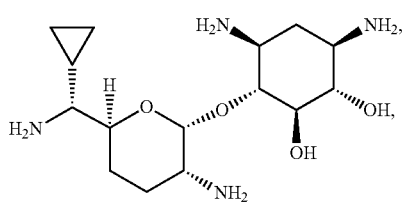
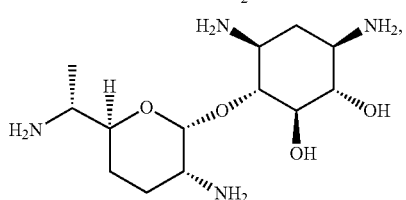
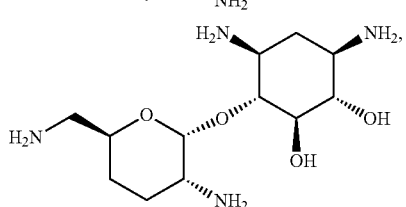
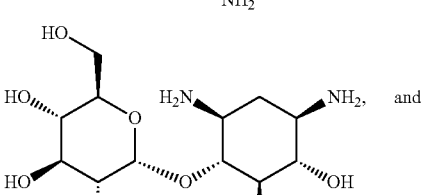
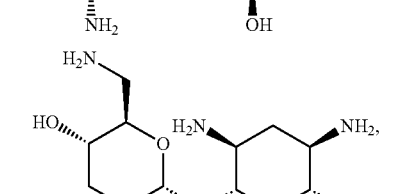
or a salt, solvate, enantiomer, or diastereomer of any of the foregoing.
In some embodiments, the compound of the present disclosure is selected from the group consisting of:
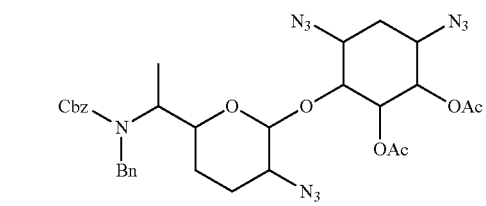

-continued
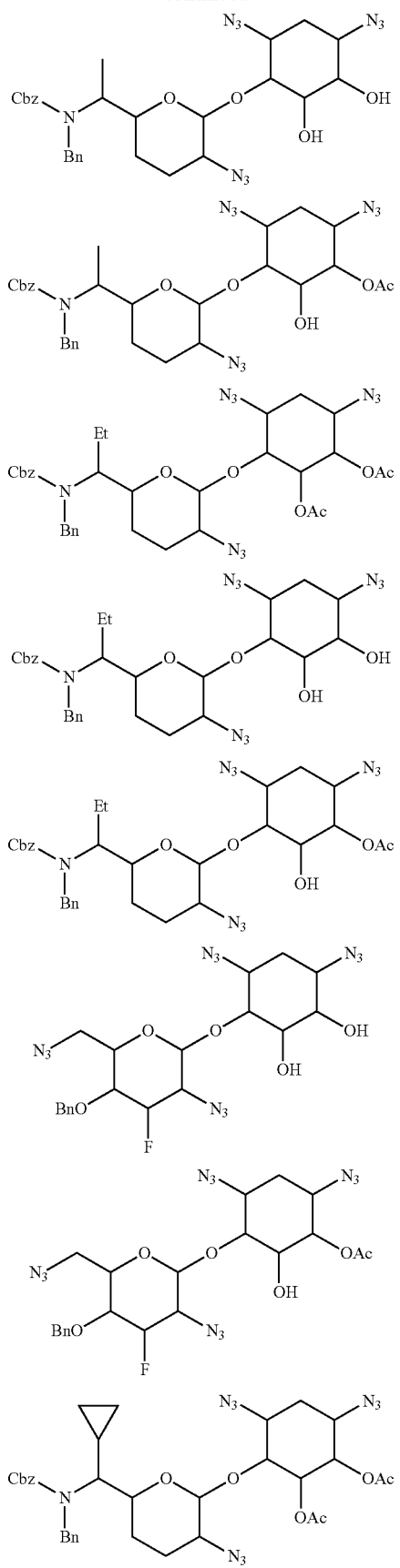
-continued
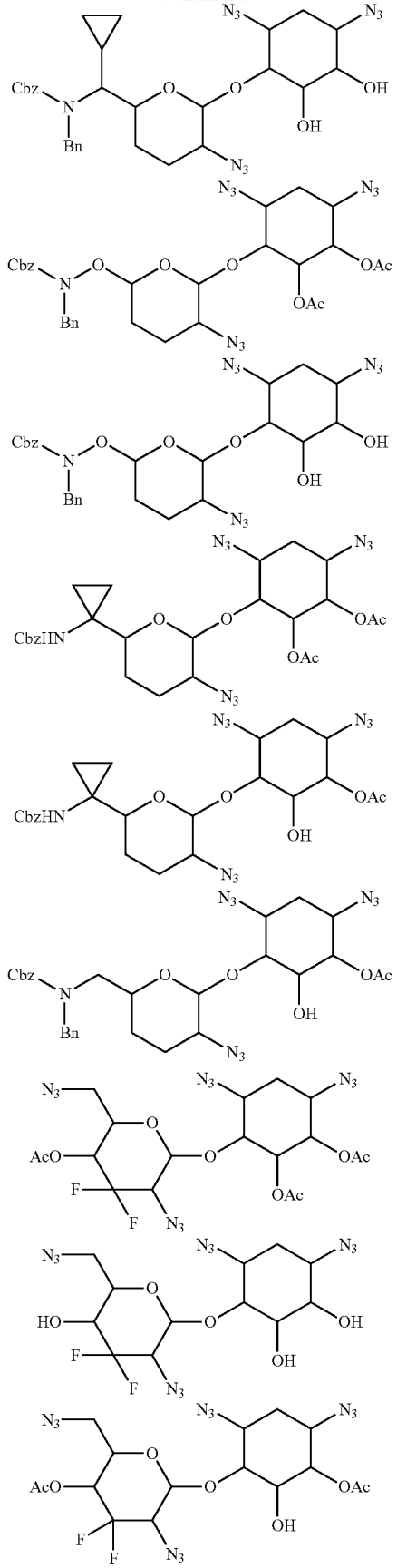

217
-continued
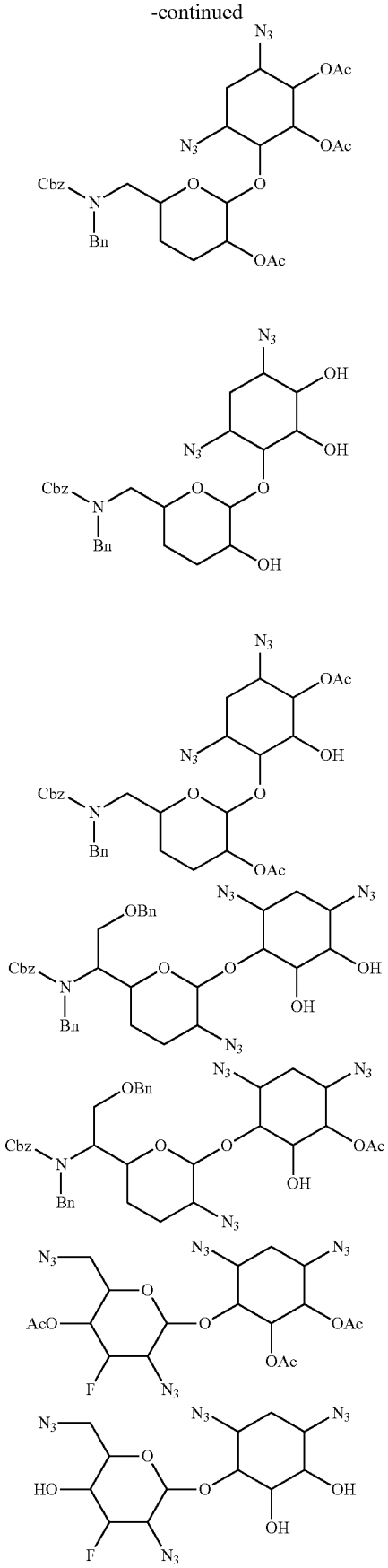
218
-continued
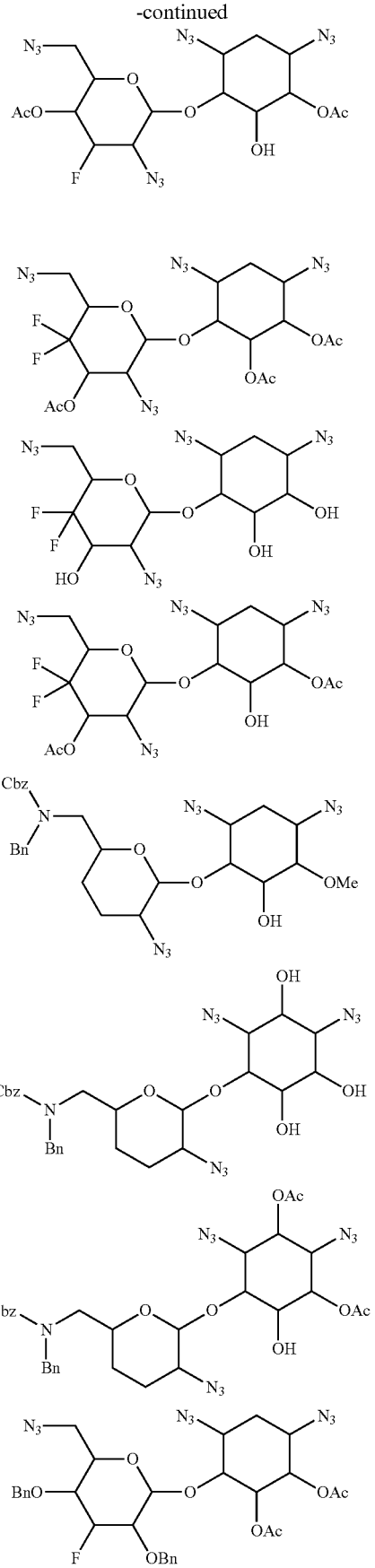

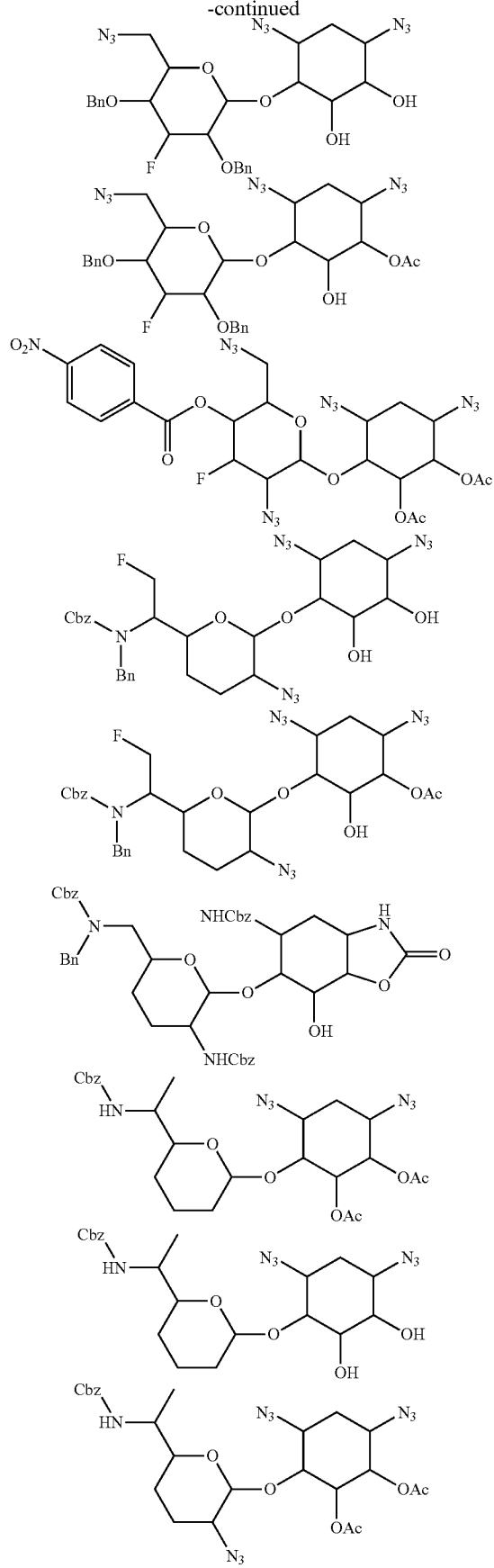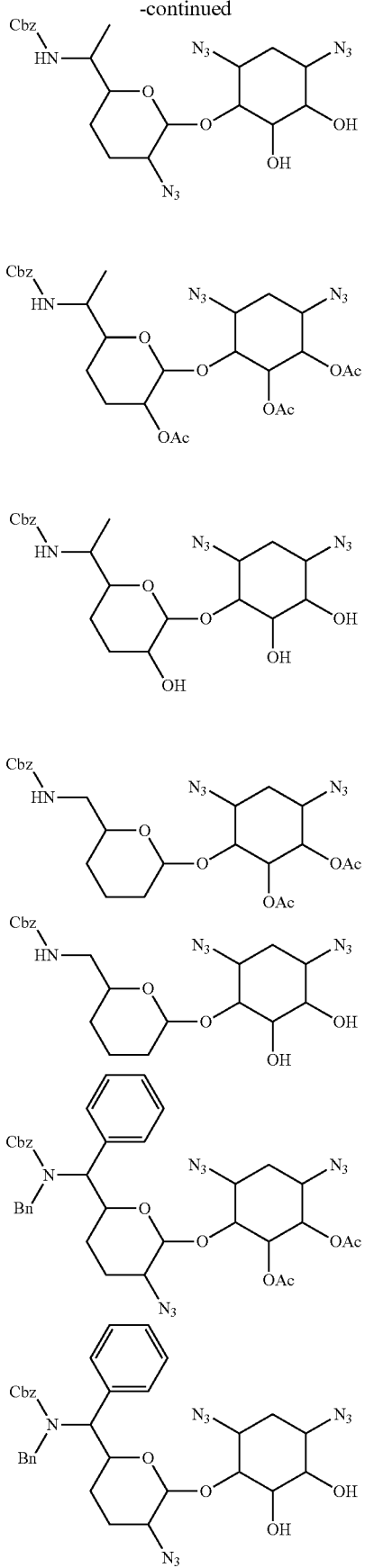

-continued
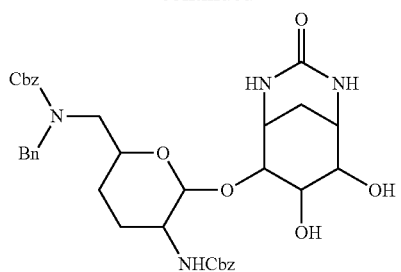
or a salt, solvate, enantiomer, or diastereomer of any of the foregoing.
In some embodiments, the compound of the present disclosure is selected from the group consisting of:
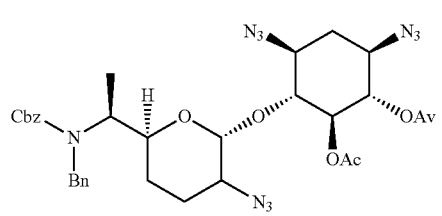
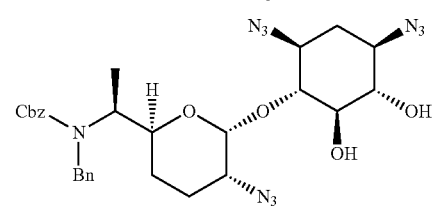
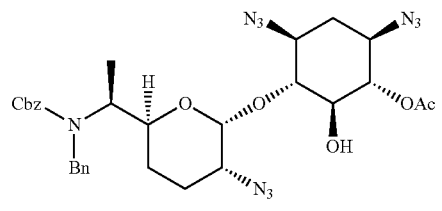
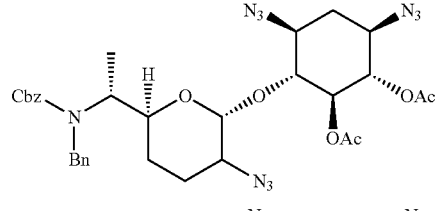
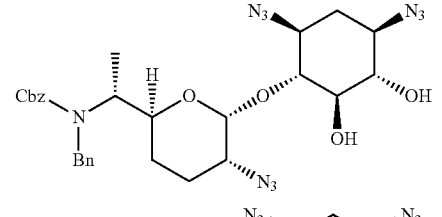
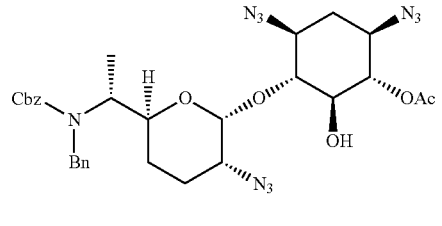
-continued
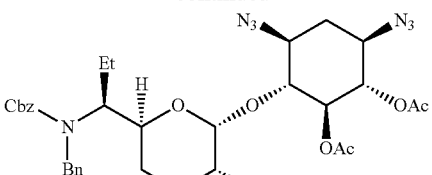
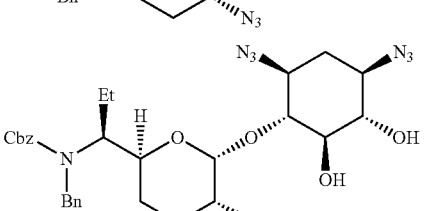
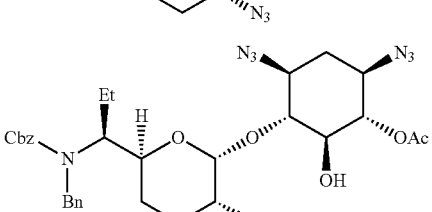
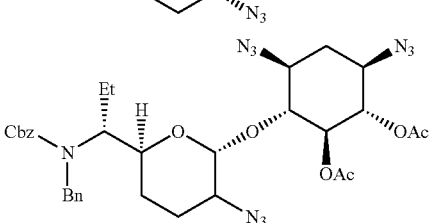
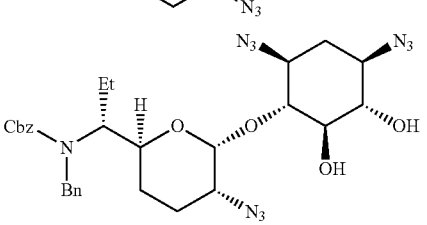
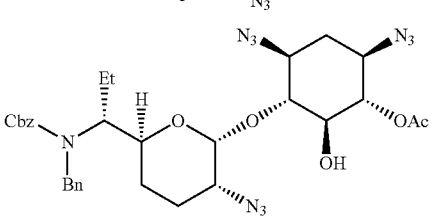
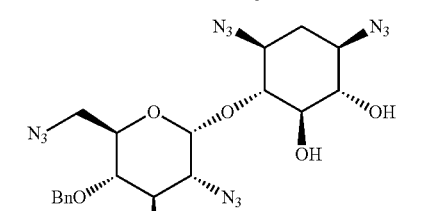
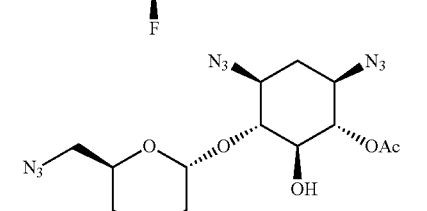
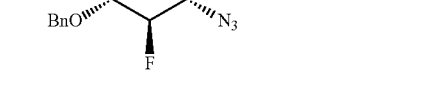

223
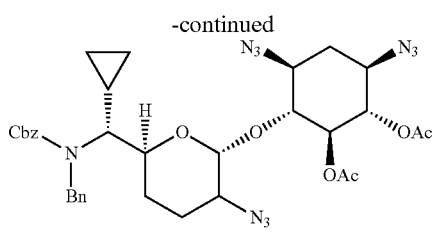
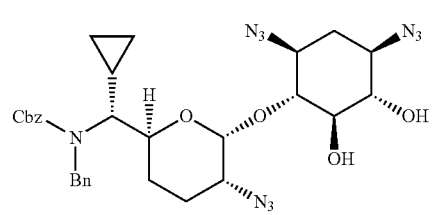
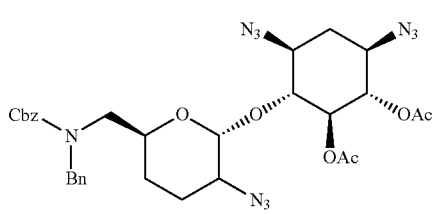
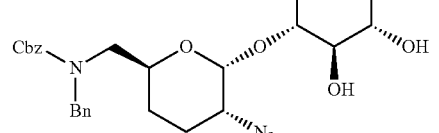
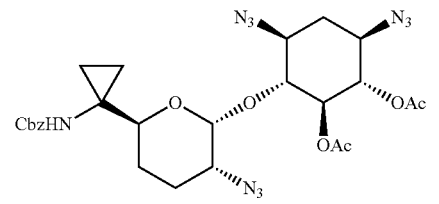
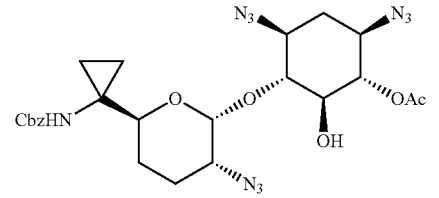
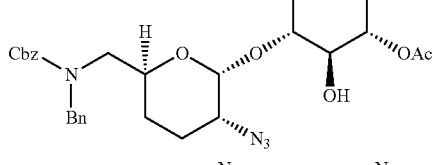
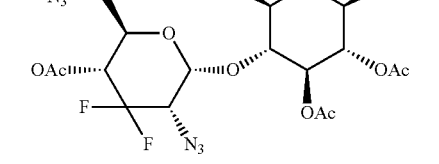
224
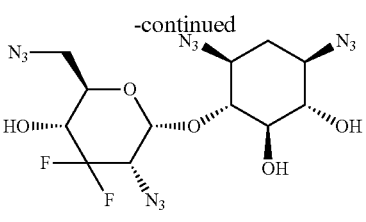
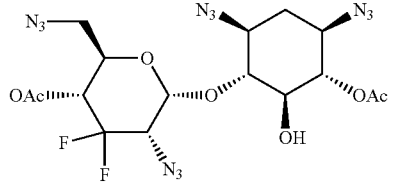
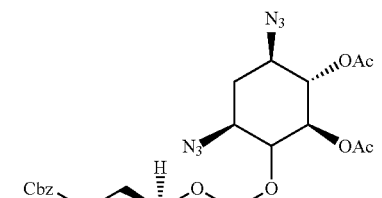
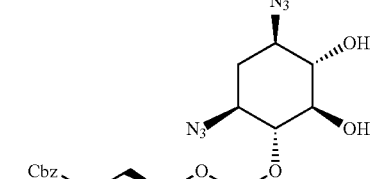
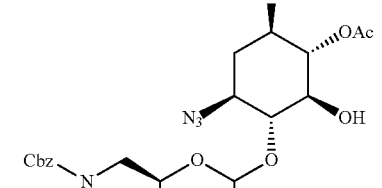
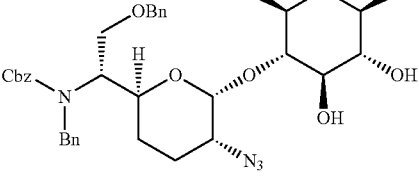
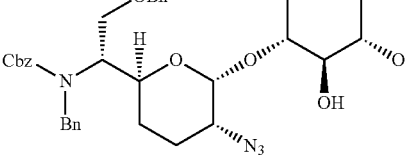

225
-continued
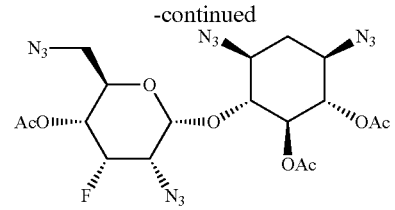
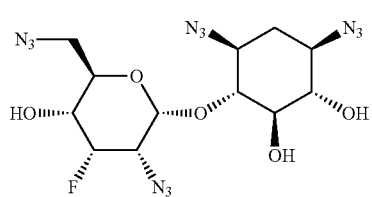
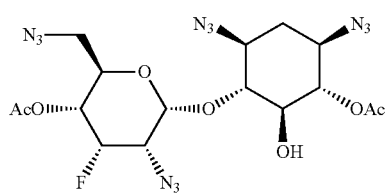
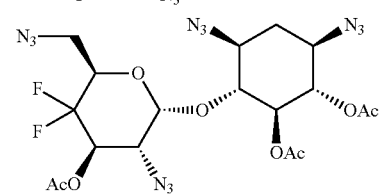
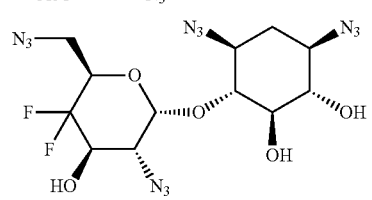
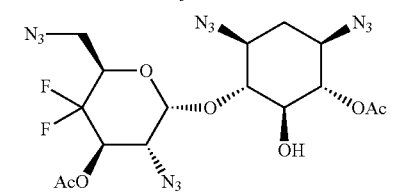
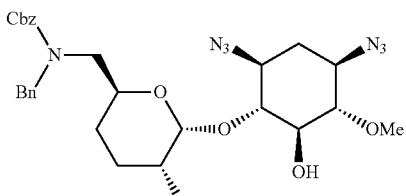
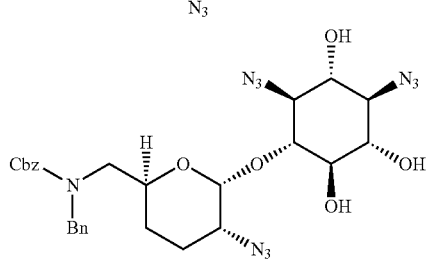
226
-continued
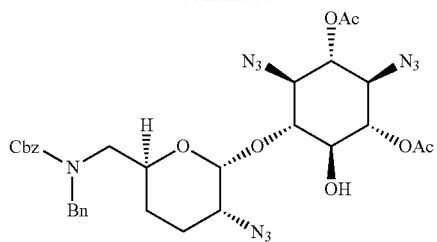
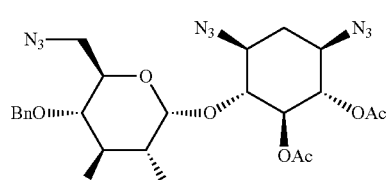
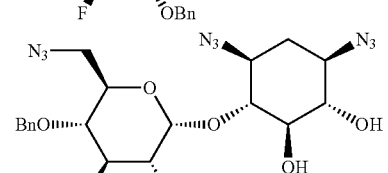
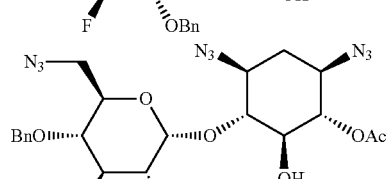
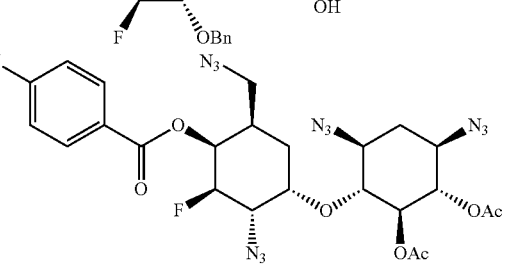
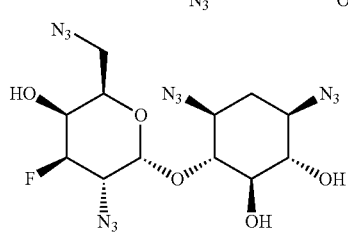
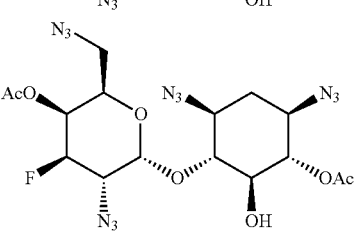
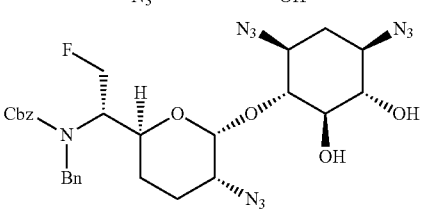

227
-continued
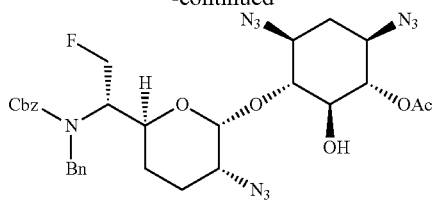
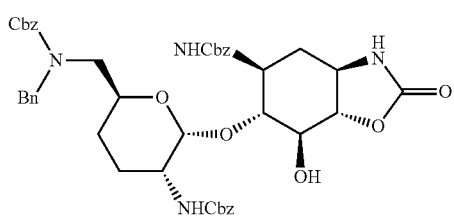
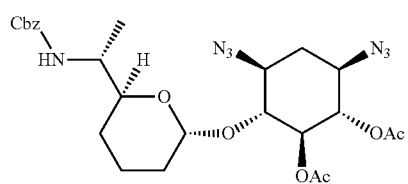
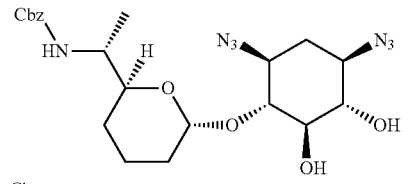
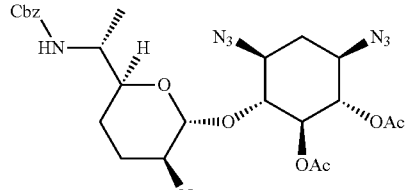
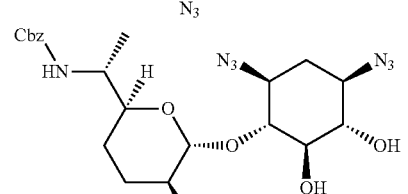
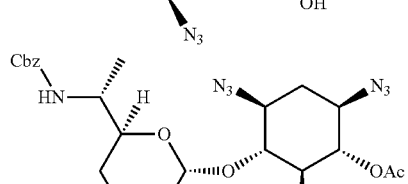
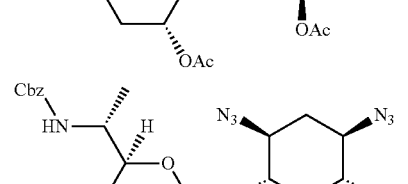
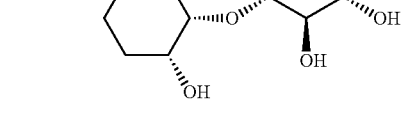
228
-continued
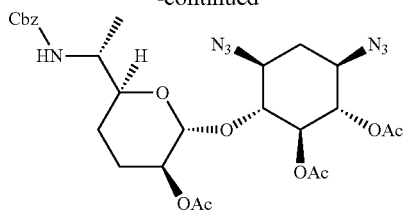
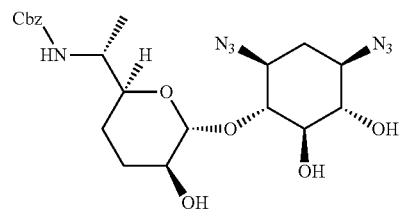
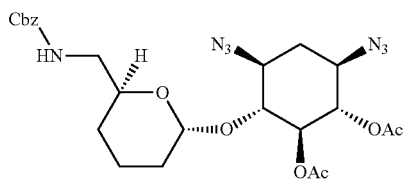
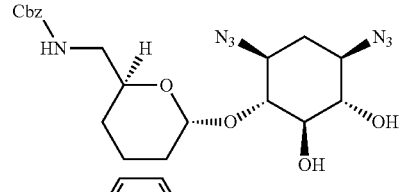
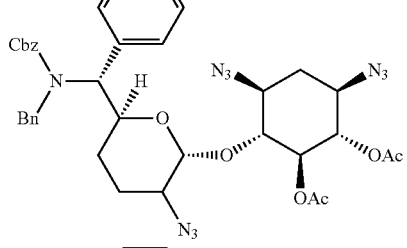
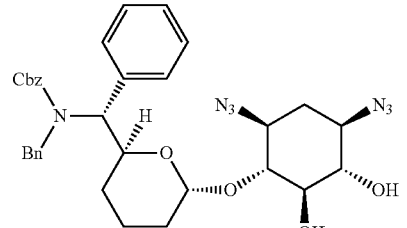
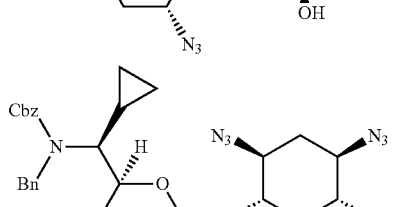
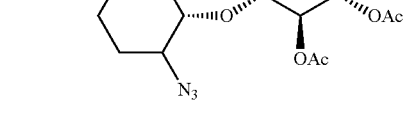

229
-continued
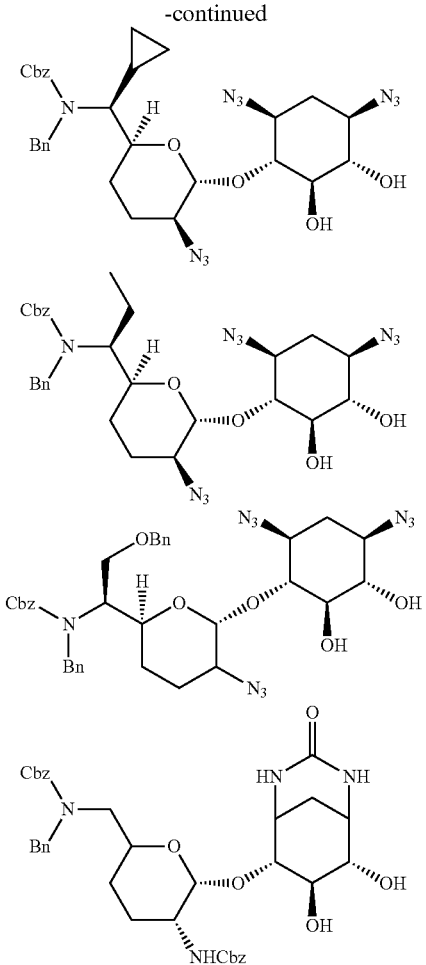
or a salt, solvate, enantiomer, or diastereomer of any of the foregoing.
In some embodiments, the compound of the present disclosure is selected from the group consisting of:
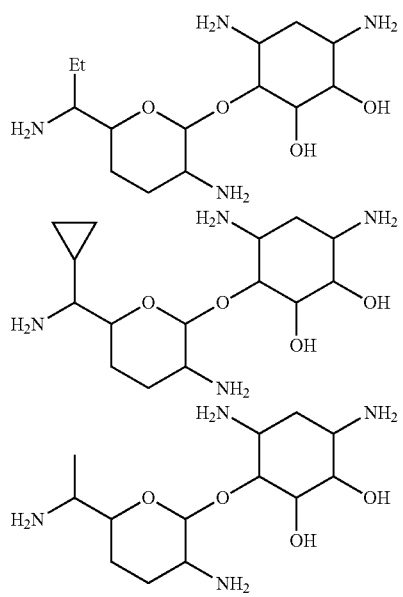
230
-continued
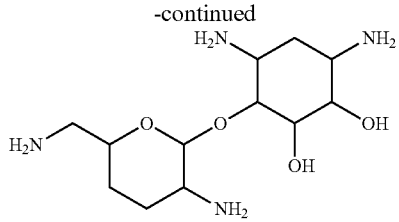
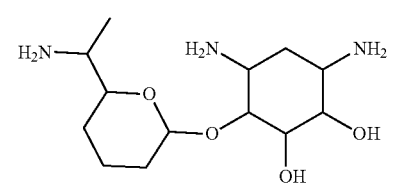
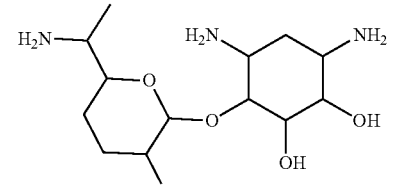
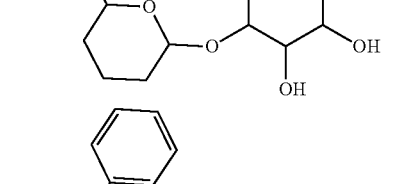
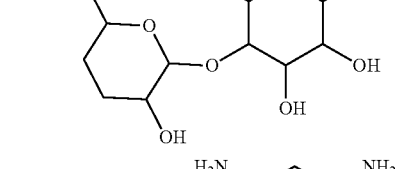
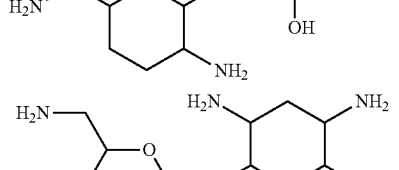
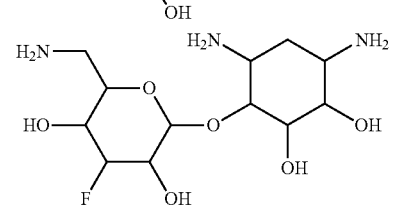

-continued
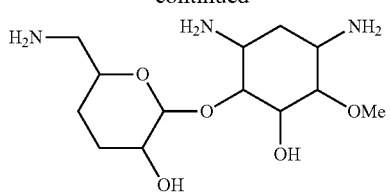
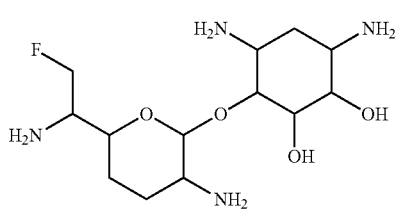
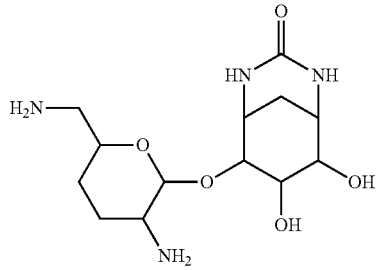
or a salt, solvate, enantiomer, or diastereomer of any of the foregoing.
In some embodiments, the compound of the present disclosure is selected from the group consisting of:
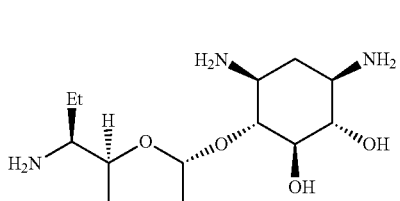
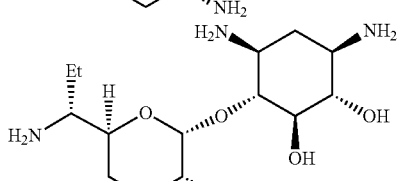

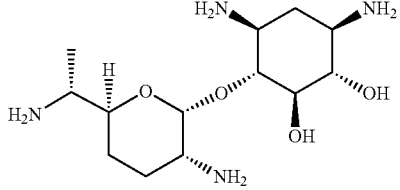
-continued
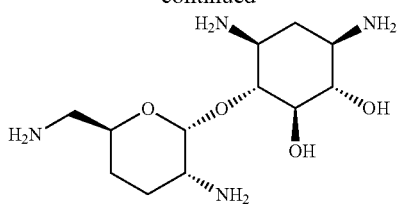
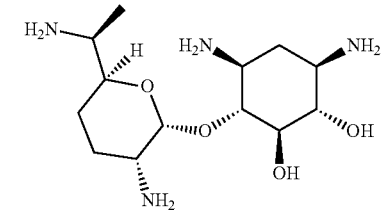
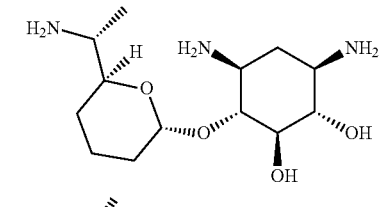
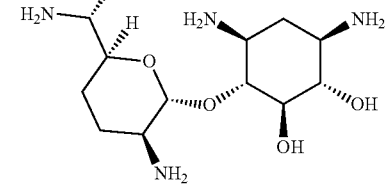
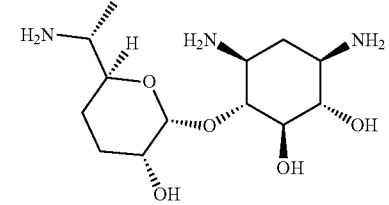
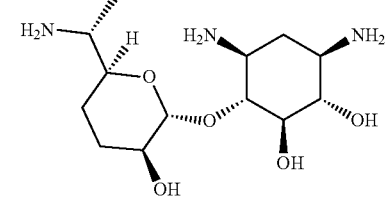
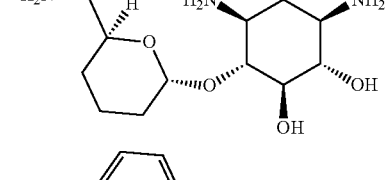
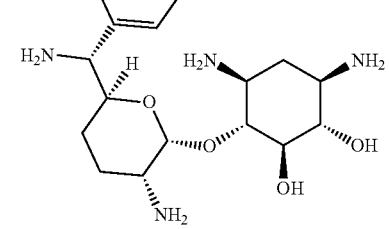

-continued
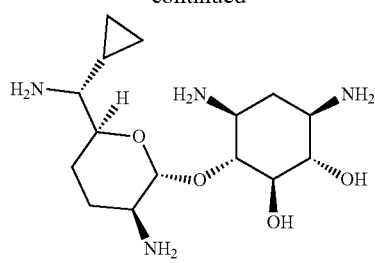
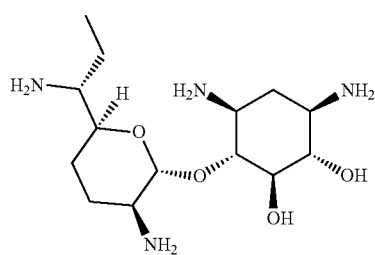
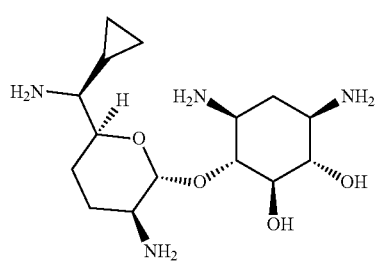
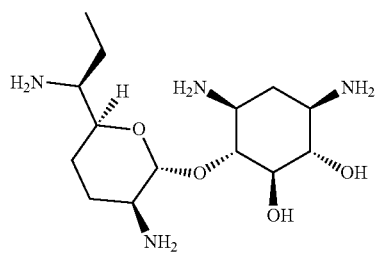
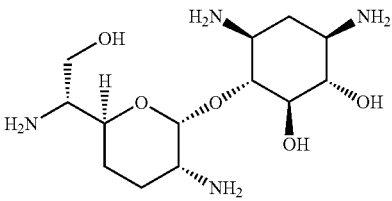
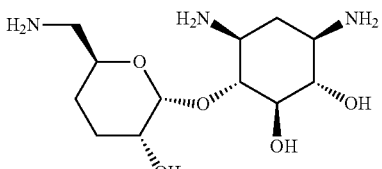
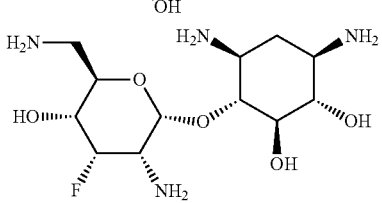
-continued
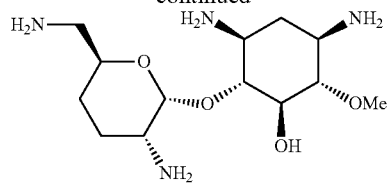
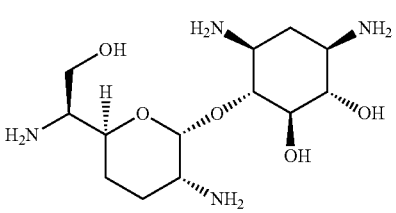
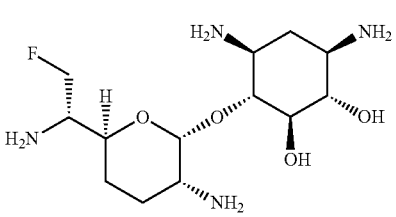
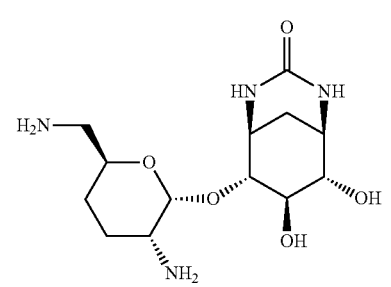
or a salt, solvate, enantiomer, or diastereomer of any of the foregoing.
In some embodiments, the compound of the present disclosure is selected from the group consisting of:
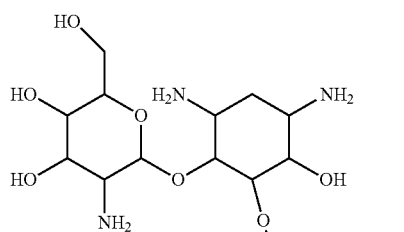
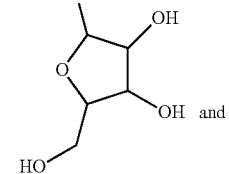
and

235

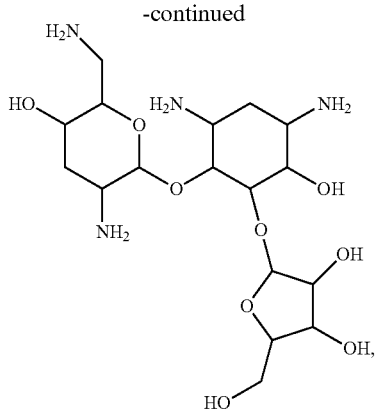

-continued or a salt, solvate, enantiomer, or diastereomer of any of the foregoing.

In some embodiments, the compound of the present disclosure is selected from the group consisting of:

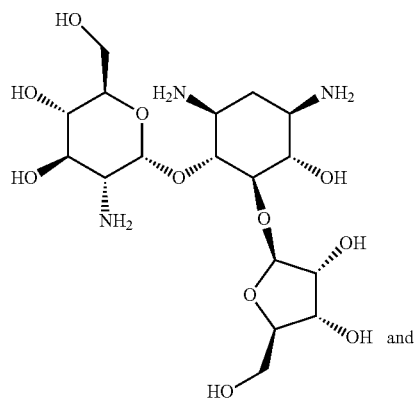

and

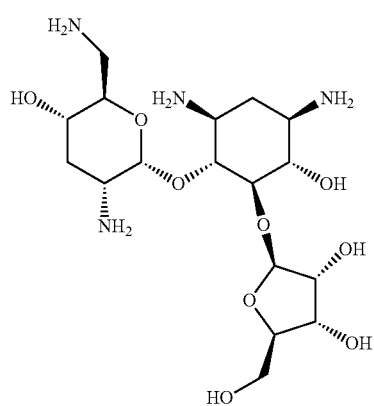

or a salt, solvate, enantiomer, or diastereomer of any of the foregoing.

In some embodiments, the compound of the present disclosure is:

236

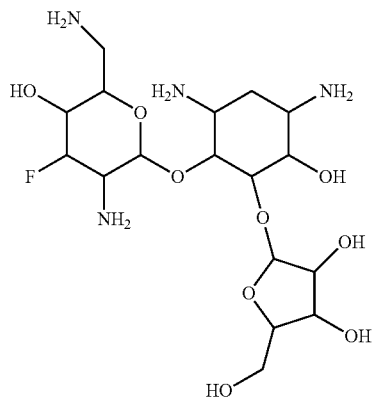 [SMILES: NCC1OC(OC2C(N)CC(N)C(O)C2OC2OC(CO)C(O)C2O)C(N)C(F)C1O]

or a salt, solvate, enantiomer, or diastereomer thereof.

In some embodiments, the compound of the present disclosure is:

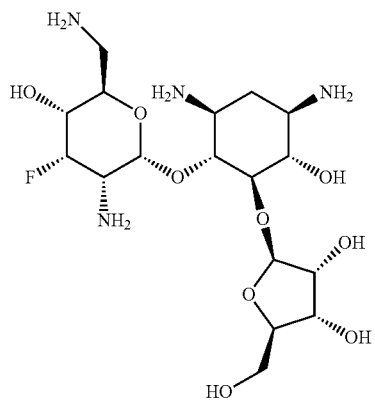 [SMILES: NC[C@H]1O[C@H](O[C@H]2[C@H](O[C@@H]3O[C@H](CO)[C@@H](O)[C@H]3O)[C@@H](O)[C@H](N)C[C@@H]2N)[C@H](N)[C@H](F)[C@@H]1O]

or a salt, solvate, enantiomer, or diastereomer thereof.

In some embodiments, the compound of the present disclosure is selected from the group consisting of:

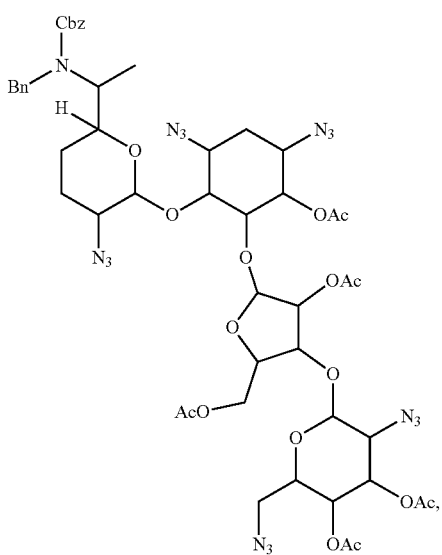

237
-continued
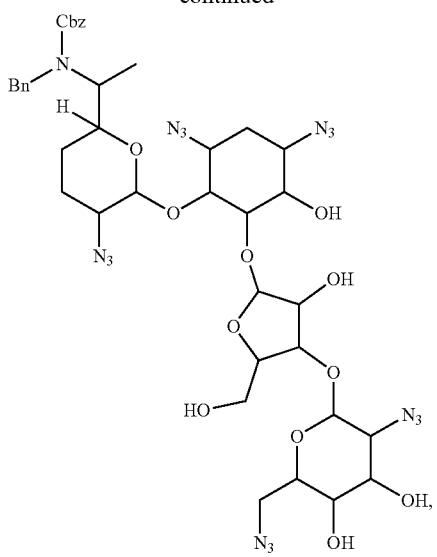
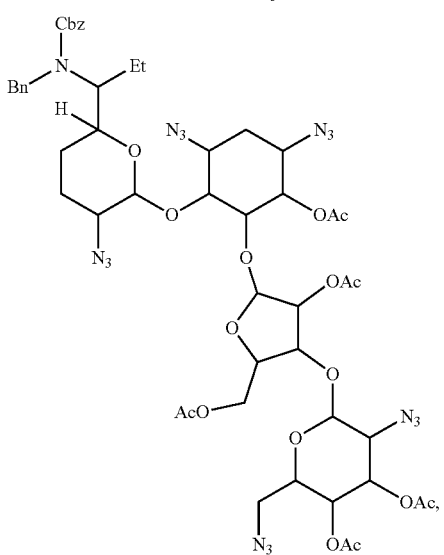
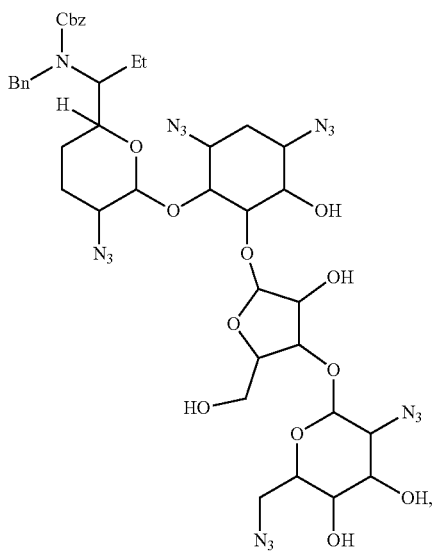
238
-continued
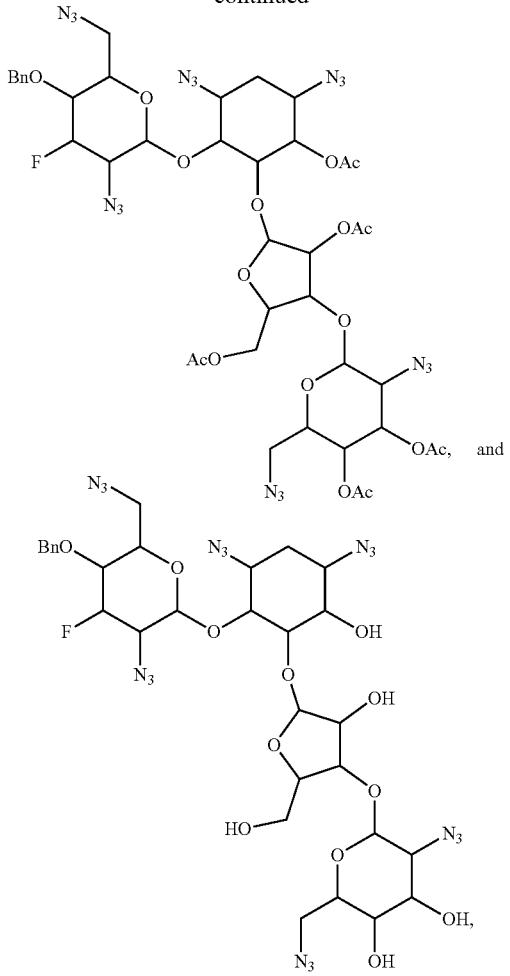
or a salt, solvate, enantiomer, or diastereomer of any of the foregoing.
In some embodiments, the compound of the present disclosure is selected from the group consisting of:
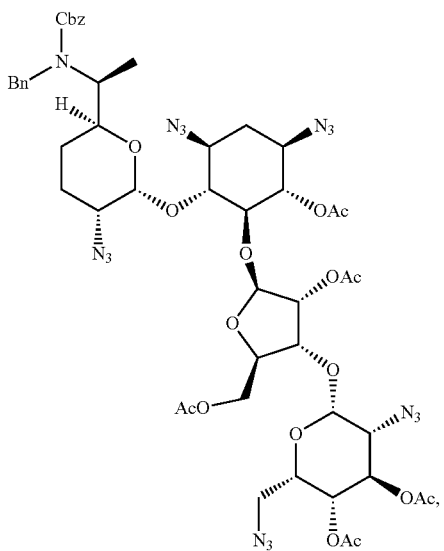

239
-continued
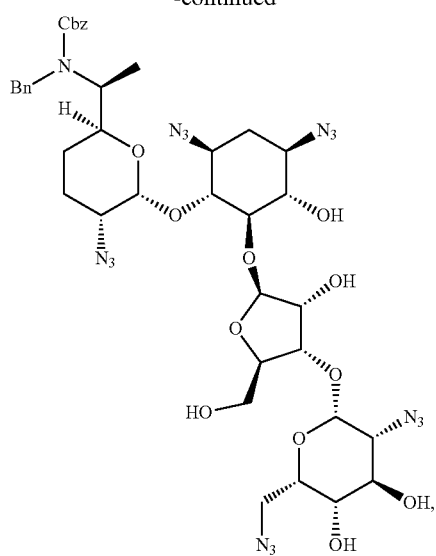
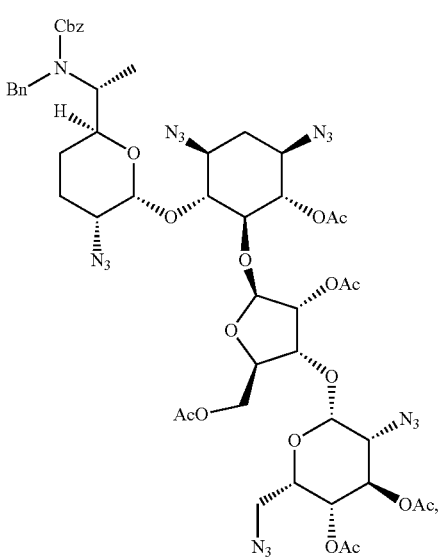
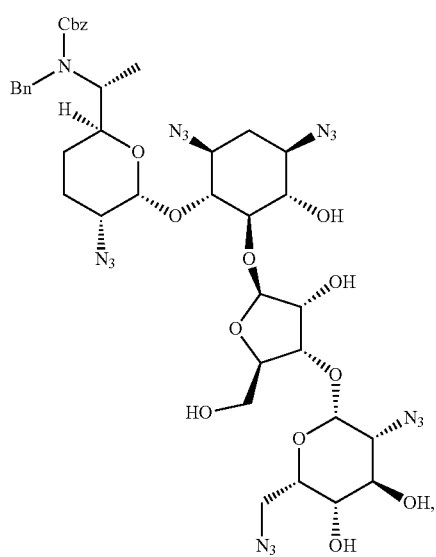
240
-continued
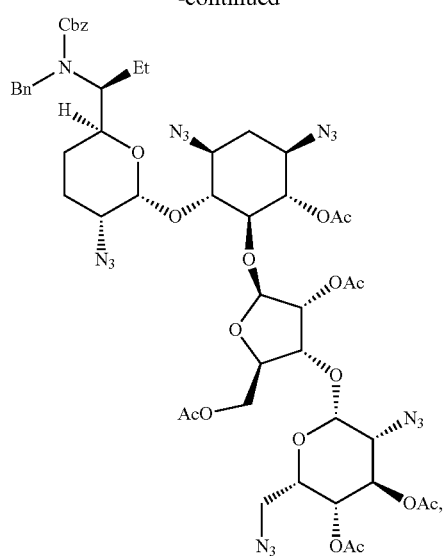
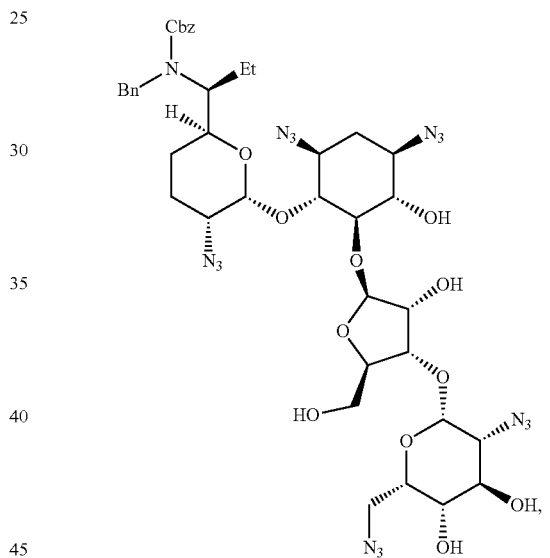
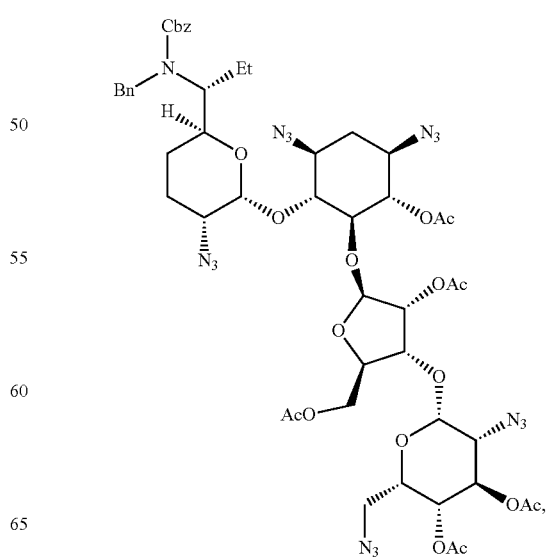

241
-continued
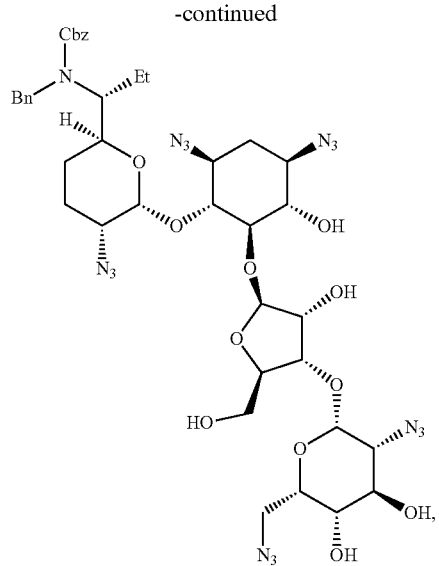
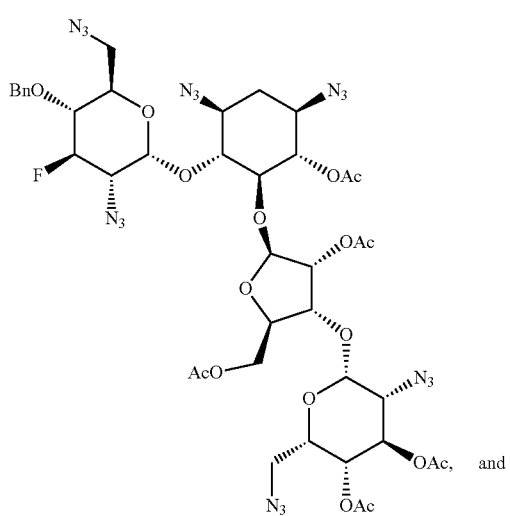
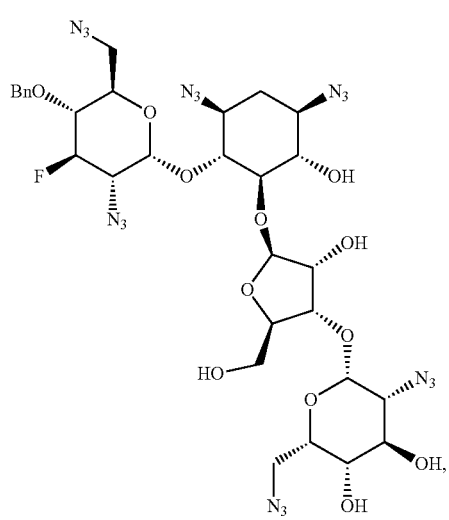 [SMILES: [N-]=[N+]=NC[C@@H]1O[C@H](O[C@H]2[C@@H](O)[C@H](O[C@@H]3[C@@H](O)[C@H](N=[N+]=[N-])C[C@H](N=[N+]=[N-])[C@H]3O[C@H]3O[C@H](CN=[N+]=[N-])[C@@H](OCc4ccccc4)[C@H](F)[C@H]3N=[N+]=[N-])O[C@@H]2CO)[C@H](N=[N+]=[N-])[C@@H](O)[C@@H]1O]
or a salt, solvate, enantiomer, or diastereomer of any of the foregoing.
242
In some embodiments, the compound of the present disclosure is selected from the group consisting of:
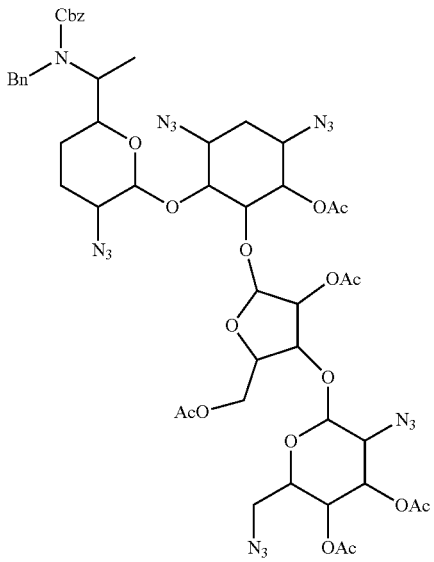
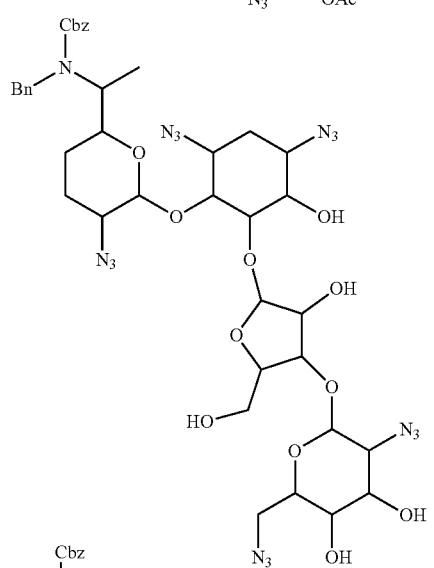
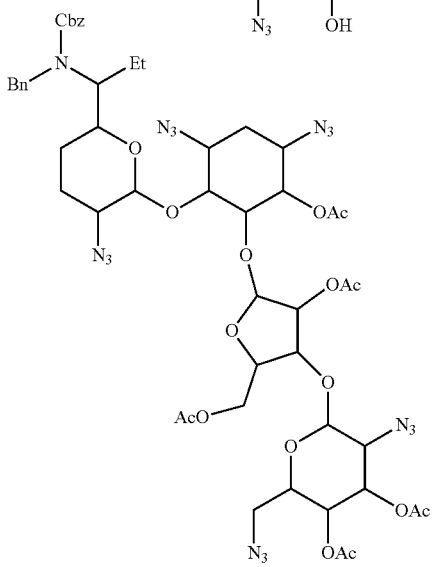

243
-continued
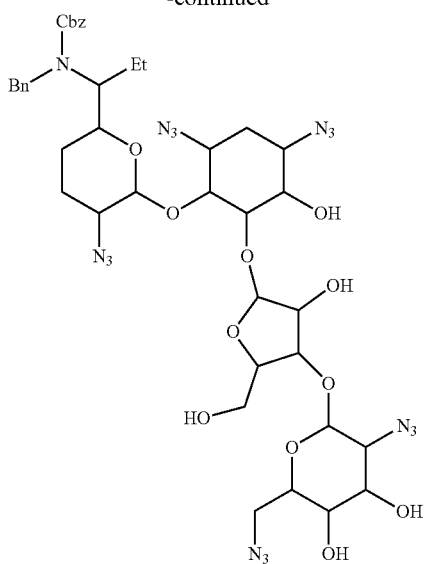
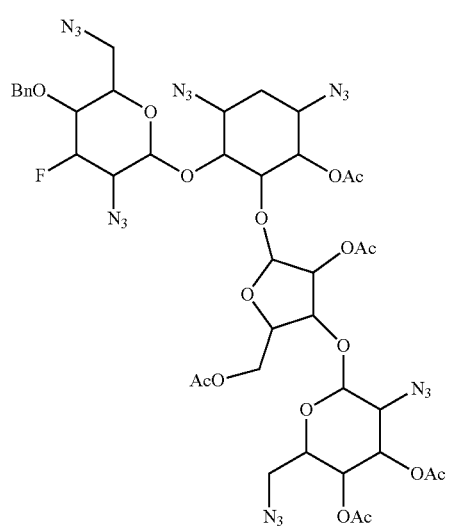
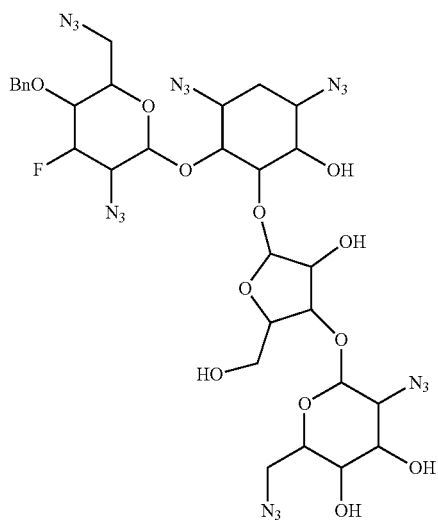
244
-continued
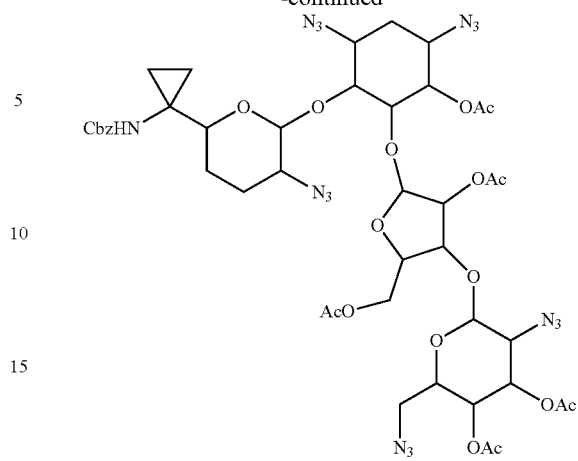
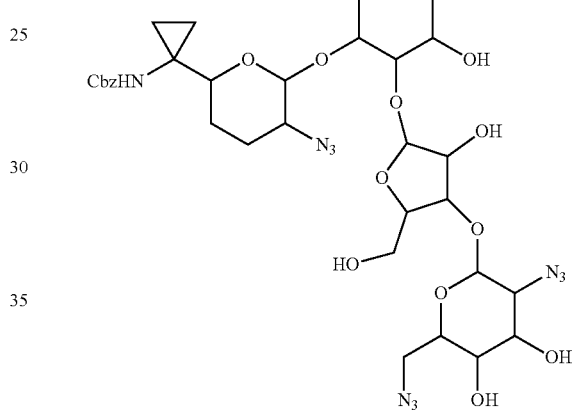
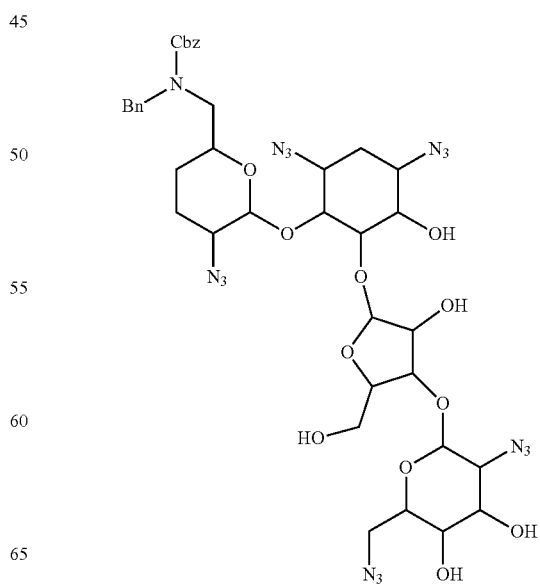

245
-continued
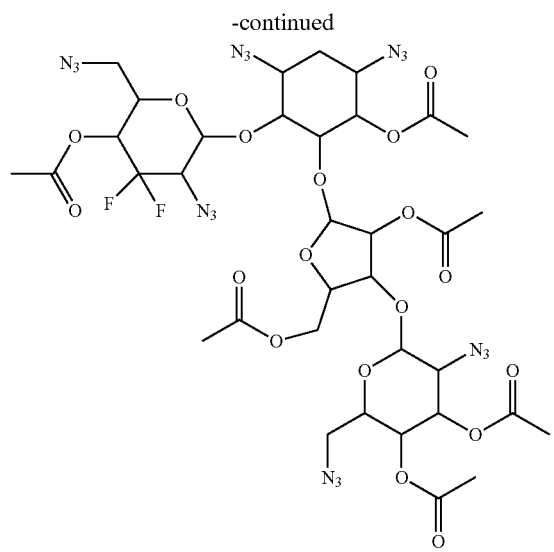
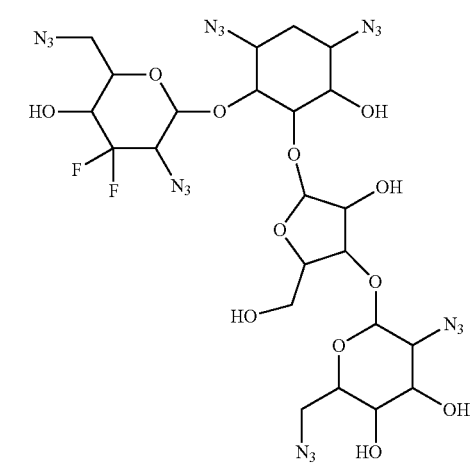
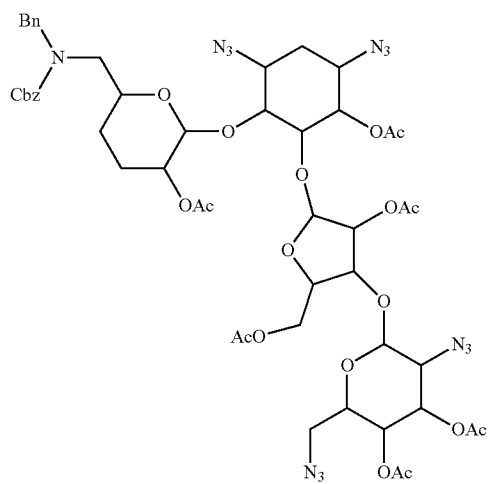
246
-continued
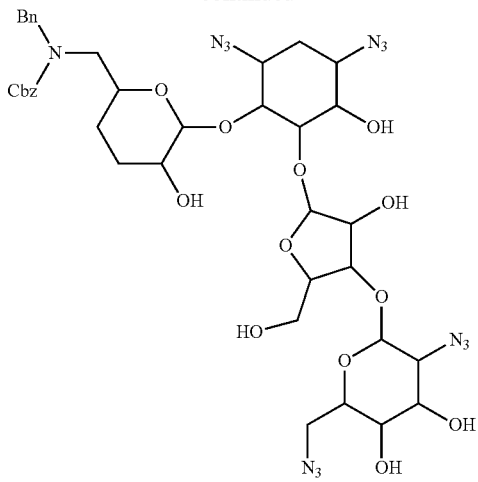
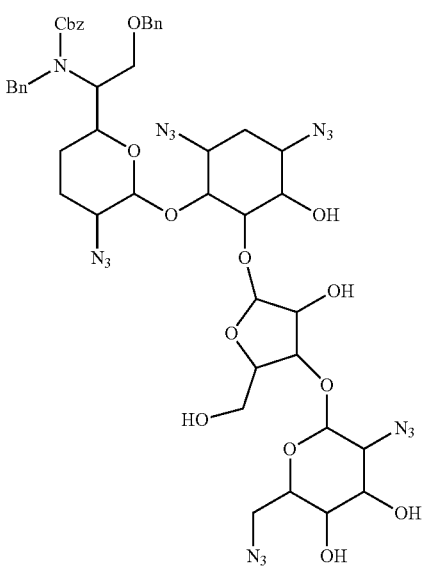

247
-continued
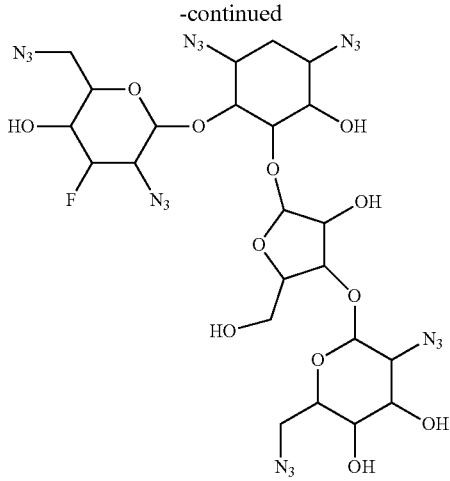
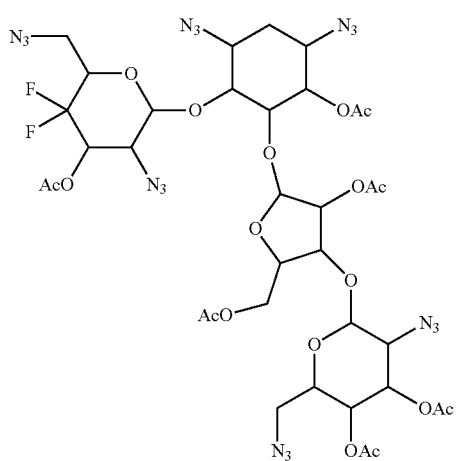
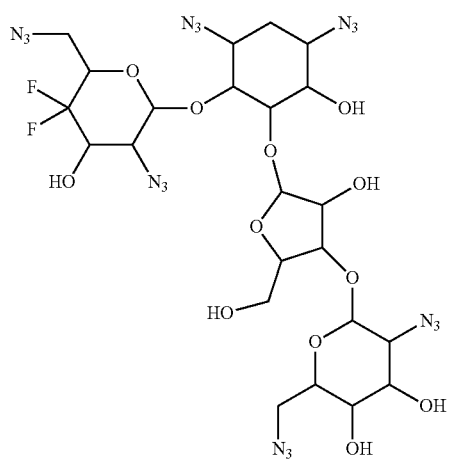
248
-continued
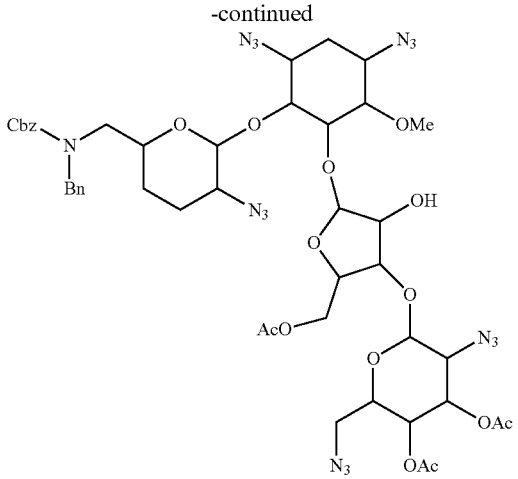
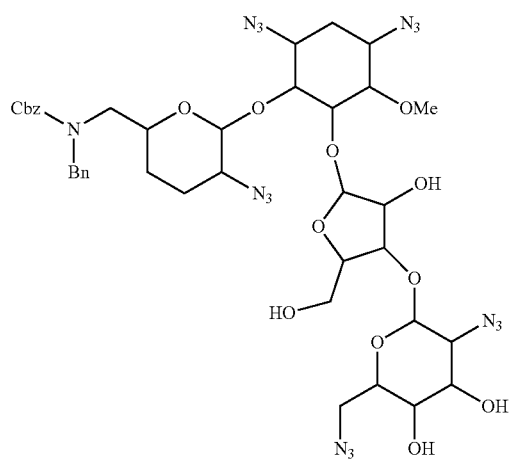
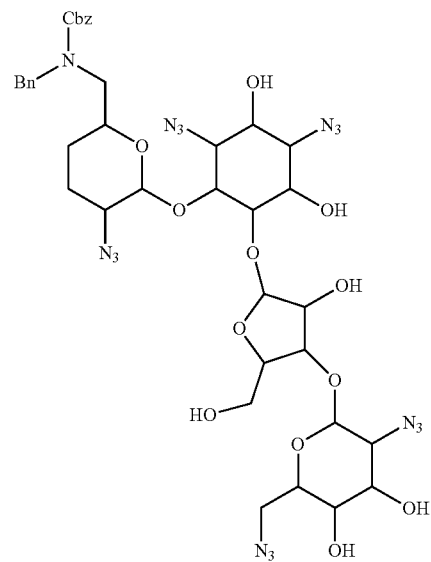

249
-continued
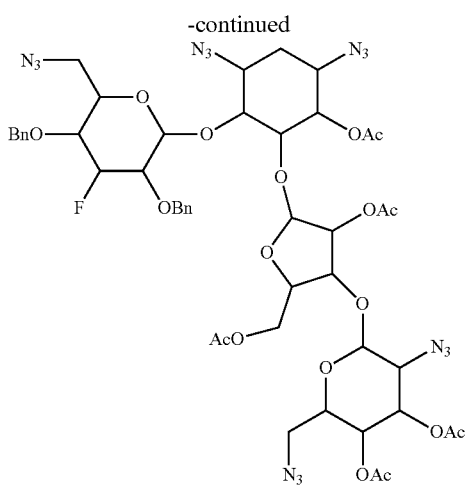
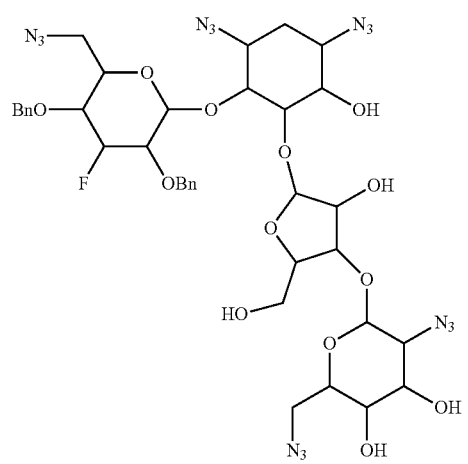
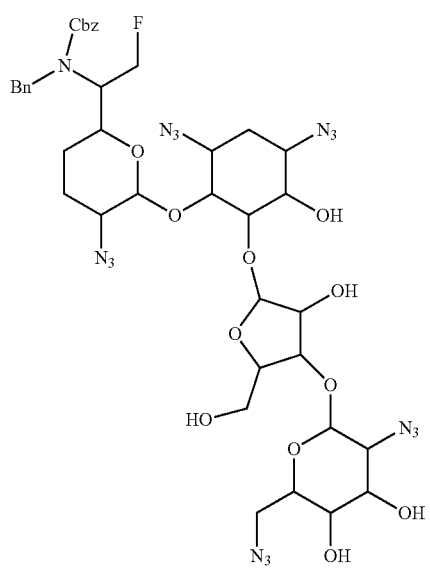
250
-continued
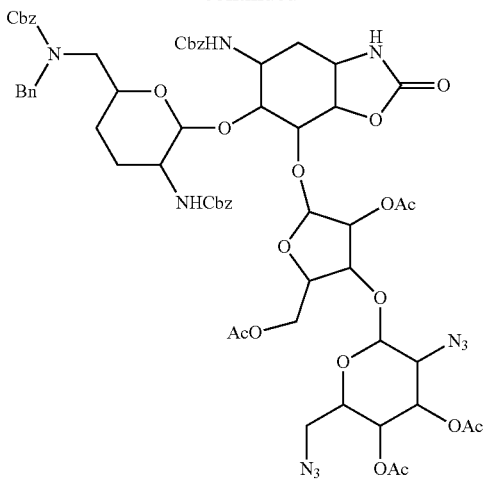
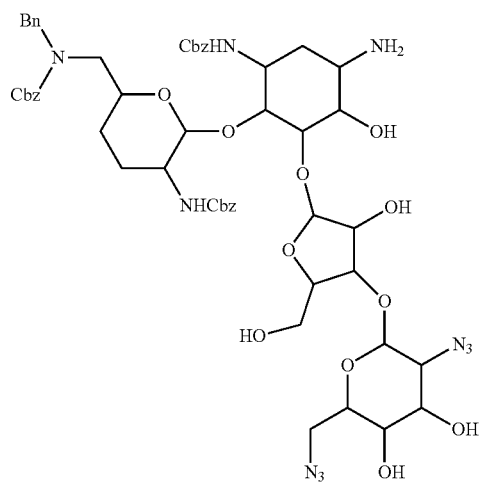

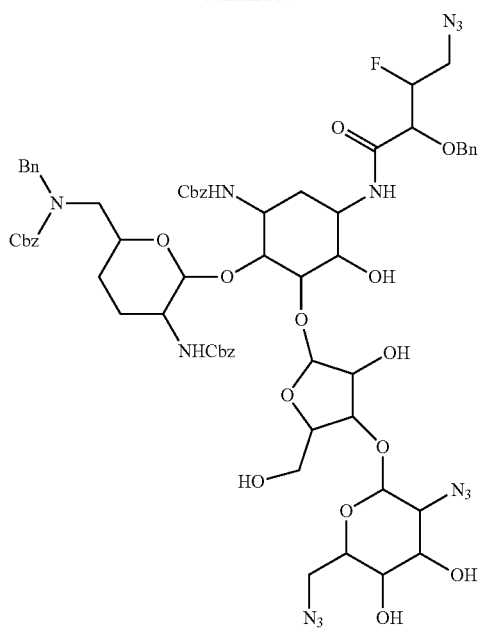 [SMILES: [N-]=[N+]=NCC(F)C(OCc1ccccc1)C(=O)NC1CC(NC(=O)OCc2ccccc2)C(OC2OC(CN(Cc3ccccc3)C(=O)OCc3ccccc3)CCC2NC(=O)OCc2ccccc2)C(OC2OC(CO)C(OC3OC(CN=[N+]=[N-])C(O)C(O)C3N=[N+]=[N-])C2O)C1O]
or a salt, solvate, enantiomer, or diastereomer of any of the foregoing.
In some embodiments, the compound of the present disclosure is selected from the group consisting of:
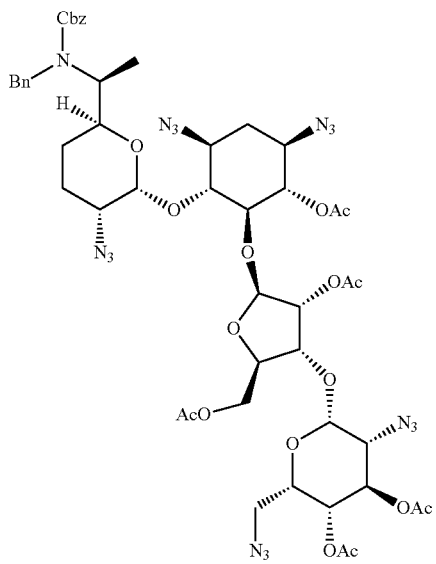
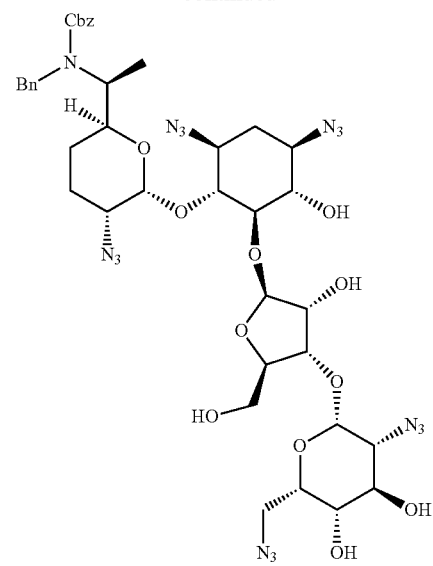
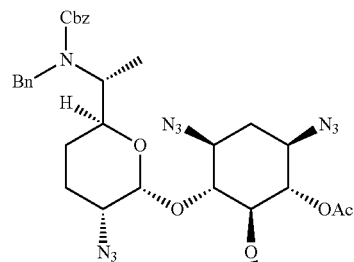
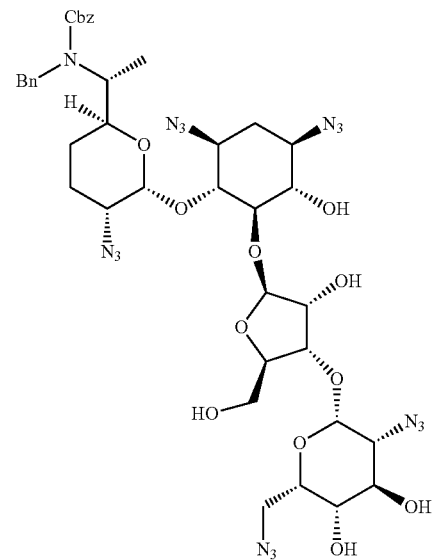

253
-continued
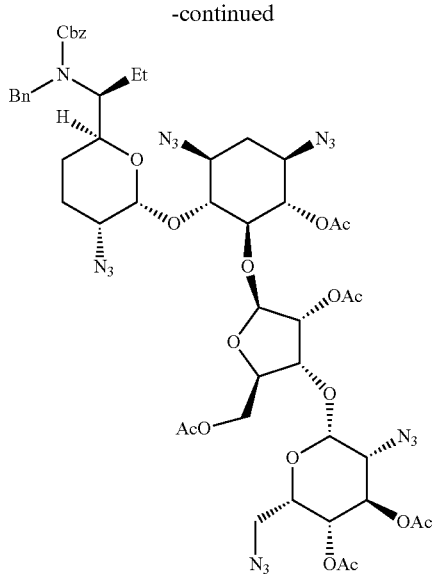
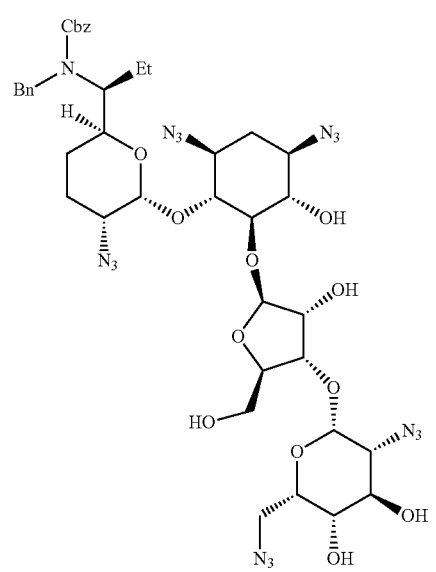
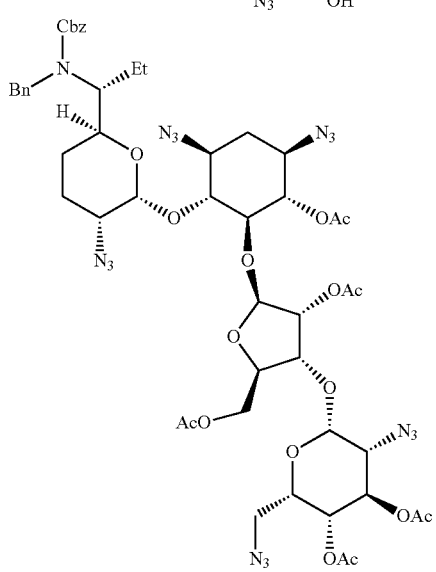
254
-continued
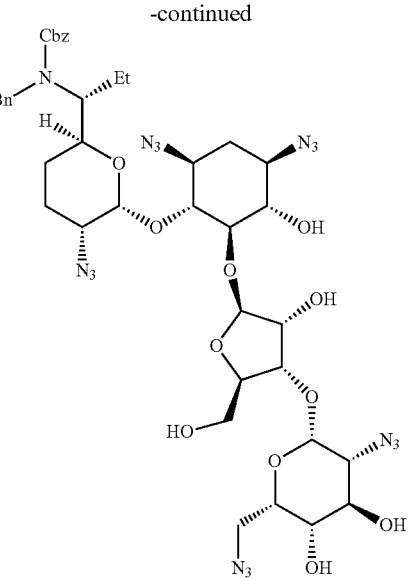
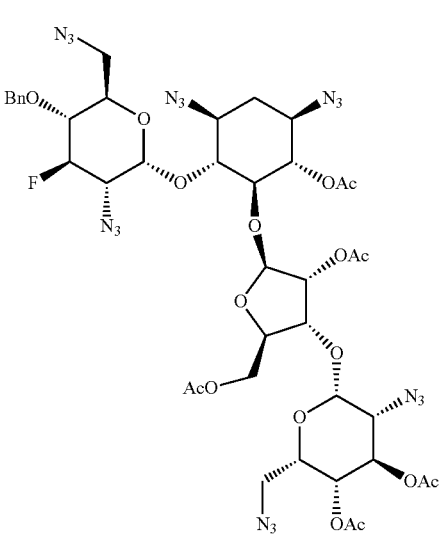

255
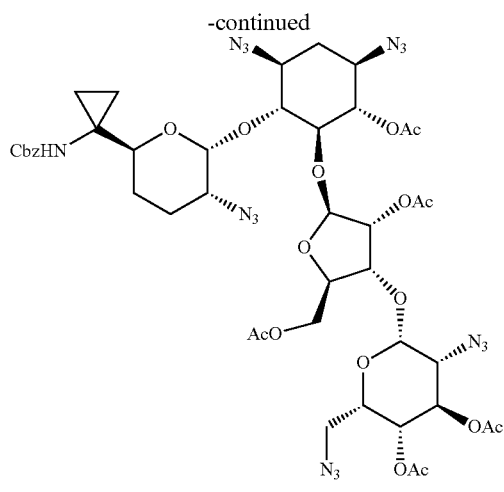
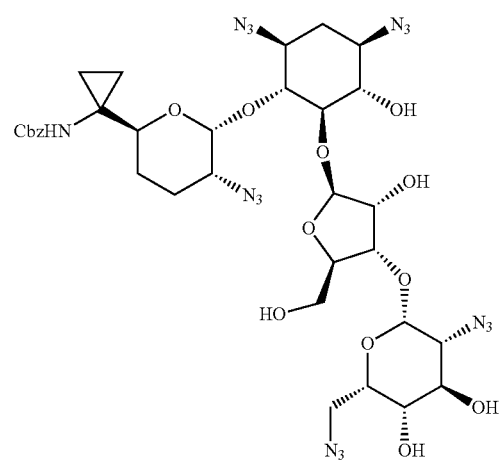
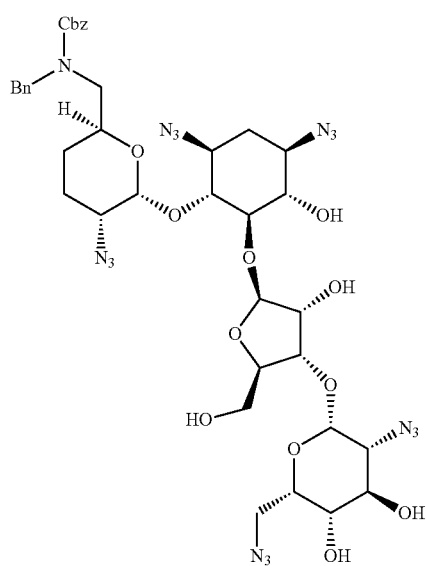
256
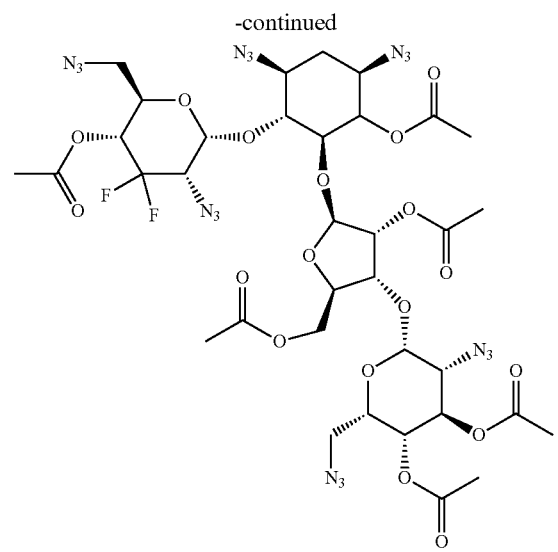
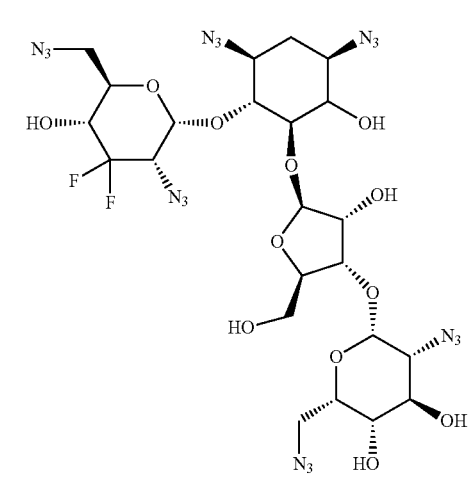
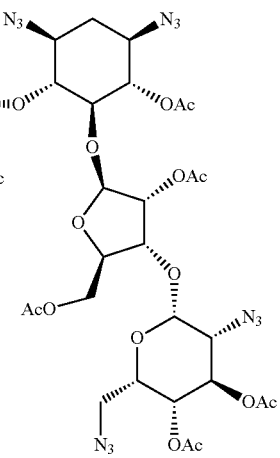

257
-continued
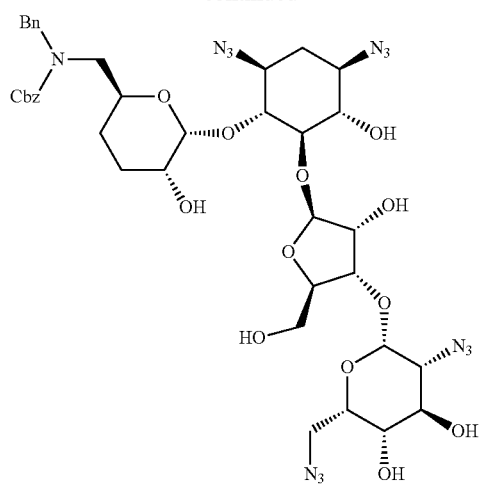
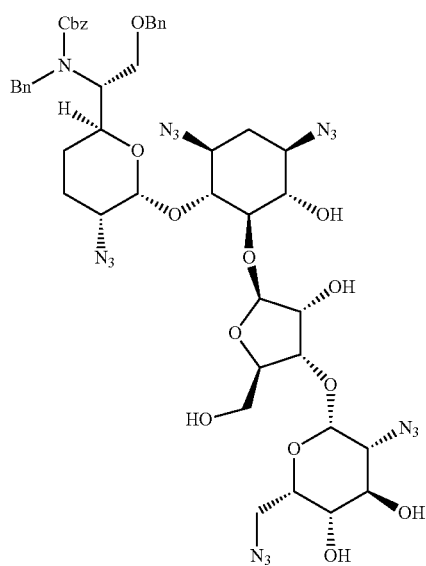
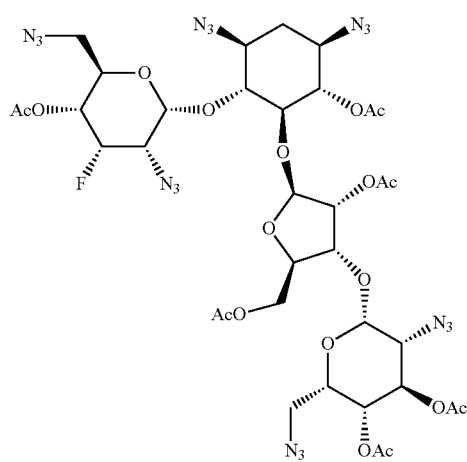
258
-continued
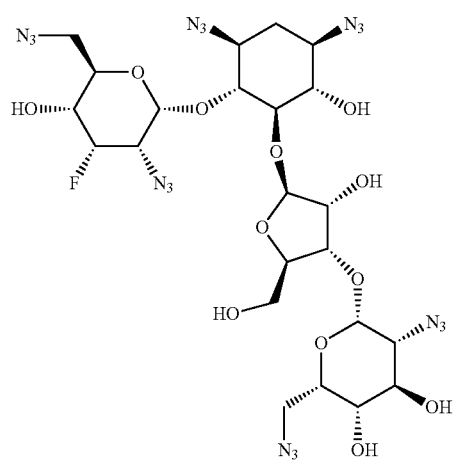
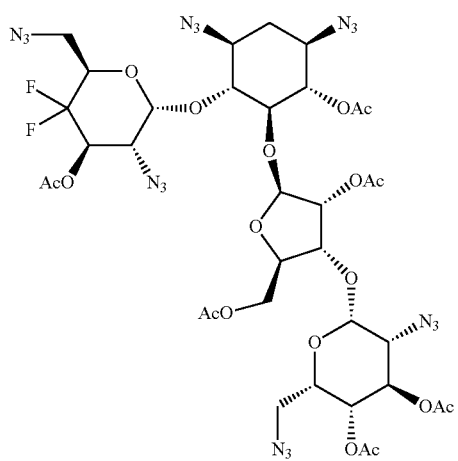
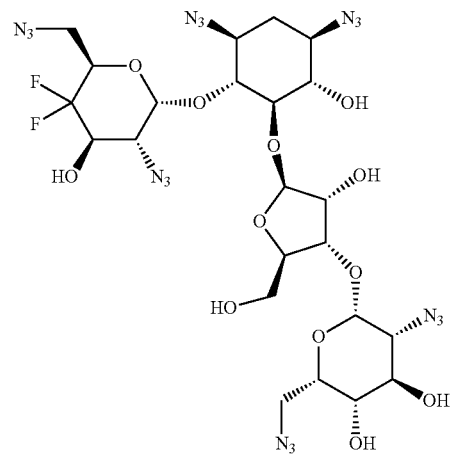

259
-continued
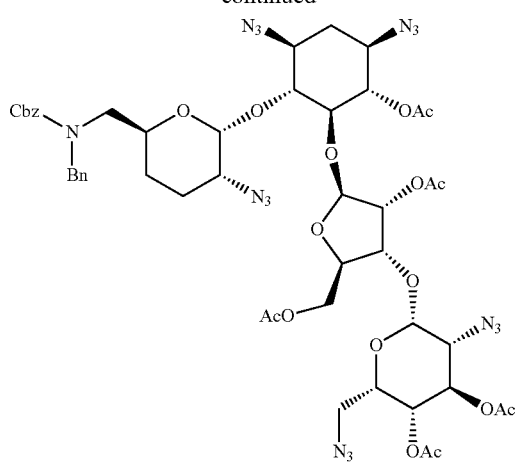
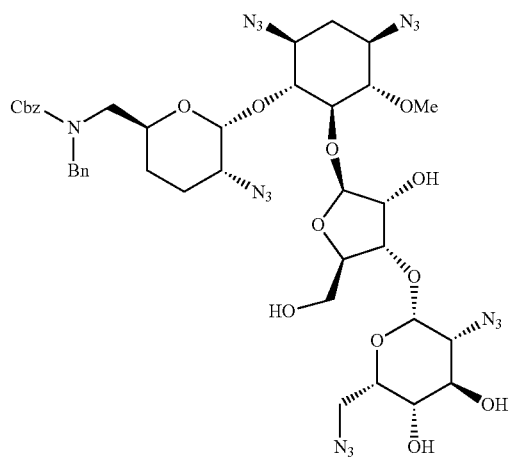
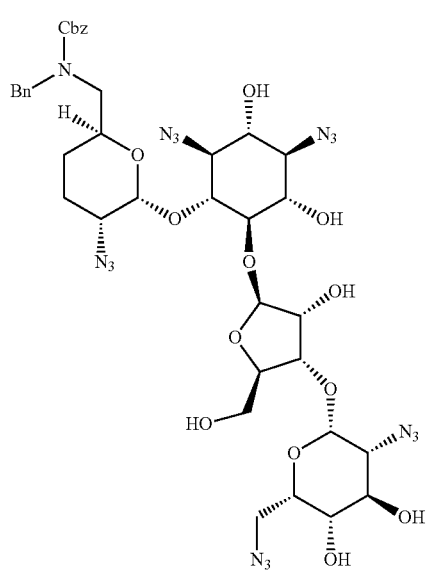
260
-continued
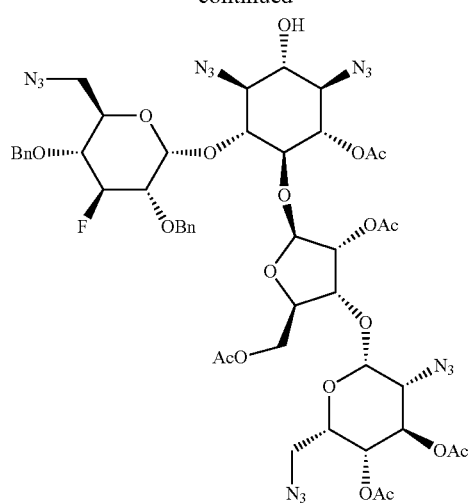
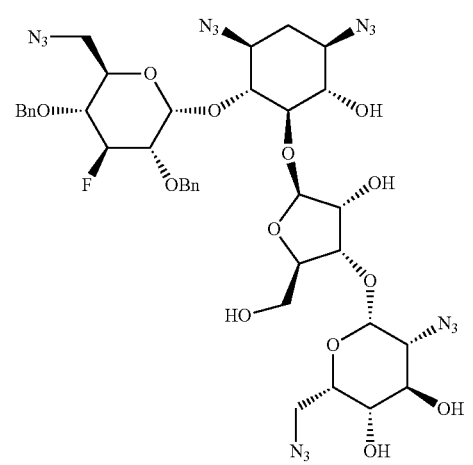
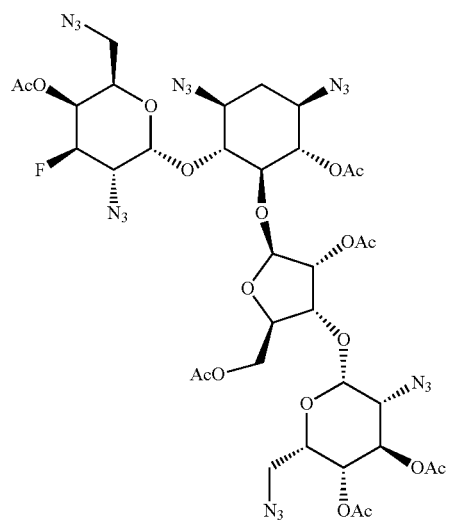

261
-continued
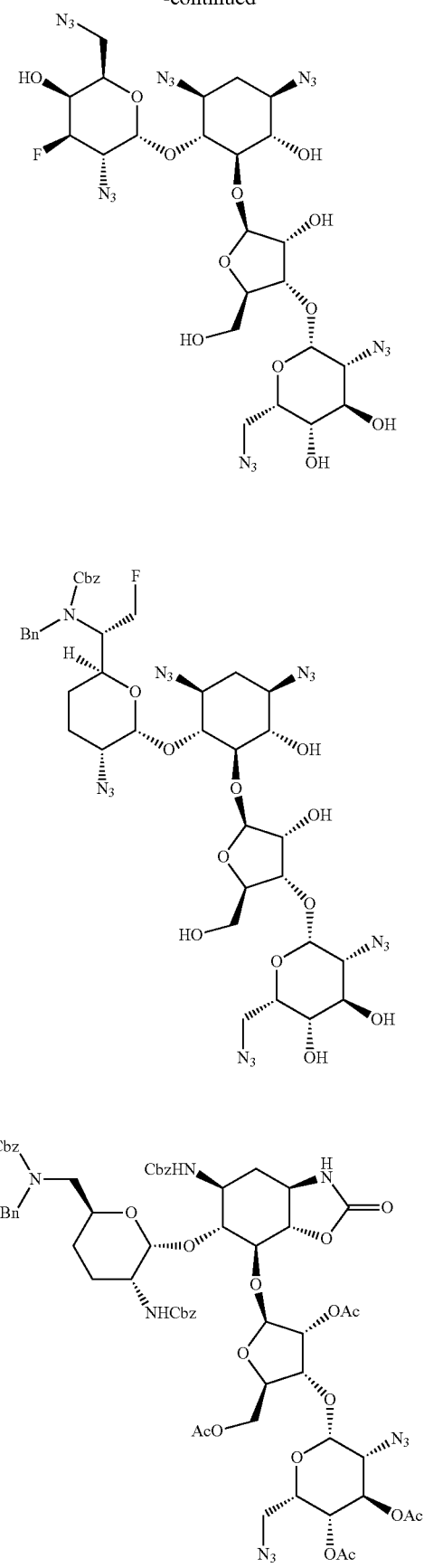
262
-continued
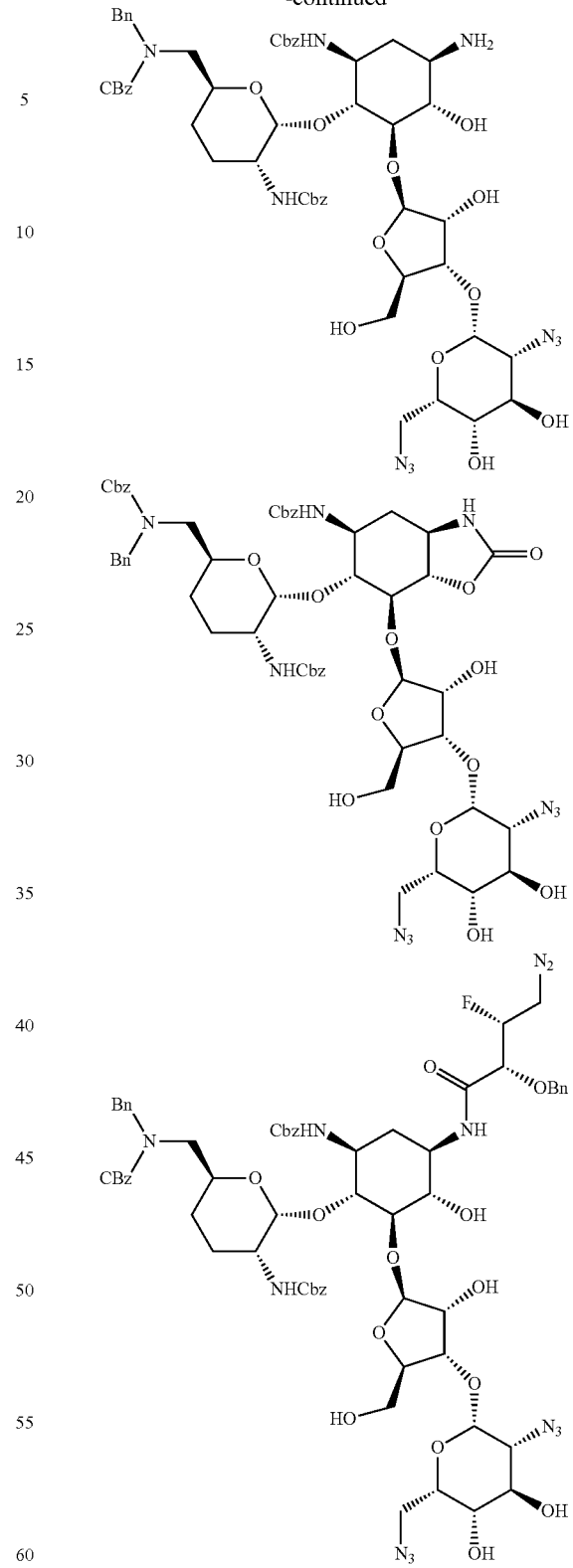
or a salt, solvate, enantiomer, or diastereomer of any of the foregoing.
Methods of Treatment
Provided herein are also methods of using compounds of formulae AB-2 and ABC-2, or a pharmaceutically acceptable salt, solvate, stereoisomer, or tautomer of any of these. In particular, provided is a method of treating a bacterial infection in a mammal, comprising administering to a mammal in need thereof a therapeutically effective amount of a compound of formulae AB-2 and ABC-2, or a pharmaceutically acceptable salt, solvate, stereoisomer, or tautomer thereof. Provided is a method of treating a bacterial infection in a mammal, comprising administering to a mammal in need thereof a therapeutically effective amount of a pharmaceutical composition comprising a compound of formulae AB-2 and ABC-2, or a pharmaceutically acceptable salt, solvate, stereoisomer, or tautomer thereof, and a pharmaceutically acceptable excipient. In some embodiments, the mammal is a human.

The bacterial infection may be a gram-positive or gram-negative bacterial infection. The bacterial infection may be infection of aerobic or anaerobic bacteria. The infection may be an infection of one or more species selected from the group consisting of *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Bacillus, Bacteroides, Peptococcus, Clostridium, Salmonella, Shigella, Serratia, Haemophilus, Brucella, Francisella, Anthracis, Yersinia, Corynebacterium, Moraxella*, and *Enterococcus*.

Bacterial infections susceptible to treatment according to the present disclosure may include primary infections and co-infections caused by a species of bacteria and one or more additional infectious agents such as, for example, bacteria, virus, parasite and fungus.

In yet a further aspect, provided herein is the use of a compound formulae AB-2 and ABC-2, or a pharmaceutically acceptable salt, solvate, stereoisomer, or tautomer thereof, in the manufacture of a medicament for treating a bacterial infection in a subject in need thereof.

In still a further aspect, provided herein is a compound formulae AB-2 and ABC-2, or a pharmaceutically acceptable salt, solvate, stereoisomer, or tautomer thereof, for use in a method of treating a bacterial infection in a subject in need thereof.

Pharmaceutical Compositions

For the purposes of administration, the compounds of the present disclosure may be administered as a raw chemical or may be formulated as pharmaceutical compositions. Pharmaceutical compositions of the present disclosure comprise a compound of formula AB-2 or ABC-2, or a pharmaceutically acceptable salt, solvate, stereoisomer, or tautomer of any of these, and a pharmaceutically acceptable carrier, diluent or excipient. The compound of formula AB-2 or ABC-2, or a pharmaceutically acceptable salt, solvate, stereoisomer, or tautomer of any of these, is present in the composition in an amount that is effective to treat a particular disease or condition of interest—for example, in an amount sufficient to treat a bacterial infection, and generally with acceptable toxicity to the patient. The antibacterial activity of compounds of formula AB-2 or ABC-2, or a pharmaceutically acceptable salt, solvate, stereoisomer, or tautomer of any of these, can be determined by one skilled in the art, for example, as described in the Examples below. Appropriate concentrations and dosages can be readily determined by one skilled in the art.

Administration of the compounds of the disclosure, such as compounds of formula AB-2 or ABC-2, or a pharmaceutically acceptable salt, solvate, stereoisomer, or tautomer of any of these, in pure form or in an appropriate pharmaceutical composition can be carried out via any of the accepted modes of administration of agents for serving similar utilities. The pharmaceutical compositions of the disclosure can be prepared by combining a compound of the disclosure with an appropriate pharmaceutically acceptable carrier, diluent or excipient, and may be formulated into preparations in solid, semi solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the disclosure can be formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the disclosure in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000).

EXEMPLARY EMBODIMENTS

Some embodiments of this disclosure are Embodiment I, as follows:

Embodiment I-1. A process for preparing a compound of formula A-5,

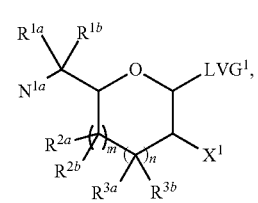

A-5 wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{12}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and C$_1$-C$_6$ alkyl, wherein each R$^{27}$, R$^{28}$, and R$^{29}$ is independently H or alkyl; wherein the C$_1$-C$_6$ alkyl or alkyl is unsubstituted or substituted with one or more substituents selected from the group consisting of halogen, —OR$^{30}$, —NR$^{31}$R$^{32}$, —SR$^{33}$, and —SO$_2$R$^{34}$;

wherein each R$^{30}$, R$^{31}$, R$^{32}$, R$^{33}$, and R$^{34}$ is independently H or alkyl substituted with one or more substituents independently selected from the group consisting of halogen, cyano, NR$^{14}$R$^{15}$, and —OR$^{16}$; or R$^{2a}$ and R$^{2b}$ form an oxo or imino group substituted with C$_1$-C$_6$ alkyl;

R$^{3a}$ and R$^{3b}$ form an oxo or imino group substituted with C$_1$-C$_6$ alkyl;

X$^1$ is —F, —Cl, —Br, or —I;

LVG$^1$ is a leaving group;

N$^{1a}$ is —NHPg$^{1a}$ or N$_3$, wherein Pg$^{1a}$ is an amino protecting group;

m is zero, 1, or 2;

n is zero, 1, or 2; and, wherein m+n is 1, 2 or 3;

or a salt, solvate, enantiomer, or diastereomer thereof, comprising:

(a) contacting a compound of formula A-1:

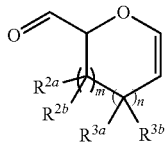

A-1 or a salt, solvate, enantiomer, or diastereomer thereof, with a chiral auxiliary reagent to yield a compound of formula A-2:

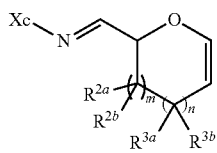

A-2 or a salt, solvate, enantiomer, or diastereomer thereof, wherein Xc is a chiral auxiliary group;

(b) contacting the compound of formula A-2 with a Grignard or organolithium reagent to yield a compound of formula A-3:

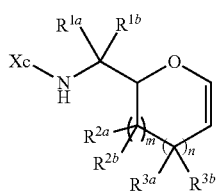

A-3 or a salt, solvate, enantiomer, or diastereomer thereof, (c) contacting the compound of formula A-3 with a halogen reagent in presence of a nucleophile reagent (Nuc-1) to yield a compound of formula A-4:

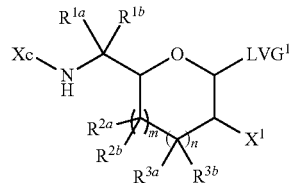

A-4 or a salt, solvate, enantiomer, or diastereomer thereof; wherein

X$^1$ is —F, —Cl, —Br, or —I;

Nuc-1 is LVG$^1$-M, wherein M is H, a metal cation, a non-metal cation, or a lone pair of electrons;

LVG$^1$ is a leaving group;

(d) exchanging the chiral auxiliary group for an amino protecting group in the compound of formula A-4 by reaction with an amino protecting group reagent to yield the compound of formula A-5:

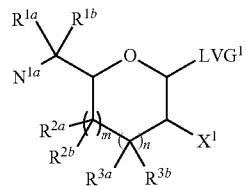

A-5 or a salt, solvate, enantiomer, or diastereomer thereof, wherein N$^{1a}$ is —NHPg$^{1a}$ or N$_3$, wherein Pg$^{1a}$ is an amino protecting group.

Embodiment I-2. The process of Embodiment I-1, wherein, when X$^1$ is not —NH$_2$, —N$_3$, a protected amino group, further comprising after step (d):

(e) converting X$^1$ in the compound of formula A-5 to X to yield a compound of formula A-6:

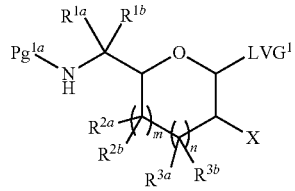

A-6 or a salt, solvate, enantiomer, or diastereomer thereof, wherein X is —NH$_2$, —N$_3$, a protected amino group, —OH, or protected hydroxyl group.

Embodiment I-3. A process for preparing a compound of formula A-5a,

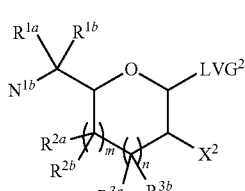

A-5a wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, and $R^{3a}$ are independently selected from the group consisting of H, —$OR^{27}$, —$NR^{28}R^{29}$, halogen, $C_1$-$C_4$ cycloalkyl, and $C_1$-$C_6$ alkyl, wherein the alkyl is unsubstituted or substituted with one or more substituents selected from the group consisting of halogen, —$OR^{30}$, —$NR^{31}R^{32}$, —$SR^{3'}$, and —$SO_2R^{34}$;

wherein each $R^{27}$, $R^{28}$, and $R^{29}$ is independently H or alkyl;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3b}$ is H;

$N^{1b}$ is —$NHPg^{1b}$ or $N_3$, wherein $Pg^{1b}$ is an amino protecting group;

$X^2$ is —F, —Cl, —Br, or —I;

$LVG^2$ is a leaving group.

m is zero, 1, or 2;

n is zero, 1, or 2;

wherein m+n is 1, 2 or 3;

or a salt, solvate, enantiomer, or diastereomer thereof, comprising:

(a) converting —OH in the compound of formula A-7

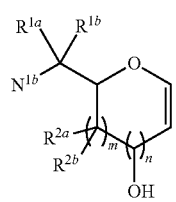

A-7 or a salt, solvate, enantiomer, or diastereomer thereof, to $R^{3a}$ to yield a compound of formula A-8:

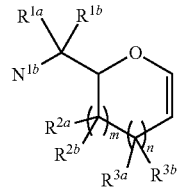

A-8 or a salt, solvate, enantiomer, or diastereomer thereof, wherein (b) contacting the compound of formula A-8 with a halogen reagent in presence of a nucleophile reagent (Nuc-2) to yield a compound of formula A-5a:

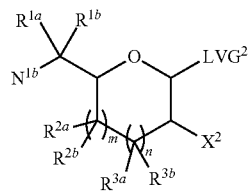

A-5a or a salt, solvate, enantiomer, or diastereomer thereof; wherein $X^2$ is —F, —Cl, —Br, or —I;

Nuc-2 is $LVG^2$-M, wherein M is H, a metal cation, a non-metal cation, or a lone pair of electrons;

$LVG^2$ is a leaving group.

Embodiment I-4. The process of Embodiment I-3, wherein when $X^2$ is not —$NH_2$, —$N_3$, a protected amino group, —OH, or protected hydroxyl group, further comprising after step (b):

(c) converting $X^2$ in the compound of formula A-5a to X to yield a compound of formula A-6a:

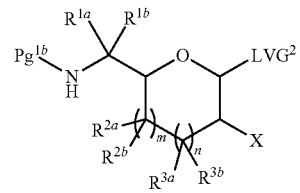

A-6a or a salt, solvate, enantiomer, or diastereomer thereof;

wherein X is —$NH_2$, —$N_3$, a protected amino group, —OH, or protected hydroxyl group.

Embodiment I-5. The process of any one of Embodiments I-1 to I-4, wherein the stereochemistry in the ring of formulae A-1, A-2, A-3, A-4, A-5, A-5a, A-6, A-6a, A-7, and A-8 is as indicated in formula (A'), wherein === is a single bond or a double bond and wherein ⌇ indicates a point of attachment to a hydrogen or a moiety: ⌇

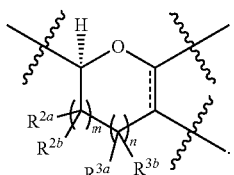

(A')

Embodiment I-6. A process for preparing a compound of formula B-6:

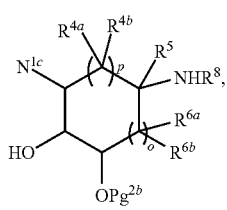

(B-6)

wherein $R^{4a}$ and $R^{4b}$ are, independently H, —OH, —OR$^{40}$, —NR$^{41}$R$^{42}$, or halogen;

wherein each $R^{40}$, $R^{41}$, and $R^{42}$ are independently H or alkyl; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^5$ is H, —CN, —CONH$_2$ or $C_1$-$C_3$alkyl, wherein the alkyl is unsubstituted or substituted with one or more substituents selected from the group consisting of —OH, —NH$_2$, —CN, —CONH$_2$, and halogen;

$R^{6a}$ and $R^{6b}$ are, independently H, halogen, NH$_2$, —OH, $C_1$-$C_3$alkoxy, —OC(O)CH$_3$, or —OPg$^{2o}$; wherein Pg$^{2o}$ is a hydroxyl protecting group;

$R^8$ is H, $C_1$-$C_6$ alkyl, an amino protecting group, or

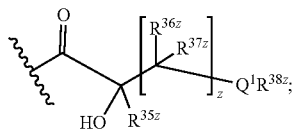

wherein $Q^1$ is NH, O, or S;
z is an integer from 0 to 4,
$R^{35z}$ is H or $C_1$-$C_3$ alkyl;
each $R^{36z}$ and $R^{37z}$ is independently selected from the group consisting of H, alkyl, halogen, and —OH, and
$R^{38z}$ is H, alkyl, or —C(=NH)NR$^{39z}$R$^{40z}$, wherein R$^{39z}$ and R$^{40z}$ are independently H or $C_1$-$C_3$ alkyl; or
$R^{35z}$ and $R^{38z}$, together with the atoms to which they are attached, form a heterocycloalkyl group comprising at least one N;
$N^{1e}$ is —NHPg$^{1e}$ or N$_3$, wherein Pg$^{1e}$ is an amino protecting group
Pg$^{2b}$ is a hydroxyl protecting group;
o is zero, 1, or 2;
p is zero, 1, or 2;
wherein o+p is 1, 2 or 3;
or a salt, solvate, enantiomer, or diastereomer thereof, comprising:

(a) contacting a compound of formula B-1:

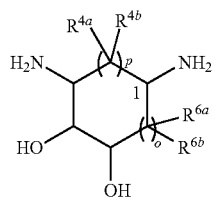

B-1 or a salt, solvate, enantiomer, or diastereomer thereof, with an amino protecting group reagent and a hydroxyl protecting group reagent to yield a compound of formula B-2:

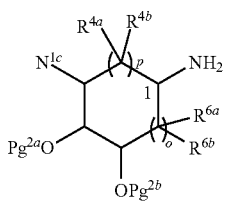

B-2 or a salt, solvate, enantiomer, or diastereomer thereof; wherein Pg$^{2a}$ is a hydroxyl protecting group;

(b) converting the amino group of the compound of formula B-2 at C1 to an azide group;

(c) converting the azide group of the compound of formula B-2 at C1 to a hydroxyl group;

(d) oxidizing the hydroxyl group of the compound of formula B-2 at C1 to an oxo group to yield a compound of formula B-3:

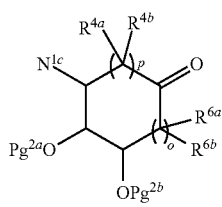

B-3 or a salt, solvate, enantiomer, or diastereomer thereof;

(e) converting the oxo group of the compound of formula B-3 to an imino group and contacting with an amino reactive reagent to yield a compound of formula B-4:

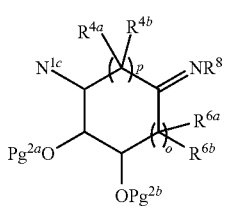

B-4 or a salt, solvate, enantiomer, or diastereomer thereof;

(f) contacting the compound of formula B-4 with a Grignard or organolithium reagent to yield a compound of formula B-5:

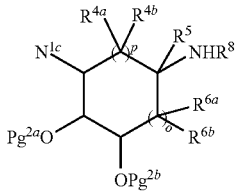

or a salt, solvate, enantiomer, or diastereomer thereof, (g) forming a hydroxyl group by selective removal of the $Pg^{2a}$ protecting group of the compound of formula B-6 to yield the compound of formula B-7:

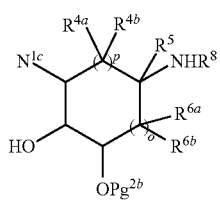

or a salt, solvate, enantiomer, or diastereomer thereof.

Embodiment I-7. A process for preparing a compound of formula B-11:

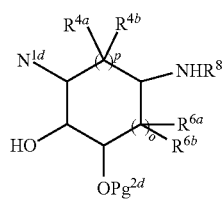

wherein $R^{4a}$ and $R^{4b}$ are, independently, H, —OH, —OR$^{40}$, —NR$^{41}$R$^{42}$, or halogen;

wherein each $R^{40}$, $R^{41}$, and $R^{42}$ are independently H or alkyl; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^{6a}$ and $R^{6b}$ are, independently H, halogen, NH$_2$, —OH, $C_1$-$C_3$alkoxy, —OC(O)CH$_3$, or —OPg$^{2o}$; wherein Pg$^{2o}$ is a hydroxyl protecting group;

$R^8$ is H, $C_1$-$C_6$ alkyl, an amino protecting group, or

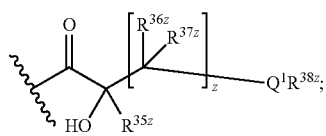

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$N^{1d}$ is —NHPg$^{1d}$ or $N_3$, wherein Pg$^{1d}$ is an amino protecting group;

Pg$^{2d}$ is a hydroxyl protecting group;

o is zero, 1, or 2;

p is zero, 1, or 2;

wherein o+p is 1, 2 or 3;

or a salt, solvate, enantiomer, or diastereomer thereof, comprising:

(a) contacting a compound of formula B-8:

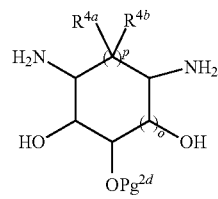

or a salt, solvate, enantiomer, or diastereomer thereof, with an amino protecting group reagent and a first selective hydroxyl protecting group reagent and a second selective hydroxyl protecting group reagent and an amino reactive reagent to yield a compound of formula B-9:

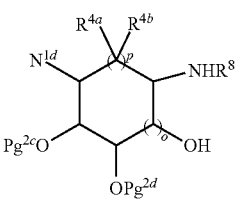

or a salt, solvate, enantiomer, or diastereomer thereof, wherein Pg$^{2c}$ is a hydroxyl protecting group;

(b) contacting the compound of formula B-9 with a electrophilic reagent to yield a compound of formula B-10:

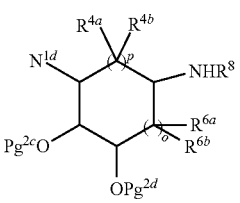

or a salt, solvate, enantiomer, or diastereomer thereof, c) forming a hydroxyl group by selective removal of the Pg$^2$C protecting group of the compound of formula B-10 to yield the compound of formula B-11:

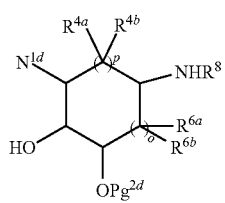

B-11 or a salt, solvate, enantiomer, or diastereomer thereof.

Embodiment I-8. The process of any one of Embodiments 1-6 to I-7, wherein the stereochemistry in the ring of formulae B-1, B-2, B-3, B-4, B-5, B-6, B-8, B-9, B-10, and B-11, is as indicated in formula (B'), wherein ⁓ indicates a point of attachment to a hydrogen or a moiety:

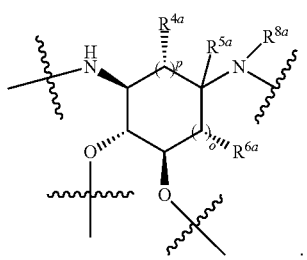

(B')

Embodiment I-9. A process for preparing a compound of formula AB-1,

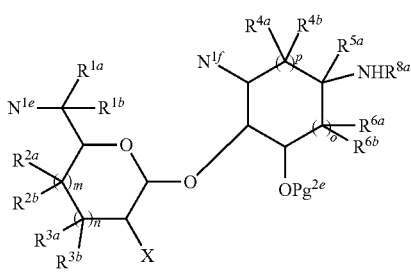

AB-1 wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$R^{4a}$ and $R^{4b}$ are, independently H, —OH, —$OR^{40}$, —$NR^{41}R^{42}$, or halogen;

wherein each $R^{40}$, $R^{41}$, and $R^{42}$ are independently H or alkyl;

wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5a}$ is H, —CN, —$CONH_2$ or $C_1$-$C_3$alkyl, wherein the alkyl is unsubstituted or substituted with one or more substituents selected from the group consisting of —OH, —$NH_2$, —CN, —$CONH_2$, and halogen;

$R^{6a}$ and $R^{6b}$ are, independently H, halogen, $NH_2$, —OH, $C_1$-$C_3$alkoxy, —$OC(O)CH_3$, or —$OPg^{2m}$; wherein $Pg^{2m}$ is a hydroxyl protecting group;

$R^{8a}$ is H, $C_1$-$C_6$ alkyl, an amino protecting group, or

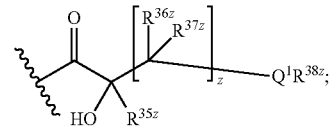

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$N^{1e}$ is —$NHPg^{1e}$ or $N_3$, wherein $Pg^{1e}$ is an amino protecting group;

$N^{1f}$ is —$NHPg^{1f}$ or $N_3$, wherein $Pg^{1f}$ is an amino protecting group;

$Pg^{2e}$ is a hydroxyl protecting group;

X is —$NH_2$, —$N_3$, protected amino group, —OH, or protected hydroxyl group;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3;

or a salt, solvate, enantiomer, or diastereomer thereof, comprising:

(a) contacting a compound of formula A-9:

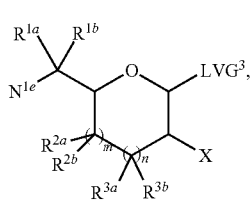

wherein LVG$^3$ is a leaving group,
with a compound of formula B-12:

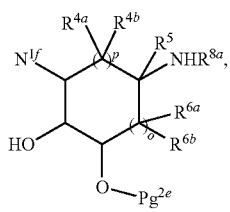

to yield the compound of formula (AB-1).

Embodiment I-10. The process of Embodiment I-9, further comprising after step (a):

(b) if amino protecting groups and hydroxyl protecting groups are present, remove the amino protecting groups and hydroxyl protecting groups to yield a compound of formula AB-2, or a salt, solvate, enantiomer, or diastereomer thereof

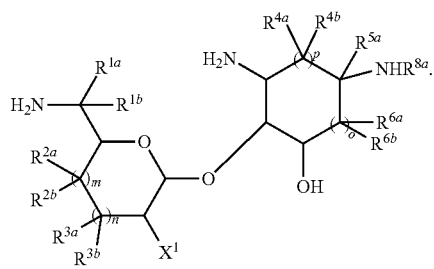

Embodiment I-11. The process of any one of Embodiments I-9 to I-10, wherein the stereochemistry of the compound of formula AB, or a salt, solvate, enantiomer, or diastereomer thereof, - is as indicated in formula (AB'):

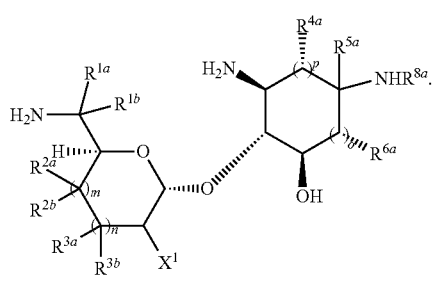

Embodiment I-12. The process of Embodiment I-9, further comprising after step (a):

(b) selectively deprotecting the compound of formula AB-1 by removing the Pg$^{2e}$ moiety to yield a compound of formula AB-3:

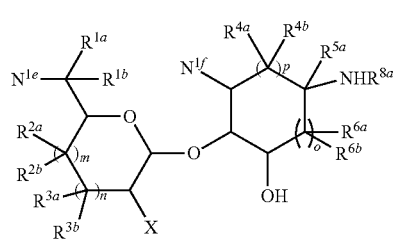

or a salt, solvate, enantiomer, or diastereomer thereof;

(c) contacting the compound of formula AB-3 with a compound of formula C-1,

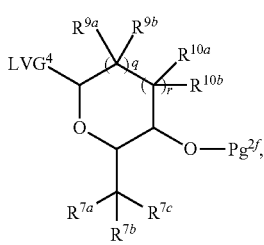

or a salt, solvate, enantiomer, or diastereomer thereof, wherein $R^{7a}$, $R^{7b}$, and $R^{7c}$ are, independently, H, NH$_2$, OH, —OR$^{71}$ or —OPg$^{2r}$;

wherein R$^{71}$ is alkyl; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

wherein Pg$^{2r}$ is a hydroxyl protecting group;

$R^{9a}$ and $R^{9b}$ are independently H, OH, or —OR$^{91}$, wherein R$^{91}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

$R^{10a}$ and $R^{10b}$ are independently H, OH, or —OR$^{101}$, wherein R$^{101}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

Pg$^{2f}$ is a hydroxyl protecting group;

LVG$^4$ is a leaving group;

q is zero, 1, or 2;

r is zero, 1, or 2;

wherein q+r is 1, 2 or 3;

to yield a compound of formula ABC-1, or a salt, solvate, enantiomer, or diastereomer thereof,

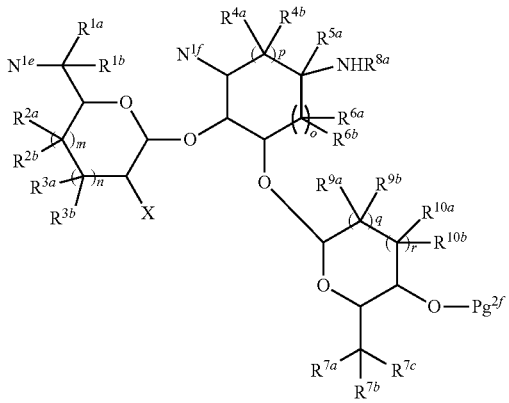

ABC-1

Embodiment I-13. The process of Embodiment I-12, further comprising after step (c):

(d) if amino protecting groups and hydroxyl protecting groups are present, remove the amino protecting groups and hydroxyl protecting groups to yield a compound of formula ABC-2, or a salt, solvate, enantiomer, or diastereomer thereof,

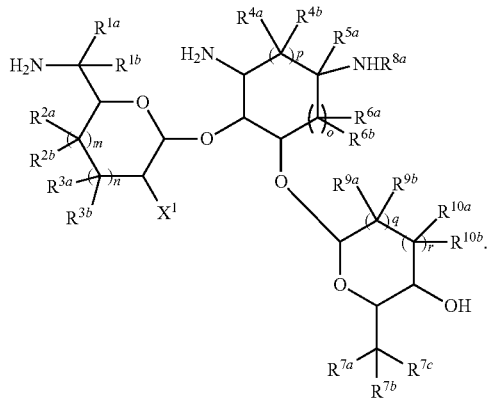

ABC-2

Embodiment I-14. The process of any one of Embodiments I-12 to I-13, wherein the stereochemistry in the ring of formulae ABC-1 and ABC-2, is as indicated in formula (ABC'),

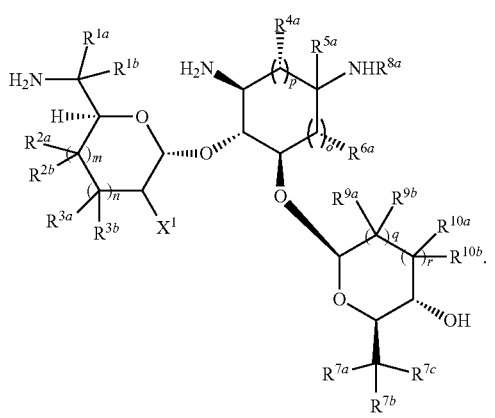

(ABC')

Embodiment I-15. The process of Embodiment I-9, further comprising after step (a):

(b) selectively deprotecting the compound of formula AB-1 by removing the $Pg^{2e}$ moiety to yield a compound of formula AB-3:

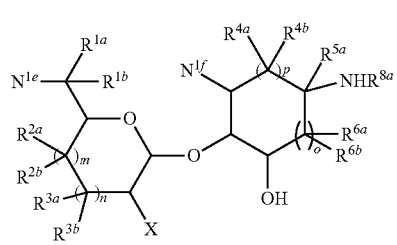

AB-3 or a salt, solvate, enantiomer, or diastereomer thereof;

(c) contacting the compound of formula AB-3 with a compound of formula CD-1,

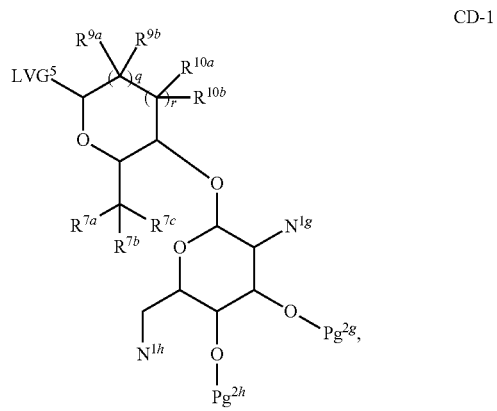

CD-1 or a salt, solvate, enantiomer, or diastereomer thereof, wherein $R^{7a}$, $R^{7b}$, and $R^{7c}$ are, independently, H, $NH_2$, OH, —$OR^{71}$ or —$OPg^{2r}$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

wherein $Pg^{2r}$ is a hydroxyl protecting group;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$LVG^5$ is a leaving group;

$N^{1g}$ is —$NHPg^{1g}$ or $N_3$, wherein $Pg^{1g}$ is an amino protecting group;

$N^{1h}$ is —$NHPg^{1h}$ or $N_3$, wherein $Pg^{1h}$ is an amino protecting group;

$Pg^{2g}$ is a hydroxyl protecting group;

$Pg^{2h}$ is a hydroxyl protecting group;

q is zero, 1, or 2;

r is zero, 1, or 2;

wherein q+r is 1, 2 or 3;

to yield a compound of formula ABCD-1, or a salt, solvate, enantiomer, or diastereomer thereof,

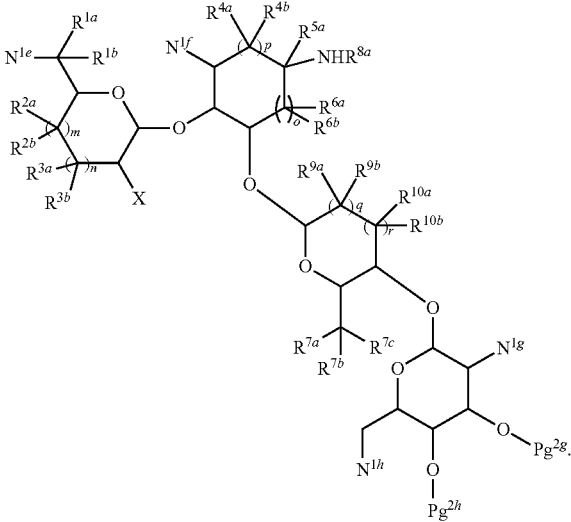

ABCD-1

Embodiment I-16. The process of Embodiment I-15, further comprising after step (c):

(d) if amino protecting groups and hydroxyl protecting groups are present, remove the amino protecting groups and hydroxyl protecting groups to yield a compound of formula ABCD-2, or a salt, solvate, enantiomer, or diastereomer thereof,

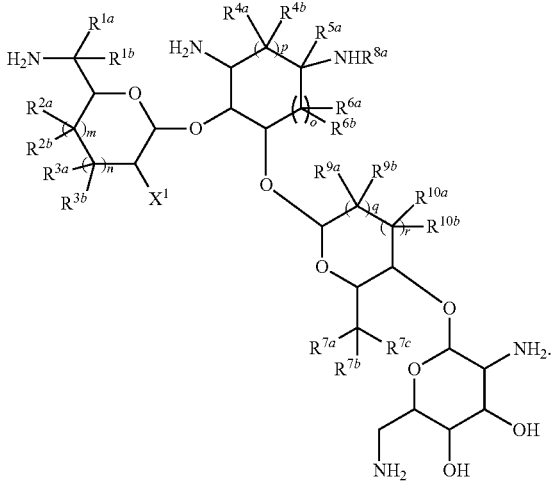

ABCD-2

Embodiment I-17. The process of any one of Embodiments I-15 to I-16, wherein the stereochemistry in the ABCD ring are indicated as in formula (ABCD'):

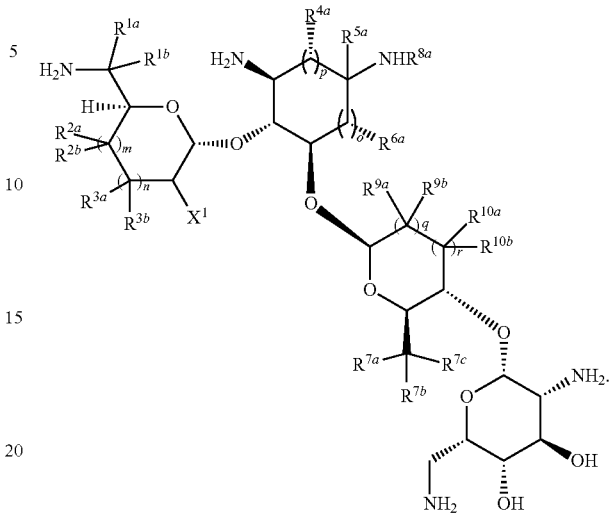

(ABCD')

Embodiment I-18. A compound of formula A-10:

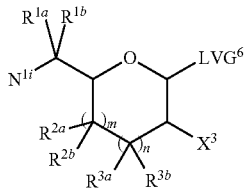

A-10 or a salt, solvate, enantiomer, or diastereomer thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{21}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$ and $-OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^3$ is selected from the group consisting of H, $NH_2$, $N_3$, protected amino group, OH, $-OPg^{2i}$, and halogen; wherein $Pg^{2i}$ is a hydroxyl protecting group;

$LVG^6$ is a leaving group;

$N^{1i}$ is $-NHPg^{1i}$-$NH_2$, or $N_3$, wherein $Pg^{1i}$ is an amino protecting group;

m is zero, 1, or 2;

n is zero, 1, or 2;

wherein m+n is 1, 2 or 3.

Embodiment I-19. The compound of Embodiment I-18, selected from the group consisting of:

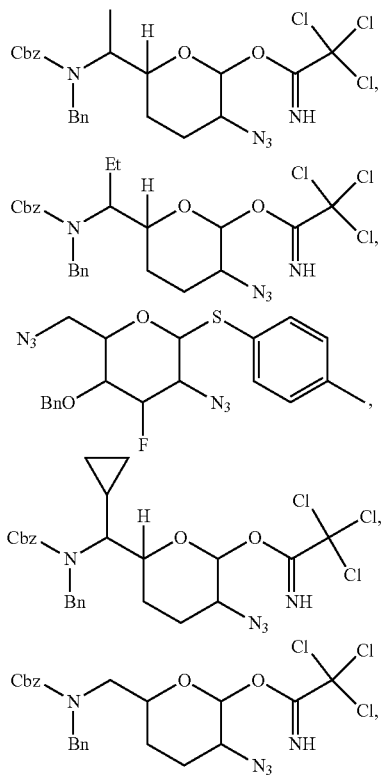

or a salt, solvate, enantiomer, or diastereomer of any of the foregoing.

Embodiment I-20. The compound of Embodiment I-18, selected from the group consisting of:

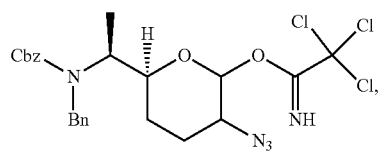

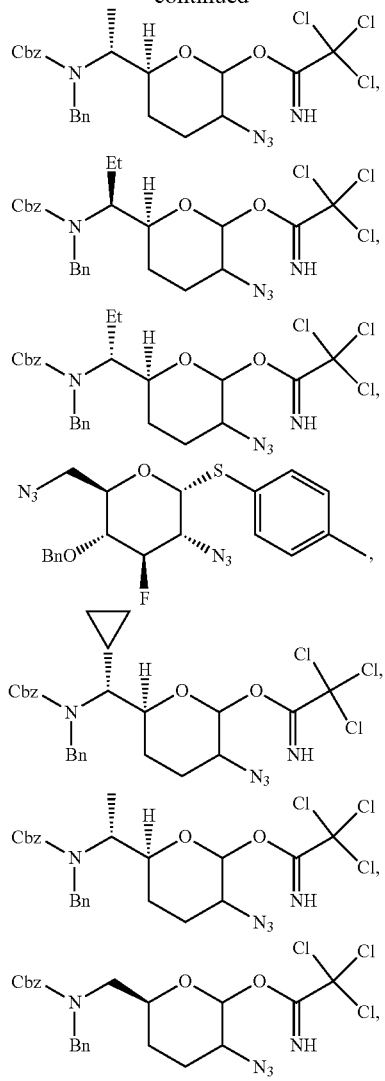

or a salt, solvate, enantiomer, or diastereomer of any of the foregoing.

Embodiment I-21. A compound of formula B-13:

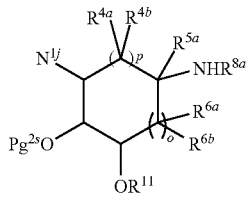

B-13 or a salt, solvate, enantiomer, or diastereomer thereof, wherein $R^{4a}$ and $R^{4b}$ are, independently H, $-OH$, $-OR^{40}$, $-NR^{41}R^{42}$, or halogen;

wherein each $R^{40}$, $R^{41}$, and $R^{42}$ are independently H or alkyl; wherein the alkyl is unsubstituted or substituted with one or more substituents selected from the group consisting of $-CONH_2$, $-OH$, $-NH_2$, $-COCH_3$, aryl, substituted aryl, heteroaryl, halogen, and substituted heteroaryl;

$R^{5a}$ is H, —CN, —CONH$_2$ or C$_1$-C$_3$alkyl, wherein the alkyl is unsubstituted or substituted with one or more substituents selected from the group consisting of —OH, —NH$_2$, —CN, —CONH$_2$, and halogen;

$R^{6a}$ and $R^{6b}$ are, independently H, halogen, NH$_2$, —OH, C$_1$-C$_3$alkoxy, —OC(O)CH$_3$, or —OPg$^{2j}$; wherein Pg$^{2j}$ is a hydroxyl protecting group;

$R^{8a}$ is H, C$_1$-C$_6$ alkyl, an amino protecting group, or

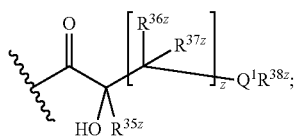

wherein $Q^1$ is NH, O, or S;

z is an integer from 0 to 4, $R^{35z}$ is H or C$_1$-C$_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein $R^{39z}$ and $R^{40z}$ are independently H or C$_1$-C$_3$ alkyl; or $R^{35z}$ and $R^{38z}$, together with the atoms to which they are attached, form a heterocycloalkyl group comprising at least one N;

$R^{11}$ is H, alkyl, —COCH$_3$, or a hydroxyl protecting group;

$N^{1j}$ is —NHPg$^{1j}$, —NH$_2$, or N$_3$, wherein Pg$^{1j}$ is an amino protecting group;

Pg$^{2s}$ is H or hydroxyl protecting group;

o is zero, 1, or 2;

p is zero, 1, or 2;

wherein o+p is 1, 2 or 3.

Embodiment I-22. The compound of Embodiment I-21, being

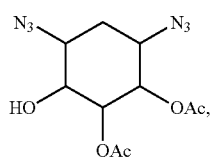

or a salt, solvate, enantiomer, or diastereomer thereof.

Embodiment I-23. The compound of Embodiment I-21, being

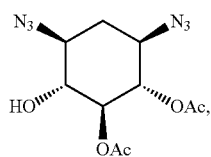

or a salt, solvate, enantiomer, or diastereomer thereof.

Embodiment I-24. A compound of formula AB-4:

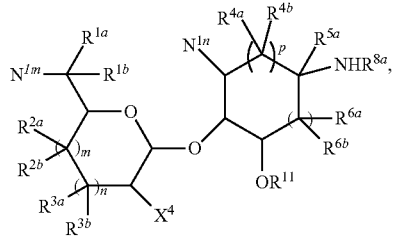

AB-4 or a salt, solvate, enantiomer, or diastereomer thereof, wherein $R^{1a}$ and $R^{1b}$ are independently selected from the group consisting of H, C$_1$-C$_{12}$ alkyl, C$_1$-C$_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —N$_3$, and —OR$^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, NR$^{14}$R$^{15}$, and —OR$^{16}$;

$R^{2a}$, $R^{2b}$, $R^{3a}$ and $R^{3b}$ are independently selected from the group consisting of H, —OR$^{27}$, —NR$^{28}$R$^{29}$, halogen, C$_1$-C$_4$ cycloalkyl, and C$_1$-C$_6$ alkyl, wherein each $R^{27}$, $R^{28}$, and $R^{29}$ is independently H or alkyl; wherein the C$_1$-C$_6$ alkyl or alkyl is unsubstituted or substituted with one or more substituents selected from the group consisting of halogen, —OR$^{30}$, —NR$^{31}$R$^{32}$, —SR$^{33}$, and —SO$_2$R$^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, NR$^{14}$R$^{15}$, and —OR$^{16}$; or $R^{2a}$ and $R^{2b}$ form an oxo or imino group substituted with C$_1$-C$_6$ alkyl;

$R^{3a}$ and $R^{3b}$ form an oxo or imino group substituted with C$_1$-C$_6$ alkyl;

$X^4$ is selected from the group consisting of H, NH$_2$, N$_3$, protected amino group, OH, —OPg$^{2k}$, and halogen; wherein Pg$^{2k}$ is a hydroxyl protecting group;

$R^{4a}$ and $R^{4b}$ are, independently, H, —OH, —OR$^{40}$, —NR$^{41}$R$^{42}$, or halogen;

wherein each $R^{40}$, $R^{41}$, and $R^{42}$ are independently H or alkyl; wherein the alkyl is unsubstituted or substituted with one or more substituents selected from the group consisting of —CONH$_2$, —OH, —NH$_2$, —COCH$_3$, aryl, substituted aryl, heteroaryl, halogen, or substituted heteroaryl;

$R^{5a}$ is H, —CN, —CONH$_2$ or C$_1$-C$_3$alkyl, wherein the alkyl is unsubstituted or substituted with one or more substituents selected from the group consisting of —OH, —NH$_2$, —CN, —CONH$_2$, and halogen;

$R^{6a}$ and $R^{6b}$ are, independently H, halogen, $NH_2$, —OH, $C_1$-$C_3$alkoxy, —OC(O)$CH_3$, or —OPg$^{2j}$;
wherein Pg$^{2j}$ is a hydroxyl protecting group;
$R^{8a}$ is H, $C_1$-$C_6$ alkyl, an amino protecting group, or

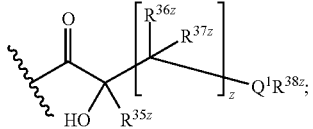

wherein
$Q^1$ is NH, O, or S;
z is an integer from 0 to 4,
$R^{35z}$ is H or $C_1$-$C_3$ alkyl;
each $R^{36z}$ and $R^{37z}$ is independently selected from the group consisting of H, alkyl, halogen, and —OH, and
$R^{38z}$ is H, alkyl, or —C(=NH)NR$^{39z}$R$^{40z}$, wherein $R^{39z}$ and $R^{40z}$ are independently H or $C_1$-$C_3$ alkyl; or
$R^{35z}$ and $R^{38z}$, together with the atoms to which they are attached, form a heterocycloalkyl group comprising at least one N;
$R^{11}$ is H, alkyl, —COCH$_3$, or a hydroxyl protecting group;
$N^{1m}$ is —NHPg$^{1m}$, —NH$_2$, or $N_3$, wherein Pg$^{1m}$ is an amino protecting group;
$N^{1n}$ is —NHPg$^{1n}$, —NH$_2$, or $N_3$, wherein Pg$^{1n}$ is an amino protecting group;
m is zero, 1, or 2;
n is zero, 1, or 2;
wherein m+n is 1, 2 or 3;
o is zero, 1, or 2;
p is zero, 1, or 2;
wherein o+p is 1, 2 or 3.

Embodiment I-25. The compound of Embodiment I-24, selected from the group consisting of:

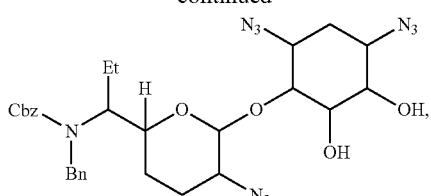
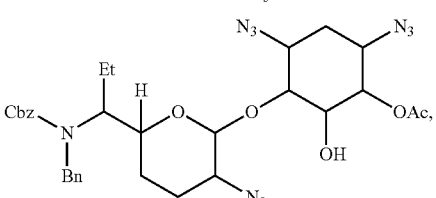
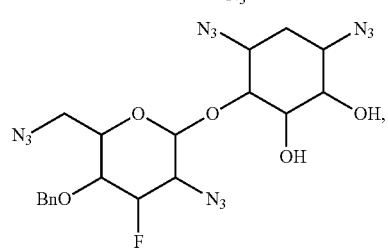
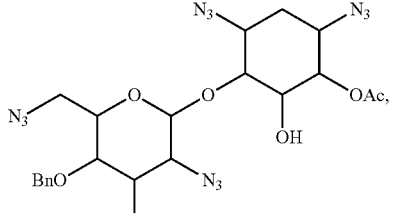
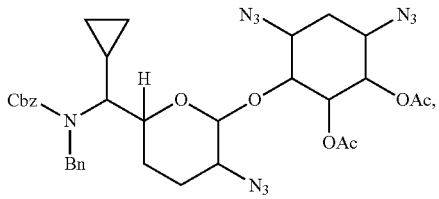
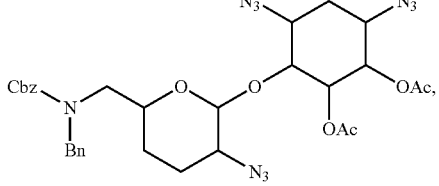
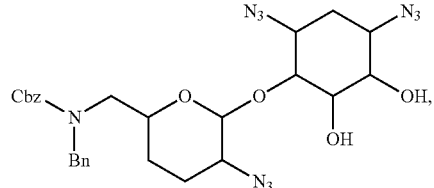
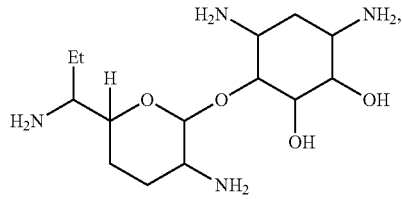

287
-continued
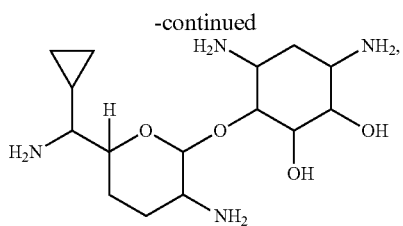
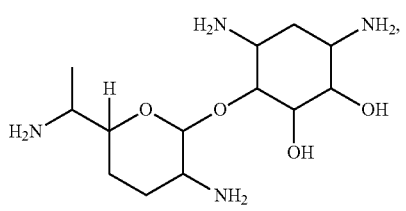
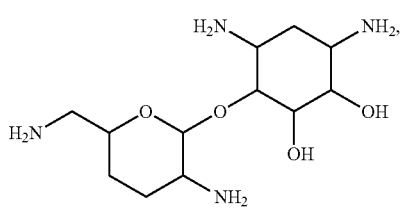
or a salt, solvate, enantiomer, or diastereomer of any of the foregoing.
Embodiment I-26. The compound of Embodiment I-24, selected from the group consisting of:
288
-continued
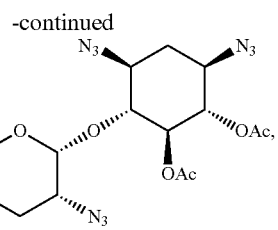
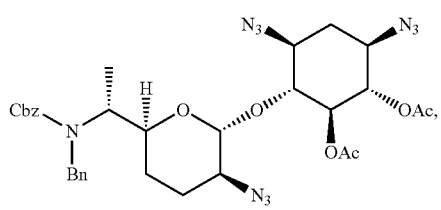
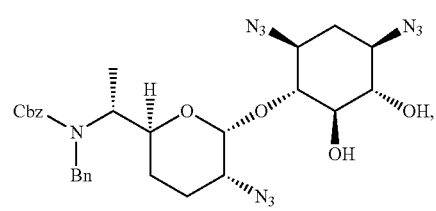
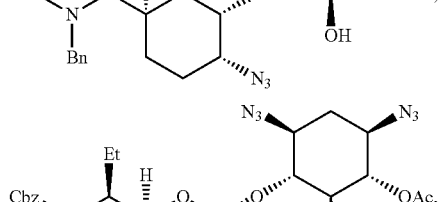
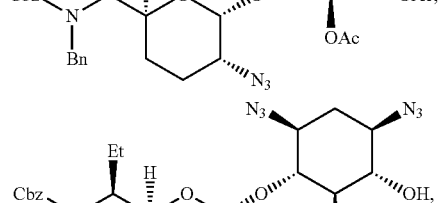
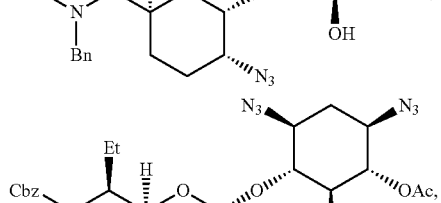
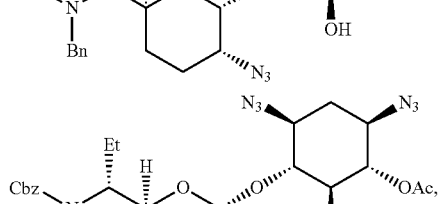
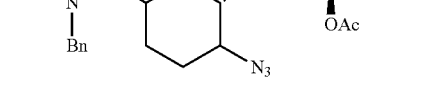

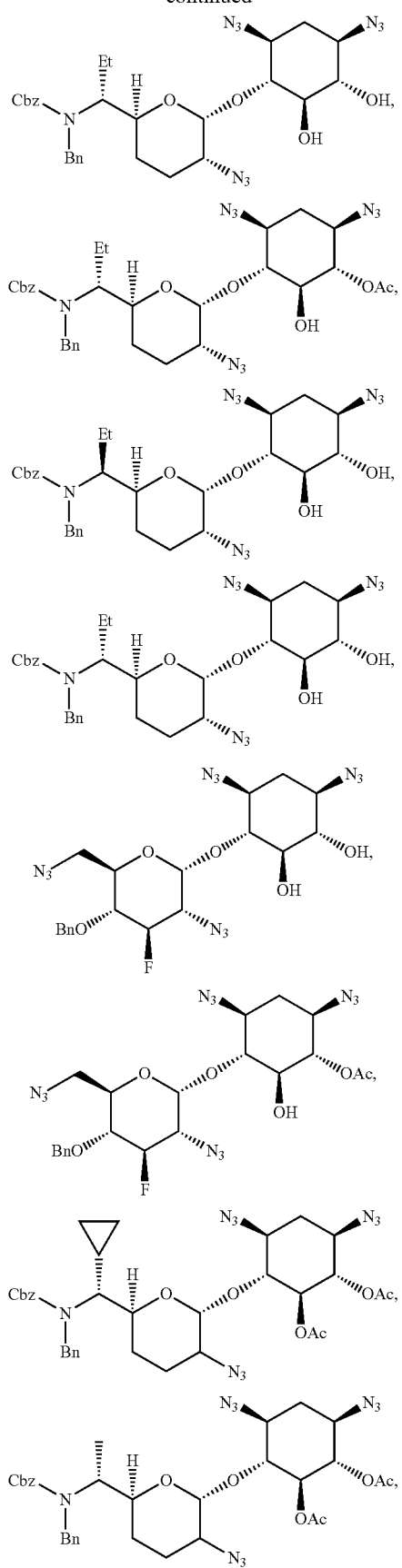
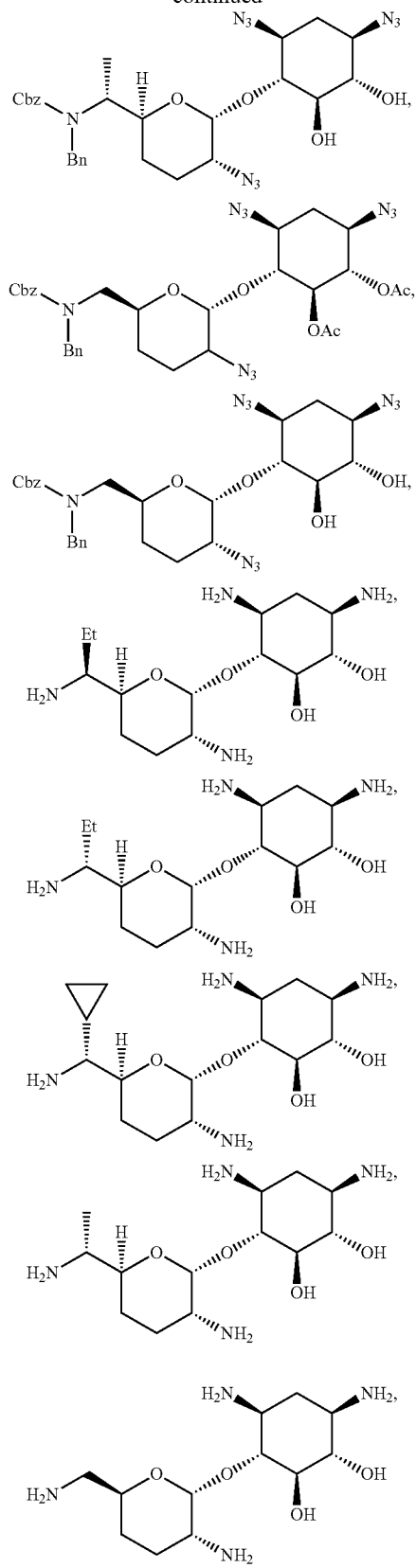
or a salt, solvate, enantiomer, or diastereomer of any of the foregoing.

Embodiment I-27. A compound of formula AB-5:

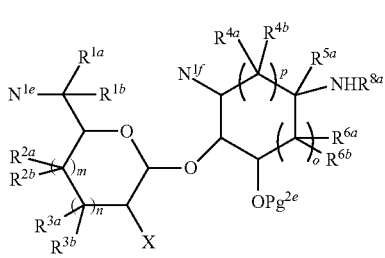

AB-5 wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$R^{4a}$ and $R^{4b}$ are, independently H, —OH, —$OR^{40}$, —$NR^{41}R^{42}$, or halogen; wherein each $R^{40}$, $R^{41}$, and $R^{42}$ are independently H or alkyl;

wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5a}$ is H, —CN, —$CONH_2$ or $C_1$-$C_3$alkyl, wherein the alkyl is unsubstituted or substituted with one or more substituents selected from the group consisting of —OH, —$NH_2$, —CN, —$CONH_2$, and halogen;

$R^{6a}$ and $R^{6b}$ are, independently H, halogen, $NH_2$, —OH, $C_1$-$C_3$alkoxy, —$OC(O)CH_3$, or —$OPg^{2m}$; wherein $Pg^{2m}$ is a hydroxyl protecting group;

$R^{8a}$ is H, $C_1$-$C_6$ alkyl, an amino protecting group, or

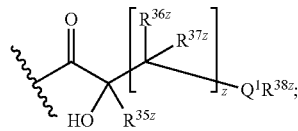

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$N^{1e}$ is —$NHPg^{1e}$ or $N_3$, wherein $Pg^{1e}$ is an amino protecting group;

$N^{1f}$ is —$NHPg^{1f}$ or $N_3$, wherein $Pg^{1f}$ is an amino protecting group;

$Pg^{2e}$ is a hydroxyl protecting group;

X is —$NH_2$, —$N_3$, protected amino group, —OH, or protected hydroxyl group;

wherein at least one of $N^{1e}$ and $N^{1f}$ is not $NH_2$ or wherein $PG^{2e}$ is not H or wherein X is not —OH or —$NH_2$;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

Embodiment I-28. The compound of Embodiment I-27, selected from the group consisting of:

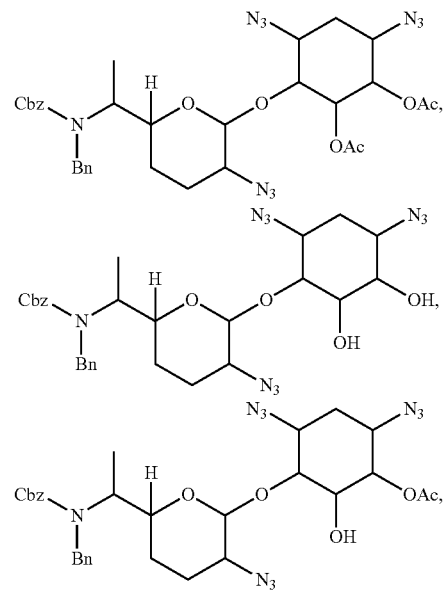

293
-continued
294
Embodiment I-29. The compound of the Embodiment I-27, selected from the group consisting of:
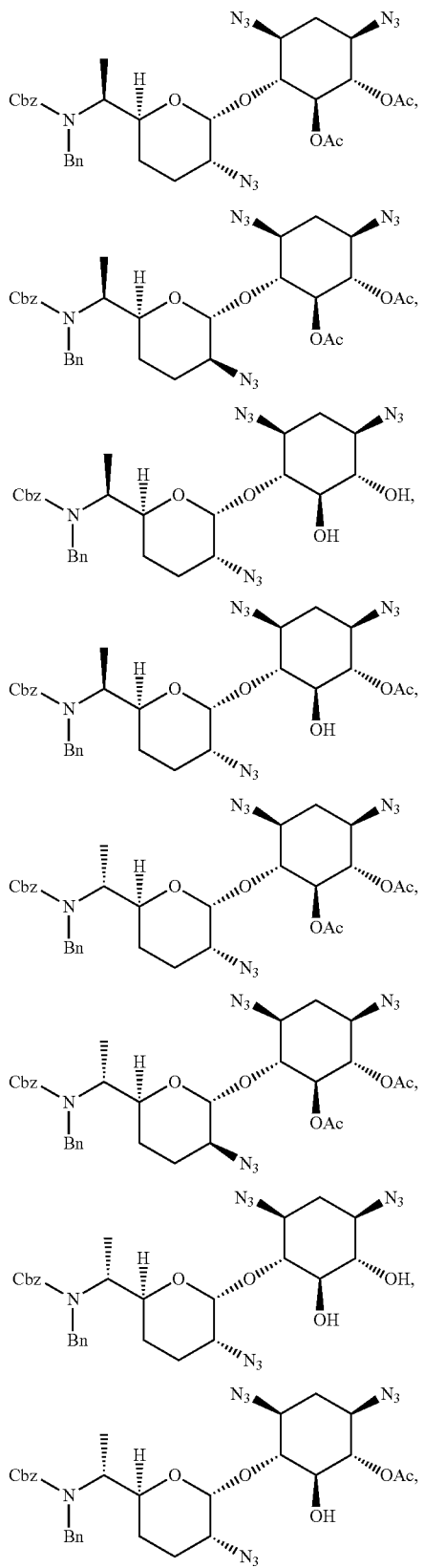
or a salt, solvate, enantiomer, or diastereomer of any of the foregoing.

295
-continued
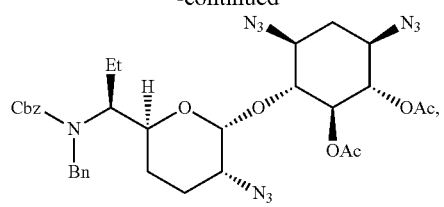
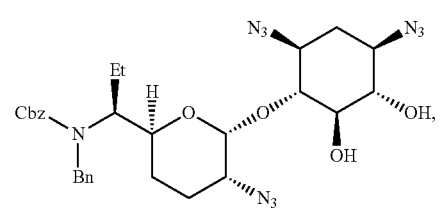
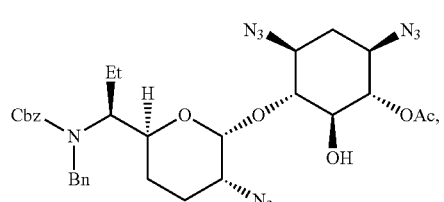
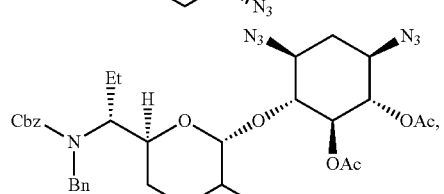
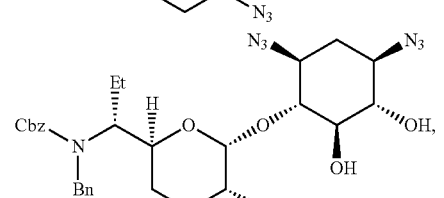

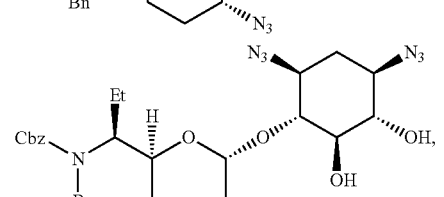
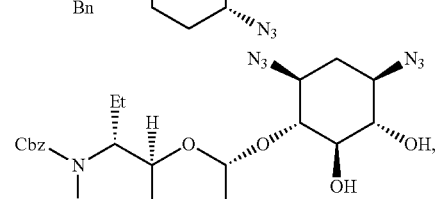
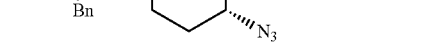
296
-continued
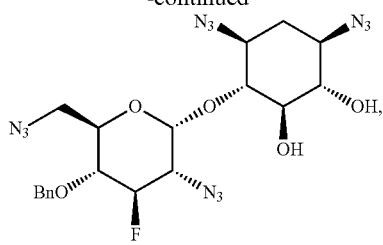
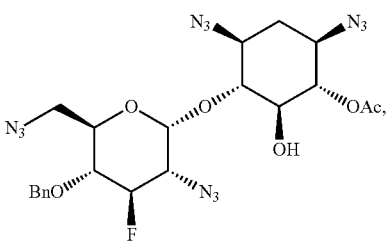
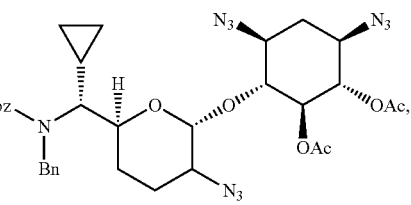
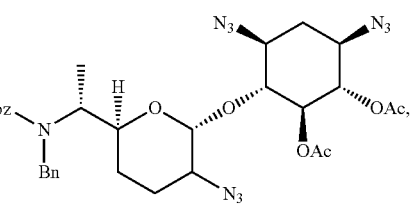
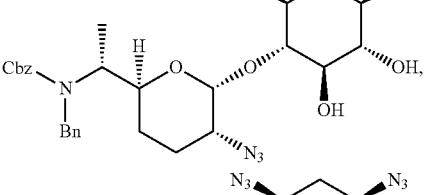
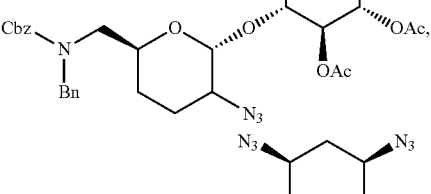
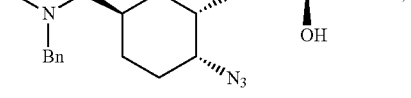
or a salt, solvate, enantiomer, or diastereomer of any of the foregoing.

Embodiment I-30. A compound of formula AB-1:

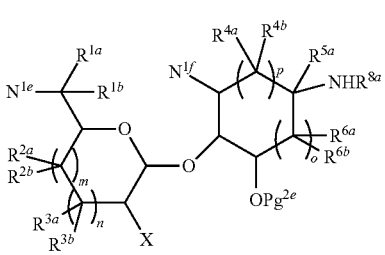

AB-1 wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^1$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{29}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$R^{4a}$ and $R^{4b}$ are, independently H, —OH, —$OR^{40}$, —$NR^{41}R^{42}$, or halogen;

wherein each $R^{40}$, $R^{41}$, and $R^{42}$ are independently H or alkyl;

wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5a}$ is H, —CN, —$CONH_2$ or $C_1$-$C_3$alkyl, wherein the alkyl is unsubstituted or substituted with one or more substituents selected from the group consisting of —OH, —$NH_2$, —CN, —$CONH_2$, and halogen;

$R^{6a}$ and $R^{6b}$ are, independently H, halogen, $NH_2$, —OH, $C_1$-$C_3$alkoxy, —$OC(O)CH_3$, or —$OPg^{2m}$; wherein $Pg^{2m}$ is a hydroxyl protecting group;

$R^{8a}$ is H, $C_1$-$C_6$ alkyl, an amino protecting group, or

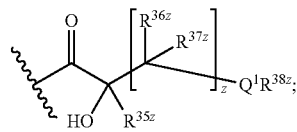

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$N^{1e}$ is —$NHPg^{1e}$ or $N_3$, wherein $Pg^{1e}$ is an amino protecting group;

$N^{1f}$ is —$NHPg^{1f}$ or $N_3$, wherein $Pg^{1f}$ is an amino protecting group;

$Pg^{2e}$ is a hydroxyl protecting group;

X is —$NH_2$, —$N_3$, protected amino group, —OH, or protected hydroxyl group;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

Embodiment I-31. A compound of formula (AB-2)

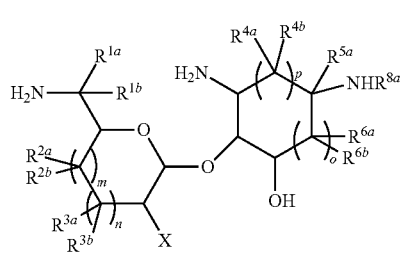

AB-2 wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$R^{4a}$ and $R^{4b}$ are, independently H, —OH, —$OR^{40}$, —$NR^{41}R^{42}$, or halogen;

wherein each $R^{40}$, $R^{41}$, and $R^{42}$ are independently H or alkyl;

wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5a}$ is H, —CN, —$CONH_2$ or $C_1$-$C_3$alkyl, wherein the alkyl is unsubstituted or substituted with one or more substituents selected from the group consisting of —OH, —$NH_2$, —CN, —$CONH_2$, and halogen;

$R^{6a}$ and $R^{6b}$ are, independently H, halogen, $NH_2$, —OH, $C_1$-$C_3$alkoxy, —OC(O)$CH_3$, or —$OPg^{2m}$; wherein $Pg^{2m}$ is a hydroxyl protecting group;

$R^{8a}$ is H, $C_1$-$C_6$ alkyl, an amino protecting group, or wherein
$Q^1$ is NH, O, or S;
z is an integer from 0 to 4,
$R^{35z}$ is H or $C_1$-$C_3$ alkyl;
each $R^{36z}$ and $R^{37z}$ is independently selected from the group consisting of H, alkyl, halogen, and —OH, and
$R^{38z}$ is H, alkyl, or —C(=NH)$NR^{39z}R^{40z}$, wherein $R^{39z}$ and $R^{40z}$ are independently H or $C_1$-$C_3$ alkyl; or
$R^{35z}$ and $R^{38z}$, together with the atoms to which they are attached, form a heterocycloalkyl group comprising at least one N;
X is —$NH_2$ or —OH;
m is zero, 1, or 2;
n is zero, 1, or 2;
wherein m+n is 1, 2 or 3;
o is zero, 1, or 2;
p is zero, 1, or 2;
wherein o+p is 1, 2 or 3;
q is zero, 1, or 2;
r is zero, 1, or 2;
wherein q+r is 1, 2 or 3.

Embodiment I-32. The compound of Embodiment I-30, selected from the group consisting of:

or a salt, solvate, enantiomer, or diastereomer of any of the foregoing.

Embodiment I-33. The compound of Embodiment I-30, selected from the group consisting of:

-continued

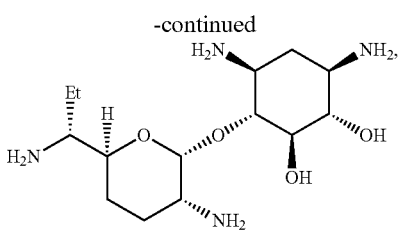

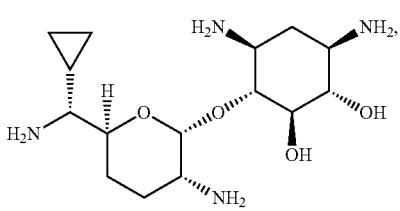

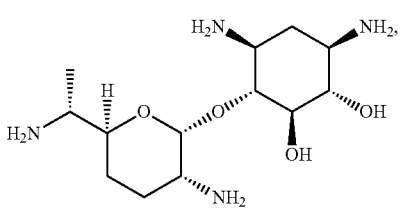

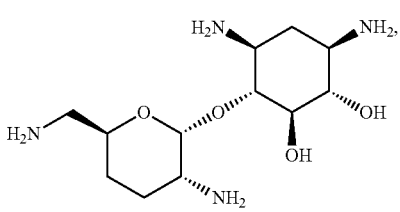

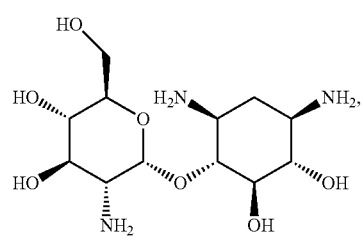

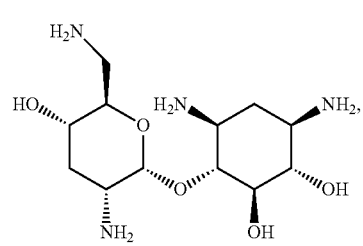

or a salt, solvate, enantiomer, or diastereomer of any of the foregoing.

Embodiment I-34. A compound of formula (ABC-3)

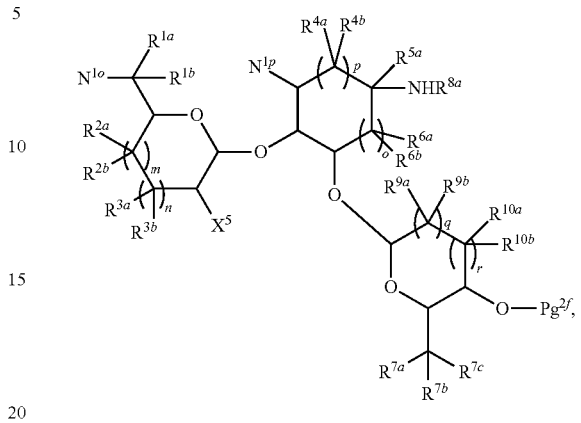

ABC-3 or a salt, solvate, enantiomer, or diastereomer thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$ and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^5$ is selected from the group consisting of H, $NH_2$, $N_3$, protected amino group, OH, —$OPg^{2l}$, and halogen; wherein $Pg^{2l}$ is a hydroxyl protecting group;

$R^{4a}$ and $R^{4b}$ are, independently H, —OH, —$OR^{40}$, —$NR^{41}R^{42}$, or halogen;

wherein each $R^{40}$, $R^{41}$, and $R^{42}$ are independently H or alkyl; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5a}$ is H, —CN, —CONH$_2$ or C$_1$-C$_3$alkyl, wherein the alkyl is unsubstituted or substituted with one or more substituents selected from the group consisting of —OH, —NH$_2$, —CN, —CONH$_2$, and halogen;

$R^{6a}$ and $R^{6b}$ are, independently H, halogen, NH$_2$, —OH, C$_1$-C$_3$alkoxy, —OC(O)CH$_3$, or —OPg$^{2j}$;

wherein Pg$^{2j}$ is a hydroxyl protecting group;

$R^{7a}$, $R^{7b}$, and $R^{7c}$ are, independently, H, OH, —OR$^{71}$ or —OPg$^2$;

wherein $R^{71}$ is alkyl; wherein the alkyl is unsubstituted or substituted with one or more substituents selected from the group consisting of —CONH$_2$, —OH, —NH$_2$, —COCH$_3$, aryl, substituted aryl, heteroaryl, and substituted heteroaryl;

wherein Pg$^2$ is a hydroxyl protecting group;

$R^{8a}$ is H, C$_1$-C$_6$ alkyl, an amino protecting group, or

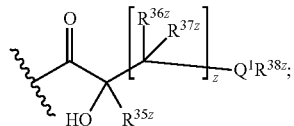

wherein

Q$^1$ is NH, O, or S;

z is an integer from 0 to 4, $R^{35z}$ is H or C$_1$-C$_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein $R^{39z}$ and $R^{40z}$ are independently H or C$_1$-C$_3$ alkyl; or $R^{35z}$ and $R^{38z}$, together with the atoms to which they are attached, form a heterocycloalkyl group comprising at least one N;

$R^{9a}$ and $R^{9b}$ are independently H, OH, or —OR$^{91}$, wherein $R^{91}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

$R^{10a}$ and $R^{10b}$ are independently H, OH, or —OR$^{101}$, wherein $R^{101}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

N$^{1o}$ is —NHPg$^{1o}$, —NH$_2$, or N$_3$, wherein Pg$^{1o}$ is an amino protecting group;

N$^{1p}$ is —NHPg$^{1p}$, —NH$_2$, or N$_3$, wherein Pg$^{1p}$ is an amino protecting group;

Pg$^{2f}$ is a hydroxyl protecting group or H;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

Embodiment I-35. A compound of formula (ABC-4)

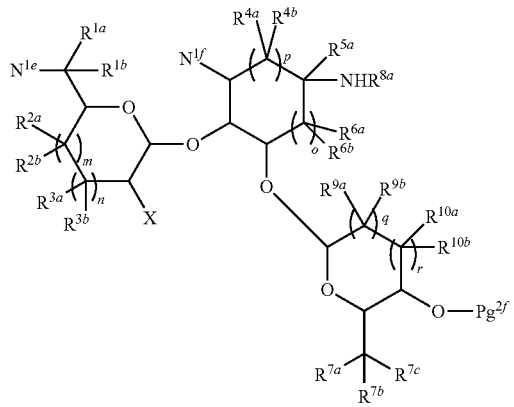

ABC-4 or a salt, solvate, enantiomer, or diastereomer thereof, wherein $R^{1a}$ and $R^{1b}$ are independently selected from the group consisting of H, C$_1$-C$_{12}$ alkyl, C$_1$-C$_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, NR$^{14}$R$^{15}$, —N$_3$, and —OR$^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, NR$^{14}$R$^{15}$, and —OR$^{16}$;

$R^{2a}$, $R^{2b}$, $R^{3a}$ and $R^{3b}$ are independently selected from the group consisting of H, —OR$^{27}$, —NR$^{28}$R$^{29}$, halogen, C$_1$-C$_4$ cycloalkyl, and C$_1$-C$_6$ alkyl, wherein each $R^{27}$, $R^{28}$, and $R^{29}$ is independently H or alkyl; wherein the C$_1$-C$_6$ alkyl or alkyl is unsubstituted or substituted with one or more substituents selected from the group consisting of halogen, —OR$^{30}$, —NR$^{31}$R$^{32}$, —SR$^{33}$, and —SO$_2$R$^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, NR$^{14}$R$^{15}$, and —OR$^{16}$; or $R^{2a}$ and $R^{2b}$ form an oxo or imino group substituted with C$_1$-C$_6$ alkyl;

$R^{3a}$ and $R^{3b}$ form an oxo or imino group substituted with C$_1$-C$_6$ alkyl;

X is —NH$_2$, —N$_3$, protected amino group, —OH, or protected hydroxyl group;

$R^{4a}$ and $R^{4b}$ are, independently H, —OH, —OR$^{40}$, —NR$^{41}$R$^{42}$, or halogen;

wherein each $R^{40}$, $R^{41}$, and $R^{42}$ are independently H or alkyl; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

$R^{5a}$ is H, —CN, —CONH$_2$ or C$_1$-C$_3$alkyl, wherein the alkyl is unsubstituted or substituted with one or more substituents selected from the group consisting of —OH, —NH$_2$, —CN, —CONH$_2$, and halogen;

$R^{6a}$ and $R^{6b}$ are, independently H, halogen, NH$_2$, —OH, C$_1$-C$_3$alkoxy, —OC(O)CH$_3$, or —OPg$^{2j}$;

wherein Pg$^{2j}$ is a hydroxyl protecting group;

$R^{7a}$, $R^{7b}$, and $R^{7c}$ are, independently, H, OH, —OR$^{71}$ or —OPg$^2$;

wherein $R^{71}$ is alkyl; wherein the alkyl is unsubstituted or substituted with one or more substituents selected from the group consisting of —CONH$_2$, —OH, —NH$_2$, —COCH$_3$, aryl, substituted aryl, heteroaryl, and substituted heteroaryl;

wherein Pg$^2$ is a hydroxyl protecting group;

$R^{8a}$ is H, C$_1$-C$_6$ alkyl, an amino protecting group, or wherein $Q^1$ is NH, O, or S;

z is an integer from 0 to 4, $R^{35z}$ is H or C$_1$-C$_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein $R^{39z}$ and $R^{40z}$ are independently H or C$_1$-C$_3$ alkyl; or $R^{35z}$ and $R^{38z}$, together with the atoms to which they are attached, form a heterocycloalkyl group comprising at least one N;

$R^{9a}$ and $R^{9b}$ are independently H, OH, or —OR$^{91}$, wherein $R^{91}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

$R^{10a}$ and $R^{10b}$ are independently H, OH, or —OR$^{101}$, wherein $R^{101}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

N$^{1e}$ is —NHPg$^{1e}$ or N$_3$, wherein Pg$^{1e}$ is an amino protecting group;

N$^{1f}$ is —NHPg$^{1f}$ or N$_3$, wherein Pg$^{1f}$ is an amino protecting group;

Pg$^{2f}$ is a hydroxyl protecting group or H;

wherein at least one of N$^{1e}$ and N$^{1f}$ is not NH$_2$ or wherein Pg$^{2f}$ is not H or wherein X is not —OH or —NH$_2$;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

Embodiment I-36. A compound of formula (ABC-1)

ABC-1 or a salt, solvate, enantiomer, or diastereomer thereof, wherein $R^{1a}$ and $R^{1b}$ are independently selected from the group consisting of H, C$_1$-C$_{12}$ alkyl, C$_1$-C$_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —SR$^{12}$, —SO$_2$R$^{13}$, —OSF$_2$NR$^{14}$R$^{15}$, —NR$^{14}$R$^{15}$, —N$_3$, and —OR$^{16}$, and wherein each $R^2$, $R^1$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —SR$^{22}$, —SO$_2$R$^{23}$, —NR$^{24}$R$^{25}$, and —OR$^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, NR$^{14}$R$^{15}$, and —OR$^{16}$;

$R^{2a}$, $R^{2b}$, $R^{3a}$ and $R^{3b}$ are independently selected from the group consisting of H, —OR$^{27}$, —NR$^{28}$R$^{29}$, halogen, C$_1$-C$_4$ cycloalkyl, and C$_1$-C$_6$ alkyl, wherein each $R^{27}$, $R^{28}$, and $R^{29}$ is independently H or alkyl; wherein the C$_1$-C$_6$ alkyl or alkyl is unsubstituted or substituted with one or more substituents selected from the group consisting of halogen, —OR$^{30}$, —NR$^{31}$R$^{32}$, —SR$^{33}$, and —SO$_2$R$^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, NR$^{14}$R$^{15}$, and —OR$^{16}$; or $R^{2a}$ and $R^{2b}$ form an oxo or imino group substituted with C$_1$-C$_6$ alkyl;

$R^{3a}$ and $R^{3b}$ form an oxo or imino group substituted with C$_1$-C$_6$ alkyl;

X is —NH$_2$, —N$_3$, protected amino group, —OH, or protected hydroxyl group;

$R^{4a}$ and $R^{4b}$ are, independently H, —OH, —OR$^{40}$, —NR$^{41}$R$^{42}$, or halogen;

wherein each $R^{40}$, $R^{41}$, and $R^{42}$ are independently H or alkyl; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5a}$ is H, —CN, —$CONH_2$ or $C_1$-$C_3$ alkyl, wherein the alkyl is unsubstituted or substituted with one or more substituents selected from the group consisting of —OH, —$NH_2$, —CN, —$CONH_2$, and halogen;

$R^{6a}$ and $R^{6b}$ are, independently H, halogen, $NH_2$, —OH, $C_1$-$C_3$ alkoxy, —OC(O)$CH_3$, or —$OPg^{2j}$;

wherein $Pg^{2j}$ is a hydroxyl protecting group;

$R^{7a}$, $R^{7b}$, and $R^{7c}$ are, independently, H, OH, —$OR^{71}$ or —$OPg^2$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, and substituted heteroaryl;

wherein $Pg^2$ is a hydroxyl protecting group;

$R^{8a}$ is H, $C_1$-$C_6$ alkyl, an amino protecting group, or

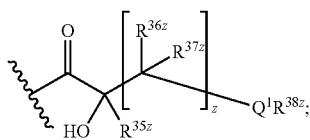

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$N^{1o}$ is —$NHPg^{1o}$ or $N_3$, wherein $Pg^{1o}$ is an amino protecting group;

$N^{1p}$ is —$NHPg^{1p}$ or $N_3$, wherein $Pg^{1p}$ is an amino protecting group;

$Pg^{2f}$ is a hydroxyl protecting group;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

Embodiment I-37. A compound of formula (ABC-2)

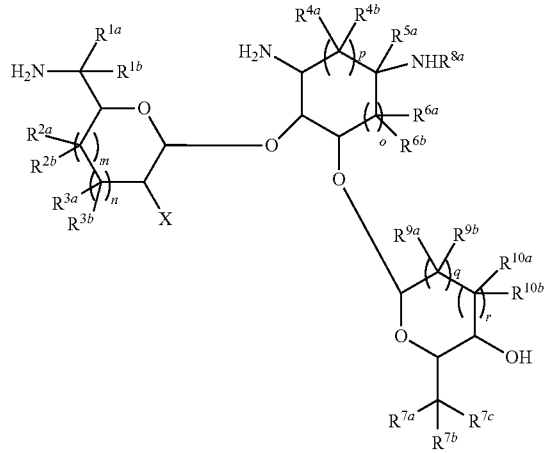

ABC-2 or a salt, solvate, enantiomer, or diastereomer thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, $NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

X is —$NH_2$ or —OH;

$R^{4a}$ and $R^{4b}$ are, independently H, —OH, —$OR^{40}$, —$NR^{41}R^{42}$, or halogen;

wherein each $R^{40}$, $R^{41}$, and $R^{42}$ are independently H or alkyl; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5a}$ is H, —CN, —CONH$_2$ or C$_1$-C$_3$alkyl, wherein the alkyl is unsubstituted or substituted with one or more substituents selected from the group consisting of —OH, —NH$_2$, —CN, —CONH$_2$, and halogen;

$R^{6a}$ and $R^{6b}$ are, independently H, halogen, NH$_2$, —OH, C$_1$-C$_3$alkoxy, —OC(O)CH$_3$, or —OPg$^{2j}$; wherein Pg$^{2j}$ is a hydroxyl protecting group;

$R^{7a}$, $R^{7b}$, and $R^{7c}$ are, independently, H, OH, —OR$^{71}$ or —OPg$^2$;

wherein $R^{71}$ is alkyl; wherein the alkyl is unsubstituted or substituted with one or more substituents selected from the group consisting of —CONH$_2$, —OH, —NH$_2$, —COCH$_3$, aryl, substituted aryl, heteroaryl, and substituted heteroaryl;

wherein Pg$^2$ is a hydroxyl protecting group;

$R^{8a}$ is H, C$_1$-C$_6$ alkyl, an amino protecting group, or

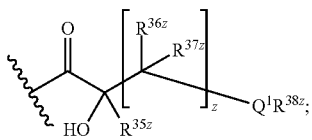

wherein

Q$^1$ is NH, O, or S;

z is an integer from 0 to 4, $R^{35z}$ is H or C$_1$-C$_3$ alkyl;

each $R^{36z}$ and $R^{37z}$ is independently selected from the group consisting of H, alkyl, halogen, and —OH, and $R^{38z}$ is H, alkyl, or —C(=NH)NR$^{39z}$R$^{40z}$, wherein R$^{39z}$ and R$^{40z}$ are independently H or C$_1$-C$_3$ alkyl; or $R^{35z}$ and $R^{38z}$, together with the atoms to which they are attached, form a heterocycloalkyl group comprising at least one N; $R^{9a}$ and $R^{9b}$ are independently H, OH, or —OR$^{91}$, wherein $R^{91}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

$R^{10a}$ and $R^{10b}$ are independently H, OH, or —OR$^{101}$, wherein $R^{101}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2;

wherein q+r is 1, 2 or 3.

Embodiment I-38. The compound of Embodiment I-34, selected from the group consisting of:

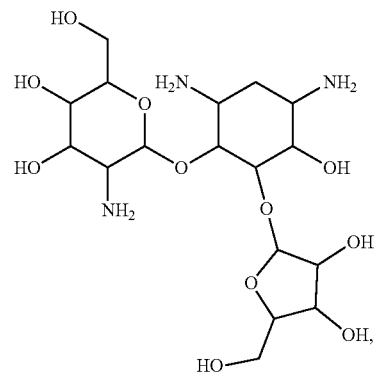

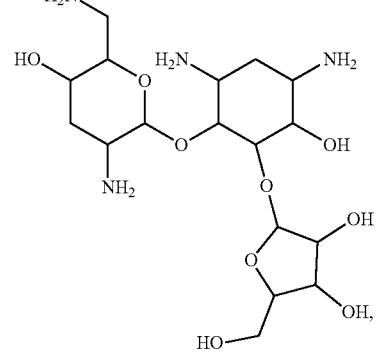

or a salt, solvate, enantiomer, or diastereomer of any of the foregoing.

Embodiment I-39. The compound of Embodiment I-34, selected from the group consisting of:

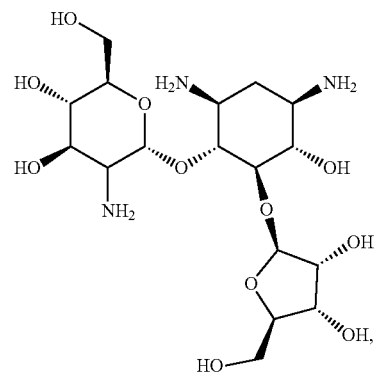

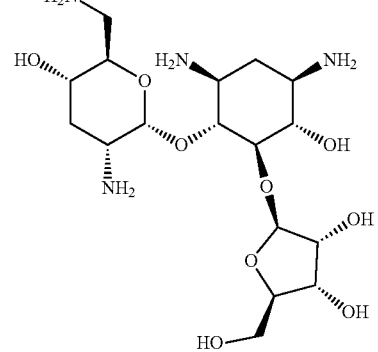

or a salt, solvate, enantiomer, or diastereomer of any of the foregoing.

Embodiment I-40. A compound of formula (ABCD-3)

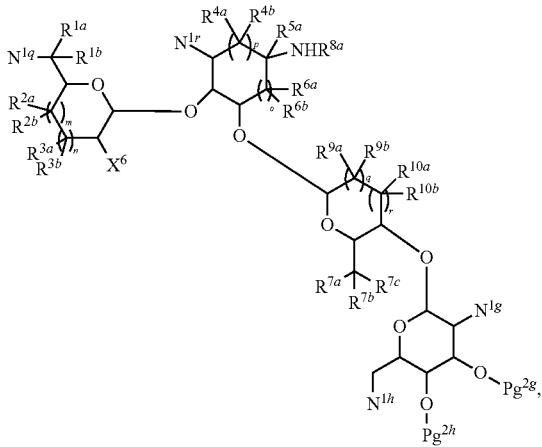

or a salt, solvate, enantiomer, or diastereomer thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, $-SR^{12}$, $-SO_2R^{3}$, $-OSF_2NR^{14}R^{15}$, $-NR^{14}R^{15}$, $-N_3$, and $-OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, $-SR^{22}$, $-SO_2R^{23}$, $-NR^{24}R^{25}$, and $-OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and $-OR^{16}$;

$R^{2a}$, $R^{2b}$, $R^{3a}$ and $R^{3b}$ are independently selected from the group consisting of H, $-OR^{27}$, $-NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, $-OR^{30}$, $-NR^{31}R^{32}$, $-SR^{33}$, and $-SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and $-OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^6$ is selected from the group consisting of H, $NH_2$, $N_3$, protected amino group, OH, $-OPg^{2m}$, and halogen; wherein $Pg^{2m}$ is a hydroxyl protecting group;

$R^{4a}$ and $R^{4b}$ are, independently, H, $-OH$, $-OR^{40}$, $-NR^{41}R^{42}$, or halogen;

wherein each $R^{40}$, $R^{41}$, and $R^{42}$ are independently H or alkyl;

wherein the alkyl is unsubstituted or substituted with one or more substituents selected from the group consisting of $-CONH_2$, $-OH$, $-NH_2$, $-COCH_3$, aryl, substituted aryl, heteroaryl, halogen, and substituted heteroaryl;

$R^{5a}$ is H, $-CN$, $-CONH_2$ or $C_1$-$C_3$ alkyl, wherein the alkyl is unsubstituted or substituted with one or more substituents selected from the group consisting of $-OH$, $-NH_2$, $-CN$, $-CONH_2$, and halogen;

$R^{6a}$ and $R^{6b}$ are, independently H, halogen, $NH_2$, $-OH$, $C_1$-$C_3$alkoxy, $-OC(O)CH_3$, or $-OPg^{2j}$; wherein $Pg^{2j}$ is a hydroxyl protecting group;

$R^{7a}$, $R^{7b}$, and $R^{7c}$ are, independently, H, OH, $-OR^{71}$ or $-OPg^{2}$;

wherein $R^{71}$ is alkyl; wherein the alkyl is unsubstituted or substituted with one or more substituents selected from the group consisting of $-CONH_2$, $-OH$, $-NH_2$, $-COCH_3$, aryl, substituted aryl, heteroaryl, and substituted heteroaryl;

wherein $Pg^2$ is a hydroxyl protecting group;

$R^{8a}$ is H, $C_1$-$C_6$ alkyl, an amino protecting group, or

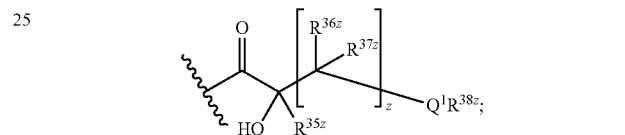

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and $-OH$, and $R^{38z}$ is H, alkyl, or $-C(=NH)NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{9a}$ and $R^{9b}$ are independently H, OH, or $-OR^{91}$, wherein $R^{91}$ is alkyl, alkenyl, or alkynyl; wherein the alkyl, alkenyl, and alkynyl is unsubstituted or substituted with one or more substituents selected from the group consisting of $-CONH_2$, $-OH$, $-NH_2$, $-COCH_3$, aryl, substituted aryl, heteroaryl, and substituted heteroaryl;

$R^{10a}$ and $R^{10b}$ are independently H, OH, or $-OR^{101}$, wherein $R^{101}$ is alkyl, alkenyl, or alkynyl; wherein the alkyl, alkenyl, and alkynyl is unsubstituted or substituted with one or more substituents selected from the group consisting of $-CONH_2$, $-OH$, $-NH_2$, $-COCH_3$, aryl, substituted aryl, heteroaryl, and substituted heteroaryl;

$N^{1q}$ is $-NHPg^{1q}$ or $N_3$, wherein $Pg^{1q}$ is an amino protecting group;

$N^{1r}$ is $-NHPg^{1r}$ or $N_3$, wherein $Pg^{1r}$ is an amino protecting group;

$N^{1g}$ is $-NHPg^{1g}$ or $N_3$, wherein $Pg^{1g}$ is an amino protecting group;

$N^{1h}$ is $-NHPg^{1h}$ or $N_3$, wherein $Pg^{1h}$ is an amino protecting group;

$Pg^{2g}$ is a hydroxyl protecting group;

$Pg^{2h}$ is a hydroxyl protecting group;

wherein at least one of $N^{1q}$, $N^{1r}$ $N^{1g}$, $N^{1h}$ is not $NH_2$ or wherein at least one of $PG^{2g}$ or $Pg^{2h}$ is not H or wherein $X^6$ is not $-OH$ or $-NH_2$;

m is zero, 1, or 2;
n is zero, 1, or 2;
wherein m+n is 1, 2 or 3;
o is zero, 1, or 2;
p is zero, 1, or 2;
wherein o+p is 1, 2 or 3;
q is zero, 1, or 2;
r is zero, 1, or 2;
wherein q+r is 1, 2 or 3.

Embodiment I-41. A compound of formula ABCD-4:

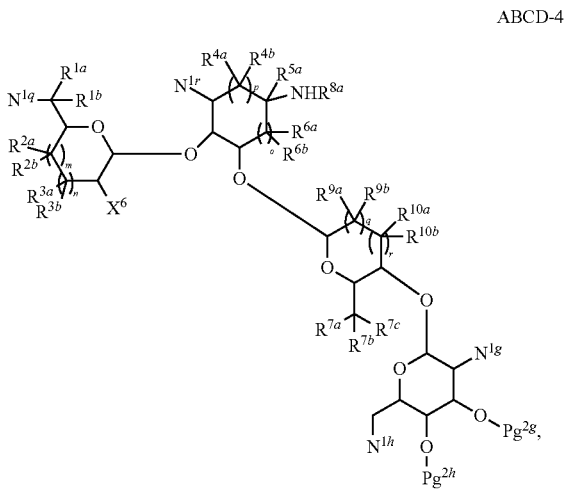

ABCD-4 or a salt, solvate, enantiomer, or diastereomer thereof, wherein $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and wherein each $R^{12}$, $R^{13}$, $R^{14}$, $R^{15}$, and $R^{16}$ is independently H or alkyl; or $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$, and —$OR^{16}$;

$R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H or alkyl; wherein the $C_1$-$C_6$ alkyl or alkyl is unsubstituted or substituted with one or more substituents selected from the group consisting of halogen, —$OR^{30}$, —$NR^{31}R^{32}$, —$SR^{33}$, and —$SO_2R^{34}$;

wherein each $R^{30}$, $R^{31}$, $R^{32}$, $R^{33}$, and $R^{34}$ is independently H or alkyl substituted with one or more substituents independently selected from the group consisting of halogen, cyano, $NR^{14}R^{15}$, and —$OR^{16}$; or $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;

$X^6$ is selected from the group consisting of H, $NH_2$, $N_3$, protected amino group, OH, —$OPg^{2m}$, and halogen; wherein $Pg^{2m}$ is a hydroxyl protecting group;

$R^{4a}$ and $R^{4b}$ are, independently, H, —OH, —$OR^{40}$, —$NR^{41}R^{42}$, or halogen;

wherein each $R^{40}$, $R^{41}$, and $R^{42}$ are independently H or alkyl;

wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

$R^{5a}$ is H, —CN, —$CONH_2$ or $C_1$-$C_3$alkyl, wherein the alkyl is unsubstituted or substituted with one or more substituents selected from the group consisting of —OH, —$NH_2$, —CN, —$CONH_2$, and halogen;

$R^{6a}$ and $R^{6b}$ are, independently H, halogen, $NH_2$, —OH, $C_1$-$C_3$alkoxy, —$OC(O)CH_3$, or —$OPg^{2j}$; wherein $Pg^{2j}$ is a hydroxyl protecting group;

$R^{7a}$, $R^{7b}$, and $R^{7c}$ are, independently, H, OH, —$OR^{71}$ or —$OPg^2$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, and substituted heteroaryl;

wherein $Pg^2$ is a hydroxyl protecting group;

$R^{8a}$ is H, $C_1$-$C_6$ alkyl, an amino protecting group, or

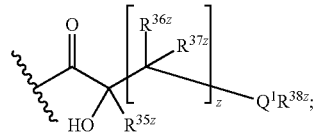

wherein $Q^1$ is NH, O, or S;

z is an integer from 0 to 4, $R^{35z}$ is H or $C_1$-$C_3$ alkyl;

each $R^{36z}$ and $R^{37z}$ is independently selected from the group consisting of H, alkyl, halogen, and —OH, and $R^{38z}$ is H, alkyl, or —C(=NH)$NR^{39z}R^{40z}$, wherein $R^{39z}$ and $R^{40z}$ are independently H or $C_1$-$C_3$ alkyl; or $R^{35z}$ and $R^{38z}$, together with the atoms to which they are attached, form a heterocycloalkyl group comprising at least one N;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$N^{1q}$ is —$NHPg^{1q}$, —$NH_2$, or $N_3$, wherein $Pg^{1q}$ is an amino protecting group;

$N^{1r}$ is —$NHPg^{1r}$, —$NH_2$, or $N_3$, wherein $Pg^{1r}$ is an amino protecting group;

$N^{1g}$ is —$NHPg^{1g}$, —$NH_2$, or $N_3$, wherein $Pg^{1g}$ is an amino protecting group;

N[1h] is —NHPg[1h], —NH$_2$, or N$_3$, wherein Pg[1h] is an amino protecting group;

Pg[2g] is H or a hydroxyl protecting group;

Pg[2h] is H or a hydroxyl protecting group;

N[1p] is —NHPg[1p], —NH$_2$, or N$_3$, wherein Pg[1p] is an amino protecting group;

wherein at least one of N[1q], N[1r], N[1g], N[1h] is not NH$_2$ or wherein at least one of PG[2g] or Pg[2h] is not H or wherein X[6] is not —OH or —NH$_2$;

m is zero, 1, or 2;

n is zero, 1, or 2;

wherein m+n is 1, 2 or 3;

o is zero, 1, or 2;

p is zero, 1, or 2;

wherein o+p is 1, 2 or 3;

q is zero, 1, or 2;

r is zero, 1, or 2.

Embodiment I-42. The compound of Embodiment I-40, selected from the group consisting of:

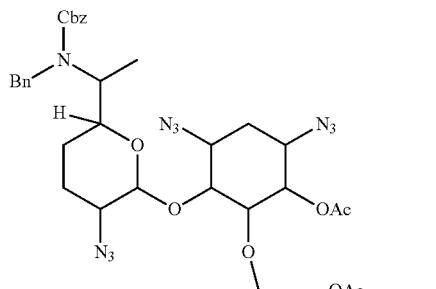


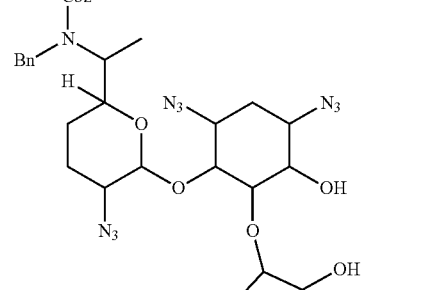

-continued

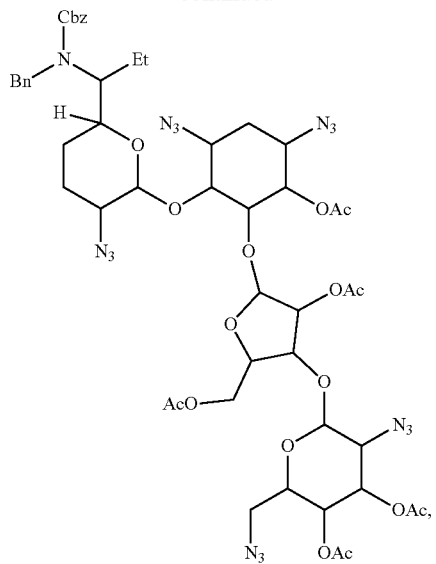

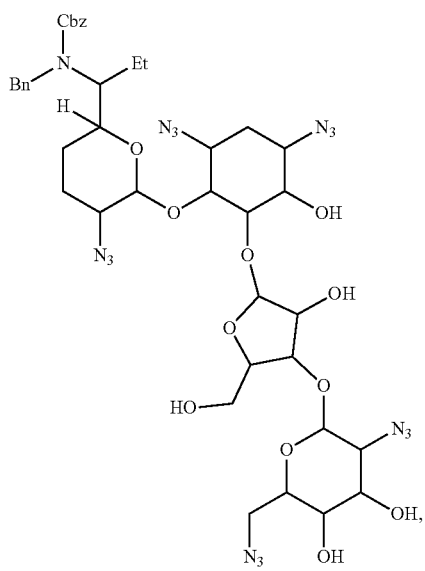

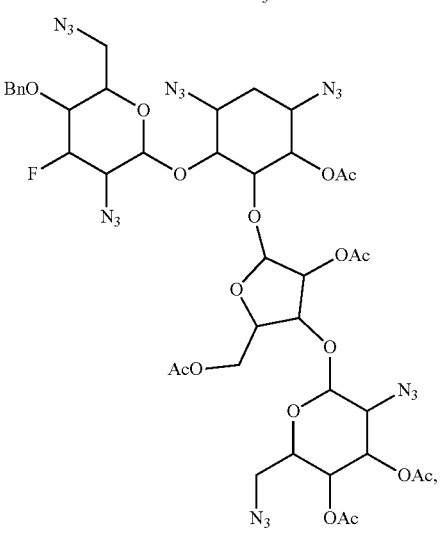

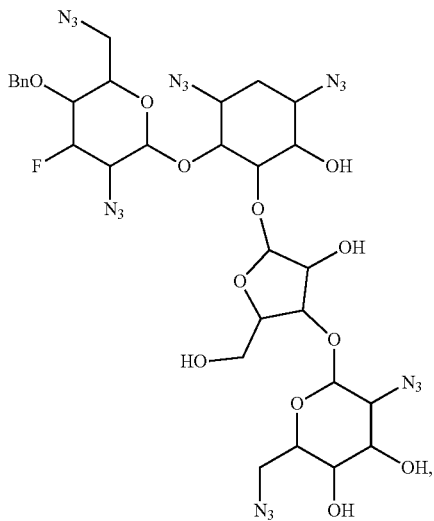
or a salt, solvate, enantiomer, or diastereomer of any of the foregoing.
Embodiment I-43. The compound of Embodiment I-40, selected from the group consisting of:
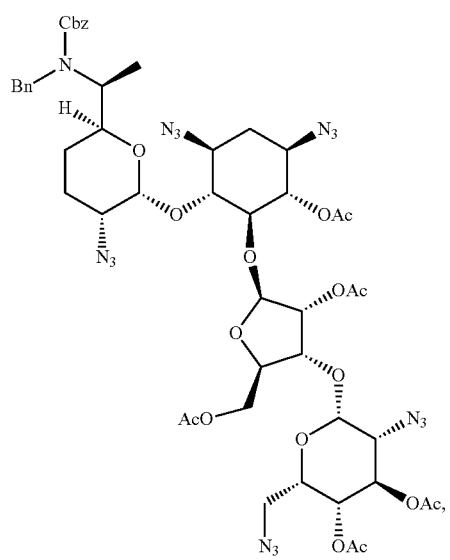
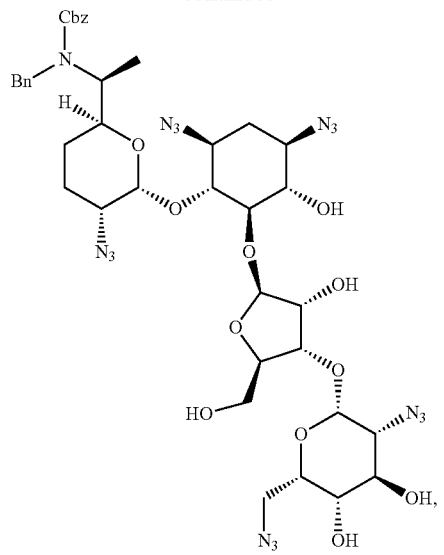
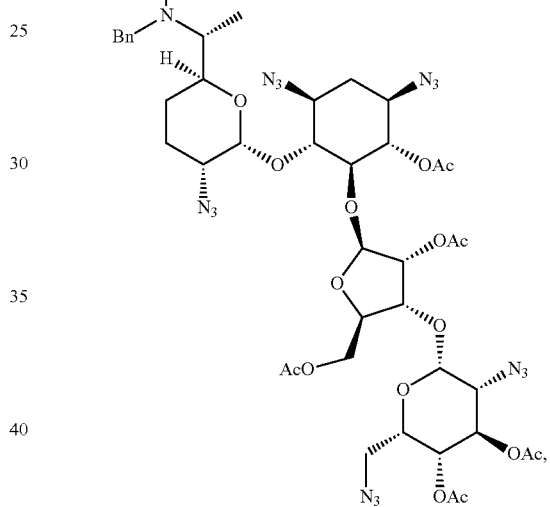
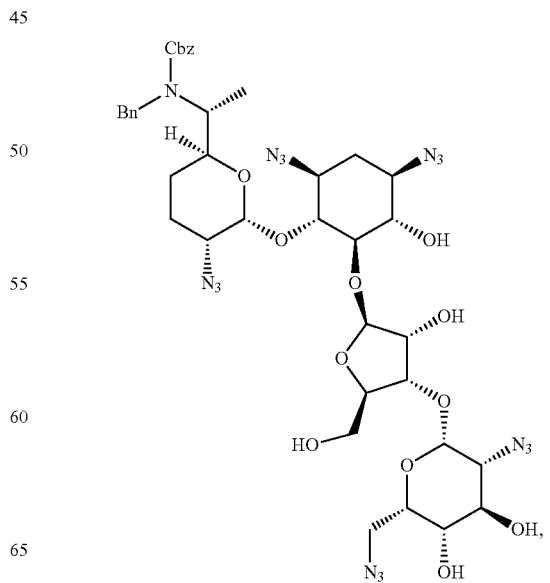

319
-continued
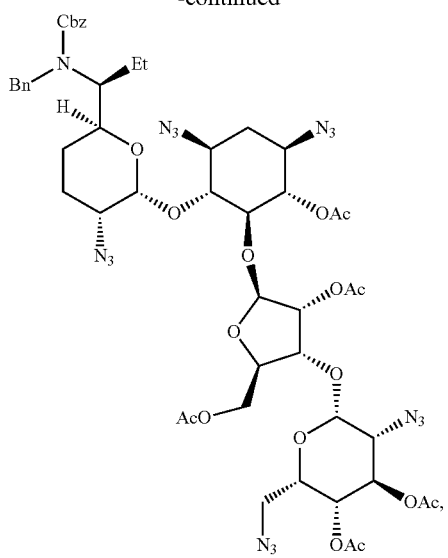
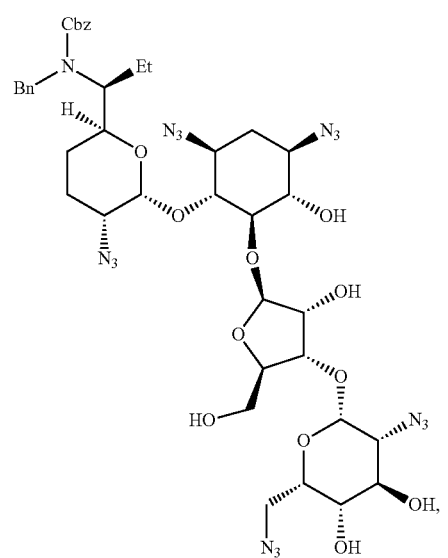
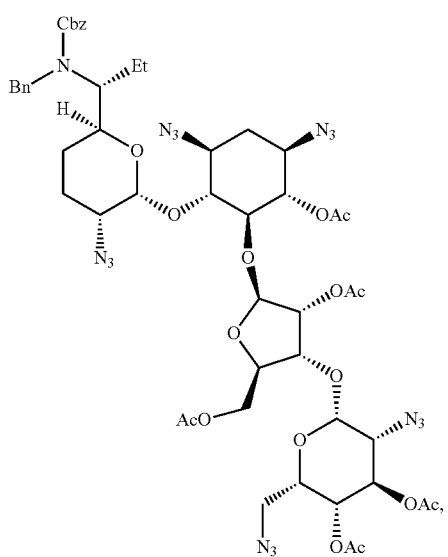
320
-continued
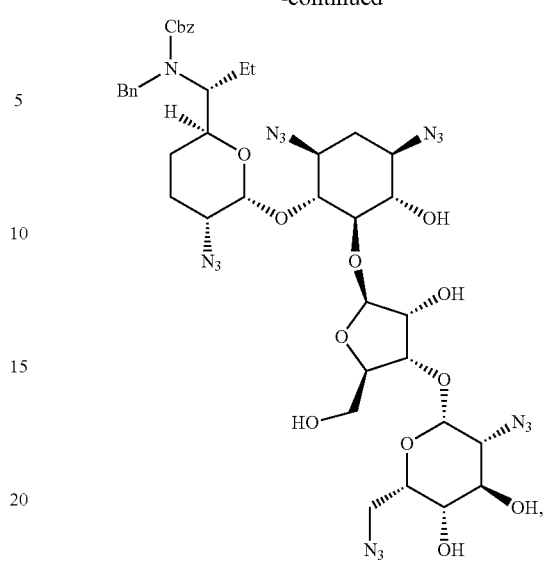
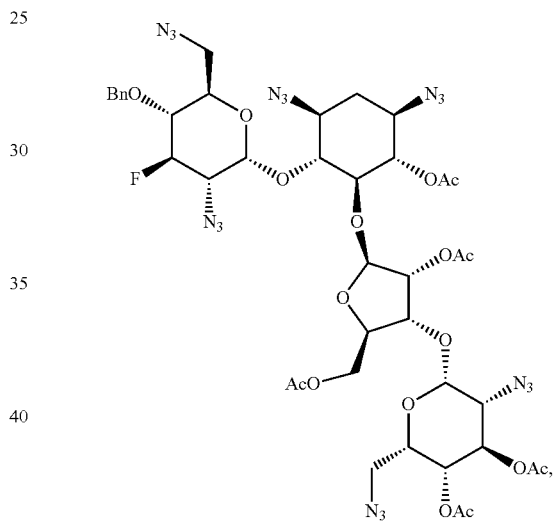
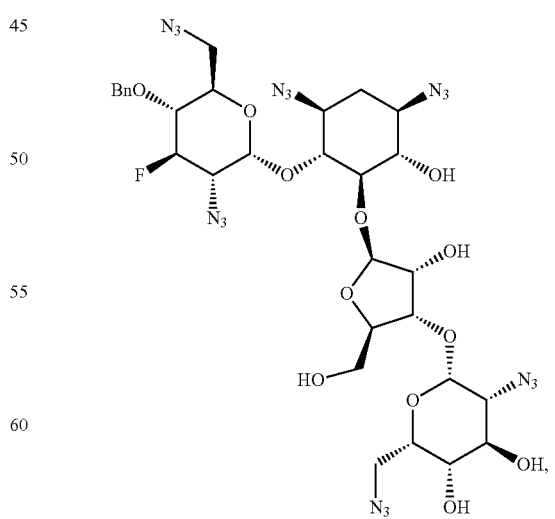
or a salt, solvate, enantiomer, or diastereomer of any of the foregoing.

Embodiment I-44. A pharmaceutical composition, comprising a compound of any one of Embodiments I-1 to I-43, or a pharmaceutically acceptable salt, solvate, stereoisomer, or tautomer thereof, and a pharmaceutically acceptable carrier.

Embodiment I-45. A method for treating a bacterial infection in a subject, comprising administering to a subject in need thereof a therapeutically effective amount of a compound of any one of Embodiment I-31 and I-37, or a pharmaceutically acceptable salt, solvate, stereoisomer, or tautomer thereof.

Embodiment I-46. A method for treating a bacterial infection in a subject, comprising administering to a subject in need thereof a therapeutically effective amount of a pharmaceutical composition according to Embodiment I-44.

Embodiment I-47. The method of Embodiment I-45 or Embodiment I-46, wherein the bacterial infection is a gram-negative bacterial infection.

Embodiment I-48. The method of Embodiment I-45 or Embodiment I-46, wherein the bacterial infection is infection of a *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Bacillus, Bacteroides, Peptococcus, Clostridium, Salmonella, Shigella, Serratia, Haemophilus, Brucella, Francisella, Anthracis, Yersinia, Corynebacterium, Moraxella*, or *Enterococcus* species.

Embodiment I-49. Use of a compound of any one of Embodiment I-31 and Embodiment I-37, or a pharmaceutically acceptable salt, solvate, stereoisomer, or tautomer thereof, in the manufacture of a medicament for treating a bacterial infection in a subject in need thereof.

Embodiment I-50. A compound of any one of Embodiment I-31 and Embodiment I-37, or a pharmaceutically acceptable salt, solvate, stereoisomer, or tautomer thereof, for use in a method of treating a bacterial infection in a subject in need thereof.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Unless otherwise noted, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

Example 1

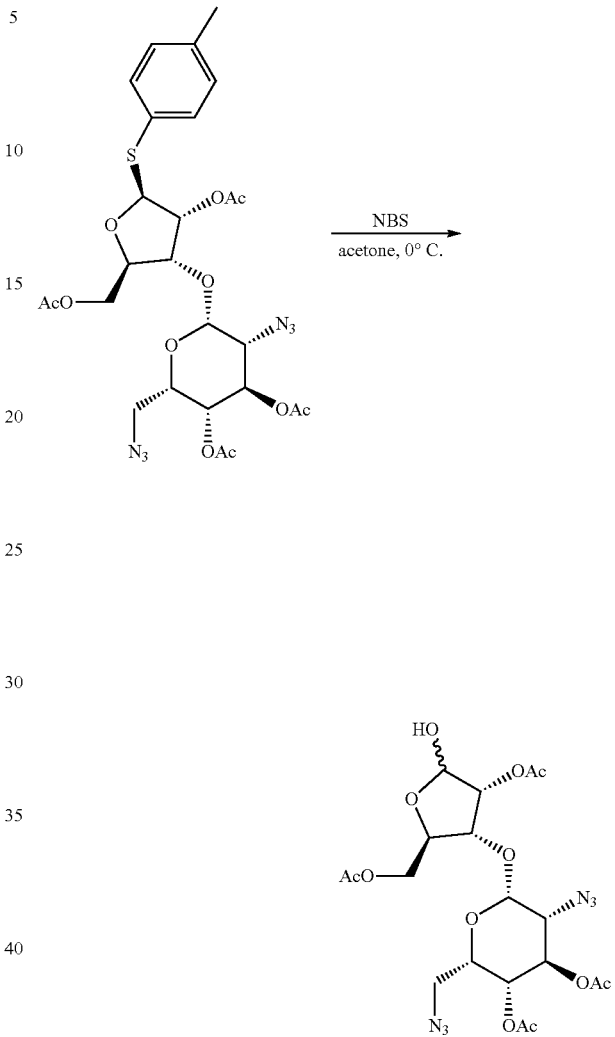

[(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate NBS (268 mg, 1.50 mmol) was added to a solution of [(2R,3R,4R,5R)-4-acetoxy-3-[(2R,3R,4R,5R,6S)-4,5-diacetoxy-3-azido-6-(azidomethyl)tetrahydropyran-2-yl]oxy-5-(p-tolylsulfanyl)tetrahydrofuran-2-yl]methyl acetate (638 mg, 1 mmol) in acetone (15.0 mL) under $N_2$ at 0° C. After 1 h, the reaction was quenched with 1:1 sat. $NaHCO_3$/$Na_2S_2O_3$ (30.0 mL) and acetone was removed under reduced pressure. The aqueous layer was extracted with DCM (3×15 mL). The combined organic layers were dried over $Na_2SO_4$, filtered and concentrated under reduced pressure. The material was purified on silica gel chromatography (25 g, dry loading) using 20% to 60% EtOAc in hexane to provide the title compound as a solid (diastereomers, 400 mg, 71%). LCMS m/z: $ES^+$ [M−OH]$^+$: 513.22, [M+NH$_4$]$^+$: 548.17.

Example 1A

Step 1

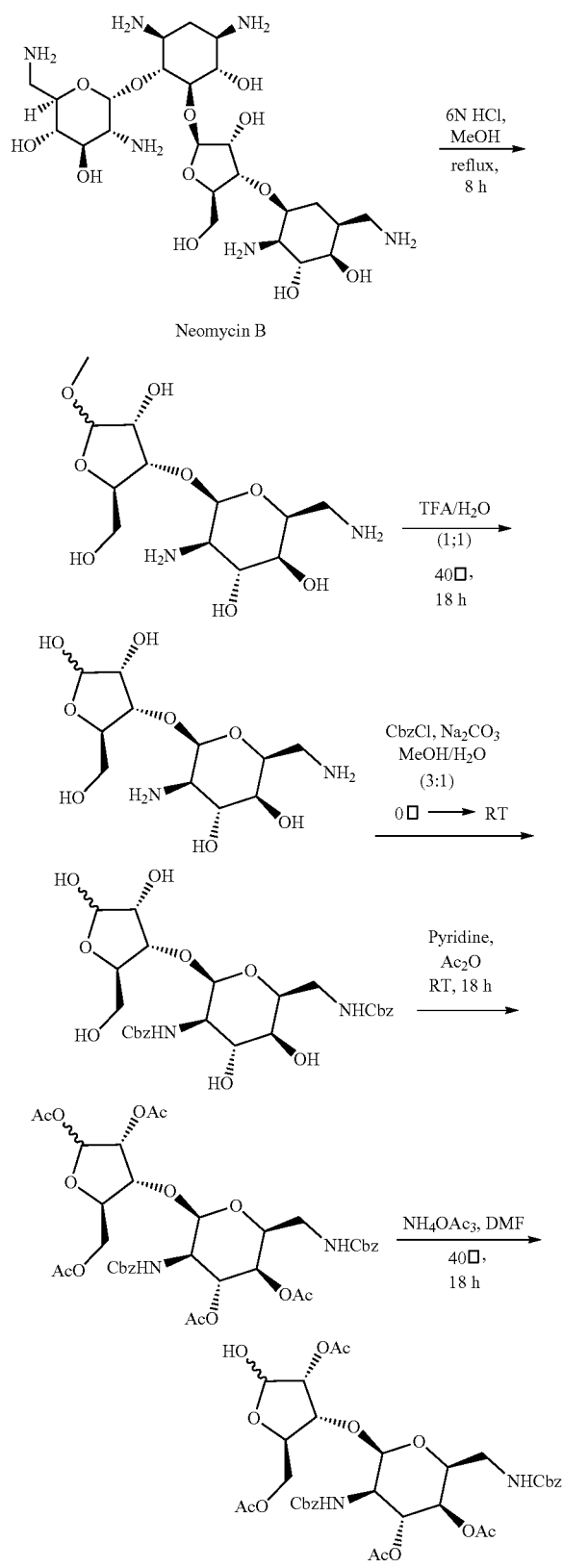

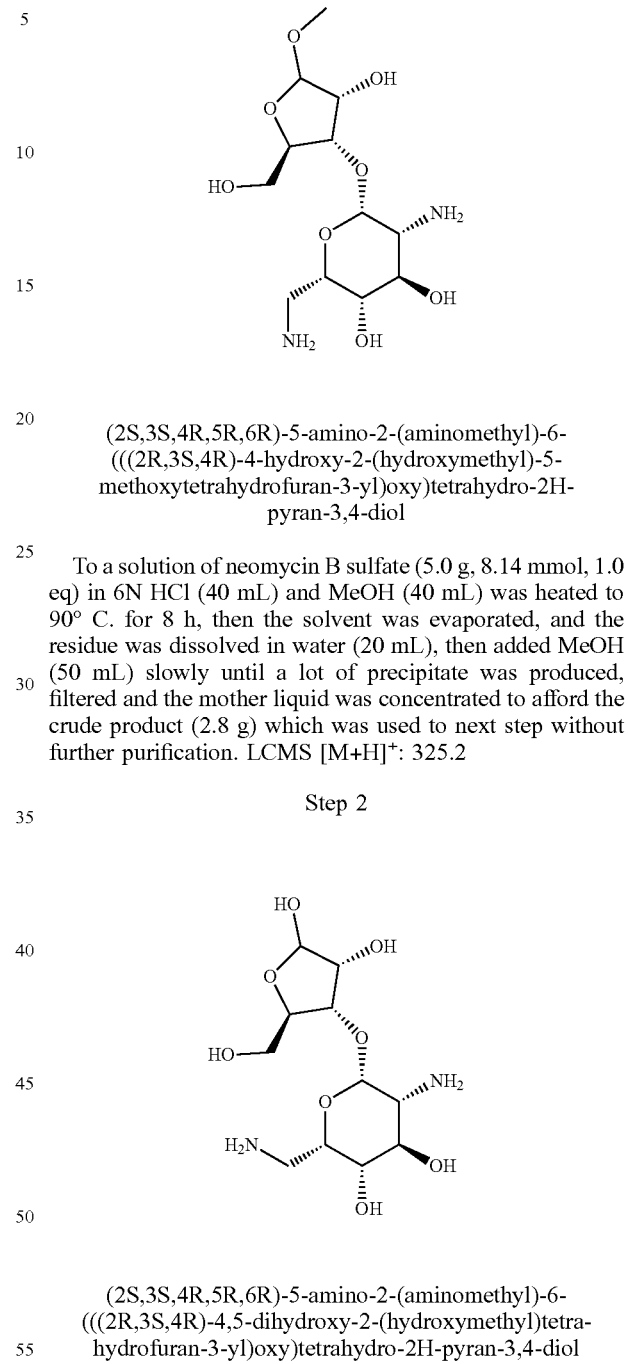

(2S,3S,4R,5R,6R)-5-amino-2-(aminomethyl)-6-
(((2R,3S,4R)-4-hydroxy-2-(hydroxymethyl)-5-
methoxytetrahydrofuran-3-yl)oxy)tetrahydro-2H-
pyran-3,4-diol To a solution of neomycin B sulfate (5.0 g, 8.14 mmol, 1.0 eq) in 6N HCl (40 mL) and MeOH (40 mL) was heated to 90° C. for 8 h, then the solvent was evaporated, and the residue was dissolved in water (20 mL), then added MeOH (50 mL) slowly until a lot of precipitate was produced, filtered and the mother liquid was concentrated to afford the crude product (2.8 g) which was used to next step without further purification. LCMS [M+H]$^+$: 325.2

Step 2

(2S,3S,4R,5R,6R)-5-amino-2-(aminomethyl)-6-
(((2R,3S,4R)-4,5-dihydroxy-2-(hydroxymethyl)tetra-
hydrofuran-3-yl)oxy)tetrahydro-2H-pyran-3,4-diol The suspended solution of the crude (2S,3S,4R,5R,6R)-5-amino-2-(aminomethyl)-6-(((2R,3S,4R)-4-hydroxy-2-(hydroxymethyl)-5-methoxytetrahydrofuran-3-yl)oxy)tetrahydro-2H-pyran-3,4-diol (2.8 g, 8.64 mmol, 1.0 eq.) in TFA/H$_2$O (25 mL/25 mL) was stirred at 40° C. for 18 h, then the solvent was evaporated, and the residue was dissolved in water (25 mL) and was added MeOH (50 mL) slowly until a lot of precipitate was produced, filtered and the mother liquid was concentrated to give the crude product (1.6 g) which was used to next step without further purification. LCMS [M+H]$^+$: 311.4

Step 3

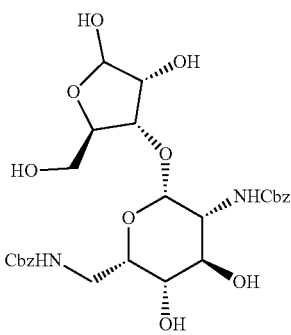 [SMILES: O=C(NC[C@@H]1O[C@H](O[C@@H]2[C@@H](CO)OC(O)[C@@H]2O)[C@H](NC(=O)OCc2ccccc2)[C@@H](O)[C@@H]1O)OCc1ccccc1]

benzyl((2R,3R,4R,5S,6S)-6-((((benzyloxy)carbonyl)amino)methyl)-2-(((2R,3S,4R)-4,5-dihydroxy-2-(hydroxymethyl)tetrahydrofuran-3-yl)oxy)-4,5-dihydroxytetrahydro-2H-pyran-3-yl)carbamate To a solution of the crude (2S,3S,4R,5R,6R)-5-amino-2-(aminomethyl)-6-(((2R,3S,4R)-4,5-dihydroxy-2-(hydroxymethyl)tetrahydrofuran-3-yl)oxy)tetrahydro-2H-pyran-3,4-diol (1.6 g, 5.14 mmol, 1.0 eq) in MeOH/H$_2$O (30 mL/10 mL) was added aq. sat. Na$_2$CO$_3$ (3.27 g, 30.84 mmol, 6.0 eq) at 0° C., followed by benzyl carbonochloridate (2.62 g, 15.42 mmol, 3.0 eq). After stirred at r.t. for 18 h, the solvent was removed at reduced pressure and wash with DCM/MeOH=10/1 (20 mL), filtered and the residue was purified by silica gel column chromatography (DCM/MeOH=10/1, v/v) to give the crude product (1.3 g). LCMS [M+Na]$^+$: 601.3

Step 4

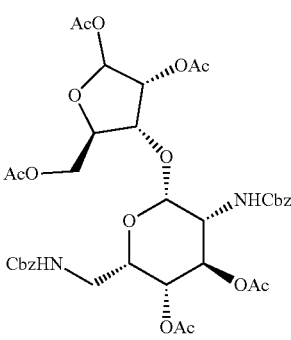 [SMILES: CC(=O)OC[C@H]1OC(OC(C)=O)[C@H](OC(C)=O)[C@@H]1O[C@H]1O[C@@H](CNC(=O)OCc2ccccc2)[C@@H](OC(C)=O)[C@H](OC(C)=O)[C@H]1NC(=O)OCc1ccccc1]

(3R,4R,5R)-5-(acetoxymethyl)-4-(((2R,3R,4R,5R,6S)-4,5-diacetoxy-3-(((benzyloxy)carbonyl)amino)-6-((((benzyloxy)carbonyl)amino)methyl)tetrahydro-2H-pyran-2-yl)oxy)tetrahydrofuran-2,3-diyl diacetate To a solution of the crude benzyl((2R,3R,4R,5S,6S)-6-((((benzyloxy)carbonyl)amino)methyl)-2-(((2R,3S,4R)-4,5-dihydroxy-2-(hydroxymethyl)tetrahydrofuran-3-yl)oxy)-4,5-dihydroxytetrahydro-2H-pyran-3-yl)carbamate (1.3 g, 2.16 mmol, 1.0 eq.) in pyridine (10 mL) was added Ac$_2$O (5 mL) in dropwise, then the mixture was stirred at r.t. for 18 h. The solvent was removed, and the residue was diluted with EA (100 mL), washed with aq. sat. NH$_4$Cl (50 mL*3), and dried over MgSO$_4$, and concentrated, purified by silica gel column chromatography (PE/EA=2:1, v/v) and prep-HPLC to afford the product (124.5 mg). LCMS [M+Na]$^+$: 811.4. $^1$H NMR (400 MHz, DMSO-d$_6$) δ 7.31-7.38 (m, 10H), 5.82-5.86 (m, 1H), 4.89-5.09 (m, 7H), 4.62-4.64 (m, 1H), 4.42-4.47 (m, 1H), 3.67-4.06 (m, 9H), 1.95-2.08 (m, 15H).

Step 5

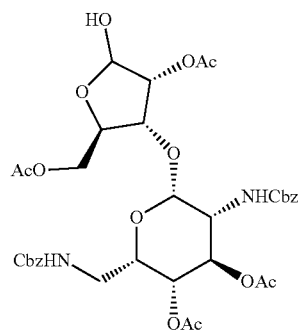 [SMILES: CC(=O)OC[C@H]1OC(O)[C@H](OC(C)=O)[C@@H]1O[C@H]1O[C@@H](CNC(=O)OCc2ccccc2)[C@@H](OC(C)=O)[C@H](OC(C)=O)[C@H]1NC(=O)OCc1ccccc1]

((2S,3R,4R,5R,6R)-6-(((2R,3R,4R)-4-acetoxy-2-(acetoxymethyl)-5-hydroxytetrahydrofuran-3-yl)oxy)-5-(((benzyloxy)carbonyl)amino)-2-((((benzyloxy)carbonyl)amino)methyl)tetrahydro-2H-pyran-3,4-diyl diacetate)

To the solution of (3R,4R,5R)-5-(acetoxymethyl)-4-(((2R,3R,4R,5R,6S)-4,5-diacetoxy-3-(((benzyloxy)carbonyl)amino)-6-((((benzyloxy)carbonyl)amino)methyl)tetrahydro-2H-pyran-2-yl)oxy)tetrahydrofuran-2,3-diyl diacetate (170.5 mg, 0.21 mmol, 1.0 eq.) in dry DMF (10 mL) was added AcOH·NH$_3$ (64.7 mg, 0.84 mmol, 4.0 eq.), then the mixture was stirred at 40° C. for 18 h. The solvent was removed, and the preparation and purification to afford product (47 mg). LCMS [M+Na]$^+$: 769.4. $^1$H NMR (400 MHz, DMSO-d$_6$) δ 7.31-7.37 (m, 10H), 6.95 (m, 1H), 5.81-5.84 (m, 1H), 4.78-5.10 (m, 10H), 4.27-4.30 (m, 1H), 3.99-4.02 (m, 2H), 3.48-3.52 (m, 2H), 3.06-3.12 (m, 2H), 1.80-2.08 (m, 12H).

Example 1B

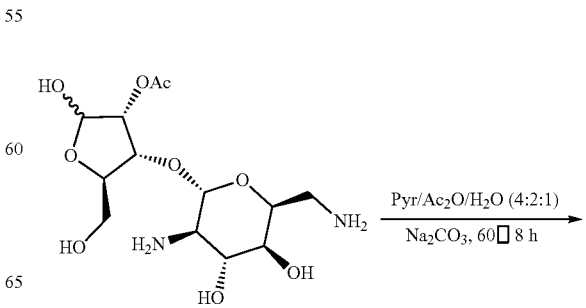

-continued

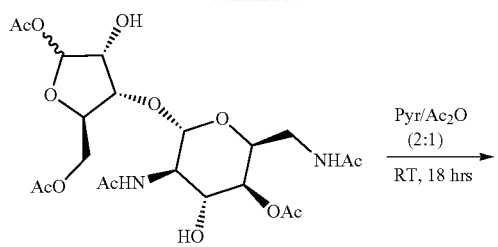

Step 1

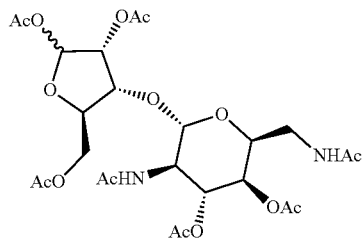

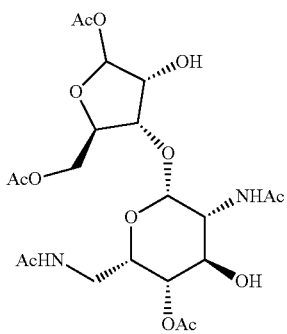 [SMILES: CC(=O)NC[C@@H]1O[C@H](O[C@@H]2[C@@H](COC(C)=O)OC(OC(C)=O)[C@@H]2O)[C@H](NC(C)=O)[C@@H](O)[C@@H]1OC(C)=O]

(2S,3S,4R,5R,6R)-5-acetamido-2-(acetamidomethyl)-6-(((2R,3S,4R)-5-acetoxy-2-(acetoxymethyl)-4-hydroxytetrahydrofuran-3-yl)oxy)-4-hydroxytetrahydro-2H-pyran-3-yl acetate The suspended solution of (2S,3S,4R,5R,6R)-5-amino-2-(aminomethyl)-6-(((2R,3S,4R)-4,5-dihydroxy-2-(hydroxymethyl)tetrahydrofuran-3-yl)oxy)tetrahydro-2H-pyran-3,4-diol (3.0 g, 9.65 mmol, 1.0 eq.) in Na₂CO₃ aq (5 mL) was added pyridine (20 mL) and Ac₂O (10 mL) in dropwise, then the mixture was stirred at 60° C. for 8 h. The solvent was evaporated, and purified by silica gel column chromatography (DCM/MeOH=20:1, v/v) to afford the product (1.31 g). LCMS [M+H]⁺: 521.4.

Step 2

(2S,3R,4R,5R,6R)-5-acetamido-2-(acetamidomethyl)-6-(((2R,3R,4R)-4,5-diacetoxy-2-(acetoxymethyl)tetrahydrofuran-3-yl)oxy)tetrahydro-2H-pyran-3,4-diyl diacetate To a solution of the (2S,3S,4R,5R,6R)-5-acetamido-2-(acetamidomethyl)-6-(((2R,3S,4R)-5-acetoxy-2-(acetoxymethyl)-4-hydroxytetrahydrofuran-3-yl)oxy)-4-hydroxytetrahydro-2H-pyran-3-yl acetate (1.31 g, 2.52 mmol, 1.0 eq.) in pyridine (10 mL) was added Ac₂O (5 mL) in dropwise, then the mixture was stirred at r.t. for 18 h. The solvent was removed, and the residue was diluted with EA (30 mL), washed with aq. sat. NH₄Cl (10 mL*3), and dried over MgSO₄, and concentrated, purified via prep-HPLC to afford the product (177.0 mg). LCMS [M+Na]⁺: 827.4. ¹H NMR (400 MHz, DMSO-d₆) δ 7.82-7.84 (m, 0.93H), 7.39-7.41 (m, 0.3H), 6.79-6.82 (m, 0.34H), 5.88-5.99 (m, 0.77H), 5.30-5.31 (m, 0.35H), 4.84-5.13 (m, 1H), 4.80-4.83 (m, 2.33H), 4.59-4.62 (m, 1H), 4.35-4.37 (m, 0.9H), 3.75-4.18 (m, 4H), 3.11-3.29 (m, 2H), 1.79-2.12 (m, 21H).

Example 2

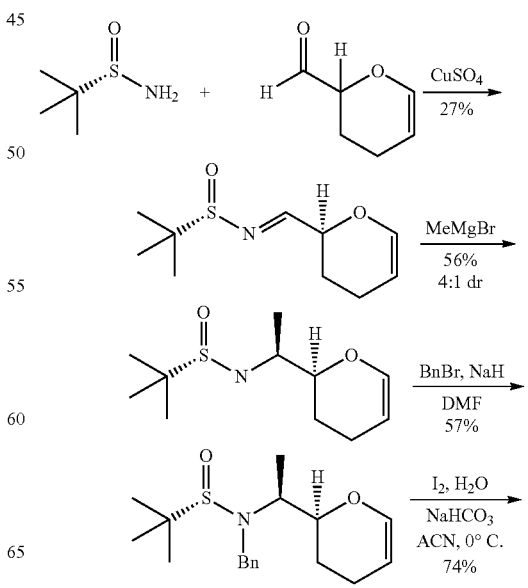

329
-continued
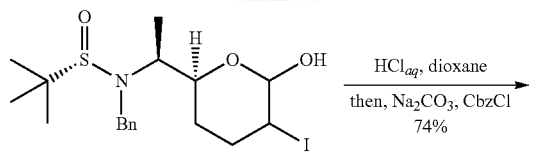
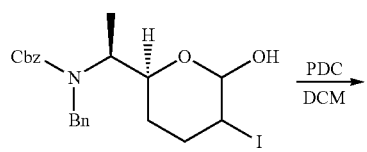
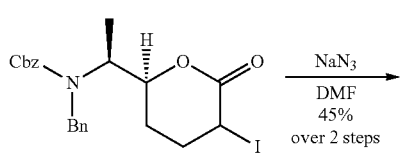
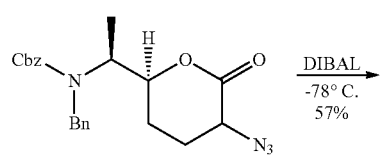
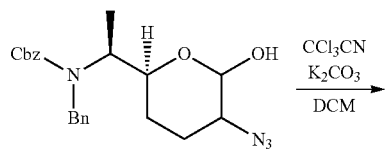
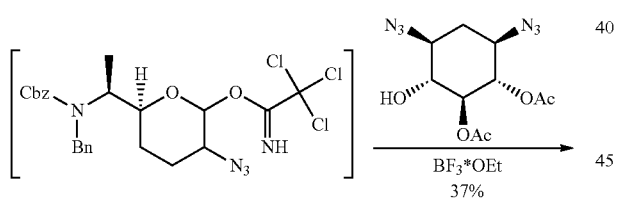
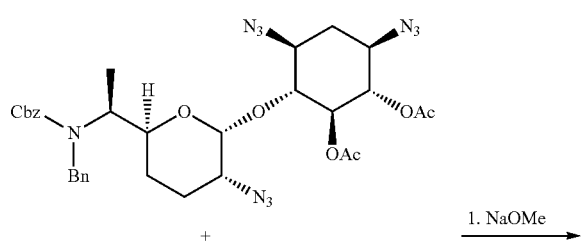
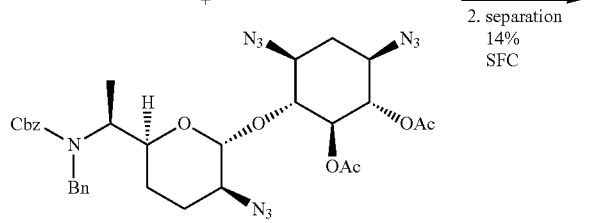
330
-continued
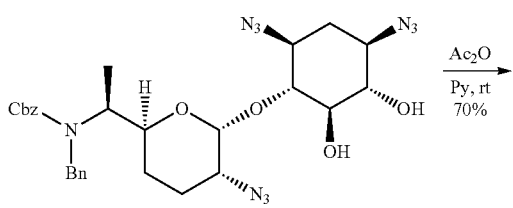
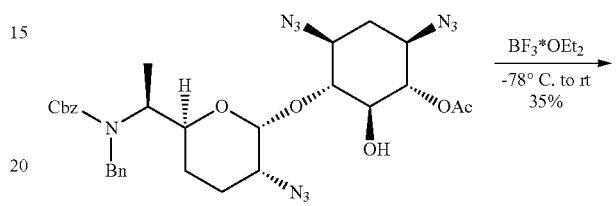
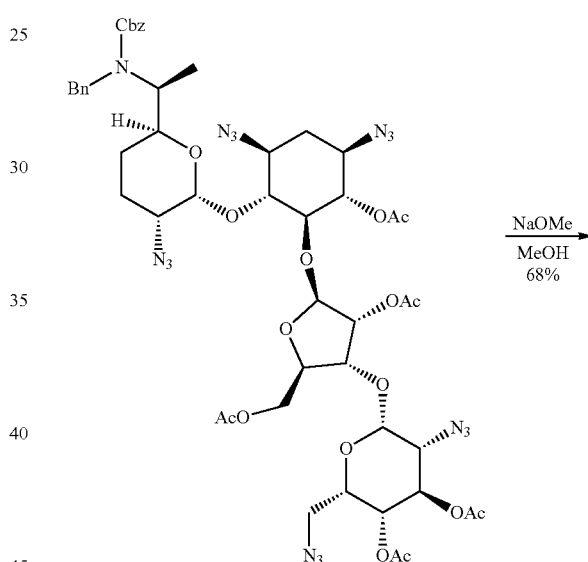
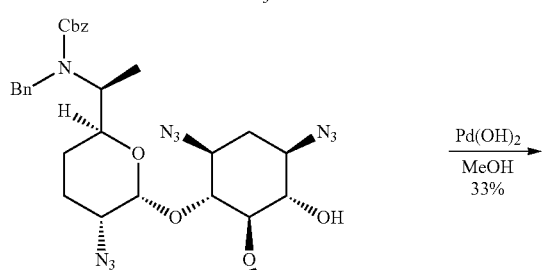
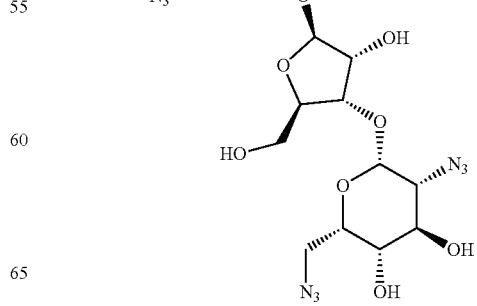

331
-continued

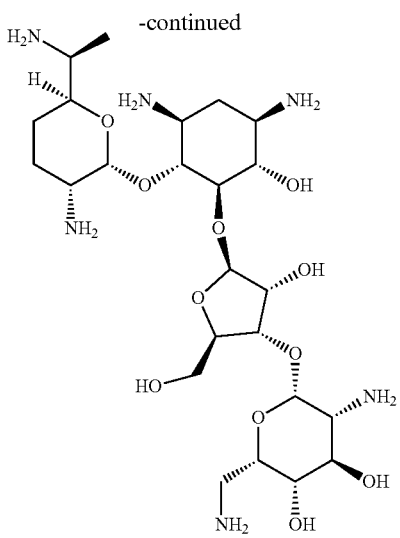

Step 1

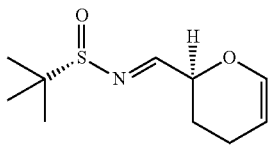

(S)—N-((E)-((S)-3,4-dihydro-2H-pyran-2-yl)methylene)-2-methylpropane-2-sulfinamide (S)-(+)-2-Methyl-2-propanesulfinamide (50 g, 412 mmol) and CuSO₄ (131.7 g, 825 mmol) were mixed in DCM (600.0 mL). A solution of 2-formyl-3,4-dihydro-2H-pyran (48.6 g, 433 mmol, Synthonix) in DCM (100.0 mL) was added over 20 min. The mixture was stirred at room temperature for 18 h, and then filtered through Celite and rinsed with DCM. The filtrate was evaporated under reduced pressure. The material was purified on silica gel (5×330 g, dry loading) by MPLC using 0-20% Et₂O in hexane as eluent to provide the title compound (23.74 g, 27%, second eluting diastereomer). ¹H NMR (400 MHz, CDCl₃) δ 8.08 (d, J=3.0 Hz, 1H), 6.47 (dt, J=6.3, 1.6 Hz, 1H), 4.81-4.72 (m, 2H), 2.19-1.94 (m, 4H), 1.24 (s, 9H).

Step 2

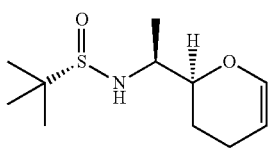

(S)—N—((S)-1-((S)-3,4-dihydro-2H-pyran-2-yl)ethyl)-2-methylpropane-2-sulfinamide (S)—N-((E)-((S)-3,4-dihydro-2H-pyran-2-yl)methylene)-2-methylpropane-2-sulfinamide (7.30 g, 33.9 mmol)

332 was dissolved in dry DCM (100 mL) and the solution was cooled to −78° C. MeMgBr (3.0 M in Et₂O, 22.6 mL, 67.8 mmol) was added dropwise to the mixture and stirring was continued at low temperature for 2 hours, before allowing the mixture to warm to room temperature. Stirring was continued at room temperature for 1 hour. Concentrated aqueous NH₄Cl (50 mL) was added, and the mixture was extracted with DCM (3×50 mL). The combined organic layers were dried (MgSO₄), and concentrated in vacuo to afford a crude oil containing a mixture of diastereomers. The material was purified using silica gel chromatography (120 g cartridge) with hexanes and ethyl acetate (0-100%) to afford the title compound as an oil (4.40 g, 56%). LCMS m/z: ES⁺ [M+H]⁺: 232.16.

Step 3

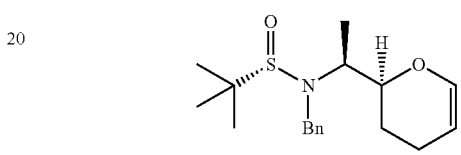

(S)—N-benzyl-N—((S)-1-((S)-3,4-dihydro-2H-pyran-2-yl)ethyl)-2-methylpropane-2-sulfinamide NaH (60% dispersion, 913 mg, 22.8 mmol) was added to a solution of (S)—N—((S)-1-((S)-3,4-dihydro-2H-pyran-2-yl)ethyl)-2-methylpropane-2-sulfinamide (4.40 g, 19.0 mmol) and benzyl bromide (3.39 mL, 28.5 mmol) in DMF (100 mL) at 0° C. The mixture was stirred at this temperature for 2 hours, then brine (100 mL) was added at 0° C. The aqueous layer was extracted with Et₂O (3×50.0 mL). The combined organic layers were dried (MgSO₄) and concentrated in vacuo to afford a residue that was purified using silica gel chromatography (120 g cartridge) using hexanes and ethyl acetate (0-100%). The pure fractions were concentrated in vacuo to afford the title compound as an oil (3.50 g, 57%). LCMS m/z: ES⁺ 322.14.

¹H NMR (500 MHz, DMSO) δ 7.45 (d, J=7.1 Hz, 2H), 7.35-7.29 (m, 2H), 7.23 (t, J=7.3 Hz, 1H), 6.38 (d, J=6.1 Hz, 1H), 4.65 (ddd, J=6.2, 4.3, 1.4 Hz, 1H), 4.35 (d, J=16.5 Hz, 1H), 3.91 (t, J=11.4 Hz, 1H), 3.80 (td, J=9.2, 2.3 Hz, 1H), 3.22-3.11 (m, 1H), 1.97-1.92 (m, 1H), 1.89-1.78 (m, 2H), 1.53-1.42 (m, 1H), 1.19 (t, J=3.4 Hz, 3H), 1.10 (s, 8H).

Step 4

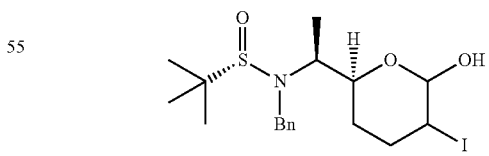

(S)—N-benzyl-N-((1S)-1-((2S)-6-hydroxy-5-iodo-tetrahydro-2H-pyran-2-yl)ethyl)-2-methylpropane-2-sulfinamide (S)—N-benzyl-N—((S)-1-((S)-3,4-dihydro-2H-pyran-2-yl)ethyl)-2-methylpropane-2-sulfinamide (4.40 g, 13.7 mmol) and NaHCO₃ (3.45 g, 41.1 mmol) were dissolved in H₂O (75.0 mL) and ACN (75.0 mL). 12 (3.82 g, 15.1 mmol) was added portionwise over 10 minutes at 0° C. The cooling bath was removed, and stirring was continued at room temperature over 90 minutes. The reaction mixture was quenched with a saturated aqueous solution of Na₂S₂O₃ (30.0 mL) and extracted with EtOAc (3×20.0 mL). The combined organic layers were dried (MgSO₄) and concentrated in vacuo to afford the title compound as a solid (4.70 g, 74%). LCMS m/z: ES⁺ [M+H]⁺: 466.04.

Step 5

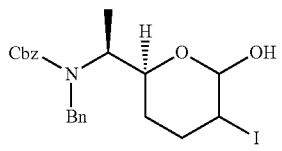 [SMILES: C[C@@H]([C@@H]1CCC(I)C(O)O1)N(Cc1ccccc1)C(=O)OCc1ccccc1]

Benzyl benzyl((1S)-1-((2S)-6-hydroxy-5-iodotetrahydro-2H-pyran-2-yl)ethyl)carbamate (S)—N-benzyl-N-((1S)-1-((2)-6-hydroxy-5-iodotetrahydro-2H-pyran-2-yl)ethyl)-2-methylpropane-2-sulfinamide (4.70 g, 10.1 mmol) was dissolved in 1,4-dioxane (150 mL), and an aqueous solution of 1 N HCl (25.2 mL, 25.2 mmol) was added. Stirring was continued at room temperature for 20 minutes, before solid Na₂CO₃ (8.56 g, 80.8 mmol) was added to the mixture. Stirring was continued for 20 minutes, and then CbzCl (1.72 mL, 12.1 mmol) was added dropwise. Stirring was continued for 2 hours. Water (200 mL) was added and the mixture was extracted with EtOAc (3×50 mL). The combined organic layers were dried (MgSO₄) and concentrated in vacuo to give a residue that was purified using silica gel chromatography (80 g cartridge) using hexanes and ethyl acetate (0-100%). The pure fractions were concentrated in vacuo to afford the title compound as an oil (3.70 g, 74%). LCMS m/z: ES⁺ [M+H]⁺: 518.04.

Step 6

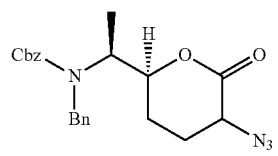 [SMILES: C[C@@H]([C@@H]1CCC(N=[N+]=[N-])C(=O)O1)N(Cc1ccccc1)C(=O)OCc1ccccc1]

Benzyl ((1S)-1-((2S)-5-azido-6-oxotetrahydro-2H-pyran-2-yl)ethyl)(benzyl)carbamate Benzyl benzyl((1S)-1-((2S)-6-hydroxy-5-iodotetrahydro-2H-pyran-2-yl)ethyl)carbamate (3.70 g, 7.47 mmol) was dissolved in DCM (350 mL). 4 Å molecular sieves (1.00 g) were suspended in the mixture, and PDC (8.43 g, 22.4 mmol) was added. Stirring was continued over 24 hours at room temperature, then filtered through a pad of celite using ethyl acetate, and concentrated in vacuo to afford crude benzyl benzyl((1S)-1-((2S)-5-iodo-6-oxotetrahydro-2H-pyran-2-yl)ethyl)carbamate as an oil, which was redissolved in DMF (50.0 mL). NaN₃ (971 mg, 14.9 mmol) was added as a solid, and stirring was continued for 2 hours at room temperature. The solvent was removed in vacuo, and the residue was dissolved in EtOAc (100 mL) and washed with water (3×25 mL). The organic layer was dried (MgSO₄) and concentrated in vacuo to afford an oil that was purified using silica gel chromatography (80 g cartridge) with ethyl acetate and hexanes (0-100%). The pure fractions were combined and concentrated in vacuo to afford the title compound as an oil (1.40 g, 46%). LCMS m/z: ES⁺ [M+Na]⁺: 431.13; calc: 431.18.

Step 7

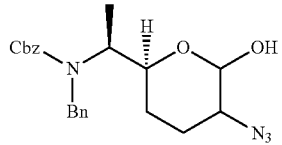 [SMILES: C[C@@H]([C@@H]1CCC(N=[N+]=[N-])C(O)O1)N(Cc1ccccc1)C(=O)OCc1ccccc1]

Benzyl ((1S)-1-((2S)-5-azido-6-hydroxytetrahydro-2H-pyran-2-yl)ethyl)(benzyl)carbamate Benzyl ((1S)-1-((2S)-5-azido-6-oxotetrahydro-2H-pyran-2-yl)ethyl)(benzyl)carbamate (1.40 g, 3.43 mmol) was dissolved in dry DCM (75.0 mL) and the mixture was cooled to −78° C. A solution of DIBAL-H (1.0 M in toluene, 6.86 mL, 6.86 mmol) was added to the mixture, and stirring was continued at low temperature for 1 hour. EtOH (2.00 mL) was added dropwise to the cold reaction mixture, which was then poured into a saturated aqueous solution of Rochelle's salt (200 mL). The mixture was stirred vigorously for 1 hour, then extracted with EtOAc (3×50.0 mL). The combined organic layers were dried (MgSO₄) and concentrated in vacuo to afford a residue that was purified using silica gel chromatography (80 g cartridge) with hexanes and ethyl acetate (0-70%). The pure fractions were collected and concentrated in vacuo to afford the title compound as a mixture of diastereomers (800 mg, 57%). LCMS m/z: ES⁺ [M+Na]⁺: 433.16; calc: 433.19.

Step 8

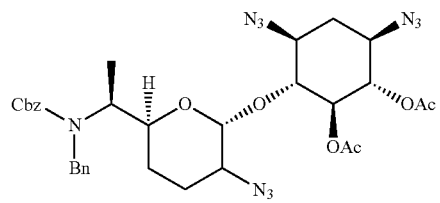 [SMILES: CC(=O)O[C@@H]1[C@@H](OC(C)=O)[C@H](N=[N+]=[N-])C[C@H](N=[N+]=[N-])[C@H]1O[C@H]1O[C@H]([C@H](C)N(Cc2ccccc2)C(=O)OCc2ccccc2)CCC1N=[N+]=[N-]]

(1S,2S,3R,4S,6R)-4,6-diazido-3-(((2R,6S)-3-azido-6-((S)-1-(benzyl((benzyloxy)carbonyl)amino)ethyl)tetrahydro-2H-pyran-2-yl)oxy)cyclohexane-1,2-diyl diacetate Benzyl ((1S)-1-((2S)-5-azido-6-hydroxytetrahydro-2H-pyran-2-yl)ethyl)(benzyl)carbamate (800 mg, 1.95 mmol)

and K$_2$CO$_3$ (808 mg, 5.85 mmol) were suspended in dry DCM (30.0 mL). CCl$_3$CN (0.977 mL, 9.75 mmol) was added dropwise to the mixture, and stirring was continued over two days. The reaction mixture was filtered through celite, and rinsed with DCM (25.0 mL). The filtrate was concentrated in vacuo to afford a residue that was redissolved in DCM (10.0 mL). [(1S,2S,3R,4S,6R)-2-acetoxy-4,6-diazido-3-hydroxy-cyclohexyl]acetate (814 mg, 2.73 mmol) was added. The mixture was cooled to −78° C., and BF$_3$·Et$_2$O (962 µL, 7.80 mmol) was added dropwise. Stirring was continued for 5 hours before the mixture was quenched with saturated aqueous NaHCO$_3$ (50.0 mL). The mixture was extracted with DCM (3×25.0 mL). The organic layers were combined, washed with brine (25.0 mL), dried (MgSO$_4$), and concentrated in vacuo to afford a crude residue that was purified using C18 reverse phase chromatography (120 g cartridge). The pure fractions were concentrated in vacuo to afford the title product as an oil (500 mg, 37%). LCMS m/z: ES$^+$ [M+Na]$^+$: 433.16; calc: 433.19.

Step 9

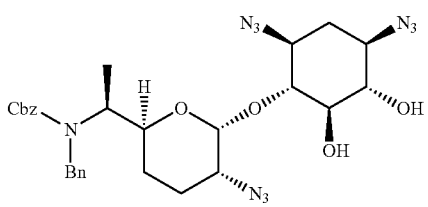

Benzyl ((S)-1-((2S,5R,6R)-5-azido-6-(((1R,2R,3S,4R,6S)-4,6-diazido-2,3-dihydroxycyclohexyl)oxy)tetrahydro-2H-pyran-2-yl)ethyl)(benzyl)carbamate (1S,2S,3R,4S,6R)-4,6-diazido-3-(((2R,6S)-3-azido-6-((S)-1-(benzyl((benzyloxy)carbonyl)amino)ethyl)tetrahydro-2H-pyran-2-yl)oxy)cyclohexane-1,2-diyl diacetate (0.500 g, 0.724 mmol) was dissolved in MeOH (25.0 mL) and NaOMe (0.235 g, 4.34 mmol) was added as a solid. Stirring was continued for 1 hour, then the mixture was quenched with AcOH (5.00 mL). The mixture was concentrated in vacuo, and submitted for SFC purification. The desired diastereomer (5.30 min. elution time) was isolated and obtained as an oil (42 mg, 13%).

Step 10

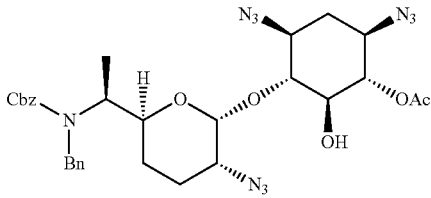 [SMILES: CC(=O)O[C@@H]1[C@@H](O)[C@H](O[C@H]2O[C@H]([C@H](C)N(Cc3ccccc3)C(=O)OCc3ccccc3)CC[C@H]2N=[N+]=[N-])[C@@H](N=[N+]=[N-])C[C@H]1N=[N+]=[N-]]

(1S,2S,3R,4S,6R)-4,6-diazido-3-(((2R,3R,6S)-3-azido-6-((S)-1-(benzyl((benzyloxy)carbonyl)amino)ethyl)tetrahydro-2H-pyran-2-yl)oxy)-2-hydroxycyclohexyl acetate Ac$_2$O (0.01 mL, 0.05 mmol) was added to a solution of benzyl ((S)-1-((2S,5R,6R)-5-azido-6-(((1R,2R,3S,4R,6S)-4,6-diazido-2,3-dihydroxycyclohexyl)oxy)tetrahydro-2H-pyran-2-yl)ethyl)(benzyl)carbamate (28 mg, 0.05 mmol) and pyridine (0.02 mL, 0.3 mmol) in dry DCM (3 mL) at room temperature. After 22 h, MeOH (0.5 mL) was added and the volatiles were removed under reduced pressure. The material was purified on silica gel (12 g, dry loading) by MPLC using hexane to 40% EtOAc in hexane to provide the title compound (21 mg, 70%) as a solid. M+H$^+$: 649.3.

Step 11

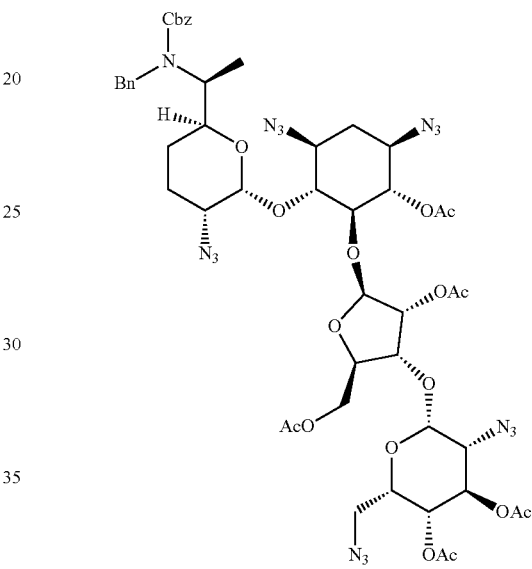

(2S,3R,4R,5R,6R)-6-(((2R,3R,4R,5S)-4-acetoxy-5-(((1S,2S,3R,5S,6R)-2-acetoxy-3,5-diazido-6-(((2R,3R,6S)-3-azido-6-((S)-1-(benzyl((benzyloxy)carbonyl)amino)ethyl)tetrahydro-2H-pyran-2-yl)oxy)cyclohexyl)oxy)-2-(acetoxymethyl)tetrahydrofuran-3-yl)oxy)-5-azido-2-(azidomethyl)tetrahydro-2H-pyran-3,4-diyl diacetate CCl$_3$CN (0.04 mL, 0.37 mol) was added dropwise to a mixture of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (39 mg, 0.07 mmol) and K$_2$CO$_3$ (31 mg, 0.22 mmol) in dry DCM (8 mL) at room temperature under N$_2$. The mixture was stirred at room temperature for 18 h, then filtered with a filter syringe and rinsed with DCM. The filtrate was concentrated under reduced pressure. (1S,2S,3R,4S,6R)-4,6-diazido-3-(((2R,3R,6S)-3-azido-6-((S)-1-(benzyl((benzyloxy)carbonyl)amino)ethyl)tetrahydro-2H-pyran-2-yl)oxy)-2-hydroxycyclohexyl acetate (16 mg, 0.03 mmol) was dissolved in DCM (8 mL) and added to the previous reaction mixture. Activated 4 Å molecular sieves were added and the mixture was cooled to −78° C., then BF$_3$·OEt$_2$ (0.02 mL, 0.12 mmol) was added dropwise. The mixture was stirred at room temperature for 5 h, then a saturated aqueous solution of NaHCO₃ (15 mL) was added. The separated aqueous layer was extracted with DCM (2×20 mL). The combined organic layer was washed with brine, dried over Na₂SO₄ and concentrated under reduced pressure. The residue was purified on C18 silica (120 g Biotage) using 50% B in A to 100% B (B=ACN 0.1% HCOOH, A=0.1% HCOOH) to provide the title compound (10 mg, 35%) as a solid. M+H⁺: 1161.7.

Step 12

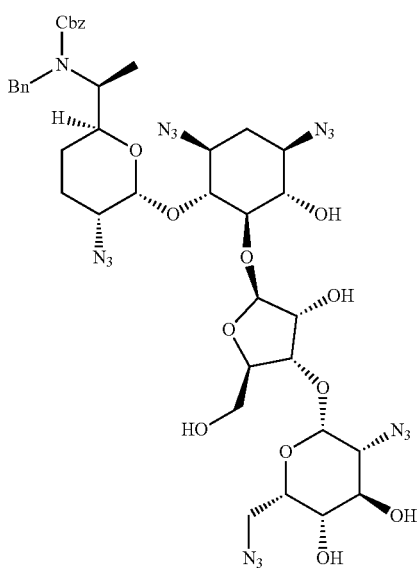 [SMILES: C[C@@H]([C@@H]1CC[C@@H](N=[N+]=[N-])[C@@H](O[C@H]2[C@H](O[C@@H]3O[C@H](CO)[C@@H](O[C@H]4O[C@@H](CN=[N+]=[N-])[C@@H](O)[C@H](O)[C@H]4N=[N+]=[N-])[C@H]3O)[C@@H](O)[C@H](N=[N+]=[N-])C[C@@H]2N=[N+]=[N-])O1)N(Cc1ccccc1)C(=O)OCc1ccccc1]

Benzyl ((S)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H-pyran-2-yl)ethyl)(benzyl)carbamate NaOMe (4.62 M in methanol, 0.01 mL, 0.06 mmol) was added dropwise to a solution of (2S,3R,4R,5R,6R)-6-(((2R,3R,4R,5S)-4-acetoxy-5-(((1S,2S,3R,5S,6R)-2-acetoxy-3,5-diazido-6-(((2R,3R,6S)-3-azido-6-((S)-1-(benzyl((benzyloxy)carbonyl)amino)ethyl)tetrahydro-2H-pyran-2-yl)oxy)cyclohexyl)oxy)-2-(acetoxymethyl)tetrahydrofuran-3-yl)oxy)-5-azido-2-(azidomethyl)tetrahydro-2H-pyran-3,4-diyl diacetate (9 mg, 0.01 mmol) in MeOH (5 mL) at room temperature. After 4 h, AcOH (4 µL, 0.07 mmol) was added to the reaction and the mixture was concentrated under reduced pressure. The residue was purified by prep-HPLC using ACN and AmFor pH 4 to provide the title compound (9 mg, 68%) as a solid. M+H⁺:951.4.

Step 13

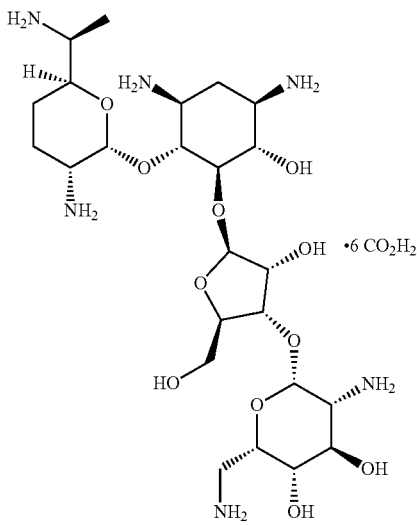 [SMILES: C[C@H](N)[C@@H]1CC[C@@H](N)[C@@H](O[C@H]2[C@H](O[C@@H]3O[C@H](CO)[C@@H](O[C@H]4O[C@@H](CN)[C@@H](O)[C@H](O)[C@H]4N)[C@H]3O)[C@@H](O)[C@H](N)C[C@@H]2N)O1]

(2S,3S,4R,5R,6R)-5-Amino-2-(aminomethyl)-6-(((2R,3S,4R,5S)-5-(((1R,2R,3S,5R,6S)-3,5-diamino-2-(((2R,3R,6S)-3-amino-6-((S)-1-aminoethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol A mixture of benzyl ((S)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H-pyran-2-yl)ethyl)(benzyl)carbamate (5 mg, 5 µmol) and Pd(OH)₂ (20% wt, 5 mg) in MeOH (8 mL) was hydrogenated for 18 h at room temperature. The mixture was degassed with N₂ for 5 min, then filtered on 0.40 µM syringe filter. The solvent was removed under reduced pressure. The material was purified on prep-HPLC using ACN and water (0.1%) formic acid to provide the title compound (1.5 mg, 32%) as the formate salt. M+H⁺: 597.3. ¹H NMR (400 MHz, CD₃OD) δ 8.51 (br, 6H), 5.87 (s, 1H), 5.36 (s, 1H), 5.25 (s, 1H), 4.50-4.42 (m, 11H), 4.39-4.31 (m, 11H), 4.33-4.25 (m, 11H), 4.23-4.15 (m, 1H), 4.12 (s, 1H), 4.00-3.91 (m, 1H), 3.91-3.82 (m, 1H), 3.75-3.61 (m, 3H), 3.54-3.33 (m, 4H), 3.26-3.16 (m, 2H), 3.16-3.01 (m, 2H), 2.79-2.68 (m, 1H), 2.28-2.17 (m, 1H), 2.08-1.89 (m, 3H), 1.64-1.41 (m, 2H), 1.29 (d, J=6.6 Hz, 3H).

Example 3

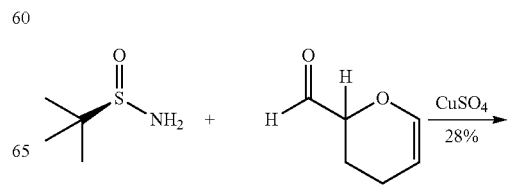

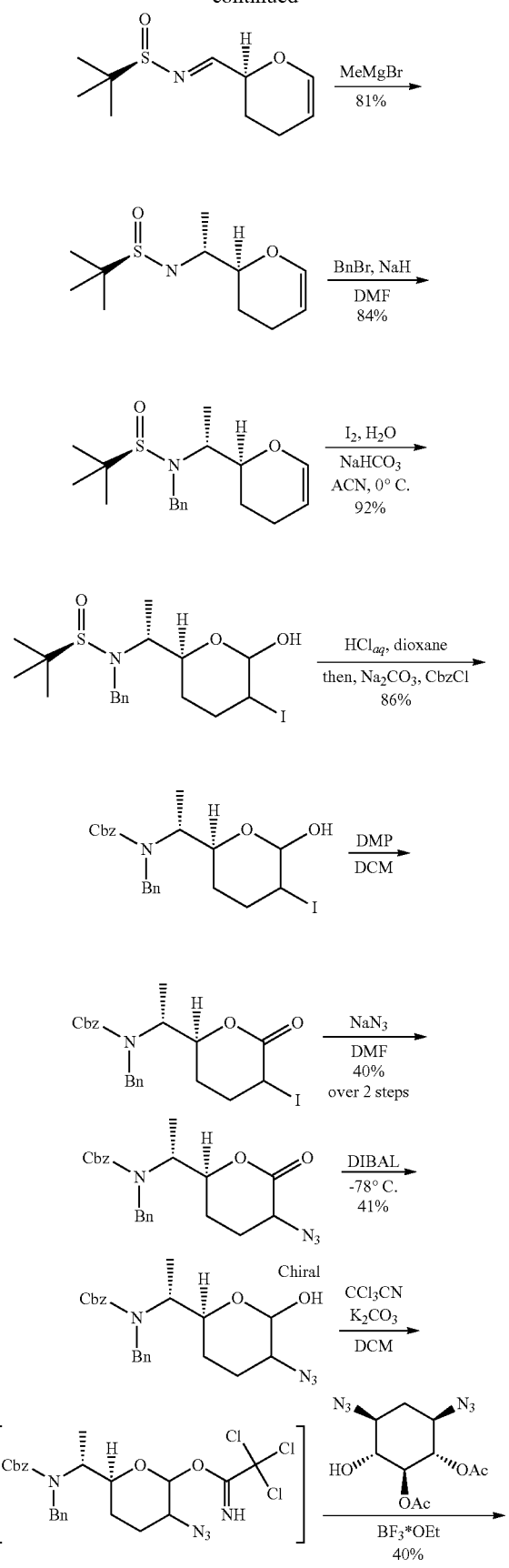
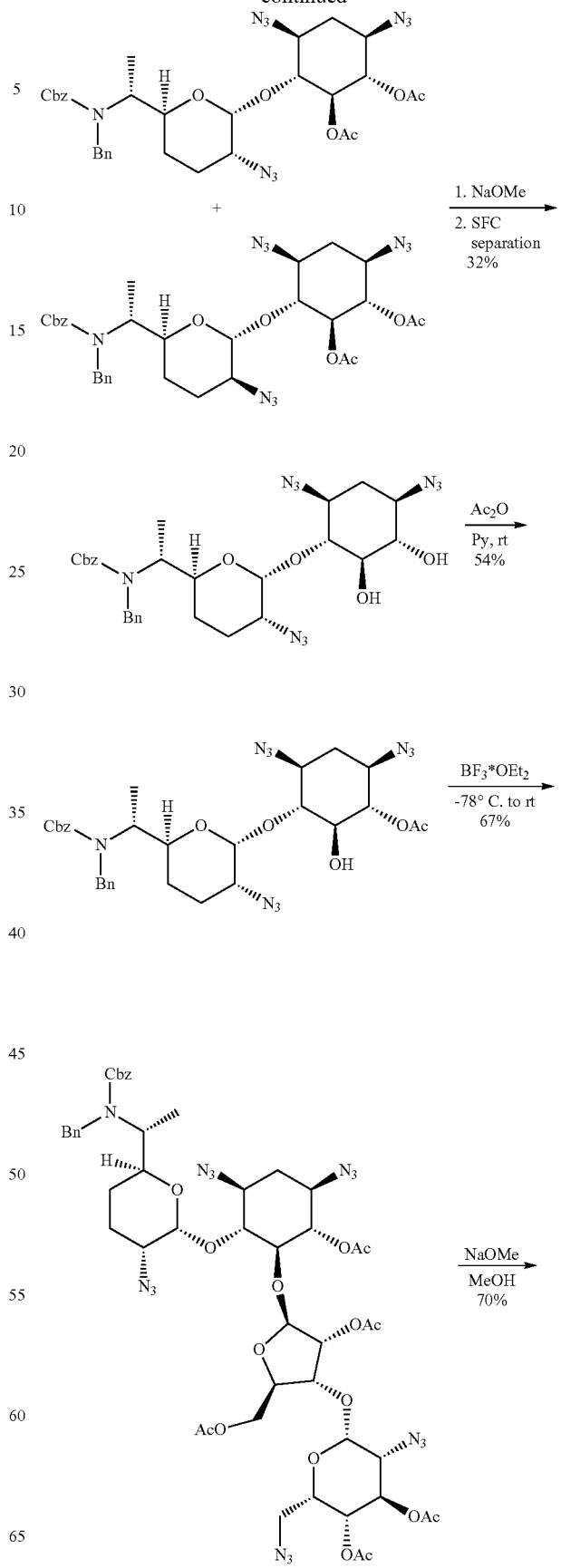

-continued

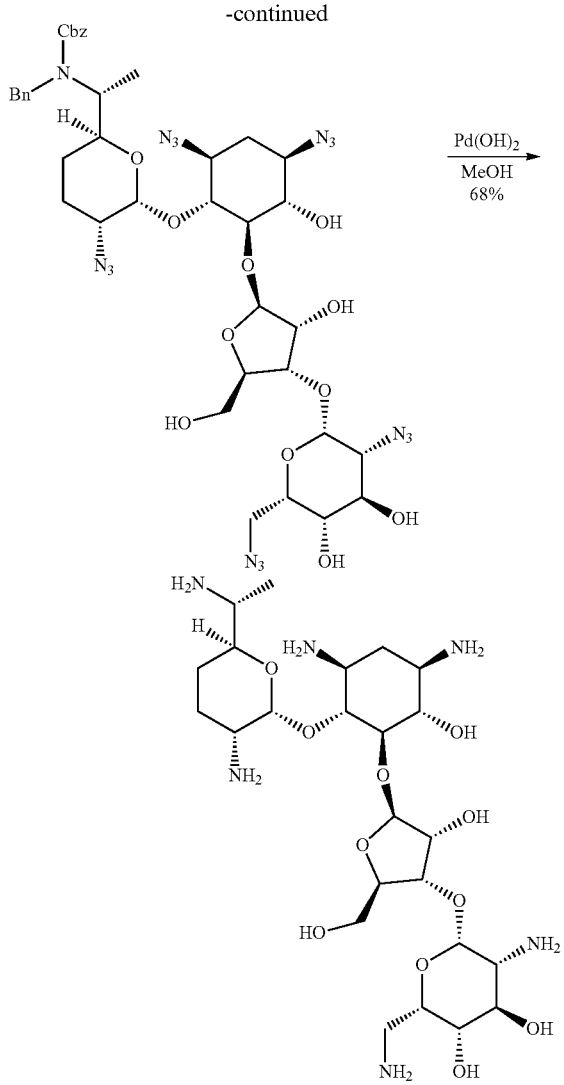

Step 1

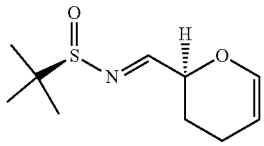

(NE)-N-[[(2S)-3,4-Dihydro-2H-pyran-2-yl]methylene]-2-methyl-propane-2-sulfinamide (R)-(+)-2-Methyl-2-propanesulfinamide (81.1 g, 669 mmol) and CuSO$_4$ (213.5 g, 1.34 mol) were mixed in DCM (700 mL). A solution of 2-formyl-3,4-dihydro-2H-pyran (75 g, 669 mmol) in DCM (100 mL) was added over 20 min. The mixture was stirred at room temperature for 72 h. The mixture was filtered through Celite and rinsed with DCM. The filtrate was evaporated under reduced pressure. The material was purified on silica gel (5×330 g, dry loading) by MPLC using 0-10% Et$_2$O in hexane to provide the title compound (28 g, 19%) as a solid. $^1$H NMR (400 MHz, CDCl$_3$) δ 8.07 (d, J=3.1 Hz, 1H), 6.40 (d, J=5.8 Hz, 1H), 4.76-4.68 (m, 1H), 4.68-4.63 (m, 1H), 2.13-1.83 (m, 4H), 1.18 (s, 9H).

Step 2

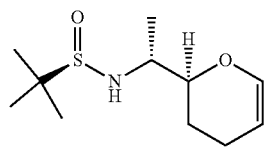

N-[(1R)-1-[(2S)-3,4-Dihydro-2H-pyran-2-yl]ethyl]-2-methyl-propane-2-sulfinamide

MeMgBr (3.0 M in Et$_2$O, 22.0 mL, 66.0 mmol) was added to a solution of (NE)-N-[[(2S)-3,4-dihydro-2H-pyran-2-yl]methylene]-2-methyl-propane-2-sulfinamide (7.10 g, 33.0 mmol) in dry DCM (110 mL) at −40° C. under N$_2$. After 2 h, the reaction was warmed to room temperature within 1 h. After another 14 h, sat. NH$_4$Cl (160 mL) was added dropwise (nota bene: gas evolution). Two phases were separated and the aqueous phase was extracted with DCM (3×20.0 mL). The combined organic layers were dried (Na$_2$SO$_4$), filtered and concentrated under reduced pressure. The residue was purified by silica gel chromatography (220 g cartridge) with EtOAc and hexanes (20-45%) to provide the title compound as a solid (6.00 g, 79%). $^1$H NMR (500 MHz, CDCl$_3$) δ 6.37 (d, J=6.1 Hz, 1H), 4.75-4.61 (m, 1H), 3.93 (ddd, J=11.2, 3.3, 2.0 Hz, 1H), 3.69 (d, J=6.1 Hz, 1H), 3.56 (pd, J=6.7, 3.5 Hz, 1H), 2.16-2.06 (m, 1H), 1.99 (dtt, J=17.1, 5.6, 1.6 Hz, 1H), 1.81 (ddd, J=13.3, 6.6, 1.8 Hz, 1H), 1.66 (dtd, J=13.3, 11.4, 5.8 Hz, 1H), 1.22 (s, 9H), 1.18 (d, J=6.7 Hz, 3H).

Step 3

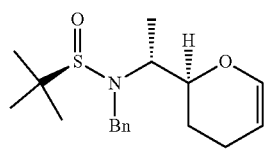 [SMILES: C[C@H]([C@@H]1CCC=CO1)N(Cc1ccccc1)[S@](=O)C(C)(C)C]

(R)—N-Benzyl-N-[(1R)-1-[(2S)-3,4-dihydro-2H-pyran-2-yl]ethyl]-2-methyl-propane-2-sulfinamide NaH (60%, 187 mg, 4.89 mmol) was added to a mixture of (R)—N-[(1R)-1-[(2S)-3,4-dihydro-2H-pyran-2-yl]ethyl]-2-methyl-propane-2-sulfinamide (1.03 g, 4.44 mmol) and BnBr (0.79 mL, 6.67 mmol) in DMF (60 mL) at 0° C. The mixture was stirred at room temperature for 1 h, then brine (250 mL) was added at 0° C. The aqueous layer was extracted with Et$_2$O (3×80 mL). The combined organic layer was dried over MgSO$_4$ and concentrated under reduced pressure. The material was purified on silica gel (40 g, dry loading) by MPLC using hexane to 60% EtOAc in hexane to provide the title compound (1.2 g, 84%) as an oil. $^1$H NMR (400 MHz, cdcl3) δ 7.37 (d, J=7.5 Hz, 2H), 7.32 (t, J=7.4 Hz, 2H), 7.26 (d, J=3.8 Hz, 1H), 6.32 (d, J=6.2 Hz, 1H), 4.64 (s, 1H), 4.39 (d, J=15.3 Hz, 1H), 4.14 (d, J=15.2 Hz, 1H), 3.66-3.57 (m, 1H), 3.32-3.20 (m, 1H), 1.98-1.80 (m, 3H), 1.54-1.43 (m, 1H), 1.37 (d, J=6.8 Hz, 3H), 1.19 (s, 9H).

Step 4

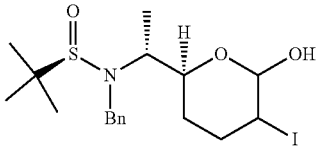 [SMILES: C[C@H]([C@@H]1CCC(I)C(O)O1)N(Cc1ccccc1)[S@](=O)C(C)(C)C]

(R)—N-Benzyl-N-[(1R)-1-[(2S)-6-hydroxy-5-iodo-tetrahydropyran-2-yl]ethyl]-2-methyl-propane-2-sulfinamide I$_2$ (947 mg, 3.73 mmol) was added portionwise to a suspension of (R)—N-benzyl-N-[(1R)-1-[(2S)-3,4-dihydro-2H-pyran-2-yl]ethyl]-2-methyl-propane-2-sulfinamide (1.2 g, 3.73 mmol) and NaHCO$_3$ (941 mg, 11.2 mmol) in ACN (50 mL) and H$_2$O (50 mL) at 0° C. The mixture was stirred at room temperature for 1 h, then a saturated aqueous solution of Na$_2$S$_2$O$_3$ (10 mL) was added. The aqueous layer was extracted with EtOAc (3×150 mL). The combined organic layer was washed with brine, dried over MgSO$_4$, filtered and concentrated under reduced pressure to provide the title compound (1.6 g, 92%) as a solid. M+H$^+$: 466.1.

Step 5

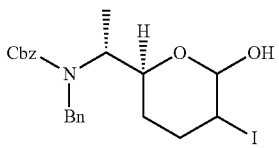 [SMILES: C[C@H]([C@@H]1CCC(I)C(O)O1)N(Cc1ccccc1)C(=O)OCc1ccccc1]

Benzyl N-benzyl-N-[(1R)-1-[(2S)-6-hydroxy-5-iodo-tetrahydropyran-2-yl]ethyl]carbamate 1N HCl (6.45 mL, 6.45 mmol) was added to a mixture of (R)—N-benzyl-N-[(1R)-1-[(2S)-6-hydroxy-5-iodo-tetrahydropyran-2-yl]ethyl]-2-methyl-propane-2-sulfinamide (1.2 g, 2.58 mmol) in dioxane (40 mL). The mixture was stirred at room temperature for 20 min, then Na$_2$CO$_3$ (2.19 g, 20.6 mmol) was added. After 20 min, CbzCl (0.51 mL, 3.61 mmol) was added dropwise. The mixture was stirred at room temperature for 2 h. Water (200 mL) was added. The separated aqueous layer was extracted with EtOAc (3×150 mL). The combined organic layer was washed with brine, dried over MgSO$_4$ and concentrated under reduced pressure. The material was purified on silical gel (80 g, dry loading) by MPLC using hexane to 80% EtOAc to provide the title compound (1.1 g, 86%) as a solid. M+H$^+$: 496.0.

Step 6

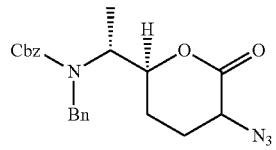 [SMILES: C[C@H]([C@@H]1CCC(N=[N+]=[N-])C(=O)O1)N(Cc1ccccc1)C(=O)OCc1ccccc1]

Benzyl N-[(1R)-1-[(2S)-5-azido-6-oxo-tetrahydro-pyran-2-yl]ethyl]-N-benzyl-carbamate Dess-Martin Periodinane (1.88 g, 4.44 mmol) was added to a solution of benzyl N-benzyl-N-[(1R)-1-[(2S)-6-hydroxy-5-iodo-tetrahydropyran-2-yl]ethyl]carbamate (1.10 g, 2.22 mmol) in DCM (100 mL) at 0° C. The mixture was stirred at room temperature for 5 h. Water (100 mL) was added following by a saturated aqueous solution of Na$_2$S$_2$O$_3$. The separated aqueous layer was extract with DCM (2×50 mL). The combined organic layer were washed with saturated aqueous NaHCO$_3$ (2×100 mL), brine (100 mL), dried over MgSO$_4$ and concentrated under reduced pressure. The residue was taken in anhydrous DMF (75 mL) and NaN$_3$ (217 mg, 3.33 mmol) was added. The mixture was stirred at room temperature for 15 min, then brine (300 mL) was added. The aqueous layer was extracted with Et$_2$O (3×100 mL). The combined organic layers were dried over MgSO$_4$ and concentrated under reduced pressure. The material was purified on silica gel (40 g, dry loading) by MPLC using hexane to EtOAc to provide the title compound (800 mg, 88%) as an oil. M+H$^+$: 409.3.

Step 7

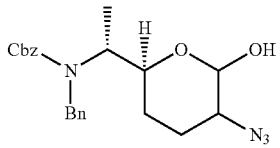

Benzyl N-[(1R)-1-[(2S)-5-azido-6-hydroxy-tetrahydropyran-2-yl]ethyl]-N-benzyl-carbamate DIBAL-H (1 M in toluene, 11.8 mL, 11.8 mmol) was added dropwise to a solution of benzyl N-[(1R)-1-[(2S)-5-azido-6-oxo-tetrahydropyran-2-yl]ethyl]-N-benzyl-carbamate (800 mg, 1.96 mmol) in DCM (60 mL) at −78° C. After 1 h at −78° C., EtOH (0.5 mL) was added dropwise. The mixture was poured into a saturated aqueous solution of Rochelle's salt (300 mL). The mixture was vigorously stirred for 1 h. The separated aqueous layer was extracted with DCM (2×75 mL). The combined organic layer was washed with brine, dried over MgSO$_4$ and concentrated under reduced pressure. The residue was purified on silica gel (40 g, dry loading) by MPLC using hexane to 60% EtOAc in hexane to provide the title compound (363 mg, 41%) as an oil. M+H$^+$: 411.2.

Step 8

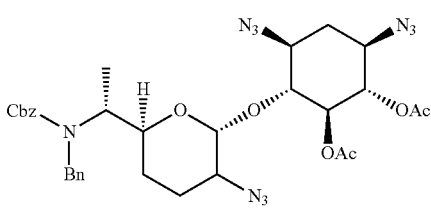

[(1S,2S,3R,4S,6R)-2-Acetoxy-4,6-diazido-3-[(2R,6S)-3-azido-6-[(1R)-1-[benzyl(benzyloxycarbonyl)amino]ethyl]tetrahydropyran-2-yl]oxy-cyclohexyl] acetate CCl$_3$CN (0.44 mL, 4.39 mol) was added dropwise to a suspension of benzyl N-[(1R)-1-[(2S)-5-azido-6-hydroxy-tetrahydropyran-2-yl]ethyl]-N-benzyl-carbamate (360 mg, 0.88 mmol) and K$_2$CO$_3$ (364 mg, 2.63 mmol) in dry DCM (10 mL) at ambient temperature under N$_2$. The mixture was stirred at room temperature for 8 h, then filtered on celite and rinsed with DCM. The filtrate was concentrated under reduced pressure. The residue was taken up in DCM (10 mL) and [(1S,2S,3R,4S,6R)-2-acetoxy-4,6-diazido-3-hydroxy-cyclohexyl]acetate (654 mg, 2.19 mmol) was added. The mixture was cooled to −78° C., then BF$_3$·OEt$_2$ (0.43 mL, 3.51 mmol) was added dropwise. The mixture was stirred at room temperature for 5 h, then a saturated aqueous solution of NaHCO$_3$ (50 mL) was added. The separated aqueous layer was extracted with DCM (2×30 mL). The combined organic layer was washed with brine, dried over Na$_2$SO$_4$ and concentrated under reduced pressure. The residue was purified on C18 silica (120 g Biotage) using 45% B in A to 100% B (B=ACN 0.1% HCOOH, A=0.1% HCOOH). The mixture of diastereoisomers was used for the next step without further purification. M+H$^+$: 691.3.

Step 9

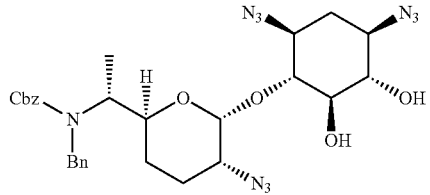 [SMILES: C[C@H]([C@@H]1CC[C@@H](N=[N+]=[N-])[C@@H](O[C@H]2[C@H](O)[C@@H](O)[C@H](N=[N+]=[N-])C[C@@H]2N=[N+]=[N-])O1)N(Cc1ccccc1)C(=O)OCc1ccccc1]

Benzyl N-[(1R)-1-[(2S,5S,6R)-5-azido-6-[(1R,2R,3S,4R,6S)-4,6-diazido-2,3-dihydroxy-cyclohexoxy]tetrahydropyran-2-yl]ethyl]-N-benzyl-carbamate NaOMe (4.62 M, 0.22 mL, 1.03 mmol) was added dropwise to a solution of [(1S,2S,3R,4S,6R)-2-acetoxy-4,6-diazido-3-[(2R,3S,6S)-3-azido-6-(benzyloxycarbonylaminomethyl)tetrahydropyran-2-yl]oxy-cyclohexyl] acetate (118 mg, 0.171 mmol) in MeOH (8 mL) at room temperature. After 60 min, AcOH (0.08 mL, 1.37 mmol) was added to the reaction and the mixture was concentrated under reduced pressure. The material was purified by chiral SFC to yield 55 mg, 53%. M+H$^+$: 607.4.

Step 10

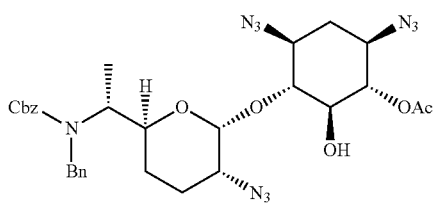

[(1S,2S,3R,4S,6R)-4,6-Diazido-3-[(2R,3R,6S)-3-azido-6-[(1R)-1-[benzyl(benzyloxycarbonyl)amino]ethyl]tetrahydropyran-2-yl]oxy-2-hydroxy-cyclohexyl] acetate Ac$_2$O (0.02 mL, 0.16 mmol) was added to a solution of N-[(1R)-1-[(2S,5R,6R)-5-azido-6-[(1R,2R,3S,4R,6S)-4,6-diazido-2,3-dihydroxy-cyclohexoxy]tetrahydropyran-2-yl]ethyl]-N-benzyl-carbamate (55 mg, 0.09 mmol) and pyridine (0.05 mL, 0.54 mmol) in dry DCM (5 mL) at room temperature. After 22 h, MeOH (0.5 mL) was added and the volatiles were removed under reduced pressure. The material was purified by prep-HPLC using ACN and AmFor (pH 4) to provide the title compound (32 mg, 54%) as a solid. M+H$^+$: 649.3.

Step 11

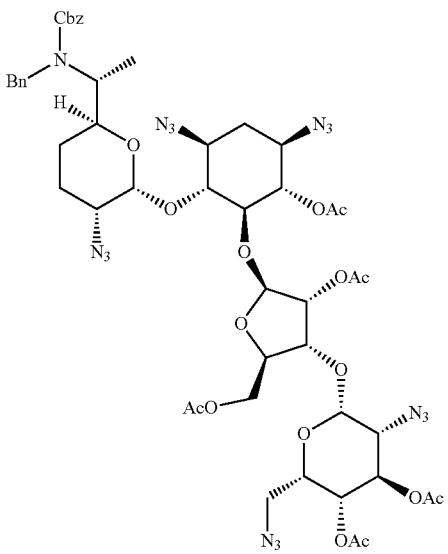 [SMILES: CC(=O)OC[C@H]1O[C@@H](O[C@@H]2[C@@H](OC(C)=O)[C@H](N=[N+]=[N-])C[C@H](N=[N+]=[N-])[C@H]2O[C@H]2O[C@H]([C@@H](C)N(Cc3ccccc3)C(=O)OCc3ccccc3)CC[C@H]2N=[N+]=[N-])[C@H](OC(C)=O)[C@@H]1O[C@H]1O[C@@H](CN=[N+]=[N-])[C@@H](OC(C)=O)[C@H](OC(C)=O)[C@H]1N=[N+]=[N-]]

(2S,3R,4R,5R,6R)-6-(((2R,3R,4R,5S)-4-Acetoxy-5-(((1S,2S,3R,5S,6R)-2-acetoxy-3,5-diazido-6-(((2S,3S,6R)-3-azido-6-((S)-1-(benzyl((benzyloxy)carbonyl)amino)ethyl)tetrahydro-2H-pyran-2-yl)oxy)cyclohexyl)oxy)-2-(acetoxymethyl)tetrahydrofuran-3-yl)oxy)-5-azido-2-(azidomethyl)tetrahydro-2H-pyran-3,4-diyl diacetate CCl$_3$CN (0.07 mL, 0.67 mol) was added dropwise to a mixture of [(2R,3R,4R)-4-acetoxy-3-[(2R,3R,4R,5R,6S)-4, 5-diacetoxy-3-azido-6-(azidomethyl)tetrahydropyran-2-yl]oxy-5-hydroxy-tetrahydrofuran-2-yl]methyl acetate (71 mg, 0.13 mmol) and K$_2$CO$_3$ (56 mg, 0.40 mmol) in dry DCM (8 mL) at room temperature under N$_2$. The mixture was stirred at room temperature for 18 h, then filtered with a filter syringe and rinsed with DCM. The filtrate was concentrated under reduced pressure.

[(1S,2S,3R,4S,6R)-4,6-diazido-3-[(2R,3R,6S)-3-azido-6-[(1R)-1-[benzyl(benzyloxycarbonyl)amino]ethyl]tetrahydropyran-2-yl]oxy-2-hydroxy-cyclohexyl] acetate (29 mg, 0.045 mmol) was dissolved in DCM (8 mL) and added to the previous reaction mixture. 4 Å molecular sieves were added and the mixture was cooled to −78° C., then BF$_3$·OEt$_2$ (0.03 mL, 0.22 mmol) was added dropwise. The mixture was stirred at room temperature for 5 h, then a saturated aqueous solution of NaHCO$_3$ (15 mL) was added. The separated aqueous layer was extracted with DCM (2×20 mL). The combined organic layer was washed with brine, dried over Na$_2$SO$_4$ and concentrated under reduced pressure. The residue was purified on C18 silica (120 g Biotage) using 50% B in A to 100% B (B=ACN 0.1% HCOOH, A=0.1% HCOOH) to provide the title compound (35 mg, 67%) as a solid. M+H$^+$: 1161.7.

Step 12

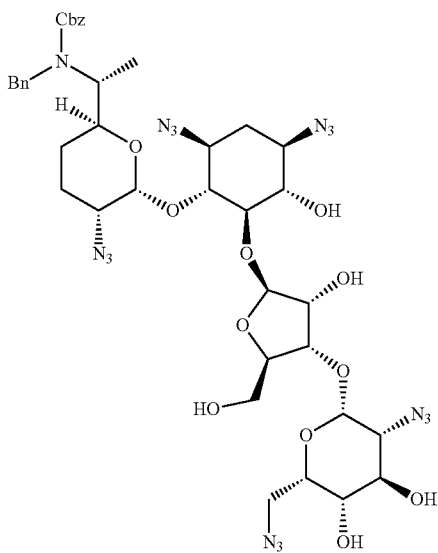 [SMILES: C[C@H]([C@@H]1CC[C@@H](N=[N+]=[N-])[C@@H](O[C@H]2[C@H](O[C@@H]3O[C@H](CO)[C@@H](O[C@H]4O[C@@H](CN=[N+]=[N-])[C@@H](O)[C@H](O)[C@H]4N=[N+]=[N-])[C@H]3O)[C@@H](O)[C@H](N=[N+]=[N-])C[C@@H]2N=[N+]=[N-])O1)N(Cc1ccccc1)C(=O)OCc1ccccc1]

Benzyl ((R)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H-pyran-2-yl)ethyl)(benzyl)carbamate NaOMe (4.62 M, 0.05 mL, 0.24 mmol) was added dropwise to a solution of (2S,3R,4R,5R,6R)-6-(((2R,3R,4R,5S)-4-acetoxy-5-(((1S,2S,3R,5S,6R)-2-acetoxy-3,5-diazido-6-(((2S,3S,6R)-3-azido-6-((S)-1-(benzyl((benzyloxy)carbonyl)amino)ethyl)tetrahydro-2H-pyran-2-yl)oxy)cyclohexyl)oxy)-2-(acetoxymethyl)tetrahydrofuran-3-yl)oxy)-5-azido-2-(azidomethyl)tetrahydro-2H-pyran-3,4-diyl diacetate (35 mg, 0.03 mmol) in MeOH (5 mL) at room temperature. After 4 h, AcOH (0.02 mL, 0.271 mmol) was added to the reaction and the mixture was concentrated under reduced pressure. The residue was purified by prep-HPLC using ACN and AmFor pH 4 to provide the title compound (20 mg, 70%) as a solid. M+H$^+$: 951.3.

Step 13

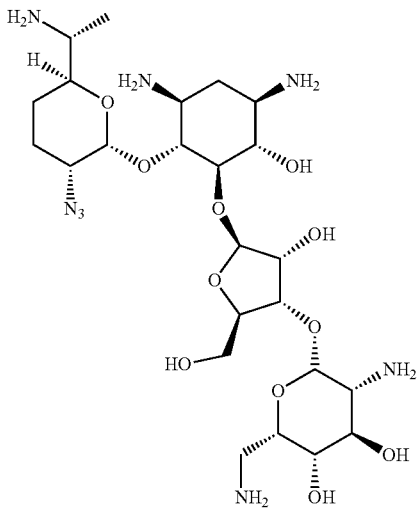

(2S,3S,4R,5R,6R)-5-Amino-2-(aminomethyl)-6-(((2R,3S,4R,5S)-5-(((1R,2R,3S,5R,6S)-3,5-diamino-2-(((2R,3R,6S)-3-amino-6-((R)-1-aminoethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol A mixture of benzyl ((R)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H-pyran-2-yl)ethyl)(benzyl)carbamate (20 mg, 0.02 mmol) and Pd(OH)$_2$ (20% wt, 10 mg, 0.02 mmol) in MeOH (8 mL) was hydrogenated for 18 h at room temperature. The mixture was degassed with N$_2$ for 5 min, then filtered on 0.40 μM syringe filter. The solvent was removed under reduced pressure to provide the title compound (8.5 mg, 68%) as a solid. M+H$^+$: 597.3 $^1$H NMR (500 MHz, MeOD) δ 5.30 (d, J=3.4 Hz, 1H), 5.23 (d, J=2.7 Hz, 1H), 4.88 (d, J=1.7 Hz, 1H), 4.32 (dd, J=6.0, 5.1 Hz, 1H), 4.14-4.11 (m, 1H), 4.03 (dt, J=6.4, 3.8 Hz, 1H), 3.90-3.80 (m, 3H), 3.78-3.70 (m, 2H), 3.66 (dd, J=12.1, 4.3 Hz, 1H), 3.50-3.45 (m, 1H), 3.45-3.43 (m, 1H), 3.35 (t, J=9.3 Hz, 1H), 3.11 (t, J=9.5 Hz, 1H), 3.00 (dd, J=13.2, 8.3 Hz, 1H), 2.97-2.90 (m, 2H), 2.87-2.74 (m, 3H), 2.59 (ddd, J=12.1, 9.8, 4.1 Hz, 1H), 1.92 (dt, J=12.9, 4.1 Hz, 1H), 1.74-1.63 (m, 3H), 1.48-1.38 (m, 1H), 1.09 (d, J=6.2 Hz, 3H).

Example 4
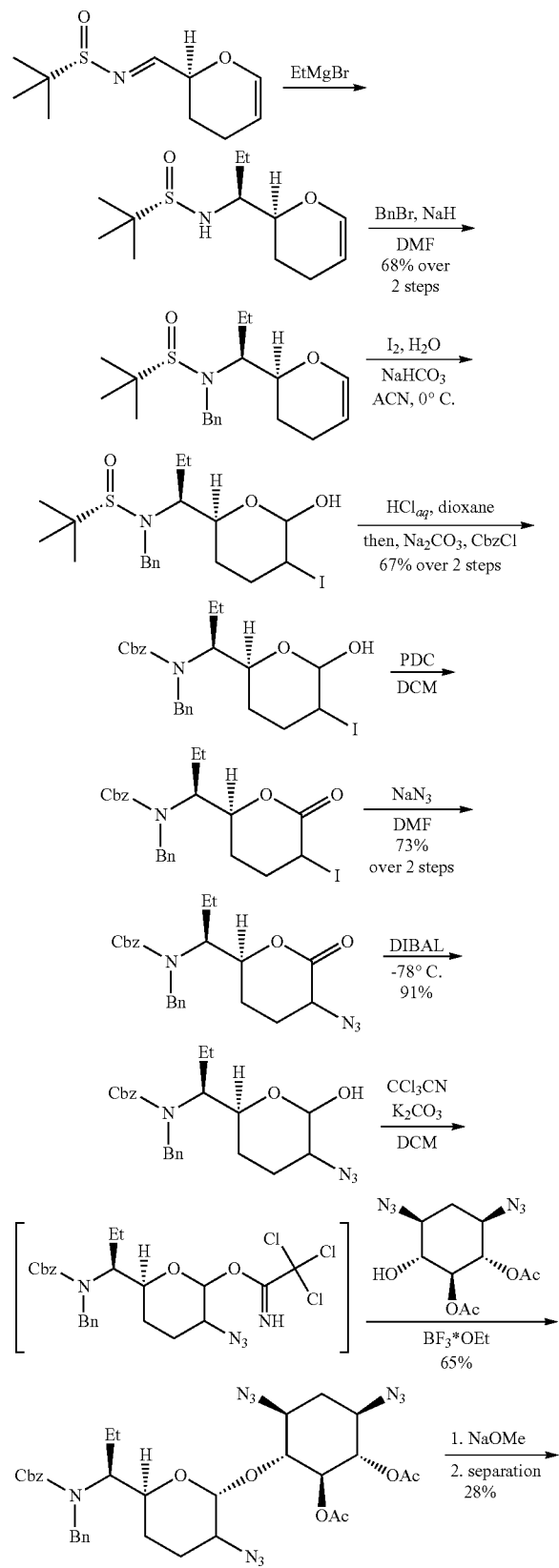
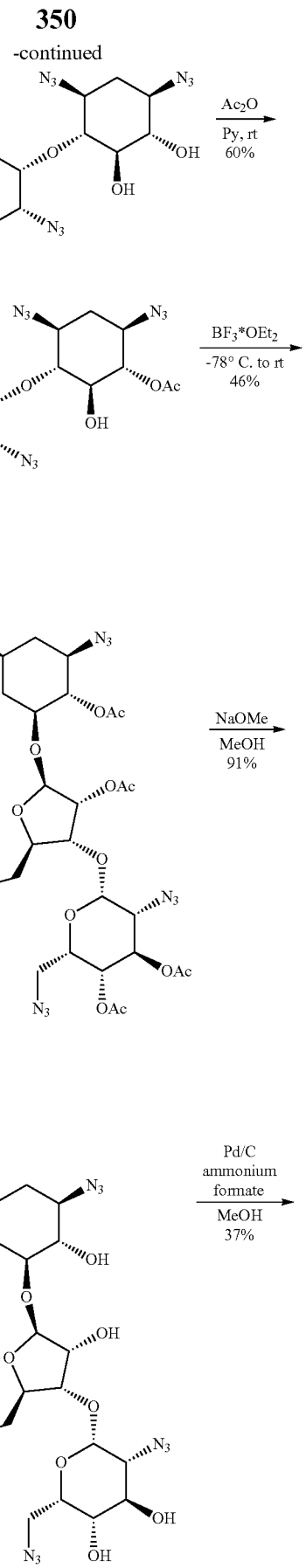

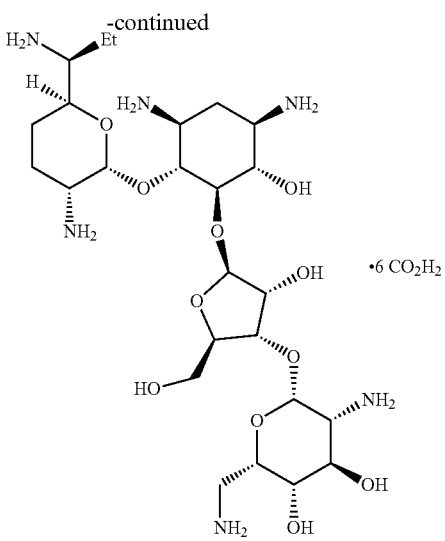

·6 CO₂H₂

Step 1

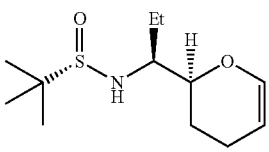 [SMILES: CC[C@H](N[S@@](=O)C(C)(C)C)[C@@H]1CCC=CO1]

(S)—N-[(1S)-1-[(2S)-3,4-Dihydro-2H-pyran-2-yl]propyl]-2-methyl-propane-2-sulfinamide EtMgBr (3.0 M in Et₂O, 9.29 mL, 27.9 mmol) was added to a solution of (NE,S)—N-[[(2S)-3,4-dihydro-2H-pyran-2-yl]methylene]-2-methyl-propane-2-sulfinamide (3.00 g, 13.9 mmol) in dry THF (100.0 mL) at −78° C. under N₂. After 1 h, the reaction was stirred at −40° C. for 1 h and then warmed to room temperature within 1 h. After 1 h, the reaction was cooled to 0° C. and sat. NH₄Cl (100.0 mL) was added dropwise (nota bene: gas evolution). THF was evaporated under reduced pressure and then the mixture was extracted with EtOAc (3×100.0 mL). The combined organic layers were dried (Na₂SO₄), filtered and concentrated under reduced pressure to provide the title compound as a liquid. The crude was clean and used in the next step without further purification. LCMS m/z ES⁺ [M+Na]⁺: 268.20, LCMS (A05) retention time=1.65 and 1.70 m.

Step 2

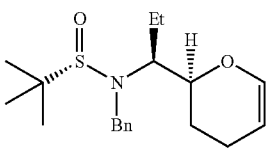 [SMILES: CC[C@@H]([C@@H]1CCC=CO1)N(Cc1ccccc1)[S@@](=O)C(C)(C)C]

(S)—N-benzyl-N—((S)-1-((S)-3,4-dihydro-2H-pyran-2-yl)propyl)-2-methylpropane-2-sulfinamide A mixture of (S)—N-[(1S)-1-[(2S)-3,4-Dihydro-2H-pyran-2-yl]propyl]-2-methyl-propane-2-sulfinamide (2.97 g, 12.1 mmol), bromomethylbenzene (2.59 mL, 21.8 mmol) in DMF (65 mL) was stirred at 0° C. NaH (0.581 g, 14.5 mmol) was then added to the reaction mixture portionwise. The mixture was allowed to stir at room temperature for 48 h. The reaction was quenched with water (200 mL) and the mixture was extract with EtOAc (3×100 mL). The organic layers were combined, washed with water and dried over sodium sulfate and then concentrated under reduced pressure. The residue was purified on silica gel (120 g) using hexane and ethyl acetate (70/30) as eluent to give the title product (2.74 g, 68%) as an oil. LCMS m/z ES⁺ [M+Na]⁺: 358.14, LCMS (B05) retention time=2.41 m.

Step 3

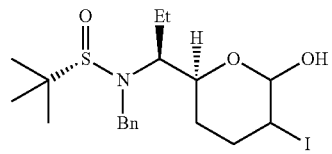 [SMILES: CC[C@@H]([C@@H]1CCC(I)C(O)O1)N(Cc1ccccc1)[S@@](=O)C(C)(C)C]

(S)—N-benzyl-N-((1S)-1-((2S)-6-hydroxy-5-iodo-tetrahydro-2H-pyran-2-yl)propyl)-2-methylpropane-2-sulfinamide Iodine (2.07 g, 8.17 mmol) was added portionwise to a suspension of (S)—N-benzyl-N—((S)-1-((S)-3,4-dihydro-2H-pyran-2-yl)propyl)-2-methylpropane-2-sulfinamide (2.74 g, 8.17 mmol) and NaHCO₃ (2.06 g, 24.5 mmol) in ACN (42.0 mL) and H₂O (42.0 mL) at 0° C. The mixture was stirred at 0° C. for 15 min. Then, the mixture was stirred at room temperature for 15 min. After completion, a saturated aqueous solution of Na₂S₂O₃ (200 mL) was added. The aqueous layer was extracted with EtOAc (3×100 mL). The combined organic layer was dried over Na₂SO₄, filtered and concentrated under reduced pressure to provide the title compound (3.92 g, 100%) as an oil. The crude was used in the next step without further purification. LCMS m/z ES⁺ [M+Na]⁺: 502.04, LCMS (B05) retention time=2.51 m.

Step 4

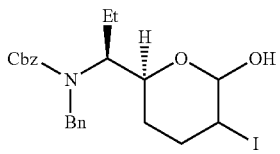 [SMILES: CC[C@@H]([C@@H]1CCC(I)C(O)O1)N(Cc1ccccc1)C(=O)OCc1ccccc1]

Benzyl benzyl((1S)-1-((2S)-6-hydroxy-5-iodotetra-hydro-2H-pyran-2-yl)propyl)carbamate Aqueous HCl (1.0 M, 49.3 mL, 49.3 mmol) was dropwise added to a solution of (S)—N-benzyl-N-((1S)-1-((2S)-6-hydroxy-5-iodotetrahydro-2H-pyran-2-yl)propyl)-2-methylpropane-2-sulfinamide (3.92 g, 8.18 mmol) in dioxane (100.0 mL) with vigorous stirring. After 1 h, solid Na₂CO₃ (6.93 g, 65.4 mmol) was added. After another 10 min, CbzCl (1.97 mL, 13.8 mmol) was added dropwise. After another 30-45 min, dioxane was evaporated and the residue was partitioned in between EtOAc (150.0 mL) and H₂O (150.0 mL). The organic phase was dried over Na₂SO₄, filtered and concentrated under reduced pressure. The crude was purified by silica gel chromatography (120 g cartridge) using hexanes and ethyl acetate (0-30%) as eluent to give the title product (diastereomers, 2.80 g, 67%) as an oil. LCMS m/z ES⁺ [M+Na]⁺: 532.90, LCMS (B05) retention time=2.41, 2.50, and 2.74 m.

Step 5

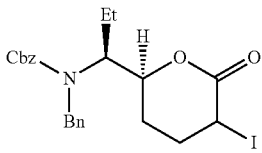 [SMILES: CC[C@@H]([C@@H]1CCC(I)C(=O)O1)N(Cc1ccccc1)C(=O)OCc1ccccc1]

Benzyl benzyl((1S)-1-((2S)-5-iodo-6-oxotetrahydro-2H-pyran-2-yl)propyl)carbamate Benzyl benzyl((1S)-1-((2S)-6-hydroxy-5-iodotetrahydro-2H-pyran-2-yl)propyl)carbamate (2.79 g, 5.48 mmol) was dissolved in DCM (120.0 mL). 4 Å molecular sieves (5.0 g) were suspended in the mixture, and PDC (6.18 g, 16.4 mmol) was added. Stirring was continued over 24 hours at room temperature, then filtered through a silica pad using ethyl acetate as eluent. The filtrate was concentrated in vacuo to afford the title compound as an oil. The crude was used in the next step without further purification. LCMS m/z: ES⁺ [M+Na]⁺: 530.95; (B05) retention time=2.41 m.

Step 6

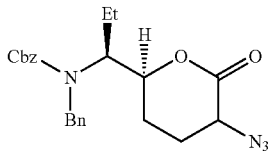 [SMILES: CC[C@@H]([C@@H]1CCC(N=[N+]=[N-])C(=O)O1)N(Cc1ccccc1)C(=O)OCc1ccccc1]

Benzyl ((1S)-1-((2S)-5-azido-6-oxotetrahydro-2H-pyran-2-yl)propyl)(benzyl)carbamate NaN₃ (0.413 mg, 6.36 mmol) was added to a solution of benzyl benzyl((1S)-1-((2S)-5-iodo-6-oxotetrahydro-2H-pyran-2-yl)propyl)carbamate (2.15 g, 4.24 mmol) in DMF (50.0 mL). The mixture was stirred for 2 hours at 0° C. Water (100.0 mL) was added and the mixture was extracted with EtOAc (3×50 mL). The organic layers were combined and then washed with water (5×100 mL). The organic layer was dried over Na₂SO₄, concentrated in vacuo and purified by silica gel chromatography (80 g cartridge) to afford the title compound as an oil (1.30 g, 73%). LCMS m/z: ES⁺ [M+Na]⁺: 445.96; (B05) retention time=2.16 m.

Step 7

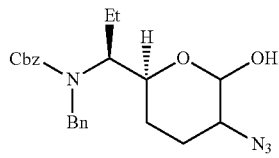 [SMILES: CC[C@@H]([C@@H]1CCC(N=[N+]=[N-])C(O)O1)N(Cc1ccccc1)C(=O)OCc1ccccc1]

Benzyl ((1S)-1-((2S)-5-azido-6-hydroxytetrahydro-2H-pyran-2-yl)propyl)(benzyl)carbamate DIBAL-H (1.00 M, 4.54 mL, 4.54 mmol) in DCM was added dropwise to a solution of benzyl ((1S)-1-((2S)-5-azido-6-oxotetrahydro-2H-pyran-2-yl)propyl)(benzyl)carbamate in DCM (75.0 mL) at −78° C. under N₂. After 1 h, acetone (1.00 mL) was added to the reaction mixture dropwise. After 5 min, sat. potassium sodium tartrate (100 mL) was added to the solution slowly, followed by the addition of water (100 mL). The mixture was allowed to warm to room temperature and vigorously stirred overnight in the presence of ethyl acetate. The organic layer was separated and the aqueous layer was extracted with ethyl acetate (3×100 mL). The combined organic layers were dried (Na₂SO₄), filtered and concentrated under reduced pressure to provide the title compound as an oil (diastereomers, 1.10 g, 91%). This mixture was used in the next step without further purification LCMS m/z: ES⁺ [M+Na]⁺: 446.93; (B05) retention time=2.31 m.

Step 8

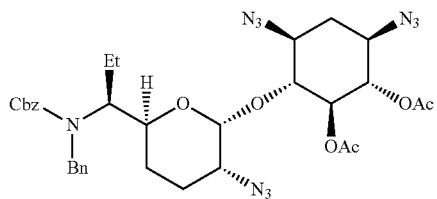 [SMILES: CC[C@@H]([C@@H]1CC[C@@H](N=[N+]=[N-])[C@@H](O[C@H]2[C@H](OC(C)=O)[C@@H](OC(C)=O)[C@H](N=[N+]=[N-])C[C@@H]2N=[N+]=[N-])O1)N(Cc1ccccc1)C(=O)OCc1ccccc1]

(1S,2S,3R,4S,6R)-4,6-diazido-3-(((2R,3R,6S)-3-azido-6-((S)-1-(benzyl((benzyloxy)carbonyl)amino)propyl)tetrahydro-2H-pyran-2-yl)oxy)cyclohexane-1,2-diyl diacetate CCl₃CN (0.877 mL, 8.75 mmol) was added dropwise to a suspension of benzyl ((1S)-1-((2S)-5-azido-6-hydroxytetrahydro-2H-pyran-2-yl)propyl)(benzyl)carbamate (0.734 g, 1.73 mmol) and K₂CO₃ (0.726 g, 5.25 mmol) in dry DCM (30.0 mL) at ambient temperature under N₂. After 12 h, the solution was filtered through Celite and the filtrate was concentrated by high-vacuum. To the crude was added [(1S,2S,3R,4S,6R)-2-acetoxy-4,6-diazido-3-hydroxy-cyclohexyl] acetate (0.418 g, 1.40 mmol) and ground 4 Å sieves (1.0 g) and the mixture was dissolved in dry DCM (30.0 mL). The suspension was stirred at ambient temperature for 25 min. The solution was cooled to 0° C. and BF₃·OEt₂ (0.864 mL, 7.00 mmol) was added dropwise with vigorous stirring. The solution was warmed to ambient temperature and stirred for another 3 hours. The reaction was quenched with sat. NaHCO$_3$ (50.0 mL). The mixture was successively extracted with DCM (3×50.0 mL) and the combined organic layer were dried (Na$_2$SO$_4$), filtered and concentrated under reduced pressure. The crude was purified by silica gel chromatography (40 g cartridge) with EtOAc and hexanes (0-30%) to produce the title compound as an oil (2 diastereomers, 0.64 g, 65%). LCMS m/z: [M+Na]$^+$: 727.13; (B05) retention time=2.61 m.

Step 9

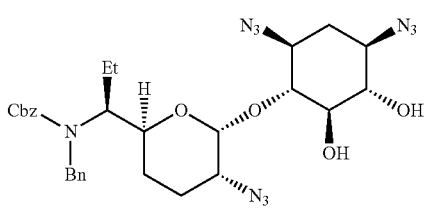 [SMILES: CC[C@@H]([C@@H]1CC[C@@H](N=[N+]=[N-])[C@@H](O[C@H]2[C@H](O)[C@@H](O)[C@H](N=[N+]=[N-])C[C@@H]2N=[N+]=[N-])O1)N(Cc1ccccc1)C(=O)OCc1ccccc1]

Benzyl N-[(1S)-1-[(2S,5R,6R)-5-azido-6-[(1R,2R,3S,4R,6S)-4,6-diazido-2,3-dihydroxy-cyclohexoxy]tetrahydropyran-2-yl]propyl]-N-benzyl-carbamate NaOMe (4.62 M, 737 µL, 3.41 mmol) was added dropwise to a solution of (1S,2S,3R,4S,6R)-4,6-diazido-3-(((2R,3R,6S)-3-azido-6-((S)-1-(benzyl((benzyloxy)carbonyl)amino)propyl)tetrahydro-2H-pyran-2-yl)oxy)cyclohexane-1,2-diyl diacetate (0.40 g, 0.568 mmol) in MeOH (35.0 mL) at room temperature. After 60 min, the reaction was neutralized with AcOH (260 µL, 4.54 mmol). Water (20.0 mL) was added and the mixture was extracted with DCM (3×30.0 mL). The organic layers were combined, dried over Na$_2$SO$_4$ and then concentrated under reduced pressure to provide a mixture of two diastereomers (0.280 g, 80%). ES$^+$ [M+Na]$^+$: 643.89; (B05) retention time=2.31 m. The desired isomer was separated on a Yamazen purification system using hexane and EtOAc to provide the desired diastereoisomer (100 mg, 28%) as a solid. ES$^+$ [M+Na]$^+$: 643.89.

Step 10

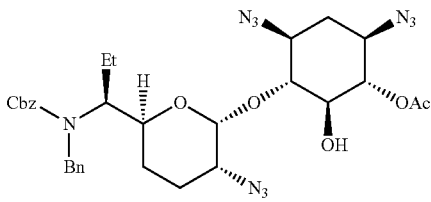 [SMILES: CC[C@@H]([C@@H]1CC[C@@H](N=[N+]=[N-])[C@@H](O[C@H]2[C@H](O)[C@@H](OC(C)=O)[C@H](N=[N+]=[N-])C[C@@H]2N=[N+]=[N-])O1)N(Cc1ccccc1)C(=O)OCc1ccccc1]

[(1S,2S,3R,4S,6R)-4,6-Diazido-3-[(2R,3R)-3-azido-6-[(1S)-1-[benzyl(benzyloxycarbonyl)amino]propyl]tetrahydropyran-2-yl]oxy-2-hydroxy-cyclohexyl] acetate Ac$_2$O (32.0 µL, 338 µmol) was added to a solution of benzyl N-[(1S)-1-[(2S, 5R,6R)-5-azido-6-[(1R,2R,3S,4R, 6S)-4,6-diazido-2,3-dihydroxy-cyclohexoxy]tetrahydropyran-2-yl]propyl]-N-benzyl-carbamate (70.0 mg, 113 µmol) and pyridine (54.7 µL, 677 µmol) in dry DCM (2.00 mL) at ambient temperature. After 18 h, all volatiles were removed under reduced pressure. The crude was purified by silica gel chromatography (25 g cartridge) with EtOAc and hexanes (5-40%) to produce the title compound as an oil (45.0 mg, 60%). LCMS m/z: ES$^+$ [M+Na]$^+$: 685.75; (B05), retention time=2.56 m.

Step 11

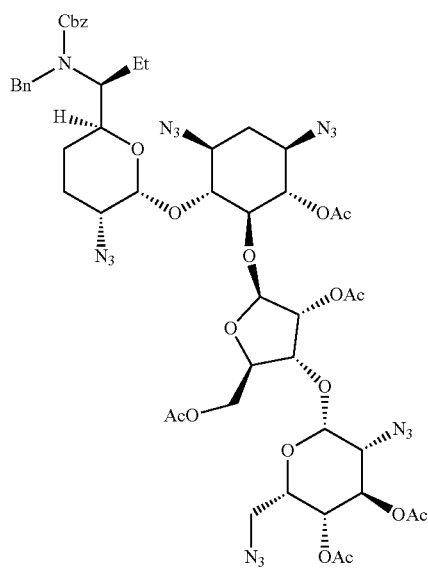 [SMILES: CC[C@@H]([C@@H]1CC[C@@H](N=[N+]=[N-])[C@@H](O[C@H]2[C@H](O[C@@H]3O[C@H](COC(C)=O)[C@@H](O[C@H]4O[C@@H](CN=[N+]=[N-])[C@@H](OC(C)=O)[C@H](OC(C)=O)[C@H]4N=[N+]=[N-])[C@H]3OC(C)=O)[C@@H](OC(C)=O)[C@H](N=[N+]=[N-])C[C@@H]2N=[N+]=[N-])O1)N(Cc1ccccc1)C(=O)OCc1ccccc1]

(2S,3R,4R,5R,6R)-6-(((2R,3R,4R,5S)-4-Acetoxy-5-(((1 S,2S,3R,5S,6R)-2-acetoxy-3,5-diazido-6-(((2S,3S,6R)-3-azido-6-((S)-1-(benzyl((benzyloxy)carbonyl)amino)ethyl)tetrahydro-2H-pyran-2-yl)oxy)cyclohexyl)oxy)-2-(acetoxymethyl)tetrahydrofuran-3-yl)oxy)-5-azido-2-(azidomethyl)tetrahydro-2H-pyran-3,4-diyl diacetate CCl$_3$CN (97.6 µL, 973 µmol) was added dropwise to a mixture of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (138 mg, 0.260 mmol) and K$_2$CO$_3$ (80.7 mg, 0.584 mmol) in dry DCM (8.00 mL) at room temperature under N$_2$. The mixture was stirred at room temperature for 16 h, then filtered through Celite and rinsed with DCM. The filtrate was concentrated under reduced pressure. The crude was dissolved in DCM (8.00 mL) and added to [(1S,2S,3R,4S,6R)-4,6-diazido-3-[(2R,3R,6S)-3-azido-6-[(1S)-1-[benzyl(benzyloxycarbonyl)amino]propyl]tetrahydropyran-2-yl]oxy-2-hydroxy-cyclohexyl] acetate (43.0 mg, 64.9 µmol). 4 Å molecular sieves (200 mg) were added and the mixture was cooled to −78° C., then BF$_3$·OEt$_2$ (40.0 μL, 324 μmol) was added dropwise. The mixture was stirred at room temperature for 5 h, then a saturated aqueous solution of NaHCO$_3$ (15.0 mL) was added. The separated aqueous layer was extracted with DCM (3×20.0 mL). The combined organic layer was washed with brine, dried over Na$_2$SO$_4$ and concentrated under reduced pressure. The residue was purified by silica gel chromatography (25 g) using hexane and ethyl acetate (0-30%) to provide the title compound (45.0 mg, 46%) as a an oil. LCMS m/z ES$^+$ [M+H]$^+$: 1175.12, LCMS (B05) retention time=2.44 m.

Step 12

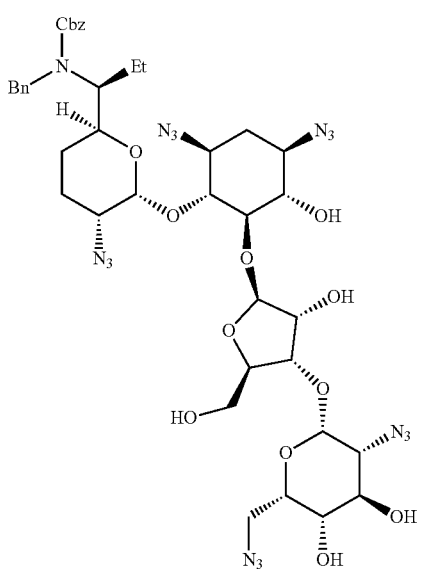 [SMILES: CC[C@@H]([C@@H]1CC[C@@H](N=[N+]=[N-])[C@@H](O[C@H]2[C@H](O[C@@H]3O[C@H](CO)[C@@H](O[C@H]4O[C@@H](CN=[N+]=[N-])[C@@H](O)[C@H](O)[C@H]4N=[N+]=[N-])[C@H]3O)[C@@H](O)[C@H](N=[N+]=[N-])C[C@@H]2N=[N+]=[N-])O1)N(Cc1ccccc1)C(=O)OCc1ccccc1]

NaOMe (25 wt %, 103 μL, 357 μmol) was added dropwise to a solution of the compound of step 11 above (35.0 mg, 298 μmol) in MeOH (5.0 mL) at ambient temperature. After 1 hour, the reaction mixture was neutralized by HOAc (~341 μL) and all volatiles were removed under reduced pressure. The crude was dissolved with EtOAc, filtered through Celite and the filtrate was concentrated under reduced pressure to produce benzyl ((S)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl) tetrahydrofuran-2-yl)oxy)-3-hydroxycyclohexyl)oxy) tetrahydro-2H-pyran-2-yl)propyl)(benzyl)carbamate as an oil (26.0 mg, 91%). LCMS m/z: ES$^+$ [M+Na]$^+$: 987.29, (B05) retention time=2.28 m.

Step 13

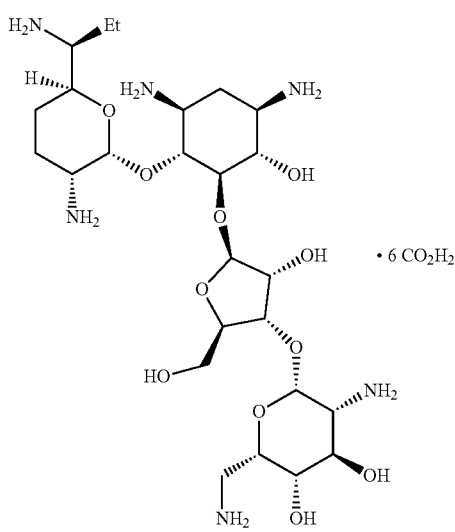 [SMILES: CC[C@H](N)[C@@H]1CC[C@@H](N)[C@@H](O[C@H]2[C@H](O[C@@H]3O[C@H](CO)[C@@H](O[C@H]4O[C@@H](CN)[C@@H](O)[C@H](O)[C@H]4N)[C@H]3O)[C@@H](O)[C@H](N)C[C@@H]2N)O1]

(2S,3S,4R,5R,6R)-5-Amino-2-(aminomethyl)-6-(((2R,3S,4R,5S)-5-(((1R,2R,3S,5R,6S)-3,5-diamino-2-(((2R,3R,6S)-3-amino-6-((S)-1-aminopropyl)tetrahydro-2H-pyran-2-yl)oxy)-6-hydroxycyclohexyl) oxy)-4-hydroxy-2-(hydroxymethyl)tetrahydrofuran-3-yl)oxy)tetrahydro-2H-pyran-3,4-diol hexaformate In a 2 neck flask equipped with a reflux condenser were added benzyl ((S)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl) tetrahydrofuran-2-yl)oxy)-3-hydroxycyclohexyl)oxy) tetrahydro-2H-pyran-2-yl)propyl)(benzyl)carbamate (26 mg, 0.033 mmol) and Pd/C (10% dry on carbon, 8.6 mg, 0.01 mmol) followed by anhydrous MeOH (4 mL). Nitrogen was bubbled for 5 min, then ammonium formate (15.3 mg, 0.24 mmol) was added. The mixture was heat at 63° C. for 30 min under N$_2$, then cooled to room temperature with an ice-bath. The mixture was filtered with a filter syringe and concentrated under reduced pressure. The material was purified by prep-HPLC using 5% B in A to 100% B (A: Amfor pH 4, B: ACN) on C18 Xbridge 30×150 mm to provide the title compound (8.9 mg, 37%) as a solid. M+H$^+$: 611.3. $^1$H NMR (500 MHz, MeOD) δ 8.51 (s, 6H), 5.74 (s, 1H), 5.36 (s, 1H), 5.26 (s, 1H), 4.48 (s, 1H), 4.42-4.24 (m, 3H), 4.13-4.09 (m, 2H), 3.96-3.76 (m, 2H), 3.76-3.61 (m, 3H), 3.42 (m, 5H), 3.13 (s, 3H), 2.31-2.25 (m, 1H), 2.13-1.92 (m, 3H), 1.89-1.50 (m, 4H), 1.05 (t, J=7.4 Hz, 3H).

Example 5

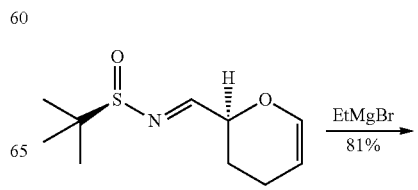

359
-continued
360
-continued
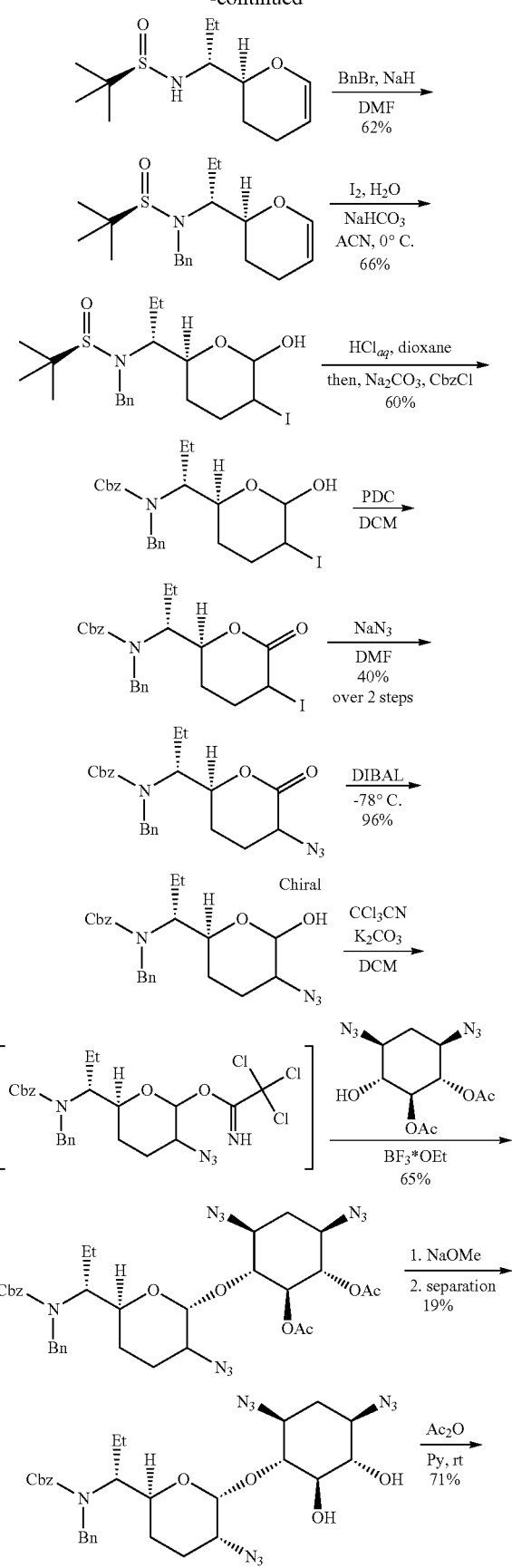
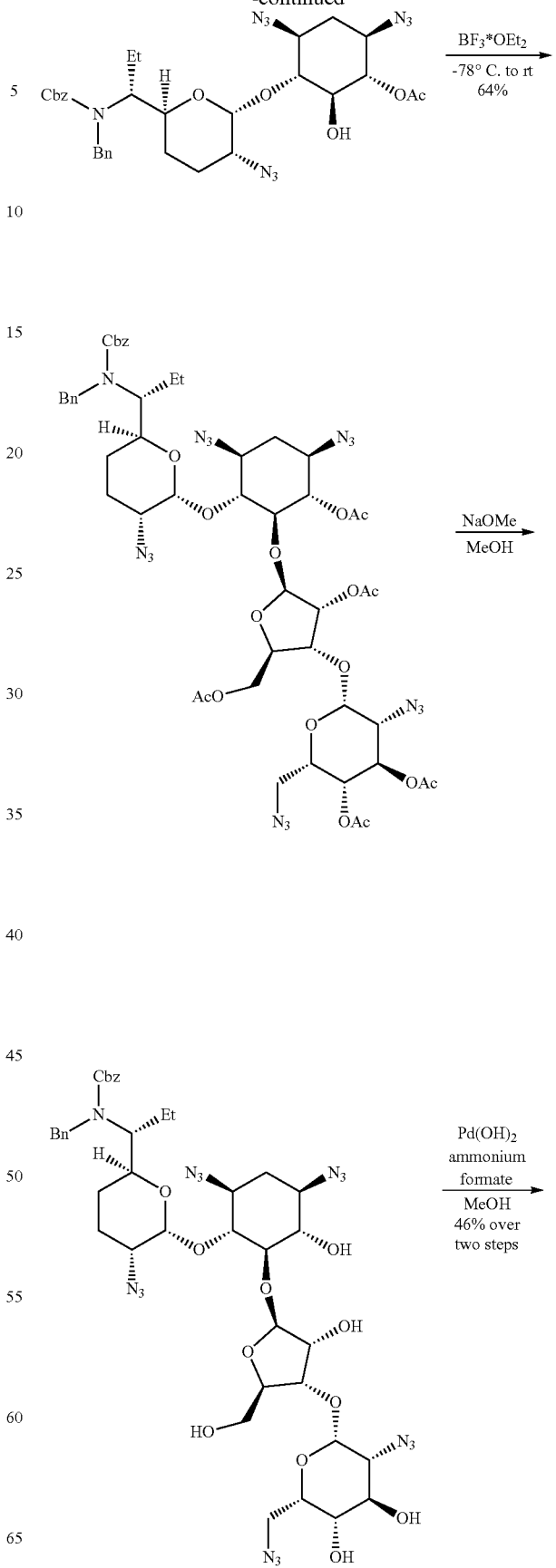

-continued

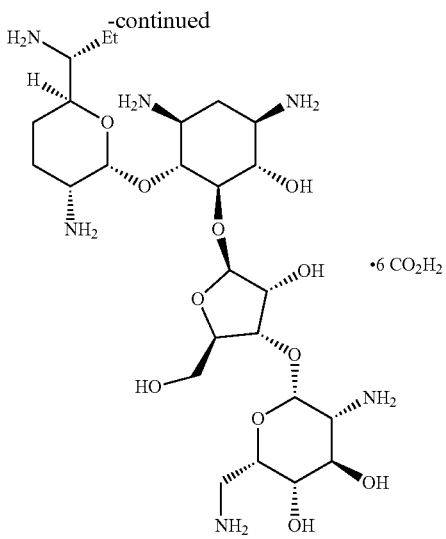

Step 1

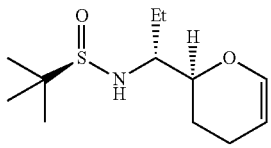 [SMILES: CC[C@@H](N[S@](=O)C(C)(C)C)[C@@H]1CCC=CO1]

(R)—N-[(1R)-1-[(2S)-3,4-Dihydro-2H-pyran-2-yl]propyl]-2-methyl-propane-2-sulfinamide EtMgBr (3.0 M in Et$_2$O, 9.29 mL, 27.9 mmol) was added to a solution of (NE)-N-[[(2S)-3,4-dihydro-2H-pyran-2-yl]methylene]-2-methyl-propane-2-sulfinamide (3.00 g, 13.9 mmol) in dry THF (75.0 mL) at −78° C. under N$_2$. After 1 h, the reaction was stirred at −40° C. for 1 h and then warmed to room temperature within 1 h. After 1 h, the reaction was cooled to 0° C. and sat. NH$_4$Cl (100.0 mL) was added dropwise (nota bene: gas evolution). THF was evaporated under reduced pressure and the resulting mixture was extracted with EtOAc (3×100.0 mL). The combined organic layers were dried (Na$_2$SO$_4$), filtered and concentrated under reduced pressure to provide the title compound as a liquid. The crude was clean and used in the next step without further purification. $^1$H NMR (500 MHz, CDCl$_3$) δ 6.35 (d, J=6.1 Hz, 1H), 4.72-4.54 (m, 1H), 4.03 (ddd, J=11.1, 3.3, 2.0 Hz, 1H), 3.64 (d, J=8.0 Hz, 1H), 3.29-3.14 (m, 1H), 2.19-2.02 (m, 1H), 2.01-1.90 (m, 1H), 1.85-1.47 (m, 4H), 1.23 (s, 9H), 0.95 (t, J=7.4 Hz, 3H). LCMS m/z ES$^+$ [M+Na]: 267.94, LCMS (A05) retention time=1.65 m.

Step 2

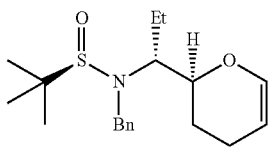 [SMILES: CC[C@H]([C@@H]1CCC=CO1)N(Cc1ccccc1)[S@](=O)C(C)(C)C]

(R)—N-benzyl-N—((R)-1-((S)-3,4-dihydro-2H-pyran-2-yl)propyl)-2-methylpropane-2-sulfinamide A mixture of (R)—N-[(1R)-1-[(2S)-3,4-Dihydro-2H-pyran-2-yl]propyl]-2-methyl-propane-2-sulfinamide (3.41 g, 13.9 mmol), bromomethylbenzene (4.28 g, 25.0 mmol) in DMF (50.0 mL) was stirred at 0° C. NaH (0.667 g, 16.7 mmol) was then added to the reaction mixture portionwise. The mixture was allowed to stir at room temperature for 48 h. The reaction was quenched with water (100 mL) and the mixture was extract with EtOAc (3×50 mL). The organic layers were combined, dried over sodium sulfate and concentrated under reduced pressure. The residue was purified on silica gel (120 g) using hexane and ethyl acetate (70/30) as eluent to give the title product (2.90 g, 62%) as a colorless oil. LCMS m/z ES$^+$ [M+H]$^+$: 335.94, LCMS (B05) retention time=2.12 m.

Step 3

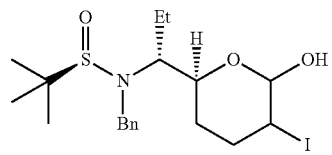 [SMILES: CC[C@H]([C@@H]1CCC(I)C(O)O1)N(Cc1ccccc1)[S@](=O)C(C)(C)C]

N-Benzyl-N-[(1R)-1-[(2S)-6-hydroxy-5-iodo-tetrahydropyran-2-yl]propyl]-2-methyl-propane-2-sulfinamide Iodine (2.33 g, 9.18 mmol) was added portionwise to a suspension of (R)—N-benzyl-N—((R)-1-((S)-3,4-dihydro-2H-pyran-2-yl)propyl)-2-methylpropane-2-sulfinamide (3.08 g, 9.18 mmol) and NaHCO$_3$ (2.31 g, 27.5 mmol) in ACN (53 mL) and H$_2$O (53 mL) at 0° C. The mixture was stirred at 0° C. for 15 min, then the mixture was stirred at room temperature for 15 min. After completion, a saturated aqueous solution of Na$_2$S$_2$O$_3$ (100 mL) was added. The aqueous layer was extracted with EtOAc (3×100 mL). The combined organic layer was dried over Na$_2$SO$_4$, filtered, concentrated under reduced pressure to provide the title compound (2.90 g, 66%) as a yellow solid. The crude was used in the next step without further purification. LCMS m/z ES$^+$ [M+Na]$^+$: 502.75, LCMS (B05) retention time=1.95 and 2.93 m.

Step 4

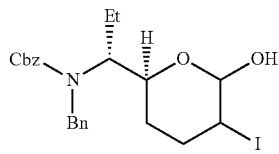 [SMILES: CC[C@H]([C@@H]1CCC(I)C(O)O1)N(Cc1ccccc1)C(=O)OCc1ccccc1]

Benzyl N-benzyl-N-[(1R)-1-[(2S)-6-hydroxy-5-iodo-tetrahydropyran-2-yl]propyl]carbamate Aqueous HCl (1.0 M, 55.3 mL, 55.3 mmol) was dropwise added to a solution of N-benzyl-N-[(1R)-1-[(2S)-6-hydroxy- 5-iodo-tetrahydropyran-2-yl]propyl]-2-methyl-propane-2-sulfinamide (4.40 g, 9.18 mmol) in dioxane (130.0 mL) with vigorous stirring. After 1 h, solid Na$_2$CO$_3$ (7.78 g, 73.4 mmol) was added. After another 10 min, CbzCl (2.21 mL, 15.5 mmol) was added dropwise. After another 30-45 min, dioxane was evaporated and the residue was partitioned in between EtOAc (100.0 mL) and H$_2$O (100.0 mL). The organic phase was dried over Na$_2$SO$_4$, filtered and concentrated under reduced pressure. The crude was purified by silica gel chromatography (120 g cartridge) using hexanes and ethyl acetate (0-30%) as eluent to give the title product (diastereomers, 2.80 g, 60%) as an oil. LCMS m/z ES$^+$ [M+Na]$^+$: 531.89, LCMS (B05) retention time=2.10 and 2.15 m.

Step 5

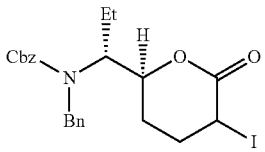 [SMILES: CC[C@H]([C@@H]1CCC(I)C(=O)O1)N(Cc1ccccc1)C(=O)OCc1ccccc1]

Benzyl N-benzyl-N-[(1R)-1-[(2S)-5-iodo-6-oxo-tetrahydropyran-2-yl]propyl]carbamate Benzyl N-benzyl-N-[(1R)-1-[(2S)-6-hydroxy-5-iodo-tetrahydropyran-2-yl]propyl]carbamate (2.80 g, 5.49 mmol) was dissolved in DCM (200.0 mL). 4 Å molecular sieves (2.0 g) were suspended in the mixture, and PDC (6.20 g, 16.4 mmol) was added. Stirring was continued over 24 hours at room temperature, then the reaction was filtered through a Silica pad using ethyl acetate as eluent. The filtrate was concentrated in vacuo to afford the title compound as an oil. The crude was used in the next step without further purification. LCMS m/z: ES$^+$ [M+H]$^+$: 507.94; (B05) retention time=2.12 m.

Step 6

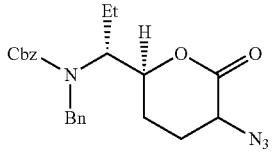

Benzyl N-[(1R)-1-[(2S)-5-azido-6-oxo-tetrahydropyran-2-yl]propyl]-N-benzyl-carbamate NaN$_3$ (633 mg, 9.47 mmol) was added to a solution of benzyl N-benzyl-N-[(1R)-1-[(2S)-5-iodo-6-oxo-tetrahydropyran-2-yl]propyl]carbamate (2.47 g, 4.87 mmol) in DMF (50.0 mL). The mixture was stirred for 2 hours at room temperature. Water (100.0 mL) was added and the mixture was extracted with EtOAc (3×50 mL). The organic layers were combined and then washed with water (5×100 mL). The organic layer was dried over Na$_2$SO$_4$, concentrated in vacuo and purified by silica gel chromatography (80 g cartridge) to afford the title compound as an oil (0.825 g, 40%). LCMS m/z: ES$^+$ [M+Na]$^+$: 444.95; (B05) retention time=2.10-2.20 m.

Step 7

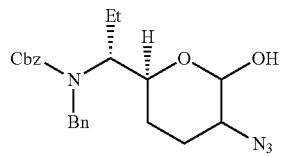

Benzyl ((1R)-1-((2S)-5-azido-6-hydroxytetrahydro-2H-pyran-2-yl)propyl)(benzyl)carbamate DIBAL-H (1 M, 2.94 mL, 2.94 mmol) in toluene was added dropwise to a solution of benzyl N-[(1R)-1-[(2S)-5-azido-6-oxo-tetrahydropyran-2-yl]propyl]-N-benzyl-carbamate (0.777 g, 1.84 mmol) in dry DCM (50.0 mL) at −78° C. under N$_2$. After 1 h, acetone (1.0 mL) was added to the reaction mixture dropwise. After 5 min, sat. potassium sodium tartrate (100.0 mL) was added to the solution slowly, followed by the addition of water (100.0 mL). The mixture was allowed to warm to room temperature and vigorously stirred for overnight in the presence of ethyl acetate. The organic layer was separated and the aqueous layer was extracted with ethyl acetate (3×100 mL). The combined organic layers were dried (Na$_2$SO$_4$), filtered and concentrated under reduced pressure to provide the title compound as an oil (diastereomers, 0.75 g, 96%). This mixture was used in the next step without further purification LCMS m/z: ES$^+$ [M+Na]$^+$: 447.91; (B05) retention time=2.10 m.

Step 8

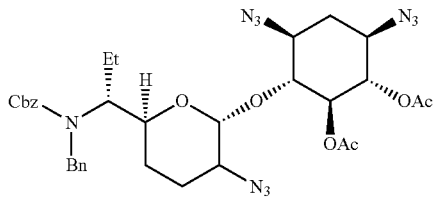

(1S,2S,3R,4S,6R)-4,6-diazido-3-(((2R,6S)-3-azido-6-((R)-1-(benzyl((benzyloxy)carbonyl)amino)propyl)tetrahydro-2H-pyran-2-yl)oxy)cyclohexane-1,2-diyl diacetate CCl$_3$CN (0.877 mL, 8.75 mmol) was added dropwise to a suspension of benzyl ((1R)-1-((2S)-5-azido-6-hydroxytetrahydro-2H-pyran-2-yl)propyl)(benzyl)carbamate (0.767 g, 5.25 mmol) and K$_2$CO$_3$ (0.726 g, 5.25 mmol) in dry DCM (30.0 mL) at ambient temperature under N$_2$. After 12 h, the solution was filtered through Celite and the filtrate was concentrated by high-vacuum. To the crude was added [(1S,2S,3R,4S,6R)-2-acetoxy-4,6-diazido-3-hydroxy-cyclohexyl] acetate (0.418 g, 1.40 mmol) and ground 4 Å sieves (1.0 g) and the mixture was dissolved in dry DCM (30.0 mL). The suspension was stirred at ambient temperature for 25 min. The solution was cooled to 0° C. and BF$_3$·OEt$_2$ (0.864 mL, 7.0 mmol) was added dropwise with vigorous stirring. The solution was warmed to ambient temperature and stirred for another 3 hours. The reaction was quenched with sat. NaHCO$_3$ (50.0 mL). The mixture was successively extracted with DCM (3×50 mL) and the combined organic layer were dried (Na$_2$SO$_4$), filtered and concentrated under reduced pressure. The crude was purified by silica gel chromatography (40 g cartridge) with EtOAc and hexanes (0-30%) to produce the title compound as an oil (2 diastereomers, 0.64 g, 65%). LCMS m/z: [M+Na]$^+$: 727.60; (B05) retention time=2.37 m.

Step 9

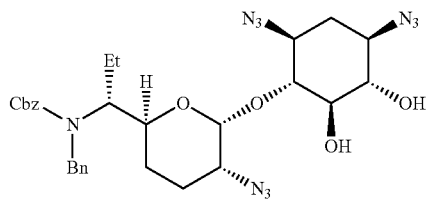 [SMILES: CC[C@H]([C@@H]1CC[C@@H](N=[N+]=[N-])[C@@H](O[C@H]2[C@H](O)[C@@H](O)[C@H](N=[N+]=[N-])C[C@@H]2N=[N+]=[N-])O1)N(Cc1ccccc1)C(=O)OCc1ccccc1]

Benzyl ((R)-1-((2S,5R,6R)-5-azido-6-(((1R,2R,3S,4R,6S)-4,6-diazido-2,3-dihydroxycyclohexyl)oxy)tetrahydro-2H-pyran-2-yl)propyl)(benzyl)carbamate NaOMe (4.62 M, 1.14 mL, 5.30 mmol) was added dropwise to a solution of (1S,2S,3R,4S,6R)-4,6-diazido-3-(((2R,6S)-3-azido-6-((R)-1-(benzyl((benzyloxy)carbonyl)amino)propyl)tetrahydro-2H-pyran-2-yl)oxy)cyclohexane-1,2-diyl diacetate (0.622 g, 0.883 mmol) in MeOH (30.0 ml) at room temperature. After 60 min, AcOH (0.404 mL, 7.06 mmol) was added to the reaction. Water (30.0 mL) was added and the mixture was extracted with DCM (3×50 mL). The organic layers were combined, dried over Na$_2$SO$_4$ and then concentrated under reduced pressure to provide a mixture of two diastereomers (0.450 g). The diastereoisomers were separated on Yamazen purification system using hexane and EtOAc to provide the title desired diastereoisomer (105 mg, 19%) as a solid. ES$^+$ [M+H]$^+$: 621.15.

Step 10

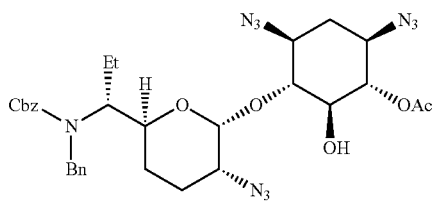 [SMILES: CC[C@H]([C@@H]1CC[C@@H](N=[N+]=[N-])[C@@H](O[C@H]2[C@H](O)[C@@H](OC(C)=O)[C@H](N=[N+]=[N-])C[C@@H]2N=[N+]=[N-])O1)N(Cc1ccccc1)C(=O)OCc1ccccc1]

(1S,2S,3R,4S,6R)-4,6-diazido-3-(((2R,3R,6S)-3-azido-6-((R)-1-(benzyl((benzyloxy)carbonyl)amino)propyl)tetrahydro-2H-pyran-2-yl)oxy)-2-hydroxycyclohexyl acetate Ac$_2$O (14.4 µL, 152 µmol) was added to a solution of benzyl ((R)-1-((2S,5R,6R)-5-azido-6-(((1R,2R,3S,4R,6S)-4,6-diazido-2,3-dihydroxycyclohexyl)oxy)tetrahydro-2H-pyran-2-yl)propyl)(benzyl)carbamate (21.0 mg, 33.8 µmol) and pyridine (16.4 µL, 203 µmol) in dry DCM (2.0 mL) at ambient temperature. After 48 h, all volatiles were removed under reduced pressure. The crude was purified by silica gel chromatography (4 g cartridge) with EtOAc and hexanes (5-20%) to produce the title compound as an oil (16.0 mg, 71%). LCMS m/z: ES$^+$ [M+Na]$^+$: 685.17; (B05) retention time=2.31 m.

Step 11

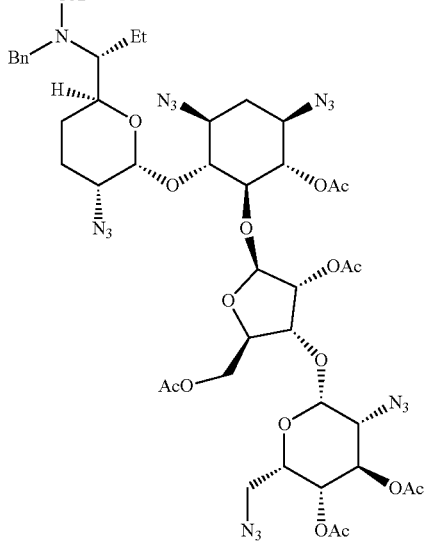

((2R,3S,4R,5S)-3-(((2R,3R,4R,5S,6S)-3-Azido-6-(azidomethyl)-4,5-dihydroxytetrahydro-2H-pyran-2-yl)oxy)-5-(((1R,2R,3S,5R,6S)-3,5-diazido-2-(((2R,3R,6S)-3-azido-6-((R)-1-(benzyl((benzyloxy)carbonyl)amino)propyl)tetrahydro-2H-pyran-2-yl)oxy)-6-hydroxycyclohexyl)oxy)-4-hydroxytetrahydrofuran-2-yl)methyl acetate CCl$_3$CN (70.4 µL, 702 µmol) was added dropwise to a mixture of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydro-furan-2-yl]methyl acetate (74.4 mg, 0.140 mmol) and K$_2$CO$_3$ (58.2 mg, 0.421 mmol) in dry DCM (8.0 mL) at room temperature under N$_2$. The mixture was stirred at room temperature for 18 h, then filtered through Celite and rinsed with DCM. The filtrate was concentrated under reduced pressure. The crude was dissolved in DCM (8 mL) and added to (1S,2S,3R,4S,6R)-4,6-diazido-3-(((2R,3R,6S)-3-azido-6-((R)-1-(benzyl((benzyloxy)carbonyl)amino)propyl)tetrahydro-2H-pyran-2-yl)oxy)-2-hydroxycyclohexyl acetate. 4 Å molecular sieves (200 mg) were added and the mixture was cooled to −78° C., then BF$_3$·OEt$_2$ (28.9 µL, 234 µmol) was added dropwise.

The mixture was stirred at room temperature for 5 h, then a saturated aqueous solution of NaHCO₃ (15 mL) was added. The separated aqueous layer was extracted with DCM (3×20 mL). The combined organic layer was washed with brine, dried over Na₂SO₄ and concentrated under reduced pressure. The residue was purified by silica gel chromatography (25 g) using hexane and ethyl acetate (0-30%) to provide the title compound (35.0 mg, 64%) as a an oil. LCMS m/z ES⁺ [M+H]⁺: 1175.29, LCMS (B05) retention time=2.46 m.

Step 12

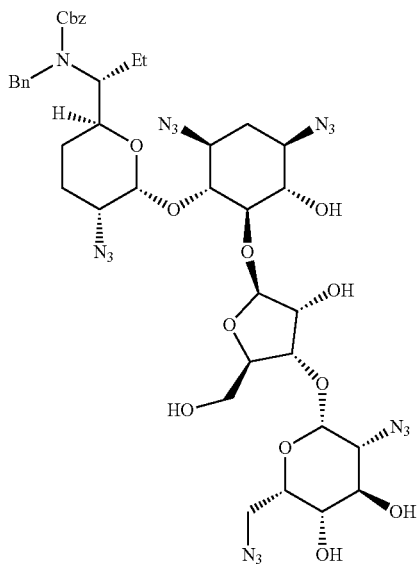 [SMILES: CC[C@H]([C@@H]1CC[C@@H](N=[N+]=[N-])[C@@H](O[C@H]2[C@H](O[C@@H]3O[C@H](CO)[C@@H](O[C@H]4O[C@@H](CN=[N+]=[N-])[C@@H](O)[C@H](O)[C@H]4N=[N+]=[N-])[C@H]3O)[C@@H](O)[C@H](N=[N+]=[N-])C[C@@H]2N=[N+]=[N-])O1)N(Cc1ccccc1)C(=O)OCc1ccccc1]

Benzyl ((R)-1-((2S,5R,6R)-5-azido-6-(((1R,2R,3S, 4R,6S)-4,6-diazido-2-(((2S,3R,4S,5R)-4-(((2R,3R, 4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H-pyran-2-yl)propyl)(benzyl)carbamate NaOMe (25 wt %, 106 µL, 368 µmol) was added dropwise to a solution of compound ((2R,3S,4R,5S)-3-(((2R,3R,4R, 5S,6S)-3-Azido-6-(azidomethyl)-4,5-dihydroxytetrahydro-2H-pyran-2-yl)oxy)-5-(((1R,2R,3S,5R,6S)-3,5-diazido-2-(((2R,3R,6S)-3-azido-6-((R)-1-(benzyl((benzyloxy)carbonyl)amino)propyl)tetrahydro-2H-pyran-2-yl)oxy)-6-hydroxycyclohexyl)oxy)-4-hydroxytetrahydrofuran-2-yl) methyl acetate (36.0 mg, 306 µmol) in MeOH (3.0 mL) at ambient temperature. After 1 hour, the reaction mixture was neutralized by HOAc (~35 µL) and all volatiles were removed under reduced pressure. The crude was dissolved with EtOAc, filtered and the filtrate was concentrated under reduced pressure to produce the title compound as an oil (29.6 mg, 100%). LCMS m/z: ES⁺ [M+Na]⁺: 987.19, (B05) retention time=2.19 m.

Step 13

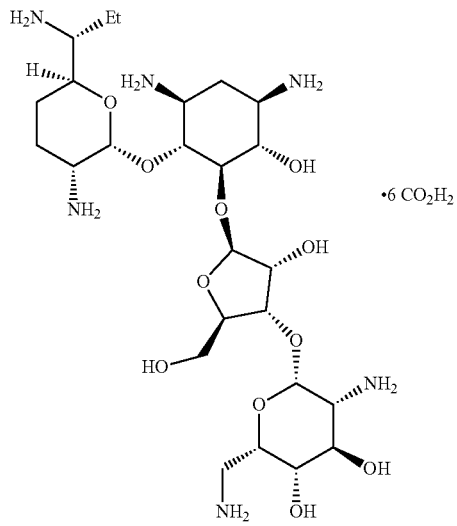 [SMILES: CC[C@@H](N)[C@@H]1CC[C@@H](N)[C@@H](O[C@H]2[C@H](O[C@@H]3O[C@H](CO)[C@@H](O[C@H]4O[C@@H](CN)[C@@H](O)[C@H](O)[C@H]4N)[C@H]3O)[C@@H](O)[C@H](N)C[C@@H]2N)O1]

(2S,3S,4R,5R,6R)-5-Amino-2-(aminomethyl)-6-(((2R,3S,4R,5S)-5-(((1R,2R,3S,5R,6S)-3,5-diamino-2-(((2R,3R,6S)-3-amino-6-((R)-1-aminopropyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol hexaformate In a 2 neck flask equipped with a reflux condenser were added benzyl ((R)-1-((2S,5R,6R)-5-azido-6-(((1R,2R,3S, 4R,6S)-4,6-diazido-2-(((2S,3R,4S,5R)-4-(((2R,3R,4R,5S, 6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H-pyran-2-yl)propyl)(benzyl)carbamate (27 mg, 0.03 mmol) and Pd/C (10% dry on carbon, 8.9 mg, 0.01 mmol) following by anhydrous MeOH (4 mL). Nitrogen was bubbled for 5 min, then ammonium formate was added. The mixture was heated at 63° C. for 30 min under N₂, then cooled to room temperature with an ice-bath. The mixture was filtered with a filter syringe and concentrated under reduced pressure. The material was purified by prep-HPLC using 5% B in A to 100% B (A: Amfor pH 4, B: ACN) on C18 Xbridge 30×150 mm to provide the title compound (7.9 mg, 46%) as a solid. M+H⁺: 611.3. ¹H NMR (400 MHz, D₂O) δ 8.58 (s, 6H), 6.03 (d, J=3.6 Hz, 1H), 5.55 (d, J=2.6 Hz, 1H), 5.45 (s, 1H), 4.67-4.61 (m, 1H), 4.53 (dd, J=4.8, 2.8 Hz, 1H), 4.47 (t, J=5.1 Hz, 1H), 4.38 (s, 2H), 4.25 (d, J=12.2 Hz, 1H), 4.16 (t, J=9.6 Hz, 1H), 4.10-4.00 (m, 2H), 3.98 (d, J=1.5 Hz, 1H), 3.92-3.80 (m, 2H), 3.74 (s, 1H), 3.72-3.43 (m, 6H), 2.62 (dd, J=8.4, 4.3 Hz, 1H), 2.26-1.94 (m, 4H), 1.91-1.60 (m, 3H), 1.14 (t, J=7.5 Hz, 3H).

Example 6

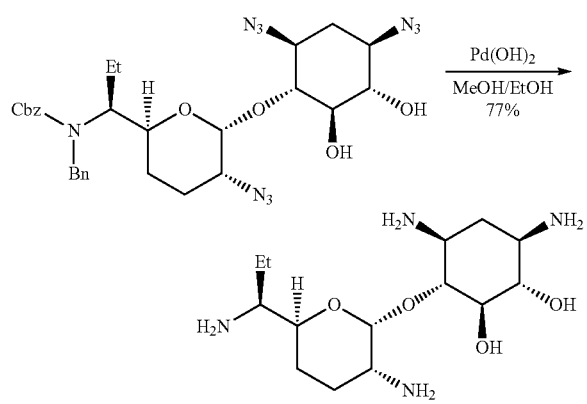

(1S,2R,3R,4S,6R)-4,6-Diamino-3-[(2R,3R,6S)-3-amino-6-[(1S)-1-aminopropyl]tetrahydropyran-2-yl]oxy-cyclohexane-1,2-diol Pd(OH)$_2$/C (20 wt %, 136 mg, 193 μmol) was added to a solution of benzyl N-[(1S)-1-[(2S,5R,6R)-5-azido-6-[(1R,2R,3S,4R,6S)-4,6-diazido-2,3-dihydroxy-cyclohexoxy]tetrahydropyran-2-yl]propyl]-N-benzyl-carbamate (made in Example 4, 30.0 mg, 48.3 mol) in MeOH (2.50 mL) and EtOH (2.50 mL). H$_2$ was bubbled through the suspension. After 16 h, the solution was filtered through a frit (0.22 m diameter) and the filtrate was concentrated under reduced pressure to give the desired product as an oil which turn into solid after lyophilization (12.1 mg, 77%). $^1$H NMR (500 MHz, MeOD) δ 5.40 (d, J=3.5 Hz, 1H), 4.14-4.07 (m, 1H), 3.47 (t, J=9.1 Hz, 1H), 3.36 (t, J=9.4 Hz, 1H), 3.23 (t, J=9.5 Hz, 1H), 3.13-3.07 (m, 1H), 3.07-3.00 (m, 1H), 2.97-2.83 (m, 2H), 2.17-2.08 (m, 1H), 1.92-1.66 (m, 5H), 1.63-1.50 (m, 2H), 1.06 (t, J=7.5 Hz, 3H).

Example 7

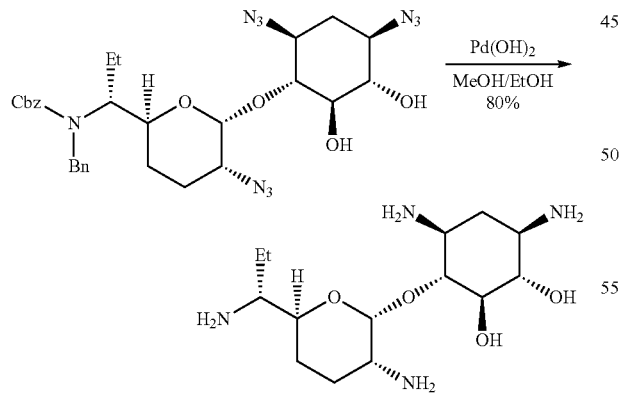

(1S,2R,3R,4S,6R)-4,6-Diamino-3-[(2R,3R,66S)-3-amino-6-[(1R)-1-aminoethyl]tetrahydropyran-2-yl]oxy-cyclohexane-1,2-diol Pd(OH)$_2$/C (20 wt %, 119 mg, 169 μmol) was added to a solution of benzyl N-[(1R)-1-[(2S,5R,6R)-5-azido-6-[(1R,2R,3S,4R,6S)-4,6-diazido-2,3-dihydroxy-cyclohexoxy]tetrahydropyran-2-yl]propyl]-N-benzyl-carbamate (made in Example 5, 35.0 mg, 56.4 mol) in MeOH (2.5 mL) and EtOH (2.5 mL). H$_2$ was bubbled through the suspension. After 17 h, the solution was filtered through a frit (0.22 m diameter) and the filtrate was concentrated under reduced pressure to give the desired product as an oil which turn into solid after lyophilization (14.3 mg, 80%). $^1$H NMR (500 MHz, MeOD) δ 5.23 (d, J=3.5 Hz, 1H), 4.01-3.92 (m, 1H), 3.43 (t, J=9.1 Hz, 1H), 3.27 (t, J=9.3 Hz, 1H), 3.13 (t, J=9.4 Hz, 1H), 2.98-2.80 (m, 3H), 2.79-2.66 (m, 1H), 2.06 (dt, J=12.8, 4.2 Hz, 1H), 1.89-1.45 (m, 7H), 1.04 (t, J=7.5 Hz, 3H).

Example 8

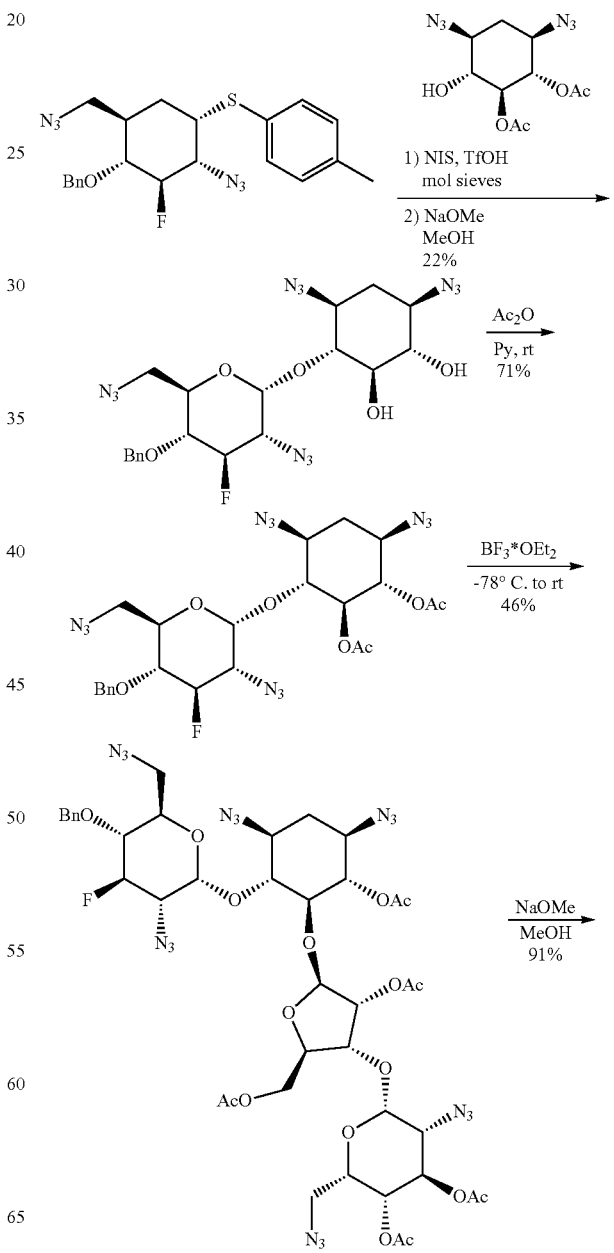

vated 4 Å molecular sieves. After stirring for 30 min at room temperature, the mixture was cooled to −40° C. NIS (500 mg, 2.22 mmol) was added and the reaction mixture was stirred for 20 min at −40° C. TfOH (0.04 mL, 0.427 mmol) was added, and the reaction was warmed to −20° C. and kept stirring for 30 min. Sodium bisulfite (200 mg), NaHCO$_3$ (200 mg), and water (10 mL) were added at 0° C., and the mixture was stirred for 10 min at room temperature. The reaction mixture was diluted with DCM (50 mL), filtered through a Celite pad, and washed with a saturated solution of aqueous NaHCO$_3$ (60 mL). The aqueous layers were extracted with DCM (50 mL×3), and the combined organic phase was washed with brine, dried over MgSO$_4$, filtered, and concentrated under reduced pressure. The residue was taken up in dry MeOH (25 mL) and NaOMe (4.62 M in MeOH, 0.56 mL, 2.56 mmol) was added. The mixture was stirred at room temperature for 1 h. Water (50 mL) was added. The aqueous layer was extracted with DCM (3×50 mL). The combined organic layer was washed with brine, dried over MgSO$_4$ and concentrated under reduced pressure. The material was purified on silica gel (40 g, dry loading) by MPLC using 0% to 50% EtOAc in hexane to provide the title compound (96 mg, 22% over 2 steps). $^1$H NMR (400 MHz, CDCl$_3$) δ 7.45-7.27 (m, 5H), 5.25-5.18 (m, 1H), 5.10-4.86 (m, 2H), 4.67-4.59 (m, 1H), 4.15-4.08 (m, 1H), 3.90-3.84 (m, 1H), 3.83-3.65 (m, 2H), 3.62-3.53 (m, 1H), 3.52-3.35 (m, 3H), 3.28-3.21 (m, 1H), 2.76 (s, 1H), 2.36-2.24 (m, 1H), 1.25 (t, J=12.0 Hz, 3H).

Step 2

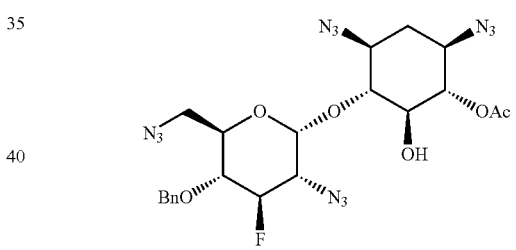

[(1S,2S,3R,4S,6R)-4,6-diazido-3-[(2R,3S,4R,5R, 6R)-3-Azido-6-(azidomethyl)-5-benzyloxy-4-fluoro-tetrahydropyran-2-yl]oxy-2-hydroxy-cyclohexyl] acetate Ac$_2$O (9 μL, 95 μmol) was added to a solution of (1 S,2R,3R,4S,6R)-4,6-diazido-3-[(2R,3S,4R,5R,6R)-3-azido-6-(azidomethyl)-5-benzyloxy-4-fluoro-tetrahydropyran-2-yl]oxy-cyclohexane-1,2-diol (24 mg, 46 μmol) and pyridine (23 μL, 278 μmol) in dry DCM (0.80 mL) at ambient temperature. After 20 h, all volatiles were removed under reduced pressure. The crude was purified by silica gel chromatography (4 g cartridge) with EtOAc and hexanes (5-20%) to produce the title compound as an oil (21 mg, 81%). $^1$H NMR (500 MHz, CDCl$_3$) δ 7.43-7.28 (m, 5H), 5.25 (t, J=3.7 Hz, 1H), 5.10-4.85 (m, 3H), 4.63 (d, J=11.0 Hz, 1H), 4.14-4.09 (m, 1H), 3.73 (dddd, J=13.3, 11.1, 9.7, 5.7 Hz, 3H), 3.62 (td, J=9.8, 2.4 Hz, 1H), 3.57 (dt, J=13.2, 2.1 Hz, 1H), 3.54-3.44 (m, 2H), 3.38-3.32 (m, 1H), 3.27 (ddd, J=12.2, 10.0, 4.5 Hz, 1H), 2.36 (dt, J=13.3, 4.5 Hz, 1H), 2.17 (s, 3H), 1.58 (dd, J=25.7, 12.5 Hz, 1H).

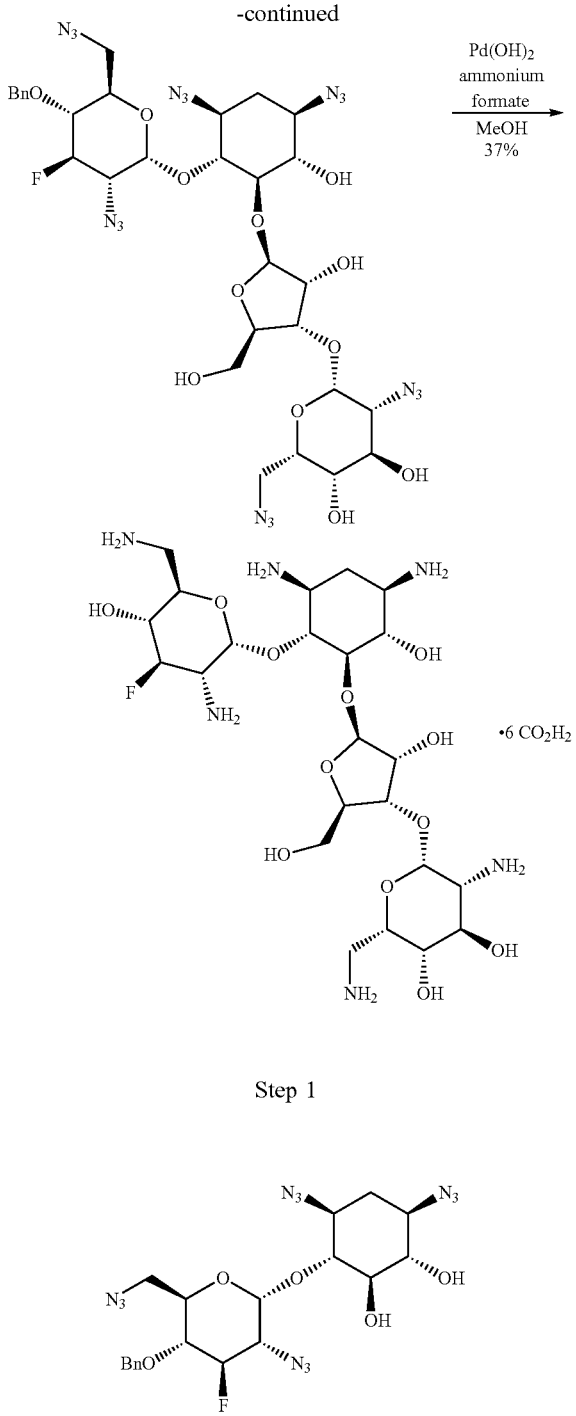

Step 1

(1S,2R,3R,4S,6R)-4,6-Diazido-3-[(2R,3S,4R,5R, 6R)-3-azido-6-(azidomethyl)-5-benzyloxy-4-fluoro-tetrahydropyran-2-yl]oxy-cyclohexane-1,2-diol (2R,3R,4R,5R,6R)-5-azido-2-(azidomethyl)-3-benzyloxy-4-fluoro-6-(p-tolylsulfanyl)tetrahydropyran (preparation below, 385 mg, 0.898 mmol) and [(1S,2S,3R,4S,6R)-2-acetoxy-4,6-diazido-3-hydroxy-cyclohexyl]acetate (255 mg, 0.855 mmol) were coevaporated with dry toluene 3 times and further dried under high vacuum. Anhydrous Et$_2$O (8 mL) and DCM (4 mL) were added followed by preacti-

Step 3

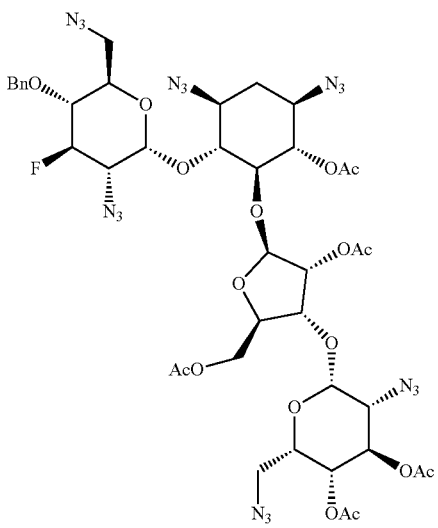 [SMILES: CC(=O)OC[C@H]1O[C@@H](O[C@@H]2[C@@H](OC(C)=O)[C@H](N=[N+]=[N-])C[C@H](N=[N+]=[N-])[C@H]2O[C@H]2O[C@H](CN=[N+]=[N-])[C@@H](OCc3ccccc3)[C@H](F)[C@H]2N=[N+]=[N-])[C@H](OC(C)=O)[C@@H]1O[C@H]1O[C@@H](CN=[N+]=[N-])[C@@H](OC(C)=O)[C@H](OC(C)=O)[C@H]1N=[N+]=[N-]]

[(2R,3R,4R,5S)-4-Acetoxy-5-[(1S,2S,3R,5S,6R)-2-acetoxy-3,5-diazido-6-[(2R,3S,4R,5R,6R)-3-azido-6-(azidomethyl)-5-benzyloxy-4-fluoro-tetrahydropyran-2-yl]oxy-cyclohexoxy]-3-[(2R,3R,4R,5R,6S)-4,5-diacetoxy-3-azido-6-(azidomethyl)tetrahydropyran-2-yl]oxy-tetrahydrofuran-2-yl] methyl acetate CCl$_3$CN (38 µL, 375 µmol) was added dropwise to a suspension of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (40 mg, 75 µmol) and K$_2$CO$_3$ (31 mg, 225 µmol) in dry DCM (1.50 mL) at ambient temperature under N$_2$. After 15 h, the solution was filtered through cotton and the filtrate was concentrated under N$_2$ stream, followed by high-vacuum. To the crude was added [(1S,2S,3R,4S,6R)-4,6-diazido-3-[(2R,3S,4R,5R,6R)-3-Azido-6-(azidomethyl)-5-benzyloxy-4-fluoro-tetrahydropyran-2-yl]oxy-2-hydroxy-cyclohexyl] acetate (21 mg, 38 µmol) in DCM (3.0 mL) and all volatiles were evaporated under N$_2$ stream. To the mixture was added ground 4 Å sieves (500 mg) and the mixture was dissolved in dry DCM (1.0 mL). The suspension was stirred at ambient temperature for 1 h. The solution was cooled to 0° C. and BF$_3$·OEt$_2$ (37 µL, 300 µmol) was added. The reaction mixture was warmed to room temperature, stirred for 30 min followed by the addition of Et$_3$N (80 µL). The crude was filtered through a silica gel pad (0.30 g) with EtOAc (5.0 mL) and all volatiles were removed under reduced pressure. The crude was purified by C18 reversed phase chromatography (40 g cartridge) with ACN and 0.1% aq. formic acid (50-100%) to produce the title compound as a solid (20 mg, 60%). LCMS m/z: ES$^+$ [M+NH$_4$]$^+$: 1090.32; (A50) retention time=2.03 m.

Step 4

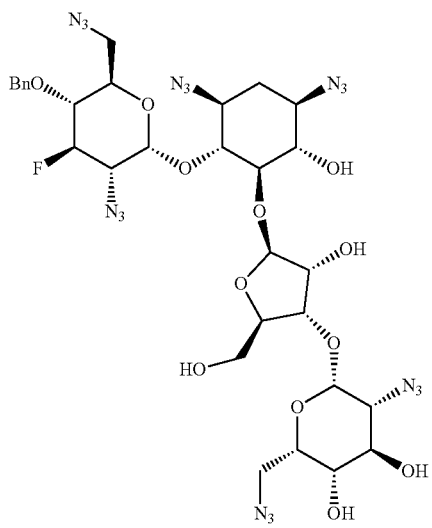 [SMILES: [N-]=[N+]=NC[C@@H]1O[C@H](O[C@H]2[C@@H](O)[C@H](O[C@@H]3[C@@H](O)[C@H](N=[N+]=[N-])C[C@H](N=[N+]=[N-])[C@H]3O[C@H]3O[C@H](CN=[N+]=[N-])[C@@H](OCc4ccccc4)[C@H](F)[C@H]3N=[N+]=[N-])O[C@@H]2CO)[C@H](N=[N+]=[N-])[C@@H](O)[C@@H]1O]

(2S,3S,4R,5R,6R)-5-Azido-2-(azidomethyl)-6-[(2R,3S,4R,5S)-5-[(1R,2R,3S,5R,6S)-3,5-diazido-2-[(2R,3S,4R,5R,6R)-3-azido-6-(azidomethyl)-5-benzyloxy-4-fluoro-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol NaOMe (25 wt %, 45 µL, 157 µmol) was added dropwise to a solution of [(2R,3R,4R,5S)-4-acetoxy-5-[(1S,2S,3R,5S,6R)-2-acetoxy-3,5-diazido-6-[(2R,3S,4R,5R,6R)-3-azido-6-(azidomethyl)-5-benzyloxy-4-fluoro-tetrahydropyran-2-yl]oxy-cyclohexoxy]-3-[(2R,3R,4R,5R,6S)-4,5-diacetoxy-3-azido-6-(azidomethyl)tetrahydropyran-2-yl]oxy-tetrahydrofuran-2-yl]methyl acetate (14 mg, 13 µmol) in MeOH (0.80 mL) at ambient temperature. After 50 min, HOAc (15 µL) was added and all volatiles were removed under reduced pressure. The crude was filtered through a silica gel pad (0.20 g) with EtOAc (6.0 mL) and the filtrate was concentrated under reduced pressure. The crude solid was washed with hexanes (3×1.0 mL) and the supernatant was decanted to produce the title compound as a solid (10 mg, 89%). $^1$H NMR (400 MHz, cdcl3) δ 7.41-7.29 (m, 5H), 5.70 (t, J=3.5 Hz, 1H), 5.37 (d, J=3.1 Hz, 1H), 5.11 (s, 1H), 5.10-4.93 (m, 1H), 4.91 (d, J=11.2 Hz, 1H), 4.63 (d, J=11.2 Hz, 1H), 4.45 (t, J=5.1 Hz, 1H), 4.29-4.17 (m, 3H), 4.11 (t, J=3.4 Hz, 1H), 4.05 (ddd, J=8.9, 3.7, 1.7 Hz, 1H), 3.94-3.76 (m, 3H), 3.76-3.52 (m, 6H), 3.50-3.32 (m, 7H), 3.13-3.00 (m, 2H), 2.28 (dt, J=13.1, 4.2 Hz, 1H), 1.75 (s, 1H), 1.47 (q, J=12.8 Hz, 1H). LCMS m/z: ES$^+$ [M+NH$_4$]$^+$: 880.37; (A05) retention time=2.54 m.

Step 5

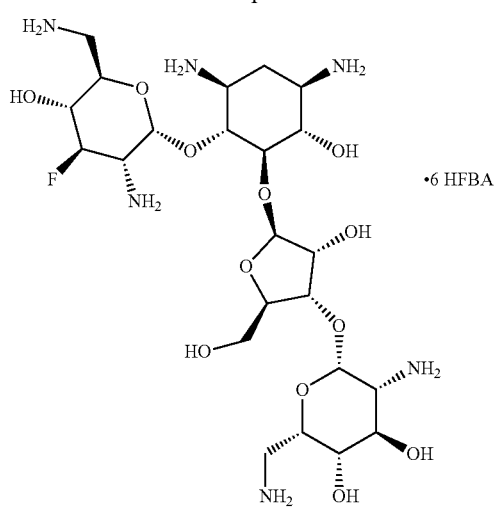

(2S,3S,4R,5R,6R)-5-Amino-2-(aminomethyl)-6-
(((2R,3S,4R,5S)-5-(((1R,2R,3S,5R,6S)-3,5-diamino-
2-(((2R,3S,4R,5R,6R)-3-amino-6-(aminomethyl)-4-
fluoro-5-hydroxytetrahydro-2H-pyran-2-yl)oxy)-6-
hydroxycyclohexyl)oxy)-4-hydroxy-2-
(hydroxymethyl)tetrahydrofuran-3-yl)oxy)
tetrahydro-2H-pyran-3,4-diol hexakis(2,2,3,3,4,4,4-
heptafluorobutanoate)

Pd(OH)$_2$/C (10 wt %, 60 mg, 43 µmol) was added to a solution of (2S,3S,4R,5R,6R)-5-azido-2-(azidomethyl)-6-[(2R,3S,4R,5S)-5-[(1R,2R,3S,5R,6S)-3,5-diazido-2-[(2R,3S,4R,5R,6R)-3-azido-6-(azidomethyl)-5-benzyloxy-4-fluoro-tetrahydropyran-2-yl]oxy-6-hydroxy-cyclohexoxy]-4-hydroxy-2-(hydroxymethyl)tetrahydropyran-3-yl]oxy-tetrahydropyran-3,4-diol (20 mg, 23 µmol) in MeOH/AcOH (2:1, 3.0 mL) under N$_2$ at ambient temperature in a test tube. The tube was then placed in a hydrogenation bottle and kept agitated for 42 h under H$_2$ (50 psi). The material was filtered through a frit (0.55 µm diameter) and the filtrate was concentrated under reduced pressure. The compound was purified by a HFBA-Coupled prep-HPLC to provide the title compound as a solid (hexa-HFBA salt, 2.2 mg, 5%). $^1$H NMR (500 MHz, MeOD) δ 6.11 (s, 1H), 5.47 (s, 1H), 5.31 (s, 1H), 4.52 (t, J=5.9 Hz, 1H), 4.38-4.18 (m, 4H), 4.14 (s, 1H), 4.00 (s, 1H), 3.93-3.84 (m, 2H), 3.81-3.56 (m, 6H), 3.56-3.41 (m, 5H), 3.19-3.09 (m, 2H), 2.50-2.37 (m, 1H), 2.22-1.98 (m, 2H).

Preparation of (2R,3R,4R,5R,6R)-5-azido-2-(azidomethyl)-3-benzyloxy-4-fluoro-6-(p-tolylsulfanyl)tetrahydropyran

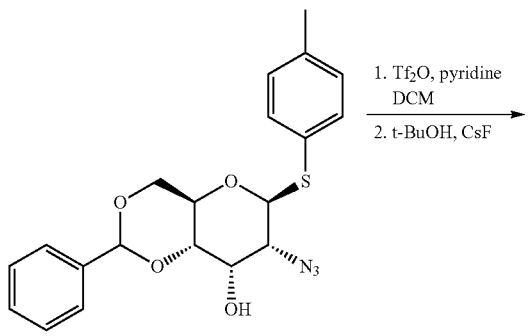

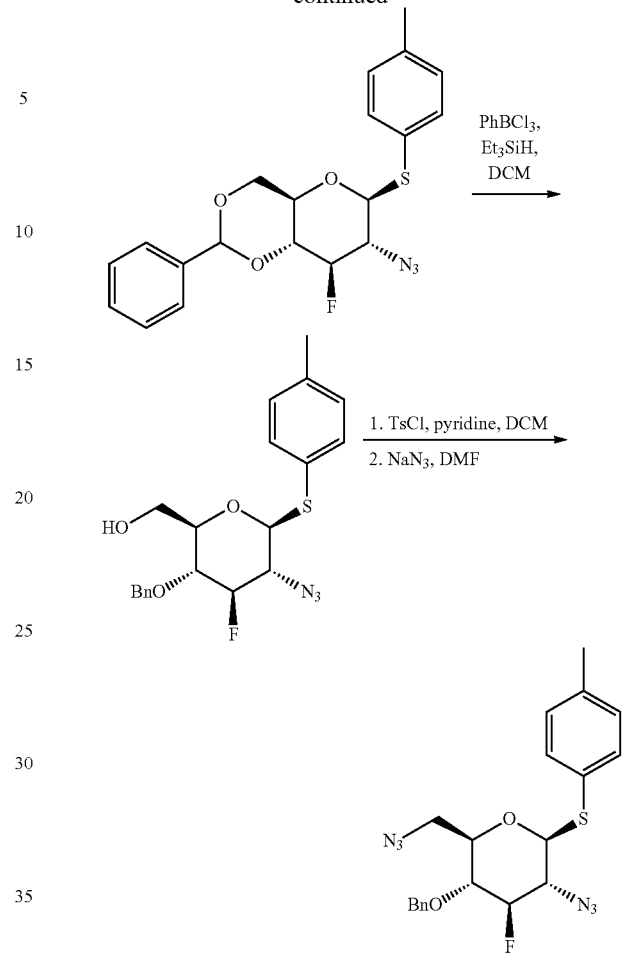

Step 1

(4aR,6S,7R,8R,8aR)-7-azido-8-fluoro-2-phenyl-6-(p-tolylthio)hexahydropyrano[3,2-d][1,3]dioxine

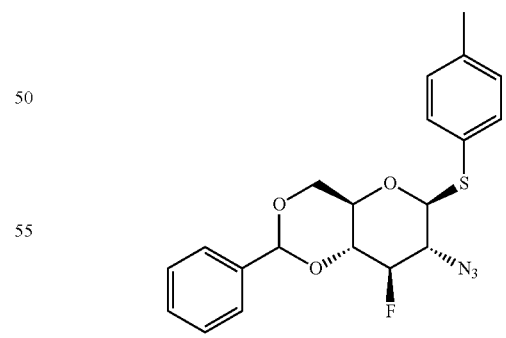

To a solution of 3.1 g of (4aR,6S,7R,8S,8aS)-7-azido-2-phenyl-6-(p-tolylthio) hexahydropyrano[3,2-d][1,3]dioxin-8-ol in 30 mL of anhydrous DCM was added 6.3 mL of pyridine and the mixture was cooled to 0° C. To this solution, 6.6 mL of triflic anhydride was added slowly and the reaction was stirred for 1 hour at the same temperature. After completion, the organic layer was diluted with DCM and washed with 1N HCl and saturated NaHCO$_3$. The organic layer was dried over anhydrous sodium sulfate and concentrated. The obtained crude was dissolved in 20 mL of tBuOH and 3.53 g of CsF was added and the reaction stirred at 50° C. until completion. The organic layer was diluted with EtOAc and washed with saturated NaHCO$_3$ and brine, then dried, filtered and concentrated. The crude was purified by flash chromatography to obtain 1.1 g of (4aR,6S,7R,8R,8aR)-7-azido-8-fluoro-2-phenyl-6-(p-tolylthio)hexahydro-pyrano[3,2-d][1,3]dioxine (35% yield).

Step 2

((2R,3R,4R,5R,6S)-5-azido-3-(benzyloxy)-4-fluoro-6-(p-tolylthio)tetrahydro-2H-pyran-2-yl)methanol

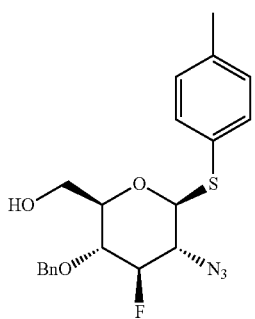 [SMILES: Cc1ccc(S[C@@H]2O[C@H](CO)[C@@H](OCc3ccccc3)[C@H](F)[C@H]2N=[N+]=[N-])cc1]

To the solution of 100 mg of (4aR,6S,7R,8R,8aR)-7-azido-8-fluoro-2-phenyl-6-(p-tolylthio) hexahydropyrano[3,2-d][1,3]dioxine in 5 mL of anhydrous dichloromethane was added 4 Å MS and the mixture was stirred for 30 min at room temperature. The solution was cooled to −78° C. and 100 µL of triethyl silane and 84 µL of PhBCl$_2$ added successively and stirred at the same temperature until completion (20 min). The reaction was quenched methanol (0.2 mL) and triethyl amine (0.2 mL). The reaction was diluted with DCM and filtered. The filtrate was washed with aqueous sodium bicarbonate and the organic layer was dried, filtered and concentrated. The crude residue was purified by flash column chromatography (30% EtOAc in Hexanes) to afford 87 mg of ((2R,3R,4R,5R,6S)-5-azido-3-(benzyloxy)-4-fluoro-6-(p-tolylthio)tetrahydro-2H-pyran-2-yl)methanol (90% yield).

Step 3

(2S,3R,4R,5R,6R)-3-azido-6-(azidomethyl)-5-(benzyloxy)-4-fluoro-2-(p-tolylthio)tetrahydro-2H-pyran

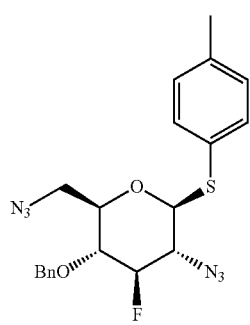 [SMILES: Cc1ccc(S[C@@H]2O[C@H](CN=[N+]=[N-])[C@@H](OCc3ccccc3)[C@H](F)[C@H]2N=[N+]=[N-])cc1]

To a solution of 850 mg of ((2R,3R,4R,5R,6S)-5-azido-3-(benzyloxy)-4-fluoro-6-(p-tolylthio) tetrahydro-2H-pyran-2-yl)methanol in anhydrous DCM was added 1.7 mL of Pyridine and 800 mg of tosyl chloride was added at 0° C. The reaction was stirred at the same temperature until completion (3 h). The reaction was diluted with 100 mL of DCM and washed with 1N HCl and aq NaHCO$_3$, then dried, filtered and concentrated. The crude was dissolved in 10 mL of anhydrous DMF and 750 mg of sodium azide was added. The reaction was stirred at 70° C. until completion. DMF was evaporated and the crude was dissolved in EtOAc and washed with water. The organic layer was dried with MgSO$_4$, filtered, concentrated and purified by flash chromatography to afford 700 mg of (2S,3R,4R,5R,6R)-3-azido-6-(azidomethyl)-5-(benzyloxy)-4-fluoro-2-(p-tolylthio)tetrahydro-2H-pyran (83% yield).

Example 9

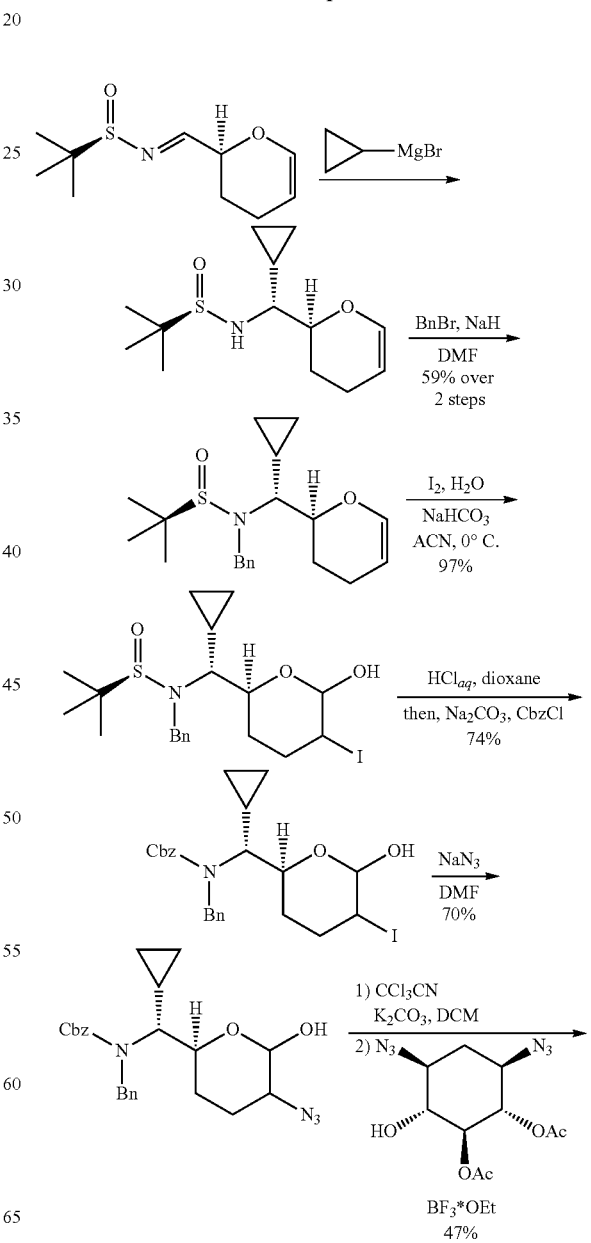

-continued

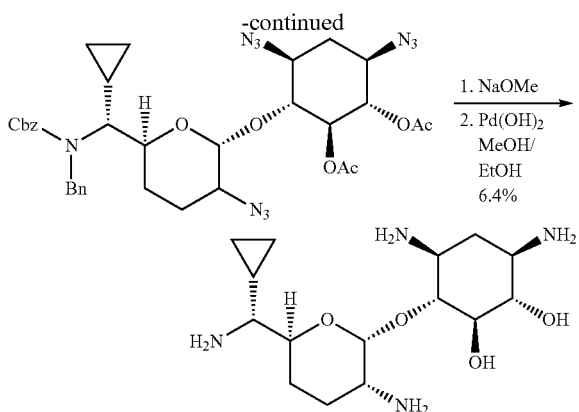

Step 1

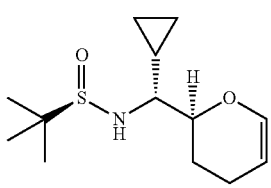 [SMILES: CC(C)(C)[S@@](=O)N[C@H](C1CC1)[C@@H]1CCC=CO1]

(R)—N—[(R)-Cyclopropyl-[(2S)-3,4-dihydro-2H-pyran-2-yl]methyl]-2-methyl-propane-2-sulfinamide Cyclopropyl MgBr (0.5 M in THF, 9.28 mL, 4.64 mmol) was added to a solution of (NE)-N-[[(2S)-3,4-dihydro-2H-pyran-2-yl]methylene]-2-methyl-propane-2-sulfinamide (500 mg, 2.32 mmol) in dry THF (15.0 mL) at −78° C. under $N_2$. After 1 h, the reaction was stirred at −40° C. for 1 h and then warmed to room temperature within 1 h. After 1 h, the reaction was cooled to 0° C. and sat. NH$_4$Cl (20.0 mL) was added dropwise (nota bene: gas evolution). The mixture was extracted with DCM (3×15.0 mL). The combined organic layers were dried (Na$_2$SO$_4$), filtered and concentrated under reduced pressure to provide the title compound as a liquid. The $^1$H NMR for crude was clean and used in the next step without further purification. $^1$H NMR (400 MHz, CDCl$_3$) δ 6.37 (d, J=5.8 Hz, 1H), 4.68 (t, J=4.9 Hz, 1H), 4.13-3.95 (m, 1H), 3.89-3.67 (m, 1H), 2.79-2.63 (m, 1H), 2.24-1.85 (m, 4H), 1.22 (s, 9H), 0.93-0.79 (m, 1H), 0.69-0.51 (m, 2H), 0.42-0.28 (m, 1H), 0.34-0.19 (m, 1H). LCMS m/z ES$^+$ [M+H]: 258.19, LCMS (B05) retention time=1.7 m.

Step 2

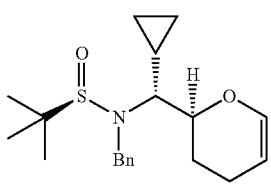 [SMILES: CC(C)(C)[S@@](=O)N(Cc1ccccc1)[C@H](C1CC1)[C@@H]1CCC=CO1]

(R)—N-Benzyl-N—[(R)-cyclopropyl(3,4-dihydro-2H-pyran-2-yl)methyl]-2-methyl-propane-2-sulfinamide A mixture of (R)—N—[(R)-cyclopropyl(3,4-dihydro-2H-pyran-2-yl)methyl]-2-methyl-propane-2-sulfinamide (0.598 g, 2.32 mmol), bromomethylbenzene (0.596 g, 3.48 mmol) in DMF (10 mL) was stirred at 0° C. NaH (92.8 mg, 2.32 mmol) was then added to the reaction mixture portionwise. The mixture was allowed to stir at room temperature for 24 h. The reaction was quenched with water and the mixture was extract with EtOAc (3×15 mL). The organic layers were combined, dried over sodium sulfate and concentrated under reduced pressure. The residue was purified on silica gel (24 g) using hexane and ethyl acetate (70/30) as eluent to give the title product as a colorless oil (473 mg, 59%). LCMS m/z ES$^+$ [M+H]$^+$: 348.20, LCMS (B05) retention time=2.17 m. Major isomer: $^1$H NMR (500 MHz, CDCl$_3$) δ 7.46-7.20 (m, 5H), 6.47 (d, J=5.5 Hz, 1H), 4.73 (t, J=5.6 Hz, 1H), 4.59 (d, J=15.0 Hz, 1H), 4.37 (d, J=14.9 Hz, 1H), 4.04 (d, J=10.7 Hz, 1H), 2.58 (d, J=8.2 Hz, 1H), 2.14-2.02 (m, 1H), 1.96-1.93 (m, 2H), 1.72 (dd, J=12.6, 5.7 Hz, 1H), 1.33-1.20 (m, 1H), 1.12 (s, 9H), 0.71 (ddd, J=14.9, 8.1, 4.3 Hz, 1H), 0.64-0.51 (m, 1H), 0.37-0.25 (m, 1H).

Step 3

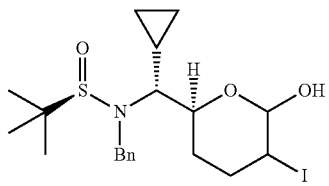 [SMILES: CC(C)(C)[S@@](=O)N(Cc1ccccc1)[C@H](C1CC1)[C@@H]1CCC(I)C(O)O1]

(R)—N-Benzyl-N-r[(R)-cyclopropyl-[(2S)-6-hydroxy-5-iodo-tetrahydropyran-2-yl]methyl]-2-methyl-propane-2-sulfinamide Iodine (1.79 g, 7.07 mmol) was added portionwise to a suspension of (R)—N-benzyl-N—[(R)-cyclopropyl-[(2S)-3,4-dihydro-2H-pyran-2-yl]methyl]-2-methyl-propane-2-sulfinamide (2.46 g, 7.07 mmol) and NaHCO$_3$ (1.78 g, 21.2 mmol) in ACN (43 mL) and H$_2$O (43 mL) at 0° C. The mixture was stirred at 0° C. for 15 min. Then, the mixture was stirred at room temperature for 15 min. After completion, a saturated aqueous solution of Na$_2$S$_2$O$_3$ (100 mL) was added. The aqueous layer was extracted with EtOAc (3×100 mL). The combined organic layer was dried over Na$_2$SO$_4$, filtered and concentrated under reduced pressure to provide the title compound (3.40 g, 97%) as a yellow solid. The crude was used in the next step without further purification. LCMS m/z ES$^+$ [M+Na]$^+$: 514.50, LCMS (B05) retention time=1.98 and 2.07 m.

Step 4

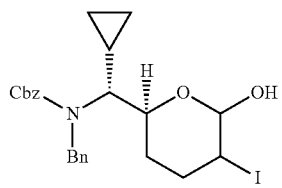 [SMILES: O=C(OCc1ccccc1)N(Cc1ccccc1)[C@H](C1CC1)[C@@H]1CCC(I)C(O)O1]

Benzyl N-benzyl-N—[(R)-cyclopropyl-[(2S)-6-hydroxy-5-iodo-tetrahydropyran-2-yl]methyl]carbamate Aqueous HCl (1.0 M, 43.6 mL, 43.6 mmol) was dropwise added to a solution of (R)—N—[(R)-[(2S)-5-azido-6-hydroxy-tetrahydropyran-2-yl]-cyclopropyl-methyl]-N-benzyl-2-methyl-propane-2-sulfinamide (3.56 g, 7.24 mmol) in dioxane (100.0 mL) with vigorous stirring. After 1 h, solid Na$_2$CO$_3$ (6.14 g, 57.9 mmol) was added. After another 10 min, CbzCl (1.74 mL, 12.2 mmol) was added dropwise. After another 30-45 min, dioxane was evaporated and the residue was partitioned in between EtOAc (100 mL) and H$_2$O (100 mL). The organic phase was dried over Na$_2$SO$_4$, filtered and concentrated under reduced pressure. The crude was purified by silica gel chromatography (80 g cartridge) with EtOAc and hexanes (0-35%) to produce the title compound (mixture of 4 diastereomers) as an oil (2.78 g, 74%). LCMS m/z: ES$^+$ [M+Na]$^+$: 544.01; (B05) retention time=2.15, 2.16, and 2.21 m.

Step 5

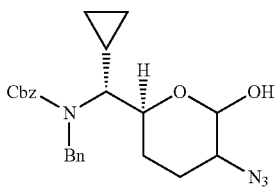

Benzyl N—[(R)-[(2S)-5-azido-6-hydroxy-tetrahydropyran-2-yl]-cyclopropyl-methyl]-N-benzyl-carbamate NaN$_3$ (1.04 g, 16.0 mmol) and K$_2$CO$_3$ (2.21 g, 16.0 mmol) was added to a solution of benzyl N-benzyl-N—[(R)-cyclopropyl-[(2S)-6-hydroxy-5-iodo-tetrahydropyran-2-yl]methyl]carbamate (2.78 g, 5.33 mmol) in dry DMF (30.0 mL) under N$_2$ at ambient temperature. After 4 h, the reaction was quenched with water (100.0 mL) and extracted with EtOAc (3×100.0 mL). The organic layer was dried over Na$_2$SO$_4$, filtered and concentrated under reduced pressure. The crude was purified by silica gel chromatography (120 g cartridge) with EtOAc and hexanes (0-30%) to produce the title compound (diastereomers) as an oil (1.63 g, 70%). ES$^+$ [M+Na]$^+$: 459.01; (B05) retention time=2.11 and 2.17 m.

Step 6

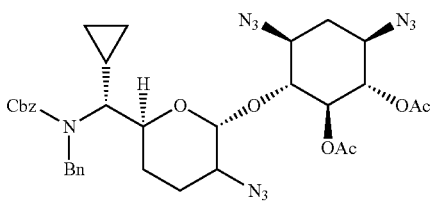

[(1S,2S,3R,4S,6R)-2-Acetoxy-4,6-diazido-3-[(2R,3R,6S)-3-azido-6-[(R)-[benzyl(benzyloxycarbonyl)amino]-cyclopropyl-methyl]tetrahydropyran-2-yl]oxy-cyclohexyl]acetate CCl$_3$CN (0.940 mL, 9.38 mmol) was added dropwise to a suspension of benzyl N—[(R)-[(2S)-5-azido-6-hydroxy-tetrahydropyran-2-yl]-cyclopropyl-methyl]-N-benzyl-carbamate (0.845 g, 1.94 mmol) and K$_2$CO$_3$ (0.777 g, 5.63 mmol) in dry DCM (30.0 mL) at ambient temperature under N$_2$. After 12 h, the solution was filtered through Celite and the filtrate was concentrated by high-vacuum. To the crude was added [(1S,2S,3R,4S,6R)-2-acetoxy-4,6-diazido-3-hydroxy-cyclohexyl]acetate (0.447 mg, 1.50 mmol) and ground 4 Å sieves (1.0 g) and the mixture was dissolved in dry DCM (30.0 mL). The suspension was stirred at ambient temperature for 30 min. The solution was cooled to 0° C. and BF$_3$·OEt$_2$ (0.926 mL, 7.50 mmol) was added dropwise with vigorous stirring. The solution was warmed to ambient temperature and stirred for another 2 hours. The reaction was quenched with sat. NaHCO$_3$ (50.0 mL). The mixture was successively extracted with DCM (3×50 mL) and the combined organic layer were dried (Na$_2$SO$_4$), filtered and concentrated under reduced pressure. The crude was purified by silica gel chromatography (80 g cartridge) with EtOAc and hexanes (5-30%) to produce the title compound as an oil (2 diastereomers, 0.510 g, 47%). LCMS m/z: [M+Na]$^+$: 739.19; (B05) retention time=2.39 m.

Step 7

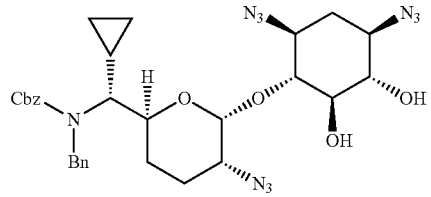 [SMILES: [N-]=[N+]=N[C@H]1C[C@@H](N=[N+]=[N-])[C@H](O)[C@@H](O)[C@@H]1O[C@H]1O[C@H]([C@@H](C2CC2)N(Cc2ccccc2)C(=O)OCc2ccccc2)CC[C@H]1N=[N+]=[N-]]

Benzyl N—[(R)-[(2S,5R,6R)-5-azido-6-[(1R,2R,3S,4R,6S)-4,6-diazido-2,3-dihydroxy-cyclohexoxy]tetrahydropyran-2-yl]-cyclopropyl-methyl]-N-benzyl-carbamate NaOMe (4.62 M, 281.0 µL, 1.29 mmol) was added dropwise to a solution of [(1S,2S,3R,4S,6R)-2-acetoxy-4,6-diazido-3-[(2R,6S)-3-azido-6-[(R)-[benzyl(benzyloxycarbonyl)amino]-cyclopropyl-methyl]tetrahydropyran-2-yl]oxy-cyclohexyl]acetate (155 mg, 0.216 mmol) in MeOH (10.0 mL) at room temperature. After 60 min, AcOH (98.9 µL, 1.73 mmol) was added to the reaction and the mixture was concentrated under reduced pressure to provide a mixture of two diastereomers. ES$^+$ [M+Na]$^+$:655.09; (B05) retention time=2.23 m. The mixture was purified by SFC. The ratio by SFC was found to be 1:7 in favor of the undesired isomer. Retention time of the undesired compound is 4.69 min. Retention time of the desired compound is 7.48. 10 mg (7.3%) of the desired compound was isolated by SFC. 65 mg of the undesired compound was isolated by SFC.

Step 8

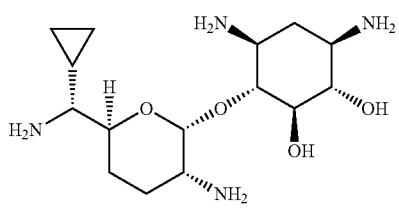

(1S,2R,3R,4S,6R)-4,6-diamino-3-(((2R,3R,6S)-3-amino-6-((R)-amino(cyclopropyl)methyl)tetrahydro-2H-pyran-2-yl)oxy)cyclohexane-1,2-diol Pd(OH)$_2$/C (20 wt %, 102 mg, 145 μmol) was added to a solution of benzyl N—[(R)-[(2S,5S,6R)-5-azido-6-[(1R,2R,3S,4R,6S)-4,6-diazido-2,3-dihydroxy-cyclohexoxy]tetrahydropyran-2-yl]-cyclopropyl-methyl]-N-benzyl-carbamate (23.0 mg, 36.4 μmol) in MeOH (2.0 mL) and EtOH (2.0 mL). H$_2$ was bubbled through the suspension. After 24 h, the solution was filtered through a frit (0.22 m diameter) and the filtrate was concentrated under reduced pressure to give the desired product as an oil which turn into solid after lyophilization (10.5 mg, 87%). $^1$H NMR (500 MHz, MeOD) δ 5.33 (d, J=3.6 Hz, 1H), 4.10-4.02 (m, 1H), 3.45 (t, J=9.1 Hz, 1H), 3.30 (t, J=9.3 Hz, 1H), 3.13 (t, J=9.4 Hz, 1H), 2.98-2.82 (m, 2H), 2.73 (ddd, J=12.2, 9.8, 4.2 Hz, 1H), 2.53-2.41 (m, 1H), 2.27 (dd, J=9.9, 3.6 Hz, 1H), 2.05 (dt, J=11.8, 4.1 Hz, 1H), 1.90-1.73 (m, 4H), 1.04-0.90 (m, 1H), 0.74-0.56 (m, 2H), 0.42-0.30 (m, 2H).

Example 10

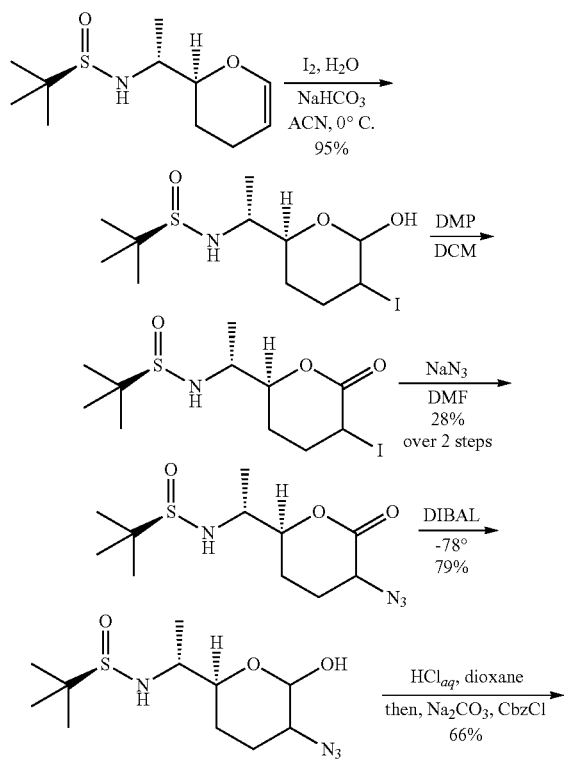

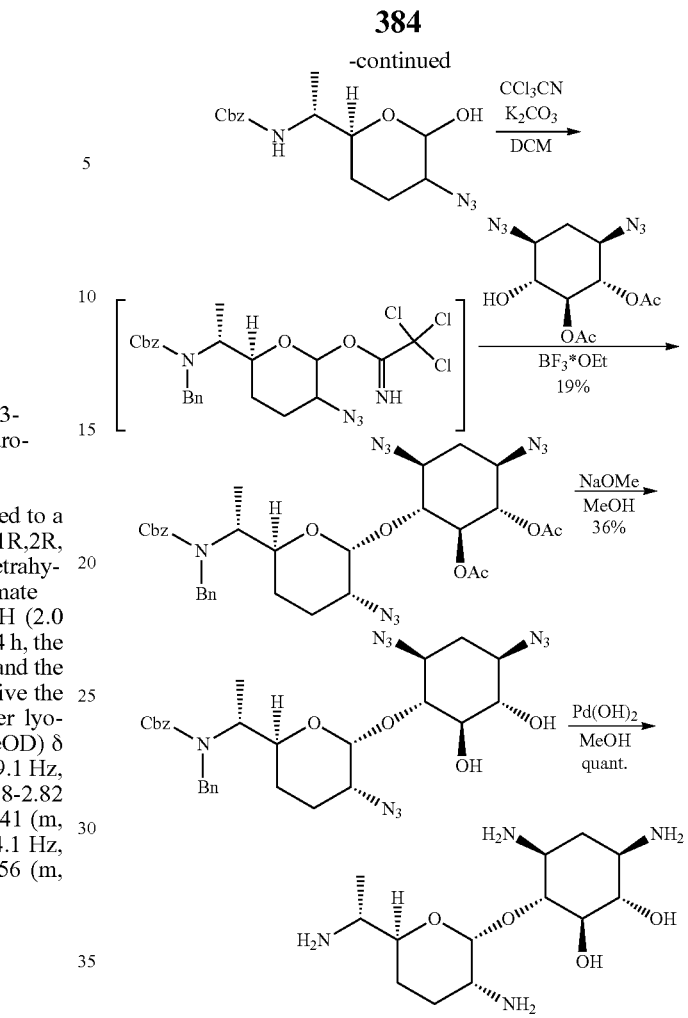

Step 1

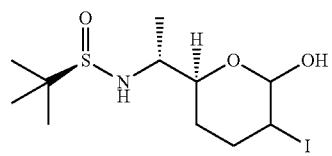 [SMILES: C[C@@H](N[S@](=O)C(C)(C)C)[C@@H]1CCC(I)C(O)O1]

(R)—N-[(1R)-1-[(2S)-6-Hydroxy-5-iodo-tetrahydropyran-2-yl]ethyl]-2-methyl-propane-2-sulfinamide Iodine (339 mg, 1.34 mmol) was added to a suspension of (R)—N-[(1R)-1-[(2S)-3,4-dihydro-2H-pyran-2-yl]ethyl]-2-methyl-propane-2-sulfinamide (303 mg, 1.31 mmol) and NaHCO$_3$ (330 mg, 3.93 mmol) in 1:1 H$_2$O/ACN (6.0 mL) at ambient temperature. After 30 min, acetonitrile was evaporated and the remaining solution was partitioned in EtOAc (25.0 mL) and water (10.0 mL). The organic layer was separated, washed with brine (10.0 mL), dried (Na$_2$SO$_4$) and filtered under reduced pressure to provide the title compounds (2 diastereomers) as a wax (490 mg, 95%). LCMS m/z: ES$^+$ [M+H]$^+$: 376.10; (A05) retention time=2.09 m. (A05) retention time=2.19 m. This material was used in the following reactions without further purifications.

Step 2

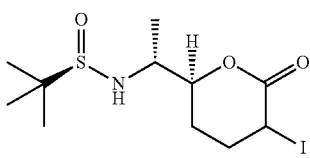 [SMILES: C[C@@H](N[S@](=O)C(C)(C)C)[C@@H]1CCC(I)C(=O)O1]

(R)—N-[(1R)-1-[(2S)-5-Iodo-6-oxo-tetrahydropyran-2-yl]ethyl]-2-methyl-propane-2-sulfinamide Dess-Martin Periodinane (631 mg, 1.48 mmol) was added to a solution of (R)—N-[(1R)-1-[(2S)-6-hydroxy-5-iodo-tetrahydropyran-2-yl]ethyl]-2-methyl-propane-2-sulfinamide (490 mg, 1.24 mmol) in DCM (15.0 mL) at ambient temperature. After 16 h, DCM was evaporated under reduced pressure and the residue was partition in between EtOAc (20.0 mL) and 1:1 sat. NaHCO$_3$/Na$_2$S$_2$O$_3$ (20.0 mL). The organic phase was successively washed with sat. NaHCO$_3$ (10.0 mL) and brine (10.0 mL), dried (Na$_2$SO$_4$), filtered and concentrated under reduced pressure to provide the title compound as an oil (463 mg, 100%). LCMS m/z: ES$^+$ [M+H]$^+$: 374.08; (A05) retention time=2.03 m.

Step 3

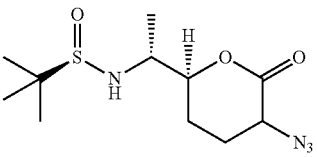 [SMILES: C[C@@H](N[S@](=O)C(C)(C)C)[C@@H]1CCC(N=[N+]=[N-])C(=O)O1]

(R)—N-[(1R)-1-[(2S)-5-Azido-6-oxo-tetrahydropyran-2-yl]ethyl]-2-methyl-propane-2-sulfinamide NaN$_3$ (282 mg, 4.34 mmol) was added to a solution of (R)—N-[(1R)-1-[(2S)-5-iodo-6-oxo-tetrahydropyran-2-yl] ethyl]-2-methyl-propane-2-sulfinamide (463 mg, 1.24 mmol) in dry DMF (4.0 mL) at ambient temperature under N$_2$. After 16 h, the solution was filtered through a silica gel plug (4.0 g) with EtOAc (50.0 mL) and the filtrate was concentrated under reduced pressure. The crude was purified by silica gel chromatography (25 g cartridge) with EtOAc and hexanes (30%-70%) to provide the title compound as an oil (2 diastereomers, 100 mg, 28%). LCMS m/z: ES$^+$ [M+H]$^+$: 289.25; (A05) retention time=1.98-2.01 m.

Step 4

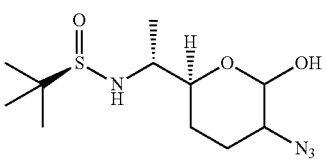

(R)—N-[(1R)-1-[(2S)-5-Azido-6-hydroxy-tetrahydropyran-2-yl]ethyl]-2-methyl-propane-2-sulfinamide DIBAL-H (1 M, 520 µL, 520 µmol) in toluene was dropwise added to a solution of (R)—N-[(1R)-1-[(2S)-5-azido-6-oxo-tetrahydropyran-2-yl]ethyl]-2-methyl-propane-2-sulfinamide (100 mg, 347 µmol) in dry DCM (4.5 mL) at −78° C. under N$_2$. After 1 h, acetone (100 µL) was added to the reaction mixture dropwise. After 5 min, sat. potassium sodium tartrate (10.0 mL) was added to the solution slowly, followed by the addition of water (10.0 mL). The mixture was allowed to warmed to room temperature and vigorously stirred for 1 h. The mixture was extracted with DCM (15.0+3×5.0 mL). The combined organic layers were dried (Na$_2$SO$_4$), filtered and concentrated under reduced pressure to provide the title compound as an oil (diastereomers, 80 mg, 79%). LCMS m/z: ES$^+$ [M+H]$^+$: 291.19; (A05) retention time=2.00 and 2.07 m. This material was used without further purifications.

Step 5

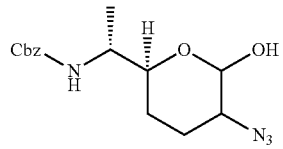

Benzyl N-[(1R)-1-[(2S)-5-azido-6-hydroxy-tetrahydropyran-2-yl]ethyl]carbamate

Aqueous HCl (1.0 M, 1.37 mL, 1.37 mmol) was added dropwise to a solution of (R)—N-[(1R)-1-[(2S)-5-azido-6-hydroxy-tetrahydropyran-2-yl]ethyl]-2-methyl-propane-2-sulfinamide (80 mg, 275 µmol) in dioxane (2.0 mL) with vigorous stirring. After 1 h, solid Na$_2$CO$_3$ (234 mg, 2.20 mmol) was added. After another 15 min, CbzCl (55 µL, 386 mmol) was added dropwise. After another 3 h, dioxane was evaporated and the residue was partitioned in between EtOAc (20.0 mL) and H$_2$O (20.0 mL). The organic phase was washed with brine (10.0 mL), dried (Na$_2$SO$_4$), filtered and concentrated under reduced pressure. The crude was purified by silica gel chromatography (4 g cartridge) with EtOAc and hexanes (10-35%) to produce the title compound (mixture of 4 diastereomers) as a solid (58 mg, 66%). LCMS m/z: ES$^+$ [M+H]$^+$: 321.33; (A05) retention time=2.21, 2.24, 2.27, and 2.30 m.

Step 6

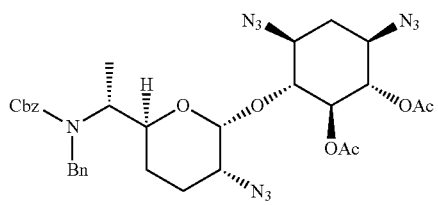 [SMILES: CC(=O)O[C@@H]1[C@@H](OC(C)=O)[C@H](N=[N+]=[N-])C[C@H](N=[N+]=[N-])[C@H]1O[C@H]1O[C@H]([C@@H](C)N(Cc2ccccc2)C(=O)OCc2ccccc2)CC[C@H]1N=[N+]=[N-]]

[(1S,2S,3R,4S,6R)-2-Acetoxy-4,6-diazido-3-[(2R,3R,6S)-3-azido-6-[(1R)-1-(benzyloxycarbonylamino)ethyl]tetrahydropyran-2-yl]oxy-cyclohexyl] acetate CCl$_3$CN (91 μL, 905 μmol) was added dropwise to a suspension of benzyl N-[(1R)-1-[(2S)-5-azido-6-hydroxy-tetrahydropyran-2-yl]ethyl]carbamate (58 mg, 181 μmol) and K$_2$CO$_3$ (75 mg, 543 μmol) in dry DCM (1.0 mL) at ambient temperature under N$_2$. After 64 h, the solution was filtered through cotton and the filtrate was concentrated under N$_2$ stream, followed by high-vacuum treatment. To the crude (96 mg) was added [(1S,2S,3R,4S,6R)-2-acetoxy-4,6-diazido-3-hydroxy-cyclohexyl] acetate (76 mg, 253 μmol) and ground 4 Å sieves (220 mg) and the mixture was dissolved in dry DCM (1.0 mL). The suspension was stirred at ambient temperature for 30 min. The solution was cooled to 0° C. and BF$_3$·OEt$_2$ (89 μL, 724 μmol) was added dropwise with vigorous stirring. The solution was warmed to ambient temperature and stirred for another 15 min. The solution was cooled to 0° C. and sat. NaHCO$_3$ (5.0 mL) was added. After another 15 min, the mixture was successively extracted with DCM (3×5.0 mL) and the combined organic layers were dried (Na$_2$SO$_4$), filtered and concentrated under reduced pressure. The crude was purified by silica gel chromatography (12 g cartridge) with EtOAc and hexanes (5-30%) to produce [(1S,2S,3R,4S,6R)-2-acetoxy-4,6-diazido-3-[(2R,3S,6S)-3-azido-6-[(1R)-1-(benzyloxycarbonylamino)ethyl]tetrahydropyran-2-yl]oxy-cyclohexyl] acetate as a solid (21 mg, 19%). $^1$H NMR (500 MHz, CDCl$_3$) δ 7.37-7.28 (m, 5H), 5.21 (d, J=8.6 Hz, 1H), 5.10 (t, J=13.1 Hz, 2H), 5.05-5.00 (m, 1H), 4.92 (t, J=10.0 Hz, 1H), 4.88 (s, 1H), 4.05 (d, J=11.8 Hz, 1H), 3.77 (s, 1H), 3.61 (t, J=9.7 Hz, 1H), 3.54 (ddd, J=12.6, 10.0, 4.6 Hz, 1H), 3.44 (ddd, J=12.4, 9.9, 4.5 Hz, 1H), 3.35 (d, J=1.5 Hz, 1H), 2.28 (dt, J=12.9, 4.0 Hz, 1H), 2.07 (s, 6H), 2.05-1.96 (m, 1H), 1.84 (dd, J=14.3, 3.2 Hz, 1H), 1.73-1.62 (m, 1H), 1.51-1.38 (m, 2H), 1.17 (d, J=6.8 Hz, 3H).

Step 7

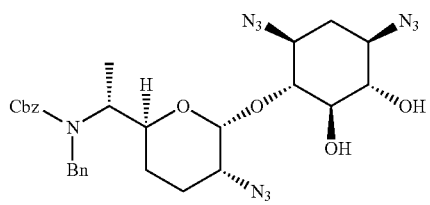 [SMILES: C[C@H]([C@@H]1CC[C@@H](N=[N+]=[N-])[C@@H](O[C@H]2[C@H](O)[C@@H](O)[C@H](N=[N+]=[N-])C[C@@H]2N=[N+]=[N-])O1)N(Cc1ccccc1)C(=O)OCc1ccccc1]

Benzyl N-[(1R)-1-[(2S,5R,6R)-5-azido-6-[(1R,2R,3S,4R,6S)-4,6-diazido-2,3-dihydroxy-cyclohexoxy]tetrahydropyran-2-yl]ethyl]carbamate NaOMe (25 wt %, 245 μL, 849 μmol) was added dropwise to a solution of [(1S,2S,3R,4S,6R)-2-acetoxy-4,6-diazido-3-[(2R,3R,6S)-3-azido-6-[(1R)-1-(benzyloxycarbonylamino)ethyl]tetrahydropyran-2-yl]oxy-cyclohexyl] acetate (85 mg, 142 μmol) in MeOH (3.0 mL) at ambient temperature. After 90 min, HOAc (245 μL, 2.55 mmol) was added to the reaction mixture dropwise and all volatiles were removed under reduced pressure. The crude was purified by silica gel chromatography (12 g cartridge) with EtOAc and hexanes (20-40%) to produce the title compound as a solid (26 mg, 36%). $^1$H NMR (500 MHz, Acetone) δ 7.44-7.23 (m, 5H), 6.25 (d, J=8.6 Hz, 1H), 5.81-5.72 (m, 1H), 5.13-4.98 (m, 2H), 4.05 (ddd, J=11.9, 5.6, 2.1 Hz, 1H), 3.73-3.65 (m, 1H), 3.65-3.57 (m, 3H), 3.57-3.51 (m, 1H), 3.44-3.32 (m, 1H), 3.15 (dt, J=12.6, 4.1 Hz, 1H), 2.25 (dt, J=13.0, 4.2 Hz, 1H), 2.14-2.06 (m, 1H), 1.92-1.82 (m, 2H), 1.53 (ddt, J=10.4, 7.6, 4.0 Hz, 1H), 1.44-1.34 (m, 1H), 1.34-1.23 (m, 2H), 1.17 (d, J=6.8 Hz, 3H). LCMS m/z: ES$^+$ [M+H]$^+$: 517.18; (A05) retention time=2.42 m.

Step 8

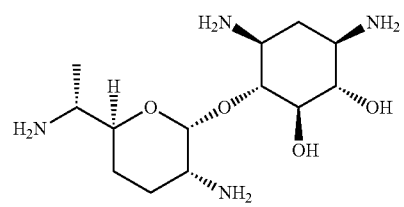 [SMILES: C[C@@H](N)[C@@H]1CC[C@@H](N)[C@@H](O[C@H]2[C@H](O)[C@@H](O)[C@H](N)C[C@@H]2N)O1]

(1S,2R,3R,4S,6R)-4,6-Diamino-3-[(2R,3R,6S)-3-amino-6-[(1R)-1-aminoethyl]tetrahydropyran-2-yl]oxy-cyclohexane-1,2-diol Pd(OH)$_2$/C (10 wt %, 7.5 mg, 5.4 μmol) was added to a solution of benzyl N-[(1R)-1-[(2S,5R,6R)-5-azido-6-[(1R,2R,3S,4R,6S)-4,6-diazido-2,3-dihydroxy-cyclohexoxy]tetrahydropyran-2-yl]ethyl]carbamate (11 mg, 21.3 μmol) in EtOH/MeOH (1:1, 3.0 mL) under N$_2$ at ambient temperature. H$_2$ was bubbled through the suspension for 10 min. After 17 h, the solution was filtered through a frit (0.22 m diameter) and the filtrate was concentrated under reduced pressure, then lyophilized to provide the title compound as a solid (8.2 mg, quantitative). $^1$H NMR (500 MHz, MeOD) δ 5.12 (d, J=3.6 Hz, 1H), 3.74 (ddd, J=12.0, 4.3, 2.1 Hz, 1H), 3.37 (t, J=9.1 Hz, 1H), 3.19 (t, J=9.2 Hz, 1H), 3.05 (t, J=9.4 Hz, 1H), 2.95-2.87 (m, 1H), 2.84-2.73 (m, 2H), 2.64 (ddd, J=12.0, 9.6, 4.1 Hz, 1H), 1.99 (dt, J=12.9, 4.1 Hz, 1H), 1.80-1.74 (m, 1H), 1.74-1.63 (m, 2H), 1.52-1.41 (m, 1H), 1.21 (dd, J=25.0, 12.2 Hz, 1H), 1.10 (d, J=6.7 Hz, 3H).

Example 11

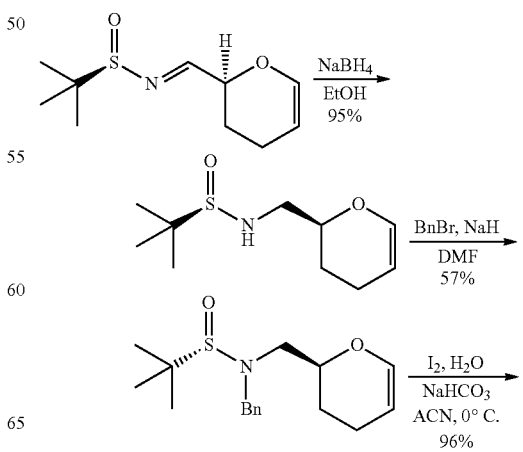

389
-continued

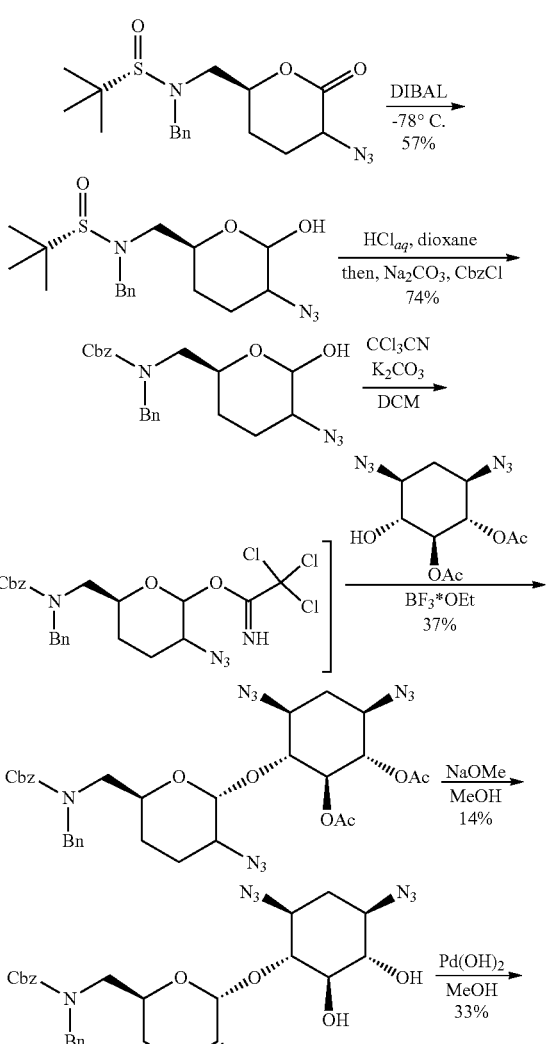

390

Step 1

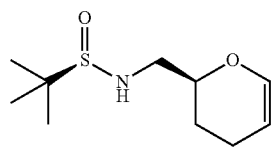

(R)—N-[[(2S)-3,4-Dihydro-2H-pyran-2-yl]methyl]-2-methyl-propane-2-sulfinamide

NaBH₄ (101 mg, 2.66 mmol) was added to a solution of (NE)-N-[[(2S)-3,4-dihydro-2H-pyran-2-yl]methylene]-2-methyl-propane-2-sulfinamide (572 mg, 2.66 mmol) in reagent alcohol (10.0 mL) at 0° C. Ice bath was removed and the reaction was kept stirring for another 30 min. The reaction was cooled to 0° C. and sat. NH₄Cl (20.0 mL) was added (nota bene: gas evolution). EtOH was evaporated under reduced pressure and the residue was extracted with EtOAc (30.0 mL). The layers were separated and the organic phase was successively washed with water (10.0 mL) and brine (10.0 mL), dried (Na₂SO₄), filtered and concentrated under reduced pressure to provide the title compound as a solid (547 mg, 95%). LCMS m/z: ES⁺ [M+H]⁺: 218.20; (A05) retention time=2.04 m. This material was used in the following steps without further purifications.

Step 2

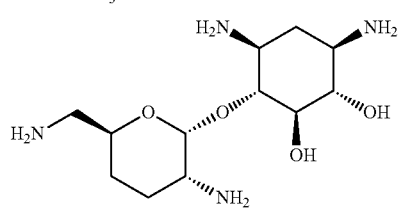

(R)—N-Benzyl-N-[[(2S)-3,4-dihydro-2H-pyran-2-yl]methyl]-2-methyl-propane-2-sulfinamide NaH (60%, 116 mg, 2.89 mmol) was added to a mixture of (R)—N-[[(2S)-3,4-dihydro-2H-pyran-2-yl]methyl]-2-methyl-propane-2-sulfinamide (547 mg, 2.52 mmol) and BnBr (448 μL, 3.78 mmol) in DMF (1.5 mL) at 0° C. The mixture was stirred at room temperature for 1 h, then cooled to 0° C. followed by addition of water (10.0 mL). The aqueous layer was extracted with EtOAc (25.0 mL) and the organic layer was successively washed with water (10.0 mL) and brine (5.0 mL), dried (Na₂SO₄), filtered and concentrated under reduced pressure. The crude was purified by silica gel chromatography (24 g cartridge) with EtOAc and hexanes (0-40%) to produce the title compound as an oil (768 mg, 99%). LCMS m/z: ES⁺ [M+H]⁺: 308.18; (A05) retention time=2.57 m.

Step 3

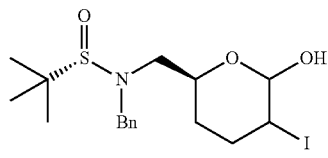 [SMILES: CC(C)(C)[S@](=O)N(Cc1ccccc1)C[C@@H]1CCC(I)C(O)O1]

(R)—N-Benzyl-N-[(1R)-1-[(2S)-6-hydroxy-5-iodo-tetrahydropyran-2-yl]ethyl]-2-methyl-propane-2-sulfinamide Iodine (272 mg, 1.07 mmol) was added to a suspension of (R)—N-benzyl-N-[(1R)-1-[(2S)-3,4-dihydro-2H-pyran-2-yl]ethyl]-2-methyl-propane-2-sulfinamide (320 mg, 1.04 mmol) and $NaHCO_3$ (262 mg, 3.12 mmol) in 1:1 $H_2O$/ACN (8.0 mL) at ambient temperature. After 30 min, MeCN was evaporated and the residue was partitioned in between EtOAc (20.0 mL) and 1:1 sat. $NaHCO_3$/sat. $Na_2S_2O_3$ (10.0 mL). The organic layer was washed with water (5.0 mL) and brine (5.0 mL), dried ($Na_2SO_4$), filtered and concentrated under reduced pressure to provide the title compound as a foam (4 diastereomers, 450 mg, 96%). LCMS m/z: $ES^+$ $[M+H]^+$: 452.06; (A05) retention time=2.30-2.50 m. This material was used in the following reactions without further purifications.

Step 4

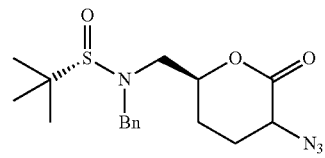 [SMILES: CC(C)(C)[S@](=O)N(Cc1ccccc1)C[C@@H]1CCC(N=[N+]=[N-])C(=O)O1]

(R)—N-[[(2S)-5-Azido-6-oxo-tetrahydropyran-2-yl]methyl]-N-benzyl-2-methyl-propane-2-sulfinamide 4 Å Sieves (500 mg) and PDC (750 mg, 1.99 mmol) was added to a solution of benzyl (R)—N-benzyl-N-[[(2S)-6-hydroxy-5-iodo-tetrahydropyran-2-yl]methyl]-2-methyl-propane-2-sulfinamide (450 mg, 997 μmol) in dry DCM (10.0 mL) under $N_2$ at ambient temperature. After 24 h, the solution was concentrated and the crude was partitioned in between EtOAc (30.0 mL) and water (15.0 mL). The organic layer was washed with water (2×10.0 mL) and brine (10.0 mL), dried ($Na_2SO_4$) and concentrated. The crude was dissolved in dry DMF (1.5 mL) under $N_2$ and $NaN_3$ (130 mg, 1.99 mmol) was added. After 1 h, the solution was partitioned in between EtOAc (30.0 mL) and water (15.0 mL). The organic layer was washed with water (2×10.0 mL) and brine (10.0 mL), dried ($Na_2SO_4$) and concentrated to provide the title compound as an oil (235 mg, 64%). LCMS m/z: $ES^+$ $[M+H]^+$: 365.17; (A05) retention time=2.37 m. This material was used in the next reactions without further purifications.

Step 5

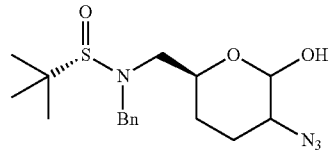

(R)—N-[[(2S)-5-Azido-6-hydroxy-tetrahydropyran-2-yl]methyl]-N-benzyl-2-methyl-propane-2-sulfinamide DIBAL-H (1 M, 1.03 mL, 1.03 mmol) in toluene was dropwise added to a solution of (R)—N-[[(2S)-5-azido-6-oxo-tetrahydropyran-2-yl]methyl]-N-benzyl-2-methyl-propane-2-sulfinamide (235 mg, 645 μmol) in dry DCM (8.0 mL) at −78° C. under $N_2$. After 100 min, sat. potassium sodium tartrate (15.0 mL) was added to the solution slowly, followed by the addition of water (15.0 mL). The mixture was allowed to warm to room temperature and vigorously stirred for 16 h. The mixture was extracted with DCM (10.0+2×5.0 mL). The combined organic layers were dried ($Na_2SO_4$), filtered and concentrated under reduced pressure. The crude was purified by silica gel chromatography (12 g cartridge) with EtOAc and hexanes (10%-50%) to provide the title compound as an oil (diastereomers, 195 mg, 74%). LCMS m/z: $ES^+$ $[M+H]^+$: 367.19; (A05) retention time=2.28-2.40 m.

Step 6

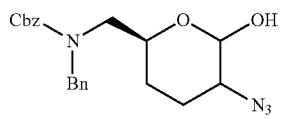 [SMILES: [N-]=[N+]=NC1CC[C@@H](CN(Cc2ccccc2)C(=O)OCc2ccccc2)OC1O]

Benzyl N-[[(2S)-5-azido-6-hydroxy-tetrahydropyran-2-yl]methyl]-N-benzyl-carbamate Aqueous HCl (1.0 M, 2.66 mL, 2.66 mmol) was dropwise added to a solution of (R)—N-[[(2S)-5-azido-6-hydroxy-tetrahydropyran-2-yl]methyl]-N-benzyl-2-methyl-propane-2-sulfinamide (195 mg, 532 μmol) in dioxane (2.7 mL) with vigorous stirring. After 1 h, solid $Na_2CO_3$ (451 mg, 4.26 mmol) was added. After another 5 min, CbzCl (106 μL, 745 mmol) was added dropwise. After another 1 h, dioxane was evaporated and the residue was partitioned in between EtOAc (20.0 mL) and $H_2O$ (20.0 mL). The organic phase was washed with brine (10.0 mL), dried ($Na_2SO_4$), filtered and concentrated under reduced pressure. The crude was purified by C18 reverse phase chromatography (80 g cartridge) with ACN and 0.1% aq. formic acid (40-70%) to produce the title compound (mixture of 4 diastereomers) as an oil (167 mg, 79%). UPLC m/z: $ES^+$ $[M-OH]^+$: 379.21; (CSH 5 to 100% ACN/AmFor pH 4) retention time=2.12, 2.15, 2.20, and 2.22 m. A portion (40 mg) of the material was purified by prep-HPLC (CSH C18 ACN/AmForm 50-70%) to provide the α-azido as a film (20 mg, 50% recovery). UPLC m/z: (CSH 5 to 100% ACN/AmFor pH 4) retention time=2.15 and 2.22 m.

Step 7

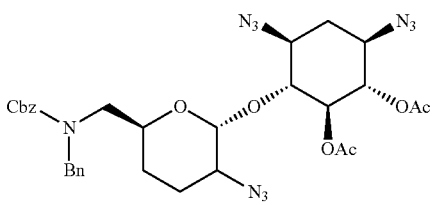

[(1S,2S,3R,4S,6R)-2-Acetoxy-4,6-diazido-3-[(2R, 6S)-3-azido-6-[[benzyl(benzyloxycarbonyl)amino] methyl]tetrahydropyran-2-yl]oxy-cyclohexyl] acetate CCl$_3$CN (145 µL, 1.44 mmol) was added dropwise to a suspension of benzyl N-[[(2S)-5-azido-6-hydroxy-tetrahydropyran-2-yl]methyl]-N-benzyl-carbamate (127 mg, 288 µmol) and K$_2$CO$_3$ (120 mg, 865 µmol) in dry DCM (2.0 mL) at ambient temperature under N$_2$. After 20 h, the solution was filtered through cotton and the filtrate was concentrated under N$_2$ stream, followed by high-vacuum. To the crude (92 mg) was added [(1S,2S,3R,4S,6R)-2-acetoxy-4,6-diazido-3-hydroxy-cyclohexyl] acetate (120 mg, 404 µmol) and ground 4 Å sieves (500 mg) and the mixture was dissolved in dry DCM (2.0 mL). The suspension was stirred at ambient temperature for 1 h. The solution was cooled to 0° C. and BF$_3$·OEt$_2$ (142 µL, 1.15 mmol) was added dropwise with vigorous stirring. The solution was warmed to ambient temperature and stirred for another 15 min. The reaction was quenched with sat. NaHCO$_3$ (10.0 mL). The mixture was successively extracted with DCM (3×8.0 mL) and the combined organic layer were dried (Na$_2$SO$_4$), filtered and concentrated under reduced pressure. The crude was purified by silica gel chromatography (24 g cartridge) with EtOAc and hexanes (5-25%) to produce [(1S,2S,3R,4S,6R)-2-acetoxy-4,6-diazido-3-[(2R,6S)-3-azido-6-[[benzyl(benzyloxycarbonyl)amino]methyl]tetrahydropyran-2-yl]oxy-cyclohexyl] acetate (2 diastereomers, 144 mg, 74%) as an oil. LCMS m/z: [M+H]$^+$: 677.20; (A05) retention time=2.86 m.

Step 8

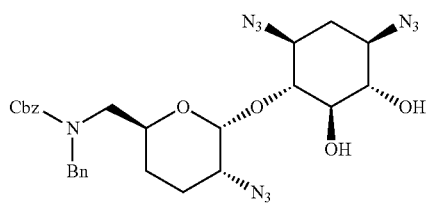 [SMILES: [N-]=[N+]=N[C@H]1C[C@@H](N=[N+]=[N-])[C@H](O)[C@@H](O)[C@@H]1O[C@H]1O[C@H](CN(Cc2ccccc2)C(=O)OCc2ccccc2)CC[C@H]1N=[N+]=[N-]]

Benzyl N-[[(2S,5R,6R)-5-azido-6-[(1R,2R,3S,4R, 6S)-4,6-diazido-2,3-dihydroxy-cyclohexoxy]tetrahydropyran-2-yl]methyl]-N-benzyl-carbamate NaOMe (25 wt %, 306 µL, 1.06 mmol) was added dropwise to a solution of [(1S,2S,3R,4S,6R)-2-acetoxy-4,6-diazido-3-[(2R,6S)-3-azido-6-[[benzyl(benzyloxycarbonyl)amino]methyl]tetrahydropyran-2-yl]oxy-cyclohexyl] acetate (92 mg, 136 µmol) in MeOH (2.0 mL) at ambient temperature. After 60 min, HOAc (122 µL, 2.13 mmol) was added to the reaction mixture dropwise and all volatiles were removed under reduced pressure. The crude was purified by silica gel chromatography (24 g cartridge) with EtOAc and hexanes (10-40%) to produce the title compound as an oil (28 mg, 22%) and benzyl N-[[(2S,5S,6R)-5-azido-6-[(1R, 2R,3S,4R,6S)-4,6-diazido-2,3-dihydroxy-cyclohexoxy]tetrahydropyran-2-yl]methyl]-N-benzyl-carbamate as a solid (38 mg, 30%). They has the same retention time and MS. LCMS m/z: ES$^+$ [M+H]$^+$: 379.27; (A05) retention time=2.63 m.

Step 9

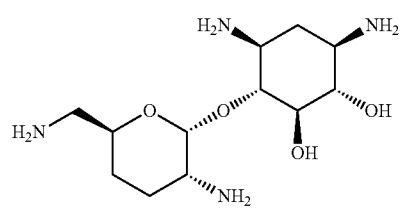 [SMILES: NC[C@@H]1CC[C@@H](N)[C@@H](O[C@H]2[C@H](O)[C@@H](O)[C@H](N)C[C@@H]2N)O1]

(1S,2R,3R,4S,6R)-4,6-Diamino-3-[(2R,3R,6S)-3-amino-6-(aminomethyl)tetrahydropyran-2-yl]oxy-cyclohexane-1,2-diol Pd(OH)$_2$/C (10 wt %, 8 mg, 5.7 µmol) was added to a solution of benzyl N-[[(2S,5R,6S)-5-azido-6-[(1R,2R,3S, 4R,6S)-4,6-diazido-2,3-dihydroxy-cyclohexoxy]tetrahydropyran-2-yl]methyl]-N-benzyl-carbamate (8 mg, 13.5 µmol) in MeOH (2.5 mL) under N$_2$ at ambient temperature. H$_2$ was bubbled through the suspension for 15 min. After 17 h, the solution was filtered through a frit (0.22 µm diameter) and the filtrate was concentrated under reduced pressure, then lyophilized to provide the title compound as a wax (3.8 mg, 92%). $^1$H NMR (500 MHz, MeOD) δ 5.22 (d, J=3.6 Hz, 1H), 3.92-3.84 (m, 1H), 3.39 (t, J=9.1 Hz, 1H), 3.24 (t, J=9.3 Hz, 1H), 3.07 (t, J=9.4 Hz, 1H), 2.86-2.79 (m, 2H), 2.77 (dd, J=13.1, 3.6 Hz, 1H), 2.70-2.63 (m, 2H), 2.01 (dt, J=8.4, 3.9 Hz, 1H), 1.78-1.67 (m, 3H), 1.44-1.38 (m, 1H), 1.24 (dd, J=24.9, 12.2 Hz, 1H).

Example 12

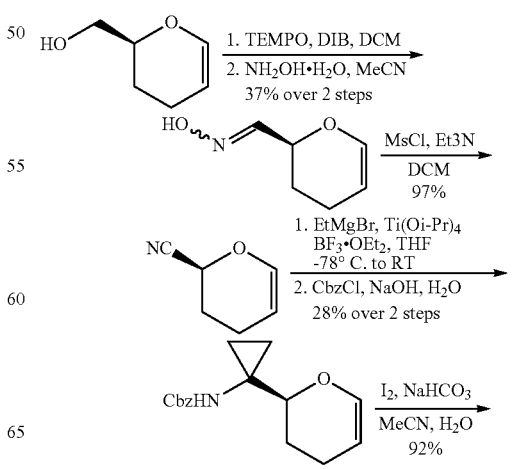

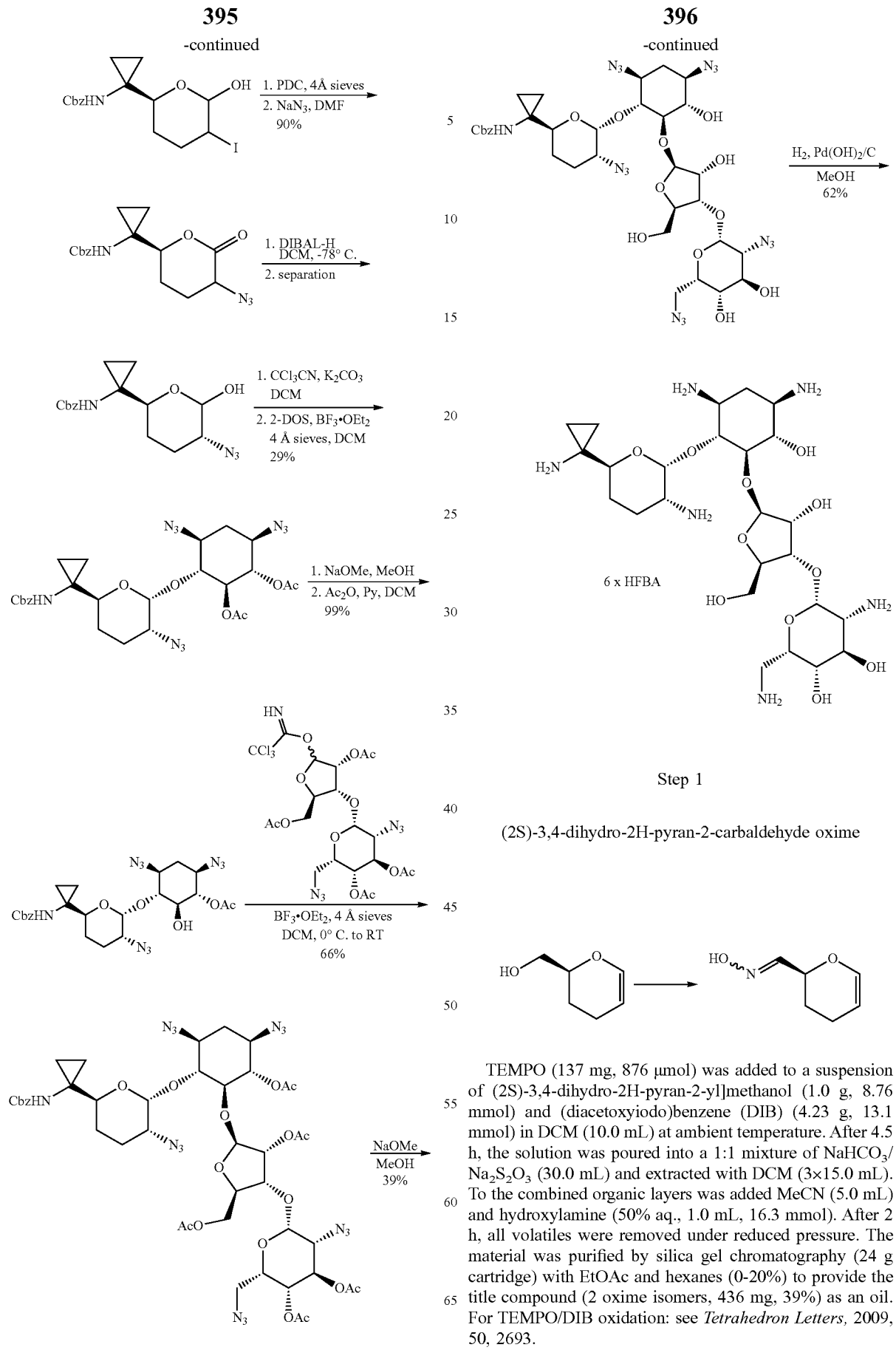

Step 1

(2S)-3,4-dihydro-2H-pyran-2-carbaldehyde oxime

TEMPO (137 mg, 876 μmol) was added to a suspension of (2S)-3,4-dihydro-2H-pyran-2-yl]methanol (1.0 g, 8.76 mmol) and (diacetoxyiodo)benzene (DIB) (4.23 g, 13.1 mmol) in DCM (10.0 mL) at ambient temperature. After 4.5 h, the solution was poured into a 1:1 mixture of NaHCO$_3$/Na$_2$S$_2$O$_3$ (30.0 mL) and extracted with DCM (3×15.0 mL). To the combined organic layers was added MeCN (5.0 mL) and hydroxylamine (50% aq., 1.0 mL, 16.3 mmol). After 2 h, all volatiles were removed under reduced pressure. The material was purified by silica gel chromatography (24 g cartridge) with EtOAc and hexanes (0-20%) to provide the title compound (2 oxime isomers, 436 mg, 39%) as an oil. For TEMPO/DIB oxidation: see *Tetrahedron Letters*, 2009, 50, 2693.

Step 2

(2S)-3,4-dihydro-2H-pyran-2-carbonitrile

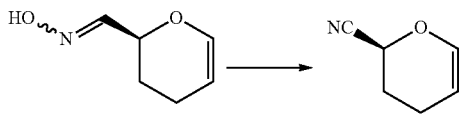 [SMILES: ON=C[C@@H]1CCC=CO1 ; N#C[C@@H]1CCC=CO1]

MsCl (398 µL, 5.14 mmol) was added dropwise (Caution: violent reaction) to a solution of (2S)-3,4-dihydro-2H-pyran-2-carbaldehyde oxime (436 mg, 3.43 mmol) and Et$_3$N (1.67 mL, 12.0 mmol) in dry DCM (6.0 mL) under N$_2$ at 0° C. and ice bath was removed. After 30 min, the material was filtered through silica gel (5.0 g) and eluted with DCM (30 mL). The filtrate was carefully concentrated and purified by silica gel chromatography (24 g cartridge, wet loading) with DCM and the fractions were carefully concentrated to provide a solution of the title compound. $^1$H NMR (400 MHz, CDCl$_3$) δ 6.30 (dt, J=6.3, 1.7 Hz, 1H), 4.91-4.82 (m, 2H), 2.34-2.19 (m, 1H), 2.17-2.03 (m, 3H). Note: The product contains 43 wt % EtOAc from ISCO system and 28 wt % DCM by $^1$H NMR. The material was not fully concentrated because of the volatility of (2S)-3,4-dihydro-2H-pyran-2-carbonitrile.

Step 3

Benzyl N-[1-[(2S)-3,4-dihydro-2H-pyran-2-yl]cyclopropyl]carbamate

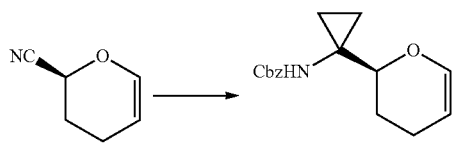 [SMILES: N#C[C@@H]1CCC=CO1 ; O=C(NC1([C@@H]2CCC=CO2)CC1)OCc1ccccc1]

Ti(OiPr)$_4$ (1.09 mL, 3.67 mmol) was added to a suspension of EtMgBr (3.0 M in ether, 2.44 mL, 7.33 mmol) in dry THF (5.0 mL) under N$_2$ at −78° C. After 30 min, a solution of (2S)-3,4-dihydro-2H-pyran-2-carbonitrile (320 mg, 2.93 mmol, carefully co-evaporated with 3×25.0 mL hexane) in dry THF (3.0 mL) was added dropwise and the mixture was warmed to room temperature. After 40 min, BF$_3$·OEt$_2$ (724 µL, 5.86 mmol) was added to the reaction mixture dropwise. After another 30 min, the solution was cooled to 0° C. and 1.0 M solution of NaOH (14.7 mL, 14.7 mmol) was added quickly dropwise. After another 10 min, CbzCl (625 µL, 4.40 mol) was added at ambient temperature and the reaction mixture was stirred for 1 h. The mixture was diluted with water (30.0 mL) and DCM (30.0 mL) The layers were separated, and the aqueous layer was extracted with DCM (2×10.0 mL). The combined organic layers were dried (Na$_2$SO$_4$), filtered and concentrated under reduced pressure. The material was purified by silica gel chromatography (25 g cartridge) using a gradient of 0-20% EtOAc in hexane as eluent to provide the title compound (225 mg, 28%) as a solid. $^1$H NMR (500 MHz, CDCl$_3$) δ 7.39-7.28 (m, 5H), 6.35 (d, J=5.4 Hz, 1H), 5.25 (s, 1H), 5.06 (s, 2H), 4.69-4.60 (m, 1H), 3.43 (d, J=10.1 Hz, 1H), 2.13-1.88 (m, 3H), 1.65 (ddd, J=25.1, 12.4, 6.2 Hz, 1H), 1.13-1.02 (m, 1H), 0.96-0.78 (m, 3H). MS ESI [M+H]$^+$ 274.0.

Step 4

Benzyl N-[1-[(2S)-6-hydroxy-5-iodo-tetrahydropyran-2-yl]cyclopropyl]carbamate

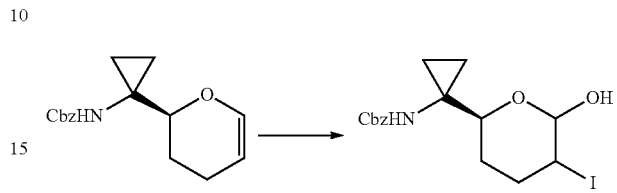

I$_2$ (71 mg, 281 µmol) was added to a suspension of N-benzyl-N-[1-[(2S)-3,4-dihydro-2H-pyran-2-yl]cyclopropyl]carbamate (100 mg, 275 µmol) and NaHCO$_3$ (46 mg, 550 mmol) in a mixture H$_2$O/MeCN (1:1) (3.0 mL) at ambient temperature. After 20 min, the volatiles were evaporated, and the residue was partitioned in between DCM (10.0 mL) and brine (10.0 mL). The aqueous layer was extracted with DCM (2×5.0 mL) and the combined organic layers were dried (Na$_2$SO$_4$), filtered and concentrated under reduced pressure to provide the title compound (>2 diastereomers, 140 mg, 92%) as a solid, which was used in the next step without further purification. MS ESI [M+H]$^+$ 417.9.

Step 5

Benzyl N-[1-[(2S)-5-azido-6-oxo-tetrahydropyran-2-yl]cyclopropyl]carbamate

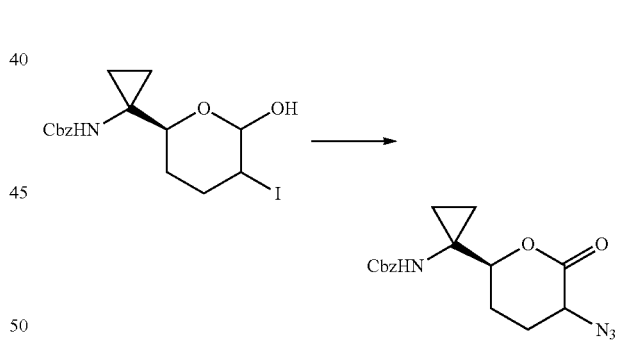

4 Å sieves (150 mg) and PDC (252 mg, 671 µmol) was added to a solution of benzyl N-[1-[(2S)-6-hydroxy-5-iodo-tetrahydropyran-2-yl]cyclopropyl]carbamate (140 mg, 336 µmol) in dry DCM (3.5 mL) under N$_2$ at ambient temperature. After 20 h, the material was filtered through a silica gel plug (1.2 mL) and was eluted with EtOAc (10.0 mL). The filtrate was concentrated under reduced pressure. The crude iodolactone (135 mg) was dissolved in dry DMF (0.40 mL) under N$_2$ and then NaN$_3$ (33 mg, 503 µmol) was added. After 1 h, the solution was filtered through a silica gel plug (1.0 mL) and eluted with EtOAc (12.0 mL). The filtrate was concentrated under reduced pressure. The mixture was re-dissolved in EtOAc and filtered through a silica gel plug (1.0 mL) and eluted with EtOAc (12.0 mL). The filtrate was concentrated under reduced pressure then lyophilized to produce the title compound (100 mg, 90%) as an oil, which was used in the next reactions without further purification. MS ESI [M+H]$^+$ 330.9.

Step 6

Benzyl N-[1-[(2S,5R)-5-azido-6-hydroxy-tetrahydropyran-2-yl]cyclopropyl]carbamate

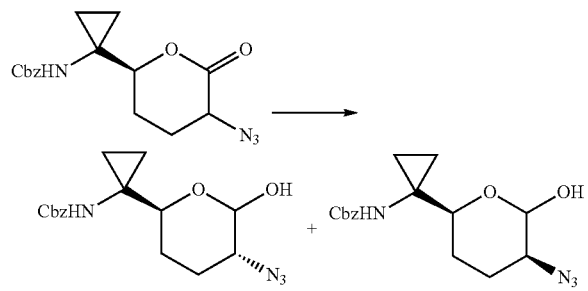

DIBAL-H (1 M, 484 µL, 484 µmol) in toluene was dropwise added to a solution of benzyl N-[1-[(2S)-5-azido-6-oxo-tetrahydropyran-2-yl]cyclopropyl]carbamate (100 mg, 303 µmol) in dry DCM (4.0 mL) at −78° C. under N$_2$ and the reaction mixture was stirred for 50 min. Acetone (150 µL) and saturated potassium sodium tartrate (5.0 mL) were added to the solution slowly. The mixture was warmed to room temperature and vigorously stirred for 16 h. The mixture was extracted with DCM (2×10 mL). The combined organic layers were dried (Na$_2$SO$_4$), filtered and concentrated under reduced pressure. The material was purified by silica gel chromatography (12 g cartridge) using a gradient of 15-40% with EtOAc and hexane as eluent and was purified by silica gel chromatography (12 g cartridge) using a gradient of 5-30% EtOAc and hexane as eluent to provide the title compound (44 mg, 44%) as a solid. MS ESI [M+Na]$^+$ 355.1.

Step 7

[(1S,2S,3R,4S,6R)-2-acetoxy-4,6-diazido-3-[(2R,3R,6S)-3-azido-6-[1-(benzyloxycarbonylamino)cyclopropyl]tetrahydropyran-2-yl]oxy-cyclohexyl] acetate

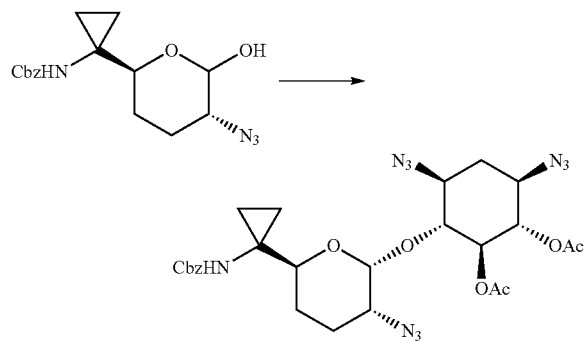

CCl$_3$CN (60 µL, 860 µmol) was added dropwise to a suspension of benzyl N-[1-[(2S,5R)-5-azido-6-hydroxy-tetrahydropyran-2-yl]cyclopropyl]carbamate (44 mg, 119 µmol) and K$_2$CO$_3$ (49 mg, 357 µmol) in dry DCM (1.0 mL) at ambient temperature under N$_2$ and the solution was stirred for 64 h. The mixture was filtered through cotton and the filtrate was concentrated under N$_2$ stream, followed by high-vacuum. To the residue was added [(1S,2S,3R,4S,6R)-2-acetoxy-4,6-diazido-3-hydroxy-cyclohexyl] acetate (50 mg, 167 µmol) and ground 4 Å sieves (300 mg) and the mixture was dissolved in dry DCM (1.0 mL). The suspension was stirred at ambient temperature for 40 min. The mixture was cooled to 0° C. and BF$_3$·OEt$_2$ (60 µL, 477 µmol) was added dropwise with vigorous stirring. The reaction mixture was warmed to ambient temperature and stirred for another 30 min. To the mixture was added Et$_3$N (100 µL) and the solution was filtered through silica gel (0.30 g) and eluted EtOAc (6.0 mL). The filtrate was concentrated and purified by preparative HPLC (BEH 30×150 mm C18 ACN/AmForm 60-70%) to provide the title compound (21 mg, 29%) as a solid. $^1$H NMR (500 MHz, CDCl$_3$) δ 7.42-7.29 (m, 5H), 5.18 (s, 1H), 5.14 (d, J=9.8 Hz, 1H), 5.11 (s, 1H), 5.05 (s, 2H), 4.91 (t, J=10.0 Hz, 1H), 3.68 (dd, J=16.4, 6.7 Hz, 2H), 3.61 (ddd, J=12.6, 10.2, 4.6 Hz, 1H), 3.54-3.41 (m, 1H), 3.00 (dt, J=6.6, 3.9 Hz, 1H), 2.34 (dt, J=13.3, 4.6 Hz, 1H), 2.07 (s, 3H), 2.07 (s, 3H), 2.03-1.92 (m, 2H), 1.92-1.85 (m, 1H), 1.57-1.45 (m, 2H), 1.10-1.02 (m, 1H), 0.91 (ddd, J=11.1, 6.6, 4.4 Hz, 1H), 0.88-0.81 (m, 1H), 0.81-0.74 (m, 1H). MS ESI [M+H]$^+$ 613.3.

Step 8

[(1S,2S,3R,4S,6R)-4,6-diazido-3-[(2R,3R,6S)-3-azido-6-[1-(benzyloxycarbonylamino)cyclopropyl]tetrahydropyran-2-yl]oxy-2-hydroxy-cyclohexyl] acetate

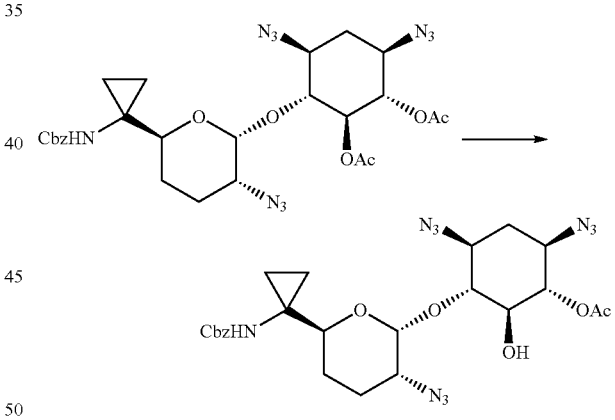

NaOMe (25 wt %, 40 µL, 173 µmol) was added dropwise to a suspension of [(1S,2S,3R,4S,6R)-2-acetoxy-4,6-diazido-3-[(2R,3R,6S)-3-azido-6-[1-(benzyloxycarbonylamino)cyclopropyl]tetrahydropyran-2-yl]oxy-cyclohexyl] acetate (21 mg, 34 µmol) in MeOH (1.0 mL) at ambient temperature and stirred for 30 min. The mixture was warmed to 40° C. and stirred for 30 min. The solution was cooled to room temperature and AcOH (20 µL, 343 µmol) was added to the reaction mixture dropwise and all volatiles were evaporated under reduced pressure. The material was filtered through silica gel (0.30 g) and eluted with EtOAc (6.0 mL). The filtrate was concentrated under reduced pressure and the residue was dissolved in dry DCM (0.50 mL) under N$_2$ and then pyridine (17 µL, 206 µmol) and Ac$_2$O (6.5 µL, 69 µmol) were added and the reaction mixture was stirred for 20 h. MeOH (100 µL) was added and all volatiles were evaporated under reduced pressure. The material was lyophilized to afford the title compound (20 mg, 99%) as a solid, which was used in the next step without further purification. $^1$H NMR (500 MHz, CDCl$_3$) δ 7.39-7.28 (m, 5H), 5.34-5.23 (m, 2H), 5.16-5.01 (m, 2H), 4.90 (dd, J=13.6, 6.3 Hz, 1H), 3.70-3.57 (m, 2H), 3.52-3.41 (m, 2H), 3.40-3.27 (m, 2H), 2.35-2.25 (m, 1H), 2.16 (s, 3H), 1.99-1.88 (m, 3H), 1.57-1.47 (m, 2H), 1.11-1.01 (m, 1H), 0.93-0.81 (m, 2H), 0.81-0.74 (m, 1H). MS ESI [M+H]$^+$ 571.2.

Step 9

[(2R,3R,4R,5S)-4-acetoxy-5-[(1S,2S,3R,5S,6R)-2-acetoxy-3,5-diazido-6-[(2R,3R,6S)-3-azido-6-[1-(benzyloxycarbonylamino)cyclopropyl]tetrahydropyran-2-yl]oxy-cyclohexoxy]-3-[(2R,3R,4R,5R,6S)-4,5-diacetoxy-3-azido-6-(azidomethyl)tetrahydropyran-2-yl]oxy-tetrahydrofuran-2-yl]methyl acetate

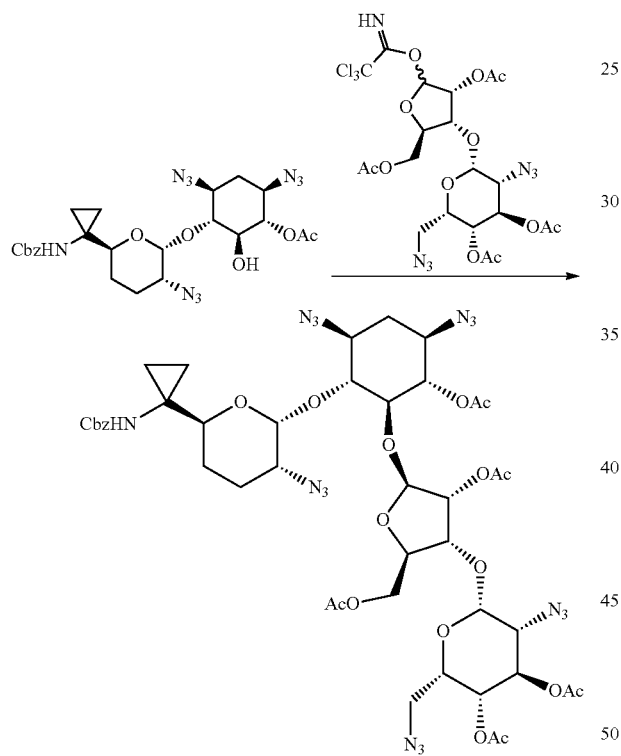

CCl$_3$CN (44 μL, 438 μmol) was added dropwise to a suspension of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (46 mg, 87 μmol) and K$_2$CO$_3$ (36 mg, 263 μmol) in dry DCM (1.0 mL) at ambient temperature under N$_2$ and stirred for 64 h. The solution was filtered through cotton and the filtrate was concentrated under N$_2$ stream, and then dried under reduced pressure. To the crude was added [(1S,2S,3R,4S,6R)-4,6-diazido-3-[(2R,3R,6S)-3-azido-6-[1-(benzyloxycarbonylamino)cyclopropyl]tetrahydropyran-2-yl]oxy-2-hydroxy-cyclohexyl] acetate (20 mg, 35 μmol) in DCM (3.0 mL) and all volatiles were evaporated under N$_2$ stream. To the mixture was added ground 4 Å sieves (300 mg) and the mixture was dissolved in dry DCM (1.0 mL). The suspension was stirred at ambient temperature for 30 min, then cooled to 0° C., followed by the addition of BF$_3$·OEt$_2$ (43 μL, 351 μmol) and the mixture was stirred at ambient temperature for another 1 h. Et$_3$N (100 μL) was added and the mixture was filtered through a silica gel pad (0.30 g) and eluted with EtOAc (5.0 mL). All volatiles were evaporated under reduced pressure and the material was purified by reversed phase chromatography (C18, 12 g cartridge) with ACN and 0.1% aqueous formic acid (50-100%) to afford the title compound (25 mg, 66%) as a solid. $^1$H NMR (500 MHz, CDCl$_3$) δ 7.40-7.30 (m, 5H), 5.76 (d, J=2.8 Hz, 1H), 5.35 (d, J=2.5 Hz, 2H), 5.06 (d, J=4.0 Hz, 2H), 5.02 (t, J=2.8 Hz, 1H), 4.93 (dd, J=12.1, 6.5 Hz, 2H), 4.87 (d, J=1.8 Hz, 1H), 4.71-4.68 (m, 1H), 4.44-4.37 (m, 2H), 4.33 (td, J=6.1, 2.1 Hz, 1H), 4.21 (dd, J=12.0, 5.7 Hz, 1H), 4.08 (ddd, J=8.1, 4.2, 1.8 Hz, 1H), 3.88 (t, J=8.6 Hz, 1H), 3.72 (t, J=8.7 Hz, 1H), 3.63-3.53 (m, 2H), 3.49-3.39 (m, 2H), 3.32 (s, 1H), 3.23 (dd, J=12.6, 4.3 Hz, 1H), 2.89 (dt, J=7.8, 3.1 Hz, 1H), 2.32-2.21 (m, 1H), 2.17 (s, 3H), 2.15 (s, 6H), 2.12 (s, 3H), 2.06-2.00 (m, 1H), 1.98-1.82 (m, 2H), 1.50-1.41 (m, 2H), 1.13-1.02 (m, 1H), 0.91-0.76 (m, 4H). MS ESI [M+H]$^+$ 1083.4.

Step 10

Benzyl N-[1-[(2S,5R,6R)-5-azido-6-[(1R,2R,3S,4R,6S)-4,6-diazido-2-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl)tetrahydrofuran-2-yl]oxy-3-hydroxy-cyclohexoxy]tetrahydropyran-2-yl]cyclopropyl]carbamate

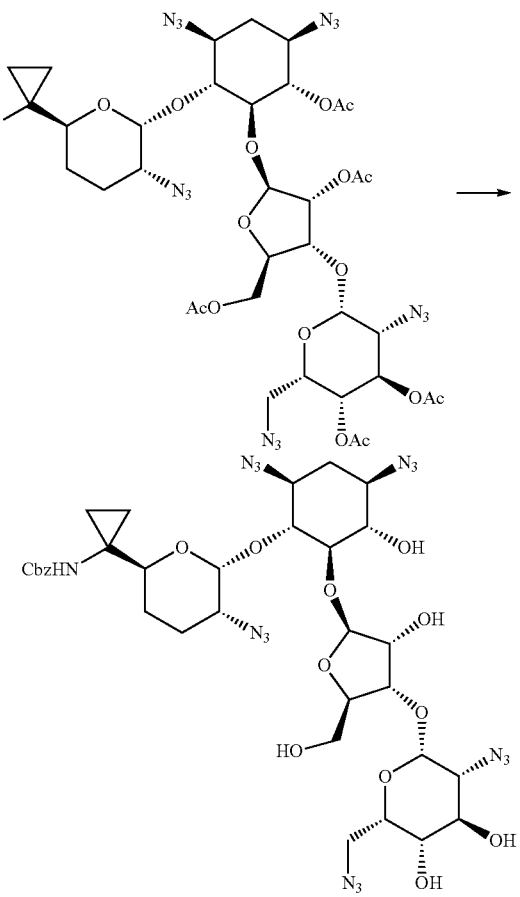

NaOMe (25 wt %, 63 μL, 277 μmol) was added dropwise to a solution of [(2R,3R,4R,5S)-4-acetoxy-5-[(1S,2S,3R,5S,6R)-2-acetoxy-3,5-diazido-6-[(2R,3R,6S)-3-azido-6-[1-(benzyloxycarbonylamino)cyclopropyl]tetrahydropyran-2-yl]oxy-cyclohexoxy]-3-[(2R,3R,4R,5R,6S)-4,5-diacetoxy-3-azido-6-(azidomethyl)tetrahydropyran-2-yl]oxy-tetrahydrofuran-2-yl]methyl acetate (25 mg, 23 μmol) in MeOH (1.0 mL) at ambient temperature and stirred for 75 min. AcOH (24 μL, 416 μmol) was added dropwise and all volatiles were evaporated under reduced pressure. The material was filtered through silica gel (0.30 g) and eluted with EtOAc (6.0 mL). The filtrate was concentrated under reduced pressure and the material was purified by silica gel chromatography (4 g cartridge) using a gradient of 50-100% EtOAc in hexane as eluent and was further purified by supercritical fluid chromatography (Lux Cellulose-2 10×250 mm-25 ACN-EtOH-10 mL/min) to provide the title compound (8 mg, 39%) as a solid. MS ESI [M+NH$_4$]$^+$ 890.3; MS ESI [M+Na]$^+$ 895.3.

Step 11

(2S,3S,4R,5R,6R)-5-amino-2-(aminomethyl)-6-[(2R,3S,4R,5S)-5-[(1R,2R,3S,5R,6S)-3,5-diamino-2-[(2R,3R,6S)-3-amino-6-(1-aminocyclopropyl)tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol;2,2,3,3,4,4,4-heptafluorobutanoic acid Pd(OH)$_2$/C (10 wt %, 2.6 mg, 1.8 μmol) was added to a solution of benzyl N-[1-[(2S,5R,6R)-5-azido-6-[(1R,2R,3S,4R,6S)-4,6-diazido-2-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl)tetrahydrofuran-2-yl]oxy-3-hydroxy-cyclohexoxy]tetrahydropyran-2-yl]cyclopropyl]carbamate (8 mg, 9 μmol) in MeOH (3.0 mL) under N$_2$ at ambient temperature. H$_2$ was bubbled into the solution for 15 min and the suspension was hydrogenated for 21 h. The material was filtered through a frit (0.45 m diameter) and the filtrate was concentrated under reduced pressure. The material was purified by a HFBA-coupled preparative HPLC to provide the title compound (hexa-HFBA salt, 10.8 mg, 62%) as a solid. $^1$H NMR (500 MHz, MeOD) δ 5.91 (d, J=3.4 Hz, 1H), 5.47 (d, J=3.0 Hz, 1H), 5.31 (d, J=1.4 Hz, 1H), 4.49 (t, J=5.3 Hz, 1H), 4.31 (dd, J=4.8, 3.1 Hz, 1H), 4.30-4.27 (m, 1H), 4.22 (td, J=5.3, 3.0 Hz, 1H), 4.17-4.10 (m, 2H), 3.99 (dd, J=12.0, 2.3 Hz, 1H), 3.91-3.83 (m, 2H), 3.74 (dd, J=12.1, 5.2 Hz, 1H), 3.70-3.66 (m, 1H), 3.66-3.60 (m, 1H), 3.55 (ddd, J=12.9, 10.4, 4.0 Hz, 1H), 3.49 (dt, J=12.9, 4.1 Hz, 1H), 3.46-3.42 (m, 1H), 3.37 (dd, J=13.4, 7.2 Hz, 1H), 3.29-3.22 (m, 2H), 2.48 (dt, J=12.4, 4.1 Hz, 1H), 2.16-2.02 (m, 2H), 1.97-1.88 (m, 1H), 1.81 (dd, J=13.3, 2.3 Hz, 1H), 1.64-1.52 (m, 1H), 1.08-0.91 (m, 4H). MS (ESI) [M+H]$^+$ 609.4.

Example 13

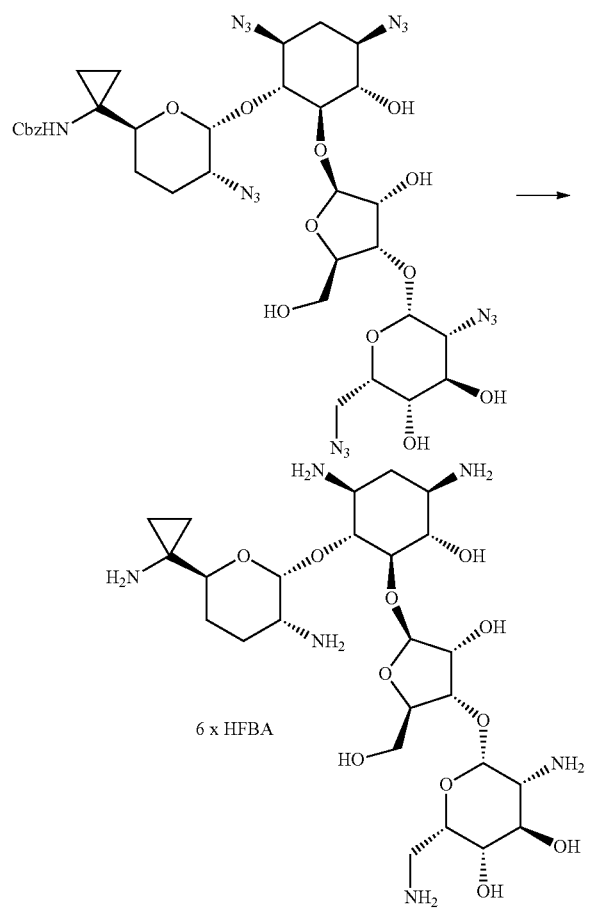

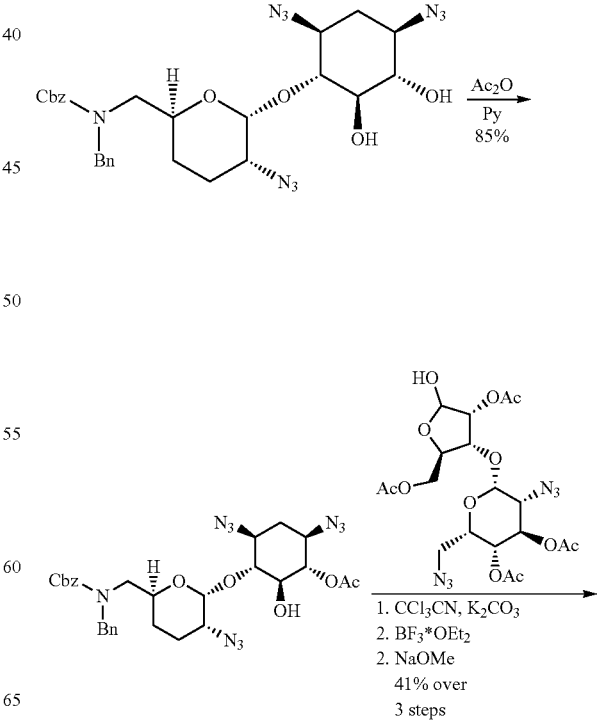

405

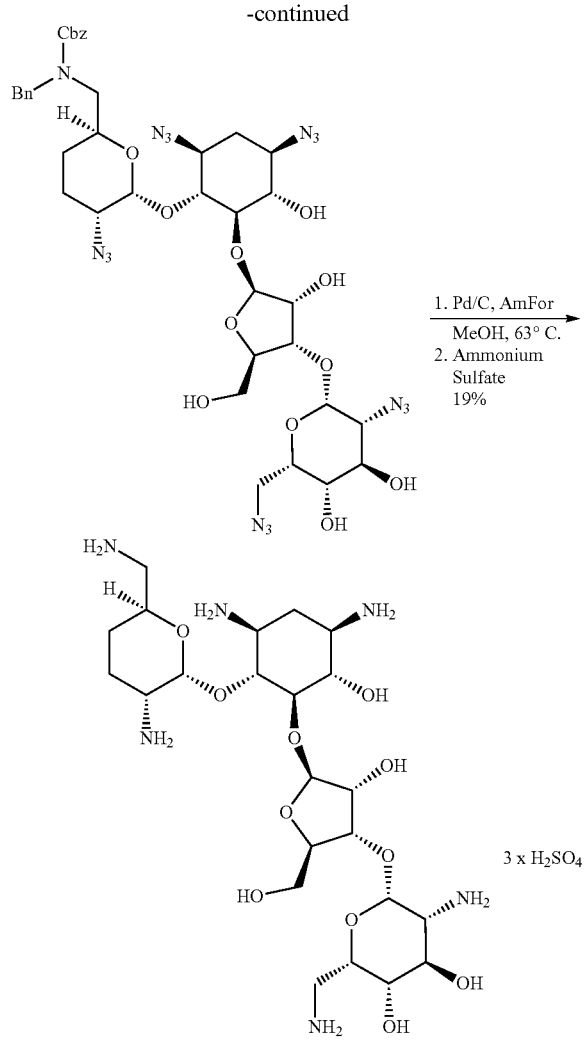

Step 1

[(1S,2S,3R,4S,6R)-4,6-diazido-3-[(2R,3R,6S)-3-azido-6-[[benzyl(benzyloxycarbonyl) amino]methyl] tetrahydropyran-2-yl]oxy-2-hydroxy-cyclohexyl] acetate

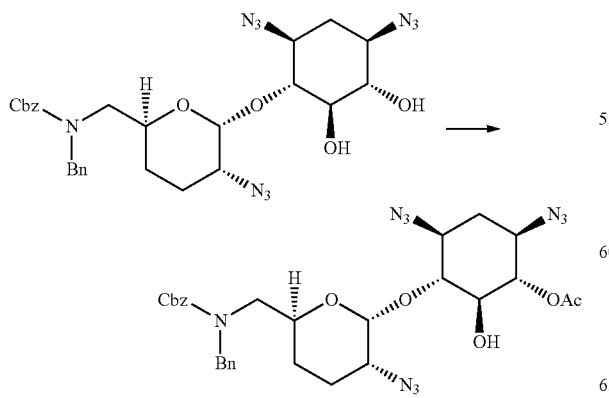

406

To a solution of benzyl N-[[(2S,5R,6R)-5-azido-6-[(1R,2R,3S,4R,6S)-4,6-diazido-2,3-dihydroxy-cyclohexoxy]tetrahydropyran-2-yl]methyl]-N-benzyl-carbamate (see Example 11 for synthesis, 4.4 g, 4.42 mmol) and pyridine (3.60 mL, 44.5 mmol) in dry DCM (400 mL) at room temperature was added $Ac_2O$ (3.51 mL, 37.1 mmol) and the reaction mixture was stirred for 20 h. MeOH (5 mL) was added, and the volatiles were removed under reduced pressure. The material was purified by MPLC on silica gel (220 g, liquid loading with toluene) using a gradient of 0-35% EtOAc in hexane as eluent to provide the title compound (4.0 g, 85%) as a solid. MS (ESI) $[M+H]^+$ 635.3.

Step 2

Benzyl ((R)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H-pyran-2-yl)ethyl)(benzyl)carbamate

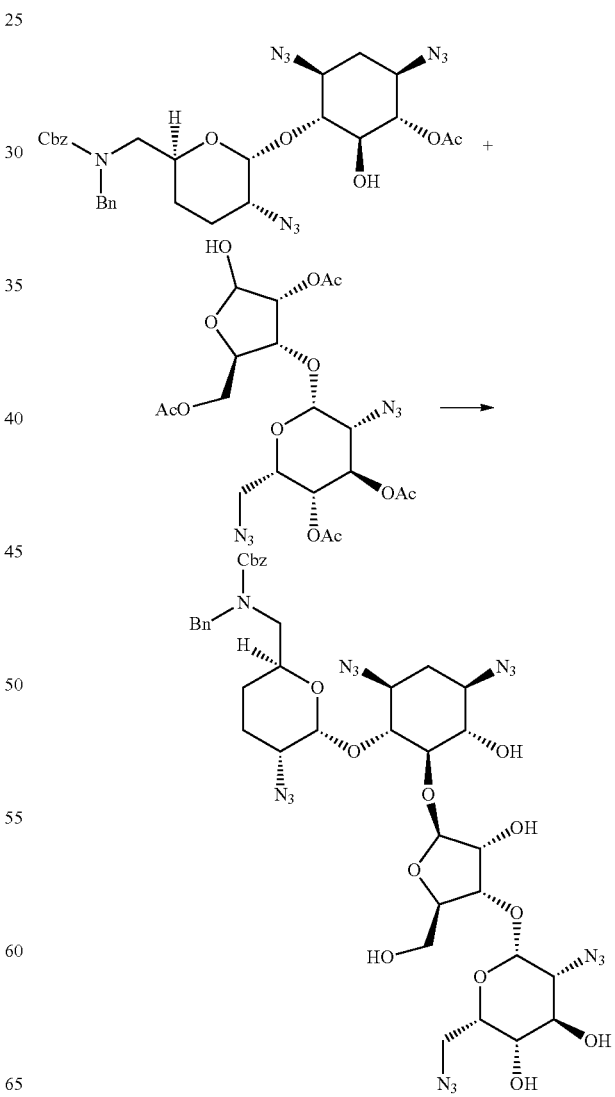

407

To a mixture of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (3.08 g, 5.80 mmol) and K₂CO₃ (2.79 g, 20.2 mmol) in DCM (500 mL) was added CCl₃CN (2.53 mL, 25.2 mmol) at room temperature. The mixture was stirred at room temperature for 18 h, then filtered on Celite, rinsed with DCM and concentrated under reduced pressure. To the above material in dry DCM (500 mL) was added [(1S,2S,3R,4S,6R)-4,6-diazido-3-[(2R,3R,6S)-3-azido-6-[(1R)-1-[benzyl(benzyloxycarbonyl)amino]ethyl]tetrahydropyran-2-yl]oxy-2-hydroxy-cyclohexyl]acetate (3.20 g, 5.04 mmol) followed by activated 3 Å sieves (5 g). The mixture was cooled to −78° C. and then BF₃·OEt₂ (1.56 mL, 12.6 mmol) was added dropwise. The acetone-dry ice bath was removed, and the reaction mixture was slowly warmed to room temperature, and then saturated NaHCO₃ (40 mL) was added. The separated aqueous layer was extracted with DCM (3×150 mL). The combined organic layers were washed with brine, then dried (MgSO₄), filtered and concentrated under reduced pressure. The residue was dissolved in MeOH (200 mL) then NaOMe (4.62 M in MeOH, 3.62 mL, 16.7 mmol) was added at room temperature and the resulting mixture was stirred for 1 h. The mixture was diluted with saturated NH₄Cl (300 mL) and the separated aqueous layer was extracted with DCM (3×300 mL). The combined organic layers were washed with brine, then dried (MgSO₄), filtered and concentrated under reduced pressure. The material was purified on C18 silica (120 g) by MPLC using a gradient of 30-100% B in A (A: 10 mm AmFor pH 3.8, B: acetonitrile) to provide the title compound (1.90 g, 410%) as a solid. MS (ESI) [M+Na]⁺ 959.4.

Step 3

(2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-(aminomethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol tris(sulfate)

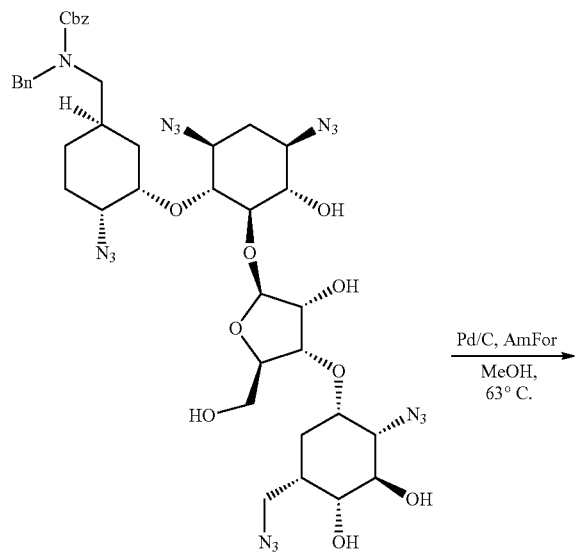

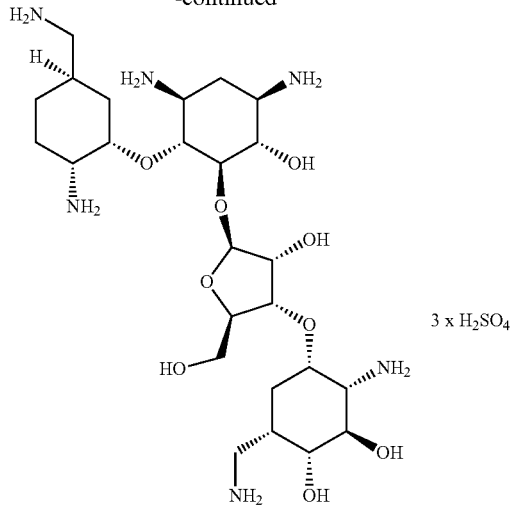

In a 2 neck flask equipped with a reflux condenser were benzyl (((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl) tetrahydrofuran-2-yl)oxy)-3-hydroxycyclohexyl)oxy)tetrahydro-2H-pyran-2-yl)methyl)(benzyl) carbamate (1.60 g, 0.04 mmol) and Pd/C (10% dry on carbon, 727 mg, 0.683 mmol) following by anhydrous MeOH (500 mL). Nitrogen was bubbled for 5 min, then ammonium formate (1.62 g, 25.6 mmol) was added. The mixture was heated at 63° C. for 5 h under N₂, then cooled to room temperature with an ice-bath. The mixture was filtered over Celite, rinsed with MeOH and concentrated under reduced pressure. The material was purified by preparative HPLC using a gradient 27-37% B in A over 6.9 min (A: 0.3% HCOOH, 0.3% HFBA, B: 0.3% HFBA in ACN) on C18 Gemini-NX 30×150 mm provide the title compound (850 mg, 27%) as a 6×HFBA salt. The salt was dissolved in water (10 mL), then the pH was adjusted to 7 using 0.1 N aqueous NH₄OH. Ammonium sulfate (3 eq, 180 mg, 1.37 mmol) was then added. The mixture was stirred at room temperature for 5 min, then filtered with 0.40 μM syringe filter and added dropwise to MeOH (450 mL) under vigorous stirring. The suspension was filter on Fine frit and rinsed with MeOH (20 mL). The mother liquor was discarded and the solid was dissolved in water (50 mL) and lyophilized to provide the title compound (282 mg, 19%) as a solid. ¹H NMR (500 MHz, D₂O) δ 5.94 (d, J=3.6 Hz, 1H), 5.44 (d, J=2.3 Hz, 1H), 5.33 (d, J=1.7 Hz, 1H), 4.56 (dd, J=6.7, 4.8 Hz, 1H), 4.47 (dd, J=4.8, 2.3 Hz, 1H), 4.36 (ddd, J=7.0, 3.8, 1.4 Hz, 1H), 4.29-4.24 (m, 2H), 4.16 (dd, J=12.6, 6.6 Hz, 2H), 3.98-3.90 (m, 2H), 3.86-3.84 (m, 1H), 3.81-3.74 (m, 2H), 3.64-3.61 (m, 1H), 3.61-3.55 (m, 1H), 3.54-3.44 (m, 2H), 3.42-3.35 (m, 2H), 3.26 (dd, J=13.4, 3.3 Hz, 1H), 3.10 (dd, J=13.5, 8.2 Hz, 1H), 2.74-2.43 (m, 1H), 2.12-1.91 (m, 4H), 1.66-1.54 (m, 1H). MS (ESI) [M+H]⁺ 583.5.

409
Example 14
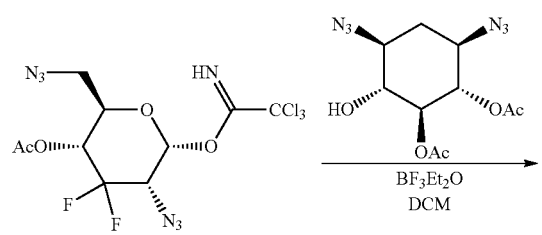
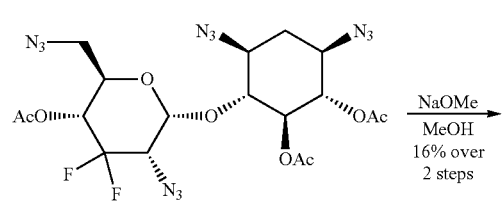
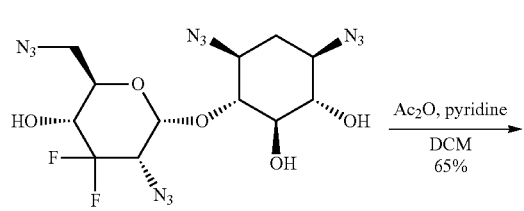
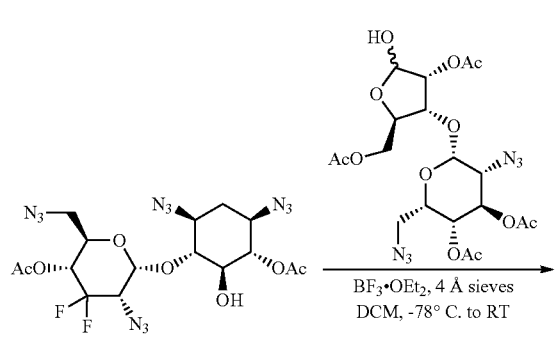
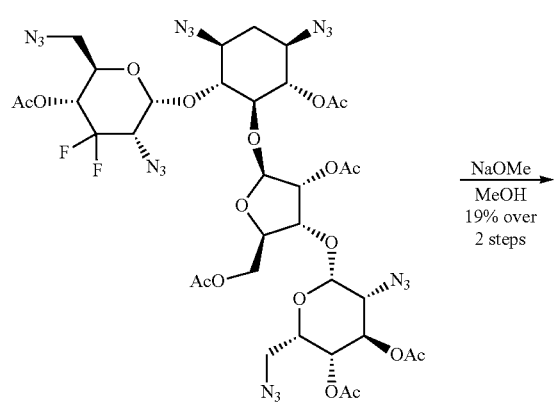
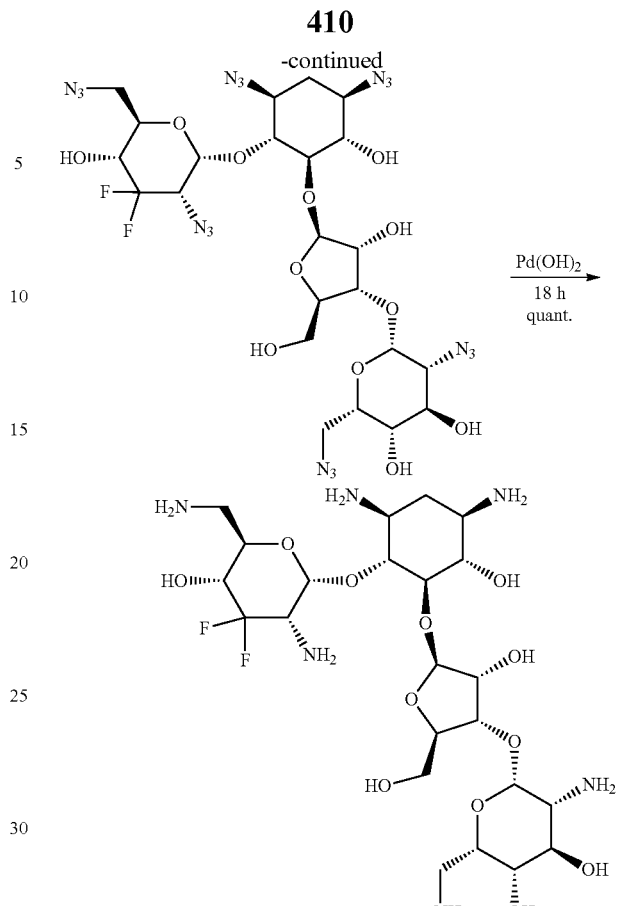
Step 1
(1S,2R,3R,4S,6R)-4,6-diazido-3-[(2R,3S,5R,6R)-3-azido-6-(azidomethyl)-4,4-difluoro-5-hydroxy-tetrahydropyran-2-yl]oxy-cyclohexane-1,2-diol

[(2R,3R,5S,6S)-5-azido-2-(azidomethyl)-4,4-difluoro-6-hydroxy-tetrahydropyran-3-yl]acetate (preparation below, 250 mg, 0.57 mmol), [(1S,2S,3R,4S,6R)-2-acetoxy-4,6-diazido-3-hydroxy-cyclohexyl] acetate (384 mg, 1.29 mmol) and grounded 4 Å molecular sieves were added to a dry round bottom flask. The mixture was dissolved in dry DCM (8.0 mL) and the suspension was stirred at ambient temperature for 45 min under $N_2$. The solution was cooled to −78° C. and then $BF_3 \cdot Et_2O$ (0.53 mL, 4.29 mmol) was added dropwise with vigorous stirring and the reaction was stirred at −78° C. for 1 h. The solution was warmed to ambient temperature and stirred for another 3 h. The reaction was quenched with saturated $NaHCO_3$ (50.0 mL) and the aqueous layer was extracted with DCM (3×50 mL). The combined organic layers were dried ($Na_2SO_4$), filtered and concentrated under reduced pressure.

Step 2

NaOMe (25 wt %, 0.56 mL, 2.58 mmol) was added dropwise to a solution of the crude in MeOH (2.0 mL) at ambient temperature. After 70 min, AcOH (0.26 mL, 4.58 mmol) was added and the volatiles were removed under reduced pressure. The material was purified by silica gel chromatography (24 g, dry loading) using a gradient of 0-40% EtOAc in hexane as eluent to provide the title compound (60.2 mg, 24%). $^1$H NMR (400 MHz, $CD_3OD$) δ 5.81 (t, J=4.2 Hz, 1H), 4.50 (ddd, J=10.1, 4.5, 2.8 Hz, 1H), 3.84-3.70 (m, 1H), 3.62-3.40 (m, 7H), 3.29 (t, J=9.5 Hz, 1H), 2.31 (dt, J=12.9, 4.4 Hz, 1H), 1.47 (dd, J=24.8, 12.2 Hz, 1H).

Step 3

[(1S,2S,3R,4S,6R)-3-[(2R,3S,5R,6R)-5-acetoxy-3-azido-6-(azidomethyl)-4,4-difluoro-tetrahydropyran-2-yl]oxy-4,6-diazido-2-hydroxy-cyclohexyl] acetate

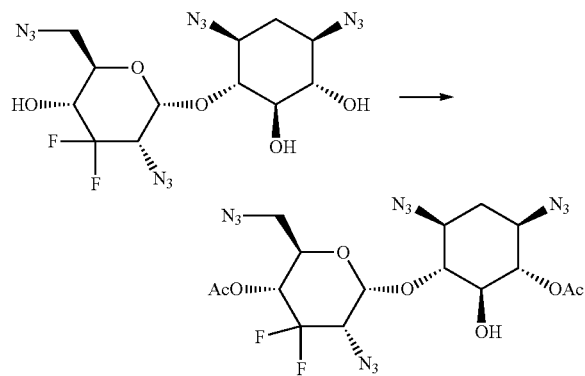

To a solution of (1S,2R,3R,4S,6R)-4,6-diazido-3-[(2R,3S,5R,6R)-3-azido-6-(azidomethyl)-4,4-difluoro-5-hydroxy-tetrahydropyran-2-yl]oxy-cyclohexane-1,2-diol (60 mg, 134 μmol) in dry DCM (2 mL) at ambient temperature, was added pyridine (87 μL, 1.08 mmol) followed by $Ac_2O$ (76 μL, 807 μmol) and the reaction mixture was stirred for 20 h. The volatiles were evaporated under reduced pressure and the material was purified silica gel chromatography (4 g, dry loading) using a gradient of 10-30% EtOAc in hexane as eluent to provide the title compound (56.9 mg, 80%). $^1$H NMR (400 MHz, $CDCl_3$) δ 5.53 (t, J=4.3 Hz, 1H), 5.17 (ddd, J=19.5, 10.4, 4.0 Hz, 1H), 4.86 (t, J=9.9 Hz, 1H), 4.52-4.43 (m, 1H), 3.71 (td, J=9.3, 4.2 Hz, 1H), 3.62 (dt, J=23.3, 4.2 Hz, 1H), 3.55-3.22 (m, 6H), 2.36 (dt, J=13.1, 4.3 Hz, 1H), 2.21-2.11 (m, 6H), 1.62-1.53 (m, 1H).

Step 4

[(2R,3R,4R,5S)-4-acetoxy-5-[(1S,2S,3R,5S,6R)-2-acetoxy-6-[(2R,5R,6R)-5-acetoxy-3-azido-6-(azidomethyl)-4,4-difluoro-tetrahydropyran-2-yl]oxy-3,5-diazido-cyclohexoxy]-3-[(2R,4R,5R,6S)-4,5-diacetoxy-3-azido-6-(azidomethyl)tetrahydropyran-2-yl]oxy-tetrahydrofuran-2-yl]methyl acetate

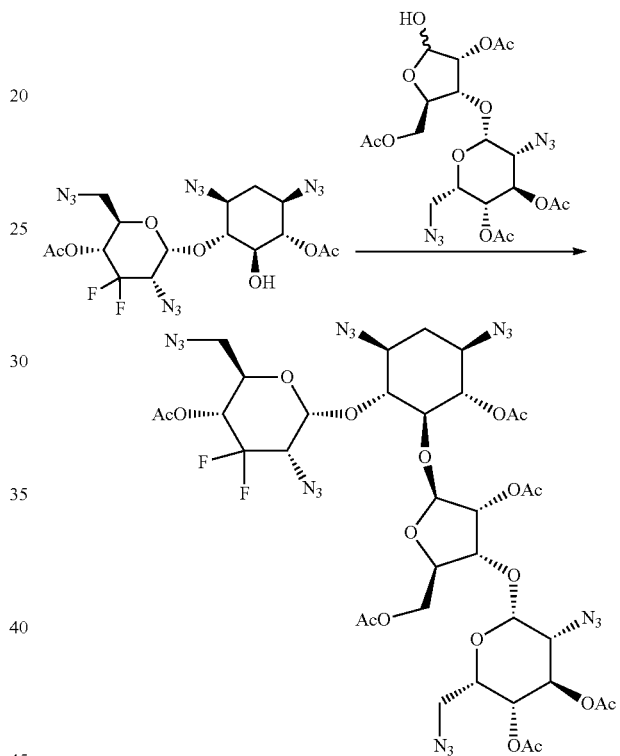

$CCl_3CN$ (0.16 mL, 1.64 mmol) was added dropwise to a mixture of [(2R,3R,4R)-4-acetoxy-3-[(2R,3R, 4R,5R,6S)-4,5-diacetoxy-3-azido-6-(azidomethyl)tetrahydropyran-2-yl]oxy-5-hydroxy-tetrahydrofuran-2-yl]methyl acetate (174 mg, 0.33 mmol) and $K_2CO_3$ (136 mg, 0.98 mmol) in dry DCM (10 mL) at room temperature under $N_2$. The mixture was stirred at room temperature for 18 h, then filtered with a filter syringe and rinsed with DCM. The filtrate was concentrated under reduced pressure and the crude imidate was used directly in the next step.

To a solution of [(1S,2S,3R,4S,6R)-3-[(2R,3S,5R,6R)-5-acetoxy-3-azido-6-(azidomethyl)-4,4-difluoro-tetrahydropyran-2-yl]oxy-4,6-diazido-2-hydroxy-cyclohexyl] acetate (58 mg, 0.11 mmol) in DCM (10 mL) was added the crude imidate followed by 4 Å molecular sieves and the mixture was stirred for 2 h and then cooled to −78° C. $BF_3 \cdot OEt_2$ (0.068 mL, 0.55 mmol) was added dropwise. The mixture was stirred at −78° C. for 2 h and then at room temperature for 2 h. The mixture was diluted with saturated $NaHCO_3$ (10 mL) and the separated aqueous layer was extracted with DCM (2×10 mL). The combined organic layers were washed with brine, dried (Na₂SO₄), filtered and concentrated under reduced pressure to afford the title compound. MS ESI [M+NH₄]⁺1060.4.

Step 5

(2S,3S,4R,5R,6R)-5-azido-2-(azidomethyl)-6-[(2R,3S,4R,5S)-5-[(1R,2R,3S,5R,6S)-3,5-diazido-2-[(2R,3S,5R,6R)-3-azido-6-(azidomethyl)-4,4-difluoro-5-hydroxy-tetrahydropyran-2-yl]oxy-6-hydroxy-cyclohexoxy]-4-hydroxy-2-(hydroxymethyl) tetrahydrofuran-3-yl]oxy-tetrahydropyran-3,4-diol

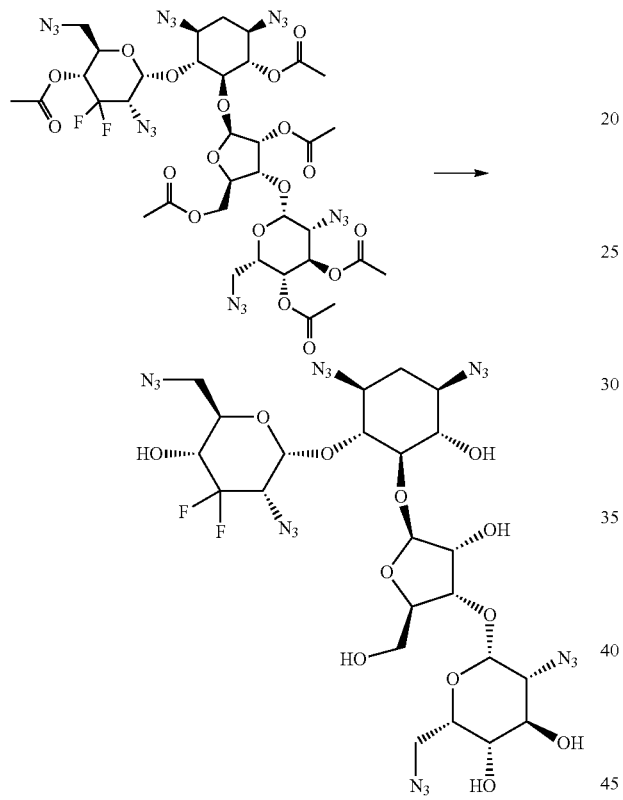

To a solution of crude [(2R,3R,4R,5S)-4-acetoxy-5-[(1S,2S,3R,5S,6R)-2-acetoxy-6-[(2R,5R,6R)-5-acetoxy-3-azido-6-(azidomethyl)-4,4-difluoro-tetrahydropyran-2-yl]oxy-3,5-diazido-cyclohexoxy]-3-[(2R,4R,5R,6S)-4,5-diacetoxy-3-azido-6-(azidomethyl)tetrahydropyran-2-yl]oxy-tetrahydrofuran-2-yl]methyl acetate (114 mg, 109 μmol) in MeOH (2 mL) at ambient temperature, was added NaOMe (25 wt %, 337 μL, 1.31 mmol) dropwise and the reaction mixture was stirred for 50 min. The mixture was diluted with AcOH (125 mL, 2.18 mmol) and the volatiles were evaporated under reduced pressure. The material was purified by silica gel chromatography (12 g cartridge) using a gradient of 5-35% EtOAc and hexane as eluent and was further purified by reverse phase (C18, 120 g Biotage) using 50% B in A to 100% B (B=ACN 0.1% HCOOH, A=H₂O 0.1% HCOOH) to provide the title compound. The material purified with preparative HPLC (ACN, AmFor, CSH column) to give the title compound (16 mg, 19%, 2 steps from [(1S,2S,3R,4S,6R)-3-[(2R,3S,5R,6R)-5-acetoxy-3-azido-6-(azidomethyl)-4,4-difluoro-tetrahydropyran-2-yl]oxy-4,6-di-azido-2-hydroxy-cyclohexyl] acetate). ¹H NMR (400 MHz, CD₃OD) δ 5.92 (t, J=4.1 Hz, 1H), 5.32 (d, J=2.0 Hz, 1H), 5.10 (d, J=1.8 Hz, 1H), 4.46 (ddd, J=10.2, 4.7, 2.6 Hz, 1H), 4.37 (dd, J=6.6, 4.6 Hz, 1H), 4.29 (dd, J=4.5, 2.0 Hz, 1H), 4.11 (td, J=6.1, 2.7 Hz, 1H), 3.99 (ddd, J=8.5, 4.4, 1.9 Hz, 1H), 3.90 (t, J=3.4 Hz, 1H), 3.82 (dd, J=11.9, 2.7 Hz, 1H), 3.74-3.29 (m, 14H), 2.23 (dt, J=12.8, 4.0 Hz, 1H), 1.46-1.32 (m, 1H). MS ESI [M+NH₄]⁺808.2.

Step 6

(2S,3S,4R,5R,6R)-5-amino-2-(aminomethyl)-6-[(2R,3S,4R,5S)-5-[(1R,2R,3S,5R,6S)-3,5-diamino-2-[(2R,3S,5R,6R)-3-amino-6-(aminomethyl)-4,4-difluoro-5-hydroxy-tetrahydropyran-2-yl]oxy-6-hydroxy-cyclohexoxy]-4-hydroxy-2-(hydroxymethyl) tetrahydrofuran-3-yl]oxy-tetrahydropyran-3,4-diol

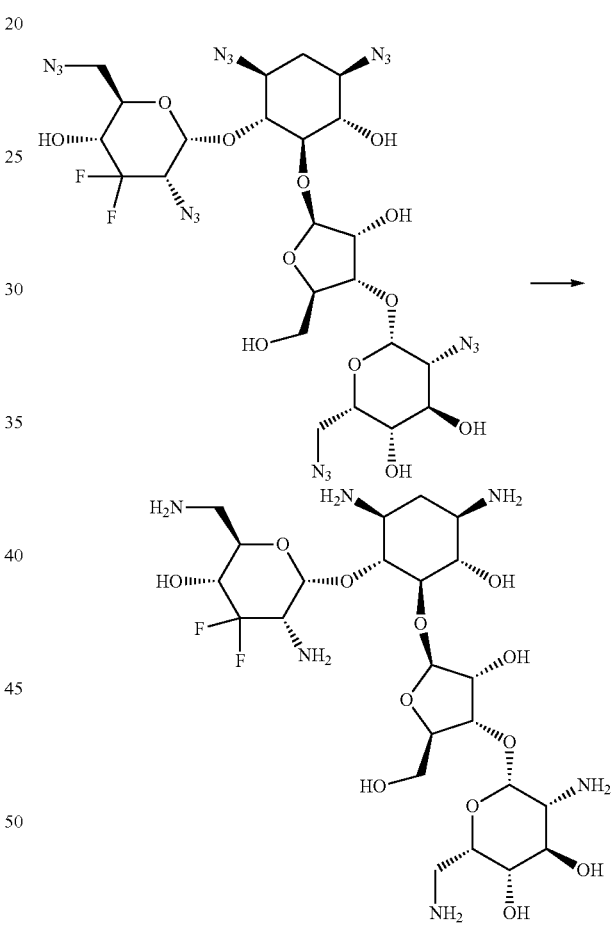

To (2S,3S,4R,5R,6R)-5-azido-2-(azidomethyl)-6-[(2R,3S,4R,5S)-5-[(1R,2R,3S,5R,6S)-3,5-diazido-2-[(2R,3S,5R,6R)-3-azido-6-(azidomethyl)-4,4-difluoro-5-hydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol (8.0 mg, 10.1 μmol) under N₂ at ambient temperature was added Pd(OH)₂/C (10 wt %, 5.0 mg, 3.5 μmol) followed by MeOH (3.0 mL) and the resulting suspension was bubbled with H₂ for 10 min. The mixture was hydrogenated under hydrogen atmosphere (1 atm, balloon) for 16 h. The suspension was filtered through a nylon filter (0.45 μm), rinsed with MeOH and the filtrate was concentrated under reduced pressure to give the title compound. The procedure was repeated to give the title compound (9.5 mg with 74% yield in total). $^1$H NMR (500 MHz, CD$_3$OD) δ 5.72 (s, 1H), 5.38 (d, J=2.1 Hz, 1H), 4.97 (d, J=1.6 Hz, 1H), 4.45 (dd, J=6.6, 5.0 Hz, 1H), 4.19 (dd, J=4.9, 2.2 Hz, 1H), 4.09 (dd, J=6.7, 3.3 Hz, 1H), 4.00-3.93 (m, 2H), 3.89 (dd, J=12.2, 5.4 Hz, 1H), 3.83 (dd, J=12.3, 2.8 Hz, 1H), 3.74 (dd, J=12.2, 3.6 Hz, 1H), 3.63 (t, J=9.2 Hz, 2H), 3.54-3.49 (m, 2H), 3.26 (t, J=9.5 Hz, 1H), 3.22-3.10 (m, 3H), 3.02 (s, 1H), 2.96 (dd, J=13.3, 3.8 Hz, 1H), 2.86 (dt, J=17.5, 8.7 Hz, 2H), 2.73-2.66 (m, 1H), 2.00 (dt, J=12.9, 4.1 Hz, 1H), 1.28-1.22 (m, 1H). MS ESI [M+H]$^+$ 635.4.

Preparation of [(2R,3R,5S,6S)-5-azido-2-(azidomethyl)-4,4-difluoro-6-hydroxy-tetrahydropyran-3-yl] acetate

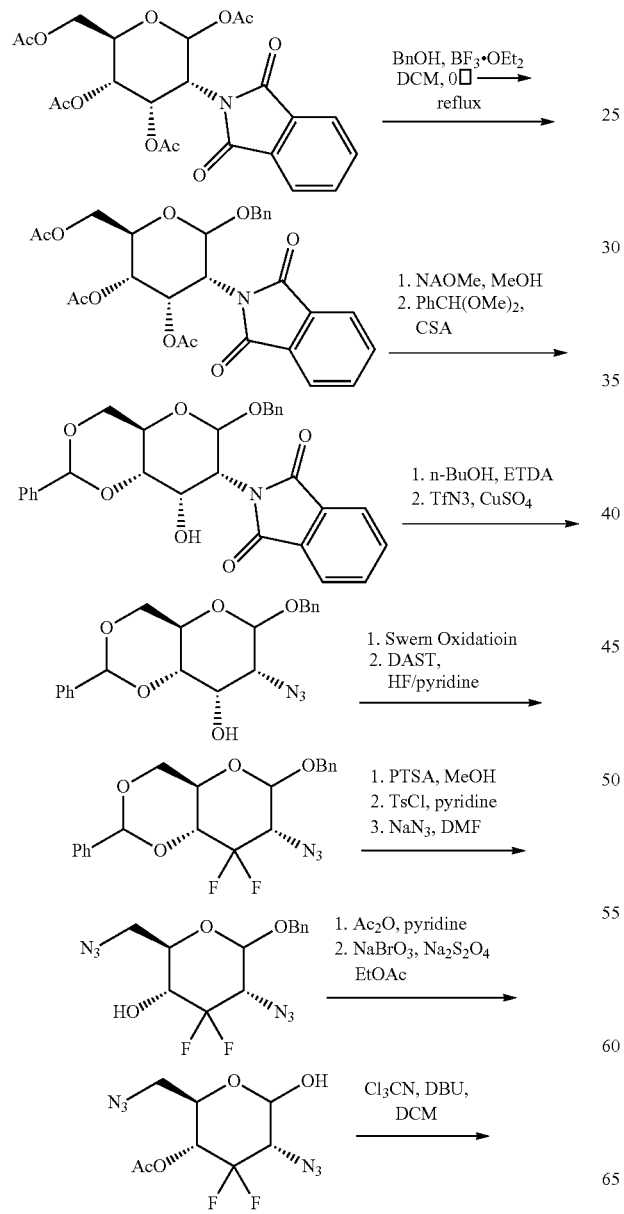

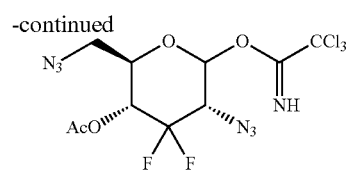

Step 1

(2R,3S,4R,5R)-2-(acetoxymethyl)-6-(benzyloxy)-5-(1,3-dioxoisoindolin-2-yl)tetrahydro-2H-pyran-3,4-diyl diacetate

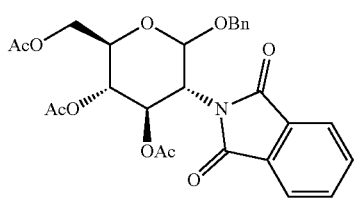 [SMILES: CC(=O)OC[C@H]1OC(OCc2ccccc2)[C@H](N2C(=O)c3ccccc3C2=O)[C@@H](OC(C)=O)[C@@H]1OC(C)=O]

To a solution of 23 g (3R,4R,5S,6R)-6-(acetoxymethyl)-3-(1,3-dioxoisoindolin-2-yl)tetrahydro-2H-pyran-2,4,5-triyl triacetate and 10.4 g of benzyl alcohol in 100 mL of anhydrous DCM was added 29.7 mL of BF$_3$ OEt$_2$ at 0° C. The temperature was raised to 35° C. and stirred for 12 hours until completion. The reaction was diluted with 250 mL of DCM and washed with 2×250 mL ice cold water and 1×250 mL aqueous sodium bicarbonate. The organic layer was dried, filtered, concentrated and purified by flash chromatography to yield 22.3 g of (3R,4R,5S,6R)-6-(acetoxymethyl)-3-(1,3-dioxoisoindolin-2-yl)tetrahydro-2H-pyran-2,4,5-triyl triacetate (88% yield).

Step 2

2-((4aR,7R,8R,8aS)-6-(benzyloxy)-8-hydroxy-2-phenylhexahydropyrano[3,2-d][1,3]dioxin-7-yl)isoindoline-1,3-dione

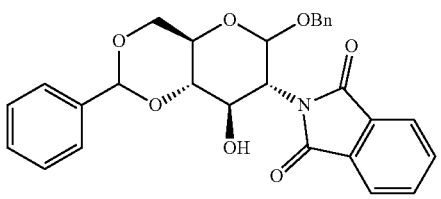

A solution of 55 g of (2R,3S,4R,5R)-2-(acetoxymethyl)-6-(benzyloxy)-5-(1,3-dioxoisoindolin-2-yl)tetrahydro-2H-pyran-3,4-diyl diacetate in 500 mL of methanol/DCM (3:2) was cooled to −10° C. 160 mL of 0.3 M sodium methoxide (in methanol) was added and the reaction continued stirring at 0° C. for two hours. The reaction was neutralized with amberlyst resin, filtered and concentrated. The concentrated residue was dissolved in 500 mL acetonitrile and 23.75 g of benzaldehyde dimethyl acetal was added, followed by 3.6 g of CSA. The reaction stirred at room temperature for one hour until completion. The reaction was quenched with triethylamine, concentrated and purified by flash chromatography (20% EtOAc in hexanes) to afford 2-((4aR,7R,8R, 8aS)-6-(benzyloxy)-8-hydroxy-2-phenylhexahydropyrano [3,2-d][1,3]dioxin-7-yl)isoindoline-1,3-dione (78% yield).

Step 3

(4aR,7R,8R,8aS)-7-azido-6-(benzyloxy)-2-phenyl-hexahydropyrano[3,2-d][1,3]dioxin-8-ol

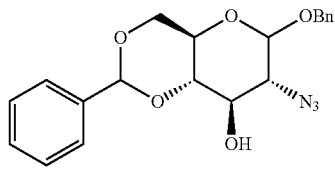

2-((4aR,7R,8R,8aS)-6-(benzyloxy)-8-hydroxy-2-phenyl-hexahydropyrano[3,2-d][1,3]dioxin-7-yl)isoindoline-1,3-dione was dissolved in n-BuOH and ethylene diamine. The solution was heated to 90° C. for 12 hours. The reaction was concentrated in vacuo, taken up in EtOAc, and washed with an equal volume of water. The organic layer was concentrated and used in the next step without further purification. 5 grams of the crude intermediate was added to a solution of 300 mL of water/methanol (1:2) containing 100 mg $CuSO_4$ and 3.85 g $K_2CO_3$. To the mixture was added 5 equivalents of $TfN_3$ in DCM at room temperature for 12 hours. 10 g of glycine was then added and the reaction stirred an additional 12 hours. The solid was filtered and washed with methanol. The filtrate was concentrated to 40% original volume and additional precipitate formed and was filtered and dissolved in DCM and dried over sodium sulfate. The dried organic portion was filtered and concentrated to yield pure (4aR,7R, 8R,8aS)-7-azido-6-(benzyloxy)-2-phenylhexahydropyrano [3,2-d][1,3]dioxin-8-ol (92% yield).

Step 4

(4aR,7S,8aR)-7-azido-6-(benzyloxy)-8,8-difluoro-2-phenylhexahydropyrano[3,2-d][1,3]dioxine

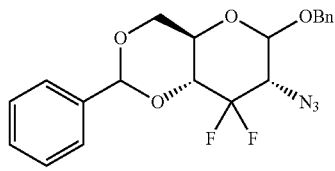

To a solution of 500 mg of (4aR,7R,8R,8aS)-7-azido-6-(benzyloxy)-2-phenylhexahydropyrano [3,2-d][1,3]dioxin-8-ol in 5 mL of DCM was added 520 μL of DAST and 15 μL of HF/Py at 0° C. and the reaction was refluxed until completion. The reaction was quenched with aqueous $NaHCO_3$ at 0° C. and the diluted with DCM. The organic layer was washed with aqueous $NaHCO_3$, dried, filtered and concentrated. The crude thus obtained was purified by column chromatography to yield 183 mg of (4aR,7S,8aR)-7-azido-6-(benzyloxy)-8,8-difluoro-2-phenylhexahydropy-rano[3,2-d][1,3]dioxine (36% yield).

Step 5

(2R,3R,5S)-5-azido-2-(azidomethyl)-6-(benzyloxy)-4,4-difluorotetrahydro-2H-pyran-3-ol

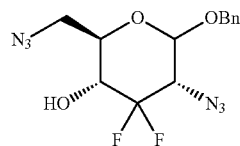 [SMILES: [N-]=[N+]=NC[C@H]1OC(OCc2ccccc2)[C@H](N=[N+]=[N-])C(F)(F)[C@@H]1O]

3.4 g of (4aR,7S,8aR)-7-azido-6-(benzyloxy)-8,8-difluoro-2-phenylhexahydropyrano[3,2-d][1,3]dioxine was dissolved in 20 mL of methanol and 219 mg of p-toluene sulfonic acid was added. The reaction was heated at 40° C. for 1 hour until completion. The reaction was quenched with 0.1 equivalents of $Et_3N$ and concentrated to dryness. The crude was purified by flash chromatography. 2.5 g of the diol was dissolved in 24 mL of DCM/pyridine (5:3) and 1.80 g of tosyl chloride was added at 0° C. The reaction was allowed to warm to room temperature and stirred for 3 hours, then diluted with DCM and washed with 1 N HCl and saturated aqueous $NaHCO_3$. The organic portion was dried, filtered and concentrated to dryness. The crude concentrate was dissolved in 30 mL of anhydrous DMF and 2.3 g of $NaN_3$ and the reaction heated at 70° C. for several hours.

The reaction was then diluted into EtOAc and washed with water. The organic portion was dried, filtered, concentrated and purified by flash chromatography to yield 2.2 g of (2R,3R,5S)-5-azido-2-(azidomethyl)-6-(benzyloxy)-4,4-di-fluorotetrahydro-2H-pyran-3-ol (77% yield).

Step 6

(2R,3R,5S)-5-azido-2-(azidomethyl)-6-(benzyloxy)-4,4-difluorotetrahydro-2H-pyran-3-yl acetate

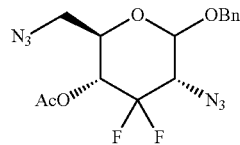 [SMILES: CC(=O)O[C@@H]1[C@@H](CN=[N+]=[N-])OC(OCc2ccccc2)[C@H](N=[N+]=[N-])C1(F)F]

(2R,3R,5S)-5-azido-2-(azidomethyl)-6-(benzyloxy)-4,4-difluorotetrahydro-2H-pyran-3-ol was dissolved in pyridine and cooled to 0° C. in an ice water bath. Acetic anhydride was added and the reaction was allowed to warm to room temperature and stir overnight. The reaction was then concentrated in vacuo, dissolved in EtOAc, and washed with 1 N HCl aq and $NaHCO_3$, then dried, filtered and concentrated. 100 mg of the crude was dissolved in 3.8 mL of EtOAc and 3 mL of aqueous sodium bromate (179 mg/3 mL) added in one portion. Next aqueous sodium dithionate (212 mg/6 mL) was added dropwise and the reaction stirred vigorously until completion. The reaction was diluted with EtOAc and washed with 1:1 aqueous $NaHCO_3$ and sodium thiosulfate. The organic layer was dried, filtered and concentrated, then purified by flash chromatography (20% EtOAc in Hexanes) to yield 70 mg of (2R,3R,5S)-5-azido-2-(azidomethyl)-6-(benzyloxy)-4,4-difluorotetrahydro-2H-pyran-3-yl acetate (93% yield).

Step 7

(2R,3R,5S)-5-azido-2-(azidomethyl)-4,4-difluoro-6-hydroxytetrahydro-2H-pyran-3-yl acetate

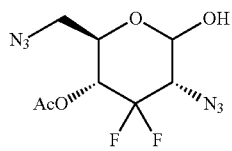 [SMILES: CC(=O)O[C@@H]1[C@@H](CN=[N+]=[N-])OC(O)[C@H](N=[N+]=[N-])C1(F)F]

1.4 grams of (2R,3R,5S)-5-azido-2-(azidomethyl)-6-(benzyloxy)-4,4-difluorotetrahydro-2H-pyran-3-yl acetate was dissolved in 54 mL EtOAc. 42 mL of aqueous sodium bromate (60 mg/mL) was added at once to the EtOAc solution, followed by 84 mL of aqueous sodium dithionate (35.3 mg/mL) was added slowly dropwise over 15 min and stirred vigorously until completion. The reaction was diluted with EtOAc and washed with 1:1 aq $NaHCO_3$ and sodium thiosulfate. The organic layer was concentrated and purified by flash column chromatography to afford 1 g of (2R,3R,5S)-5-azido-2-(azidomethyl)-4,4-difluoro-6-hydroxytetrahydro-2H-pyran-3-yl acetate (94% yield).

Step 8

(2R,3R,5S,6S)-5-azido-2-(azidomethyl)-4,4-difluoro-6-(2,2,2-trichloro-1-iminoethoxy) tetrahydro-2H-pyran-3-yl acetate

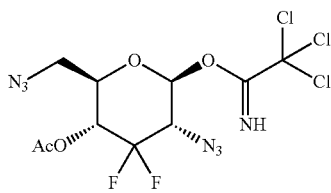 [SMILES: CC(=O)O[C@@H]1[C@@H](CN=[N+]=[N-])O[C@@H](OC(=N)C(Cl)(Cl)Cl)[C@H](N=[N+]=[N-])C1(F)F]

To a solution of 700 mg of (2R,3R,5S)-5-azido-2-(azidomethyl)-4,4-difluoro-6-hydroxytetrahydro-2H-pyran-3-yl acetate in 25 mL of anhydrous DCM was added 720 μL of trichloroacetonitrile at 0° C. To this solution, 103 μL of DBU was slowly added at the same temperature. The reaction was stirred until completion at room temperature. The reaction was diluted with DCM and washed with 1 N HCl, brine and the organic layer was concentrated. The crude thus obtained was purified by flash column chromatography (20% EtOAc in hexanes) to afford 750 mg of (2R,3R,5S,6S)-5-azido-2-(azidomethyl)-4,4-difluoro-6-(2,2,2-trichloro-1-iminoethoxy) tetrahydro-2H-pyran-3-yl acetate (75% yield).

Example 15

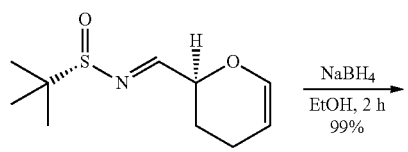

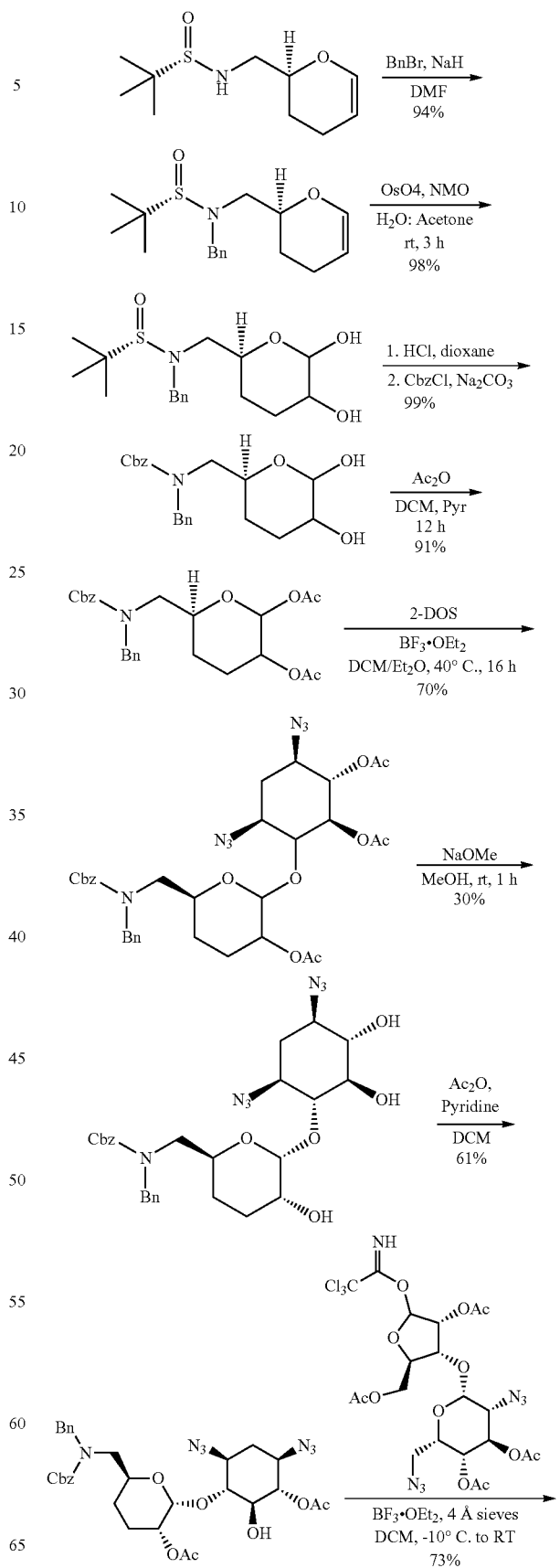

-continued

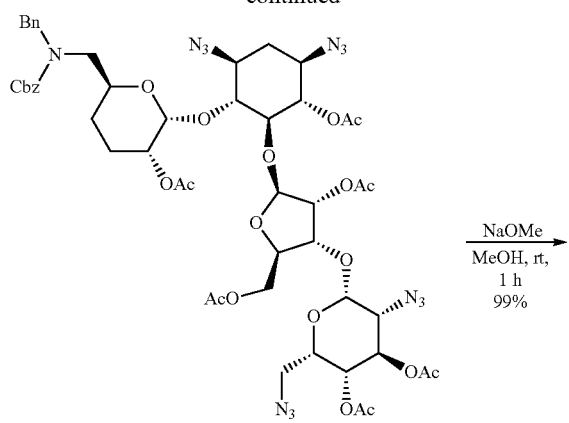

Step 1

(S)—N-[[(2S)-3,4-dihydro-2H-pyran-2-yl]methyl]-2-methyl-propane-2-sulfinamide

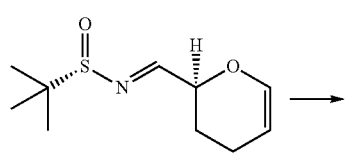

-continued

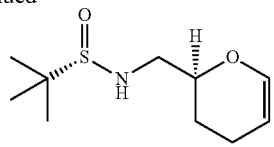

To a solution of (NE, S)—N-[[(2S)-3,4-dihydro-2H-pyran-2-yl]methylene]-2-methyl-propane-2-sulfinamide (3.00 g, 13.9 mmol) in ethanol (60.0 mL) at 0° C., was added NaBH$_4$ (0.527 g, 13.9 mmol) and the ice bath was removed and the reaction mixture was stirred 30 min. The reaction was cooled to 0° C. and saturated NH$_4$Cl (40.0 mL) was added (CAUTION: gas evolution). The volatiles were evaporated under reduced pressure and the residue was extracted with EtOAc (3×40.0 mL). The combined organic layers were dried (Na$_2$SO$_4$), filtered and concentrated under reduced pressure to provide the title compound (3.00 g, 99%) as a solid, which was in the next step without further purification. MS (ESI) [M+H]$^+$ 218.0.

Step 2

(S)—N-benzyl-N-[[(2S)-3,4-dihydro-2H-pyran-2-yl]methyl]propane-2-sulfinamide

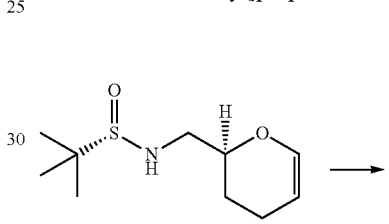

NaH (60%, 0.635 g, 15.9 mmol) was added to a mixture of (S)—N-[[(2S)-3,4-dihydro-2H-pyran-2-yl]methyl]-2-methyl-propane-2-sulfinamide (3.00 g, 13.8 mmol) and BnBr (2.46 mL, 20.7 mmol) in DMF (10.0 mL) at 0° C. and the reaction mixture was stirred at room temperature for 3 h. The mixture was cooled to 0° C. and then water was added (20.0 mL). The aqueous layer was extracted with EtOAc (3×25.0 mL) and the combined organic layers were washed with water (5×20.0 mL), then dried (Na$_2$SO$_4$), filtered and concentrated under reduced pressure. The material was purified by silica gel chromatography (80 g cartridge) using a gradient of EtOAc and hexane (0-40%) to afford the title compound (4.00 g, 94%) as an oil. MS (ESI) [M+Na]$^+$ 330.2.

Step 3

(S)—N-benzyl-N-[[(2S)-5,6-dihydroxytetrahydropyran-2-yl]methyl]-2-methyl-propane-2-sulfinamide

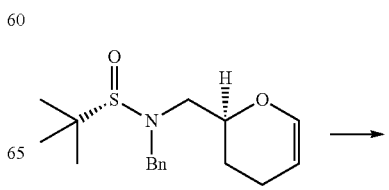

423
-continued

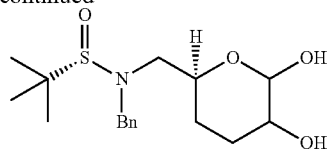

OsO₄ (4% solution in water, 3.91 mL, 0.615 mmol) was added to a solution of (S)—N-benzyl-N-[[(2S)-3,4-dihydro-2H-pyran-2-yl]methyl]propane-2-sulfinamide (3.78 g, 12.3 mmol) and NMO (2.97 g, 24.6 mmol) in a mixture acetone and H₂O (100 mL, 5:1) at ambient temperature and the reaction mixture was stirred at room temperature for 3 h. The volatiles were removed under reduced pressure (CAUTION: OsO₄ is volatile) and the residue was diluted with saturated solution of sodium thiosulfate (200 mL). The aqueous layer was then extracted with EtOAc (3×100 mL). The combined organic layers were dried (Na₂SO₄), filtered and evaporated under reduced pressure. The material was purified by silica gel chromatography (80 g cartridge) using a gradient of EtOAc and hexane (10-50%) as eluent to produce the title compound (mixture of diastereomers) (4.10 g, 98%) as an oil. MS (ESI) [M+Na]⁺ 364.9.

Step 4

Benzyl N-benzyl-N-[[(2S)-5,6-dihydroxytetrahydropyran-2-yl]methyl]carbamate

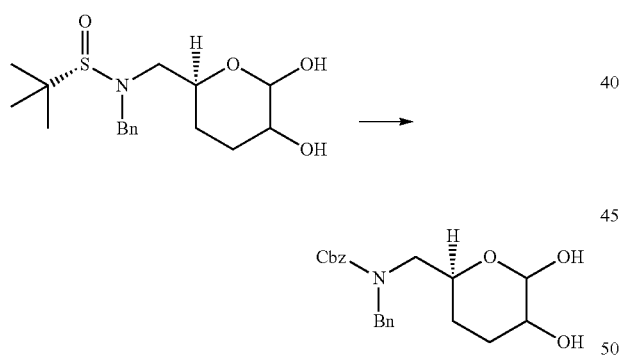

Aqueous HCl (1.0 M, 74.4 mL, 72.4 mmol) was dropwise added to a solution of N-benzyl-N-[[(2S)-5,6-dihydroxytetrahydropyran-2-yl]methyl]-2-methyl-propane-2 sulfinamide (4.10 g, 12.0 mmol) in dioxane (100.0 mL) with vigorous stirring. After 1 h, solid Na₂CO₃ (10.2 g, 96.1 mmol) was added. After another 10 min, CbzCl (2.89 mL, 20.3 mmol) was added dropwise and the reaction mixture was stirred for 3 h. The volatiles were evaporated, and the residue was partitioned in between EtOAc (150 mL) and H₂O (150 mL). The layers were separated, and the organic phase was dried (Na₂SO₄), filtered and concentrated under reduced pressure. The material was purified by silica gel chromatography (120 g cartridge) using a gradient of ethyl acetate in hexane (0-40%) as eluent to afford the title compound (diastereomers, 4.40 g, 99%) as an oil. MS (ESI) [M+Na]⁺ 394.8.

424

Step 5

[(6S)-2-acetoxy-6-[[benzyl(benzyloxycarbonyl)amino]methyl]tetrahydropyran-3-yl] acetate

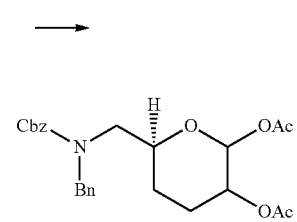

To a solution of benzyl N-benzyl-N-[[(2S)-5,6-dihydroxytetrahydropyran-2-yl]methyl]carbamate (4.40 g, 11.8 mmol) in a mixture pyridine (10 mL) and DCM (75.0 mL) at 0° C., was added acetic anhydride (5.60 mL, 59.2 mmol) and the reaction mixture was stirred at room temperature for 48 h. The mixture was diluted with 5% of sulfuric acid (100 mL) and the aqueous layer was extracted with EtOAc (3×100 mL). The combined organic layers were dried (Na₂SO₄), filtered and concentrated under reduced pressure. The material was purified by silica gel chromatography (120 g cartridge) using a gradient ethyl acetate of hexane (0-30%) as eluent to afford the title compound (diastereomers, 4.90 g, 91%) as an oil. MS (ESI) [M+Na]⁺ 478.8.

Step 6

[(2R,3R,6S)-6-[[benzyl(benzyloxycarbonyl)amino]methyl]-2-[(1R,2S,3S,4R,6S)-2,3-diacetoxy-4,6-diazido-cyclohexoxy]tetrahydropyran-3-yl] acetate

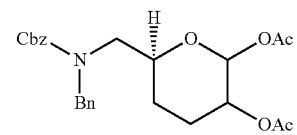

A microwave tube was charged with [(6S)-2-acetoxy-6-[[benzyl(benzyloxycarbonyl)amino]methyl]tetrahydropyran-3-yl] acetate (0.70 g, 0.154 mmol), [(1S,2S,3R,4S,6R)-2-acetoxy-4,6-diazido-3-hydroxy-cyclohexyl] acetate (0.504 g, 1.69 mmol) and 4 Å molecular sieves (3.00 g) and then a mixture of solvent (DCM/Ether; 5:1, 10.0 mL) was added followed BF₃·Et₂O (0.948 mL, 7.68 mmol). The reaction mixture was stirred at 50° C. for 24 h. The mixture was quenched with saturated NaHCO₃, and the aqueous layer was extracted with DCM (3×20.0 mL). The organic combined layers were dried (Na₂SO₄), filtered and concentrated under reduced pressure. The material was purified by silica gel chromatography (180 g) using a gradient of ethyl acetate in hexane (0-50%) as eluent to provide the title compound (0.750 g, 70%) as mixture of diastereomers. MS (ESI) [M+Na]⁺ 716.1.

Step 7

Benzyl N-benzyl-N-[[(2S,5R,6R)-6-[(1R,2R,3S,4R,6S)-4,6-diazido-2,3-dihydroxy-cyclohexoxy]-5-hydroxy-tetrahydropyran-2-yl]methyl]carbamate NaOMe (25 wt %, 1.59 mL, 5.54 mmol) was added dropwise to a solution of [(2R,3R,6S)-6-[[benzyl(benzyloxycarbonyl)amino]methyl]-2-[(1R,2S,3S,4R,6S)-2,3-diacetoxy-4,6-diazido-cyclohexoxy]tetrahydropyran-3-yl] acetate (0.640 g, 0.923 mmol) in MeOH (25.0 mL) at ambient temperature and the reaction mixture was stirred for 60 min. The mixture was neutralized by AcOH (0.950 mL, 16.6 mmol) and the volatiles were removed under reduced pressure. The material was purified by silica gel chromatography (120 g) using a mixture MeOH (2%) in DCM as eluent to afford the title compound (second eluting, 156 mg, 30%) as an oil. Note: three spots appeared on TLC plate and the middle spot corresponds to the desired diastereomer benzyl N-benzyl-N [[(2S,5R,6R)-6-[(1R,2R,3S,4R,6S)-4,6-diazido-2,3-dihydroxy-cyclohexoxy]-5-hydroxy-tetrahydropyran-2-yl]methyl]carbamate. ¹H NMR (500 MHz, MeOD) δ 7.55-7.13 (m, 1H), 5.38-5.11 (m, 3H), 4.83 (dd, J=15.7, 4.3 Hz, 1H), 4.60 (d, J=15.7 Hz, 1H), 4.39-4.19 (m, 1H), 3.76-3.62 (m, 6H), 3.58-3.31 (m, 1H), 3.18 (dt, J=14.2, 7.1 Hz, 1H), 2.23 (dt, J=12.8, 4.1 Hz, 1H), 1.99-1.56 (m, 3H), 1.48-1.24 (m, 2H). MS (ESI) [M+Na]⁺ 590.1.

Step 8

[(2R,3R,6S)-2-[(1R,2S,3S,4R,6S)-3-acetoxy-4,6-diazido-2-hydroxy-cyclohexoxy]-6-[[benzyl(benzyloxycarbonyl)amino]methyl]tetrahydropyran-3-yl] acetate

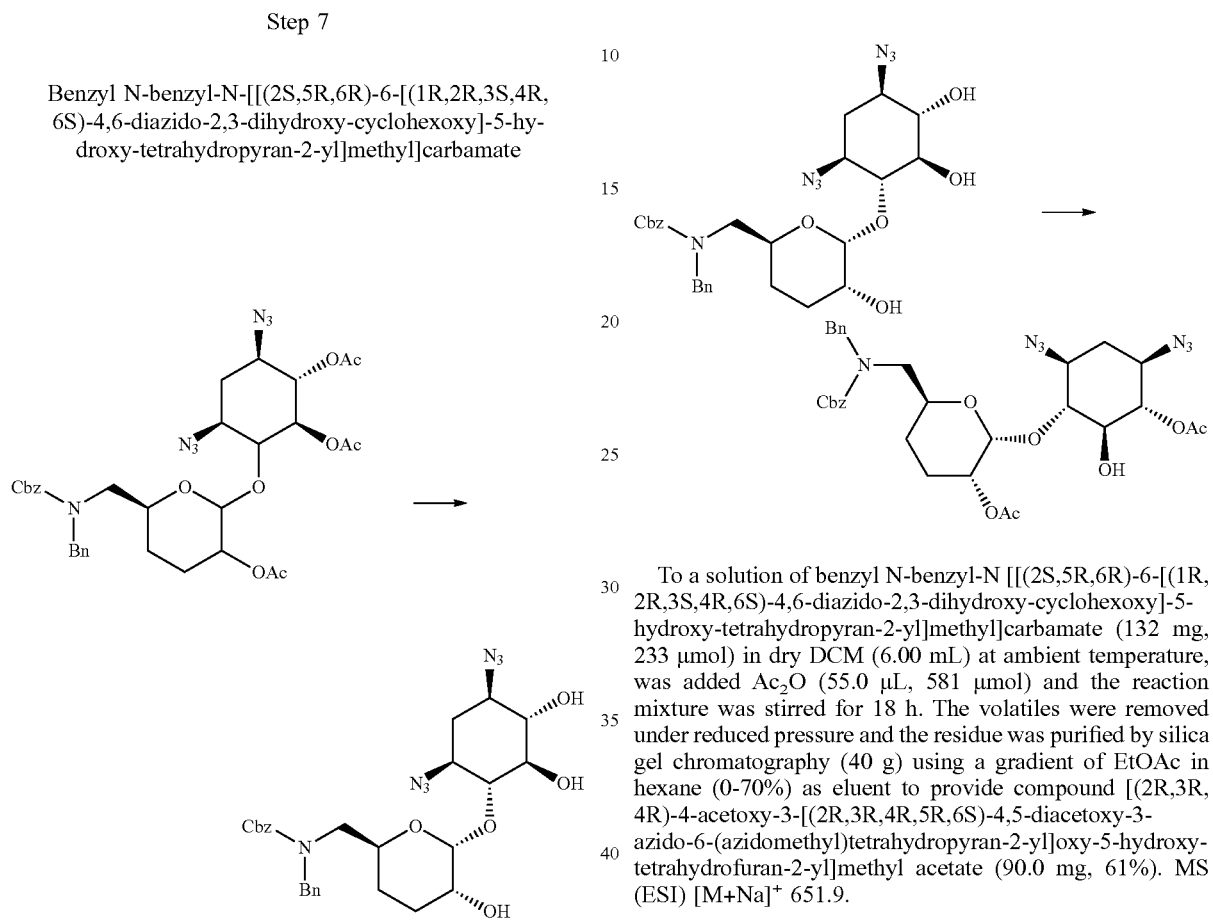

To a solution of benzyl N-benzyl-N [[(2S,5R,6R)-6-[(1R,2R,3S,4R,6S)-4,6-diazido-2,3-dihydroxy-cyclohexoxy]-5-hydroxy-tetrahydropyran-2-yl]methyl]carbamate (132 mg, 233 μmol) in dry DCM (6.00 mL) at ambient temperature, was added Ac₂O (55.0 μL, 581 μmol) and the reaction mixture was stirred for 18 h. The volatiles were removed under reduced pressure and the residue was purified by silica gel chromatography (40 g) using a gradient of EtOAc in hexane (0-70%) as eluent to provide compound [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (90.0 mg, 61%). MS (ESI) [M+Na]⁺ 651.9.

Step 9

[(2R,3R,4R,5S)-4-acetoxy-5-[(1S,2S,3R,5S,6R)-2-acetoxy-6-[(2R,3R,6S)-3-acetoxy-6-[[benzyl(benzyloxycarbonyl)amino]methyl]tetrahydropyran-2-yl]oxy-3,5-diazido-cyclohexoxy]-3-[(2R,3R,4R,5R,6S)-4,5-diacetoxy-3-azido-6-(azidomethyl)tetrahydropyran-2-yl]oxy-tetrahydrofuran-2-yl] methyl acetate

427

-continued

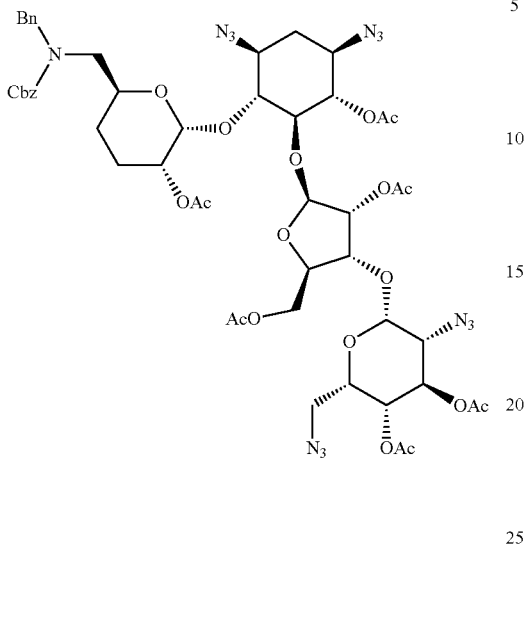

CCl$_3$CN (0.212 mL, 2.12 mmol) was added dropwise to a mixture of [(2R,3R,4R)-4-acetoxy-3-[(2R,3R, 4R,5R,6S)-4,5-diacetoxy-3-azido-6-(azidomethyl)tetrahydropyran-2-yl]oxy-5-hydroxy-tetrahydrofuran-2-yl]methyl acetate (225 mg, 0.424 mmol) and K$_2$CO$_3$ (176 mg, 1.27 mmol) in dry DCM (12.0 mL) at room temperature under N$_2$. The mixture was stirred at room temperature for 18 h, then filtered through Celite and rinsed with dry DCM. The filtrate was concentrated under reduced pressure.

To a solution of [(2R,3R,6S)-2-[(1R,2S,3S,4R,6S)-3-acetoxy-4,6-diazido-2-hydroxy-cyclohexoxy]-6-[[benzyl(benzyloxycarbonyl)amino]methyl]tetrahydropyran-3-yl]acetate (92.0 mg, 0.141 mmol) in DCM (12.0 mL) was added to the above material. 4 Å molecular sieves were then added and the mixture was cooled to −10° C. and then BF$_3$·Et$_2$O (87.1 μL, 0.706 mmol) was added dropwise. The mixture warmed slowly at room temperature and stirred for 5 h. The mixture was diluted with saturated NaHCO$_3$ (10.0 mL) and the separated aqueous layer was extracted with DCM (3×20.0 mL). The combined organic layers were washed with brine, then dried (Na$_2$SO$_4$), filtered and concentrated under reduced pressure. The material was purified by silica gel chromatography (40 g) using gradient of EtOAc in hexane (0-40%) as eluent to provide title product [(2R,3R,4R,5S)-4-acetoxy-5-[(1S,2S,3R,5S,6R)-2-acetoxy-6-[(2R,3R,6S)-3-acetoxy-6-[[benzyl(benzyloxycarbonyl)amino]methyl]tetrahydropyran-2-yl]oxy-3,5-diazido-cyclohexoxy]-3-[(2R,3R,4R,5R,6S)-4,5-diacetoxy-3-azido-6-(azidomethyl)tetrahydropyran-2-yl]oxy-tetrahydrofuran-2-yl]methyl acetate (120 mg, 73%) as an oil. MS (ESI) [M+Na]$^+$ 1186.0.

428

Step 10

Benzyl N-benzyl-N-[[(2S,5R,6R)-6-[(1R,2R,3S,4R,6S)-4,6-diazido-2-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl)tetrahydrofuran-2-yl]oxy-3-hydroxy-cyclohexoxy]-5-hydroxy-tetrahydropyran-2-yl]methyl]carbamate

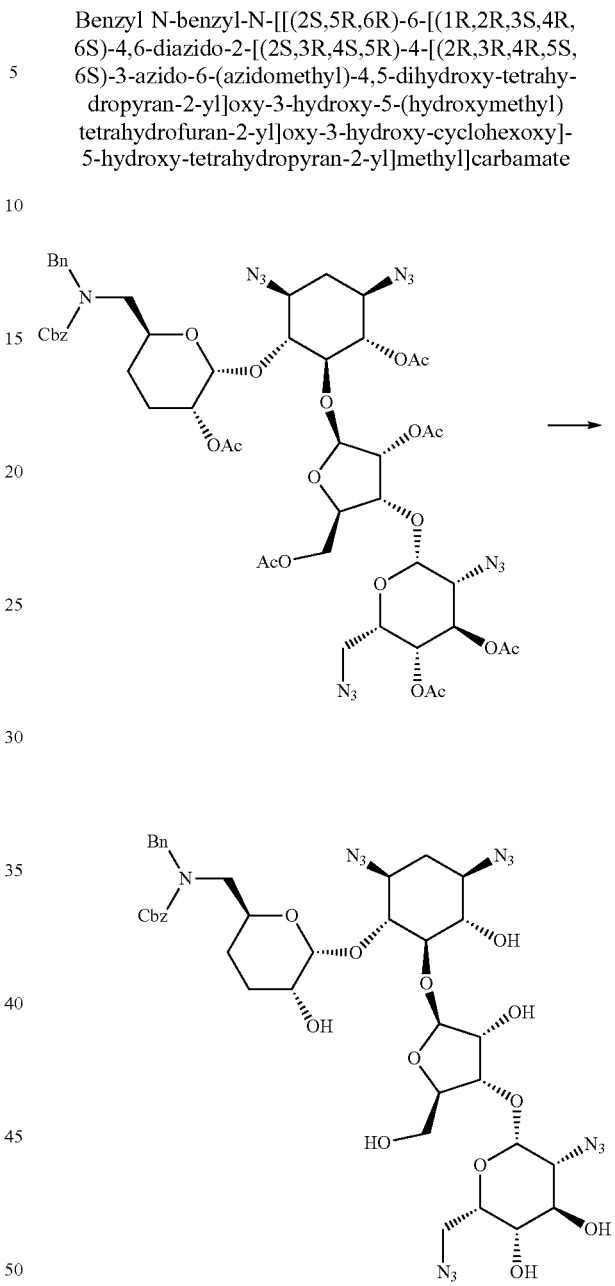

NaOMe (25 wt %, 356 μL, 124 μmol) was added dropwise to a solution of [(2R,3R,4R,5S)-4-acetoxy-5-[(1S,2S,3R,5S,6R)-2-acetoxy-6-[(2R,3R,6S)-3-acetoxy-6-[[benzyl(benzyloxycarbonyl)amino]methyl]tetrahydropyran-2-yl]oxy-3,5-diazido-cyclohexoxy]-3-[(2R,3R,4R,5R,6S)-4,5-diacetoxy-3-azido-6-(azidomethyl)tetrahydropyran-2-yl]oxy-tetrahydrofuran-2-yl]methyl acetate (120 mg, 103 μmol) in MeOH (5.00 mL) at ambient temperature and the reaction mixture was stirred for 1 h. The mixture was neutralized by AcOH (~118 μL) and the volatiles were removed under reduced pressure. The material was dissolved with EtOAc, filtered through silica gel pad and the filtrate was concentrated under reduced pressure to produce the title compound (90.0 mg, 96%) as an oil. MS (ESI) [M+Na]$^+$ 934.1.

429

Step 11

(2S,3S,4R,5R,6R)-5-amino-2-(aminomethyl)-6-[(2R,3S,4R,5S)-5[(1R,2R,3S,5R,6S)-3,5-diamino-2-[(2R,3R,6S)-6-(aminomethyl)-3-hydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol; formate

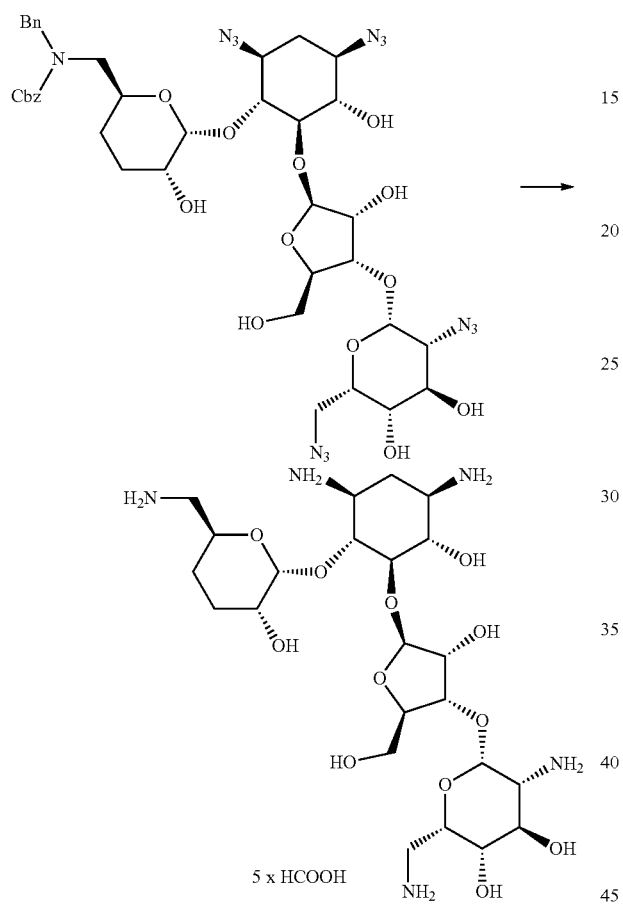

Pd(OH)$_2$/C (20 wt %, 194 mg, 276 μmol) was added to a solution of benzyl N-benzyl-N-[[(2S,5R,6R)-6-[(1R,2R,3S,4R,6S)-4,6-diazido-2-[(2S,3R,4S,5R)-4-[(2R,3R,4R,5S,6S)-3-azido- 6-(azidomethyl)-4,5-dihydroxy-tetrahydropyran-2-yl]oxy-3-hydroxy-5-(hydroxymethyl)tetrahydrofuran-2-yl]oxy-3-hydroxy-cyclohexoxy]-5-hydroxy-tetrahydropyran-2-yl]methyl]carbamate (42.0 mg, 46.1 μmol) in MeOH (3.60 mL) and EtOH (3.60 mL). H$_2$ was bubbled and the suspension was hydrogenated under hydrogen atmosphere for 16 h. The mixture was filtered through a frit (0.22 m diameter) and the filtrate was concentrated under reduced pressure. The material was purified by preparative HPLC to provide the title compound (12.5 mg, 43%) as a formate salt. $^1$H NMR (400 MHz, MeOD) δ 8.46 (s, 5H), 5.46 (d, J=3.2 Hz, 1H), 5.33 (d, J=2.1 Hz, 1H), 5.22 (s, 1H), 4.57-4.48 (m, 1H), 4.32-4.20 (m, 2H), 4.16-4.04 (m, 3H), 3.87-3.52 (m, 7H), 3.41-3.30 (m, 2H), 3.13-3.05 (m, 4H), 2.92 (dd, J=13.1, 8.5 Hz, 1H), 2.27 (d, J=11.6 Hz, 1H), 1.97-1.61 (m, 4H), 1.43 (dd, J=25.9, 14.0 Hz, 1H). MS (ESI) [M+Na]$^+$ 606.8.

430

Example 16

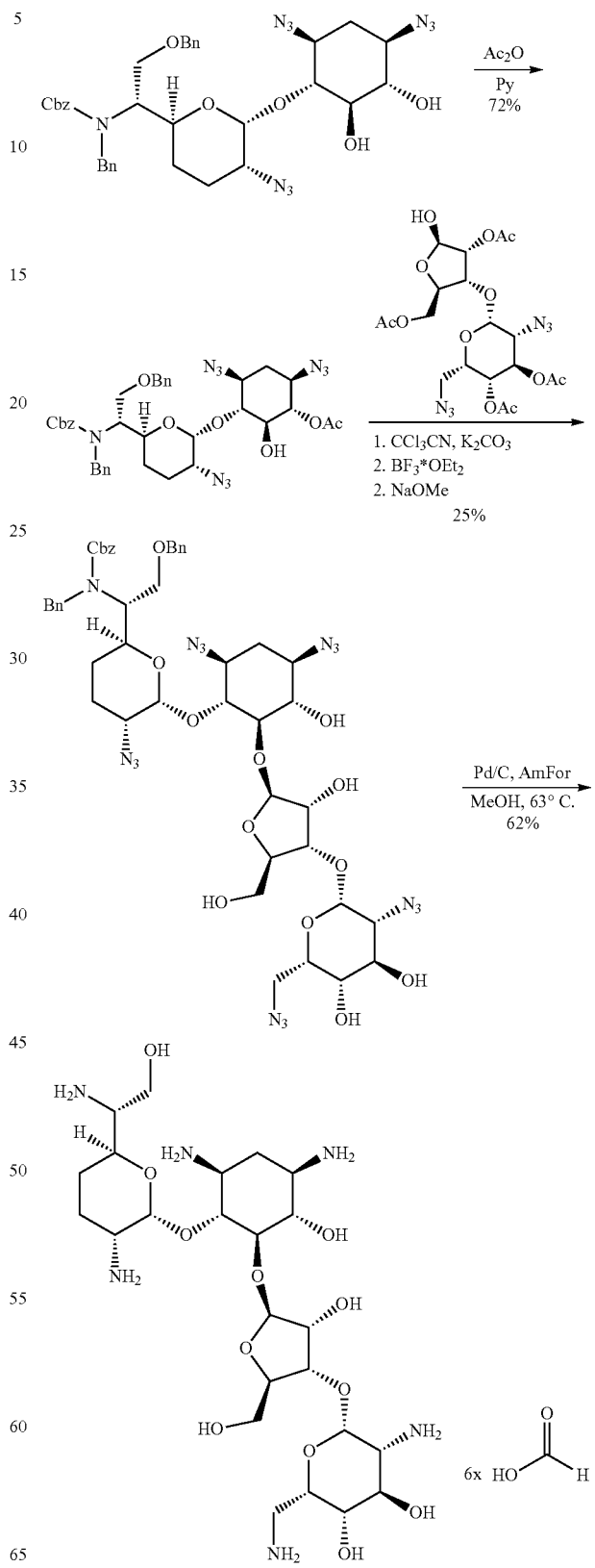

Step 1

Benzyl N-[(1R)-1-[(2S,5R,6R)-5-azido-6-[(1R,2R,3S,4R,6S)-4,6-diazido-2,3-dihydroxy-cyclohexoxy]tetrahydropyran-2-yl]-2-benzoxy-ethyl]-N-benzyl-carbamate

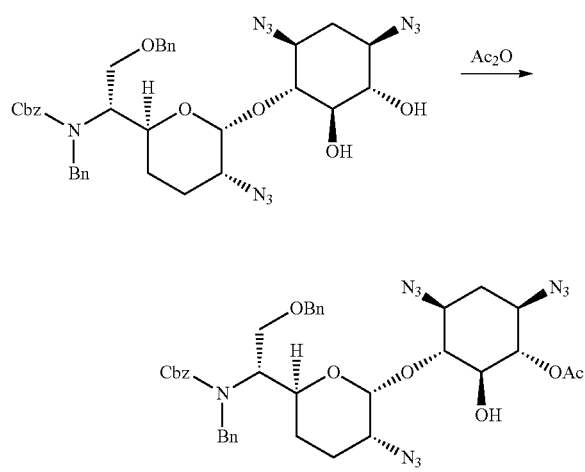 [SMILES: "Ac2O" ; [N-]=[N+]=N[C@H]1C[C@@H](N=[N+]=[N-])[C@H](O)[C@@H](O)[C@@H]1O[C@H]1O[C@H]([C@@H](COCc2ccccc2)N(Cc2ccccc2)C(=O)OCc2ccccc2)CC[C@H]1N=[N+]=[N-] ; CC(=O)O[C@@H]1[C@@H](O)[C@H](O[C@H]2O[C@H]([C@@H](COCc3ccccc3)N(Cc3ccccc3)C(=O)OCc3ccccc3)CC[C@H]2N=[N+]=[N-])[C@@H](N=[N+]=[N-])C[C@H]1N=[N+]=[N-]]

To a solution of benzyl N-[(1R)-1-[(2S,6R)-5-azido-6-[(1R,2R,3S,4R,6S)-4,6-diazido-2,3-dihydroxy-cyclohexoxy]tetrahydropyran-2-yl]-2-benzyloxy-ethyl]-N-benzyl-carbamate (see Example 36 for synthesis, 134 mg, 0.19 mmol) and pyridine (9 µL, 1.13 mmol) in dry DCM (5.0 mL) at room temperature was added Ac$_2$O (9 µL, 94 µmol) and the reaction mixture was stirred for 20 h. The volatiles were removed under reduced pressure. The material was purified by MPLC on silica gel (40 g, liquid loading with toluene) using a gradient of 0-45% EtOAc in hexane as eluent to provide the title compound (72 mg, 96%) as a solid. MS (ESI) [M+H]$^+$ 755.4.

Step 2

Benzyl ((R)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl) tetrahydrofuran-2-yl)oxy)-3-hydroxycyclohexyl)oxy)tetrahydro-2H-pyran-2-yl)-2-(benzyloxy) ethyl)(benzyl)carbamate

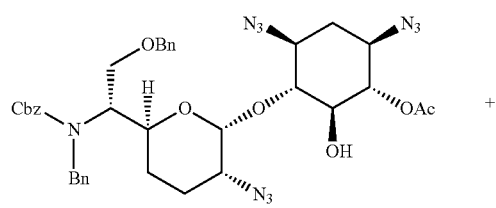

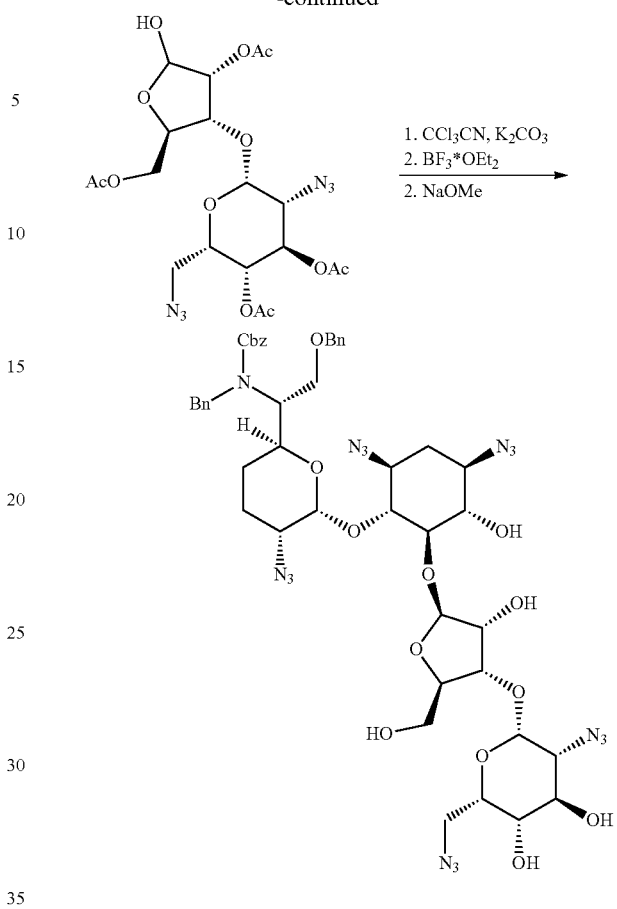

To a mixture of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (155 mg, 0.29 mmol) and K$_2$CO$_3$ (88 mg, 0.64 mmol) in DCM (5.0 mL) was added CCl$_3$CN (0.08 mL, 0.76 mmol) at room temperature. The mixture was stirred at room temperature for 18 h, then filtered on Celite, rinsed with DCM and concentrated under reduced pressure. To the above material in dry DCM (20 mL) was added [(1S,2S,3R,4S,6R)-4,6-diazido-3-[(2R,3R,6S)-3-azido-6-[(1R)-1-[benzyl(benzyloxycarbonyl) amino]-2-benzyloxy-ethyl]tetrahydropyran-2-yl]oxy-2-hydroxy-cyclohexyl] acetate (96 mg, 0.13 mmol) followed by activated 3 Å sieves (1 g). The mixture was cooled to −78° C. and then BF$_3$·OEt$_2$ (0.06 mL, 0.51 mmol) was added dropwise. The acetone-dry ice bath was removed, and the reaction mixture was slowly warmed to room temperature, and then saturated NaHCO$_3$ (10 mL) was added. The separated aqueous layer was extracted with DCM (3×15 mL). The combined organic layers were washed with brine, dried (MgSO$_4$), filtered and concentrated under reduced pressure. The residue was taken in MeOH (10 mL) then NaOMe (4.62 M in MeOH, 0.39 mL, 1.78 mmol) was added at room temperature and the reaction mixture was stirred for 1 h. The mixture was diluted with saturated NH$_4$Cl (10 mL) and the separated aqueous layer was extracted with DCM (3×15 mL). The combined organic layers were washed with brine, dried (MgSO$_4$), filtered and concentrated under reduced pressure. The material was purified by preparative HPLC to provide the title compound (47 mg, 35%) as a solid. MS (ESI) [M+Na]+1079.4.

Step 3

(2S,3S,4R,5R,6R)-5-amino-2-(aminomethyl)-6-
(((2R,3S,4R,5S)-5-(((1R,2R,3S,5R,6S)-3,5-diamino-
2-(((2R,3R,6S)-3-amino-6-((R)-1-amino-2-hydroxy-
ethyl)tetrahydro-2H-pyran-2-yl)oxy)-6-
hydroxycyclohexyl)oxy)-4-hydroxy-2-
(hydroxymethyl)tetrahydrofuran-3-yl)oxy)
tetrahydro-2H-pyran-3,4-diol syringe and concentrated under reduced pressure. The material was purified by preparative HPLC using isocratic 10% B in A (A: Amfor pH 4, B: ACN) on C18 Xbridge 30×150 mm to provide the title compound (22.3 mg, 62%) as a solid. $^1$H NMR (500 MHz, MeOD) δ 8.41 (s, 6H), 5.48 (s, 1H), 5.15 (s, 1H), 5.09 (d, J=1.5 Hz, 1H), 4.39-4.34 (m, 1H), 4.30-4.17 (m, 3H), 4.10-3.99 (m, 3H), 3.81-3.71 (m, 3H), 3.68-3.53 (m, 2H), 3.50-3.42 (m, 3H), 3.32-3.24 (m, 3H), 3.16-2.99 (m, 3H), 2.26-2.14 (m, 2H), 1.87-1.78 (m, 1H), 1.71-1.57 (m, 3H). MS (ESI) [M+H]$^+$ 613.4.

Example 17

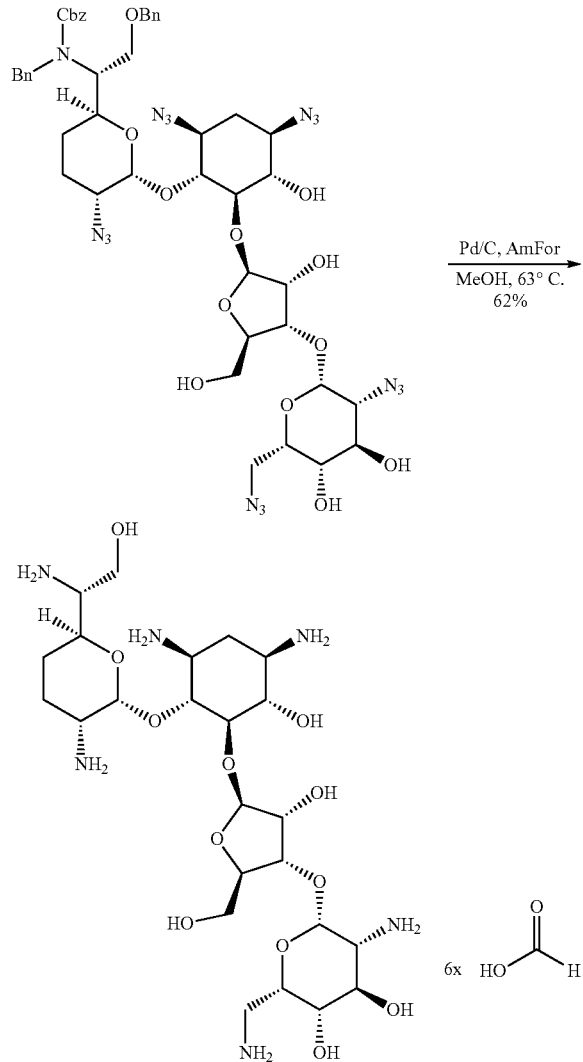

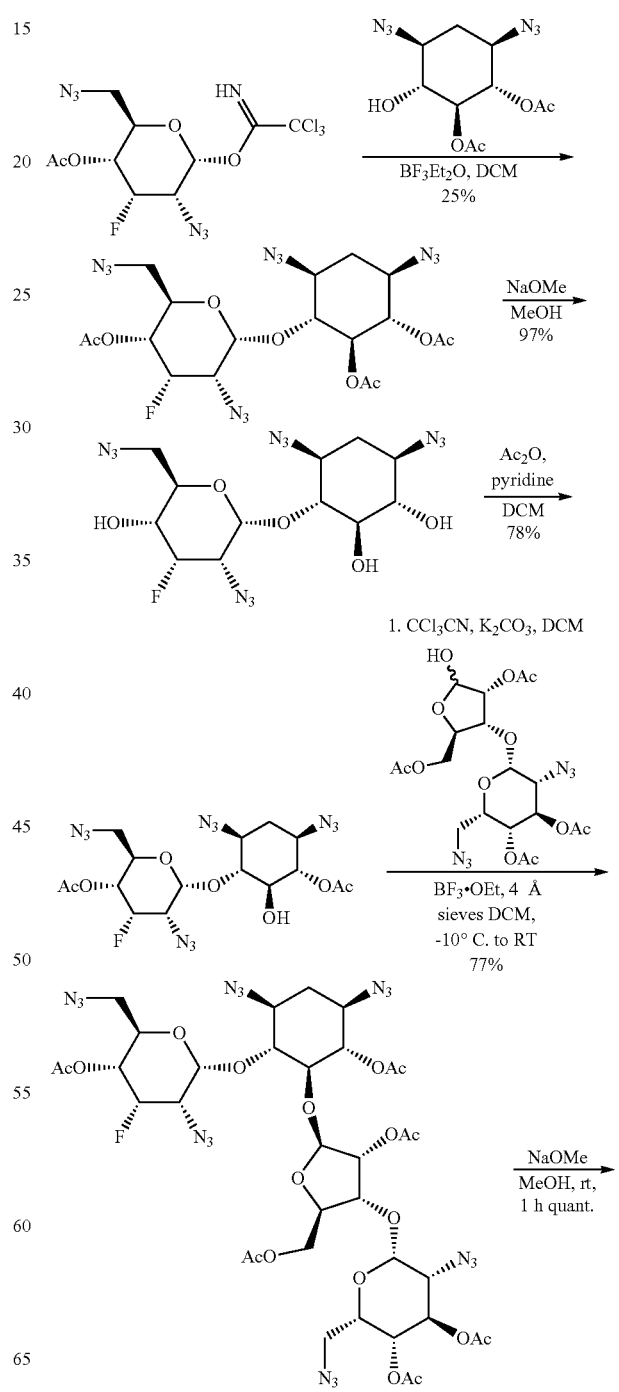

In a 2 neck flask equipped with a reflux condenser were added benzyl ((R)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H-pyran-2-yl)-2-(benzyloxy) ethyl)(benzyl)carbamate (43 mg, 0.04 mmol) and Pd/C (10% dry on carbon, 19.5 mg, 0.02 mmol) following by anhydrous MeOH (8 mL). Nitrogen was bubbled for 5 min, then ammonium formate (44 mg, 0.69 mmol) was added. The mixture was heated at 63° C. for 5 h under N$_2$, then cooled to room temperature with an ice-bath. The mixture was filtered with a filter

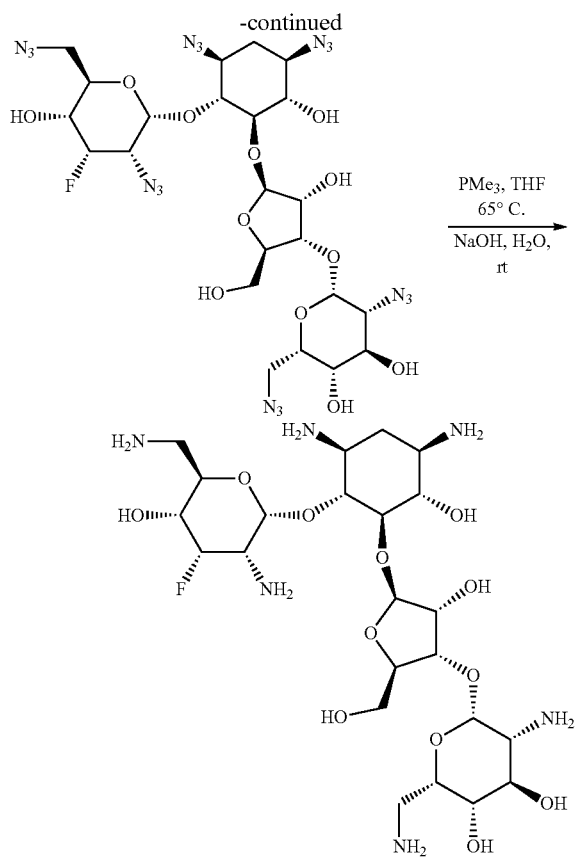

Step 1

(1S,2R,3R,4S,6R)-4,6-diazido-3-[(2R,3S,4S,5R,6R)-3-azido-6-(azidomethyl)-4-fluoro-5-hydroxy-tetrahydropyran-2-yl]oxy-cyclohexane-1,2-diol To (2R,3R,4S,5S)-5-azido-2-(azidomethyl)-4-fluoro-6-(2,2,2-trichloro-1-iminoethoxy) tetrahydro-2H-pyran-3-yl acetate (preparation below, 1.00 g, crude) was added [(1S, 2S,3R,4S,6R)-2-acetoxy-4,6-diazido-3-hydroxy-cyclohexyl] acetate (500 mg, 1.68 mmol) and grounded 4 Å sieves (3.70 g). Dry DCM (18.0 mL) was added and the suspension was stirred at ambient temperature for 30 min. The mixture was cooled to −10° C. and then BF$_3$·Et$_2$O (1.18 mL, 9.56 mmol) was added dropwise with vigorous stirring. The solution was warmed to ambient temperature slowly and stirred for another 5 h. The reaction was quenched with saturated NaHCO$_3$ (10.0 mL) and the aqueous layer was extracted with DCM (3×20.0 mL). The combined organic layers were dried (Na$_2$SO$_4$), filtered and concentrated under reduced pressure. The material was purified by silica gel chromatography (80 g) using a gradient of EtOAc in hexane (0-30%) as eluent to provide the title compound as an oil (220 mg, 25%). MS (ESI) [M+Na]$^+$ 576.9.

NaOMe (25 wt %, 686 µL, 2.38 mmol) was added dropwise to a solution of [(1S,2S,3R,4S,6R)-2-acetoxy-3-[(2R,3S,4S,5R,6R)-5-acetoxy-3-azido-6-(azidomethyl)-4-fluoro-tetrahydropyran-2-yl]oxy-4,6-diazido-cyclohexyl] acetate (220 mg, 397 µmol) in MeOH (15.0 mL) at ambient temperature and the reaction mixture was stirred for 60 min. The mixture was neutralized with AcOH (408 µL, 7.14 mmol) and the volatiles were removed under reduced pressure. The material was filtered through a silica gel pad and eluted with EtOAc to afford the title compound (165 mg, 97%) as a solid. $^1$H NMR (500 MHz, MeOD) δ 5.75 (d, J=4.5 Hz, 1H), 5.12 (dt, J=53.8, 2.2 Hz, 1H), 4.59 (ddd, J=10.1, 5.1, 2.4 Hz, 1H), 3.72-3.43 (m, 7H), 3.32 (t, J=9.5 Hz, 1H), 3.18 (ddd, J=35.0, 4.4, 2.4 Hz, 1H), 2.34 (dt, J=13.0, 4.3 Hz, 1H), 1.50 (dd, J=24.7, 12.3 Hz, 1H).

Step 2

[(1S,2S,3R,4S,6R)-3-[(2R,3S,4S,5R,6R)-5-acetoxy-3-azido-6-(azidomethyl)-4-fluoro-tetrahydropyran-2-yl]oxy-4,6-diazido-2-hydroxy-cyclohexyl] acetate

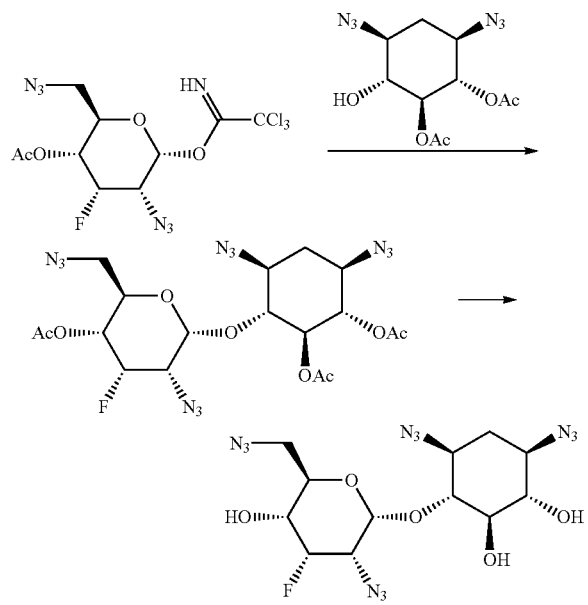

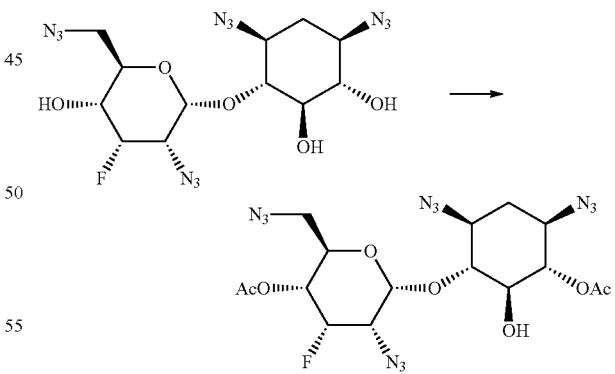

Ac$_2$O (179 µL, 1.89 mmol) was added to a solution of (1S,2R,3R,4S,6R)-4,6-diazido-3-[(2R,3S,4S,5R,6R)-3-azido-6-(azidomethyl)-4-fluoro-5-hydroxy-tetrahydropyran-2-yl]oxy-cyclohexane-1,2-diol (135 mg, 0.315 mmol) and pyridine (204 µL, 2.52 mmol) in dry DCM (8.0 mL) at ambient temperature. The reaction mixture was stirred for 20 h and then the volatiles were removed under reduced pressure. The material was purified by silica gel chromatography (40 g cartridge) using a gradient of EtOAc in hexane (0-30%) as eluent to afford the title compound (126 mg, 78%) as an oil. MS (ESI) [M+Na]+ 535.0.

Step 3

(2S,3R,4R,5R,6R)-6-(((2R,3R,4R,5S)-4-acetoxy-5-(((1S,2S,3R,5S,6R)-2-acetoxy-6-(((2R,3S,4S,5R,6R)-5-acetoxy-3-azido-6-(azidomethyl)-4-fluorotetrahydro-2H-pyran-2-yl)oxy)-3,5-diazidocyclohexyl)oxy)-2-(acetoxymethyl)tetrahydrofuran-3-yl)oxy)-5-azido-2-(azidomethyl)tetrahydro-2H-pyran-3,4-diyl diacetate

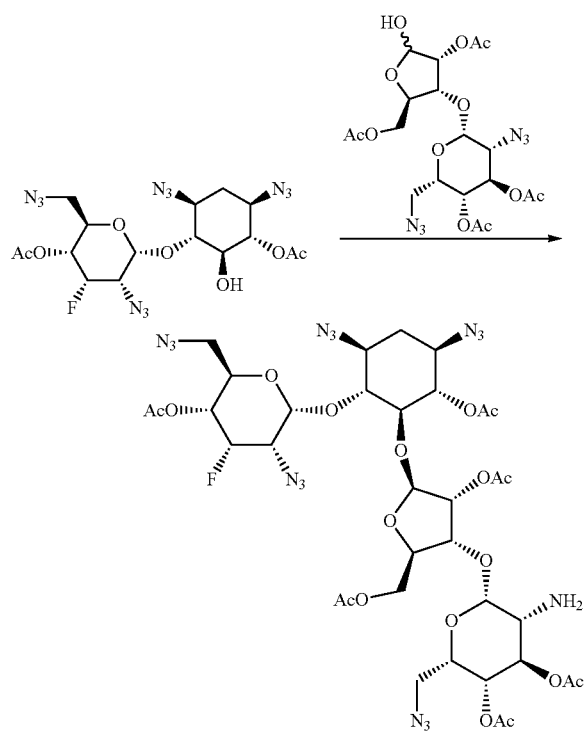

CCl3CN (0370 mL, 3.69 mmol) was added dropwise to a mixture of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (391 mg, 0.738 mmol) and K2CO3 (306 mg, 2.21 mmol) in dry DCM (15.0 mL) at room temperature under N2. The reaction mixture was stirred at room temperature for 18 h, then filtered through Celite pad and washed with dry DCM. The filtrate was concentrated under reduced pressure and used in the next step without purification.

To a solution of [(1 S,2S,3R,4S,6R)-3-[(2R,3S,4S,5R,6R)-5-acetoxy-3-azido-6-(azidomethyl)-4-fluoro-tetrahydropyran-2-yl]oxy-4,6-diazido-2-hydroxy-cyclohexyl] acetate (126 mg, 0.246 mmol) in dry DCM (15.0 mL), was added the above material followed by molecular sieves 4 Å and the mixture was cooled to −10° C. BF3·OEt2 (0.152 mL, 1.23 mmol) was then added dropwise and the reaction mixture was warmed slowly at room temperature and then stirred for 5 h. The mixture was diluted with saturated NaHCO3 (10.0 mL) and the separated aqueous layer was extracted with DCM (3×20.0 mL). The combined organic layer was washed with brine, then dried (Na2SO4), filtered and concentrated under reduced pressure. The material was purified on silica gel chromatography (40 g cartridge) using a gradient of EtOAc in hexane (0-40%) as eluent to provide the title compound (194 mg, 77%) as a solid. MS (ESI) [M+Na]+ 1047.9.

Step 4

(2S,3S,4R,5R,6R)-5-azido-2-(azidomethyl)-6-(((2R,3S,4R,5S)-5-(((1R,2R,3S,5R,6S)-3,5-diazido-2-(((2R,3S,4S,5R,6R)-3-azido-6-(azidomethyl)-4-fluoro-5-hydroxytetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol

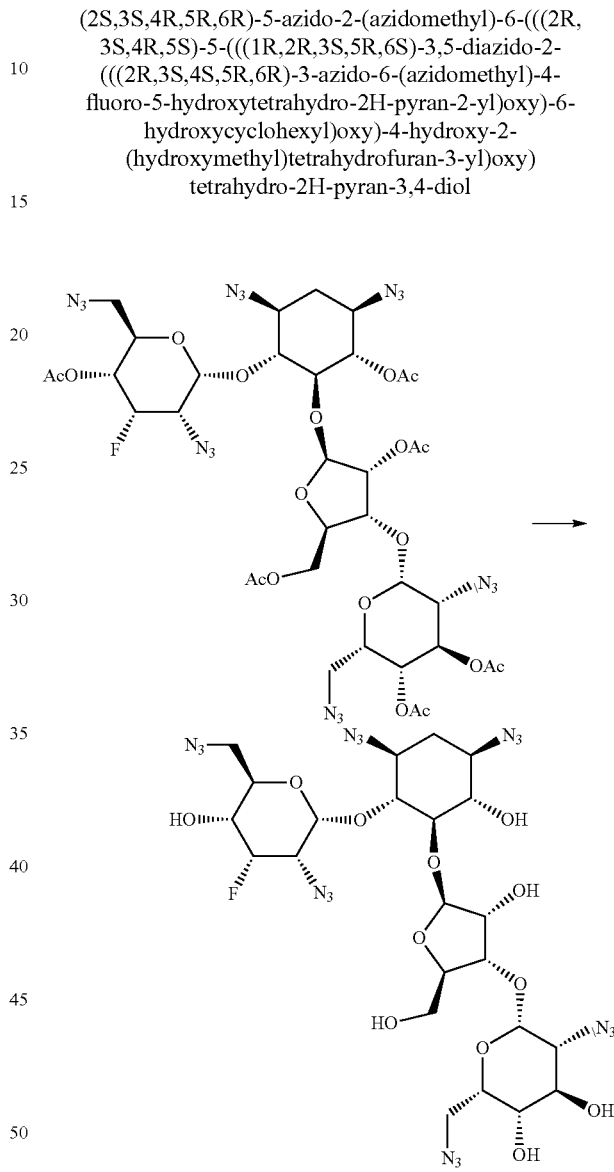

NaOMe (25 wt %, 0.654 mL, 2.27 mmol) was added dropwise to a solution of (2S,3R,4R,5R,6R)-6-(((2R,3R,4R,5S)-4-acetoxy-5-(((1S,2S,3R,5S,6R)-2-acetoxy-6-(((2R,3S,4S,5R,6R)-5-acetoxy-3-azido-6-(azidomethyl)-4-fluorotetrahydro-2H-pyran-2-yl)oxy)-3,5-diazidocyclohexyl)oxy)-2-(acetoxymethyl)tetrahydrofuran-3-yl)oxy)-5-azido-2-(azidomethyl)tetrahydro-2H-pyran-3,4-diyl diacetate (194 mg, 0.189 mmol) in MeOH (6.00 mL) at ambient temperature and the reaction mixture was stirred for 60 min. The mixture was neutralized with AcOH (217 μL, 3.79 mmol) and then the volatiles were removed under reduced pressure. The material was purified on silica gel pad using EtOAc as eluent to provide the title compound (145 mg, 99%) as a solid. MS (ESI) [M+Na]+ 795.2.

Step 5

(2S,3S,4R,5R,6R)-5-amino-2-(aminomethyl)-6-[(2R,3S,4R,5S)-5-[(1R,2R,3S,5R,6S)-3,5-diamino-2-[(2R,3S,4S,5R,6R)-3-amino-6-(aminomethyl)-4-fluoro-5-hydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol

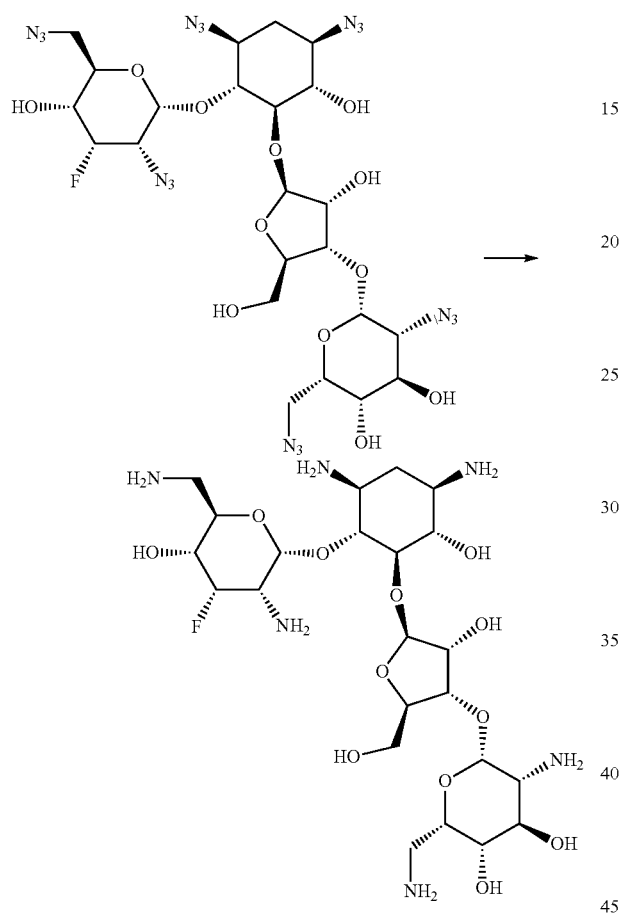

To a solution of (2S,3S,4R,5R,6R)-5-azido-2-(azidomethyl)-6-(((2R,3S,4R,5S)-5-(((1R,2R,3S,5R,6S)-3,5-diazido-2-(((2R,3S,4S,5R,6R)-3-azido-6-(azidomethyl)-4-fluoro-5-hydroxytetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (15.0 mg, 19.4 μmol) in THF (2.00 mL) was added trimethylphosphine (777 μL, 777 μmol) at ambient temperature and the reaction mixture was stirred at room temperature for 16 h. The mixture was diluted with water (2.00 mL) and then NaOH (0.3 mL, 0.1 M) were added. The resulting mixture was then stirred for 3 h at ambient temperature, concentrated under reduced pressure. The material was purified by Sephadex C-25 column using water and ammonium hydroxide (0.25%) as eluent to afford the title compound (6.90 mg, 58%) as a white solid after lyophilization. $^{1}$H NMR (400 MHz, MeOD) δ 5.57 (d, J=4.4 Hz, 11H), 5.28 (s, 1H), 4.93 (d, J=1.5 Hz, 11H), 4.75 (d, J=53.4 Hz, 11H), 4.22 (t, J=4.7 Hz, 11H), 4.12 (dt, J=8.9, 4.6 Hz, 2H), 3.91 (t, J=3.1 Hz, 1H), 3.85-3.60 (m, 4H), 3.47 (dtt, J=28.5, 19.0, 9.4 Hz, 5H), 3.19 (t, J=9.3 Hz, 1H), 3.01 (ddd, J=21.8, 13.4, 5.5 Hz, 3H), 2.90-2.67 (m, 3H), 2.60 (dd, J=16.9, 8.7 Hz, 1H), 1.96 (dd, J=8.3, 3.4 Hz, 1H), 1.31-1.16 (m, 1H). MS (ESI) [M+Na]$^{+}$ 639.1.

Preparation of (2R,3R,4S,5S)-5-azido-2-(azidomethyl)-4-fluoro-6-(2,2,2-trichloro-1-iminoethoxy)tetrahydro-2H-pyran-3-yl acetate

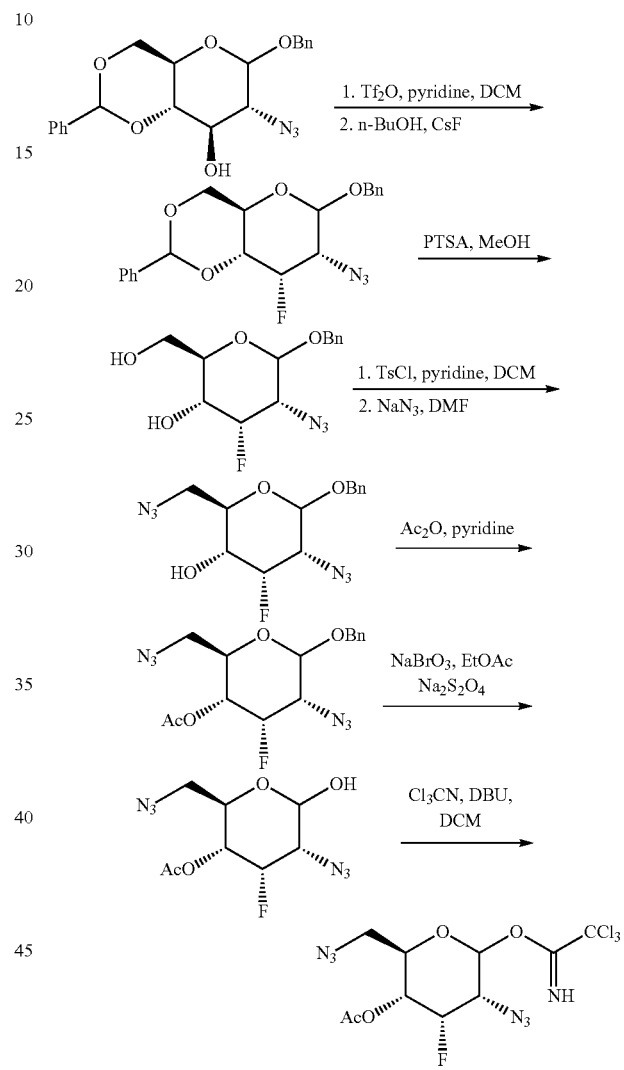

Step 1

(4aR,7S,8S,8aR)-7-azido-6-(benzyloxy)-8-fluoro-2-phenylhexahydropyrano[3,2-d][1,3]dioxine

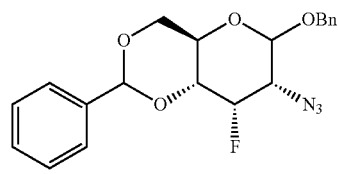

To a solution of 7.7 g of (4aR,7S,8S,8aR)-7-azido-6-(benzyloxy)-8-fluoro-2-phenylhexahydropyrano[3,2-d][1,3]dioxine in 60 mL of anhydrous DCM was added 16.1 mL of pyridine and the reaction was cooled to 0° C. To this solution, 6.8 mL of Triflic anhydride was added slowly and the reaction stirred for 1 hour at the same temperature. After completion, the organic layer was diluted with DCM and washed with 1 N HCl and saturated NaHCO₃. The organic layer was dried over anhydrous sodium sulfate, filtered and concentrated. The obtained crude was dissolved in 50 mL BuOH and 30 mL of toluene and 9.1 g of CsF was added and the reaction stirred at 70° C. until completion. The organic layer was diluted with EtOAc and washed with saturated NaHCO₃, brine and concentrated. The crude was purified by column chromatography (20% EtOAc in hexanes) to afford 5.5 g of (4aR,7S,8S,8aR)-7-azido-6-(benzyloxy)-8-fluoro-2-phenylhexahydropyrano[3,2-d][1,3] dioxine (72% yield).

Step 2

(2R,3R,4S,5S)-5-azido-6-(benzyloxy)-4-fluoro-2-(hydroxymethyl)tetrahydro-2H-pyran-3-ol

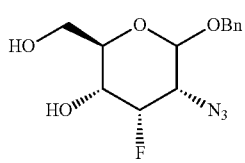 [SMILES: [N-]=[N+]=N[C@H]1C(OCc2ccccc2)O[C@H](CO)[C@@H](O)[C@H]1F]

To a solution of 6.2 g of (4aR,7S,8S,8aR)-7-azido-6-(benzyloxy)-8-fluoro-2-phenylhexahydro-pyrano [3,2-d][1,3] dioxine in 100 mL of MeOH was added 420 mg of p-toluenesulfonic acid at room temperature. The reaction was stirred at room temperature until completion (4 hours). The reaction was quenched with 0.1 eq of Et₃N and concentrated. The crude was purified by flash column chromatography (EtOAc/Hexanes 2:3) to afford 4.5 g of (2R,3R,4S,5S)-5-azido-6-(benzyloxy)-4-fluoro-2-(hydroxymethyl)tetrahydro-2H-pyran-3-ol (95% yield).

Step 3

(2R,3R,4S,5S)-5-azido-2-(azidomethyl)-6-(benzyloxy)-4-fluorotetrahydro-2H-pyran-3-ol

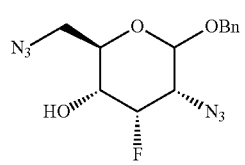 [SMILES: [N-]=[N+]=NC[C@H]1OC(OCc2ccccc2)[C@H](N=[N+]=[N-])[C@H](F)[C@@H]1O]

To a solution of 4.5 g of (2R,3R,4S,5S)-5-azido-6-(benzyloxy)-4-fluoro-2-(hydroxymethyl)tetrahydro-2H-pyran-3-ol in anhydrous DCM/pyridine (5:3), 3.75 g of Tosyl Chloride was added at 0° C. The reaction was stirred at the same temperature until completion (3 h). The reaction was diluted with 100 mL of DCM and washed with 1 N HCl and aqueous NaHCO₃, dried, filtered and concentrated. The crude was dissolved in anhydrous DMF and 4.9 g of sodium azide was added. The reaction was further stirred at 70° C. until completion. DMF was evaporated and the residue was dissolved in EtOAc and washed with water. The organic layer was dried, filtered, concentrated and purified by flash chromatography to afford 2.9 g of (2R,3R,4S,5S)-5-azido-2-(azidomethyl)-6-(benzyloxy)-4-fluorotetrahydro-2H-pyran-3-ol (60% yield).

Step 4

(2R,3R,4S,5S)-5-azido-2-(azidomethyl)-6-(benzyloxy)-4-fluorotetrahydro-2H-pyran-3-yl acetate

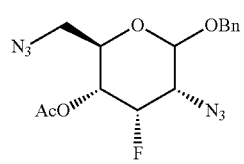

(2R,3R,4S,5S)-5-azido-2-(azidomethyl)-6-(benzyloxy)-4-fluorotetrahydro-2H-pyran-3-ol was dissolved in anhydrous pyridine and the solution was cooled to 0° C. Acetic anhydride was slowly added and the reaction was allowed to warm to room temperature and stirred overnight. The reaction was concentrated to dryness, resuspended in EtOAc, and washed with aqueous NaHCO₃ and brine. The organic portion was dried, filtered, concentrated and purified by flash chromatography to yield (2R,3R,4S,5S)-5-azido-2-(azidomethyl)-6-(benzyloxy)-4-fluorotetrahydro-2H-pyran-3-yl acetate (89% yield).

Step 5

(2R,3R,4S,5S)-5-azido-2-(azidomethyl)-4-fluoro-6-hydroxytetrahydro-2H-pyran-3-yl acetate

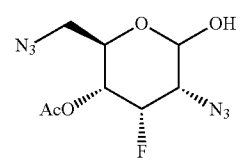 [SMILES: CC(=O)O[C@H]1[C@@H](F)[C@@H](N=[N+]=[N-])C(O)O[C@@H]1CN=[N+]=[N-]]

1.5 g of (2R,3R,4S,5S)-5-azido-2-(azidomethyl)-6-(benzyloxy)-4-fluorotetrahydro-2H-pyran-3-yl acetate was dissolved in 38 mL of EtOAc. 30 mL of aqueous sodium bromate (0.62 M) was added at once to the EtOAc solution. 60 mL aqueous sodium dithionate (0.27 M) was added slowly dropwise over 15 min and the reaction was stirred vigorously until completion. The reaction was then diluted with EtOAc and washed with 1:1 aq NaHCO₃ and sodium thiosulfate. The organic layer was dried, filtered, concentrated and purified by flash column chromatography (30% EtOAc in hexanes) to afford 921 mg of (2R,3R,4S,5S)-5-azido-2-(azidomethyl)-4-fluoro-6-hydroxytetrahydro-2H-pyran-3-yl acetate (82% yield).

Step 6

(2R,3R,4S,5S)-5-azido-2-(azidomethyl)-4-fluoro-6-(2,2,2-trichloro-1-iminoethoxy) tetrahydro-2H-pyran-3-yl acetate

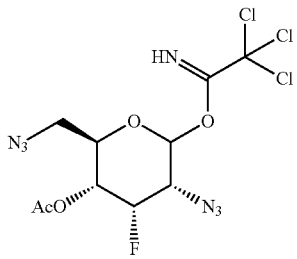 [SMILES: CC(=O)O[C@H]1[C@@H](F)[C@@H](N=[N+]=[N-])C(OC(=N)C(Cl)(Cl)Cl)O[C@@H]1CN=[N+]=[N-]]

To a solution of 950 mg of (2R,3R,4S,5S)-5-azido-2-(azidomethyl)-4-fluoro-6-hydroxytetrahydro-2H-pyran-3-yl acetate in 20 mL of anhydrous DCM was added 970 μL of trichloroacetonitrile at 0° C. To this solution, 143 μL of DBU was slowly added at the same temperature. The reaction was stirred until completion at room temperature (~5 minutes). The reaction was diluted with DCM and washed with 1N HCl, brine and the organic layer was dried, filtered and concentrated. The crude thus obtained was purified by flash column chromatography (20% EtOAc in hexanes) to afford 1.04 g of (2R,3R,4S,5S)-5-azido-2-(azidomethyl)-4-fluoro-6-(2,2,2-trichloro-1-iminoethoxy) tetrahydro-2H-pyran-3-yl acetate (78% yield).

Example 18

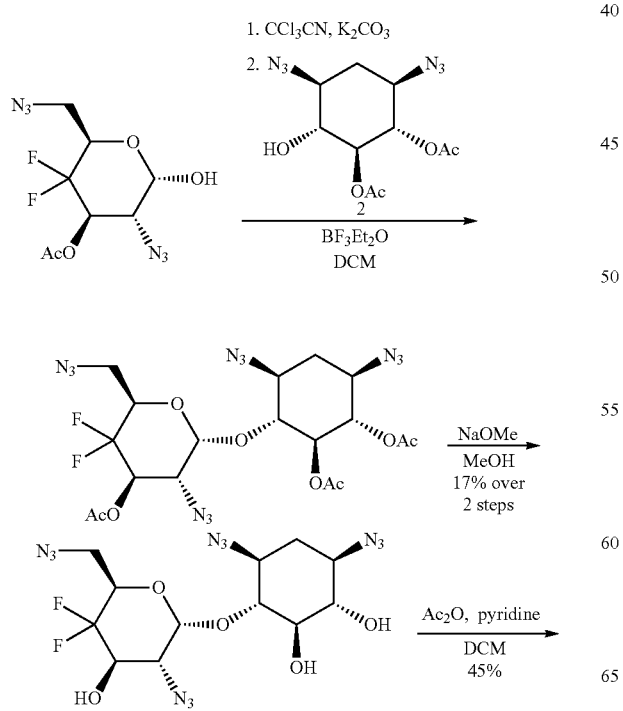

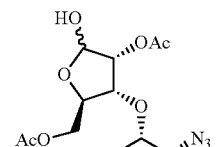

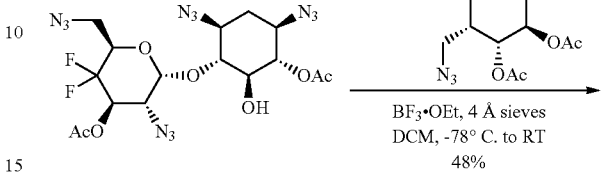

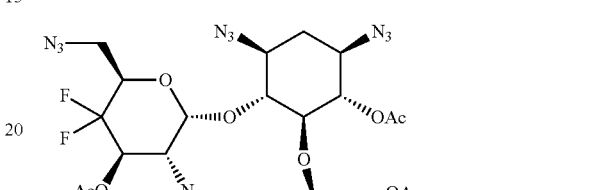

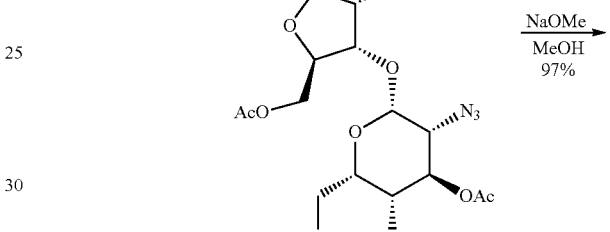

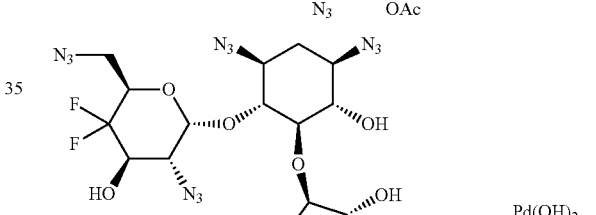

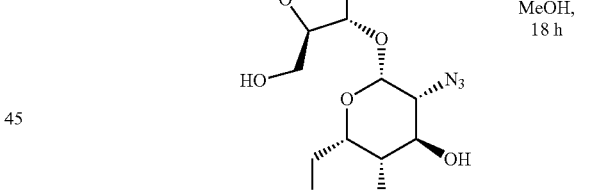

Step 1

(1S,2R,3R,4S,6R)-4,6-diazido-3-[(2S,3R,4R,6R)-3-azido-6-(azidomethyl)-5,5-difluoro-4-hydroxy-tetrahydropyran-2-yl]oxy-cyclohexane-1,2-diol

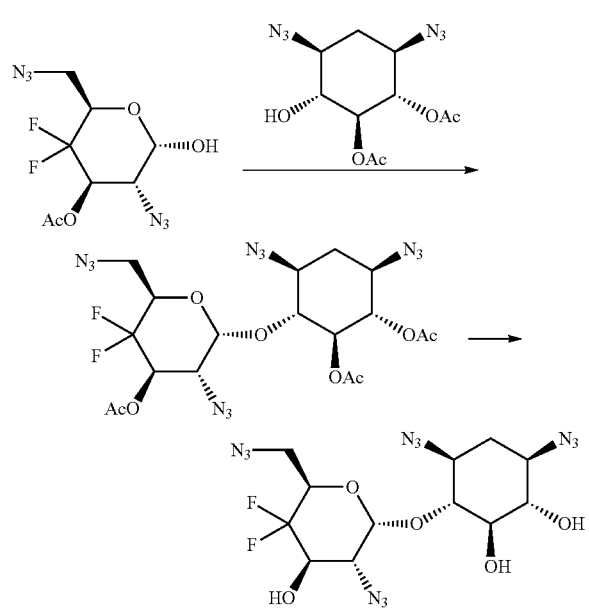

CCl₃CN (0.34 mL, 3.42 mmol) was added dropwise to a suspension of [(2R,4R,5R)-5-azido-2-(azidomethyl)-3,3-difluoro-6-hydroxy-tetrahydropyran-4-yl] acetate (preparation below, 200 mg, 0.68 mmol) and K₂CO₃ (284 mg, 2.05 mmol) in dry DCM (20 mL) at ambient temperature under N₂. After 72 h, the solution was filtered through cotton and the filtrate was concentrated under N₂ stream, followed by high-vacuum.

To the above material was added [(1S,2S,3R,4S,6R)-2-acetoxy-4,6-diazido-3-hydroxy-cyclohexyl] acetate (408 mg, 1.37 mmol) and ground 4 Å sieves and then dry DCM (20 mL) was added. The suspension was stirred at ambient temperature for 1 h. The solution was cooled to −78° C. and BF₃·Et₂O (0.34 mL, 2.74 mmol) was added dropwise with vigorous stirring and the resulting mixture was stirred at −78° C. for 1 h. The mixture was warmed to ambient temperature and stirred for another hour. The reaction was diluted with saturated NaHCO₃ (100.0 mL) and the aqueous layer mixture was extracted with DCM (3×50 mL). The combined organic layers were dried (Na₂SO₄), filtered and concentrated under reduced pressure to afford an acetylated dimer.

NaOMe (25 wt %, 0.44 mL, 2.05 mmol) was added dropwise to a solution of the crude acetylated dimer in MeOH (2.0 mL) at ambient temperature and the reaction mixture was stirred for 70 min. The mixture was diluted with AcOH (0.23 mL, 4.11 mmol) and the volatiles were removed under reduced pressure. The residue was purified by silica gel chromatography (24 g cartridge) using a gradient of EtOAc in hexane (0-50%) as eluent to afford the title compound (49.5 mg, 16%, 3 steps).

Step 2

[(1S,2S,3R,4S,6R)-3-[(2S,3R,4R,6R)-4-acetoxy-3-azido-6-(azidomethyl)-5,5-difluoro-tetrahydropyran-2-yl]oxy-4,6-diazido-2-hydroxy-cyclohexyl] acetate

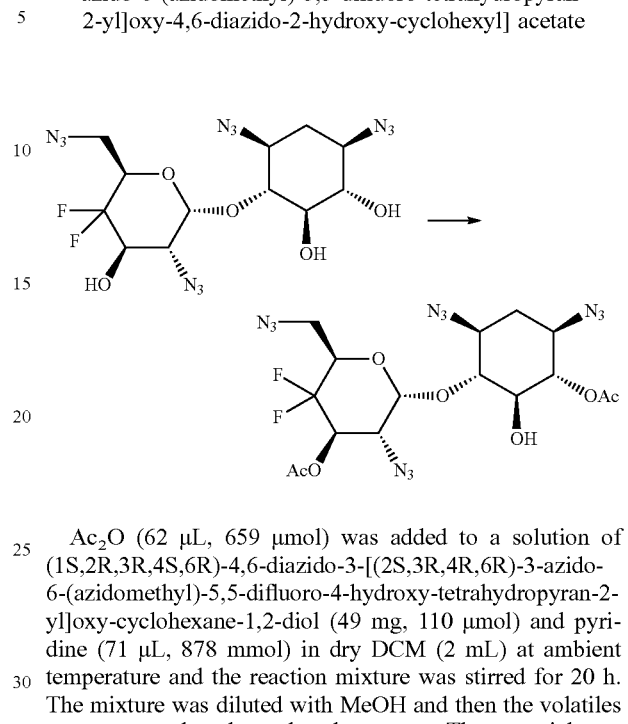

Ac₂O (62 μL, 659 μmol) was added to a solution of (1S,2R,3R,4S,6R)-4,6-diazido-3-[(2S,3R,4R,6R)-3-azido-6-(azidomethyl)-5,5-difluoro-4-hydroxy-tetrahydropyran-2-yl]oxy-cyclohexane-1,2-diol (49 mg, 110 μmol) and pyridine (71 μL, 878 mmol) in dry DCM (2 mL) at ambient temperature and the reaction mixture was stirred for 20 h. The mixture was diluted with MeOH and then the volatiles were removed under reduced pressure. The material was purified by silica gel chromatography (12 g cartridge) using a gradient of EtOAc and hexane (5-25%) as eluent to afford the title compound as an oil along with beta anomer (~25%). The mixture was repurified by silica gel chromatography (12 g cartridge) using a gradient of EtOAc and hexane (15-30%) as eluent to afford the title compound (26.0 mg, 45%) as an oil. ¹H NMR (500 MHz, CDCl₃) δ 5.61-5.50 (m, 1H), 5.42-5.37 (m, 1H), 4.84 (t, J=9.9 Hz, 1H), 4.46 (ddd, J=24.0, 8.1, 2.9 Hz, 1H), 3.70 (dd, J=10.9, 3.6 Hz, 1H), 3.62 (td, J=9.4, 3.8 Hz, 1H), 3.56-3.32 (m, 7H), 2.38-2.32 (m, 1H), 2.16 (s, 3H), 2.11 (s, 3H), 1.65-1.52 (m, 1H).

Step 3

(2S,3S,4R,5R,6R)-5-azido-2-(azidomethyl)-6-[(2R,3S,4R,5S)-5-[(1R,2R,3S,5R,6S)-3,5-diazido-2-[(2S,3R,4R,6R)-3-azido-6-(azidomethyl)-5,5-difluoro-4-methyl-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol

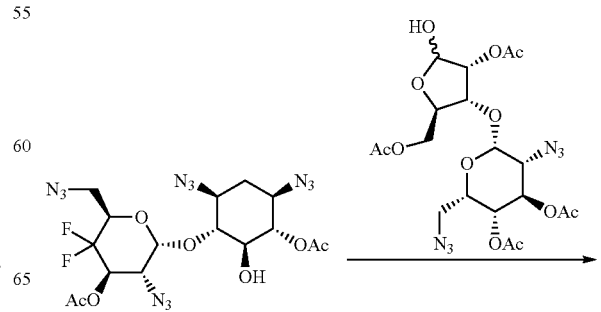

-continued

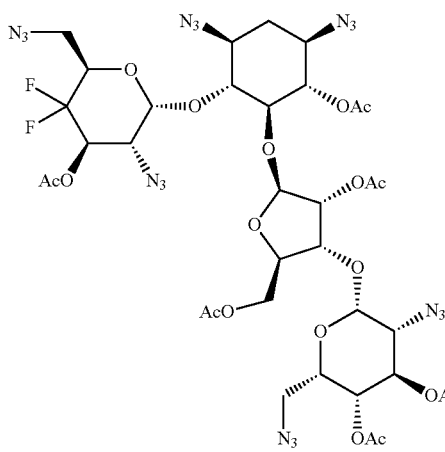

CCl$_3$CN (0.074 mL, 0.74 mmol) was added dropwise to a mixture of [(2R,3R,4R)-4-acetoxy-3-[(2R,3R, 4R,5R,6S)-4,5-diacetoxy-3-azido-6-(azidomethyl)tetrahydropyran-2-yl]oxy-5-hydroxy-tetrahydrofuran-2-yl]methyl acetate (78 mg, 0.15 mmol) and K$_2$CO$_3$ (61 mg, 0.44 mmol) in dry DCM (5 mL) at room temperature under N$_2$. The mixture was stirred at room temperature for 18 h, then filtered through a 45 μm nylon filter and rinsed with DCM. The filtrate was concentrated under reduced pressure and used in the next step without further purification.

To a solution of [(1S,2S,3R,4S,6R)-3-[(2S,3R,4R,6R)-4-acetoxy-3-azido-6-(azidomethyl)-5,5-difluoro-tetrahydropyran-2-yl]oxy-4,6-diazido-2-hydroxy-cyclohexyl] acetate (26 mg, 0.049 mmol) in DCM (5 mL) was added the above material followed 4 Å molecular sieves and the mixture was cooled to −78° C. BF$_3$·Et$_2$O (0.030 mL, 0.25 mmol) was then added dropwise and the reaction mixture was stirred at room temperature for 4 h. The mixture was diluted with saturated NaHCO$_3$ (8 mL) and the separated aqueous layer was extracted with DCM (2×8 mL). The combined organic layer was washed with brine, then dried (Na$_2$SO$_4$), filtered and concentrated under reduced pressure. The material was purified by flash column chromatography (12 g) using a gradient of EtOAc in hexane (0-45%) as eluent to afford the title compound (24.5 mg, 48%). $^1$H NMR (500 MHz, CDCl$_3$) δ 6.04 (d, J=2.6 Hz, 1H), 5.57 (ddd, J=19.6, 11.2, 4.6 Hz, 1H), 5.33 (d, J=2.6 Hz, 1H), 5.02 (t, J=2.8 Hz, 1H), 4.95 (t, J=9.8 Hz, 1H), 4.92-4.85 (m, 2H), 4.73-4.63 (m, 2H), 4.45-4.38 (m, 2H), 4.32-4.25 (m, 2H), 4.10-4.06 (m, 1H), 3.89 (t, J=9.0 Hz, 1H), 3.72-3.67 (m, 1H), 3.60-3.40 (m, 5H), 3.33-3.25 (m, 3H), 2.40 (dt, J=13.2, 4.5 Hz, 1H), 2.21 (s, 3H), 2.17-2.14 (m, 9H), 2.11 (s, 3H), 2.09 (s, 3H), 1.70-1.62 (m, 1H). MS (ESI) [M+NH$_4$]$^+$ 1060.4.

Step 4

(2S,3S,4R,5R,6R)-5-azido-2-(azidomethyl)-6-[(2R, 3S,4R,5S)-5-[(1R,2R,3S,5R,6S)-3,5-diazido-2-[(2S, 3R,4R,6R)-3-azido-6-(azidomethyl)-5,5-difluoro-4-hydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol

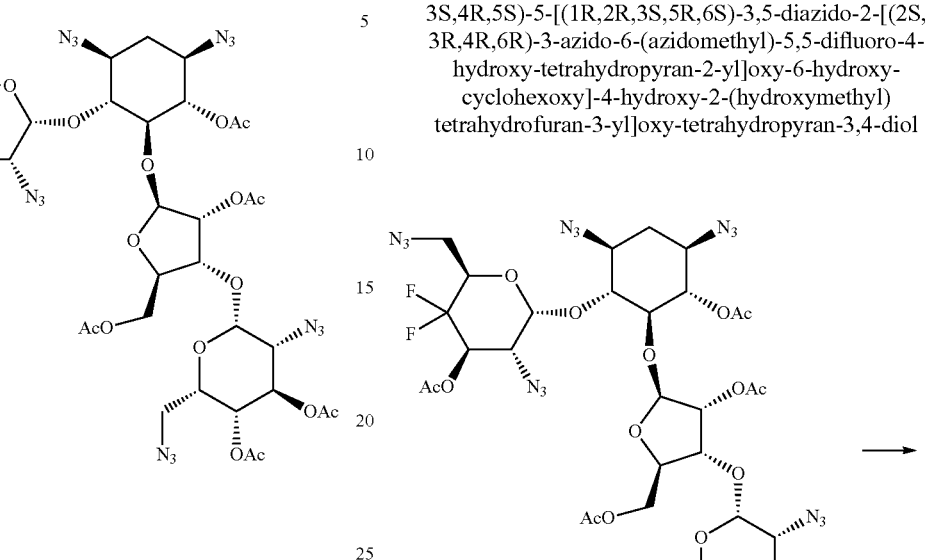

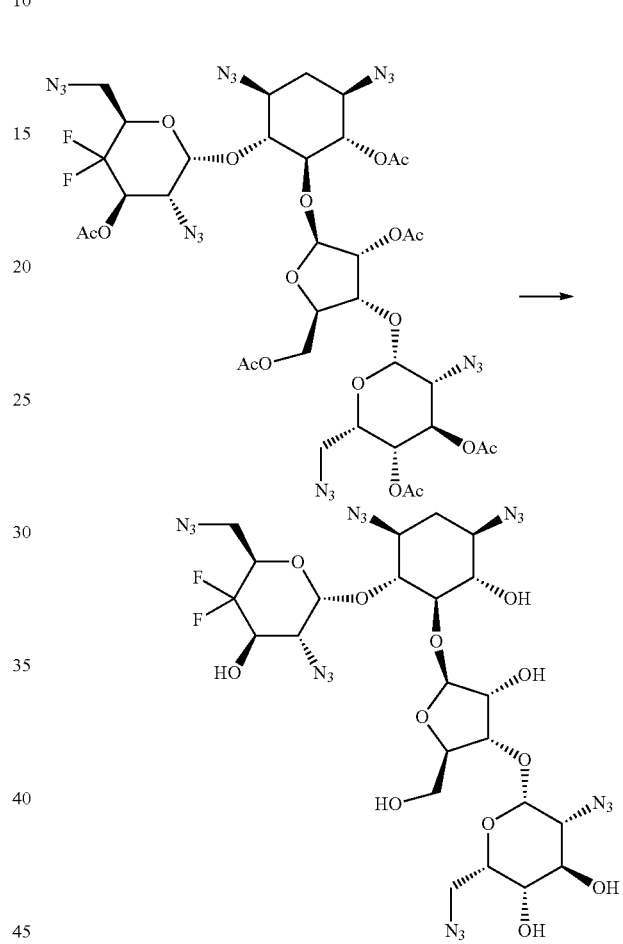

NaOMe (25 wt %, 41 μL, 0.14 mmol) was added dropwise to a solution of (2S,3S,4R,5R,6R)-5-azido-2-(azidomethyl)-6-[(2R,3S,4R,5S)-5-[(1R,2R,3S,5R,6S)-3,5-diazido-2-[(2S,3R,4R,6R)-3-azido-6-(azidomethyl)-5,5-difluoro-4-methyl-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol (24.5 mg, 0.024 mmol) in MeOH (2 mL) at ambient temperature and the reaction mixture was stirred for 75 min. The mixture was diluted with AcOH (0.013 mL, 0.24 mmol) and the volatiles were removed under reduced pressure. The residue was diluted in EtOAc and the organic layer was washed with saturated NaHCO$_3$ and brine, then dried (Na$_2$SO$_4$), filtered and concentrated under reduced pressure to give the title compound (18.0 mg, 97%). $^1$H NMR (500 MHz, MeOD) δ 5.91 (s, 1H), 5.29 (d, J=2.1 Hz, 1H), 5.04 (d, J=1.7 Hz, 1H), 4.49-4.36 (m, 1H), 4.31 (dd, J=6.3, 4.7 Hz, 1H), 4.21 (dd, J=4.5, 2.2 Hz, 1H), 4.10-4.01 (m, 2H), 3.92 (ddd, J=8.4, 4.5, 1.9 Hz, 1H), 3.84 (t, J=3.3 Hz, 1H), 3.78-3.71 (m, 1H), 3.64-3.24 (m, 13H), 2.18-2.09 (m, 1H), 1.32-1.25 (m, 1H).

Step 5

(2S,3S,4R,5R,6R)-5-amino-2-(aminomethyl)-6-[(2R,3S,4R,5S)-5-[(1R,2R,3S,5R,6S)-3,5-diamino-2-[(2S,3R,4R,6R)-3-amino-6-(aminomethyl)-5,5-difluoro-4-hydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol

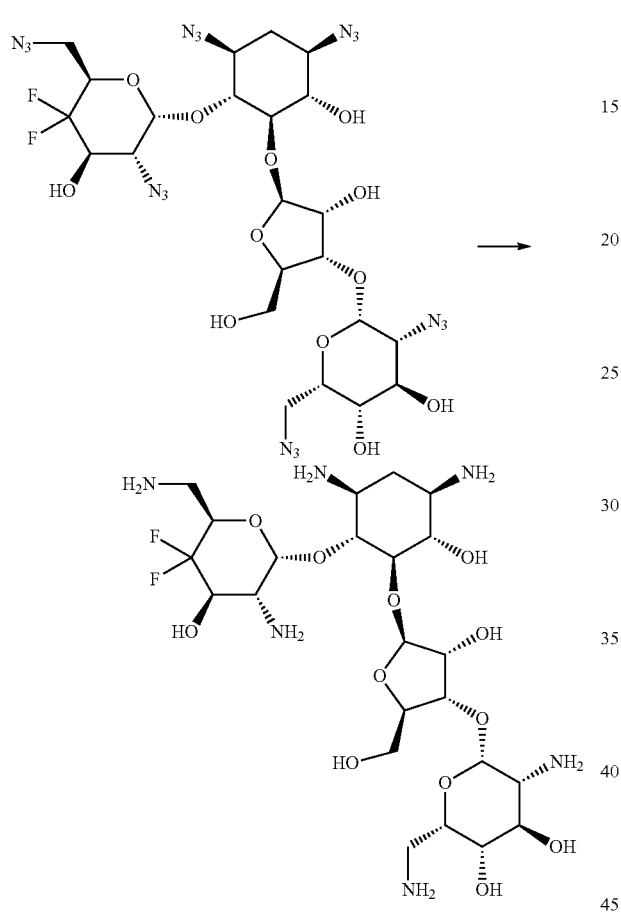

Pd(OH)$_2$ (2.8 mg, 2.0 μmol) was added to a solution of (2S,3S,4R,5R,6R)-5-azido-2-(azidomethyl)-6-[(2R,3S,4R,5S)-5-[(1R,2R,3S,5R,6S)-3,5-diazido-2-[(2S,3R,4R,6R)-3-azido-6-(azidomethyl)-5,5-difluoro-4-hydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol (4.5 mg, 5.7 μmol) in MeOH (3.0 mL) under N$_2$ at ambient temperature. The suspension was bubbled with H$_2$ for 10 min and then hydrogenated for 16 h under hydrogen atmosphere (1 atm, balloon). The mixture was filtered through a frit (nylon, 0.45 m diameter), rinsed with MeOH and the filtrate was concentrated under reduced pressure to give the title compound. Note: the exact procedure was repeated (on 13.5 mg, 17.1 μmol scale) to give the title compound (16.4 mg overall amount). $^1$H NMR (500 MHz, MeOD) δ 5.54 (s, 1H), 5.35 (d, J=2.8 Hz, 1H), 4.98 (d, J=1.7 Hz, 1H), 4.43-4.39 (m, 1H), 4.19-4.07 (m, 3H), 4.01-3.93 (m, 3H), 3.86-3.81 (m, 1H), 3.74 (dd, J=12.3, 3.9 Hz, 1H), 3.61 (t, J=9.2 Hz, 1H), 3.54-3.47 (m, 2H), 3.25 (t, J=9.5 Hz, 1H), 3.15 (dd, J=13.2, 8.4 Hz, 1H), 3.06-3.00 (m, 2H), 2.98-2.90 (m, 3H), 2.90-2.84 (m, 1H), 2.68 (ddd, J=12.2, 9.8, 4.1 Hz, 1H), 2.04-1.96 (m, 1H), 1.30-1.20 (m, 1H).

Preparation of [(2R,4R,5R)-5-azido-2-(azidomethyl)-3,3-difluoro-6-hydroxy-tetrahydropyran-4-yl] acetate

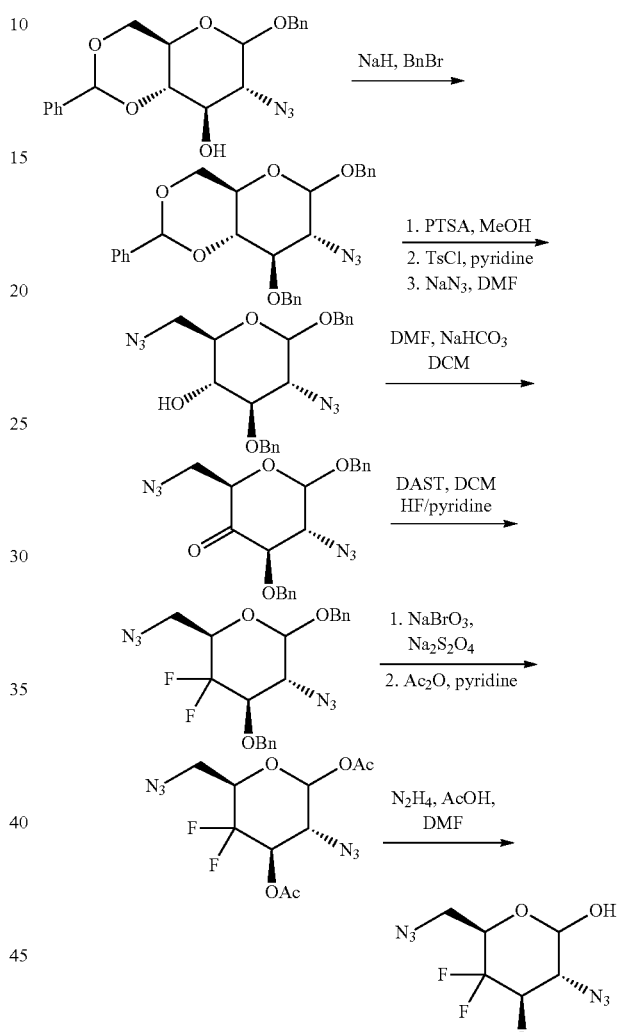

Step 1

(4aR,7R,8R,8aS)-7-azido-6,8-bis(benzyloxy)-2-phenylhexahydropyrano[3,2-d][1,3]dioxine

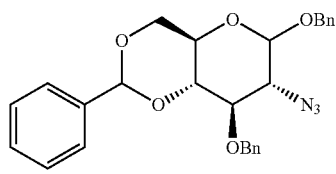

To a solution of 4.8 g of (4aR,7R,8R,8aS)-7-azido-6-(benzyloxy)-2-phenylhexahydropyrano[3,2-d][1,3]dioxin- 8-ol in 50 mL of anhydrous DMF at 4° C., was added 750 mg of NaH in several portions. The reaction was stirred at 0° C. for 30 minutes. 2.2 g of benzyl bromide was added to the reaction and the vessel was removed from the ice bath and allowed to warm to room temperature. After completion, the reaction was quenched with cold water and concentrated in vacuo. The concentrate was dissolved in DCM and washed with equal volumes of 1 N HCl and brine. The organic portion was dried, filtered and concentrated to dryness. The residue was then purified by flash chromatography (10% EtOAc in hexanes) to yield 5.7 g of (4aR,7R,8R,8aS)-7-azido-6,8-bis(benzyloxy)-2-phenylhexahydropyrano[3,2-d][1,3]dioxine (96% yield).

Step 2

(2R,3R,4R,5R)-5-azido-2-(azidomethyl)-4,6-bis(benzyloxy)tetrahydro-2H-pyran-3-ol

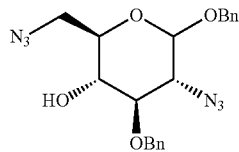 [SMILES: [N-]=[N+]=NC[C@H]1OC(OCc2ccccc2)[C@H](N=[N+]=[N-])[C@@H](OCc2ccccc2)[C@@H]1O]

To a solution of 15 g of (4aR,7R,8R,8aS)-7-azido-6,8-bis(benzyloxy)-2-phenylhexahydropyrano[3,2-d][1,3]dioxine in 100 mL of methanol, was added 540 mg of p-toluene sulfonic acid at room temperature. The reaction was stirred at room temperature for 4 hours until completion. The reaction was then quenched with 0.1 equivalent of triethylamine, concentrated, and purified by flash chromatography (10% EtOAC in DCM) to yield 5.6 g of the diol intermediate. The diol was dissolved in 15 mL of DCM, cooled to 0° C., and 9 mL of pyridine was added, followed by 3.6 g of Tosyl chloride. The reaction was stirred at 0° C. for 3 hours until completion. The reaction was then diluted with 100 mL of DCM and washed with an equal volume of 1 N HCl followed by aqueous sodium bicarbonate. The organic portion was dried, filtered and concentrated. The crude concentrate was dissolved in mL DMF, 4.7 g of sodium azide was added, and the reaction heated at 70° C. for hours. The DMF was removed by evaporation and the crude was dissolved in EtOAc and washed with water. The organic portion was dried, filtered, and concentrated then purified by flash chromatography to yield 5.8 g of (2R,3R,4R,5R)-5-azido-2-(azidomethyl)-4,6-bis(benzyloxy)tetrahydro-2H-pyran-3-ol (97% yield).

Step 3

(2R,4R,5R)-5-azido-2-(azidomethyl)-4,6-bis(benzyloxy)dihydro-2H-pyran-3 (4H)-one

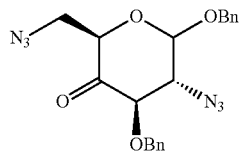 [SMILES: [N-]=[N+]=NC[C@H]1OC(OCc2ccccc2)[C@H](N=[N+]=[N-])[C@@H](OCc2ccccc2)C1=O]

To a solution of 5.9 g of the alcohol (2R,3R,4R,5R)-5-azido-2-(azidomethyl)-4,6-bis(benzyloxy)tetrahydro-2H-pyran-3-ol in 50 mL of DCM was added 1.57 g of NaHCO$_3$ and 7.93 g of DMP at 0° C. and the reaction was allowed to warm to room temperature and stirred until completion. The reaction was quenched with aqueous sodium bicarbonate, diluted with DCM, and washed with an equal volume of aqueous sodium bicarbonate. The organic portion was dried, filtered, concentrated, and purified by flash chromatography to yield a white solid. The solid was washed with Et$_2$O to obtain 5.0 g of pure product (85% yield).

Step 4

(2R,4R,5R)-5-azido-2-(azidomethyl)-4,6-bis(benzyloxy)-3,3-difluorotetrahydro-2H-pyran

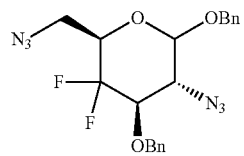 [SMILES: [N-]=[N+]=NC[C@H]1OC(OCc2ccccc2)[C@H](N=[N+]=[N-])[C@@H](OCc2ccccc2)C1(F)F]

To a solution of 2.6 g of (2R,4R,5R)-5-azido-2-(azidomethyl)-4,6-bis(benzyloxy)dihydro-2H-pyran-3 (4H)-one in 30 mL DCM was added 3.5 g of DAST and 291 mg HF/pyridine at 0° C. The reaction was then heated to reflux until the reaction was complete. The reaction was then cooled to 0° C. and quenched with aqueous sodium bicarbonate, then diluted with DCM and washed with an equal volume of aqueous sodium bicarbonate. The organic portion was dried, filtered and concentrated, then purified by flash chromatography (15:85 EtOAc/Hexanes) to yield 1.8 grams of (2R,4R,5R)-5-azido-2-(azidomethyl)-4,6-bis(benzyloxy)-3,3-difluorotetrahydro-2H-pyran (66% yield).

Step 5

(3R,4R,6R)-3-azido-6-(azidomethyl)-5,5-difluorotetrahydro-2H-pyran-2,4-diyl diacetate

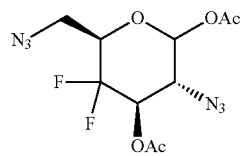 [SMILES: CC(=O)OC1O[C@H](CN=[N+]=[N-])C(F)(F)[C@H](OC(C)=O)[C@H]1N=[N+]=[N-]]

The starting material, (2R,4R,5R)-5-azido-2-(azidomethyl)-4,6-bis(benzyloxy)-3,3-difluorotetrahydro-2H-pyran, was dissolved in 7.2 mL EtOAc. 6 mL of aqueous sodium bromate (69 mM) was added to the reaction in one portion. Next, aqueous sodium dithionate was slowly added dropwise over 15 minutes and the reaction stirred vigorously until completion. The reaction was diluted with EtOAc and washed with 1:1 aqueous sodium bicarbonate and sodium thiosulfate. The organic layer was concentrated and dissolved in 10 mL anhydrous pyridine. 3 mL of acetic anhydride was added slowly and the reaction stirred at room temperature until completion. The reaction was concentrated to dryness, dissolved in 100 mL DCM, and washed with 1 N HCl aq, followed by saturated aqueous sodium bicarbonate. The organic portion was concentrated, dissolved in DCM, and purified by flash chromatography (3:7 EtOAc/

Hexanes) to yield 135 mg of (3R,4R,6R)-3-azido-6-(azidomethyl)-5,5-difluorotetrahydro-2H-pyran-2,4-diyl diacetate (88% yield).

Step 6

(2R,4R,5R)-5-azido-2-(azidomethyl)-3,3-difluoro-6-hydroxytetrahydro-2H-pyran-4-yl acetate

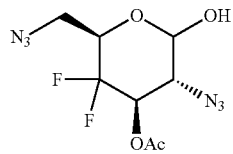 [SMILES: CC(=O)O[C@@H]1[C@@H](N=[N+]=[N-])C(O)O[C@H](CN=[N+]=[N-])C1(F)F]

To a solution of 140 mg (3R,4R,6R)-3-azido-6-(azidomethyl)-5,5-difluorotetrahydro-2H-pyran-2,4-diyl diacetate in 2 mL of anhydrous DMF, was added 40 mg of hydrazine acetate. The reaction was heated at 50° C. for 1 hour. The reaction was concentrated to dryness and the residue taken up in 100 mL DCM. The organic layer was washed with 1 N HCl and aqueous sodium bicarbonate. The washed organic portion was concentrated and purified by flash chromatography (3:7 EtOAc/Hexanes). 110 mg of (2R,4R,5R)-5-azido-2-(azidomethyl)-3,3-difluoro-6-hydroxytetrahydro-2H-pyran-4-yl acetate was isolated (92% yield).

Example 19

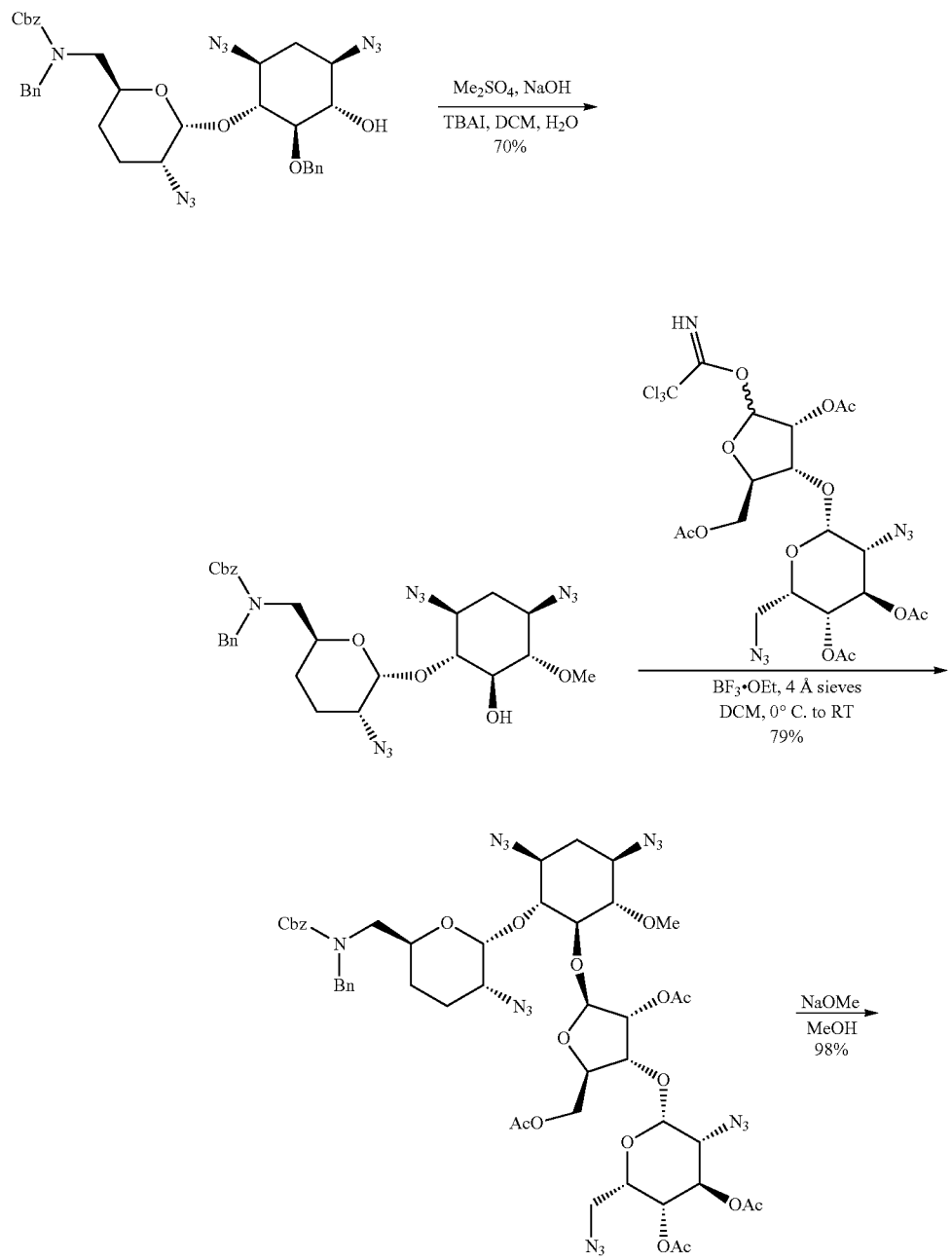

455

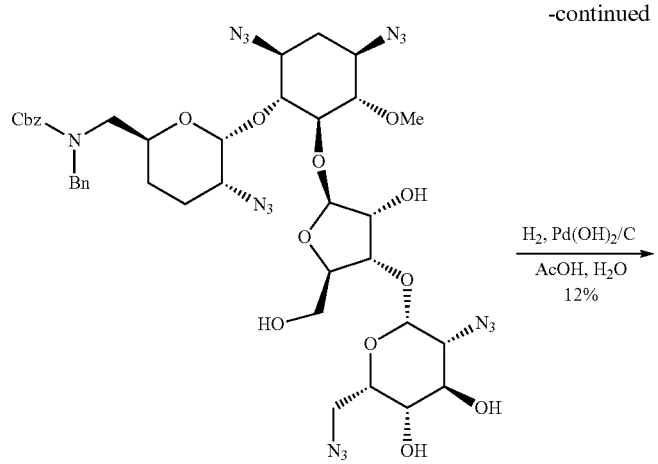

456

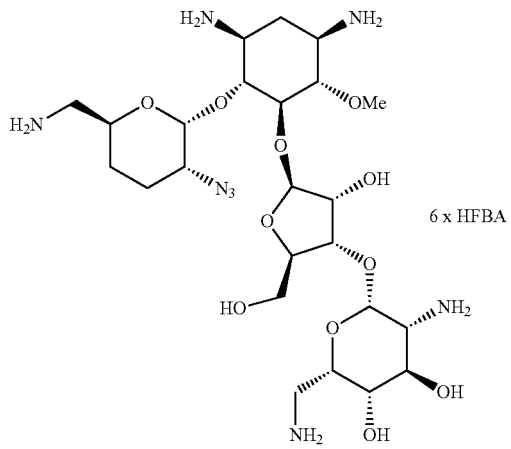

-continued

Step 1

Benzyl N-[[(2S, 5R,6R)-5-azido-6-[(1R,2R,3S,4R, 6S)-4,6-diazido-2-hydroxy-3-methoxy-cyclohexoxy] tetrahydropyran-2-yl]methyl]-N-benzyl-carbamate

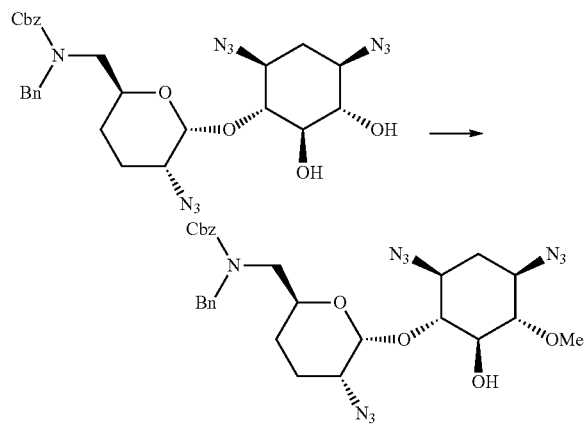

Me$_2$SO$_4$ (128 µL, 1.35 mmol) was added to a vigorously stirring suspension of benzyl N-[[(5R,6R)-5-azido-6-[(1R, 2R,3S,4R,6S)-4,6-diazido-2,3-dihydroxy-cyclohexoxy]tetrahydropyran-2-yl]methyl]-N-benzyl-carbamate (see Example 21 for synthesis, 100 mg, 169 µmol) and TBAI (9 mg, 25 µmol) in DCM (2.5 mL) and NaOH solution (1.0 M aq., 2.5 mL, 2.5 mmol) at ambient temperature. After 2 h, concentrated NH$_4$OH (300 µL) was added and the mixture was partitioned in between water (10.0 mL) and DCM (10.0 mL). The aqueous layer was extracted with DCM (2×5.0 mL). The combined organic layers were dried (Na$_2$SO$_4$), filtered and concentrated under reduced pressure. The residue was filtered through silica gel (0.30 g) and eluted with EtOAc (6.0 mL). The filtrate was concentrated under reduced pressure and the material was purified by preparative HPLC (BEH 30×150 mm C18 ACN/AmForm 70-80%) to provide the title compound (rotamers, 72 mg, 70%) as a solid. $^1$H NMR (500 MHz, CDCl$_3$) δ 7.39-7.13 (m, 10H), 5.34-5.08 (m, 3H), 4.81-4.69 (m, 1H), 4.56-4.45 (m, 1H), 4.27 (d, J=43.5 Hz, 1H), 3.69 (s, 3H), 3.61-3.14 (m, 8H), 2.99 (t, J=9.5 Hz, 1H), 2.22 (dt, J=13.2, 4.5 Hz, 1H), 2.08-1.96 (m, 1H), 1.96-1.87 (m, 1H), 1.87-1.68 (m, 1H), 1.50-1.30 (m, 2H). MS ESI [M+H]$^+$ 607.3.

Step 2

[(2R,3R,4R,5S)-4-acetoxy-3-[(2R,3R,4R,5R,6S)-4, 5-diacetoxy-3-azido-6-(azidomethyl)tetrahydropyran-2-yl]oxy-5-[(1R,2R,3S,5R,6S)-3,5-diazido-2-[(2R,3R,6S)-3-azido-6-[[benzyl(benzyloxycarbonyl) amino]methyl]tetrahydropyran-2-yl]oxy-6-methoxycyclohexoxy]tetrahydrofuran-2-yl]methyl acetate

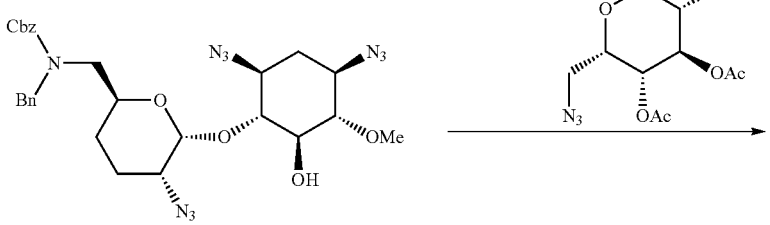

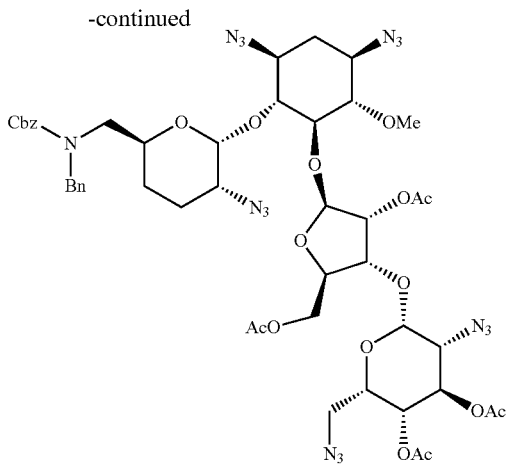

CCl₃CN (119 μL, 1.19 mmol) was added dropwise to a suspension of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (126 mg, 237 μmol) and K₂CO₃ (98 mg, 712 μmol) in dry DCM (2.0 mL) at ambient temperature under N₂. After 18 h, the solution was filtered through cotton and the filtrate was concentrated under N₂ stream, followed by high-vacuum. To the crude material was added a solution of benzyl N-[[(2S,5R,6R)-5-azido-6-[(1R,2R,3S,4R,6S)-4,6-diazido-2-hydroxy-3-methoxy-cyclohexoxy]tetrahydropyran-2-yl]methyl]-N-benzyl-carbamate (72 mg, 119 μmol) in DCM (3.0 mL) and then all volatiles were evaporated under N₂ stream. To the mixture was added ground 4 Å sieves (500 mg) and the mixture was dissolved in dry DCM (2.0 mL). The suspension was stirred at ambient temperature for 60 min, then cooled to 0° C., and then BF₃·OEt₂ (43 μL, 351 μmol) was added. The mixture was stirred at ambient temperature for 1 h and then Et₃N (200 μL) was added. The mixture was filtered through a silica gel pad (0.50 g) and eluted with EtOAc (10.0 mL). The volatiles were evaporated under reduced pressure and the material was purified by reversed phase chromatography (C18, 30 g cartridge) with ACN and 0.1% aqueous formic acid (50-100%) to produce the title compound (105 mg, 79%) as a solid. MS ESI [M+H]⁺ 1019.4.

Step 3

Benzyl N-[[(2S,5R,6R)-5-azido-6-[(1R,2R,3S,4R,6S)-4,6-diazido-2-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl)tetrahydrofuran-2-yl]oxy-3-methoxy-cyclohexoxy]tetrahydropyran-2-yl]methyl]-N-benzyl-carbamate

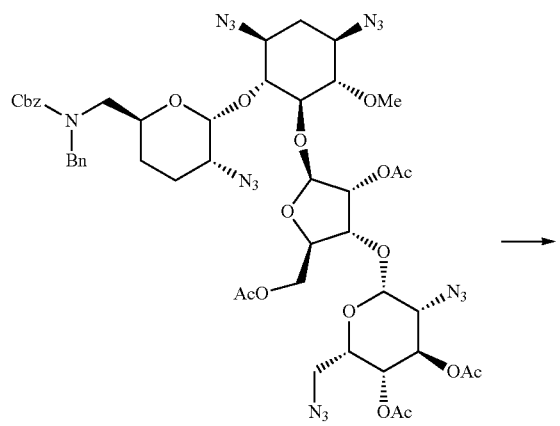

→

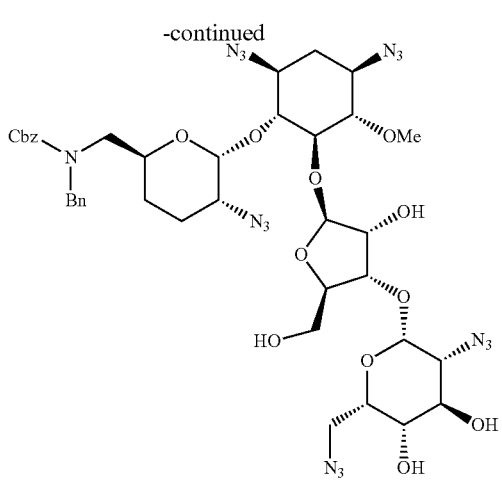

NaOMe (25 wt %, 77 μL, 336 μmol) was added dropwise to a solution of [(2R,3R,4R,5S)-4-acetoxy-3-[(2R,3R,4R,5R,6S)-4,5-diacetoxy-3-azido-6-(azidomethyl)tetrahydropyran-2-yl]oxy-5-[(1R,2R,3S,5R,6S)-3,5-diazido-2-[(2R,3R,6S)-3-azido-6-[[benzyl(benzyloxycarbonyl)amino]methyl]tetrahydropyran-2-yl]oxy-6-methoxy-cyclohexoxy]tetrahydrofuran-2-yl]methyl acetate (47 mg, 42 μmol) in MeOH (1.0 mL) at ambient temperature and the reaction mixture was stirred for 75 min. AcOH (29 μL, 504 μmol) was added dropwise and all volatiles were evaporated under reduced pressure. The material was filtered through silica gel (0.30 g) and eluted with EtOAc (8.0 mL) to provide the title compound (rotamers, 39 mg, 98%) as a solid. ¹H NMR (500 MHz, CDCl₃) δ 7.39-7.25 (m, 9H), 7.18 (d, J=7.1 Hz, 1H), 5.73 (d, J=25.1 Hz, 1H), 5.40 (d, J=4.6 Hz, 1H), 5.30-5.07 (m, 3H), 4.85-4.65 (m, 1H), 4.59-4.46 (m, 1H), 4.39-4.22 (m, 2H), 4.16 (s, 1H), 4.11-4.08 (m, 1H), 4.02 (ddd, J=8.5, 4.5, 1.9 Hz, 1H), 3.99 (dd, J=5.8, 4.8 Hz, 1H), 3.88 (dd, J=12.6, 2.3 Hz, 1H), 3.83-3.73 (m, 3H), 3.69-3.60 (m, 4H), 3.52 (t, J=9.5 Hz, 1H), 3.47-3.33 (m, 5H), 3.28-3.13 (m, 1H), 3.12-2.88 (m, 3H), 2.23-2.15 (m, 1H), 2.15-2.09 (m, 1H), 1.93-1.69 (m, 2H).

Step 4

(2S,3S,4R,5R,6R)-5-amino-2-(aminomethyl)-6-[(2R,3S,4R,5S)-5-[(1R,2R,3S,5R,6S)-3,5-diamino-2-[(2R,3R,6S)-3-amino-6-(aminomethyl)tetrahydropyran-2-yl]oxy-6-methoxy-cyclohexoxy]-4-hydroxy-2-(hydroxymethyl)tetrahydrofuran-3-yl]oxy-tetrahydropyran-3,4-diol;2,2,3,3,4,4,4-heptafluorobutanoic acid

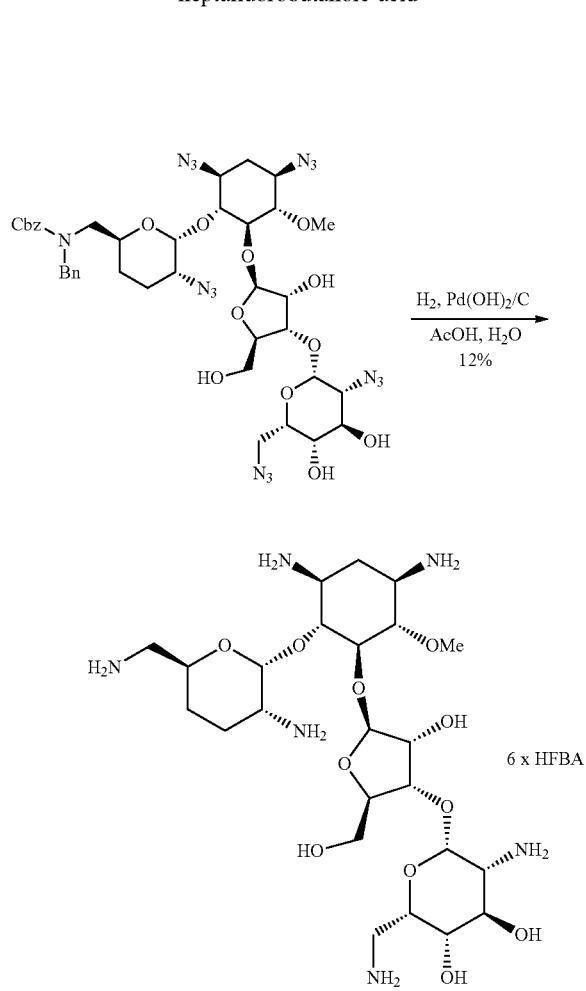

Pd(OH)₂/C (10 wt %, 18 mg, 13 µmol) was added to a solution of benzyl N-[[(2S,5R,6R)-5-azido-6-[(1R,2R,3S,4R,6S)-4,6-diazido-2-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl)tetrahydrofuran-2-yl]oxy-3-methoxy-cyclohexoxy]tetrahydropyran-2-yl]methyl]-N-benzyl-carbamate (18 mg, 19 µmol) in 4:1 AcOH/H₂O (0.50 mL) under N₂ at ambient temperature. H₂ was bubbled into the solution for 20 min and the resulting mixture was for 20 h. The mixture was filtered through a frit (0.45 µm diameter), washed with water (5.0 mL) and the filtrate was lyophilized. The material was purified by a HFBA-coupled preparative HPLC to provide the title compound (4.4 mg, 12%) as a solid. ¹H NMR (500 MHz, MeOD) δ 6.08 (d, J=3.5 Hz, 1H), 5.40 (d, J=3.9 Hz, 1H), 5.32 (d, J=1.3 Hz, 1H), 4.40 (t, J=5.7 Hz, 1H), 4.29 (dd, J=6.0, 4.1 Hz, 1H), 4.24 (t, J=9.5 Hz, 1H), 4.16-4.07 (m, 4H), 3.95 (t, J=8.9 Hz, 1H), 3.90 (dd, J=12.2, 2.4 Hz, 1H), 3.76 (dd, J=12.1, 5.3 Hz, 1H), 3.69-3.67 (m, 1H), 3.67 (s, 3H), 3.56-3.46 (m, 3H), 3.41-3.35 (m, 3H), 3.26 (dd, J=13.4, 3.9 Hz, 1H), 3.15 (dd, J=13.2, 2.4 Hz, 1H), 2.95 (dd, J=13.2, 8.6 Hz, 1H), 2.46 (dt, J=12.1, 3.7 Hz, 1H), 2.23-2.08 (m, 2H), 1.96-1.83 (m, 2H), 1.57-1.46 (m, 1H). MS (ESI) [M+H]⁺ 597.4.

Example 20

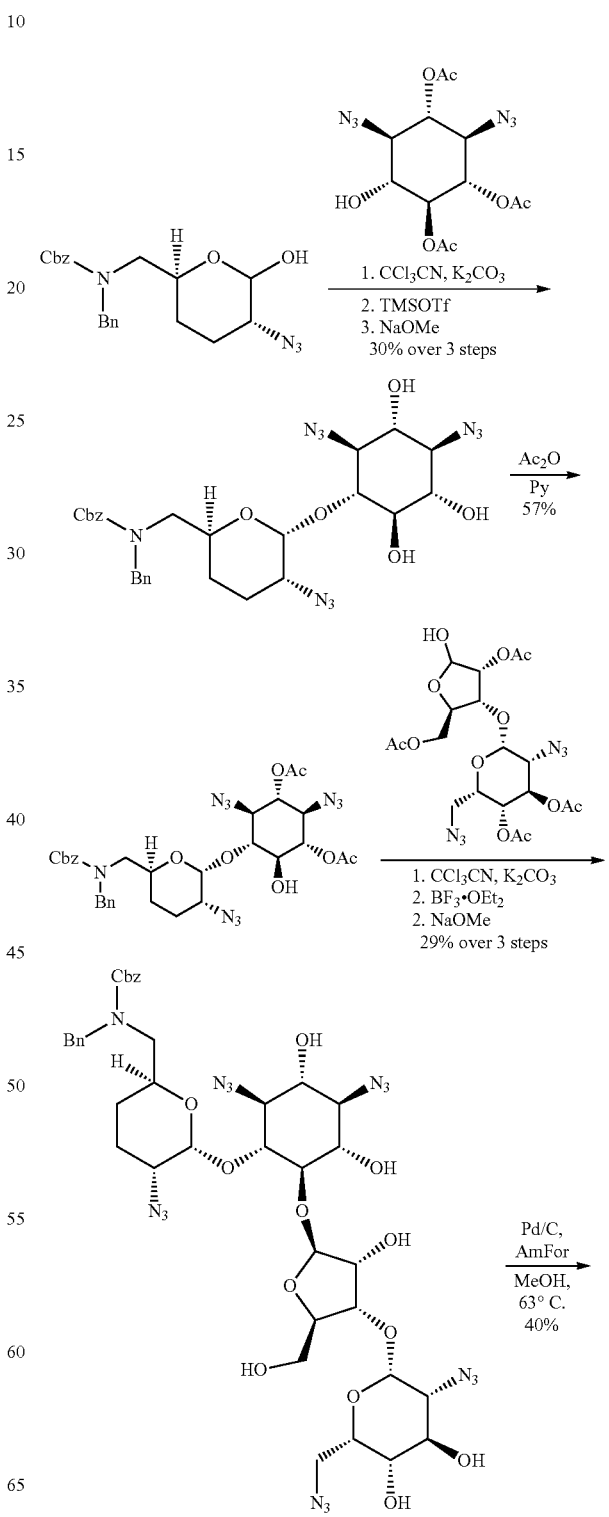

-continued

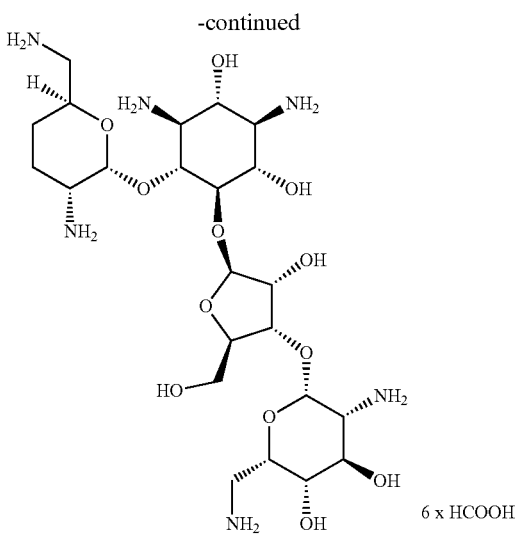

6 x HCOOH

Step 1

Benzyl N-[[(2S,5R,6R)-5-azido-6-[(1R,2S,3R,4R,5S,6R)-2,4-diazido-3,5,6-trihydroxy-cyclohexoxy]tetrahydropyran-2-yl]methyl]-N-benzyl-carbamate

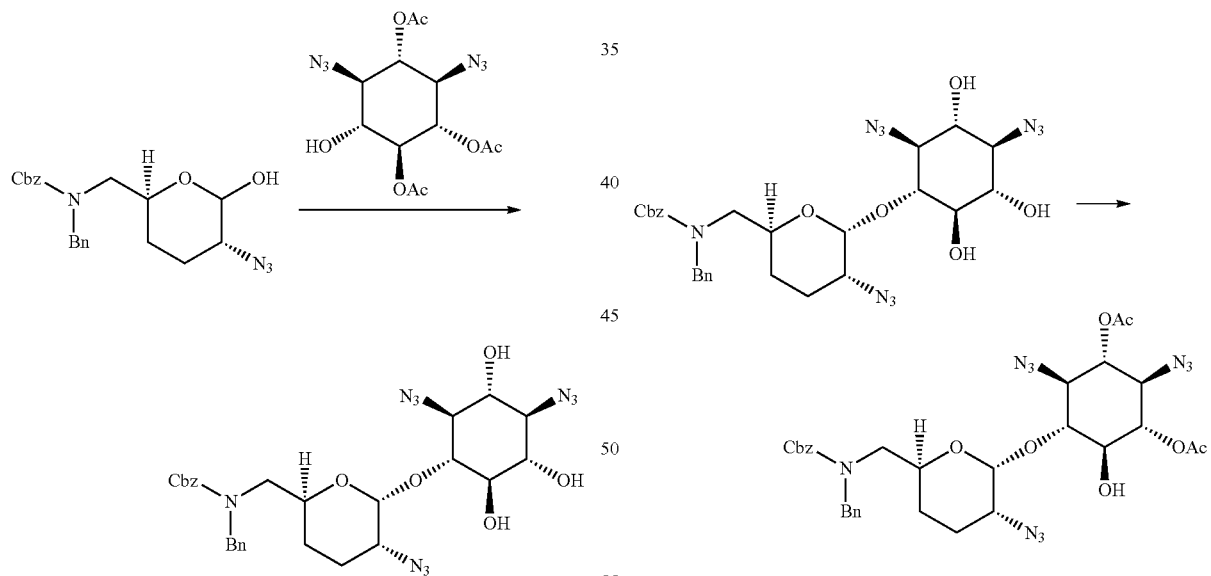

To a suspension of benzyl N-[[(2S,5R)-5-azido-6-hydroxy-tetrahydropyran-2-yl]methyl]-N-benzyl-carbamate (see Example 11 for synthesis, 101 mg, 0.26 mmol) and $K_2CO_3$ (155 mg, 1.12 mmol) in DCM (3 mL) was added $CCl_3CN$ (0.14 mL, 1.40 mmol). The mixture was stirred at room temperature for 18 h, then filtered on Celite, rinsed with DCM and concentrated under reduced pressure. [(1S,2R,3S,4S,5R,6R)-3,4-diacetoxy-2,6-diazido-5-hydroxy-cyclohexyl]acetate (70 mg, 0.20 mmol) was added to the above material, and the mixture was co-evaporated with anhydrous toluene (3×10 mL) and then was dried under reduced pressure for 2 h. To a solution of above material in anhydrous $Et_2O$ (10 mL) were added activated 3 Å (0.5 g) and 4 Å sieves (0.5 g). The mixture was stirred at room temperature for 1 h, then cooled to −45° C. TMSOTf (0.01 mL, 0.06 mmol) was added dropwise and the mixture was stirred at −40° C. for 2 h, then warmed to room temperature. A saturated solution of $NaHCO_3$ (20 mL) was added and the separated aqueous layer was extracted with EtOAc (3×30 mL). The combined organic layers were dried ($MgSO_4$), filtered and concentrated under reduced pressure. To a solution of above material in MeOH (6 mL), NaOMe (4.62 M in MeOH, 0.34 mL, 1.57 mmol) was added and the mixture was stirred at room temperature for 1 h. The volatiles were evaporated under reduced pressure. The residue was dissolved in DCM (25 mL) and a saturated solution of $NH_4Cl$ (25 mL) was added. The separated aqueous layer was extracted with DCM (2×30 mL). The combined organic layers were dried ($MgSO_4$), filtered and concentrated under reduced pressure. The material was purified by MPLC on silica (24 g, liquid loading with toluene) using a gradient of 0-50% EtOAc in hexane as eluent to provide the title compound (70 mg, 59% over 3 steps) as a solid. MS (ESI) $[M+H]^+$ 609.2

Step 2

[(1S,2R,3S,4S,5R,6S)-3-acetoxy-2,6-diazido-5-[(2R,3R,6S)-3-azido-6-[[benzyl (benzyloxycarbonyl)amino]methyl]tetrahydropyran-2-yl]oxy-4-hydroxy-cyclohexyl] acetate

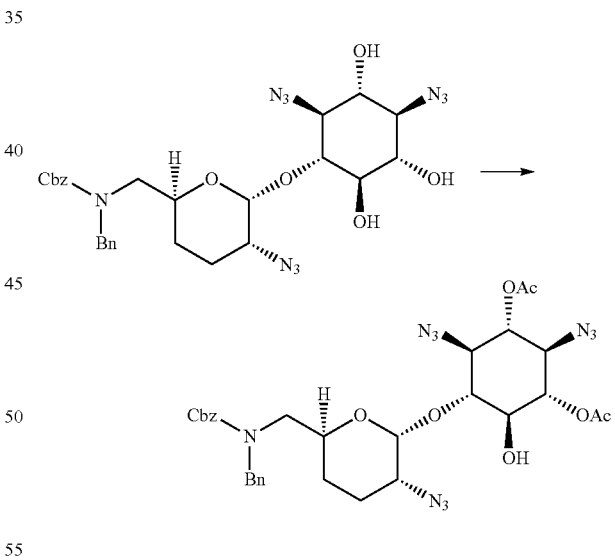

To a solution of benzyl N-[[(2S,5R,6R)-5-azido-6-[(1R,2S,3R,4R,5S,6R)-2,4-diazido-3,5,6-trihydroxy-cyclohexoxy]tetrahydropyran-2-yl]methyl]-N-benzyl-carbamate (70 mg, 0.115 mmol) in DCM (3 mL) was added pyridine (0.07 mL, 0.81 mmol) followed by $Ac_2O$ (0.07 mL, 0.69 mmol) and the reaction mixture was stirred at room temperature for 18 h. MeOH (1 mL) was then added and the mixture was concentrated under reduced pressure. The material was purified by MPLC on silica gel (24 g, liquid loading with toluene) using a gradient of 0-45% EtOAc in hexane as eluent to provide the title compound (45 mg, 57%) as a solid.

Step 3

Benzyl (((2S,5R,6R)-5-azido-6-(((1R,2S,3R,4R,5S,6R)-2,4-diazido-6-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3,5-dihydroxycyclohexyl)oxy)tetrahydro-2H-pyran-2-yl)methyl)(benzyl)carbamate

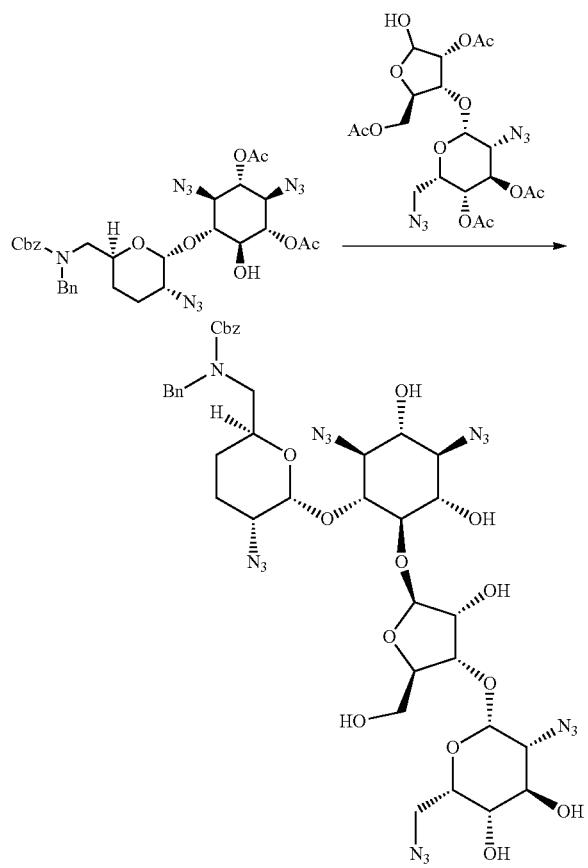

To a mixture of [(2R,3R,4R)-4-acetoxy-3-[(2R,3R,4R,5R,6S)-4,5-diacetoxy-3-azido-6-(azidomethyl) tetrahydropyran-2-yl]oxy-5-hydroxy-tetrahydrofuran-2-yl]methyl acetate (76 mg, 0.14 mmol) and K$_2$CO$_3$ (54 mg, 0.07 mmol) in DCM (10 mL) was added CCl$_3$CN (0.05 mL, 0.52 mmol) at room temperature. The mixture was stirred at room temperature for 18 h, then filtered on Celite, rinsed with DCM and concentrated under reduced pressure. To the above material in dry DCM (10 mL) was added (1 S,2R, 3S,4S,5R,6S)-2,4-diazido-5-(((2R,3R,6S)-3-azido-6-((benzyl((benzyloxy)carbonyl)amino)methyl)tetrahydro-2H-pyran-2-yl)oxy)-6-hydroxycyclohexane-1,3-diyl diacetate (45 mg, 0.07 mmol) followed by activated 3 Å sieves (1 g). The mixture was cooled to −78° C. and then BF$_3$·OEt$_2$ (0.03 mL, 0.23 mmol) was added dropwise. The acetone-dry ice bath was removed, and the reaction mixture was slowly warmed to room temperature, and then saturated NaHCO$_3$ (10 mL) was added. The separated aqueous layer was extracted with DCM (3×15 mL). The combined organic layers were washed with brine, dried (MgSO$_4$), filtered and concentrated under reduced pressure. To a solution of the above material in MeOH (10 mL), NaOMe (4.62 M in MeOH, 0.14 mL, 0.65 mmol) was added at room temperature and the reaction mixture was stirred for 1 h. The mixture was diluted with saturated NH$_4$Cl (10 mL) and the separated aqueous layer was extracted with DCM (3×15 mL). The combined organic layers were washed with brine, dried (MgSO$_4$), filtered and concentrated under reduced pressure. The material was purified by preparative HPLC to provide the title compound (18 mg, 29% over 3 steps) as a solid. MS (ESI) [M+Na]$^+$ 953.3.

Step 4

(2S,3S,4R,5R,6R)-5-amino-2-(aminomethyl)-6-(((2R,3S,4R,5S)-5-(((1R,2R, 3S,4R,5R,6S)-3,5-diamino-2-(((2R,3R,6S)-3-amino-6-(aminomethyl) tetrahydro-2H-pyran-2-yl)oxy)-4,6-dihydroxycyclohexyl)oxy)-4-hydroxy-2-(hydroxymethyl) tetrahydrofuran-3-yl)oxy) tetrahydro-2H-pyran-3,4-diol; 6 HCOOH

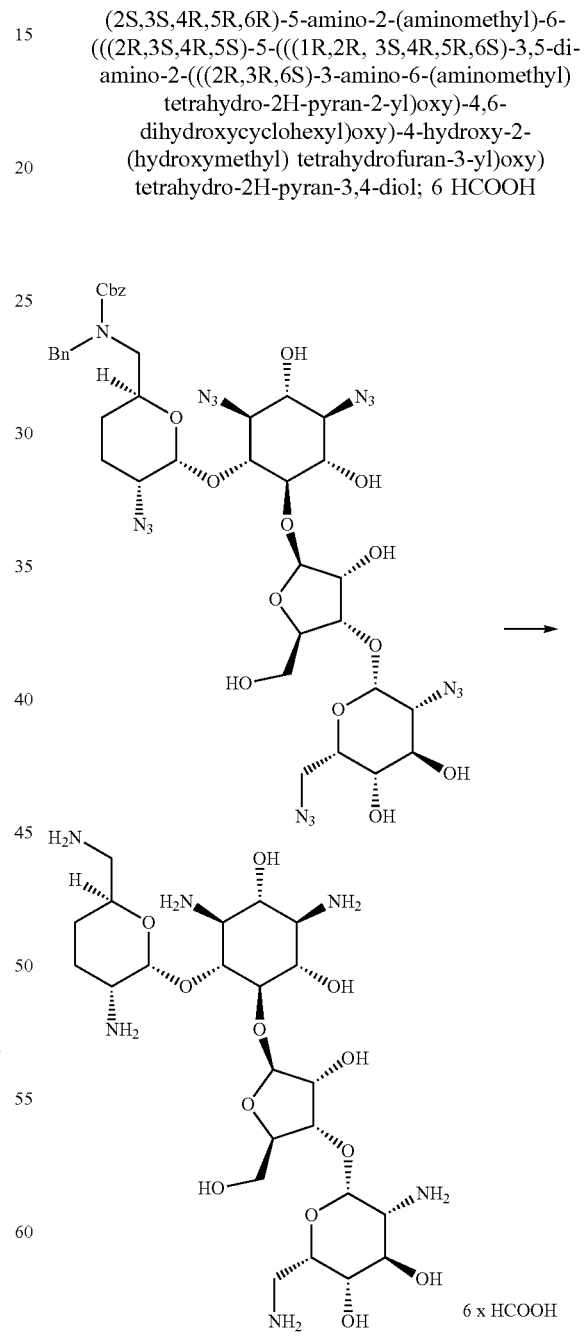

MeOH (5.0 mL) was added to a mixture of Pd/C (10% on carbon, 8.0 mg, 0.01 mmol) and benzyl (((2S,5R,6R)-5- azido-6-(((1R,2S,3R,4R,5S,6R)-2,4-diazido-6-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3,5-dihydroxycyclohexyl)oxy)tetrahydro-2H-pyran-2-yl)methyl)(benzyl)carbamate (18 mg, 0.02 mmol) under N$_2$. The suspension was degassed for 5 min, then ammonium formate (18 mg, 0.28 mmol) was added. The septum was replaced by a reflux condenser, followed by 3 vacuum/nitrogen cycles and the reaction mixture was heated at 63° C. for 5 h, then cooled to room temperature. The mixture was filtered with a syringe filter and concentrated under reduced pressure. The material was purified by preparative HPLC (Waters XBridge C18, 30×150 mm; 40 mL/min) using isocratic 10% acetonitrile in water (10 mM AmForm pH 3.8) over 7 min to provide the title compound (6.60 mg, 40%) as a solid. $^1$H NMR (500 MHz, D$_2$O) δ 8.47 (br, 6H), 5.91 (d, J=3.3 Hz, 1H), 5.44 (d, J=2.5 Hz, 1H), 5.33 (s, 1H), 4.51 (t, J=5.5 Hz, 1H), 4.42-4.39 (m, 1H), 4.36-4.33 (m, 1H), 4.28-4.18 (m, 3H), 4.05-3.91 (m, 3H), 3.87-3.84 (m, 1H), 3.80-3.71 (m, 3H), 3.64-3.61 (m, 1H), 3.60-3.55 (m, 1H), 3.49-3.38 (m, 2H), 3.34-3.23 (m, 3H), 3.11 (dd, J=13.5, 7.6 Hz, 1H), 2.12-1.99 (m, 2H), 1.98-1.91 (m, 1H), 1.66-1.55 (m, 1H). MS (ESI) [M+H]$^+$ 599.4.

Example 21

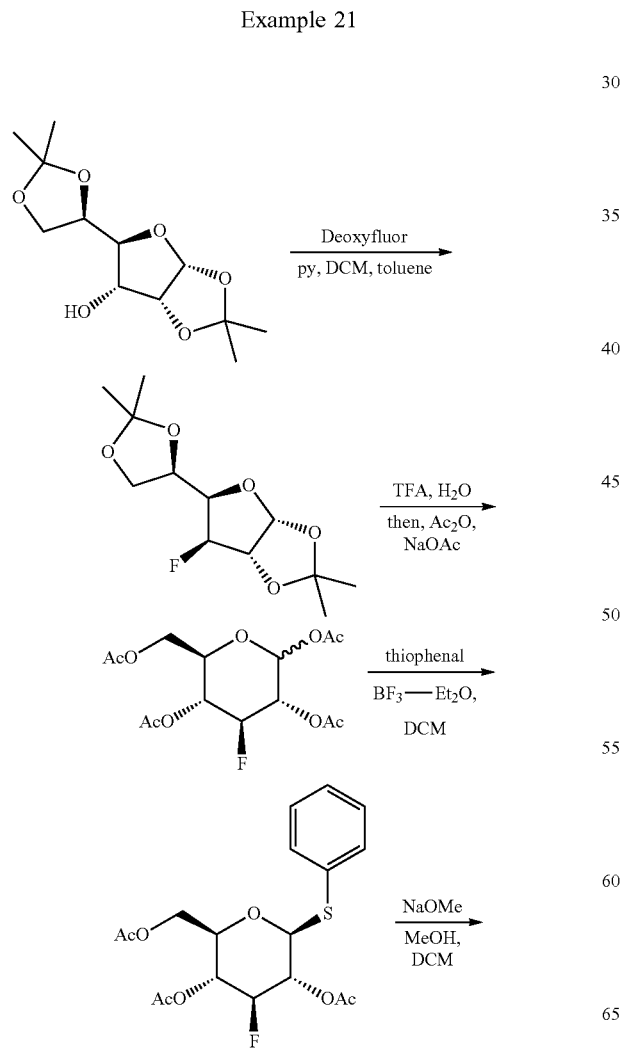

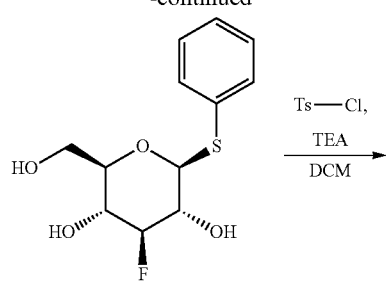

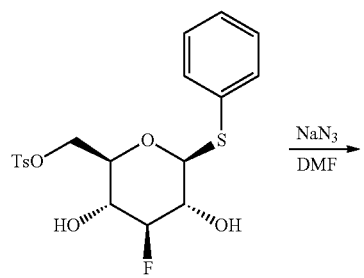

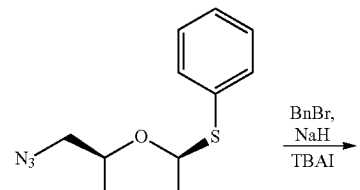

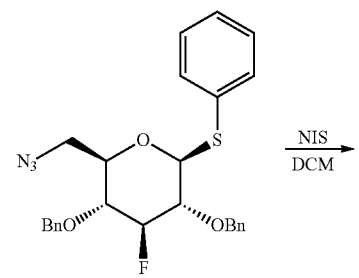

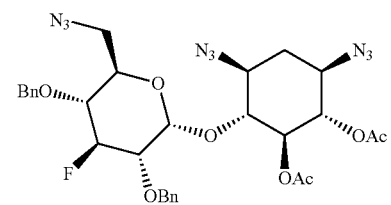

Step 1

(3aR,5R,6S,6aS)-5-[(4R)-2,2-dimethyl-1,3-dioxolan-4-yl]-6-fluoro-2,2-dimethyl-3a,5,6,6a-tetrahydrofuro[2,3-d][1,3]dioxole

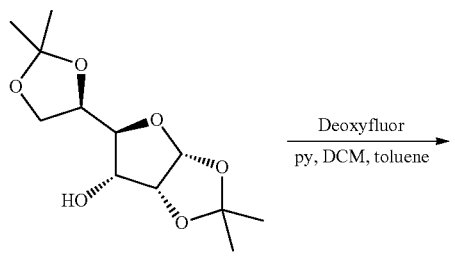

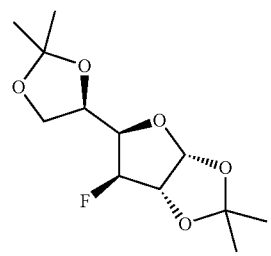

Allofuranose diacetonide (10 g, 38.4 mmol) was dissolved in 35 mL of dry DCM and pyridine at −78° C. To the cold solution, 2.7 M Deoxyfluor in toluene (20 mL, 54 mmol) was added dropwise. The reaction was stirred for 7 days at 40° C. The reaction was quenched with sat NaHCO$_3$, and the aqueous phase was extracted with DCM (3×50 mL). Combined organic phases were washed with NaHCO$_3$ (100 mL) and dried with Na$_2$SO$_4$. The crude material was purified by MPLC to afford the title compound (9.54 g, 36.4 mmol, 95%). Acetonides fragment on mass spec: MS (ESI) [M−both acetonides+Na]$^+$=205.1.

Step 2

[(2R)-2-[(3aR,5R,6S,6aS)-6-fluoro-2,2-dimethyl-3a,5,6,6a-tetrahydrofuro[2,3-d][1,3]dioxol-5-yl]-2-acetoxy-ethyl] acetate; [(2R,3R,4S,5S)-3,5,6-triacetoxy-4-fluoro-tetrahydropyran-2-yl]methyl acetate

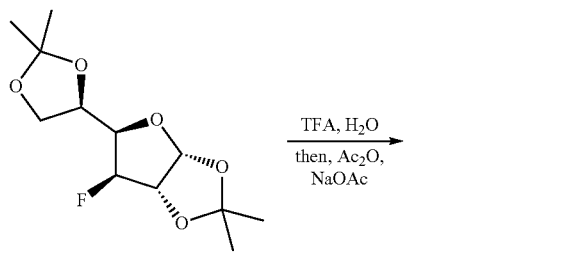

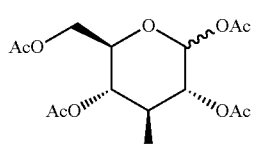

Fluorinated allofuranose diacetonide (9.5 g, 36.2 mmol) was dissolved in 10 mL of THF and 100 mL of 5% TFA in water was added to the solution. The reaction was stirred for 14 hours at room temperature. The solution was rotovaped and co-evaporated with toluene (100 mL). Then dissolved in 40 mL of acetic anhydride and refluxed for 30 min with 6 equiv (1.3 g) of sodium acetate. After that the reaction was cooled to room temperature and quenched with sat NaHCO$_3$/CH$_2$Cl$_2$=300 mL/300 mL twice. The organic phase was washed with brine and aqueous phase was backwashed with EtOAc 300 mL. Combined org phases were dried over Na$_2$SO$_4$ and reduced to an oil which was purified by MPLC to afford the title compound (7.66 g, 11.7 mmol, 60%) MS (ESI) [M+NH$_4$]$^+$=368.1.

Step 3

[(2R,3R,4S,5R,6S)-3,5-diacetoxy-4-fluoro-6-phenylsulfanyl-tetrahydropyran-2-yl]methyl acetate

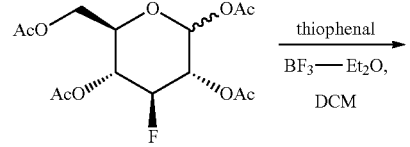

3-deoxy-3-fluoro-allopyranose tetracetate (7.7 g, 22.0 mmol) and thiophenol (4.85 g, 4.50 mmol) were dissolved in DCM (100 mL) with 10 g of activated 4 Å molecular sieves and stirred for at least 24 hours at room temperature under dry nitrogen. The suspension was treated with BF$_3$·Et$_2$O and the reaction suspension was stirred overnight. The crude material was purified by MPLC to afford the title compound (2.5 g, 6.24 mmol, 28%) MS (ESI) [M+NH$_4$]$^+$=418.2.

Step 4

(2R,3R,4S,5R,6S)-4-fluoro-2-(hydroxymethyl)-6-phenylsulfanyl-tetrahydropyran-3,5-diol -continued

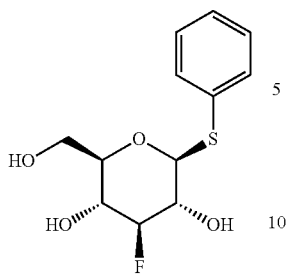

1-phenylthio-3-deoxy-3-fluoro-allopyranoside peracetate (2.5 g, 6.24 mmol) was dissolved in 25 mL of 4:1=MeOH:DCM mixture and treated with 5 mL of 25% NaOMe in MeOH. The reaction was stirred for 1 h at room temperature. The reaction was quenched with Amberlyst 15 resin which was filtered and washed with 20 mL of MeOH, solvent was evaporated and the crude material was used in the next step without any further purification. MS (ESI) [M+NH₄]⁺ =292.3.

Step 5

[(2R,3R,4S,5R,6S)-4-fluoro-3,5-dihydroxy-6-phenylsulfanyl-tetrahydropyran-2-yl]methyl 4-methyl-benzenesulfonate

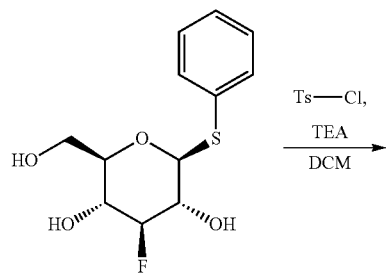

1-phenylthio-3-deoxy-3-fluoro-allopyranoside (2.28 g, 8.31 mmol) was dissolved in 5 mL of DCM at 0° C. and Et₃N (4.20 g, 41.6 mmol) with TsCl (1.91 g, 10 mmol) were added sequentially. After 3 hours the crude reaction in DCM was purified by MPLC to afford the title compound (1.92 g, 4.62 mmol, 38%) MS (ESI) [M+NH₄]*=446.1.

Step 6

(2R,3R,4S,5R,6S)-2-(azidomethyl)-4-fluoro-6-phenylsulfanyl-tetrahydropyran-3,5-diol

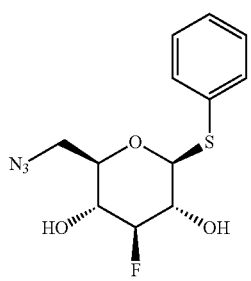

1-phenylthio-3-deoxy-3-fluoro-6-OTs-allopyranoside (1.98 g, 4.62 mmol) was dissolved in 17 mL of DMF and NaN₃ (0.36 g, 5.54 mmol) was added. The reaction was stirred at 80° C. for 5 hours. The reaction was washed with NaHCO₃ (7 mL) and extracted with EtOAc (3×10 mL) and the combined organic phases were washed with brine, and dried with Na₂SO₄. The crude was used in the next step without further purification (1.36 g, 4.54 mmol, 98%).

Step 7

(2R,3R,4S,5R,6S)-2-(azidomethyl)-3,5-dibenzyloxy-4-fluoro-6-phenylsulfanyl-tetrahydropyran

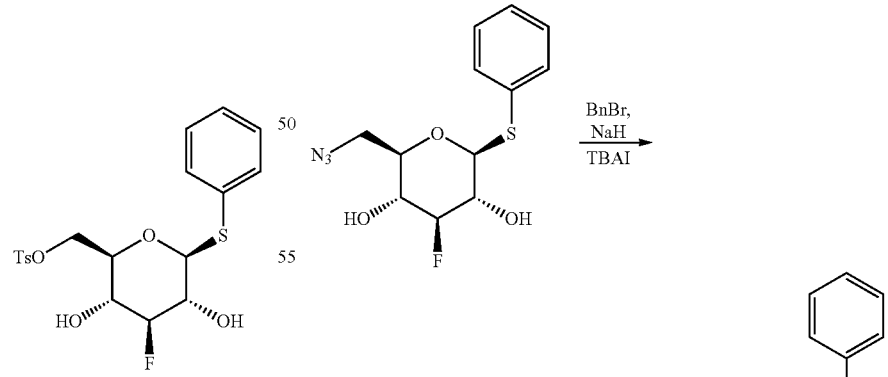

1-phenylthio-3-deoxy-3-fluoro-6-azido-allopyranoside (1.36 g, 4.54 mmol) and BnBr (2.33 g, 13.6 mmol) were dissolved in 16 mL of DMF with catalytic TBAI (0.18 g, 0.45 mmol). Dry NaH (0.44 g, 18.2 mmol) was added to the mixture at 0° C. The reaction was stirred at room temperature for 3 hours after which the reaction was quenched with 5 M $NH_4Cl$ and extracted with $Et_2O$ (3×100 mL), which washed with brine. The crude was purified by MPLC to provide the title compound (1.37 g, 2.86 mmol, 63%) MS (ESI) $[M+Na]^+=497.2$.

Step 8

[(1S,2S,3R,4S,6R)-2-acetoxy-4,6-diazido-3-[(2R,3S,4S,5R,6R)-6-(azidomethyl)-3,5-dibenzyloxy-4-fluoro-tetrahydropyran-2-yl]oxy-cyclohexyl] acetate

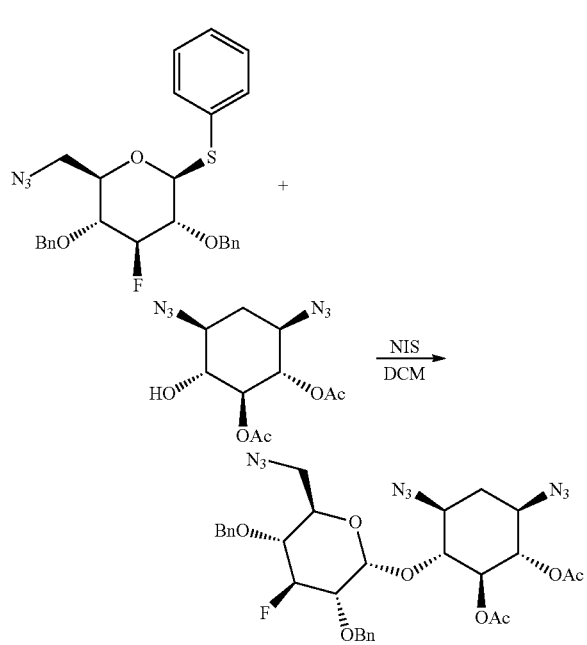

1-phenylthio-3-deoxy-3-fluoro-6-$N_3$-allopyranoside and 1,3-$N_3$-5,6-Ac-2-DOS were coevaporated with toluene (3×5 mL) and dried in high vacuum, were dissolved in DCM (12 mL) with 2 g of activated 4 Å mol sieves. The suspension was stirred at room temperature for 14 hours and cooled to −78° C. followed by a quick addition of NIS (dried in high vacuum for 12 hours). The reaction was allowed to stir for 30 min at −78° C. and catalytic TfOH was added. The reaction was stirred at −78° C. for 1 hour and allowed to warm up to room temperature over 2 hours. The reaction turned to dark brown-purple color. TLC showed product formation with $R_f$~0.55 in 20% EtOAc in hexanes as a single spot. The reaction was quenched with $Et_3N$ and filtered and the molecular sieves were washed on filter with 50 mL of DCM. Organic phase was washed with 30 mL of sat. $NaHCO_3$ and 50 mL of water. Aqueous phases were dried with $Na_2SO_4$ and crude after concentration was taken up in 3 mL of DCM and purified by MPLC to afford the title compound (0.82 g, 1.23 mmol, 88%. MS (ESI) $[M+Na]^+=690.3$.

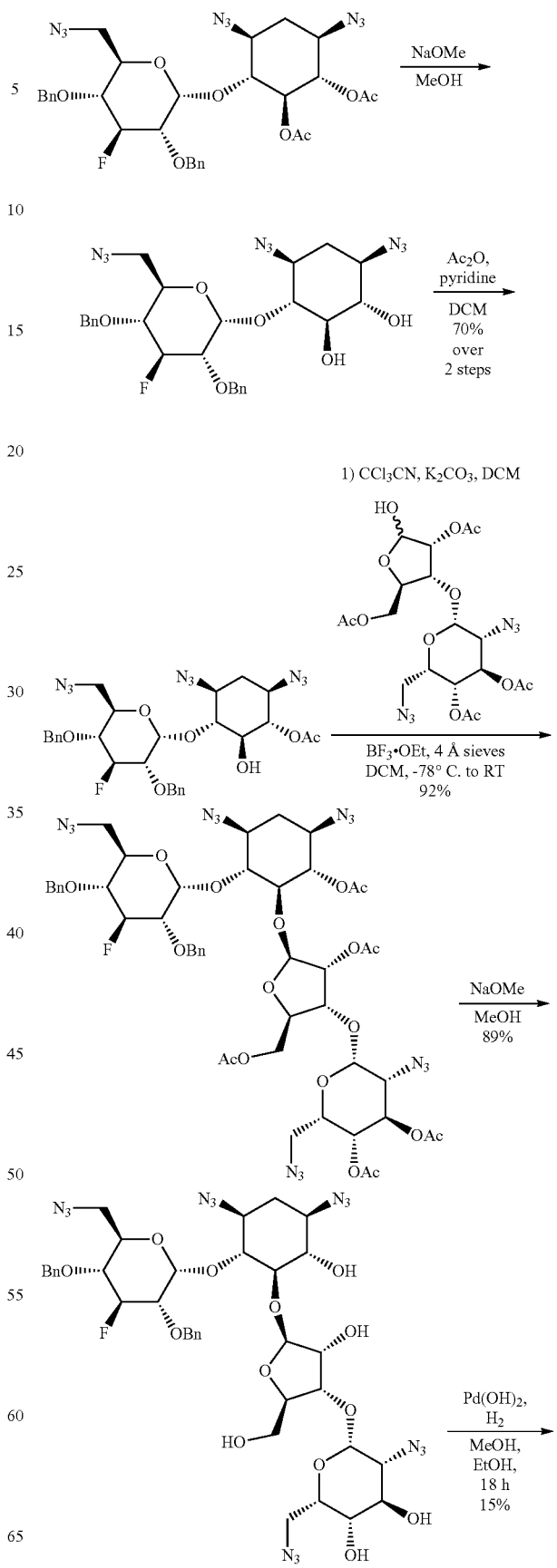

-continued

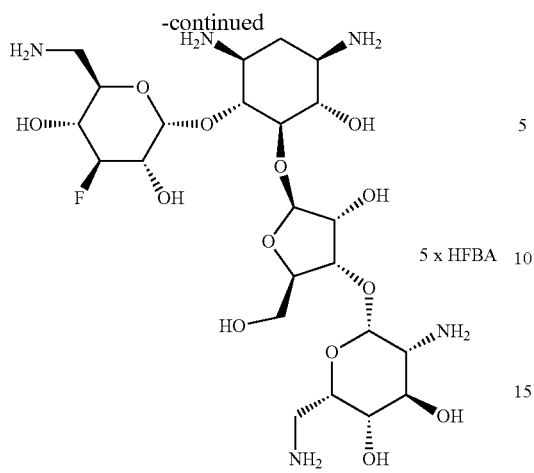

5 x HFBA

Step 9

[(1S,2S,3R,4S,6R)-4,6-diazido-3-[(2R,3S,4S,5R,6R)-6-(azidomethyl)-3,5-dibenzyloxy-4-fluoro-tetrahydropyran-2-yl]oxy-2-hydroxy-cyclohexyl] acetate

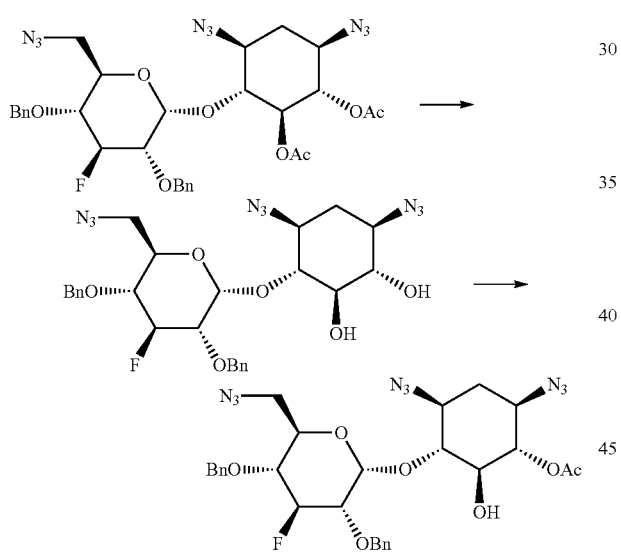

NaOMe (25 wt %, 518 µL, 1.80 mmol) was added dropwise to a solution of [(1S,2S,3R,4S,6R)-2-acetoxy-4,6-diazido-3-[(2R,3S,4S,5R,6R)-6-(azidomethyl)-3,5-dibenzyloxy-4-fluoro-tetrahydropyran-2-yl]oxy-cyclohexyl] acetate (200 mg, 300 µmol) in MeOH (15.0 mL) at ambient temperature and the reaction mixture was stirred for 60 min. The mixture was neutralized with AcOH (308 µL, 5.39 mmol) and the volatiles were removed under reduced pressure. The material was purified through a silica gel plug using EtOAc as eluent to afford the title compound, which was used in the next without further purification. MS (ESI) [M+Na]+ 606.9.

Ac2O (162 µL, 1.72 mmol) was added to a solution of (1S,2R,3R,4S,6R)-4,6-diazido-3-[(2R,3S,4S,5R,6R)-6-(azidomethyl)-3,5-dibenzyloxy-4-fluoro-tetrahydropyran-2-yl]oxy-cyclohexane-1,2-diol (167 mg, 0.286 mmol) and pyridine (185 µL, 2.29 mmol) in dry DCM (10.0 mL) at ambient temperature and the reaction mixture was stirred for 16 h. The volatiles were removed under reduced pressure and the material was purified by silica gel chromatography (40 g cartridge) using a gradient of EtOAc in hexane (0-30%) as eluent to afford the title compound (128 mg, 70%) as an oil. MS (ESI) [M+Na]+ 648.1.

Step 10

[(2R,3R,4R,5S)-4-acetoxy-5-[(1S,2S,3R,5S,6R)-2-acetoxy-3,5-diazido-6-[(2R,3S,4S,5R,6R)-6-(azidomethyl)-3,5-dibenzyloxy-4-fluoro-tetrahydropyran-2-yl]oxy-cyclohexoxy]-3-[(2R,3R,4R,5R,6S)-4,5-diacetoxy-3-azido-6-(azidomethyl)tetrahydropyran-2-yl]oxy-tetrahydrofuran-2-yl] methyl acetate

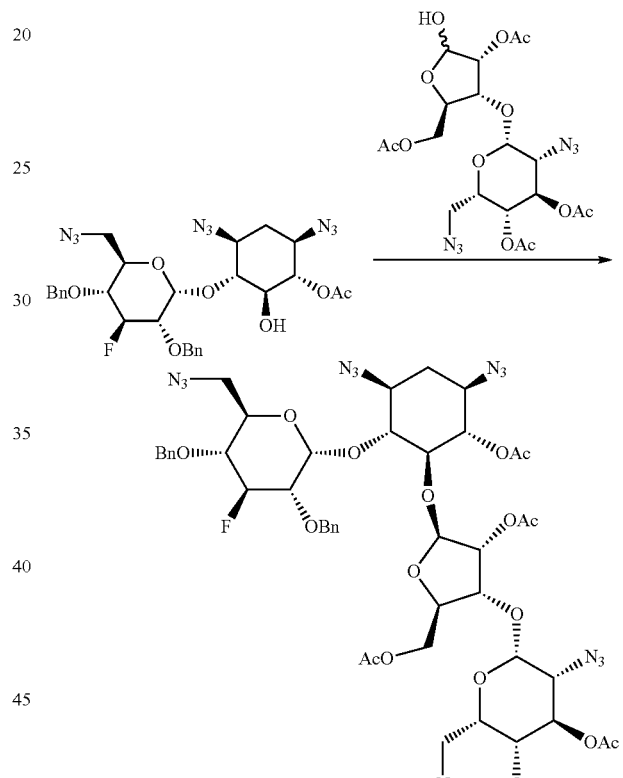

CCl3CN (0.308 mL, 3.07 mol) was added dropwise to a mixture of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (326 mg, 0.614 mmol) and K2CO3 (254 mg, 1.84 mmol) in dry DCM (15.0 mL) at room temperature under N2. The reaction mixture was stirred at room temperature for 18 h, then filtered through a Celite pad, washed with dry DCM and the filtrate was concentrated under reduced pressure.

To a solution of [[(1S,2S,3R,4S,6R)-4,6-diazido-3-[(2R,3S,4R,5R,6R)-6-(azidomethyl)-3,5-dibenzyloxy-4-fluoro-tetrahydropyran-2-yl]oxy-2-hydroxy-cyclohexyl] acetate (128 mg, 0.205 mmol) in DCM (15.0 mL) was added the above material followed molecular sieves 4 Å were added and the mixture was cooled to −10° C. BF3·OEt2 (0.126 mL, 1.02 mmol) was then added dropwise and the mixture was warmed slowly at room temperature and stirred for 4 h. The mixture was diluted with saturated NaHCO$_3$ (10.0 mL) and the separated aqueous layer was extracted with DCM (3×20.0 mL). The combined organic layer was washed with brine, then dried (Na$_2$SO$_4$), filtered and concentrated under reduced pressure. The material was purified on silica gel chromatography (40 cartridge) using a gradient of EtOAc in hexane (0-40%) as eluent to provide the title compound (213 mg, 92%) as an oil. $^1$H NMR (400 MHz, CDCl$_3$) δ 7.45-7.26 (m, 10H), 5.83 (t, J=3.5 Hz, 1H), 5.26 (s, 1H), 5.08-5.01 (m, 2H), 4.99 (d, J=4.5 Hz, 1H), 4.95-4.86 (m, 3H), 4.85 (d, J=1.8 Hz, 1H), 4.77 (q, J=11.2 Hz, 2H), 4.72-4.67 (m, 1H), 4.61 (d, J=11.3 Hz, 1H), 4.46 (dd, J=12.1, 2.4 Hz, 1H), 4.41 (dd, J=7.5, 4.6 Hz, 1H), 4.27-4.04 (m, 5H), 3.79-3.24 (m, 12H), 2.31 (dt, J=13.2, 4.6 Hz, 1H), 2.17 (s, 6H), 2.07 (s, 3H), 2.04 (s, 3H), 1.58 (dd, J=24.7, 12.3 Hz, 1H). MS (ESI) [M+Na]$^+$ 1161.3.

Step 11

(2S,3S,4R,5R,6R)-5-azido-2-(azidomethyl)-6-[(2R,3S,4R,5S)-5-[(1R,2R,3S,5R,6S)-3,5-diazido-2-[(2R,3S,4S,5R,6R)-6-(azidomethyl)-3,5-dibenzyloxy-4-fluoro-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol

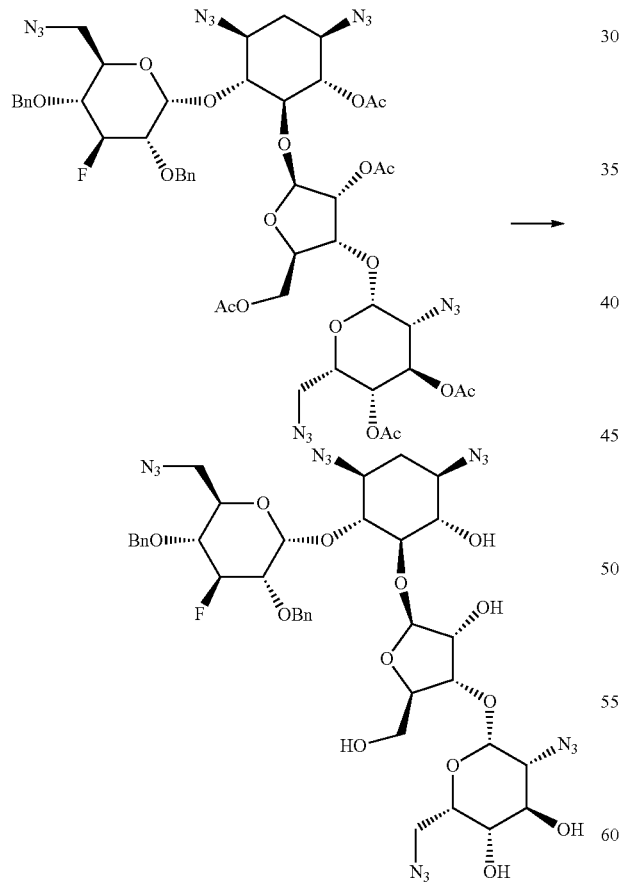

NaOMe (25 wt %, 0.647 mL, 2.25 mmol) was added dropwise to a solution of [(2R,3R,4R,5S)-4-acetoxy-5-[(1S,2S,3R,5S,6R)-2-acetoxy-3,5-diazido-6-[(2R,3S,4S,5R,6R)-6-(azidomethyl)-3,5-dibenzyloxy-4-fluoro-tetrahydropyran-2-yl]oxy-cyclohexoxy]-3-[(2R,3R,4R,5R,6S)-4,5-diacetoxy-3-azido-6-(azidomethyl)tetrahydropyran-2-yl]oxy-tetrahydrofuran-2-yl]methyl acetate (213 mg, 0.187 mmol) in MeOH (10.0 mL) at ambient temperature and the reaction mixture was stirred for 60 min. The mixture was neutralized by adding AcOH (214 μL, 3.74 mmol) and the volatiles were removed under reduced pressure. The material was purified on silica plug using EtOAc as eluent to provide the title compound (155 mg, 89%) as a solid. $^1$H NMR (500 MHz, MeOD) δ 7.73-7.22 (m, 1H), 6.22 (t, J=3.5 Hz, 1H), 5.39 (d, J=1.9 Hz, 1H), 5.15 (d, J=1.8 Hz, 1H), 5.07-4.91 (m, 3H), 4.76 (d, J=11.2 Hz, 1H), 4.68 (d, J=11.4 Hz, 1H), 4.44 (dd, J=6.5, 4.5 Hz, 1H), 4.35 (dd, J=4.5, 1.9 Hz, 1H), 4.20 (td, J=6.2, 2.8 Hz, 2H), 4.04 (ddd, J=8.2, 4.8, 2.0 Hz, 1H), 3.99 (t, J=3.4 Hz, 1H), 3.88 (dd, J=11.9, 2.8 Hz, 1H), 3.83-3.76 (m, 1H), 3.75-3.54 (m, 8H), 3.53-3.40 (m, 5H), 2.26-2.15 (m, 1H), 1.37 (m, 1H). MS (ESI) [M+Na]$^+$ 950.8.

Step 12

(2S,3S,4R,5R,6R)-5-amino-2-(aminomethyl)-6-[(2R,3S,4R,5S)-5-[(1R,2R,3S,5R,6S)-3,5-diamino-2-[(2R,3S,4S,5R,6R)-6-(aminomethyl)-4-fluoro-3,5-dihydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol

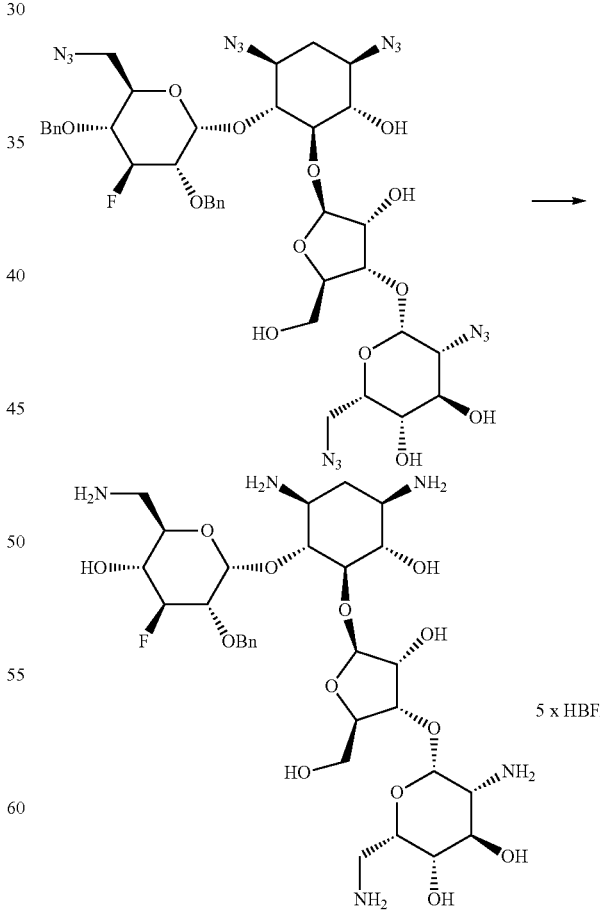

Pd(OH)$_2$ (20 wt %, 109 mg, 155 μmol) was added to a solution of (2S,3S,4R,5R,6R)-5-azido-2-(azidomethyl)-6-

477

[(2R,3S,4R,5S)-5-[(1R,2R,3S,5R,6S)-3,5-diazido-2-[(2R,3S,4S,5R,6R)-6-(azidomethyl)-3,5-dibenzyloxy-4-fluoro-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol (24.0 mg, 25.9 µmol) in a mixture MeOH (2.00 mL) and EtOH (2.00 mL). H$_2$ was bubbled for 5 min and the suspension was hydrogenated for 16 h. The mixture was filtered through a frit (0.22 µm diameter) and the filtrate was concentrated under reduced pressure. The material was purified by preparative HPLC to provide (2S,3S,4R,5R,6R)-5-amino-2-(aminomethyl)-6-[(2R,3S,4R,5S)-5-[(1R,2R,3S,5R,6S)-3,5-diamino-2-[(2R,3S,4S,5R,6R)-6-(aminomethyl)-4-fluoro-3,5-dihydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol_(13.4 mg, 15%) as HFBA salt. $^1$H NMR (400 MHz, MeOD) δ 5.67 (t, J=3.5 Hz, 1H), 5.37 (d, J=2.4 Hz, 1H), 5.25 (d, J=1.6 Hz, 1H), 4.60 (dt, J=52.2, 8.2 Hz, 1H), 4.52-4.46 (m, 1H), 4.29 (dd, J=4.9, 2.4 Hz, 1H), 4.27-4.21 (m, 1H), 4.17-4.09 (m, 3H), 3.98 (ddd, J=10.2, 6.7, 3.9 Hz, 1H), 3.85 (dd, J=15.0, 5.8 Hz, 1H), 3.81-3.71 (m, 3H), 3.69-3.47 (m, 4H), 3.43-3.30 (m, 2H), 3.25-3.08 (m, 4H), 2.49-2.35 (m, 1H), 1.91 (dd, J=25.0, 12.5 Hz, 1H). MS (ESI) [M+H]$^+$ 618.4.

Example 22

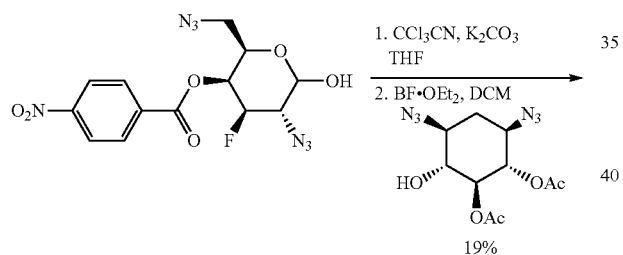

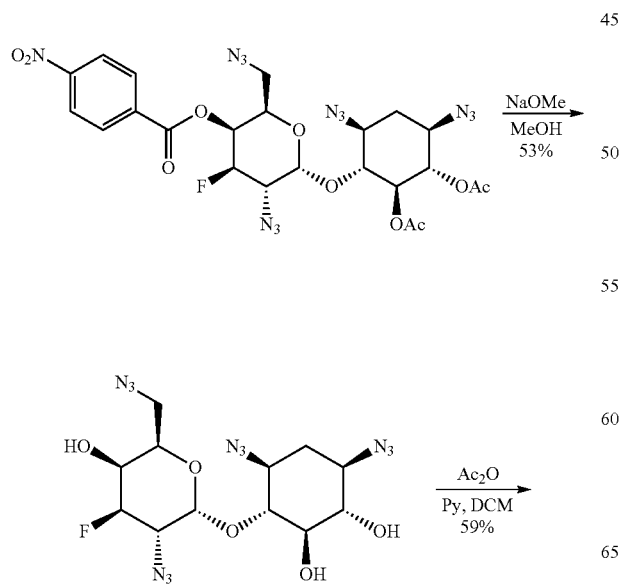

478

-continued

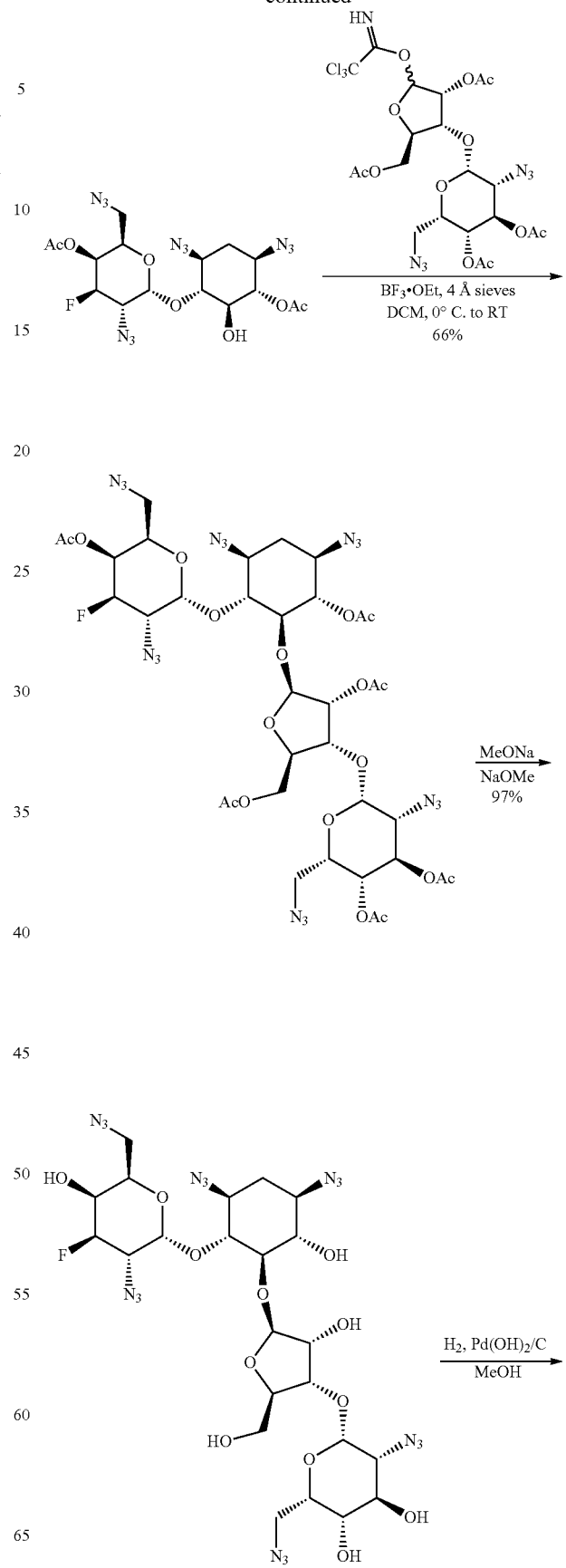

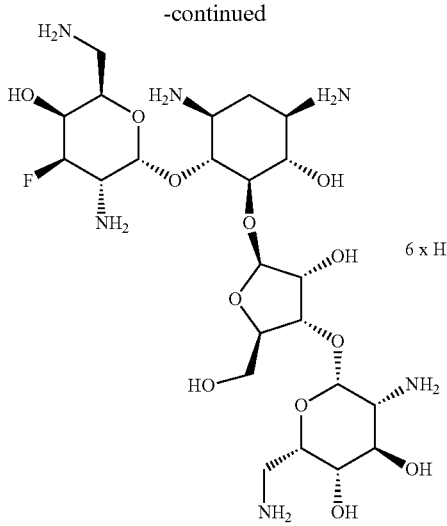

6 x HCOOH

Step 1

[(2R,3S,4R,5R,6R)-5-azido-2-(azidomethyl)-4,6-difluoro-tetrahydropyran-3-yl] 4-nitrobenzoate

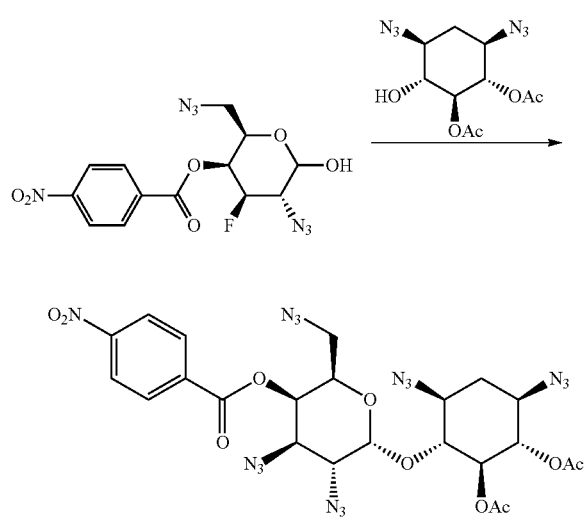

CCl₃CN (241 µL, 2.40 mmol) was added dropwise to a suspension of [(2R,3S,4R,5S)-5-azido-2-(azidomethyl)-4-fluoro-6-hydroxy-tetrahydropyran-3-yl] 4-nitrobenzoate (preparation below, 183 mg, 480 µmol) and K₂CO₃ (199 mg, 1.44 mmol) in dry THF (2.0 mL) at ambient temperature under N₂ and the reaction mixture was stirred for 18 h. The mixture was filtered through cotton and the filtrate was concentrated under N₂ stream, and then dried under high-vacuum. To the above material was added [(1S,2S,3R,4S,6R)-2-acetoxy-4,6-diazido-3-hydroxy-cyclohexyl] acetate (2-DOS, 179 mg, 600 µmol) and ground 4 Å sieves (750 mg) and the mixture was dissolved in dry DCM (2.5 mL). The suspension was stirred at ambient temperature for 60 min. The mixture was cooled to 0° C. and BF₃·OEt₂ (237 µL, 1.92 mmol) was added dropwise with vigorous stirring. The reaction mixture was warmed to ambient temperature and stirred for another 60 min. The reaction was quenched with saturated NaHCO₃ (5.0 mL) and the aqueous layer was extracted with DCM (3×5.0 mL). The combined organic layers were dried (Na₂SO₄), filtered and concentrated under reduced pressure. The material was purified by silica gel chromatography (25 g cartridge) using a gradient of with EtOAc and hexane (5-50%) as eluent to provide the title compound (60 mg, 19%) as a solid. ¹H NMR (500 MHz, CDCl₃) δ 8.34 (d, J=9.0 Hz, 2H), 8.24 (d, J=9.0 Hz, 2H), 5.92-5.85 (m, 1H), 5.31 (t, J=4.2 Hz, 1H), 5.22-5.05 (m, 2H), 4.96 (t, J=10.0 Hz, 1H), 4.64 (t, J=5.9 Hz, 1H), 3.84 (td, J=10.2, 3.9 Hz, 1H), 3.73-3.61 (m, 2H), 3.57-3.45 (m, 2H), 3.31 (dd, J=13.0, 5.3 Hz, 1H), 2.46 (dt, J=13.4, 4.6 Hz, 1H), 2.12 (s, 3H), 2.10 (s, 3H), 1.65 (dd, J=25.9, 12.5 Hz, 1H).

Step 2

(1S,2R,3R,4S,6R)-4,6-diazido-3-[(2R,3S,4R,5S,6R)-3-azido-6-(azidomethyl)-4-fluoro-5-hydroxy-tetrahydropyran-2-yl]oxy-cyclohexane-1,2-diol

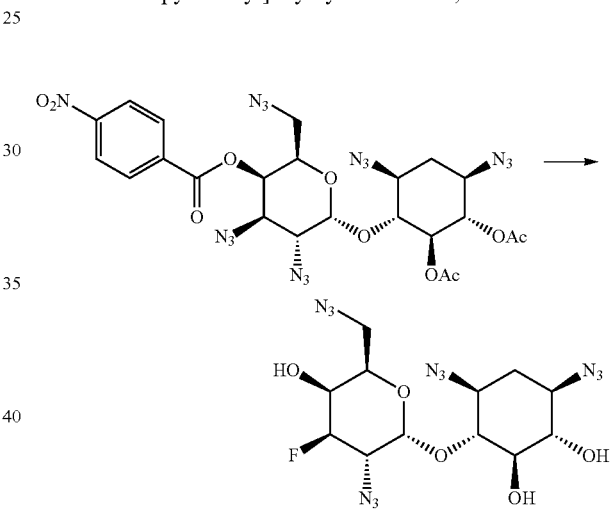

NaOMe (25 wt %, 138 µL, 605 µmol) was added dropwise to a solution of [(2R,3S,4R,5S,6R)-5-azido-2-(azidomethyl)-6-[(1R,2S,3S,4R,6S)-2,3-diacetoxy-4,6-diazido-cyclohexoxy]-4-fluoro-tetrahydropyran-3-yl] 4-nitrobenzoate (80 mg, 121 µmol) in MeOH (1.0 mL) at ambient temperature. The solution was warmed to 50° C. and stirred for 60 min. The solution was cooled to ambient temperature and the volatiles were evaporated under reduced pressure. The residue was diluted with saturated NaHCO₃ (5.0 mL) and DCM (5.0 mL). The separated aqueous layer was extracted with DCM (5.0 mL). The combined organic layers were dried (Na₂SO₄), filtered and concentrated under reduced pressure. The material was purified by C18 reverse phase chromatography (12 g cartridge) using a gradient of ACN and 0.1% formic acid (10-45%) to provide the title compound (30 mg, 53%) as a solid. ¹H NMR (500 MHz, CDCl₃) δ 5.34 (t, J=4.2 Hz, 1H), 4.93 (ddd, J=49.4, 10.1, 3.2 Hz, 1H), 4.31-4.21 (m, 2H), 4.12 (td, J=10.4, 3.8 Hz, 1H), 3.84 (s, 1H), 3.63 (dd, J=12.3, 6.6 Hz, 1H), 3.53-3.37 (m, 4H), 3.35-3.26 (m, 2H), 2.87 (s, 1H), 2.39 (s, 1H), 2.36-2.26 (m, 1H), 1.57-1.46 (m, 1H). MS (ESI) [M−H]⁻ 427.3.

Step 3

[(1S,2S,3R,4S,6R)-3-[(2R,3S,4R,5S,6R)-5-acetoxy-3-azido-6-(azidomethyl)-4-fluoro-tetrahydropyran-2-yl]oxy-4,6-diazido-2-hydroxy-cyclohexyl] acetate

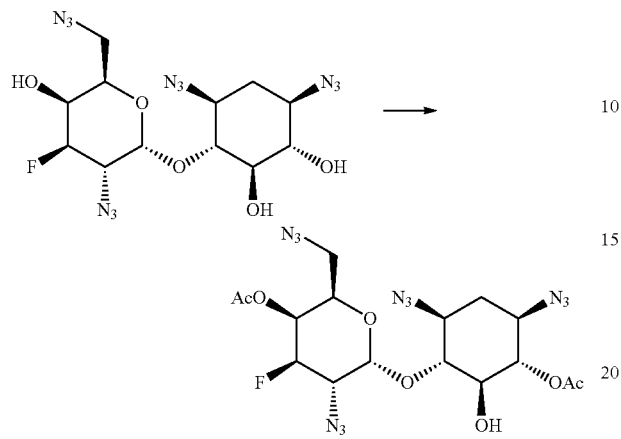

Ac$_2$O (17 μL, 180 μmol) was added to a solution of (1S,2R,3R,4S,6R)-4,6-diazido-3-[(2R,3S,4R,5S,6R)-3-azido-6-(azidomethyl)-4-fluoro-5-hydroxy-tetrahydropyran-2-yl]oxy-cyclohexane-1,2-diol (17 mg, 40 μmol) and pyridine (32 μL, 397 μmol) in dry DCM (1.0 mL) at ambient temperature and the reaction mixture was stirred for 18 h. MeOH (100 μL) was added and the volatiles were evaporated under reduced pressure. The material was purified by C18 reverse phase chromatography (4 g cartridge) using a gradient of ACN and 0.1% aq formic acid (20-70%) to provide the title compound (12 mg, 59%) as a solid. $^1$H NMR (500 MHz, CDCl$_3$) δ 5.64-5.54 (m, 1H), 5.41 (t, J=4.2 Hz, 1H), 5.08-4.89 (m, 2H), 4.37 (dd, J=6.9, 5.4 Hz, 1H), 4.01 (td, J=10.3, 3.8 Hz, 1H), 3.65 (dd, J=11.7, 5.3 Hz, 2H), 3.52 (ddd, J=12.5, 10.0, 4.6 Hz, 1H), 3.48-3.38 (m, 2H), 3.34 (ddd, J=12.2, 10.0, 4.5 Hz, 1H), 3.25 (dd, J=12.9, 5.1 Hz, 1H), 2.38 (dt, J=13.3, 4.5 Hz, 1H), 2.19 (s, 3H), 2.18 (s, 3H), 1.64-1.56 (m, 1H).

Step 4

[(2R,3R,4R,5S)-4-acetoxy-5-[(1S,2S,3R,5S,6R)-2-acetoxy-6-[(2R,3S,4R,5S,6R)-5-acetoxy-3-azido-6-(azidomethyl)-4-fluoro-tetrahydropyran-2-yl]oxy-3,5-diazido-cyclohexoxy]-3-[(2R,3R,4R,5R,6S)-4,5-diacetoxy-3-azido-6-(azidomethyl)tetrahydropyran-2-yl]oxy-tetrahydrofuran-2-yl]methyl acetate

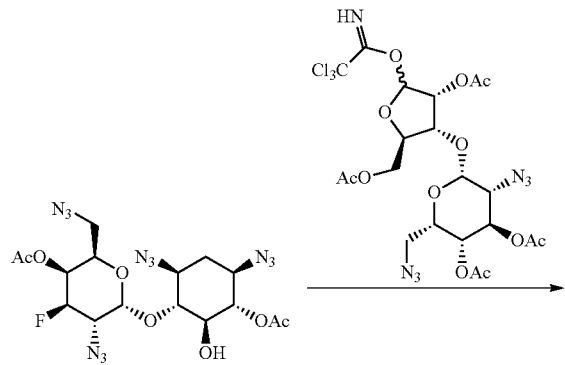

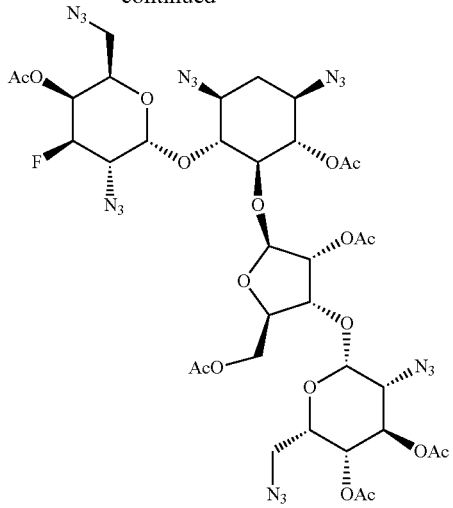

CCl$_3$CN (94 μL, 940 μmol) was added dropwise to a suspension of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (99 mg, 187 μmol) and K$_2$CO$_3$ (78 mg, 562 μmol) in dry DCM (1.5 mL) at ambient temperature under N$_2$ and the reaction mixture was stirred for 18 h. The mixture was filtered through a Celite pad and the filtrate was concentrated under N$_2$ stream, and then dried under high-vacuum. To the above material was added [(1S,2S,3R,4S,6R)-3-[(2R,3S,4R,5S,6R)-5-acetoxy-3-azido-6-(azidomethyl)-4-fluoro-tetrahydropyran-2-yl]oxy-4,6-diazido-2-hydroxy-cyclohexyl] acetate (48 mg, 94 μmol) in DCM (3.0 mL) and the volatiles were evaporated under N$_2$ stream. To the mixture was added ground 4 Å sieves (300 mg) followed by dry DCM (1.5 mL). The suspension was stirred at ambient temperature for 90 min, then cooled to 0° C. BF$_3$·OEt$_2$ (92 μL, 749 μmol) was added and the reaction mixture was stirred at ambient temperature for another 1 h. Et$_3$N (200 μL) was added and the mixture was filtered through a silica gel pad (0.30 g) and eluted with EtOAc. The filtrate was evaporated under reduced pressure and the material was purified by C18 reversed phase chromatography (12 g cartridge) using a gradient of ACN and 0.1% aq. formic acid (50-100%) as eluent to afford the title compound (63 mg, 66%) as a solid. $^1$H NMR (500 MHz, CDCl$_3$) δ 6.05 (t, J=4.0 Hz, 1H), 5.56 (dd, J=5.7, 3.6 Hz, 1H), 5.34 (d, J=2.5 Hz, 1H), 5.03-4.86 (m, 5H), 4.73-4.66 (m, 1H), 4.49-4.39 (m, 3H), 4.33-4.28 (m, 1H), 4.24 (dd, J=12.2, 4.9 Hz, 1H), 4.09 (ddd, J=8.0, 4.4, 1.7 Hz, 1H), 3.87 (t, J=9.0 Hz, 1H), 3.70-3.65 (m, 1H), 3.65-3.55 (m, 2H), 3.49 (ddd, J=12.6, 9.9, 4.5 Hz, 1H), 3.45-3.36 (m, 2H), 3.34-3.29 (m, 1H), 3.28 (dd, J=13.0, 4.4 Hz, 1H), 3.21 (dd, J=12.9, 4.2 Hz, 1H), 2.35 (dt, J=13.2, 4.5 Hz, 1H), 2.17 (s, 3H), 2.16 (s, 3H), 2.15 (s, 3H), 2.15 (s, 3H), 2.12 (s, 3H), 2.11 (s, 3H), 1.59 (dd, J=25.7, 12.7 Hz, 11H). MS (ESI) [M+NH$_4$]$^+$ 1042.2.

Step 5

(2S,3S,4R,5R,6R)-5-azido-2-(azidomethyl)-6-[(2R,3S,4R,5S)-5-[(1R,2R,3S,5R,6S)-3,5-diazido-2-[(2R,3S,4R,5S,6R)-3-azido-6-(azidomethyl)-4-fluoro-5-hydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol

Step 6

(2S,3S,4R,5R,6R)-5-amino-2-(aminomethyl)-6-[(2R,3S,4R,5S)-5-[(1R,2R,3S,5R,6S)-3,5-diamino-2-[(2R,3S,4R,5S,6R)-3-amino-6-(aminomethyl)-4-fluoro-5-hydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol; formic acid

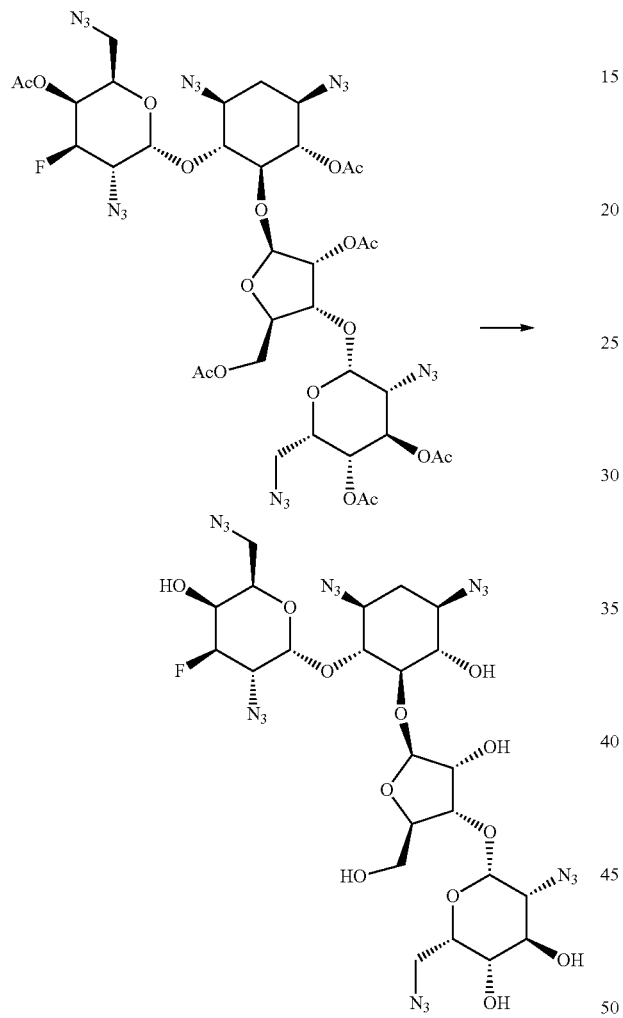

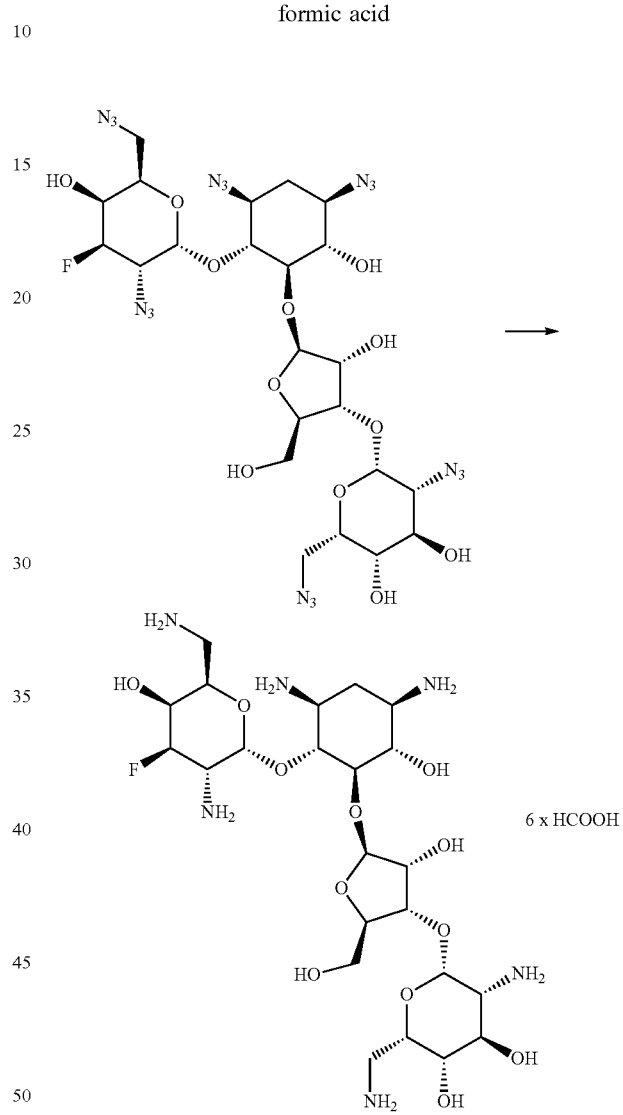

NaOMe (25 wt %, 141 μL, 615 μmol) was added dropwise to a solution of [(2R,3R,4R,5S)-4-acetoxy-5-[(1S,2S,3R,5S,6R)-2-acetoxy-6-[(2R,3S,4R,5S,6R)-5-acetoxy-3-azido-6-(azidomethyl)-4-fluoro-tetrahydropyran-2-yl]oxy-3,5-diazido-cyclohexoxy]-3-[(2R,3R,4R,5R,6S)-4,5-diacetoxy-3-azido-6-(azidomethyl)tetrahydropyran-2-yl]oxy-tetrahydrofuran-2-yl]methyl acetate (63 mg, 62 μmol) in MeOH (2.0 mL) at ambient temperature and the reaction mixture was stirred for 90 min. AcOH (53 μL, 922 μmol) was added and the volatiles were evaporated under reduced pressure. The material was filtered through silica gel (0.50 g) and eluted with EtOAc (10.0 mL). The filtrate was concentrated under reduced pressure to provide the title compound (46 mg, 97%) as a solid, which was used in the next step without further purification. MS (ESI) [M+NH$_4$]$^+$790.3.

Pd(OH)$_2$/C (10 wt %, 7.6 mg, 5.4 μmol) was added to a solution of (2S,3S,4R,5R,6R)-5-azido-2-(azidomethyl)-6-[(2R,3S,4R,5S)-5-[(1R,2R,3S,5R,6S)-3,5-diazido-2-[(2R,3S,4R,5S,6R)-3-azido-6-(azidomethyl)-4-fluoro-5-hydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol (21 mg, 27 μmol) in MeOH (3.0 mL) under N$_2$ at ambient temperature. H$_2$ was bubbled into the solution for 15 min and then the suspension was hydrogenated under hydrogen atmosphere for 18 h. The mixture was filtered through a frit (0.45 m diameter) and then formic acid (40 μL) was added to the filtrate. The filtrate was concentrated under reduced pressure and then lyophilization to provide the title compound (hexa-formate salt, 20.5 mg, 82%) as a solid. $^1$H NMR (500 MHz, MeOD) δ 8.49 (s, 6H), 6.01 (t, J=4.2 Hz, 1H), 5.41 (d, J=2.1 Hz, 1H), 5.27 (d, J=1.5 Hz, 1H), 5.09 (ddd, J=49.5, 10.9, 3.0 Hz, 1H), 4.51 (dd, J=6.7, 4.7 Hz, 1H), 4.40-4.33 (m, 2H), 4.30 (ddd, J=4.7, 3.4, 0.8 Hz, 1H), 4.22 (dd, J=8.5, 1.9 Hz, 1H), 4.20-4.17 (m, 1H), 4.16 (t, J=3.1 Hz, 1H), 3.94-3.86 (m, 2H), 3.82 (t, J=9.5 Hz, 1H), 3.78-3.71 (m, 2H), 3.69-3.66 (m, 1H), 3.56-3.50 (m, 1H), 3.43-3.40 (m, 1H), 3.40-3.33 (m, 2H), 3.26-3.13 (m, 4H), 2.31 (dt, J=12.5, 4.2 Hz, 1H), 1.79-1.68 (m, 1H). MS (ESI) [M+H]+ 617.51.

Preparation of [(2R,3S,4R,5S)-5-azido-2-(azidomethyl)-4-fluoro-6-hydroxy-tetrahydropyran-3-yl] 4-nitrobenzoate

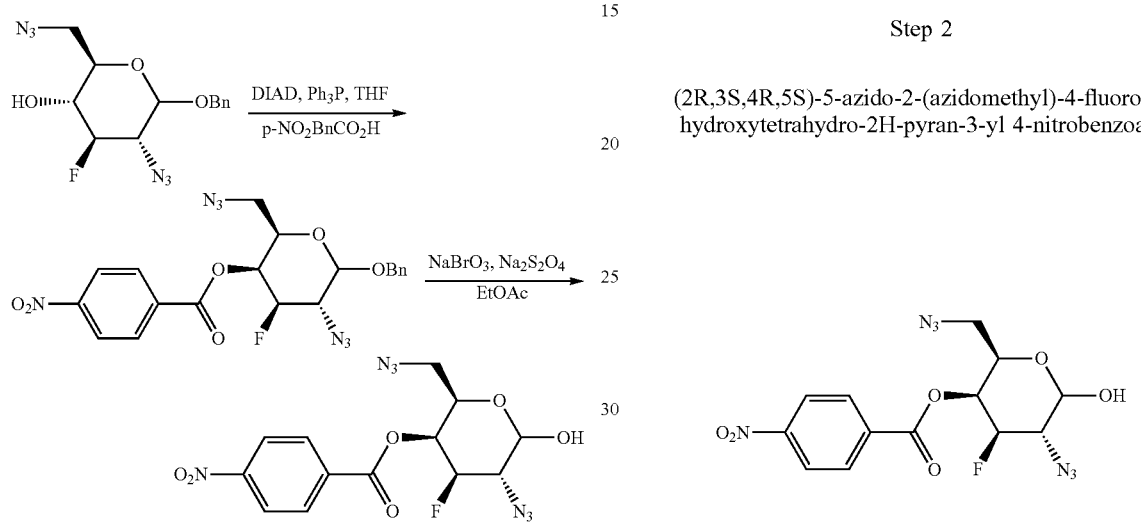

Step 1

(2R,3S,4R,5S)-5-azido-2-(azidomethyl)-6-(benzyloxy)-4-fluorotetrahydro-2H-pyran-3-yl 4-nitrobenzoate

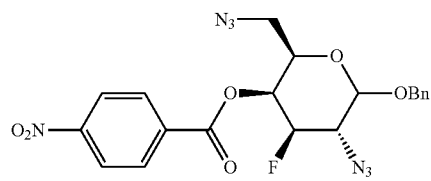 [SMILES: [N-]=[N+]=NC[C@H]1OC(OCc2ccccc2)[C@H](N=[N+]=[N-])[C@@H](F)[C@H]1OC(=O)c1ccc([N+](=O)[O-])cc1]

To a solution of 4.52 g of DIAD in 30 mL of THF was added 5.13 g of triphenylphosphine at 0° C. and stirred for 1 h at the same temperature. To this solution, was added p-nitrobenzoic acid at the same temperature and stirred for 1 hour. To this solution, (2R,3R,4R,5S,6R)-5-azido-2-(azidomethyl)-6-(benzyloxy)-4-fluorotetrahydro-2H-pyran-3-ol in 30 mL of anhydrous THF was slowly added at 0° C. and the reaction allowed to reach room temperature. The reaction mixture was stirred until completion of the reaction. The reaction was purified by flash chromatography (30% EtOAc in Hexanes) to afford 1.85 g of (2R,3S,4R,5S)-5-azido-2-(azidomethyl)-6-(benzyloxy)-4-fluorotetrahydro-2H-pyran-3-yl 4-nitrobenzoate (74% yield).

Step 2

(2R,3S,4R,5S)-5-azido-2-(azidomethyl)-4-fluoro-6-hydroxytetrahydro-2H-pyran-3-yl 4-nitrobenzoate To a solution of 2 g of (2R,3S,4R,5S)-5-azido-2-(azidomethyl)-6-(benzyloxy)-4-fluorotetrahydro-2H-pyran-3-yl 4-nitrobenzoate in EtOAc was added 3 g of NaBrO₃ dissolved in 30 mL of water. To this mixture, 3.14 g sodium dithionate dissolved in 60 mL of water was added over 30 min. The reaction mixture was vigorously stirred until completion (3-6 h). The organic layer was separated and washed with 200 mL of 1:1 mixture of aqueous sodium thiosulfate (5%) and saturated aqueous NaHCO₃. The organic layer was dried over anhydrous sodium sulfate and concentrated. The obtained crude was purified by flash chromatography (EtOAc/Hexanes 1:3) to afford 1 g of (2R,3S,4R,5 S)-5-azido-2-(azidomethyl)-4-fluoro-6-hydroxytetrahydro-2H-pyran-3-yl 4-nitrobenzoate (63% yield).

Example 23

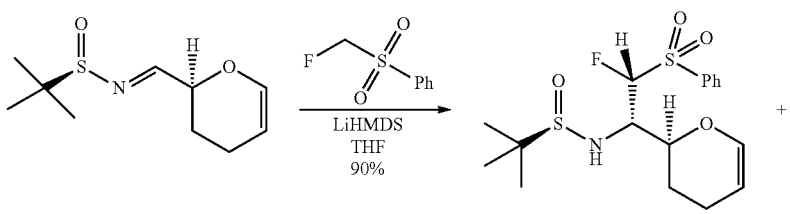

-continued
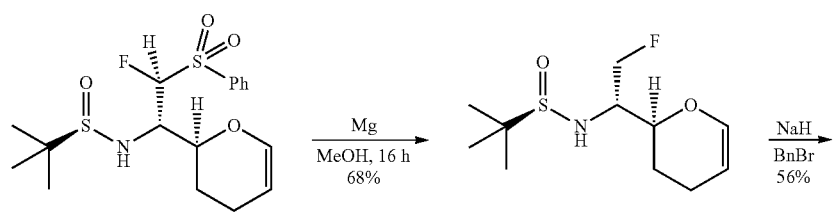
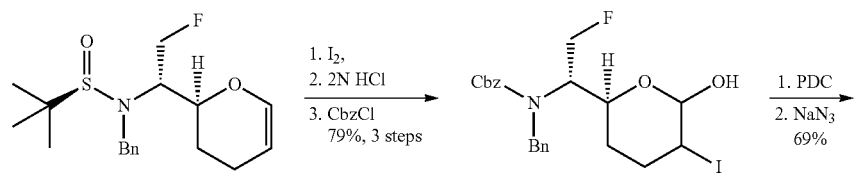
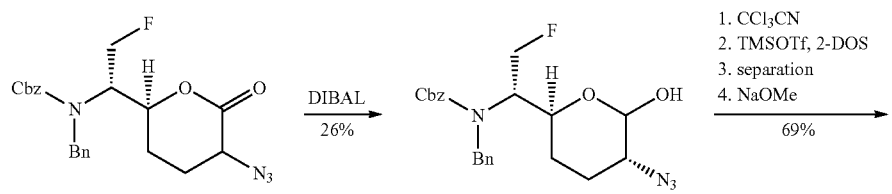
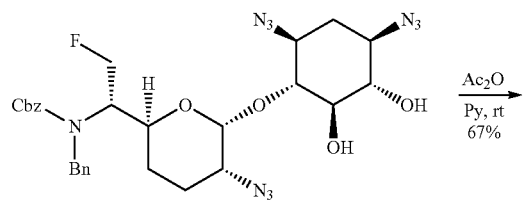
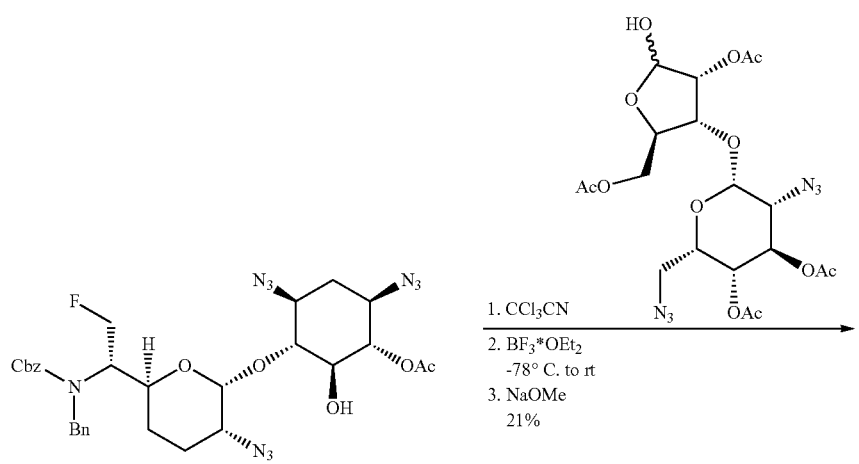

489

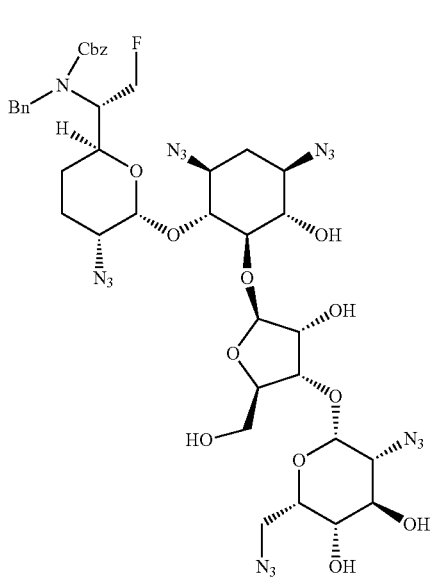

490

-continued

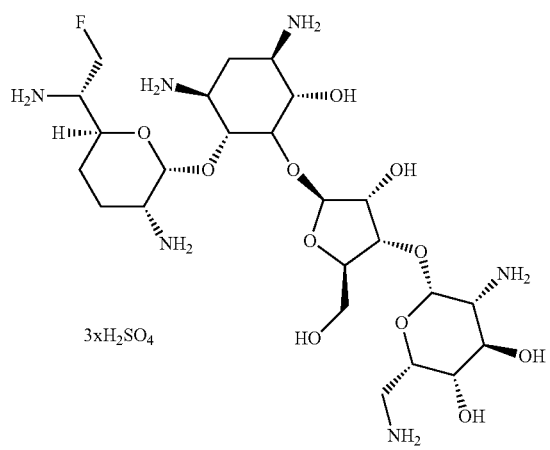

Pd/C
AmFor

3xH₂SO₄

Step 1

(R)—N-[(1S,2R)-2-(benzenesulfonyl)-1-[(2S)-3,4-dihydro-2H-pyran-2-yl]-2-fluoro-ethyl]-2-methyl-propane-2-sulfinamide

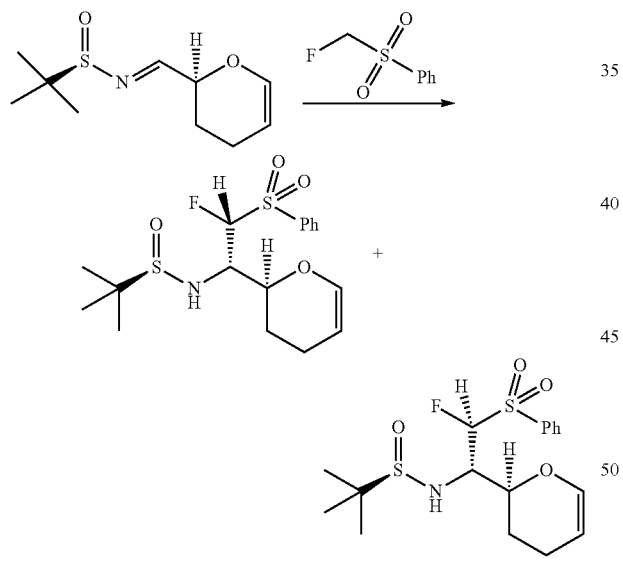

To a solution of (NE,R)—N-[[(2S)-3,4-dihydro-2H-pyran-2-yl]methylene]-2-methyl-propane-2-sulfinamide (4.82 g, 22.4 mmol) and fluoromethylsulfonylbenzene (3.90 g, 22.4 mmol) in anhydrous THF (100 mL), at −78° C. was added LiHMDS (1.00 M in THF, 23.5 mL, 23.5 mmol) and the reaction mixture was stirred at −78° C. for 1 h. The mixture was warmed to 20° C. and quenched with saturated NaHCO₃ (50 mL). The mixture was diluted with EtOAc (150 mL) and water (100 mL). The separated organic phase was dried (Na₂SO₄), filtered and concerted under reduced pressure. The material was purified by column chromatography on silica gel (120 g, dry pack) using a gradient of 20-50% EtOAc in hexane as eluent to afford the title compound (7.84 g, 90%, 1:1 mixture). MS (ESI) [M+Na]⁺ 412.3.

Step 2

(R)—N-[(1S)-1-[(2S)-3,4-dihydro-2H-pyran-2-yl]-2-fluoro-ethyl]-2-methyl-propane-2-sulfinamide

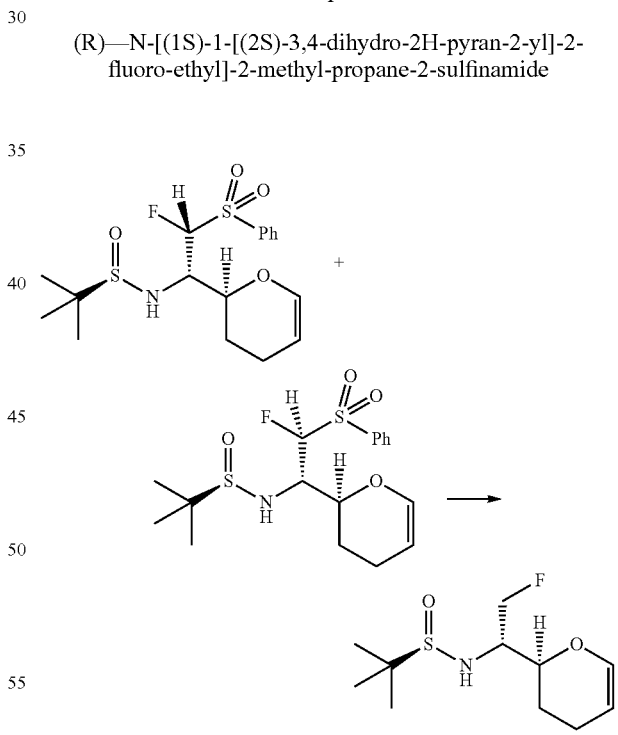

To a solution of (R)—N-[(1S)-2-(benzenesulfonyl)-1-[(2S)-3,4-dihydro-2H-pyran-2-yl]-2-fluoro-ethyl]-2-methyl-propane-2-sulfinamide (8.4 g, 21.6 mmol) in MeOH (75 mL), was added Mg (2.10 g, 86 mmol) in 4 portions over 1 h (bubbles) and the reaction mixture was stirred overnight at room temperature. The mixture was concentrated under reduced pressure and then saturated NH₄Cl and Et₂O was added. The separated organic phase was washed with brine (100 mL), then dried (Na₂SO₄), filtered and concentrated under reduced pressure to provide title product (R)—N-[(1S)-1-[(2S)-3,4-dihydro-2H-pyran-2-yl]-2-fluoro-ethyl]-2-methyl-propane-2-sulfinamide (3.65 g, 68%). $^1$H NMR (400 MHz, CDCl$_3$) δ 6.31-6.26 (m, 1H), 4.67 (tdd, J=6.3, 3.1, 2.0 Hz, 1H), 4.54 (dd, J=4.9, 1.4 Hz, 1H), 4.42 (dd, J=4.9, 1.3 Hz, 1H), 3.98 (dd, J=10.2, 5.5 Hz, 1H), 3.68 (d, J=8.3 Hz, 1H), 3.59-3.45 (m, 1H), 2.08-1.91 (m, 3H), 1.76-1.63 (m, 1H), 1.18 (s, 9H). MS (ESI) [M+H]$^+$ 250.4.

Step 3

(R)—N-benzyl-N-[(1S)-1-[(2S)-3,4-dihydro-2H-pyran-2-yl]-2-fluoro-ethyl]-2-methyl-propane-2-sulfinamide

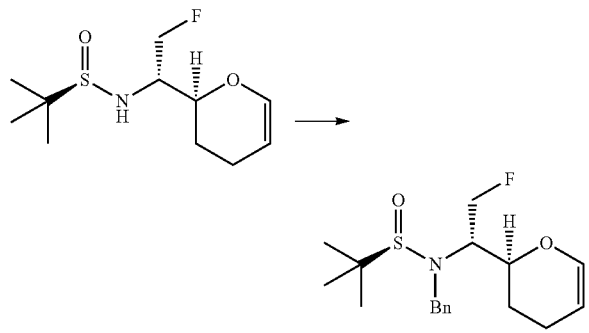

To a solution of (R)—N-[(1S)-1-[(2S)-3,4-dihydro-2H-pyran-2-yl]-2-fluoro-ethyl]-2-methyl-propane-2-sulfinamide (3.65 mg, 14.6 mmol) and benzyl bromide (2.61 mL, 22.0 mmol) in DMF (30 mL) at 0° C., was added sodium hydride (60.0%, 703 mg, 17.6 mmol) and the reaction mixture was stirred at 20° C. for 1 h. The mixture was quenched with brine (100 mL) and the aqueous layer was extracted with EtOAc (150 mL). The organic phase was dried (Na$_2$SO$_4$), filtered and concentrated under reduced pressure. The material was purified by column chromatography on silica gel (120 g) using a gradient of 0-40% EtOAc in hexane as eluent to afford the title compound (2.76 g, 56%). MS (ESI) [M+Na]$^m$ 362.4.

Step 4

Benzyl-N-benzyl-N-[(1S)-2-fluoro-1-[(2S)-6-hydroxy-5-iodo-tetrahydropyran-2-yl]ethyl]carbamate

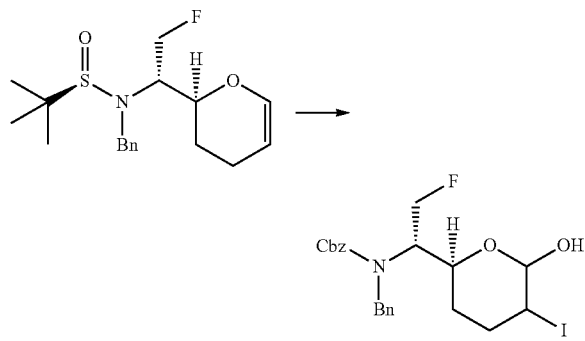

To a suspension of (R)—N-benzyl-N-[(1S)-1-[(2S)-3,4-dihydro-2H-pyran-2-yl]-2-fluoro-ethyl]-2-methyl-propane-2-sulfinamide (2.78 g, 8.19 mmol) and NaHCO$_3$ (2.06 g, 24.6 mmol) in a mixture of ACN (30 mL) and H$_2$O (30 mL) at 0° C., was added I2 (3.12 g, 12.3 mmol) portionwise and the reaction mixture was stirred at 20° C. for 90 min. The mixture was diluted with saturated aqueous solution of Na$_2$S$_2$O$_3$ (100 mL) and the aqueous layer was extracted with EtOAc (100 mL). The organic layer was dried (Na$_2$SO$_4$), filtered, and concentrated under reduced pressure to provide the iodolactol. MS (ESI) [M+Na]$^+$ 506.2.

To a solution of above material (3.96 g, 8.19 mmol) in dioxane (100 mL) with vigorous stirring, was added 1.0 M aqueous HCl (32.8 mL, 32.8 mmol) and the reaction mixture was stirred for 1 h. Solid Na$_2$CO$_3$ (6.94 g, 65.5 mmol) was then added and the mixture was stirred for 10 min. CbzCl (1.63 mL, 11.5 mmol) was added dropwise and the reaction mixture was stirred for 30 min. The mixture was partitioned in between EtOAc (50 mL) and H$_2$O (50 mL). The aqueous layer was extracted with EtOAc (50 mL) and the combined organic layers were combined were dried (Na$_2$SO$_4$), filtered and concentrated under reduced pressure. The material was purified by column chromatography on silica gel (120 g) using a gradient of 0-55% EtOAc in hexane as eluent to provide the title compound (3.30 g, 79%). MS (ESI) [M+Na]$^+$ 536.2.

Step 5

Benzyl N-[(1S)-1-[(2S)-5-azido-6-oxo-tetrahydropyran-2-yl]-2-fluoro-ethyl]-N-benzyl-carbamate

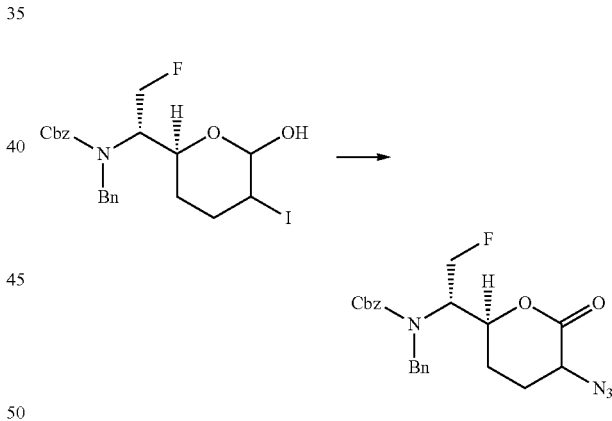

To a solution of benzyl N-benzyl-N-[(1S)-2-fluoro-1-[(2S)-6-hydroxy-5-iodo-tetrahydropyran-2-yl]ethyl]carbamate (3.30 g, 6.43 mmol) in DCM (200 mL), was added 4 Å molecular sieves (2.00 g) followed by PDC (10.9 g, 28.9 mmol) and the suspension was stirred for 18 h. The mixture was filtered on a silica pad, rinsed with EtOAc and concentrated under reduced pressure. The residue material was dissolved in DMF (30 mL) and then cooled at 0° C. NaN$_3$ (0.46 g, 7.07 mmol) was added and the reaction mixture was stirred for 1 h at room temperature. The mixture was diluted with brine (250 mL) and the separated aqueous layer was extracted with Et$_2$O. The combined organic layers were dried over (Na$_2$SO$_4$), filtered and concentrated under reduced pressure to provide the title compound as a mixture of diastereomers (1.9 g, 69%), which was used in the next step without further purification. MS (ESI) [M+Na]$^+$ 449.3.

Step 6

Benzyl N-[(1S)-1-[(2S,5R)-5-azido-6-hydroxy-tetrahydropyran-2-yl]-2-fluoro-ethyl]-N-benzyl-carbamate

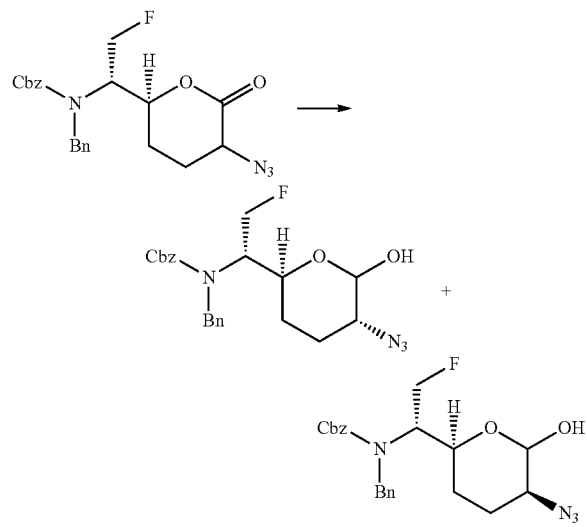

DIBAL-H (1 M in toluene, 8.96 mL, 8.96 mmol) was added dropwise to a solution of benzyl N-[(1S)-1-[(2S)-5-azido-6-oxo-tetrahydropyran-2-yl]-2-benzyloxy-ethyl]-N-benzyl-carbamate (1.91 g, 4.48 mmol) in DCM (50 mL) at −78° C. and the reaction mixture was stirred at room temperature for 1 h. EtOH (1 mL) was added dropwise and the mixture was poured into a saturated aqueous solution of Rochelle's salt (300 mL) and then was stirred vigorously stirred for 1 h. The separated aqueous layer was extracted with DCM (2×75 mL). The combined organic layer was washed with brine, then dried (Na₂SO₄), filtered and concentrated under reduced pressure. The material was purified flash chromatography on silica gel (120 g) using a gradient of 25-70% Et₂O in hexane to provide benzyl N-[(1S)-1-[(2S,5R,6R)-5-azido-6-[(1R,2R,3S,4R,6S)-4,6-diazido-2,3-dihydroxy-cyclohexoxy]tetrahydropyran-2-yl]-2-fluoro-ethyl]-N-benzyl-carbamate (first eluting, 489 mg, 26%) and a diastereomer (second eluting, 283 mg, 15%). MS (ESI) [M+Na]⁺ 451.1. (5.69 and 5.86 min are the first eluting diastereomer; 5.57 and 5.78 min are the first eluting diastereomer).

Step 7

(1S,2R,3R,4S,6R)-4,6-diazido-3-[(2R,3R,6S)-3-azido-6-[(1S)-1-[benzyl(methyl)aminol-2-fluoro-ethyl]tetrahydropyran-2-yl]oxy-cyclohexane-1,2-diol

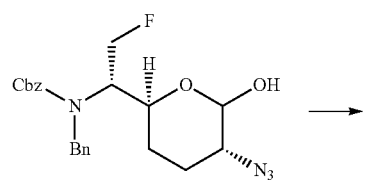

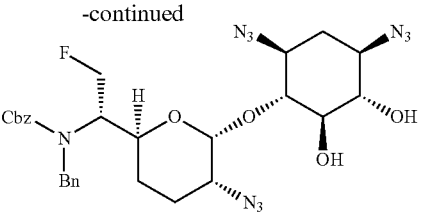

To a suspension of benzyl N-[(1S)-1-[(2S,5R,6R)-5-azido-6-[(1R,2R,3S,4R,6S)-4,6-diazido-2,3-dihydroxy-cyclohexoxy]tetrahydropyran-2-yl]-2-fluoro-ethyl]-N-benzyl-carbamate (150 mg, 0.58 mmol) and K₂CO₃ (174 mg, 1.26 mmol) in DCM (5 mL) under N₂ was added CCl₃CN (0.20 mL, 2.01 mmol). The mixture was stirred at room temperature for 66 h, then the filtered through Celite, rinsed with DCM and concentrated under reduced pressure.

[(1S,2S,3R,4S,6R)-2-acetoxy-4,6-diazido-3-hydroxy-cyclohexyl] acetate (150 mg, 0.50 mmol) was added to the above material, and the mixture was co-evaporated with anhydrous toluene (2×10 mL) and then was dried under reduced pressure for 2 h. The material was dissolved in anhydrous Et₂O (5 mL) and then grounded activated 3 Å (0.5 g) and 4 Å sieves (0.5 g) were added. The mixture was stirred at room temperature for 1 h, then cooled to −40° C. TMSOTf (0.027 mL, 0.15 mmol) was then added dropwise and the mixture was stirred at −40° C. for 2 h, then warmed to room temperature. A saturated solution of NaHCO₃ (200 mL) was added and the separated aqueous layer was extracted with EtOAc (3×200 mL). The combined organic layers were dried (MgSO₄), filtered and concentrated under reduced pressure. The material was purified by flash chromatography (24 g, liquid loading) using a gradient of 0-40% EtOAc in hexane as eluent to afford intermediate A (minor, first eluting) and intermediate B (major, second eluting). MS (ESI) [M+Na]⁺ 731.5.

To a solution of intermediate B in MeOH (5 mL), NaOMe (4.62 M in MeOH, 0.87 mL, 4.02 mmol) was added and the reaction mixture was stirred at room temperature for 1 h. The mixture was concentrated under reduced pressure and the residue was dissolved in DCM (25 mL) and then a saturated solution of NH₄Cl (25 mL) was added. The separated aqueous layer was extracted with DCM (2×20 mL). The combined organic layers were dried (MgSO₄), filtered and concentrated under reduced pressure to provide the title compound (70.0 mg, 22%) MS (ESI) [M+Na]⁺ 647.5.

Step 8

Benzyl N-[(1S)-1-[(2S,5R,6R)-5-azido-6-[(1R,2R,3S,4R,6S)-4,6-diazido-2,3-dihydroxy-cyclohexoxy]tetrahydropyran-2-yl]-2-fluoro-ethyl]-N-benzyl-carbamate

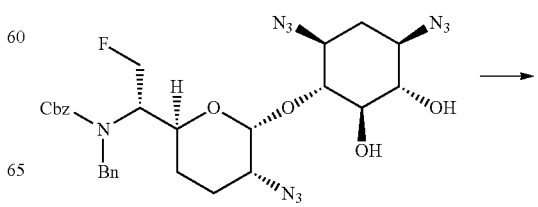

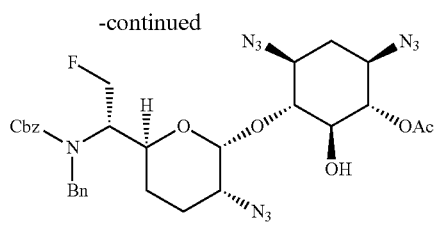

To a solution of benzyl N-[(1S)-1-[(2S,6R)-5-azido-6-[(1R,2R,3S,4R,6S)-4,6-diazido-2,3-dihydroxy-cyclohexoxy]tetrahydropyran-2-yl]-2-fluoro-ethyl]-N-benzyl-carbamate (88.0 mg, 0.14 mmol) in dry DCM (8 mL), was added pyridine (67 µL, 0.85 mmol) followed by Ac₂O (67 µL, 0.70 mmol) at room temperature and the reaction mixture was stirred for 20 h. MeOH was added and the volatiles were evaporated under reduced pressure. The material was purified by flash chromatography (12 g, liquid loading with toluene) using a gradient 0-45% EtOAc in hexane as eluent to provide the title compound (63 mg, 67%). MS (ESI) [M+H]⁺ 667.7.

Step 9

Benzyl-N-[(1S)-1-[(2S,5R,6R)-5-azido-6-[(1R,2R,3S,4R,6S)-4,6-diazido-2-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl)tetrahydrofuran-2-yl]oxy-3-hydroxy-cyclohexoxy]tetrahydropyran-2-yl]-2-fluoro-ethyl]-N-benzyl-carbamate

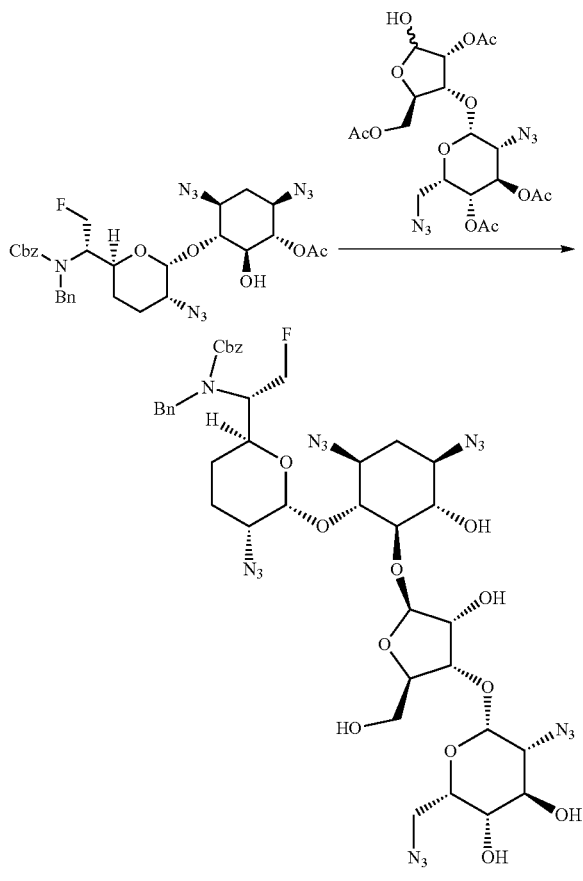

To a suspension of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (150 mg, 0.28 mmol) and K₂CO₃ (78.4 mg, 0.57 mmol) in dry DCM (5.0 mL) at ambient temperature under N₂, was added CCl₃CN (0.095 mL, 0.95 mmol) dropwise and the reaction mixture was stirred for 15 h. The mixture was filtered through 45 µm nylon filter and the volatiles were evaporated under reduced pressure.

To the above material was added a solution of [(1S,2S,3R,4S,6R)-4,6-diazido-3-[(2R,3R,6S)-3-azido-6-[(1S)-1-[benzyl(benzyloxycarbonyl)amino]-2-fluoro-ethyl]tetrahydropyran-2-yl]oxy-2-hydroxy-cyclohexyl] acetate (63.0 mg, 0.095 mmol) in DCM (1.0 mL) and the volatiles were evaporated under reduced pressure. To the residue was added ground 4 Å sieves (200 mg) followed by dry DCM (5.0 mL). The suspension was stirred at ambient temperature for 1 h. The solution was cooled to 0° C. and then BF₃·Et₂O (0.093 mL, 0.76 mmol) was added. The reaction mixture was stirred for 2 h, and then the reaction was quenched with NaHCO₃. The layers were separated, and the aqueous layer was extracted with EtOAc (5.0 mL). The organic phase was dried (Na₂SO₄), filtered and concentrated under reduced pressure. The material was purified by reversed phase chromatography on C18 (80 g) using ACN in water and 0.1% aqueous. formic acid (40-100%) to afford the title compound. MS (ESI) [M+Na]⁺ 1201.8.

To a solution of the above material in MeOH (1.0 mL) at ambient temperature, was added NaOMe (25 wt %, 0.33 mL, 1.13 mmol) dropwise and the reaction mixture was stirred for 45 min. The volatiles were removed under reduced pressure. The residue was diluted with EtOAc and the organic layer was washed with saturated NH₄Cl and brine, then dried (Na₂SO₄), filtered, and concentrated under reduced pressure. The material was purified by preparative HPLC (CSH ACN/AmForm 60-80%) to afford the title compound (19 mg, 21%, 3 steps). MS (ESI) [M+H]⁺ 969.7.

Step 10

(2S,3S,4R,5R,6R)-5-amino-2-(aminomethyl)-6-[(2R,3S,4R,5S)-5-[(1R,2R,3S,5R,6S)-3,5-diamino-2-[(2R,3R,6S)-3-amino-6-[(1S)-1-amino-2-fluoro-ethyl]tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol; Sulfate

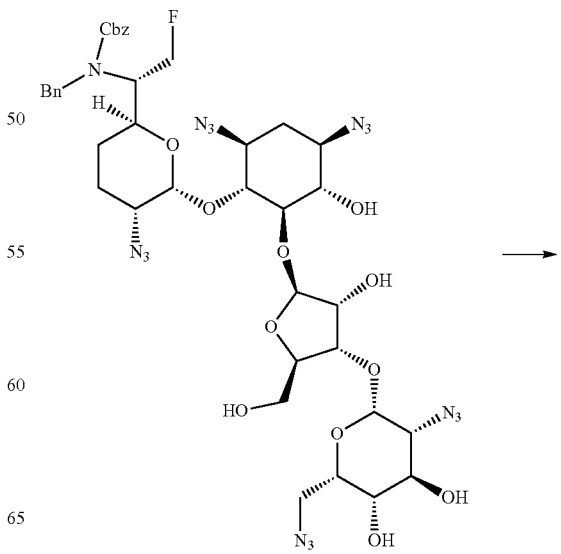

497

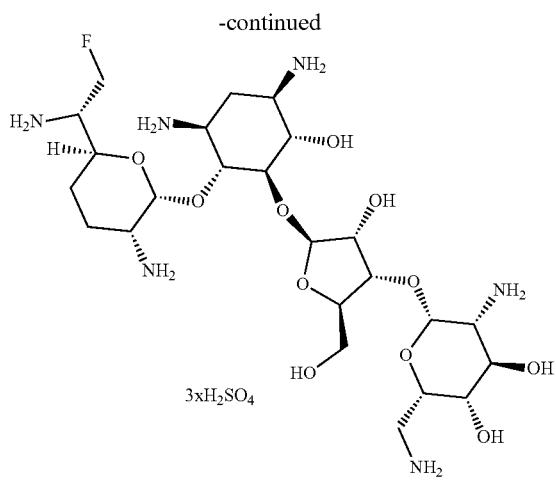

3xH₂SO₄

To a solution of benzyl N-[(1S)-1-[(2S,5R,6R)-5-azido-6-[(1R,2R,3S,4R,6S)-4,6-diazido-2-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl)tetrahydrofuran-2-yl]oxy-3-hydroxy-cyclohexoxy]tetrahydropyran-2-yl]-2-fluoro-ethyl]-N-benzyl-carbamate

498

(19 mg, 0.020 mmol) and Pd/C (10% dry on carbon, 10.4 mg, 0.0098 mmol) following by anhydrous MeOH (1 mL). Nitrogen was bubbled for 5 min, then ammonium formate (18.5 mg, 0.29 mmol) was added and the mixture was heated at 63° C. for 6 h. The mixture was then cooled and filtered through a nylon filter (45 m) and the volatiles were evaporated under reduced pressure to provide the title compound (7.7 mg, 64%). The material was purified by preparative HPLC (with A: 0.3% HFBA, 0.3% HCOOH in water B: 0.3% HFBA Acetonitrile; Flow rate: 40 mL/min; Column: C18, 30×150 mm, 27% B in A to 37% B in A over 7 minutes provided 8 mg of the title compound as a HFBA salt. The salt swap with ammonium sulfate provided the title product (0.7 mg, 6%). $^1$H NMR (500 MHz, D$_2$O) δ 5.86 (d, J=3.5 Hz, 1H), 5.35 (d, J=2.3 Hz, 1H), 5.24 (d, J=1.7 Hz, 1H), 4.83-4.74 (m, 1H), 4.68-4.63 (m, 1H), 4.47 (dd, J=6.7, 4.9 Hz, 1H), 4.38 (dd, J=4.8, 2.3 Hz, 1H), 4.30-4.25 (m, 1H), 4.22-4.14 (m, 3H), 4.00 (s, 1H), 3.88-3.82 (m, 2H), 3.79-3.64 (m, 4H), 3.56-3.52 (m, 1H), 3.52-3.46 (m, 1H), 3.43-3.24 (m, 4H), 2.36 (dt, J=6.9, 4.6 Hz, 1H), 2.02-1.93 (m, 2H), 1.93-1.83 (m, 2H), 1.70-1.58 (m, 1H). MS (ESI) [M+H]$^+$ 615.0.

Example 24

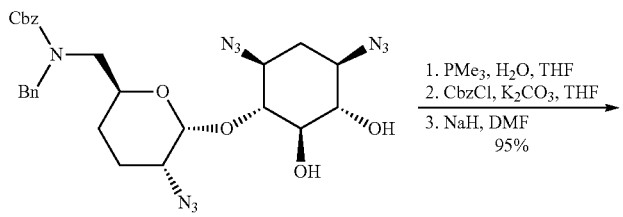

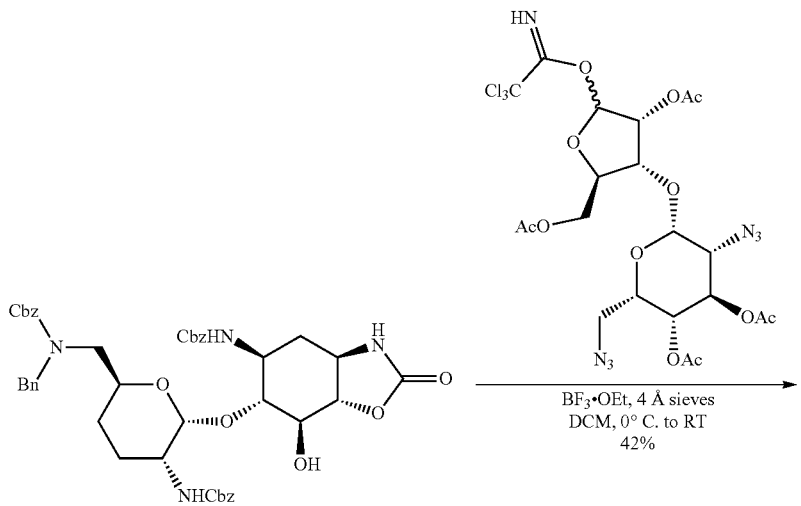

499
-continued
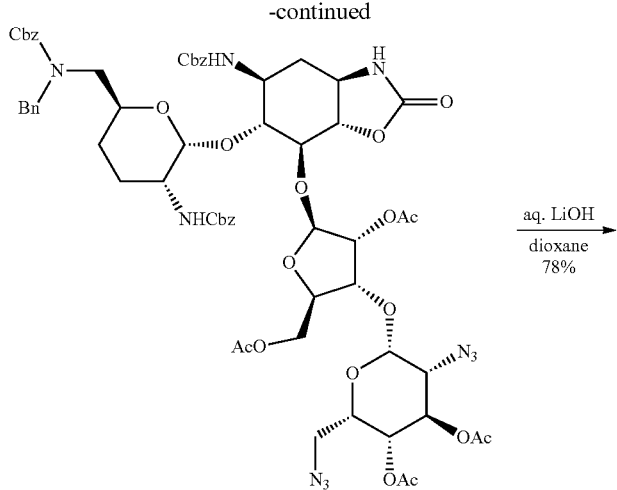
aq. LiOH
dioxane
78%
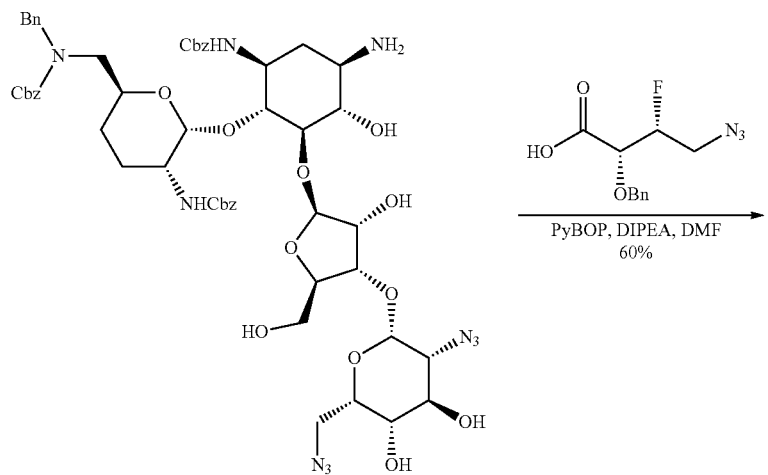
PyBOP, DIPEA, DMF
60%
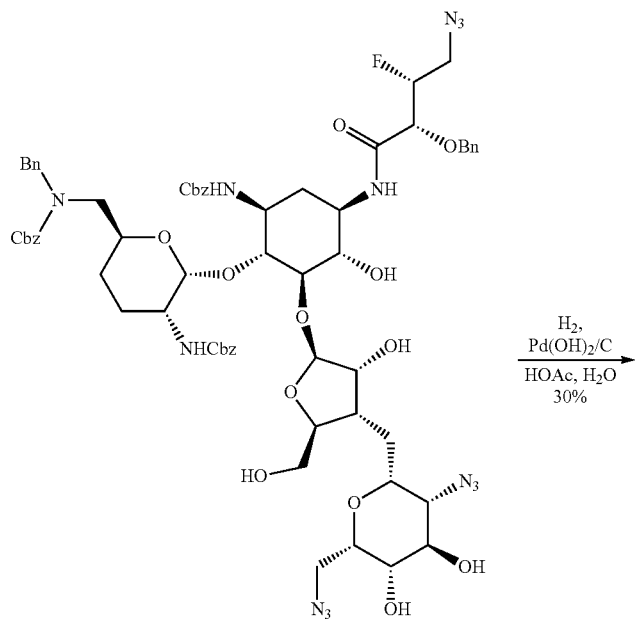
H₂,
Pd(OH)₂/C
HOAc, H₂O
30%

-continued

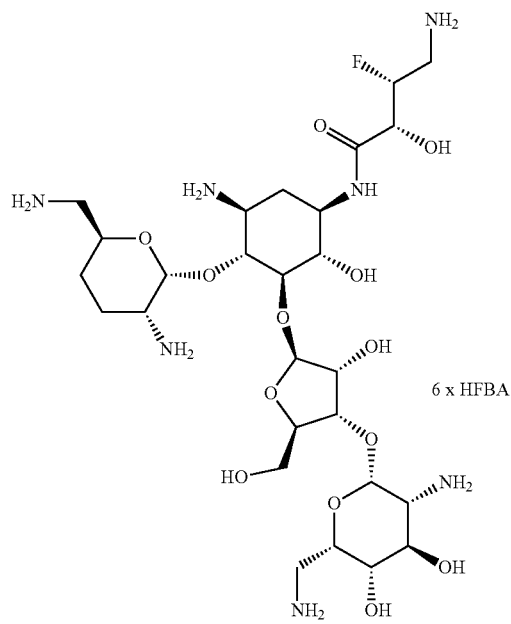

6 x HFBA

Step 1

Benzyl N-[[(2S,5R,6R)-6-[[(3aR,5S,6R,7S,7aS)-5-(benzyloxycarbonylamino)-7-hydroxy-2-oxo-3a,4,5,6,7,7a-hexahydro-3H-1,3-benzoxazol-6-yl]oxy]-5-(benzyloxycarbonylamino)tetrahydropyran-2-yl]methyl]-N-benzyl-carbamate

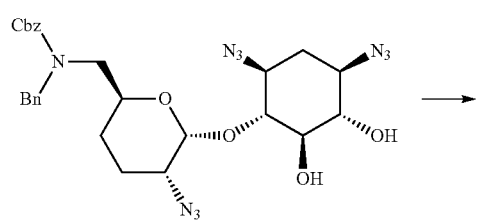

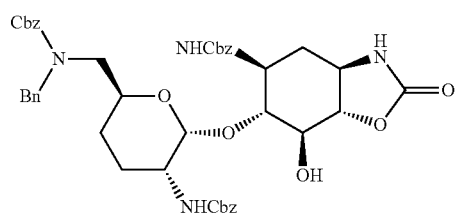

To a solution of benzyl N-[[(2S,5R,6R)-5-azido-6-[(1R,2R,3S,4R,6S)-4,6-diazido-2,3-dihydroxy-cyclohexoxy]tetrahydropyran-2-yl]methyl]-N-benzyl-carbamate (see Example 11 for synthesis, 335 mg, 565 μmol) and water (350 μL, 19.4 mmol) in THF (12.0 mL) under $N_2$ at, was added $PMe_3$ (1.0 M in THF, 2.54 mL, 2.54 mmol) ambient temperature. The reaction mixture was heated to 40° C. and stirred for 18 h. The mixture was cooled to room temperature and then $K_2CO_3$ (703 mg, 5.09 mmol) was added and stirred for 10 min. CbzCl (362 μL, 2.54 mmol) was added dropwise and the reaction mixture was stirred for 60 min. Silica gel (5.0 g) was added and all volatiles were evaporated under reduced pressure. The material was purified by silica gel chromatography (25 g cartridge, drypack) using a gradient of MeOH and DCM (0-10%) as eluent to afford benzyl N-benzyl-N-[[(2S,5R,6R)-5-(benzyloxycarbonylamino)-6-[(1R,2R,3S,4R,6S)-4,6-bis(benzyloxycarbonylamino)-2,3-dihydroxy-cyclohexoxy]tetrahydropyran-2-yl]methyl]carbamate (725 mg) as a solid.

A portion of benzyl N-benzyl-N-[[(2S,5R,6R)-5-(benzyloxycarbonylamino)-6-[(1R,2R,3S,4R,6S)-4,6-bis(benzyloxycarbonylamino)-2,3-dihydroxy-cyclohexoxy]tetrahydropyran-2-yl]methyl]carbamate (200 mg) was dissolved in anhydrous DMF (0.80 mL) and then NaH (60%, 42 mg, 1.05 mmol) was added under $N_2$ at 0° C. The flask was warmed to ambient temperature and stirred for 40 min. The mixture was cooled to 0° C. and then acetic acid (69 μL, 1.20 mmol) was added dropwise. The material was directly purified by silica gel chromatography (12 g cartridge) using a gradient of MeOH and DCM (0-10%) as eluent to afford the title compound (120 mg, 95% over 3 steps) as a solid. MS (ESI) $[M+H]^+$ 809.4.

Step 2

[(2R,3R,4R,5S)-5-[[(3aR,5S,6R,7S,7aS)-6-[(2R,3R,6S)-6-[[benzyl(benzyloxycarbonyl)amino]methyl]-3-(benzyloxycarbonylamino)tetrahydropyran-2-yl]oxy-5-(benzyloxycarbonylamino)-2-oxo-3a,4,5,6,7,7a-hexahydro-3H-1,3-benzoxazol-7-yl]oxy]-4-acetoxy-3-[(2R,3R,4R,5R,6S)-4,5-diacetoxy-3-azido-6-(azidomethyl)tetrahydropyran-2-yl]oxy-tetrahydrofuran-2-yl]methyl acetate

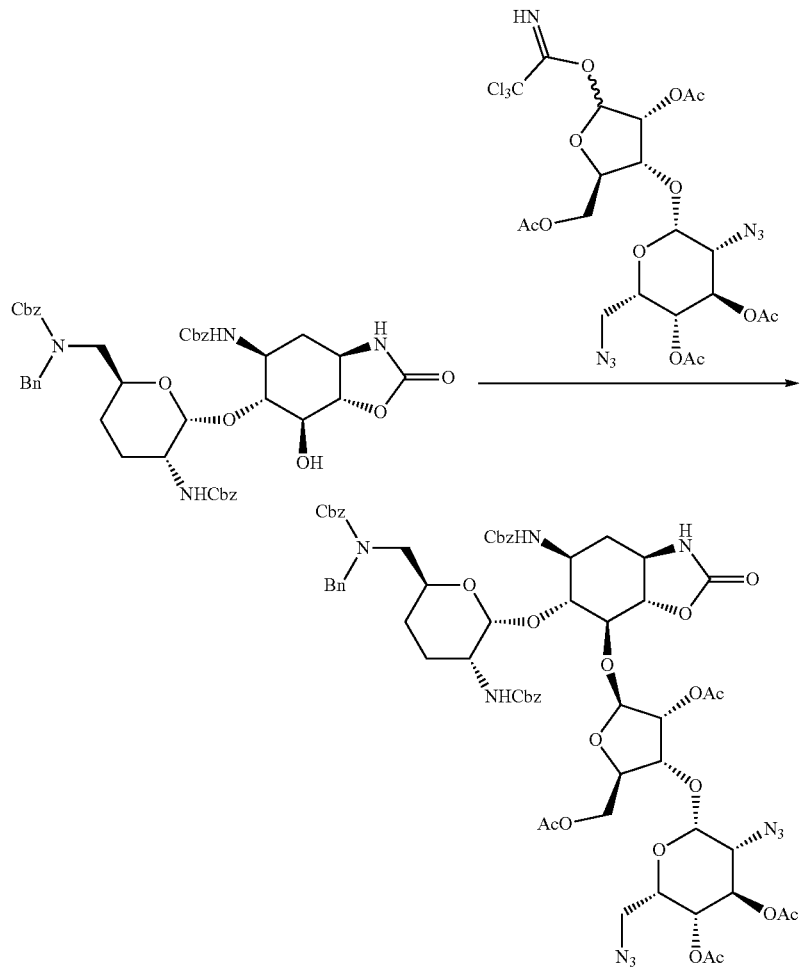

CCl$_3$CN (149 μL, 1.48 mmol) was added dropwise to a suspension of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (157 mg, 297 μmol) and K$_2$CO$_3$ (123 mg, 890 μmol) in dry DCM (1.8 mL) at ambient temperature under N$_2$. After 17 h, the solution was filtered through a Celite pad and the filtrate was concentrated under N$_2$ stream, and then dried under high-vacuum. To the above material was added benzyl N-[[(2S,5R,6R)-6-[[(3aR,5S,6R,7S,7aS)-5-(benzyloxycarbonylamino)-7-hydroxy-2-oxo-3a,4,5,6,7,7a-hexahydro-3H-1,3-benzoxazol-6-yl]oxy]-5-(benzyloxycarbonylamino)tetrahydropyran-2-yl]methyl]-N-benzyl-carbamate (120 mg, 148 μmol) in DCM (1.8 mL) and all volatiles were evaporated under N$_2$ stream. To the mixture was added ground 4 Å sieves (450 mg) and the mixture was dissolved in dry DCM (1.8 mL). The suspension was stirred at ambient temperature for 90 min, and then cooled to 0° C. BF$_3$·OEt$_2$ (146 μL, 1.19 mmol) was added and then stirred at ambient temperature for another 1 h. Et$_3$N (300 μL) was added and the mixture was filtered through a silica gel pad (0.30 g) and washed with EtOAc (20.0 mL). The volatiles were evaporated under reduced pressure and the material was purified by silica gel chromatography (12 g cartridge) using a gradient of MeOH and DCM (0-5%) as eluent and was further purified by C18 reversed phase chromatography (30 g cartridge) using ACN and 0.1% aq. formic acid (40-100%) to provide the title compound (83 mg, 42%) as a solid. MS (ESI) [M+H]$^+$ 1322.8.

Step 3

Benzyl N-[[(2S,5R,6R)-6-[(1R,2R,3S,4R,6S)-4-amino-2-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl)tetrahydrofuran-2-yl]oxy-6-(benzyloxycarbonylamino)-3-hydroxy-cyclohexoxy]-5-(benzyloxycarbonylamino)tetrahydropyran-2-yl]methyl]-N-benzyl-carbamate

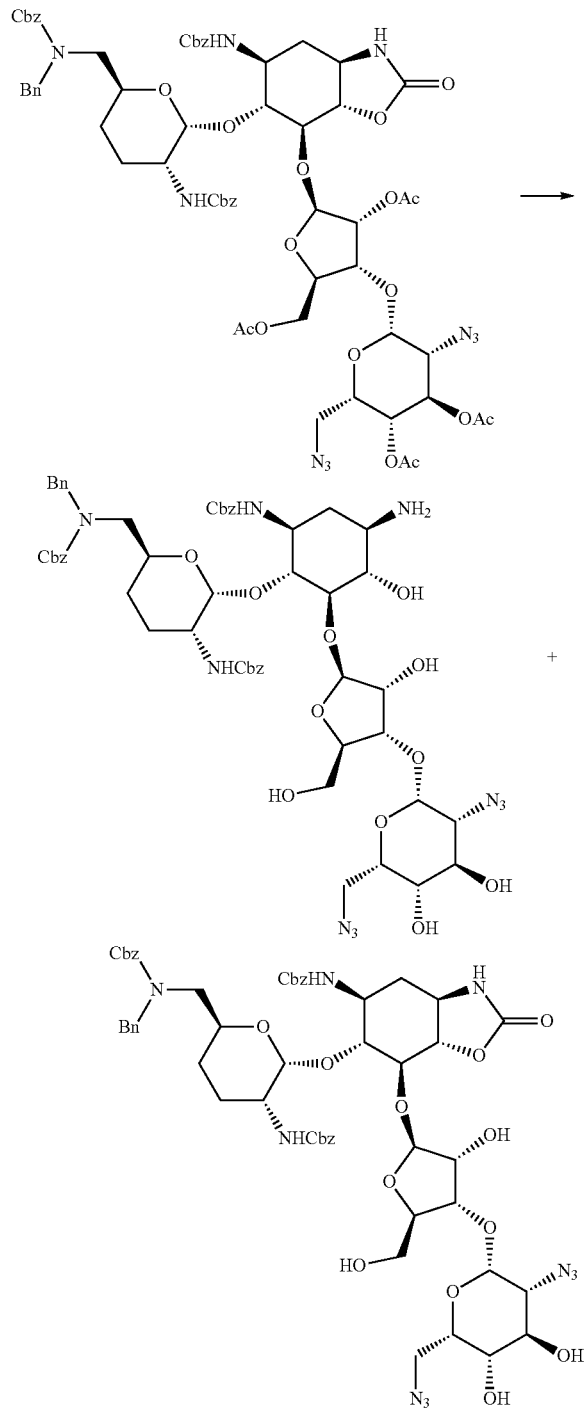

LiOH·H$_2$O (12 mg, 280 μmol) was added to a suspension of [(2R,3R,4R,5S)-5-[[(3aR,5S,6R,7S,7aS)-6-[(2R,3R,6S)-6-[[benzyl(benzyloxycarbonyl)amino]methyl]-3-(benzyloxycarbonylamino)tetrahydropyran-2-yl]oxy-5-(benzyloxycarbonylamino)-2-oxo-3a,4,5,6,7,7a-hexahydro-3H-1,3-benzoxazol-7-yl]oxy]-4-acetoxy-3-[(2R,3R,4R,5R,6S)-4,5-diacetoxy-3-azido-6-(azidomethyl)tetrahydropyran-2-yl]oxy-tetrahydrofuran-2-yl]methyl acetate (37 mg, 28 μmol) in a mixture dioxane and water (2.0 mL, 1:1) at ambient temperature. After 2 h, LiOH·H$_2$O (12 mg, 280 μmol) was added and the reaction mixture was stirred for 18 h. All volatiles were removed under reduced pressure and the material was purified by silica gel chromatography (4 g cartridge) using a gradient of MeOH and DCM (0-20%) as eluent to provide the title compound (21 mg, 66%) as a solid. MS (ESI) [M+H]$^+$ 1127.8.

Also from the same chromatography, benzyl N-[[(2S,5R,6R)-6-[[(3aR,5S,6R,7S,7aS)-7-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl)tetrahydrofuran-2-yl]oxy-5-(benzyloxycarbonylamino)-2-oxo-3a,4,5,6,7,7a-hexahydro-3H-1,3-benzoxazol-6-yl]oxy]-5-(benzyloxycarbonylamino)tetrahydropyran-2-yl]methyl]-N-benzyl-carbamate (8 mg, 25%). MS (ESI) [M+H]$^+$ 1154.6.

To a suspension of [(2R,3R,4R,5S)-5-[[(3aR,5S,6R,7S,7aS)-6-[(2R,3R,6S)-6-[[benzyl(benzyloxycarbonyl)amino]methyl]-3-(benzyloxycarbonylamino)tetrahydropyran-2-yl]oxy-5-(benzyloxycarbonylamino)-2-oxo-3a,4,5,6,7,7a-hexahydro-3H-1,3-benzoxazol-7-yl]oxy]-4-acetoxy-3-[(2R,3R,4R,5R,6S)-4,5-diacetoxy-3-azido-6-(azidomethyl)tetrahydropyran-2-yl]oxy-tetrahydrofuran-2-yl]methyl acetate (45 mg, 34 μmol) and benzyl N-[[(2S,5R,6R)-6-[[(3aR,5S,6R,7S,7aS)-7-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl)tetrahydrofuran-2-yl]oxy-5-(benzyloxycarbonylamino)-2-oxo-3a,4,5,6,7,7a-hexahydro-3H-1,3-benzoxazol-6-yl]oxy]-5-(benzyloxycarbonylamino)tetrahydropyran-2-yl]methyl]-N-benzyl-carbamate (8 mg, 7 μmol) in a mixture dioxane and water (1:1; 2.0 mL) at ambient temperature was added LiOH·H$_2$O (43 mg, 1.02 mmol) and the reaction mixture was stirred for 18 h.

All volatiles were evaporated under reduced pressure and the material was purified by silica gel chromatography (12 g cartridge) using a gradient of MeOH and DCM (0-20%) as eluent to provide the title compound (34 mg, 74%) as a solid. MS (ESI) [M+H]$^+$ 1127.8.

Overall, the hydrolysis of [(2R,3R,4R,5S)-5-[[(3aR,5S,6R,7S,7aS)-6-[(2R,3R,6S)-6-[[benzyl(benzyloxycarbonyl)amino]methyl]-3-(benzyloxycarbonylamino)tetrahydropyran-2-yl]oxy-5-(benzyloxycarbonylamino)-2-oxo-3a,4,5,6,7,7a-hexahydro-3H-1,3-benzoxazol-7-yl]oxy]-4-acetoxy-3-[(2R,3R,4R,5R,6S)-4,5-diacetoxy-3-azido-6-(azidomethyl)tetrahydropyran-2-yl]oxy-tetrahydrofuran-2-yl]methyl acetate (82 mg, 62 μmol) afforded the title compound (55 mg) with 78% yield.

Step 4

Benzyl N-[[(2S,5R,6R)-6-[(1R,2R,3S,4R,6S)-2-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl)tetrahydrofuran-2-yl]oxy-4-[[(2R,3R)-4-azido-2-benzyloxy-3-fluoro-butanoyl]amino]-6-(benzyloxycarbonylamino)-3-hydroxy-cyclohexoxy]-5-(benzyloxycarbonylamino)tetrahydropyran-2-yl]methyl]-N-benzyl-carbamate

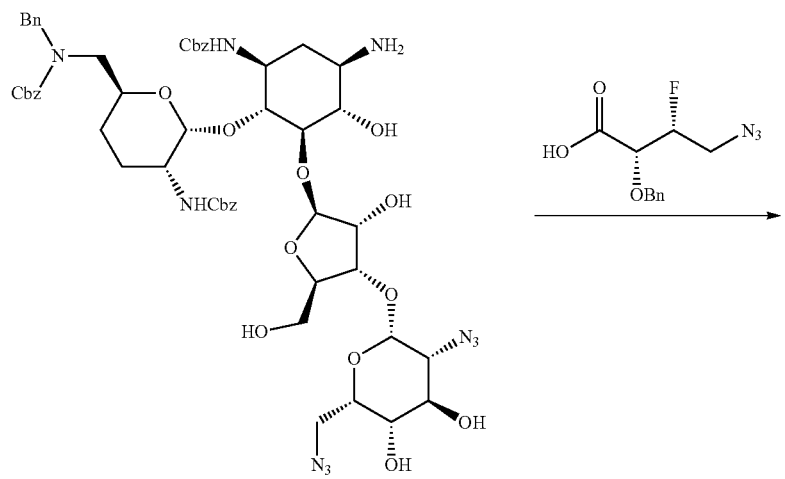

PyBOP (30 mg, 59 μmol) was added to a solution of benzyl N-[[(2S,5R,6R)-6-[(1R,2R,3S,4R,6S)-4-amino-2-[(2S,3R,4S,5R)-4-[(2R,3R,4R,5S,6S)-3-azido-6-(azidom- ethyl)-4,5-dihydroxy-tetrahydropyran-2-yl]oxy-3-hydroxy-5-(hydroxymethyl)tetrahydrofuran-2-yl]oxy-6-(benzyloxycarbonylamino)-3-hydroxy-cyclohexoxy]-5-(benzyloxycarbonylamino)tetrahydropyran-2-yl]methyl]-N-benzyl-carbamate (55 mg, 49 μmol), (2R,3R)-4-azido-2-benzyloxy-3-fluoro-butanoic acid (14 mg, 56 μmol) and DIPEA (20 μL, 146 μmol) in dry DMF (0.40 mL) under $N_2$ and the reaction mixture was stirred for 60 min. The mixture was directly purified by C18 reverse phase chromatography (12 g cartridge) using ACN and 0.1% aq formic acid (30-100%) as eluent to provide the title compound (40 mg, 60%) as a solid. MS (ESI) [M+H]$^+$ 1363.9.

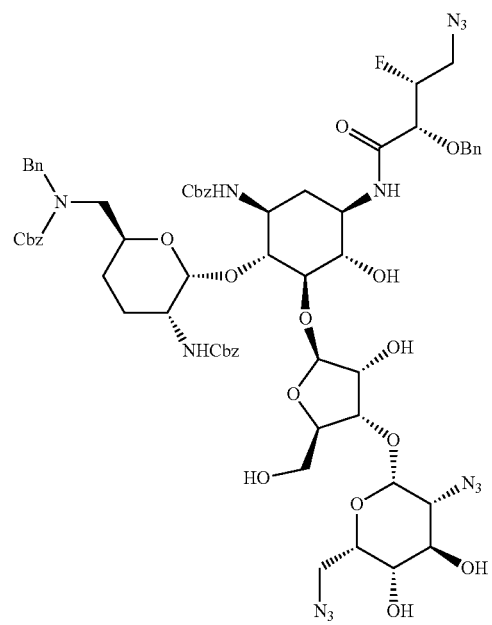

Step 5

(2R,3R)-4-amino-N-[(1R,2S,3R,4R,5S)-5-amino-3-[(2S,3R,4S,5R)-4-[(2R,3R,4R,5S,6S)-3-amino-6-(aminomethyl)-4,5-dihydroxy-tetrahydropyran-2-yl]oxy-3-hydroxy-5-(hydroxymethyl)tetrahydrofuran-2-yl]oxy-4-[(2R,3R,6S)-3-amino-6-(aminomethyl)tetrahydropyran-2-yl]oxy-2-hydroxy-cyclohexyl]-3-fluoro-2-hydroxy-butanamide;2,2,3,3,4,4,4-heptafluorobutanoic acid

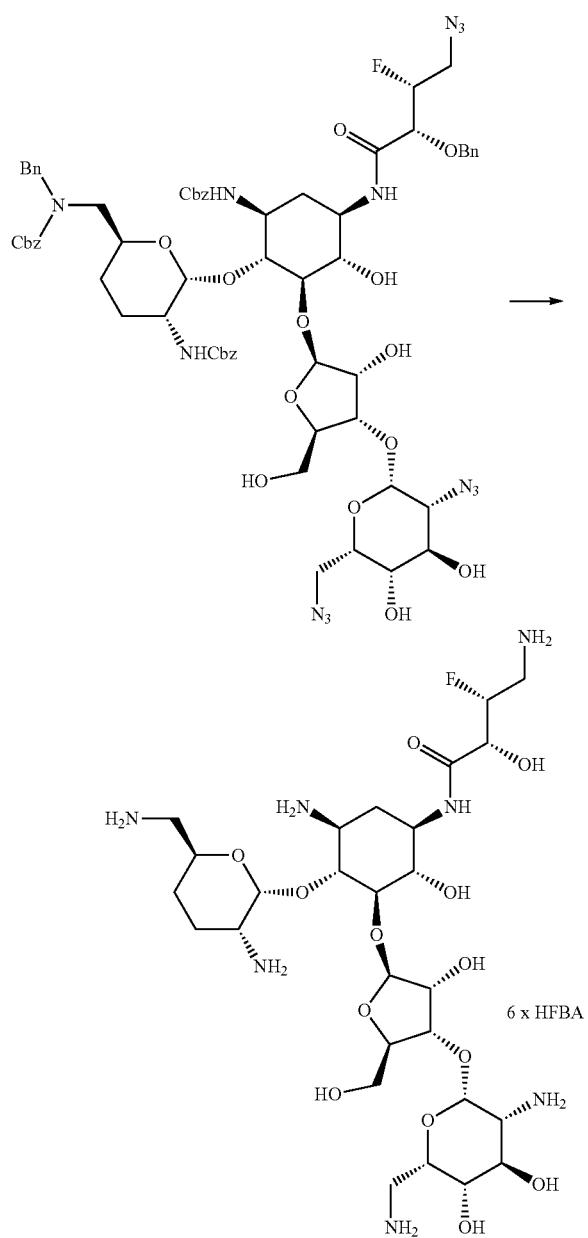

6 x HFBA

Pd(OH)$_2$/C (10 wt %, 82 mg, 59 µmol) was added to a solution of benzyl N-[[(2S,5R,6R)-6-[(1R,2R,3S,4R,6S)-2-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl)tetrahydrofuran-2-yl]oxy-4-[[(2R,3R)-4-azido-2-benzyloxy-3-fluoro-butanoyl]amino]-6-(benzyloxycarbonylamino)-3-hydroxy-cyclohexoxy]-5-(benzyloxycarbonylamino)tetrahydropyran-2-yl]methyl]-N-benzyl-carbamate (21 mg, 27 µmol) in a mixture 4:1 AcOH/H$_2$O (2.0 mL) under N$_2$ at ambient temperature. H$_2$ was bubbled into the solution for 15 min and the suspension was hydrogenated under hydrogen atmosphere for 18 h. The material was filtered through a frit (0.45 m diameter) and concentrated under reduced pressure. The material was purified by preparative HPLC (BEH 30×100 mm ACN/AmForm 10-15%) and was further purified by HFBA-coupled preparative HPLC (HFBA 25-40%) to provide the title compound (hexa-HFBA salt, 17.5 mg, 30%) as a solid. $^1$H NMR (500 MHz, D$_2$O) δ 5.91 (d, J=3.3 Hz, 1H), 5.42 (d, J=1.8 Hz, 1H), 5.37-5.21 (m, 2H), 4.52-4.41 (m, 2H), 4.38 (dd, J=4.5, 2.1 Hz, 1H), 4.33 (t, J=4.4 Hz, 1H), 4.27-4.21 (m, 2H), 4.17-4.10 (m, 1H), 4.08-3.97 (m, 2H), 3.95 (dd, J=12.3, 2.5 Hz, 1H), 3.90 (t, J=9.1 Hz, 1H), 3.86 (s, 1H), 3.76 (dd, J=12.2, 5.4 Hz, 1H), 3.67 (t, J=9.8 Hz, 1H), 3.61 (s, 1H), 3.59-3.53 (m, 2H), 3.53-3.37 (m, 4H), 3.27 (dd, J=13.5, 3.1 Hz, 1H), 3.12 (dd, J=13.5, 7.0 Hz, 1H), 2.34-2.26 (m, 1H), 2.11-2.01 (m, 2H), 1.99-1.91 (m, 1H), 1.89-1.78 (m, 1H), 1.68-1.56 (m, 1H). MS (ESI) [M+H]$^+$ 702.4.

Example 25

(1S,2R,3R,4S,6R)-4,6-diamino-3-(((2R,3R,6S)-3-amino-6-((S)-1-aminoethyl)tetrahydro-2H-pyran-2-yl)oxy)cyclohexane-1,2-diol

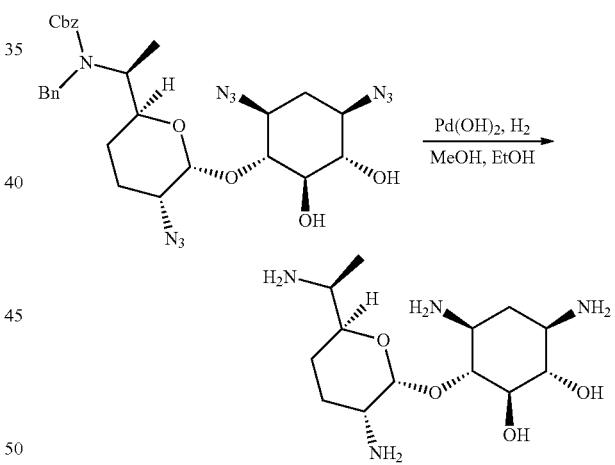

Pd(OH)$_2$/C (20 wt %, 145 mg, 206 µmol) was added to a solution of benzyl N-[(1S)-1-[(2S,5R,6R)-5-azido-6-[(1R,2R,3S,4R,6S)-4,6-diazido-2,3-dihydroxycyclohexoxy]tetrahydropyran-2-yl]ethyl]-N-benzyl-carbamate (see Example 2 for synthesis, 25.0 mg, 41.2 µmol) in MeOH (2.50 mL) and EtOH (2.50 mL). H$_2$ was bubbled and the suspension was hydrogenated under hydrogen atmosphere for 16 h. The mixture was filtered through a frit (0.22 m diameter) and the filtrate was concentrated under reduced pressure to afford the title compound (11.0 mg, 88%) as a solid. $^1$H NMR (500 MHz, MeOD) δ 5.47 (d, J=3.5 Hz, 1H), 3.75-3.68 (m, 1H), 3.43 (t, J=9.1 Hz, 1H), 3.37-3.31 (m, 1H), 3.12 (t, J=9.5 Hz, 1H), 3.07-3.00 (m, 1H), 2.95-2.86 (m, 2H), 2.79-2.72 (m, 1H), 2.06-2.00 (m, 1H), 1.87-1.73 (m, 3H), 1.46-1.36 (m, 1H), 1.28-1.14 (m, 4H). MS (ESI) [M+H]$^+$ 305.0.

Example 26

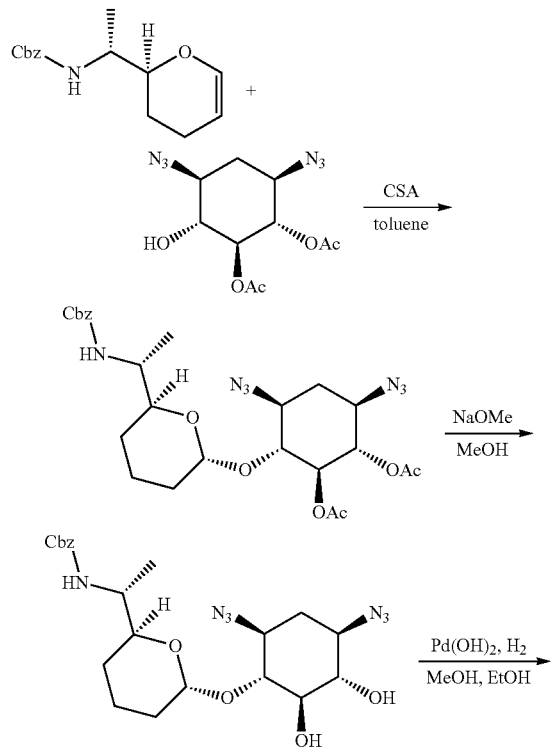

Step 1

[(1S,2S,3R,4S,6R)-2-acetoxy-4,6-diazido-3-[(6S)-6-[(1R)-1-(benzyloxycarbonylamino)ethyl]tetrahydro-pyran-2-yl]oxy-cyclohexyl] acetate

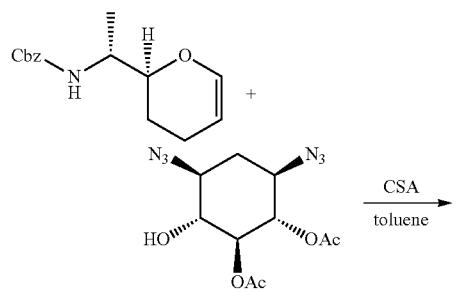

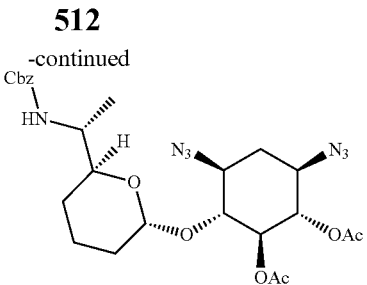

CSA (97.8 mg, 0.42 mmol) was added to a solution of benzyl N-[(1R)-1-[(2S)-3,4-dihydro-2H-pyran-2-yl]ethyl]carbamate (see Example 27, 100 mg, 0.38 mmol) and DL-[(1S,2S,3R,4S,6R)-2-acetoxy-4,6-diazido-3-hydroxy-cyclohexyl] acetate (126 mg, 0.42 mmol) in toluene (5 mL) at room temperature. The mixture was stirred at room temperature for 5 h, then a saturated aqueous solution of NaHCO₃ (5 mL) was added. The aqueous layer was extracted with DCM. The combined organic layer was driven over MgSO₄ and concentrated under reduced pressure. The material was purified by prep HPLC (ACN, AmFor, BEH column) to provide the title compound (103 mg) with 48% as a solid. 1H NMR (500 MHz, CDCl₃) δ 7.33-7.23 (m, 5H), 5.08-5.02 (m, 2H), 4.96-4.88 (m, 3H), 4.53 (dd, J=9.5, 1.8 Hz, 1H), 3.74-3.63 (m, 1H), 3.58-3.50 (m, 1H), 3.50-3.42 (m, 2H), 3.26 (dd, J=11.0, 4.5 Hz, 1H), 2.20 (dt, J=13.4, 4.5 Hz, 1H), 2.01 (s, 3H), 1.95 (s, 3H), 1.84-1.74 (m, 2H), 1.45-1.34 (m, 3H), 1.27-1.17 (m, 2H), 1.13 (d, J=6.7 Hz, 3H).

Step 2

Benzyl N-[(1R)-1-[(2S,6R)-6-[(1R,2R,3S,4R,6S)-4,6-diazido-2,3-dihydroxy-cyclohexoxy]tetrahydropyran-2-yl]ethyl]carbamate

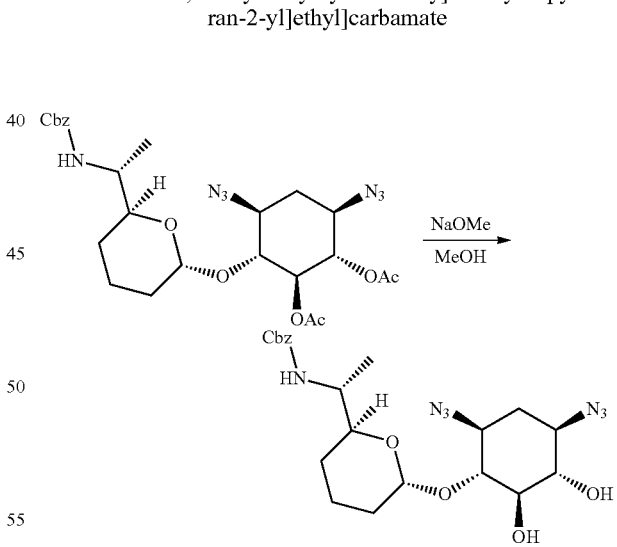

A MeONa solution (0.50 M, 1.47 mL, 736 μmol) in MeOH was added dropwise to a solution of [(1S,2S,3R,4S,6R)-2-acetoxy-4,6-diazido-3-[(2R,6S)-6-[(1R)-1-(benzyloxycarbonylamino)ethyl]tetrahydropyran-2-yl]oxy-cyclohexyl] acetate (103 mg, 184 μmol) in methanol (4.6 mL). After 1 h, AcOH (63 μL, 1.10 mmol) was added to the solution. All volatiles were evaporated, and the crude was purified by silica gel chromatography (4 g cartridge) with EtOAc and hexanes (10-50%) to provide the title compound, which was further purified by prep-HPLC to produce the title compound as a solid (29 mg, 32%). ¹H NMR (500 MHz, DMSO) δ 7.40-7.26 (m, 5H), 7.11 (d, J=8.9 Hz, 1H), 5.51 (t, J=4.4 Hz, 2H), 5.29 (d, J=5.6 Hz, 1H), 5.01 (d, J=12.5 Hz, 1H), 4.97 (d, J=12.5 Hz, 1H), 3.81-3.73 (m, 1H), 3.56-3.44 (m, 2H), 3.44-3.34 (m, 2H), 3.27-3.20 (m, 1H), 3.14 (td, J=9.4, 5.5 Hz, 1H), 2.03 (dt, J=12.5, 4.4 Hz, 1H), 1.76-1.61 (m, 2H), 1.52 (ddd, J=18.9, 16.5, 8.5 Hz, 3H), 1.18 (dd, J=24.8, 12.4 Hz, 2H), 1.06 (d, J=6.8 Hz, 3H). LCMS m/z: ES⁺ [M+H]⁺: 476.24; (A05) retention time=2.35 in.

Step 3

(1S,2R,3R,4S,6R)-4,6-diamino-3-[(2R,6S)-6-[(1R)-1-aminoethyl]tetrahydropyran-2-yl]oxy-cyclohexane-1,2-diol

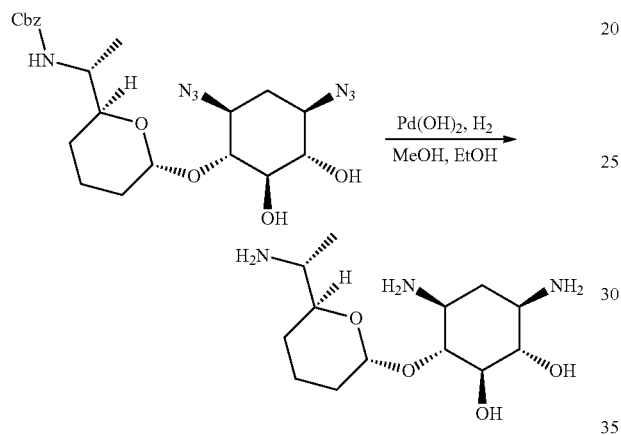

A solution of benzyl N-[(1R)-1-[(2S,6R)-6-[(1R,2R,3S,4R,6S)-4,6-diazido-2,3-dihydroxy-cyclohexoxy] tetrahydropyran-2-yl]ethyl]carbamate (8.5 mg, 0.02 mmol) and 20% wt Pd(OH)₂ (2.5 mg, 0.004 mmol) in MeOH/EtOH (5 mL, 1:1) was hydrogenated at room temperature for 18 hours. The mixture was degassed with N₂ and filtered on celite. The mixture was concentrated under reduced pressure to provide the title compound (4.66 mg, 90%) as a solid. M+Na+: 312.1. ¹H NMR (500 MHz, MeOD) δ 5.50 (d, J=3.0 Hz, 1H), 3.94-3.89 (m, 1H), 3.26-3.19 (m, 2H), 3.12-3.06 (m, 1H), 3.02-2.97 (m, 1H), 2.80-2.73 (m, 1H), 2.62 (ddd, J=12.0, 9.7, 4.2 Hz, 1H), 1.94 (dt, J=12.8, 4.2 Hz, 1H), 1.85-1.78 (m, 2H), 1.65-1.53 (m, 3H), 1.35 (qd, J=12.2, 3.7 Hz, 1H), 1.23-1.18 (m, 1H), 1.15 (d, J=5.2 Hz, 3H).

Example 27

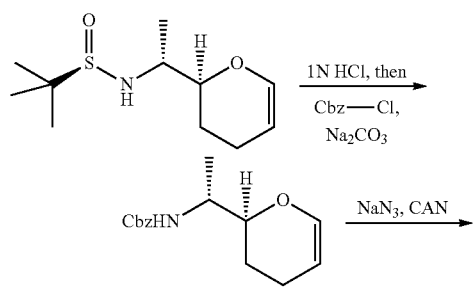

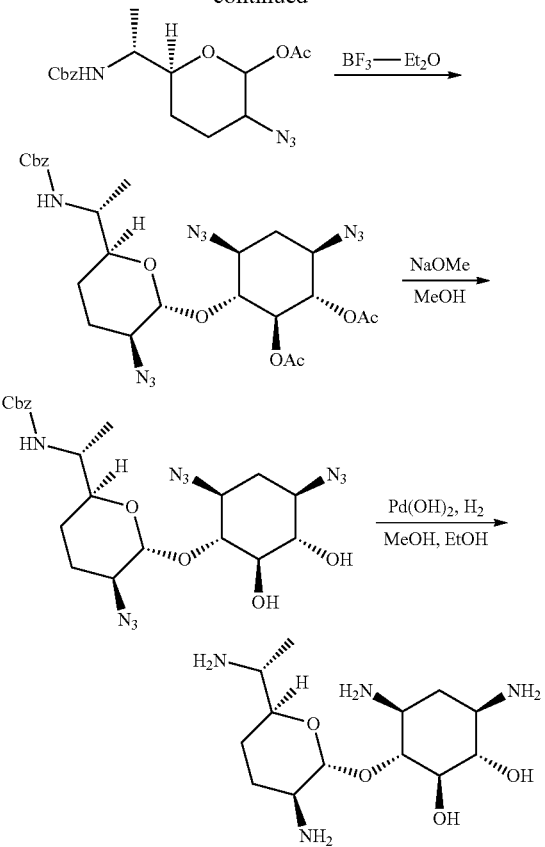

Step 1

Benzyl N-[(1R)-1-[(2S)-3,4-dihydro-2H-pyran-2-yl]ethyl]carbamate

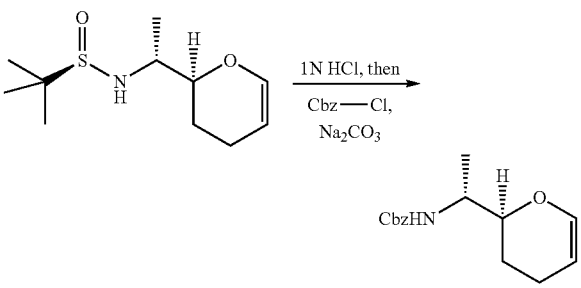

HCl (4 M, 842 μL, 3.37 mmol) was added dropwise into a solution of N-[(1R)-1-[(2S)-3,4-dihydro-2H-pyran-2-yl]ethyl]-2-methyl-propane-2-sulfinamide (780 mg, 3.37 mmol) and isopropanol (309 μL, 4.05 mmol) in EtOAc (7.0 mL) at ambient temperature. After 90 min, triethylamine (600 μL, 4.30 mmol) was added and all volatiles were removed under reduced pressure. The crude was dissolved in THF (12.0 mL) and water (3.0 mL) followed by the addition of K₂CO₃ (932 mg, 6.74 mmol). After 15 min, CbzCl (575 μL, 4.05 mmol) was dropwise added to the solution. After another 2 h, THF was evaporated and the remainder was partitioned in between EtOAc (20.0 mL) and water (20.0 mL). The organic layer was washed with brine (10.0 mL), dried (Na$_2$SO$_4$), filtered and concentrated under reduced pressure. The crude was purified by silica gel chromatography (25 g cartridge) with EtOAc and hexanes (5%-20%) to provide the title compound as a solid (125 mg, 13%). LCMS m/z: ES$^+$ [M+H]$^+$: 262.16; (A05) retention time=2.44 m.

Step 2

[(6S)-3-azido-6-[(1R)-1-(benzyloxycarbonylamino)ethyl]tetrahydropyran-2-yl] acetate

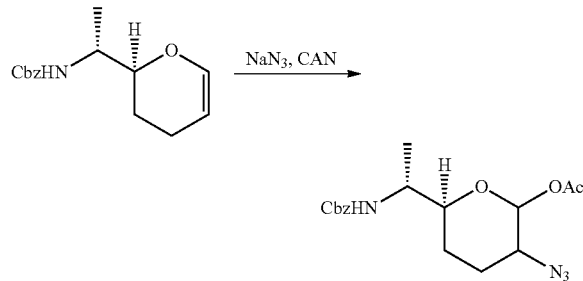

A solution of benzyl N-[(1R)-1-[(2S)-3,4-dihydro-2H-pyran-2-yl]ethyl]carbamate (112 mg, 429 μmol) in dry MeCN (1.0 mL) was added to solid CAN (0.705 g, 1.29 mmol) and NaN$_3$ (56 mg, 857 μmol) at −20° C. dropwise under N$_2$. After the addition, dry MeCN (0.50+0.50 mL) was used to transfer all material. The solution was kept within ~25~−15° C. for 7 h. The solution was diluted with water (20.0 mL) and Et$_2$O (20.0 mL) and the organic layer was successively washed with water (10.0 mL) and brine (5.0 mL), dried (Na$_2$SO$_4$), filtered and concentrated under reduced pressure. The crude was dissolved in HOAc (2.0 mL) and was added NaOAc (11 mg, 129 μmol). After 20 h, all solvents were removed under reduced pressure and the crude was purified by silica gel chromatography (4 g cartridge) with EtOAc and hexanes (10-40%) to produce the title compound (mixture of diastereomers) as an oil (79 mg, 48%). LCMS m/z: ES$^+$ [M+H]$^+$: 363.04, [M−OAc]$^+$: 303.27; (A05) retention time=2.40 and 2.44 m.

Step 3

[(1S,2S,3R,4S,6R)-2-acetoxy-4,6-diazido-3-[(2R,3S,6S)-3-azido-6-[(1R)-1-(benzyloxycarbonylamino)ethyl]tetrahydropyran-2-yl]oxy-cyclohexyl] acetate

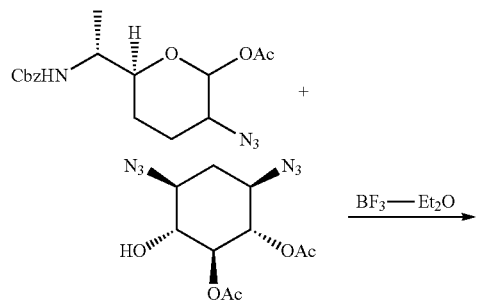

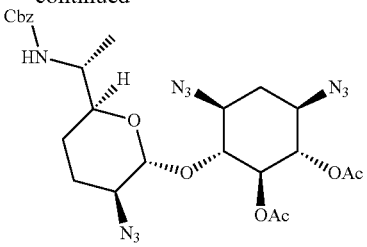

Dry DCM (2.0 mL) was added into a solid mixture of [(6S)-3-azido-6-[(1R)-1-(benzyloxycarbonylamino)ethyl]tetrahydropyran-2-yl] acetate (75 mg, 207 μmol), [(1S,2S,3R,4S,6R)-2-acetoxy-4,6-diazido-3-hydroxy-cyclohexyl] acetate (80 mg, 268 μmol) and pulverized 4 Å molecular sieves (600 mg) under N$_2$. After 1 h, the solution was cooled to 0° C. and BF$_3$·OEt$_2$ (89 μL, 717 μmol) was added dropwise with rapid stirring. After 1 h, the solution was warmed to room temperature. After another 22 h, another portion of BF$_3$·OEt$_2$ (89 μL, 717 μmol) was added dropwise with rapid stirring. After another 6 h, sat. NaHCO$_3$ (5.0 mL) was added to the reaction mixture. The mixture was extracted by EtOAc (10.0 mL) and the organic layer was successively washed with water (5.0 mL) and brine (5.0 mL). The crude was purified by silica gel chromatography (12 g cartridge) with EtOAc and hexanes (5-30%) to provide the title compound as a solid (12 mg, 10%). LCMS m/z: ES$^+$ [M+H]$^+$: 601.28, [M-DOS]$^+$: 303.24; (A05) retention time=2.69 m.

Step 4

Benzyl N-[(1R)-1-[(2S,5S,6R)-5-azido-6-[(1R,2R,3S,4R,6S)-4,6-diazido-2,3-dihydroxy-cyclohexoxy]tetrahydropyran-2-yl]ethyl]carbamate

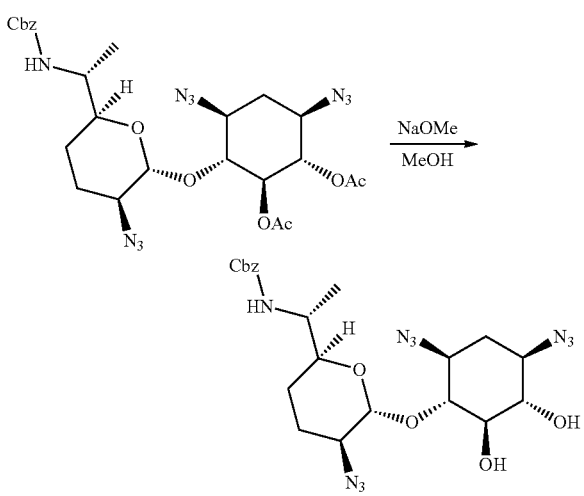

A MeONa solution (25 wt %, 23 μL, 100 μmol) in MeOH was added dropwise to a solution of [(1S,2S,3R,4S,6R)-2-acetoxy-4,6-diazido-3-[(2R,6S)-6-[(1R)-1-(benzyloxycarbonylamino)ethyl]tetrahydropyran-2-yl]oxy-cyclohexyl] acetate (12 mg) in methanol (1.0 mL). After 1 h, HOAc (30 μL, 525 mmol) was added to the solution. All volatiles were evaporated and the crude was purified by silica gel chromatography (4 g cartridge) with EtOAc and hexanes (20-50%) to provide the title compound as a film (7 mg, 66%). ¹H NMR (500 MHz, MeOD) δ 7.45-7.22 (m, 5H), 5.50 (s, 1H), 5.16-5.04 (m, 2H), 4.16-4.03 (m, 1H), 3.75-3.66 (m, 1H), 3.64 (s, 1H), 3.55-3.45 (m, 2H), 3.43-3.35 (m, 2H), 3.23 (t, J=9.5 Hz, 1H), 2.22-2.08 (m, 2H), 1.85 (dd, J=14.0, 2.6 Hz, 1H), 1.66 (qd, J=13.2, 3.7 Hz, 1H), 1.46 (d, J=13.7 Hz, 1H), 1.24 (dt, J=12.8, 9.4 Hz, 1H), 1.19 (d, J=6.9 Hz, 3H). LCMS m/z: ES⁺ [M+H]⁺: 517.25; (A05) retention time=2.39

Step 5

(1S,2R,3R,4S,6R)-4,6-diamino-3-[(2R,3S,6S)-3-amino-6-[(1R)-1-aminoethyl]tetrahydropyran-2-yl]oxy-cyclohexane-1,2-diol

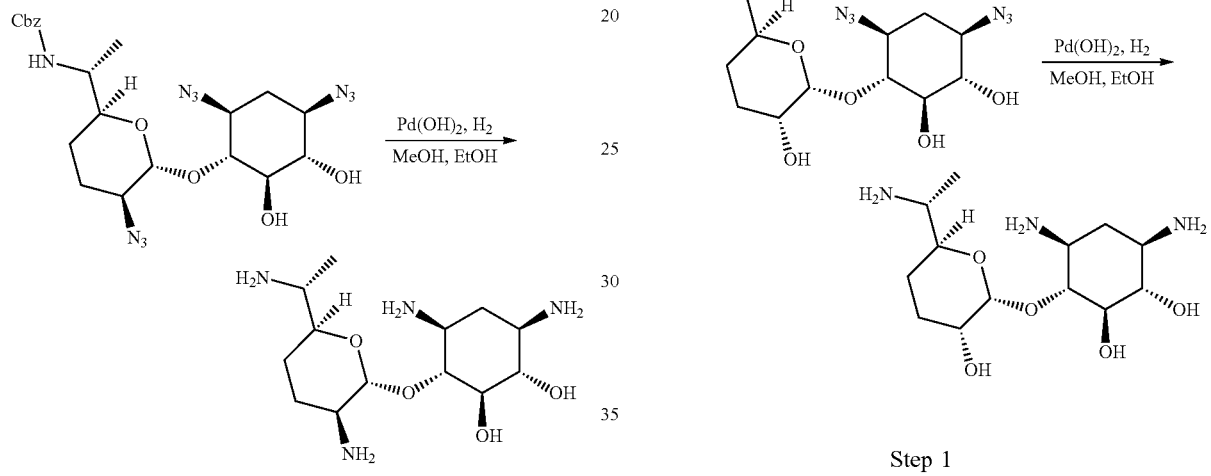

Pd(OH)₂/C (10 wt %, 4.5 mg, 3.3 µmol) was added to a solution of benzyl N-[(1R)-1-[(2S,5S,6R)-5-azido-6-[(1R,2R,3S,4R,6S)-4,6-diazido-2,3-dihydroxy-cyclohexoxy]tetrahydropyran-2-yl]ethyl]carbamate (7 mg, 13.6 µmol) in EtOH/MeOH (1:1, 3.0 mL) under N₂ at ambient temperature. H₂ was bubbled through the suspension for 10 min. After 17 h, the solution was filtered through a frit (0.22 µm diameter) and the filtrate was concentrated under reduced pressure, then lyophilized to provide the title compound as a solid (4.7 mg, 114%). ¹H NMR (500 MHz, MeOD) δ 5.06 (d, J=1.9 Hz, 1H), 3.87-3.79 (m, 1H), 3.30 (t, J=9.1 Hz, 1H), 3.23 (t, J=9.2 Hz, 1H), 3.05 (t, J=9.4 Hz, 1H), 3.02-2.98 (m, 1H), 2.96 (dd, J=6.2, 3.8 Hz, 1H), 2.76 (ddd, J=12.2, 9.4, 4.2 Hz, 1H), 2.64 (ddd, J=12.0, 9.6, 4.1 Hz, 1H), 2.12-2.04 (m, 1H), 2.01 (dt, J=12.9, 4.2 Hz, 1H), 1.75-1.62 (m, 2H), 1.51-1.44 (m, 1H), 1.28-1.22 (m, 1H), 1.15 (d, J=6.7 Hz, 3H). LCMS m/z: [M+H]⁺: 305.19; [M+Na]⁺: 327.14.

Example 28

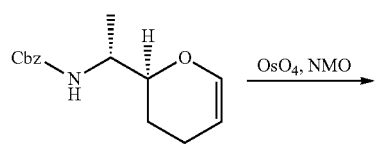

Step 1

[(6S)-2-acetoxy-6-[(1R)-1-(benzyloxycarbonylamino)ethyl]tetrahydropyran-3-yl] acetate OsO₄ (4.0 mg, 0.02 mmol) was added to a solution of benzyl N-[(1R)-1-[(2S)-3,4-dihydro-2H-pyran-2-yl]ethyl]carbamate (210 mg, 0.80 mmol) and NMO (235 mg, 2.01 mmol) in acetone (10 mL). The mixture was stirred at room temperature for 18 h, then filtered on Florisil, rinsed with EtOAc and concentrated under reduced pressure. The residue was taken in dry pyridine (10 mL) and acetic anhydride (0.30 mL, 3.21 mmol) was added. The mixture was stirred at room temperature for 18 h, then water (50 mL) was added. The separated aqueous layer was extracted with DCM. The combined organic was washed with brine, dried over MgSO₄ and concentrated under reduced pressure. The material was purified on silica gel (40 g, dry loading) by MPLC using 0% to 50% EtOAc in hexane to provide the title compound (280 mg, 92%) as a mixture of 3 diastereoisomers.

Step 2

[(6S)-6-[(1R)-1-(benzyloxycarbonylamino)ethyl]-2-[(1R,2S,3S,4R,6S)-2,3-diacetoxy-4,6-diazido-cyclohexoxy]tetrahydropyran-3-yl] acetate

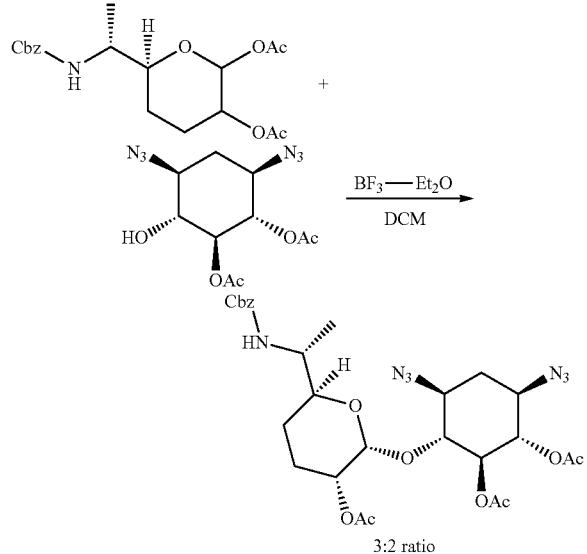

3:2 ratio

BF$_3$·OEt$_2$ (0.09 mL, 0.7 mL) was added to a mixture of [rac-(6S)-2-acetoxy-6-[rac-(1R)-1-(benzyloxycarbonylamino)ethyl]tetrahydropyran-3-yl] acetate (180 mg, 0.474 mmol) and [(1S,2S,3R,4S,6R)-2-acetoxy-4,6-diazido-3-hydroxy-cyclohexyl] acetate (283 mg, 0.95 mmol) in DCM (50 mL) at −78° C. The acetone/dry ice bath was removed, and the mixture was stirred 6 h at room temperature. A saturated aqueous solution of NaHCO$_3$ (50 mL) was added. The aqueous layer was extracted with DCM. The combined organic layers were dried over Na$_2$SO$_4$ and concentrated under reduced pressure. The product was purified by prep HPLC and provided a mixture of 3 diastereoisomers. 195 mg (2 dia)-32% yield.

Step 3

Benzyl N-[(1R)-1-[(2S,5R,6R)-6-[(1R,2R,3S,4R,6S)-4,6-diazido-2,3-dihydroxy-cyclohexoxy]-5-hydroxy-tetrahydropyran-2-yl]ethyl]carbamate

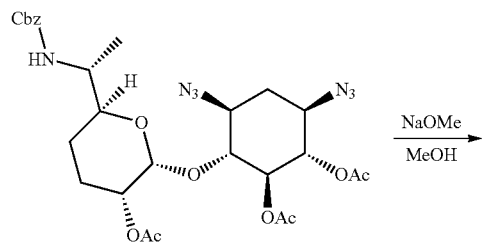

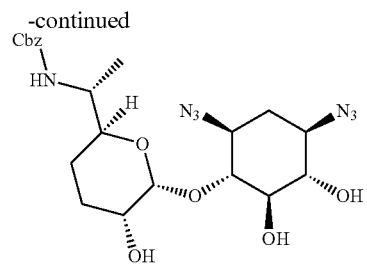

Sodium methoxide (4.62 M in methanol, 0.17 mL, 0.77 mmol) was added to a solution of [(6S)-6-[(1R)-1-(benzyloxycarbonylamino)ethyl]-2-[(1R,2S,3S,4R,6S)-2,3-diacetoxy-4,6-diazido-cyclohexoxy]tetrahydropyran-3-yl] acetate (95 mg, 0.157 mmol) in dry MeOH (6.0 mL). The mixture was stirred at room temperature for 4 h, then AcOH (0.05 mL, 0.923 mmol) was added. The mixture was concentrated under reduced pressure. The material was purified by prep-HPLC to provide the desired compound (major anomer: 37 mg, 48%) $^1$H NMR (500 MHz, MeOD) δ 7.44-7.23 (m, 5H), 5.28 (d, J=3.1 Hz, 1H), 4.01-3.87 (m, 1H), 3.70-3.56 (m, 2H), 3.52-3.43 (m, 2H), 3.43-3.34 (m, 2H), 3.30-3.24 (m, 1H), 2.24-2.13 (m, 1H), 1.89-1.80 (m, 1H), 1.80-1.72 (m, 1H), 1.69 (d, J=12.8 Hz, 1H), 1.50-1.36 (m, 1H), 1.36-1.26 (m, 1H), 1.14 (d, J=6.7 Hz, 3H).

Step 4

(1S,2R,3R,4S,6R)-4,6-diamino-3-[(2R,3R,6S)-6-[(1R)-1-aminoethyl]-3-hydroxy-tetrahydropyran-2-yl]oxy-cyclohexane-1,2-diol

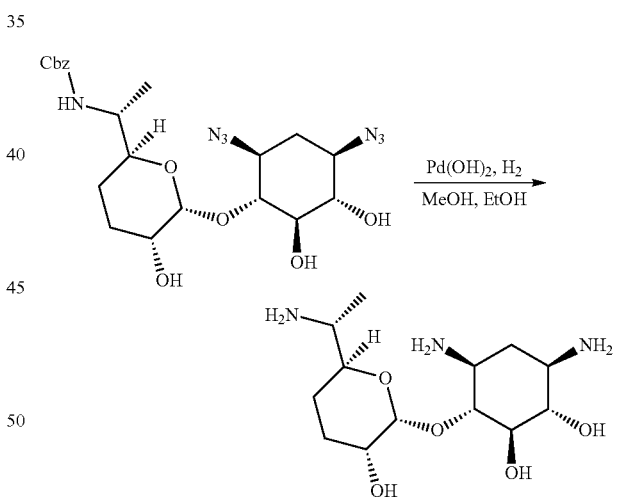

A mixture of benzyl N-[(1R)-1-[(2S,5R,6R)-6-[(1R,2R,3S,4R,6S)-4,6-diazido-2,3-dihydroxy-cyclohexoxy]-5-hydroxy-tetrahydropyran-2-yl]ethyl]carbamate (12 mg, 0.024 mmol) and Pd(OH)$_2$ (20% on dry support, 3.5 mg, 0.005 mmol) in MeOH/EtOH (5 mL, 1:1) was hydrogenated at room temperature for 18 h. The mixture was filtered with a 0.45 μM filter syringe and the solvent was removed under reduced pressure to provide the title compound (5.66 mg, 76%) as a solid. M+Na$^+$: 329.7 $^1$H NMR (500 MHz, D$_2$O) δ 5.31 (d, J=3.5 Hz, 1H), 4.03-3.97 (m, 1H), 3.85-3.77 (m, 1H), 3.55 (t, J=9.3 Hz, 1H), 3.40-3.32 (m, 2H), 3.26 (t, J=9.6 Hz, 1H), 2.96 (ddd, J=12.1, 9.7, 4.3 Hz, 1H), 2.86 (ddd, J=12.1, 9.9, 4.2 Hz, 1H), 2.07 (dt, J=12.9, 4.2 Hz, 1H), 1.92-1.88 (m, 1H), 1.87-1.78 (m, 2H), 1.58-1.47 (m, 1H), 1.35-1.27 (m, 1H), 1.23 (d, J=6.8 Hz, 3H).

Example 29

Step 1

Benzyl ((R)-1-((2S,5S,6R)-6-(((1R,2R,3S,4R,6S)-4,6-diazido-2,3-dihydroxycyclohexyl)oxy)-5-hydroxytetrahydro-2H-pyran-2-yl)ethyl)carbamate

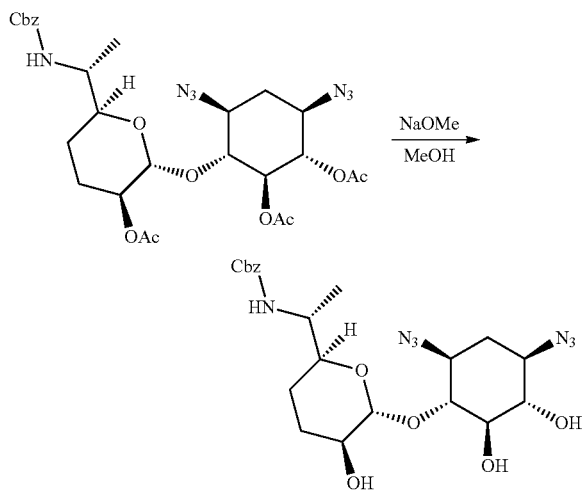

Sodium methoxide (4.62 M in methanol, 0.05 mL, 0.22 mmol) was added to a solution of [(6S)-6-[(1R)-1-(benzyloxycarbonylamino)ethyl]-2-[(1R,2S,3S,4R,6S)-2,3-diacetoxy-4,6-diazido-cyclohexoxy]tetrahydropyran-3-yl] acetate (as made in Example 28, 23 mg, 0.037 mmol) in dry MeOH (6.0 mL). The mixture was stirred at room temperature for 4 h, then AcOH (0.02 mL, 0.261 mmol) was added. The mixture was concentrated under reduced pressure. The material was purified by prep-HPLC to provide the title compound (11 mg, 59%) as a solid. M+H⁺ 492.34.

Step 2

(1S,2R,3R,4S,6R)-4,6-diamino-3-[(2R,3S,6S)-6-[(1R)-1-aminoethyl]-3-hydroxy-tetrahydropyran-2-yl]oxy-cyclohexane-1,2-diol

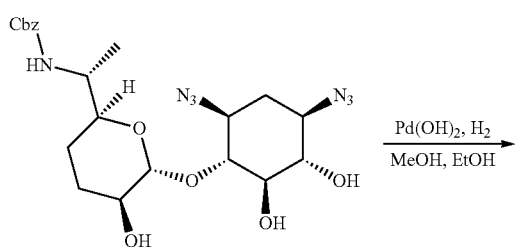

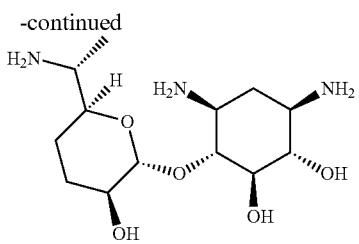

A mixture of benzyl N-[(1R)-1-[(2S,5S,6R)-6-[(1R,2R,3S,4R,6S)-4,6-diazido-2,3-dihydroxy-cyclohexoxy]-5-hydroxy-tetrahydropyran-2-yl]ethyl]carbamate (8 mg, 0.016 mmol) and Pd(OH)₂ (20% on dry support, 2.3 mg, 0.003 mmol) in MeOH/EtOH (5 mL, 1:1) was hydrogenated at room temperature for 18 h. The mixture was filtered with a 0.45 uM filter syringe and the solvent was removed under reduced pressure to provide the title compound (3.64 mg, 73%) as a solid. M+H⁺: 306.2. ¹H NMR (500 MHz, D₂O) δ 5.19 (s, 1H), 4.05 (dt, J=12.0, 2.9 Hz, 1H), 3.86-3.80 (m, 1H), 3.49-3.37 (m, 4H), 3.18-3.10 (m, 1H), 3.10-3.01 (m, 1H), 2.21 (dt, J=12.5, 4.0 Hz, 1H), 1.99-1.90 (m, 1H), 1.81-1.75 (m, 1H), 1.69-1.43 (m, 3H), 1.22 (d, J=6.9 Hz, 3H).

Example 30

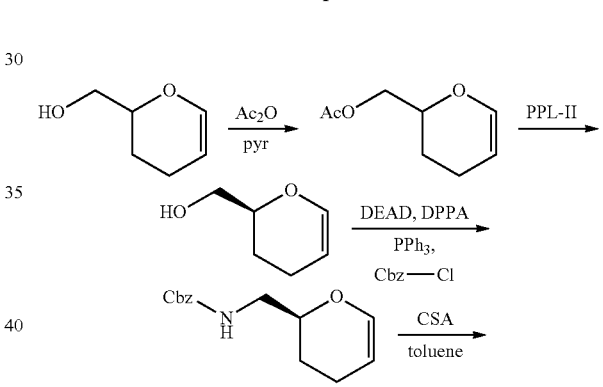

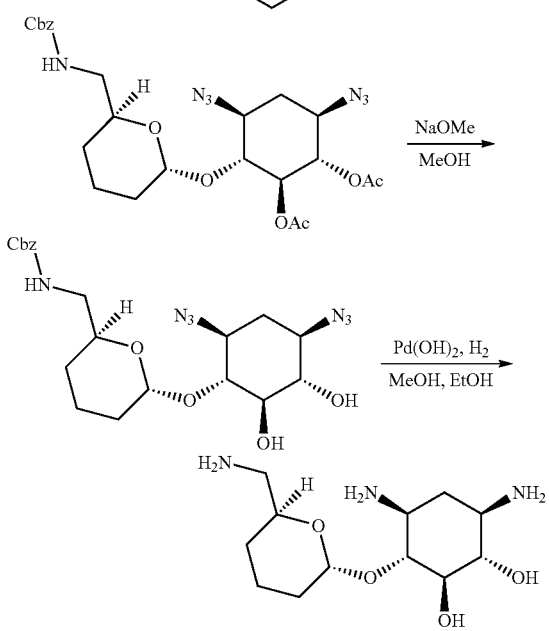

Step 1

3,4-Dihydro-2H-pyran-2-ylmethyl acetate

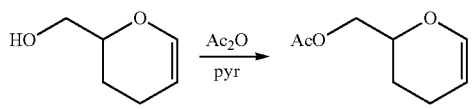

Ac$_2$O (10.0 mL, 106 mmol) was added to a solution of 3,4-dihydro-2H-pyran-2-ylmethanol (5.00 g, 43.8 mmol) in dry pyridine (20.0 mL). After 30 min, most of volatiles were removed under reduced pressure, then MeOH (10.0 mL) was added. All volatiles were removed under reduced pressure to yield the title compound as a liquid (7.80 g, 93%). This material was used in the next steps without further purification. $^1$H NMR (400 MHz, CDCl$_3$) δ 6.35 (d, J=5.9 Hz, 1H), 4.76-4.63 (m, 1H), 4.21-4.08 (m, 2H), 4.08-3.98 (m, 1H), 2.10-1.93 (m, 7H), 1.88-1.77 (m, 1H), 1.73-1.60 (m, 1H).

Step 2

[(2S)-3,4-dihydro-2H-pyran-2-yl]methanol

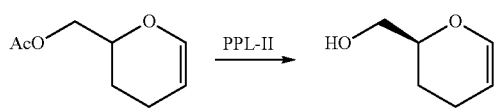 [SMILES: CC(=O)OCC1CCC=CO1 ; "PPL-II" ; OC[C@@H]1CCC=CO1]

A solution of DL-3,4-dihydro-2H-pyran-2-ylmethyl acetate (3.20 g, 19.5 mmol) in acetone (10.0 mL) was added to a pH 7.4 phosphate buffer (0.010 M, 1.10 L, containing 343 mg NaH$_2$PO$_4$·H$_2$O and 1210 mg Na$_2$HPO$_4$) with vigorous stirring in an Erlenmeyer flask. More acetone (3×9.0 mL) was used to quantitatively transfer all material. PPL-II (300 mg) was added to the reaction mixture and the solution was stirred at ambient temperature (20° C.) for 16 h. The reaction mixture was then successively extracted with EtOAc (200+100+100+100 mL). The combined organic layers were dried (Na$_2$SO$_4$), filtered and concentrated under reduced pressure. The crude was purified by silica gel chromatography (80 g cartridge) with EtOAc and hexanes (40-50%) to provide the title compound as a volatile oil (540 mg, 72%). This material was used in the next step without further purification.

Step 3

Benzyl N-[[(2S)-3,4-dihydro-2H-pyran-2-yl]methyl]carbamate

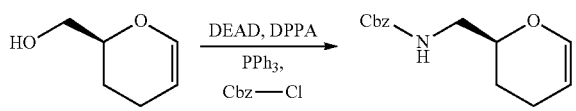

DEAD (922 μL, 5.68 mmol) was added to a solution of [(2S)-3,4-dihydro-2H-pyran-2-yl]methanol (540 mg, 4.73 mmol) and PPh$_3$ (1.49 g, 5.68 mmol) in dry THF (19.0 mL) dropwise at 0° C. under N$_2$. Then DPPA (1.22 mL, 5.68 mmol) was added to the reaction mixture dropwise. The solution was warmed to ambient temperature and stirred for 16 h. PPh$_3$ (1.49 g, 5.68 mmol) was added to the reaction mixture (CAUTION: gas evolution). After 30 min, deionized water (1.6 mL, 90.0 mmol) was added to the solution and the reaction was warmed to 50° C. under a refluxing condenser. After another 4 h, the solution was cooled to room temperature and K$_2$CO$_3$ (1.31 g, 9.46 mmol) was added. After another 30 min, CbzCl (0.81 mL, 5.68 mmol) was added dropwise. After another 60 min, THF was evaporated under reduced pressure and the residue was diluted with sat. NaHCO$_3$ (20.0 mL), successively extracted with ether (30.0+20.0+20.0 mL). The combined organic layer was dried (Na$_2$SO$_4$), filtered and concentrated under reduced pressure. The residue was purified by silica gel chromatography (25 g cartridge) with EtOAc and hexanes (5-20%) to produce the title compound as a solid (860 mg, 73%). LCMS m/z: ES$^+$ [M+H]$^+$: 248.33; (A05) retention time=2.37 m.

Step 4

(1S,2S,3R,4S,6R)-2-acetoxy-4,6-diazido-3-[(2R,6S)-6-(benzyloxycarbonylaminomethyl)tetrahydropyran-2-yl]oxy-cyclohexyl] acetate

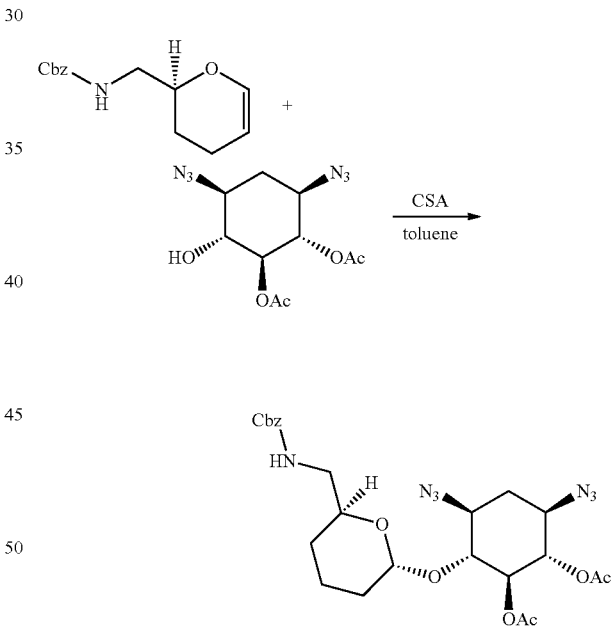

CSA (207 mg, 0.89 mmol) was added to a solution of benzyl N-[[(2S)-3,4-dihydro-2H-pyran-2-yl]methyl]carbamate (200 mg, 0.81 mmol) and DL-[(1S,2S,3R,4S,6R)-2-acetoxy-4,6-diazido-3-hydroxy-cyclohexyl] acetate (265 mg, 0.89 mmol) in toluene (15 mL) at room temperature. The mixture was stirred at room temperature for 4 h, then a saturated aqueous solution of NaHCO$_3$ (10 mL) was added. The aqueous layer was extracted with DCM. The combined organic layer was dried over MgSO$_4$ and concentrated under reduced pressure. The crude was purified was purified by prep HPLC (ACN, AmFor, BEH column) to provide the title compound (along with some water left).

Step 5

Benzyl N-[[(2S,6R)-6-[(1R,2R,3S,4R,6S)-4,6-di-azido-2,3-dihydroxy-cyclohexoxy]tetrahydropyran-2-yl]methyl]carbamate

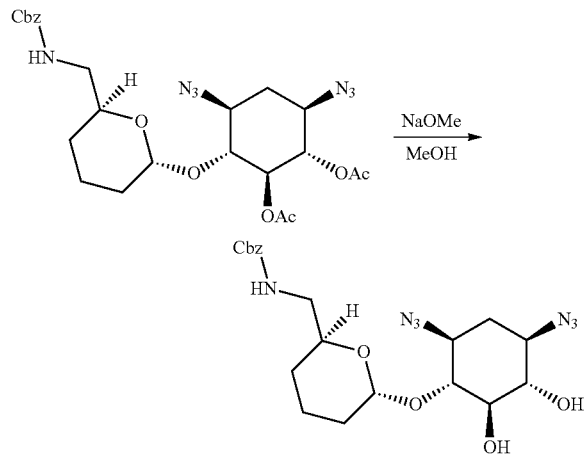

Sodium methoxide (4.62 M in methanol, 0.86 mL, 4.04 mmol) was added to a solution of [(1S,2S,3R,4S,6R)-2-acetoxy-4,6-diazido-3-[(2R,6S)-6-(benzyloxycarbonylaminomethyl)tetrahydropyran-2-yl]oxy-cyclohexyl] acetate (441 mg, 0.81 mmol) in dry methanol (10.0 mL). After 1 h, HOAc (1.21 mL, 21.2 mmol) was added to the solution. All volatiles were evaporated, and the crude was purified by quick silica gel chromatography (4 g cartridge) with EtOAc and hexanes (20-70%) to give the product with slight impurity (60 mg) followed by prep HPLC (ACN, AmFor, BEH column) to give the title product (30 mg, 8% over two steps). LCMS m/z: ES$^+$ [M+H]$^+$: 462.16; ES$^+$ [M−2DOS+H]$^+$: 248.16. (A05) retention time=2.3 min. $^1$H NMR (500 MHz, MeOD) δ 7.30-7.11 (m, 5H), 5.41 (s, 1H), 4.97 (s, 2H), 4.00 (dd, J=14.2, 7.1 Hz, 1H), 3.39-3.05 (m, 7H), 2.92 (dd, J=13.8, 7.7 Hz, 1H), 2.03 (ddd, J=8.2, 6.8, 3.6 Hz, 1H), 1.89 (s, 2H), 1.84-1.71 (m, 1H), 1.71-1.60 (m, 1H), 1.53-1.43 (m, 3H), 1.22-1.08 (m, 3H).

Step 6

(1S,2R,3R,4S,6R)-4,6-diamino-3-[(2R,6S)-6-(aminomethyl)tetrahydropyran-2-yl]oxy-cyclohexane-1,2-diol

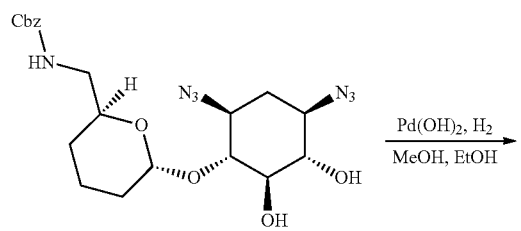

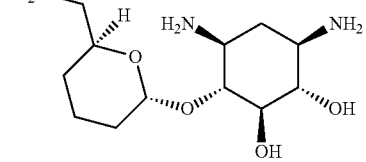

Pd(OH)$_2$/C (10 wt %, 7.6 mg, 5.4 μmol) was added to a flask containing benzyl benzyl N-[[(2S,6R)-6-[(1R,2R,3S,4R,6S)-4,6-diazido-2,3-dihydroxy-cyclohexoxy]tetrahydropyran-2-yl]methyl]carbamate (10 mg, 21.7 μmol) under N$_2$ at ambient temperature. EtOH/MeOH (1:1, 2.0 mL) was added after which H$_2$ was bubbled through the suspension for 10 min. After 17 h under hydrogen atmosphere (1 atm, balloon), the solution was filtered through a frit (0.45 μm diameter), rinsed with MeOH and the filtrate was concentrated under reduced pressure, then lyophilized to provide the title product (6.9 mg). $^1$H NMR (500 MHz, D$_2$O) δ 5.41 (s, 1H), 4.05-3.96 (m, 1H), 3.36-3.30 (m, 2H), 3.15-3.08 (m, 1H), 2.93 (dd, J=13.3, 3.6 Hz, 1H), 2.87-2.76 (m, 2H), 2.76-2.67 (m, 1H), 1.95 (dt, J=13.0, 4.2 Hz, 1H), 1.78-1.59 (m, 5H), 1.35-1.25 (m, 1H), 1.25-1.15 (m, 1H).

Example 31

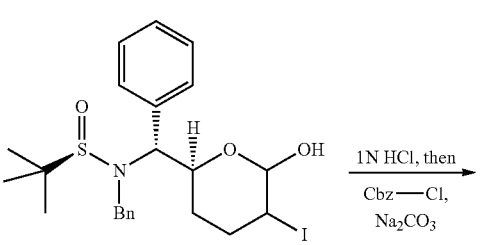

527
-continued

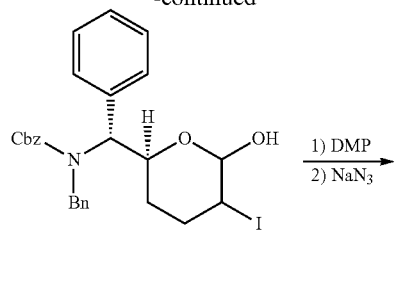

1) DMP
2) NaN₃

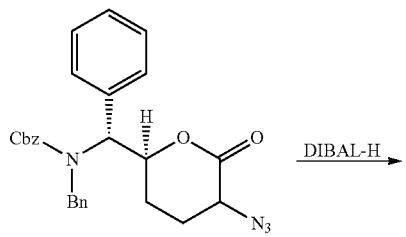

DIBAL-H

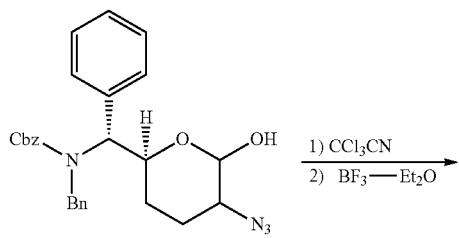

1) CCl₃CN
2) BF₃—Et₂O

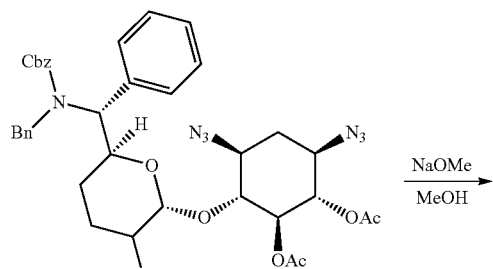

NaOMe
MeOH

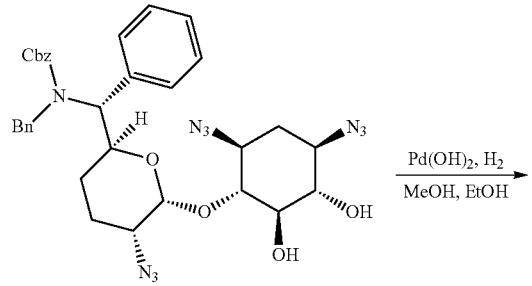

Pd(OH)₂, H₂
MeOH, EtOH

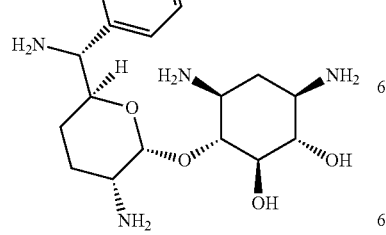

528

Step 1

(R)—N—[(R)-[(2S)-3,4-dihydro-2H-pyran-2-yl]-phenyl-methyl]-2-methyl-propane-2-sulfinamide

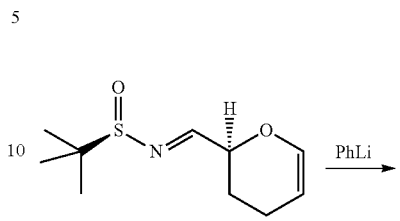

PhLi

PhLi (1.9 M in dibutyl ether, 12.2 mL, 23.22 mmol) was added to a solution of (NE,R)—N-[[(2S)-3,4-dihydro-2H-pyran-2-yl]methylene]-2-methyl-propane-2-sulfinamide (2.50 g, 11.61 mmol) in dry Toluene (100 mL) at −78° C. under N₂. After 3 h, the reaction was warmed to −30° C. The reaction was quenched with adding sat. NH₄Cl dropwise dropwise (CAUTION: gas evolution). Two phases were separated, and the aqueous phase was extracted with DCM. The combined organic layers were dried (Na₂SO₄), filtered and concentrated under reduced pressure. Purified by flash chromatography (80 g cartridge, 20-50% EtOAc in hexanes as eluent) to give the title product (3.55 g total, 87% based on both reactions). LCMS m/z: ES⁺ [M+H]⁺: 294.09 (A05) retention time=2.41 min.

¹H NMR (400 MHz, cdcl3) δ 7.41-7.24 (m, 5H), 6.35 (d, J=5.8 Hz, 1H), 4.73-4.56 (m, 2H), 4.14-3.96 (m, 3H), 2.00-1.83 (m, 2H), 1.76-1.67 (m, 1H), 1.52-1.40 (m, 1H), 1.20 (s, 9H).

Step 2

(R)—N-benzyl-N—[(R)-[(2S)-3,4-dihydro-2H-pyran-2-yl]-phenyl-methyl]-2-methyl-propane-2-sulfinamide

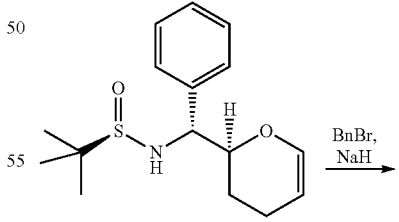

BnBr,
NaH

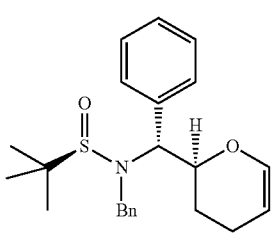

NaH (60%, 367 mg, 9.19 mmol) was added to a mixture of (R)—N—[(R)-[(2S)-3,4-dihydro-2H-pyran-2-yl]-phenyl-methyl]-2-methyl-propane-2-sulfinamide (2.45 g, 8.35 mmol) and BnBr (1.49 mL, 12.52 mmol) in DMF (100 mL) at 0° C. The mixture was stirred at room temperature for 1 h, then brine (250 mL) was added at 0° C. The aqueous layer was extracted with Et₂O (3×80 mL). The combined organic layer was dried over MgSO₄ and concentrated under reduced pressure. The material was purified on silica gel (80 g cartridge, 10-40% EtOAc in hexane) to provide the title compound (2.18 g, 68%) as a sticky foam. LCMS m/z: ES⁺ [M+H]⁺: 384.18. (A05) retention time=2.77 min. ¹H NMR (400 MHz, cdcl3) δ 7.46-7.17 (m, 9H), 6.21 (d, J=6.0 Hz, 1H), 4.63 (d, J=13.0 Hz, 1H), 4.36 (d, J=15.9 Hz, 1H), 4.25 (t, J=8.5 Hz, 1H), 4.13-3.99 (m, 1H), 3.83 (d, J=15.9 Hz, 1H), 2.16-2.04 (m, 1H), 2.04-1.92 (m, 1H), 1.85 (d, J=16.9 Hz, 1H), 1.59-1.42 (m, 1H), 1.24 (s, 9H).

Step 3

(R)—N-benzyl-N—[(R)-[(2S)-6-hydroxy-5-iodo-tetrahydropyran-2-yl]-phenyl-methyl]-2-methyl-propane-2-sulfinamide

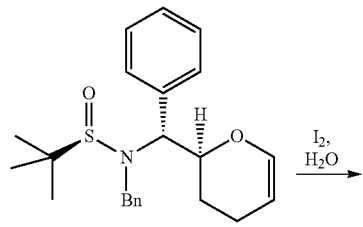

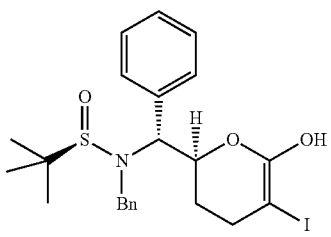

I₂ (1.59 g, 6.25 mmol) was added portionwise to a suspension of (R)—N-benzyl-N—[(R)-[(2S)-3,4-dihydro-2H-pyran-2-yl]-phenyl-methyl]-2-methyl-propane-2-sulfinamide (2.18 g, 5.68 mmol) and NaHCO₃ (1.43 g, 17.05 mmol) in ACN (25 mL) and H₂O (25 mL) at 0° C. The mixture was stirred at room temperature for 90 min, then a saturated aqueous solution of Na₂S₂O₃ (10 mL) was added. The aqueous layer was extracted with EtOAc (3×20 mL). The combined organic layer was washed with brine, dried over Na₂SO₄, filtered and concentrated under reduced pressure to provide the title compound. M+Na⁺ m/z: 550.02 (A05), retention time=2.6 min.

Step 4 benzyl N-benzyl-N—[(R)-[(2S)-6-hydroxy-5-iodo-tetrahydropyran-2-yl]-phenyl-methyl]carbamate

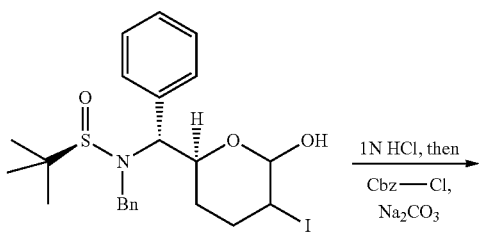

1 N HCl (11.3 mL, 11.36 mmol) was added to a mixture of (R)—N-benzyl-N—[(R)-[(2S)-6-hydroxy-5-iodo-tetra-hydropyran-2-yl]-phenyl-methyl]-2-methyl-propane-2-sulfinamide (3.0 g, 5.68 mmol) in dioxane (80 mL). The mixture was stirred at room temperature for 20 min, LCMS indicated no starting material. Na₂CO₃ (4.8 g, 45.44 mmol) and water (10 mL) was added. After 20 min, CbzCl (1.1 mL, 7.95 mmol) was added dropwise. The mixture was stirred at room temperature overnight. Water (100 mL) was added. The separated aqueous layer was extracted with EtOAc (3×50 mL). The combined organic layer was washed with brine, dried over MgSO₄ and concentrated under reduced pressure. The material was purified on silica gel (80 g, dry loading) by MPLC using hexane to 60% EtOAc to provide the title compound (1.69 g, 53%, over 3 steps) as a solid. [M+Na⁺] m/z: 580.04. (A05) retention time=~2.8 min, several diastereomers.

Step 5 benzyl N—[(R)-[(2S)-5-azido-6-oxo-tetrahydropy-ran-2-yl]-phenyl-methyl]-N-benzyl-carbamate

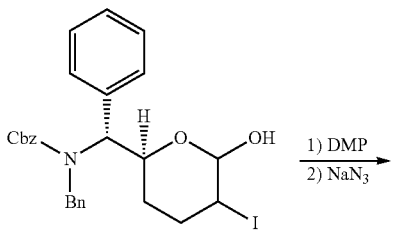

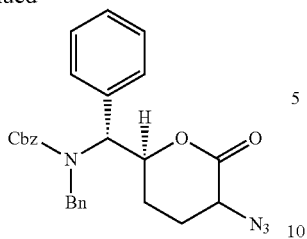

Dess-Martin Periodinane (1.93 g, 4.55 mmol) was added to a solution of benzyl N-benzyl-N—[(R)-[(2S)-6-hydroxy-5-iodo-tetrahydropyran-2-yl]-phenyl-methyl]carbamate (1.69 g, 3.03 mmol, includes impurity) in DCM (100 mL) at 0° C. The mixture was stirred at room temperature for 5 h. Water (100 mL) was added following by a saturated aqueous solution of $Na_2S_2O_3$. The separated aqueous layer was extract with DCM (2×50 mL). The combined organic layer were washed with saturated aqueous $NaHCO_3$ (2×100 mL), brine (100 mL), dried over $MgSO_4$ and concentrated under reduced pressure.

The residue was taken in anhydrous DMF (75 mL) and $NaN_3$ (296 mg, 4.55 mmol) was added. The mixture was stirred at room temperature for 15 min, then brine (300 mL) was added. The aqueous layer was extracted with EtOAc (3×100 mL). The combined organic layers was dried over $MgSO_4$ and concentrated under reduced pressure. The material was purified on silica gel (40 g, dry loading) by MPLC using hexane to EtOAc to provide the title compound (603 mg, 42%) as an yellow oil. $M+H^+$: 471 and/or M+Na 493.

Step 6

Benzyl N—[(R)-[(2S)-5-azido-6-hydroxy-tetrahydropyran-2-yl]-phenyl-methyl]-N-benzyl-carbamate

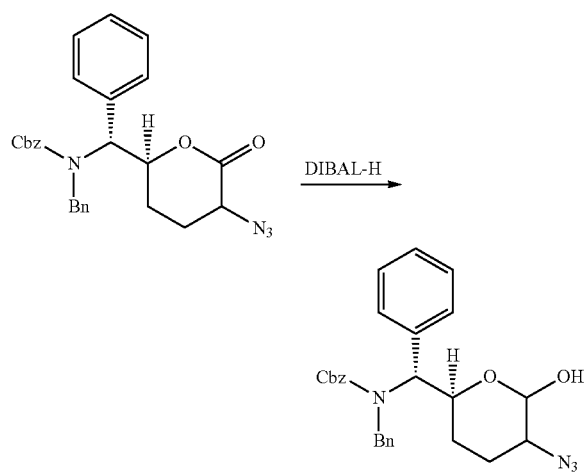

DIBAL-H (1 M in toluene, 7.65 mL, 7.65 mmol) was added dropwise to a solution of benzyl N—[(R)-[(2S)-5-azido-6-oxo-tetrahydropyran-2-yl]-phenyl-methyl]-N-benzyl-carbamate (600 mg, complex mixture) in DCM (60 mL) at −78° C. After 1 h at −78° C., EtOH (0.5 mL) was added dropwise. The mixture was poured into a saturated aqueous solution of Rochelle's salt (300 mL). The mixture was vigorously stirred for 1.5 h. The separated aqueous layer was extracted with DCM (2×75 mL). The combined organic layer was washed with brine, dried over $MgSO_4$ and concentrated under reduced pressure. The residue was purified on silica gel (24 g, dry loading) by MPLC using hexane to 60% EtOAc in hexane to provide the title compound (482 mg, 72%). $[M+H^+]$ m/z: 473.11 retention time=2.71 min.

Step 7

[(1S,2S,3R,4S,6R)-2-acetoxy-4,6-diazido-3-[(2R,6S)-3-azido-6-[(R)-[benzyl(benzyloxycarbonyl)amino]-phenyl-methyl]tetrahydropyran-2-yl]oxy-cyclohexyl] acetate

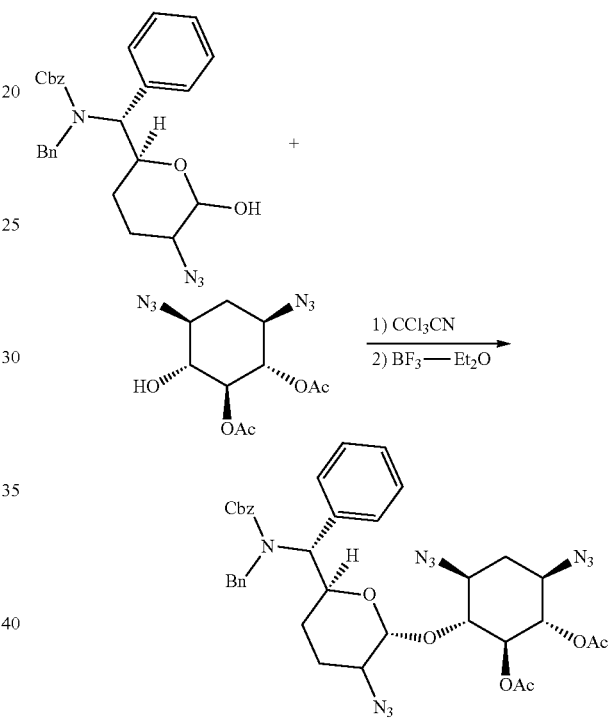

$CCl_3CN$ (0.44 mL, 4.39 mol) was added dropwise to a suspension of benzyl N—[(R)-[(2S)-5-azido-6-hydroxy-tetrahydropyran-2-yl]-phenyl-methyl]-N-benzyl-carbamate (360 mg, 0.88 mmol) and $K_2CO_3$ (364 mg, 2.63 mmol) in dry DCM (10 mL) at ambient temperature under $N_2$. The mixture was stirred at room temperature for 8 h, then filtered on celite and rinsed with DCM. The filtrate was concentrated under reduced pressure. The residue was taken in DCM (10 mL) and [(1 S,2S,3R,4S,6R)-2-acetoxy-4,6-diazido-3-hydroxy-cyclohexyl]acetate (654 mg, 2.19 mmol) was added. The mixture was cooled to −78° C., then $BF_3·OEt_2$ (0.43 mL, 3.51 mmol) was added dropwise. The mixture was stirred at room temperature for 5 h, then a saturated aqueous solution of $NaHCO_3$ (50 mL) was added. The separated aqueous layer was extracted with DCM (2×30 mL). The combined organic layer was washed with brine, dried over $Na_2SO_4$ and concentrated under reduced pressure. The residue was purified on C18 silica (120 g Biotage) using 50% B in A to 100% B (B=ACN 0.1% HCOOH, A=$H_2O$ 0.1% HCOOH); out at 90% to give the title products (19 mg, 5%). LCMS m/z: $ES^+$ $[M+H]^+$: 753.34. (A05) retention time=3.02 min.

Step 8

Benzyl N—[(R)-[(2S,5R,6R)-5-azido-6-[(1R,2R,3S,4R,6S)-4,6-diazido-2,3-dihydroxy-cyclohexoxy]tetrahydropyran-2-yl]-phenyl-methyl]-N-benzyl-carbamate

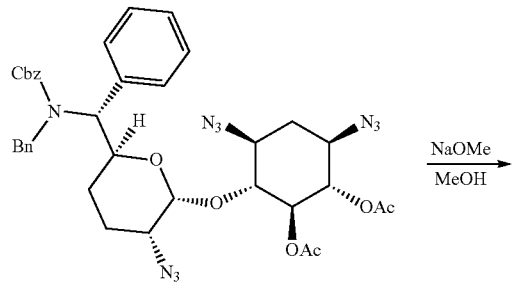

NaOMe (4.62 M, 0.033 mL, 0.15 mmol) was added dropwise to a solution of [(1S,2S,3R,4S,6R)-2-acetoxy-4,6-diazido-3-[(2R,6S)-3-azido-6-[(R)-[benzyl(benzyloxycarbonyl)amino]-phenyl-methyl]tetrahydropyran-2-yl]oxy-cyclohexyl] acetate (19 mg, 0.025 mmol) in MeOH (1 mL) at room temperature. After 60 min, AcOH (0.012 mL, 0.20 mmol) was added to the reaction and the mixture was concentrated under reduced pressure. HPLC provided the desired product (6 mg, 36%).

Step 9

(1S,2R,3R,4S,6R)-4,6-diamino-3-[(2R,3R,6S)-3-amino-6-[(R)-amino(phenyl)methyl]tetrahydropyran-2-yl]oxy-cyclohexane-1,2-diol

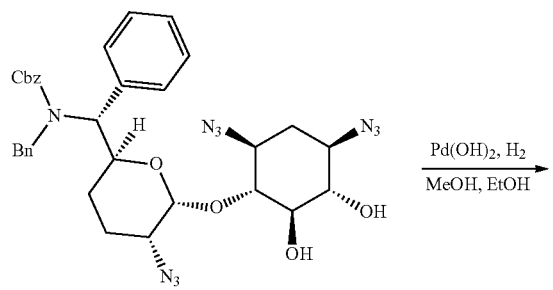

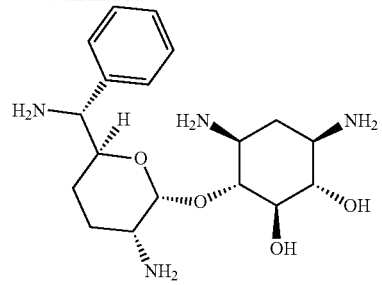

Pd(OH)$_2$/C (10 wt %, 18.6 mg, 13.3 μmol) was added to a flask containing benzyl N—[(R)-[(2S,5R,6R)-5-azido-6-[(1R,2R,3S,4R,6S)-4,6-diazido-2,3-dihydroxy-cyclohexoxy]tetrahydropyran-2-yl]-phenyl-methyl]-N-benzyl-carbamate (6.0 mg, 89.7 μmol) under N$_2$ at ambient temperature. MeOH (3.0 mL) was added after which H$_2$ was bubbled through the suspension for 10 min. After 16 h under hydrogen atmosphere (1 atm, balloon), the solution was filtered through a frit (0.45 μm), rinsed with MeOH and the filtrate was concentrated under reduced pressure to give the title product (2.7 mg, 82%). $^1$H NMR (500 MHz, D$_2$O) δ 7.55-7.42 (m, 5H), 4.91 (s, 1H), 4.25-4.16 (m, 1H), 4.10 (d, J=8.1 Hz, 1H), 3.40-3.34 (m, 1H), 3.21 (t, J=9.7 Hz, 1H), 3.12 (s, 1H), 2.95-2.88 (m, 2H), 2.68 (t, J=8.7 Hz, 1H), 2.16-2.06 (m, 1H), 2.05-1.95 (m, 1H), 1.90-1.67 (m, 3H), 1.20-1.08 (m, 1H).

Example 32

(1S,2R,3R,4S,6R)-4,6-diamino-3-(((2R,3S,6S)-3-amino-6-((R)-amino(cyclopropyl)methyl)tetrahydro-2H-pyran-2-yl)oxy)cyclohexane-1,2-diol

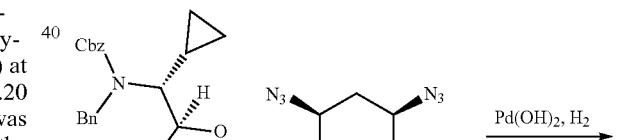

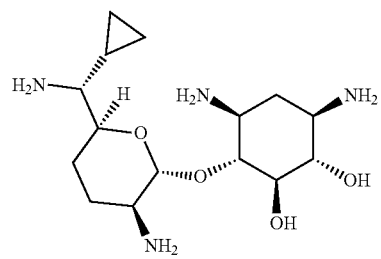

Pd(OH)$_2$ (20 wt %, 133 mg, 190 μmol) was added to a solution of benzyl N—[(R)-[(2S,5S,6R)-5-azido-6-[(1R,2R,3S,4R,6S)-4,6-diazido-2,3-dihydroxy-cyclohexoxy]tetrahydropyran-2-yl]-cyclopropyl-methyl]-N-benzyl-carbamate (prepared in Example 9, 40.0 mg, 63.2 μmol) in MeOH (2.5 mL) and EtOH (2.5 mL). H$_2$ was bubbled through the suspension. After 17 h, the solution was filtered through a frit (0.22 μm diameter) and the filtrate was concentrated under reduced pressure to give the desired product as an oil which turn into solid after lyophilization (19.0 mg, 91%). $^1$H NMR (500 MHz, MeOD) δ 5.10 (s, 1H), 4.09-4.04 (m, 1H), 3.34-3.24 (m, 2H), 3.07 (t, J=9.3 Hz, 1H), 3.01 (d, J=2.0 Hz, 1H), 2.83-2.71 (m, 1H), 2.66 (ddd, J=12.1, 9.7, 4.1 Hz, 1H), 2.17-2.09 (m, 2H), 2.03 (d, J=13.0 Hz, 1H), 1.99-1.86 (m, 2H), 1.74-1.63 (m, 1H), 1.60-1.48 (m, 1H), 1.00-0.82 (m, 1H), 0.60 (dq, J=17.9, 8.8 Hz, 2H), 0.39-0.24 (m, 2H).

Example 33

(1S,2R,3R,4S,6R)-4,6-diamino-3-(((2R,3S,6S)-3-amino-6-((R)-1-aminopropyl)tetrahydro-2H-pyran-2-yl)oxy)cyclohexane-1,2-diol

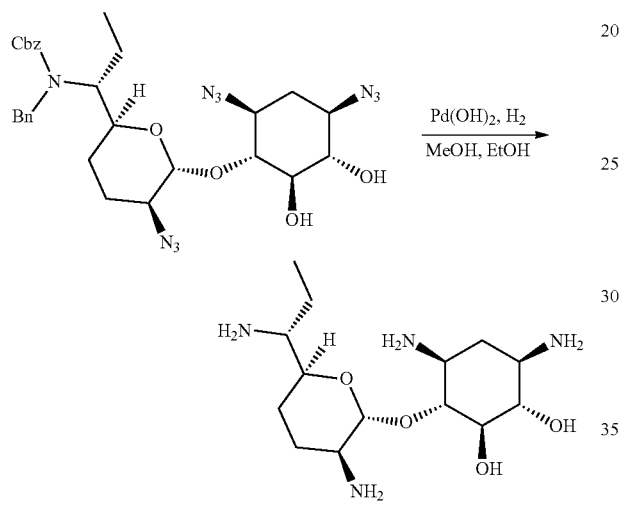

Pd(OH)$_2$/C (wet, 20 wt %, 249 mg, 354 μmol) was added to a solution of benzyl N-[(1R)-1-[(2S,5S,6R)-5-azido-6-[(1R,2R,3S,4R,6S)-4,6-diazido-2,3-dihydroxy-cyclohexoxy]tetrahydropyran-2-yl]propyl]-N-benzyl-carbamate (made in Example 5, 55.0 mg, 88.6 μmol) in MeOH (3.0 mL) and EtOH (3.0 mL). H$_2$ was bubbled through the suspension. After 24 h, the solution was filtered through a frit (0.22 μm diameter) and the filtrate was concentrated under reduced pressure to give the desired product as an oil which turned into a solid after lyophilization (26.1 mg, 93%). $^1$H NMR (500 MHz, MeOD) δ 4.97 (d, J=1.4 Hz, 1H), 3.91-3.84 (m, 1H), 3.19-3.08 (m, 2H), 2.95 (t, J=9.3 Hz, 1H), 2.89 (dd, J=5.8, 3.6 Hz, 1H), 2.83-2.74 (m, 1H), 2.66 (ddd, J=12.2, 9.4, 4.3 Hz, 1H), 2.60-2.49 (m, 1H), 1.99-1.84 (m, 2H), 1.66-1.45 (m, 3H), 1.39-1.26 (m, 3H), 0.90 (t, J=7.5 Hz, 3H).

Example 34

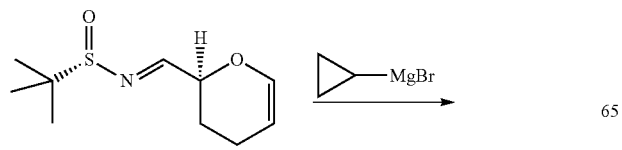

-continued

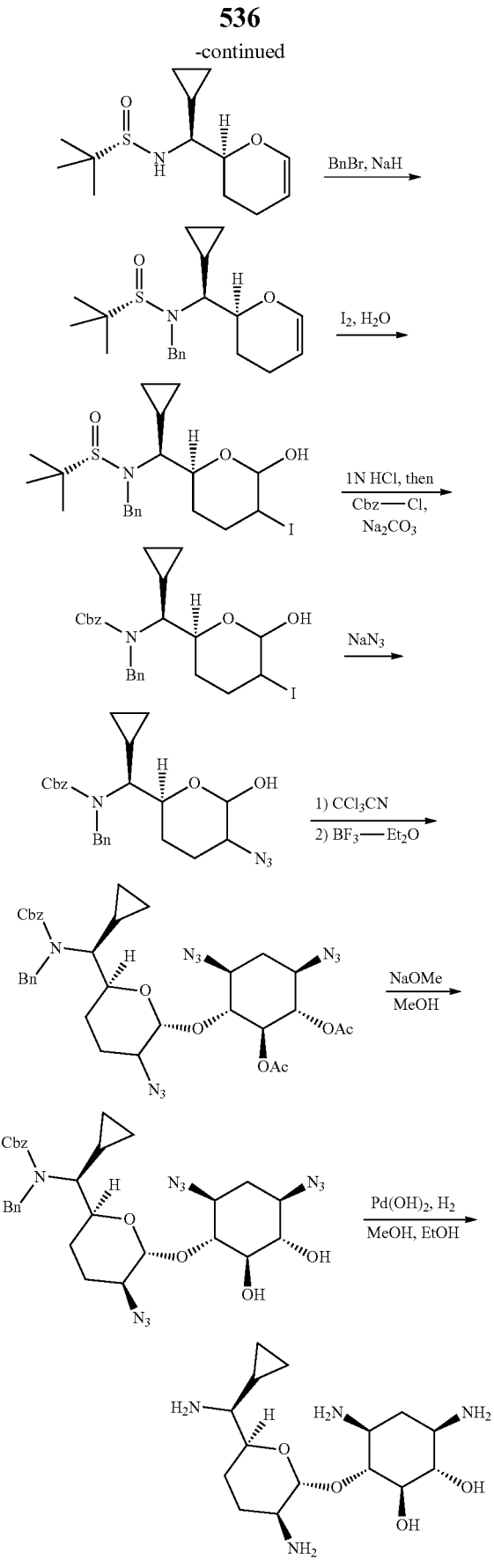

Step 1

(S)—N—[(S)-cyclopropyl-[(2S)-3,4-dihydro-2H-pyran-2-yl]methyl]-2-methyl-propane-2-sulfinamide

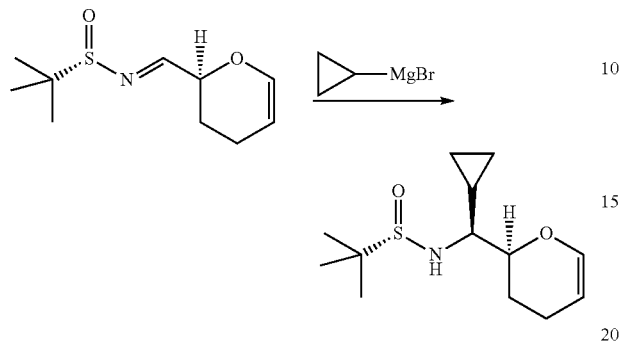

Cyclopropyl MgBr (0.5 M in THF, 55.7 mL, 27.8 mmol) was added to a solution of ((NE,S)—N-[[(2S)-3,4-dihydro-2H-pyran-2-yl]methylene]-2-methyl-propane-2-sulfinamide (3.00 g, 13.9 mmol) in dry THE (100.0 mL) at −78° C. under N₂. After 1 h, the reaction was stirred at −40° C. for 1 h and then warmed to room temperature within 1 h. After 1 h, the reaction was cooled to 0° C. and sat. NH₄Cl (100.0 mL) was added dropwise (CAUTION: gas evolution). THE was evaporated under reduced pressure and then the mixture was extracted with DCM (3×50 mL). The combined organic layers were dried (Na₂SO₄), filtered and concentrated under reduced pressure to provide the title compound as a liquid. The ¹H NMR for crude was clean and used in the next step without further purification. ¹H NMR (500 MHz, CDCl₃) δ 6.37 (d, J=6.1 Hz, 1H), 4.76-4.60 (m, 1H), 3.96-3.86 (m, 1H), 3.43 (d, J=6.1 Hz, 1H), 2.56 (ddd, J=9.6, 6.2, 3.2 Hz, 1H), 2.19-1.75 (m, 4H), 1.22 (s, 9H), 1.09-0.97 (m, 1H), 0.74-0.56 (m, 2H), 0.46-0.39 (m, 2H). LCMS m/z ES⁺ [M+H]⁺: 258.19, LCMS (B05) retention time=1.78 m.

Step 2

(S)—N-benzyl-N—[(S)-cyclopropyl(3,4-dihydro-2H-pyran-2-yl)methyl]-2-methyl-propane-2-sulfinamide

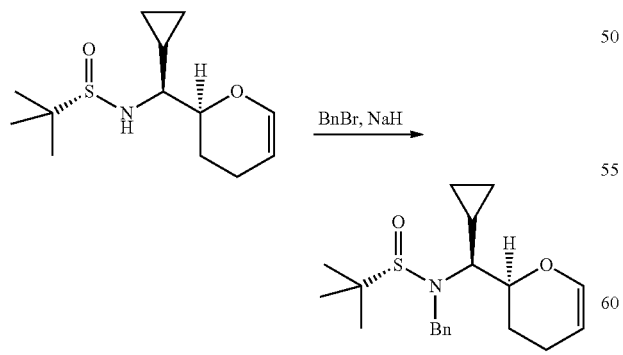

A mixture of (S)—N—[(S)-cyclopropyl(3,4-dihydro-2H-pyran-2-yl)methyl]-2-methyl-propane-2-sulfinamide (3.58 g, 13.9 mmol), bromomethylbenzene (2.97 mL, 25.0 mmol) in DMF (50.0 mL) was stirred at 0° C. NaH (0.667 g, 16.7 mmol) was then added to the reaction mixture portionwise. The mixture was stirred at room temperature for 12 h. The reaction was quenched with water (100 mL) and the mixture was extract with EtOAc (3×50 mL). The organic layers were combined, washed with water and dried over sodium sulfate and then concentrated under reduced pressure. The residue was purified on silica gel (120 g) using hexane and ethylacetate (70/30) as eluent to give the title product (2.88 g, 60%) as an oil. LCMS m/z ES⁺ [M+H]⁺: 348.16, LCMS (B05) retention time=2.10 m.

Step 3

(S)—N-benzyl-N—[(S)-cyclopropyl-[(2S)-6-hydroxy-5-iodo-tetrahydropyran-2-yl]methyl]-2-methyl-propane-2-sulfinamide

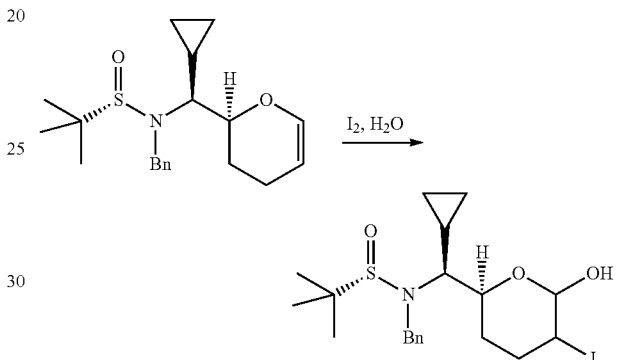

I₂ (1.59 g, 6.30 mmol) was added portionwise to a suspension of N-benzyl-N—[(S)-cyclopropyl-[(2S)-3,4-dihydro-2H-pyran-2-yl]methyl]-2-methyl-propane-2-sulfinamide (2.19 g, 6.30 mmol) and NaHCO₃ (1.58 g, 18.9 mmol) in ACN (38 mL) and H₂O (38 mL) at 0° C. The mixture was stirred at 0° C. for 15 min. Then, the mixture was stirred at room temperature for 15 min. After completion, a saturated aqueous solution of Na₂S₂O₃ (100 mL) was added. The aqueous layer was extracted with EtOAc (3×100 mL). The combined organic layer was dried over Na₂SO₄, filtered and concentrated under reduced pressure to provide the title compound (2.90 g, 94%) as an yellow solid. The crude was used in the next step without further purification. LCMS m/z ES⁺ [M+Na]⁺: 514.50, LCMS (B05) retention time=2.10 and 2.21 m.

Step 4

Benzyl N-benzyl-N—[(S)-cyclopropyl-[(2S)-6-hydroxy-5-iodo-tetrahydropyran-2-yl]methyl]carbamate

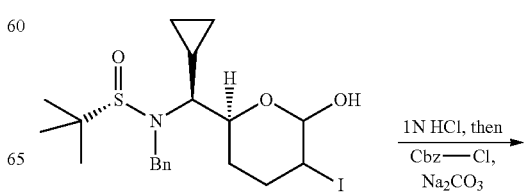

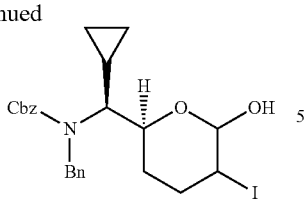

Aqueous HCl (1.0 M, 35.3 mL, 35.3 mmol) was dropwise added to a solution of N-benzyl-N—[(S)-cyclopropyl-[(2S)-6-hydroxy-5-iodo-tetrahydropyran-2-yl]methyl]-2-methyl-propane-2-sulfinamide (2.88 g, 5.86 mmol) in dioxane (82.0 mL) with vigorous stirring. After 1 h, solid $Na_2CO_3$ (4.96 g, 46.8 mmol) was added. After another 10 min, CbzCl (1.41 mL, 9.91 mmol) was added dropwise. After another 30-45 min, dioxane was evaporated and the residue was partitioned in between EtOAc (100.0 mL) and $H_2O$ (100.0 mL). The organic phase was dried over $Na_2SO_4$, filtered and concentrated under reduced pressure. The crude was purified by silica gel chromatography (120 g cartridge) using hexanes and ethyl acetate (0-30%) as eluent to give the title product (diastereomers, 1.50 g, 49%) as an oil. LCMS m/z $ES^+$ $[M+Na]^+$: 544.01, LCMS (B05) retention time=2.19 and 2.22 m.

Step 5

Benzyl N—[(S)-[(2S)-5-azido-6-hydroxy-tetrahy-dropyran-2-yl]-cyclopropyl-methyl]-N-benzyl-carbamate

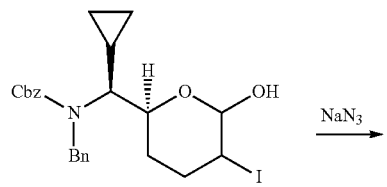

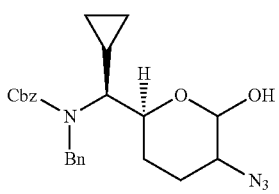

$NaN_3$ (0.561 g, 8.63 mmol) and $K_2CO_3$ (1.19 g, 8.63 mmol) was added to a solution of benzyl N-benzyl-N—[(S)-cyclopropyl-[(2S)-6-hydroxy-5-iodo-tetrahydropyran-2-yl]methyl]carbamate (1.50 g, 2.87 mmol) in dry DMF (22.0 mL) under $N_2$ at ambient temperature. After 4 h, the mixture was diluted with water (50.0 mL) and extracted with EtOAc (50.0 mL). The organic layer was dried over $Na_2SO_4$, filtered and concentrated under reduced pressure. The crude was purified by silica gel chromatography (40 g cartridge) with EtOAc and hexanes (10-30%) to produce the title compound (diastereomers) as an oil (0.80 g, 63%). LCMS m/z: $ES^+$ $[M+Na]^+$: 459.10; (B 05) retention time=2.16 m.

Step 6

(1S,2S,3R,4S,6R)-4,6-diazido-3-(((2R,6S)-3-azido-6-((S)-(benzyl((benzyloxy)carbonyl)amino)(cyclopropyl)methyl)tetrahydro-2H-pyran-2-yl)oxy)cyclohexane-1,2-diyl diacetate

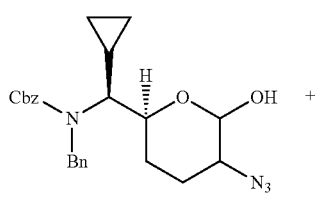

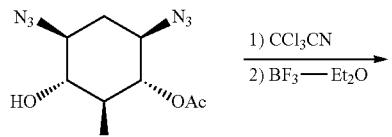

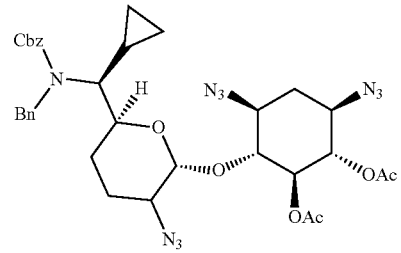

$CCl_3CN$ (0.567 mL, 5.66 mmol) was added dropwise to a suspension of benzyl N—[(S)-[(2S)-5-azido-6-hydroxy-tetrahydropyran-2-yl]-cyclopropyl-methyl]-N-benzyl-carbamate (0.494 g, 1.13 mmol) and $K_2CO_3$ (0.469 g, 3.39 mmol) in dry DCM (20.0 mL) at ambient temperature under $N_2$. After 12 h, the solution was filtered through Celite and the filtrate was concentrated by high-vacuum. To the crude was added [(1S,2S,3R,4S,6R)-2-acetoxy-4,6-diazido-3-hydroxy-cyclohexyl]acetate (270 mg, 0.905 mmol) and ground 4 Å sieves (1.0 g) and the mixture was dissolved in dry DCM (20.0 mL). The suspension was stirred at ambient temperature for 30 min. The solution was cooled to 0° C. and $BF_3·OEt_2$ (0.559 mL, 4.53 mmol) was added dropwise with vigorous stirring. The solution was warmed to ambient temperature and stirred for another 2 hours. The reaction was quenched with sat. $NaHCO_3$ (20.0 mL). The mixture was successively extracted with DCM (3×20 mL) and the combined organic layer were dried ($Na_2SO_4$), filtered and concentrated under reduced pressure. The crude was purified by silica gel chromatography (40 g cartridge) with EtOAc and hexanes (0-30%) to produce the title compound as an oil (diastereomers, 0.510 mg, 79%). LCMS m/z: $[M+H]^+$: 716.97; (B05) retention time=2.39 m.

Step 7

Benzyl N—[(S)-[(2S,5S,6R)-5-azido-6-[(1R,2R,3S,4R,6S)-4,6-diazido-2,3-dihydroxy-cyclohexoxy]tetrahydropyran-2-yl]-cyclopropyl-methyl]-N-benzyl-carbamate

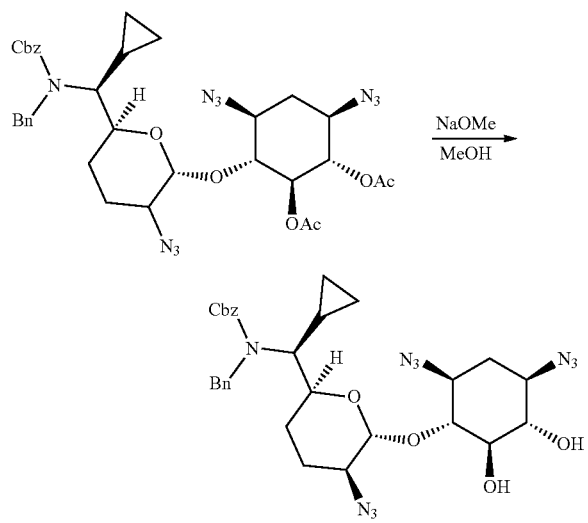

NaOMe (4.62 M, 924 μL, 4.27 mmol) was added dropwise to a solution of (1S,2S,3R,4S,6R)-4,6-diazido-3-(((2R,6S)-3-azido-6-((S)-(benzyl((benzyloxy)carbonyl)amino)(cyclopropyl)methyl)tetrahydro-2H-pyran-2-yl)oxy)cyclohexane-1,2-diyl diacetate (0.510 g, 0.712 mmol) in MeOH (30.0 mL) at room temperature. After 60 min, AcOH (326 μL, 5.69 mmol) was added to the reaction. Water (20.0 mL) was added and the mixture was extracted with DCM (3×30 mL). The organic layers were combined, dried over Na$_2$SO$_4$ and then concentrated under reduced pressure to provide a mixture of two diastereomers (0.350 g, 78%) in a 7:1 ratio in favor of the trans product (see note for more details). ES$^+$ [M+Na]$^+$: 655.06; (B05) retention time=2.23 m.

Step 8

(1S,2R,3R,4S,6R)-4,6-diamino-3-(((2R,3S,6S)-3-amino-6-((S)-amino(cyclopropyl)methyl)tetrahydro-2H-pyran-2-yl)oxy)cyclohexane-1,2-diol

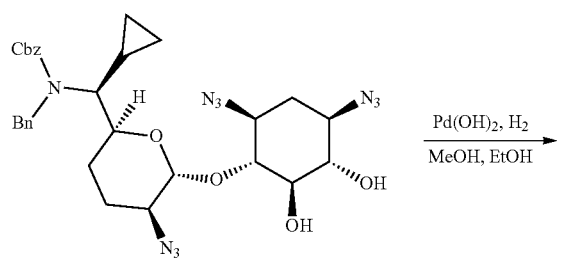

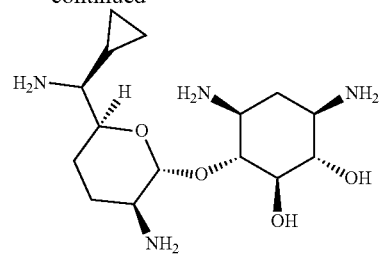

Pd(OH)$_2$/C (20 wt %, 300 mg, 427 μmol) was added to a solution of benzyl N—[(S)-[(2S,5S,6R)-5-azido-6-[(1R,2R,3S,4R,6S)-4,6-diazido-2,3-dihydroxy-cyclohexoxy]tetrahydropyran-2-yl]-cyclopropyl-methyl]-N-benzyl-carbamate (45.0 mg, 71.1 μmol) in MeOH (2.5 mL) and EtOH (2.5 mL). H$_2$ was bubbled through the suspension. After 24 h, the solution was filtered through a frit (0.22 μm diameter) and the filtrate was concentrated under reduced pressure to give the desired product as an oil which turn into solid after lyophilization (20.0 mg, 85%). $^1$H NMR (500 MHz, MeOD) δ 5.34 (s, 1H), 4.24-4.19 (m, 1H), 3.40-3.35 (m, 2H), 3.15 (t, J=9.3 Hz, 1H), 3.06 (d, J=1.6 Hz, TH), 2.92-2.84 (m, TH), 2.79 (ddd, J=12.1, 9.9, 4.2 Hz, 1H), 2.52-2.40 (m, 2H), 2.20-2.11 (m, 1H), 2.10-2.03 (m, 1H), 1.99-1.88 (m, 1H), 1.78-1.69 (m, 1H), 1.60-1.51 (m, 1H), 1.15-1.05 (m, 1H), 0.79-0.63 (m, 2H), 0.46-0.36 (m, 2H).

Example 35

(1S,2R,3R,4S,6R)-4,6-diamino-3-[(2R,3S,6S)-3-amino-6-[(1S)-1-aminopropyl]tetrahydropyran-2-yl]oxy-cyclohexane-1,2-diol

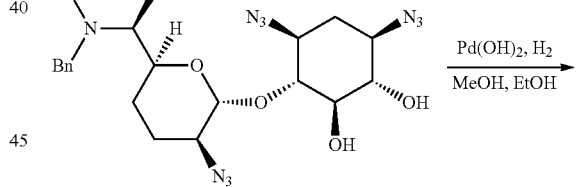

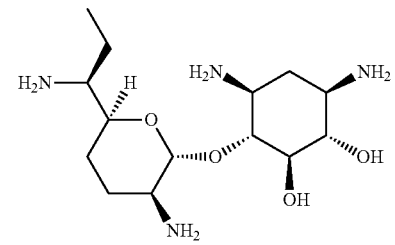

In a round bottom flask equipped with a reflux condenser were added benzyl N-[(1S)-1-[(2S,5S,6R)-5-azido-6-[(1R,2R,3S,4R,6S)-4,6-diazido-2,3-dihydroxy-cyclohexoxy]tetrahydropyran-2-yl]propyl]-N-benzyl-carbamate (made in Example 4, 38.0 mg, 0.0612 mmol) and Pd/C (10% dry on carbon, 19.5 mg, 0.0184 mmol) following by anhydrous MeOH (6.00 mL). Nitrogen was bubbled for 5 min, then ammonium format was added. The mixture was heat at 63° C. for 30 min under N$_2$, then cooled to room temperature with an ice-bath. The mixture was filtered through a fritted funnel and then concentrated under reduced pressure to give the titled product as a liquid which then lyophilized to give a solid (11.1 mg, 57%). LCMS m/z: ES+ [M+Na]: 341, (A05) retention time=0.97 m. ¹H NMR (400 MHz, CD₃OD) δ 5.09 (s, 1H), 4.00 (d, J=10.8 Hz, 1H), 3.35-3.20 (m, 2H), 3.15-2.97 (m, 2H), 2.93-2.58 (m, 3H), 2.19-1.97 (m, 2H), 1.86-1.58 (m, 4H), 1.56-1.36 (m, 2H), 1.06 (t, J=7.4 Hz, 3H).

Example 36

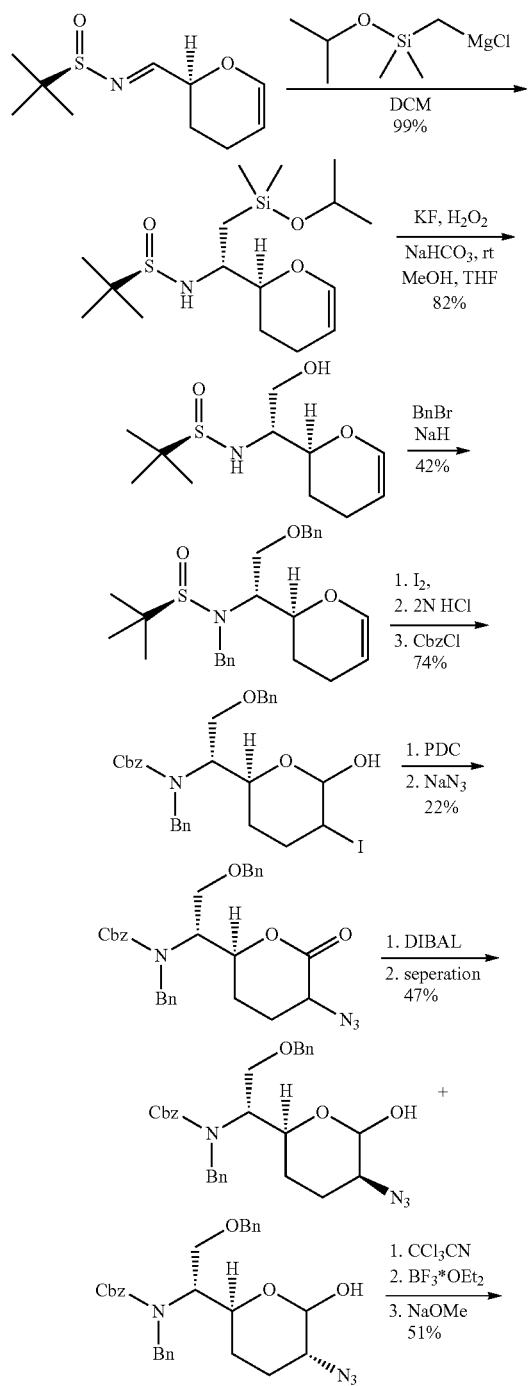

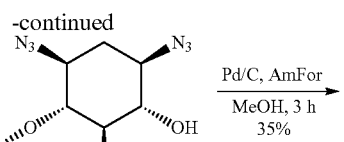

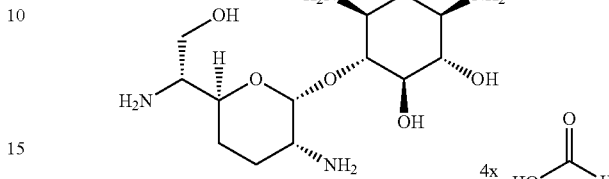

Step 1

(R)—N-[(1S)-1-[(2S)-3,4-dihydro-2H-pyran-2-yl]-2-[isopropoxy(dimethyl)silyl]ethyl]-2-methyl-propane-2-sulfinamide

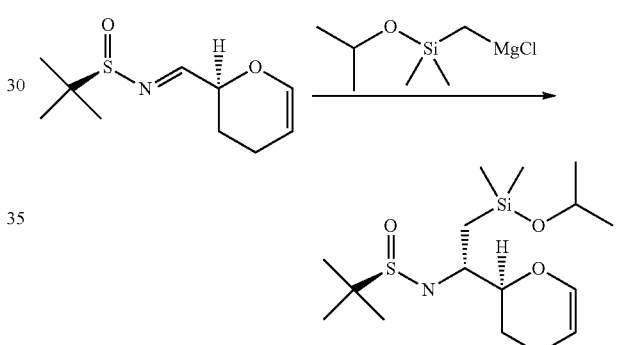

A suspension of magnesium filings (4.85 g, 199 mmol) in dry THF (125 mL) was heated at 65° C. with high agitation under an atmosphere of nitrogen. 1,2-Dibromoethane (0.52 mL, 6 mmol) was added over 1 min, followed by slow addition of chloromethyl dimethylisopropoxysilane (25 g, 150 mmol) over 15 min. The reaction was stirred at 65° C. for 90 min, then cooled to room temperature to give 1 M solution which was kept in a freezer (maximum 2 weeks).

To a solution of (NE,R)—N-[[(2S)-3,4-dihydro-2H-pyran-2-yl]methylene]-2-methyl-propane-2-sulfinamide (10 g, 46.4 mmol) in DCM (600 mL) was added dropwise chloro-[[isopropoxy (dimethyl)silyl]methyl]magnesium (1 M in THF, 93 mL, 93 mmol) at −78° C. The reaction mixture was stirred at −78° C. for 1 h, then warmed to room temperature and stirred for 3 h. The mixture was diluted with saturated NaHCO₃ (400 mL) and the layers were separated. The aqueous layer was extracted with DCM (3×300 mL). The combined organic layers were washed with brine, dried (MgSO₄), filtered and concentrated under reduced pressure to provide the title compound (11 g, 68%). ¹H NMR (400 MHz, CDCl₃) δ 6.36 (d, J=6.1 Hz, 1H), 4.69-4.63 (m, 1H), 4.04 (ddd, J=11.1, 3.5, 1.9 Hz, 1H), 3.97 (dt, J=12.1, 6.1 Hz, 1H), 3.90 (d, J=7.3 Hz, 1H), 3.61 (ddd, J=14.6, 7.3, 3.6 Hz, 1H), 2.14-2.03 (m, 1H), 2.00-1.91 (m, 1H), 1.89-1.81 (m, 1H), 1.70-1.55 (m, 1H), 1.21 (s, 9H), 1.13 (d, J=3.3 Hz, 3H), 1.12 (d, J=3.3 Hz, 3H), 0.83 (dd, J=15.0, 6.8 Hz, 1H), 0.15 (d, J=2.8 Hz, 3H), 0.13 (s, 3H). (NH was not observed) MS (ESI) [M+Na]+ 370.1.

Step 2

(R)—N-[(1R)-1-[(2S)-3,4-dihydro-2H-pyran-2-yl]-2-hydroxy-ethyl]-2-methyl-propane-2-sulfinamide

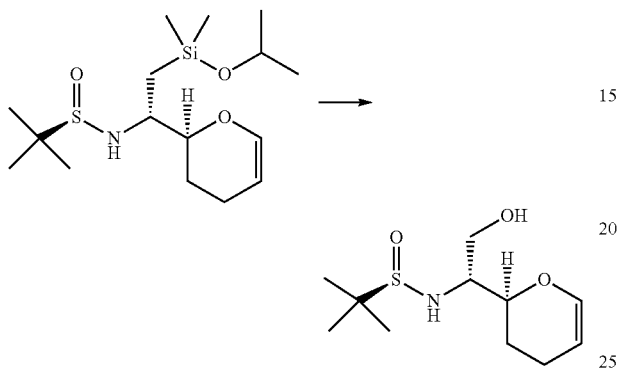

To a solution of (R)—N-[(1S)-1-[(2S)-3,4-dihydro-2H-pyran-2-yl]-2-[isopropoxy(dimethyl)silyl] ethyl]-2-methyl-propane-2-sulfinamide (11 g, 3.16 mmol) in MeOH (600 mL) was added KF (3.11 g, 3.64 mmol) and NaHCO₃ (3.19 g, 38 mmol). H₂O₂ (35% wt in water, 5.44 mL, 63.3 mL) was added dropwise over 5 min and the reaction mixture was stirred at room temperature for 16 h. The mixture was diluted with saturated solution of Na₂S₂O₃ (400 mL) and the aqueous layer was extracted with EtOAc (3×600 mL). The combined organic layers were washed with brine (1.0 L), dried (MgSO₄), filtered and concentrated under reduced pressure to provide the title compound (7.9 g, 99%) as an oil. ¹H NMR (500 MHz, CDCl₃) δ 6.34 (d, J=6.4 Hz, 1H), 4.75-4.70 (m, 1H), 4.09 (ddd, J=10.5, 5.6, 1.7 Hz, 1H), 3.94 (d, J=7.6 Hz, 1H), 3.87-3.82 (m, 1H), 3.80-3.74 (m, 1H), 3.44-3.37 (m, 1H), 2.65 (dd, J=9.2, 4.3 Hz, 1H), 2.15-2.06 (m, 1H), 2.03-1.98 (m, 1H), 1.74-1.66 (m, 1H), 1.26 (s, 9H).

Step 3

(R)—N-benzyl-N-[(1R)-2-benzyloxy-1-[(2S)-3,4-dihydro-2H-pyran-2-yl]ethyl]-2-methyl-propane-2-sulfinamide

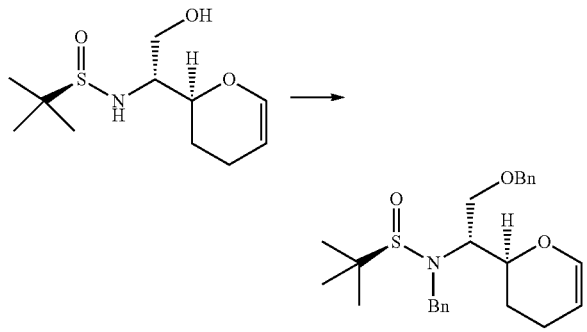

To a solution of BnBr (4.90 mL, 41.2 mmol) and (R)—N-[(1R)-1-[(2S)-3,4-dihydro-2H-pyran-2-yl]-2-hydroxy-ethyl]-2-methyl-propane-2-sulfinamide (3.40 g, 13.7 mmol) in DMF (120 mL) at 0° C., was added NaH (60% oil dispersion, 1.15 g, 28.9 mmol). The reaction mixture was stirred at 0° C. for 1 h, then brine (500 mL) was added at 0° C. The aqueous layer was extracted with Et₂O (3×150 mL). The combined organic layers were dried (MgSO₄), filtered and concentrated under reduced pressure. The material was purified by silica gel (80 g, dry loading) by MPLC using a gradient of 0-50% EtOAc in hexane as eluent to provide the title compound (2.30 g, 39%) as a solid. MS (ESI) [M+Na]+ 450.1.

Step 4

Benzyl N-benzyl-N-[(1R)-2-benzyloxy-1-[(2S)-6-hydroxy-5-iodo-tetrahydropyran-2-yl]ethyl]carbamate

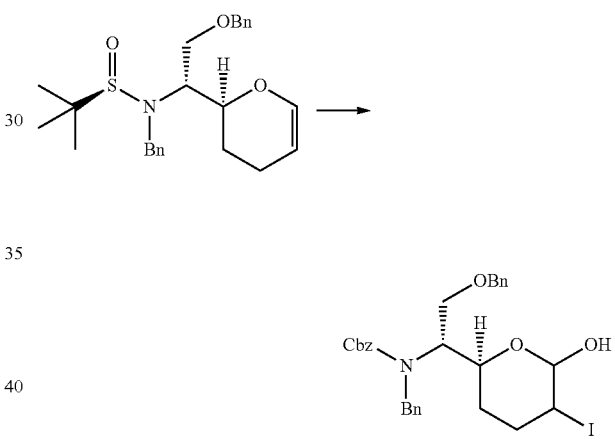

To a solution of (R)—N-benzyl-N-[(1R)-2-benzyloxy-1-[(2S)-3,4-dihydro-2H-pyran-2-yl]ethyl]-2-methyl-propane-2-sulfinamide (2.30 g, 5.38 mmol) and NaHCO₃ (1.36 g, 16.1 mmol) in ACN (100 mL) and water (100 mL) at 0° C., was added I2 (1.50 g, 5.92 mmol). The reaction mixture was stirred at 0° C. for 45 min, then a saturated solution of Na₂S₂O₃ (200 mL) was added following by EtOAc (250 mL). The layers were separated, and the aqueous layer was extracted with EtOAc (3×150 mL). The combined organic layers were washed with brine (500 mL), dried (MgSO₄), filtered and concentrated under reduced pressure. The residue was taken in dioxane (50 mL) and 2M HCl (8.07 mL, 16.1 mmol) was added dropwise. The mixture was stirred at room temperature for 30 min, then Na₂CO₃ (3.42 g, 32.3 mmol) was added. After 10 min at room temperature, CbzCl (1.54 mL, 10.7 mmol) was added dropwise. The mixture was stirred at room temperature for 2 h, then water (100 mL) was added. The aqueous layer was extracted with EtOAc (3×100 mL). The combined organic layers were washed with brine, dried (MgSO₄), filtered and concentrated under reduced pressure. The material was purified by silica gel (120 g, dry loading) by MPLC using a gradient of 0-50% EtOAc in hexane as eluent to provide the title compound (2.40 g, 74% over 3 steps) as a solid. MS (ESI) [M+H]+ 602.4.

Step 5 benzyl N-[(1R)-1-[(2S)-5-azido-6-oxo-tetrahydropyran-2-yl]-2-benzyloxy-ethyl]-N-benzyl-carbamate

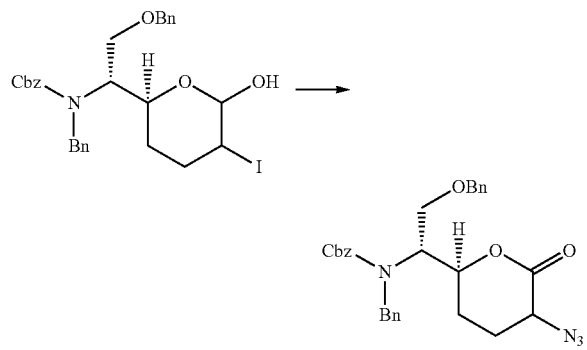

To a mixture of benzyl N-benzyl-N-[(1R)-2-benzyloxy-1-[(2S)-6-hydroxy-5-iodo-tetrahydro-pyran-2-yl]ethyl]carbamate (2.40 g, 3.99 mmol) and 4 Å molecular sieves (1.00 g) in DCM (150 mL) was added PDC (6.76 g, 18.0 mmol) at room temperature. After 18 h, the mixture was filtered on silica pad, rinsed with EtOAc and concentrated under reduced pressure. The residue was taken in DMF (25 mL) and cooled at 0° C. NaN₃ (285 mg, 4.39 mmol) was added and the mixture was stirred for 1 h at 0° C. The mixture was diluted with brine (250 mL) and the aqueous layer was extracted with Et₂O (3×150 mL). The combined organic layers were dried (MgSO₄), filtered and concentrated under reduced pressure. The residue was purified by silica (40 g, dry loading) by MPLC using a gradient of 0-40% EtOAc in hexane as eluent to provide the title compound (450 mg, 22% over 2 steps) as a solid. MS (ESI) [M+H]⁺ 515.2.

Step 6

Benzyl N-[(1R)-1-[(2S,5R)-5-azido-6-hydroxy-tetrahydropyran-2-yl]-2-benzyloxy-ethyl]-N-benzyl-carbamate

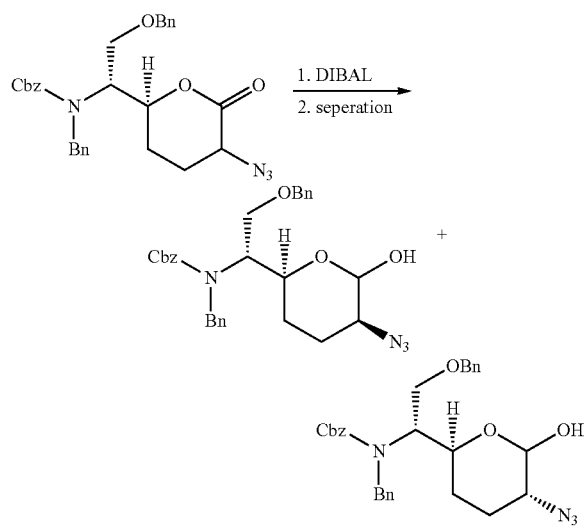

To a solution of benzyl N-[(1R)-1-[(2S)-5-azido-6-oxo-tetrahydropyran-2-yl]-2-benzyloxy-ethyl]-N-benzyl-carbamate (400 mg, 0.78 mmol) in DCM (18 mL) at −78° C., DIBAL-H (1M in toluene, 1.55 mL, 1.55 mmol) was added dropwise and the reaction mixture was stirred for 1 h. EtOH (0.5 mL) was added dropwise and the mixture was poured into a saturated solution of Rochelle's salt (300 mL). The mixture was vigorously stirred for 1 h at room temperature. The aqueous layer was extracted with DCM (2×75 mL). The combined organic layers were washed with brine, dried (MgSO₄) and concentrated under reduced pressure. The residue was purified by silica gel (40 g, dry loading) by MPLC using a gradient of 0-40% EtOAc in hexane as eluent to provide benzyl N-[(1R)-1-[(2S,5S)-5-azido-6-hydroxy-tetrahydropyran-2-yl]-2-benzyloxy-ethyl]-N-benzyl-carbamate (96 mg, 24%) and the desired diastereoisomer benzyl N-[(1R)-1-[(2S,5R)-5-azido-6-hydroxy-tetrahydropyran-2-yl]-2-benzyloxy-ethyl]-N-benzyl-carbamate (188 mg, 47%) as an oil. MS (ESI) [M+H]⁺ 517.3.

Step 7

Benzyl N-[(1R)-1-[(2S,5R,6R)-5-azido-6-[(1R,2R,3S,4R,6S)-4,6-diazido-2,3-dihydroxy-cyclohexoxy]tetrahydropyran-2-yl]-2-benzyloxy-ethyl]-N-benzyl-carbamate

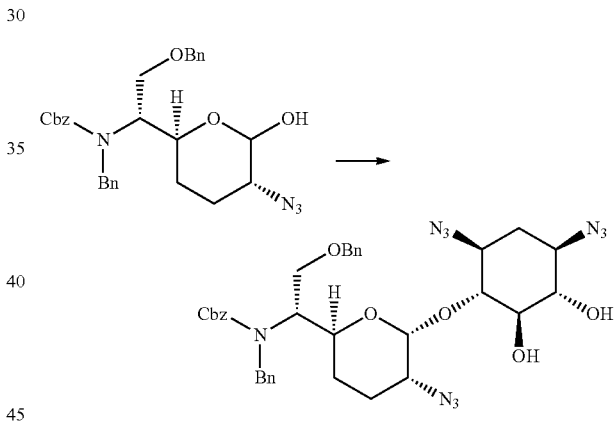

To a mixture of benzyl N-[(1R)-1-[(2S,5R)-5-azido-6-hydroxy-tetrahydropyran-2-yl]-2-benzyloxy-ethyl]-N-benzyl-carbamate (188 mg, 0.36 mmol) and K₂CO₃ (352 mg, 2.55 mmol) in dry DCM (10 mL) at room temperature was added CCl₃CN (0.29 mL, 2.91 mmol). The mixture was stirred at room temperature for 16 h, then filtered on celite and rinsed with DCM. The filtrate was concentrated under reduced pressure. The residue was taken in anhydrous DCM (10 mL) and [(1S,2S,3R,4S,6R)-2-acetoxy-4,6-diazido-3-hydroxy-cyclohexyl]acetate (239 mg, 0.80 mmol) was added. The mixture was cooled to −78° C., then BF₃·OEt₂ (0.14 mL, 1.13 mmol) was added dropwise. The reaction mixture was warmed to 0° C. and stirred for 1 h. The mixture was diluted with saturated NaHCO₃ (50 mL) and the aqueous layer was extracted with DCM (2×30 mL). The combined organic layers were washed with brine, dried (Na₂SO₄), filtered and concentrated under reduced pressure. The residue was taken in MeOH (10 mL) and NaOMe (4.62 M in MeOH, 0.55 mL, 2.55 mmol) was added. The reaction mixture was stirred at room temperature for 2 h, then concentrated under reduced pressure. The residue was

549 diluted with DCM (20 mL) and saturated NH₄Cl (80 mL). The layers were separated, and the aqueous layer was extracted with DCM (2×30 mL). The combined organic layers were washed with brine, dried (Na₂SO₄), filtered and concentrated under reduced pressure. The material was purified by reverse phase chromatography (C18) using a gradient of 5-100% ACN in water (contains 0.1% formic acid) to provide the title compound (134 mg, 52% over 3 steps) as a solid. MS (ESI) [M+H]⁺ 713.3.

Step 8

(1S,2R,3R,4S,6R)-4,6-diamino-3-[(2R,6S)-3-amino-6-[(1R)-1-amino-2-hydroxy-ethyl]tetrahydropyran-2-yl]oxy-cyclohexane-1,2-diol formate

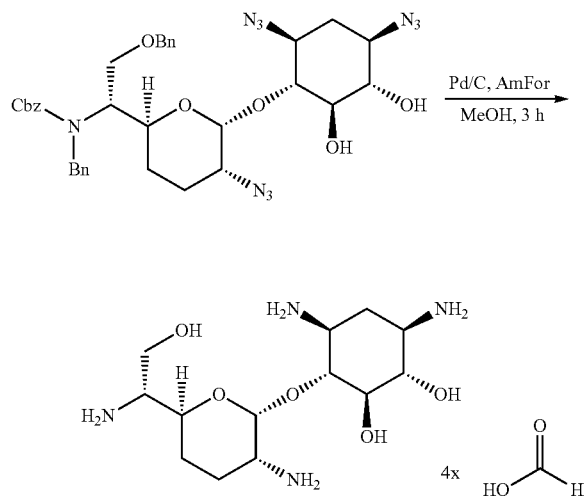

In a 2 neck flask equipped with a reflux condenser were added (1S,2R,3R,4S,6R)-4,6-diazido-3-(((2R,3R,6S)-3-azido-6-((R)-1-(benzyl(methyl)amino)-2-(benzyloxy)ethyl)tetrahydro-2H-pyran-2-yl)oxy)cyclohexane-1,2-diol (16 mg, 0.02 mmol) and Pd/C (10% dry on carbon, 7.2 mg, 0.01 mmol) followed by MeOH (5 mL). Nitrogen was bubbled for 5 min, then ammonium formate (15.6 mg, 0.25 mmol) was added. The mixture was heated at 63° C. for 3 h under N₂. The mixture was cooled with an ice-bath and then filtered with a filter syringe and the filtrate was concentrated under reduced pressure. The material was purified by preparative HPLC (Waters XBridge C18 30×150 mm; Flow rate: 40 mL/min) using a gradient of 10-25% ACN in Amfor pH 3.8 over 7 min to provide the title compound (3.90 mg, 34%) as a solid. ¹H NMR (400 MHz, CD₃OD) δ 8.45 (br, 4H), 5.64 (s, 1H), 4.27-4.17 (m, 1H), 3.84-3.69 (m, 3H), 3.62-3.55 (m, 1H), 3.51-3.44 (m, 1H), 3.40-3.31 (m, 2H), 3.16-3.02 (m, 3H), 2.35-2.21 (m, 1H), 1.97-1.92 (m, 1H), 1.86-1.80 (m, 1H), 1.66-1.57 (m, 2H). MS (ESI) [M+H]⁺ 321.4.

550

Example 37

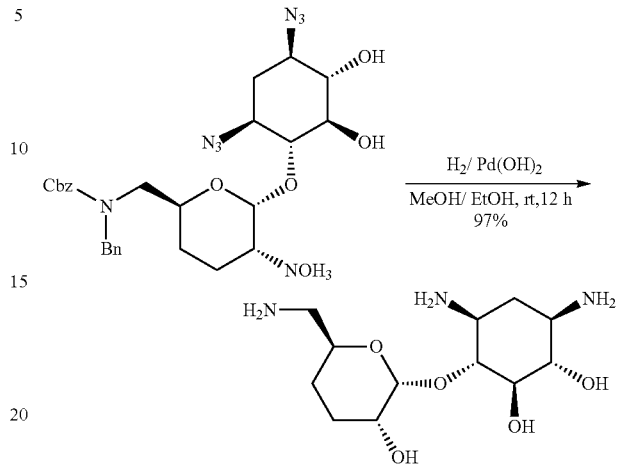

(1S,2R,3R,4S,6R)-3-[(2R,3R,6S)-6-(aminomethyl)-3-hydroxy-tetrahydropyran-2-yl]oxy-4,6-diazido-cyclohexane-1,2-diol Pd(OH)₂ (20 wt %, 129 mg, 0.183 mmol) was added to a solution of benzyl N-benzyl-N-[[(2S,5R,6R)-6-[(1R,2R,3S,4R,6S)-4,6-diazido-2,3-dihydroxy-cyclohexoxy]-5-hydroxy-tetrahydropyran-2-yl]methyl]carbamate (see Example 15 for synthesis, 26.0 mg, 45.8 μmol) in MeOH (2.50 mL) and EtOH (2.50 mL). H₂ was bubbled and the suspension was hydrogenated under hydrogen atmosphere for 12 h. The suspension was filtered through a frit (0.22 m diameter) and the filtrate was concentrated under reduced pressure to afford the title compound (13.0 mg, 97%) as a solid. ¹H NMR (400 MHz, MeOD) δ 5.17 (d, J=3.4 Hz, 1H), 4.07-3.97 (m, 1H), 3.72 (ddd, J=11.4, 5.1, 3.6 Hz, 1H), 3.47 (t, J=9.2 Hz, 1H), 3.28 (t, J=9.5 Hz, 1H), 3.17 (t, J=9.4 Hz, 1H), 2.90 (ddd, J=23.0, 12.6, 3.8 Hz, 2H), 2.82-2.70 (m, 2H), 2.09 (dt, J=12.7, 4.1 Hz, 1H), 1.94-1.69 (m, 4H), 1.30 (q, J=12.5 Hz, 1H). MS (ESI) [M+H]⁺ 325.2.

Example 38

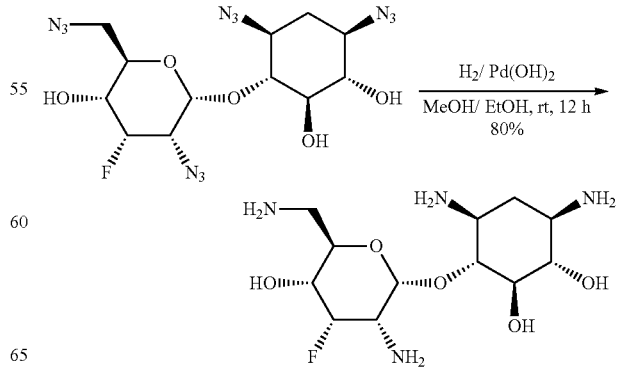

551

(1S,2R,3R,4S,6R)-4,6-diamino-3-[(2R,3S,4S,5R,6R)-3-amino-6-(aminomethyl)-4-fluoro-5-hydroxy-tetrahydropyran-2-yl]oxy-cyclohexane-1,2-diol Pd(OH)$_2$ (20 wt %, 105 mg, 0.149 mmol) was added to a solution of (1S,2R,3R,4S,6R)-4,6-diazido-3-(((2R,3S,4S,5R,6R)-3-azido-6-(azidomethyl)-4-fluoro-5-hydroxytetrahydro-2H-pyran-2-yl)oxy)cyclohexane-1,2-diol (see Example 22 for synthesis, 20.0 mg, 49.7 μmol) in MeOH (2.0 mL) and EtOH (2.0 mL). H$_2$ was bubbled and the suspension was hydrogenate under hydrogen atmosphere for 12 h. The mixture was filtered through a frit (0.22 m diameter) and the filtrate was concentrated under reduced pressure to afford the title compound (12.9 mg, 80%) as a solid. $^1$HNMR (500 MHz, MeOD) δ 5.48 (d, J=4.6 Hz, 1H), 4.78 (t, J=53.0, 2.2 Hz, 1H), 4.01 (ddd, J=10.5, 5.5, 2.1 Hz, 1H), 3.56-3.44 (m, 2H), 3.31 (t, J=9.3 Hz, 1H), 3.22 (dd, J=13.2, 2.9 Hz, 1H), 3.16 (t, J=9.5 Hz, 1H), 3.05 (ddd, J=33.9, 4.6, 2.5 Hz, 1H), 2.95-2.84 (m, 2H), 2.77 (ddd, J=12.1, 9.8, 4.2 Hz, 1H), 2.07 (dt, J=12.8, 4.2 Hz, 1H), 1.32 (dd, J=24.8, 12.3 Hz, 1H).

Example 39

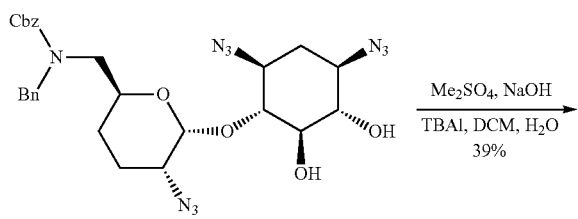

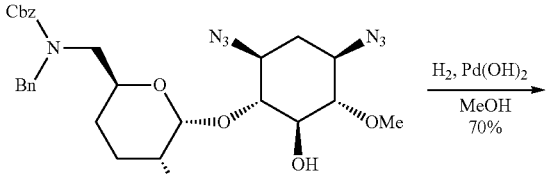

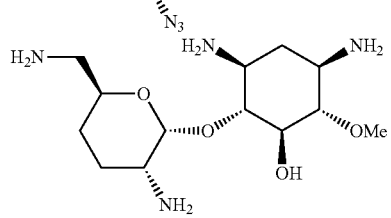

Step 1

Benzyl N-[[(5R,6R)-5-azido-6-[(1R,2R,3S,4R,6S)-4,6-diazido-2-hydroxy-3-methoxy-cyclohexoxy]tetrahydropyran-2-yl]methyl]-N-benzyl-carbamate

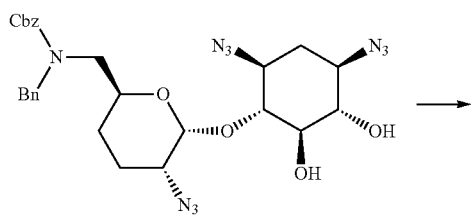

552

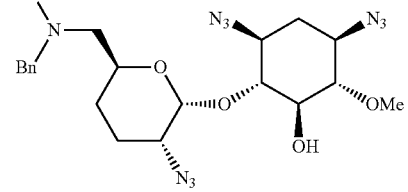

Me$_2$SO$_4$ (51 μL, 68 mmol) was added to a vigorously stirring suspension of benzyl N-[[(5R,6R)-5-azido-6-[(1R,2R,3S,4R,6S)-4,6-diazido-2,3-dihydroxy-cyclohexoxy]tetrahydropyran-2-yl]methyl]-N-benzyl-carbamate (see Example 11 for synthesis, 40 mg, 67 μmol) and TBAI (4 mg, 10 μmol) in a mixture DCM (1.0 mL) and NaOH solution (1.0 M aq., 1.0 mL, 1.0 mmol) at ambient temperature. After 2 h, concentrated NH$_4$OH (200 μL) was added and the mixture was partitioned in between water (10.0 mL) and DCM (10.0 mL). The aqueous layer was extracted with DCM (5.0 mL) and the combined organic layers were dried (Na$_2$SO$_4$), filtered and concentrated under reduced pressure. The material was purified by silica gel chromatography (12 g cartridge) using a gradient of 10-40% EtOAc in hexane as eluent and was further purified by preparative HPLC (BEH 30×150 mm C18 ACN/AmForm 70-80%) to provide the title compound (rotamers, 16 mg, 39%) as a solid. $^1$H NMR (400 MHz, CDCl$_3$) δ 7.48-7.04 (m, 1H), 5.32-5.04 (m, 3H), 4.72 (d, J=15.9 Hz, 1H), 4.47 (d, J=16.0 Hz, 1H), 4.34-4.12 (m, 1H), 3.66 (s, 3H), 3.59-3.10 (m, 8H), 2.96 (t, J=9.5 Hz, 1H), 2.19 (dt, J=13.2, 4.5 Hz, 1H), 2.06-1.92 (m, 1H), 1.92-1.81 (m, 1H), 1.73-1.51 (m, 1H), 1.47-1.28 (m, 2H). MS ESI [M+H]$^+$ 607.2.

Step 2

(1R,2R,3S,5R,6S)-3,5-diamino-2-[(2R,3R,6S)-3-amino-6-(aminomethyl)tetrahydropyran-2-yl]oxy-6-methoxy-cyclohexanol; formic acid

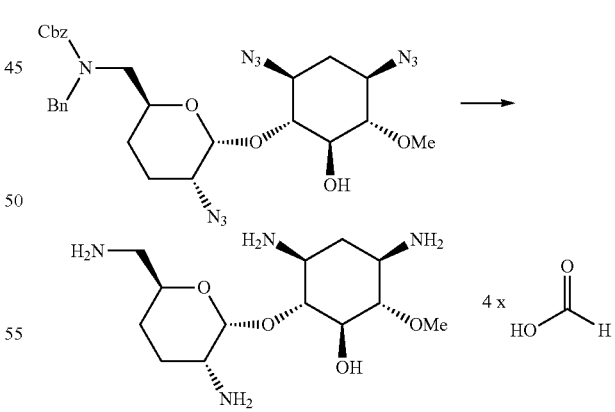

Pd(OH)$_2$ (10 wt %, 9.3 mg, 6.6 μmol) was added to a solution of benzyl N-[[(2S,5R,6R)-5-azido-6-[(1R,2R,3S,4R,6S)-4,6-diazido-2-hydroxy-3-methoxy-cyclohexoxy]tetrahydropyran-2-yl]methyl]-N-benzyl-carbamate (16 mg, 26.4 μmol) in MeOH (1.5 mL) under N$_2$ at ambient temperature. H$_2$ was bubbled through the suspension for 15 min and then the suspension was stirred for 18 h. The solution was filtered through a frit (0.22 m diameter) and the filtrate was concentrated under reduced pressure. The material was purified by preparative HPLC (BEH 30×150 mm C18 ACN/AmForm 10-25%) to provide the title compound (9 mg, 70%). $^1$H NMR (500 MHz, D$_2$O) δ 8.53 (s, 3H), 5.79 (d, J=3.3 Hz, 1H), 4.26-4.16 (m, 1H), 3.96 (t, J=9.8 Hz, 1H), 3.82 (t, J=8.8 Hz, 1H), 3.64 (s, 3H), 3.62-3.53 (m, 1H), 3.53-3.44 (m, 1H), 3.43-3.35 (m, 2H), 3.27 (dd, J=13.5, 3.2 Hz, 1H), 3.12 (dd, J=13.6, 7.3 Hz, 1H), 2.50 (dt, J=5.5, 3.1 Hz, 1H), 2.11-1.98 (m, 2H), 1.98-1.82 (m, 2H), 1.70-1.57 (m, 1H). MS ESI [M+H]$^+$ 350.2

Example 40

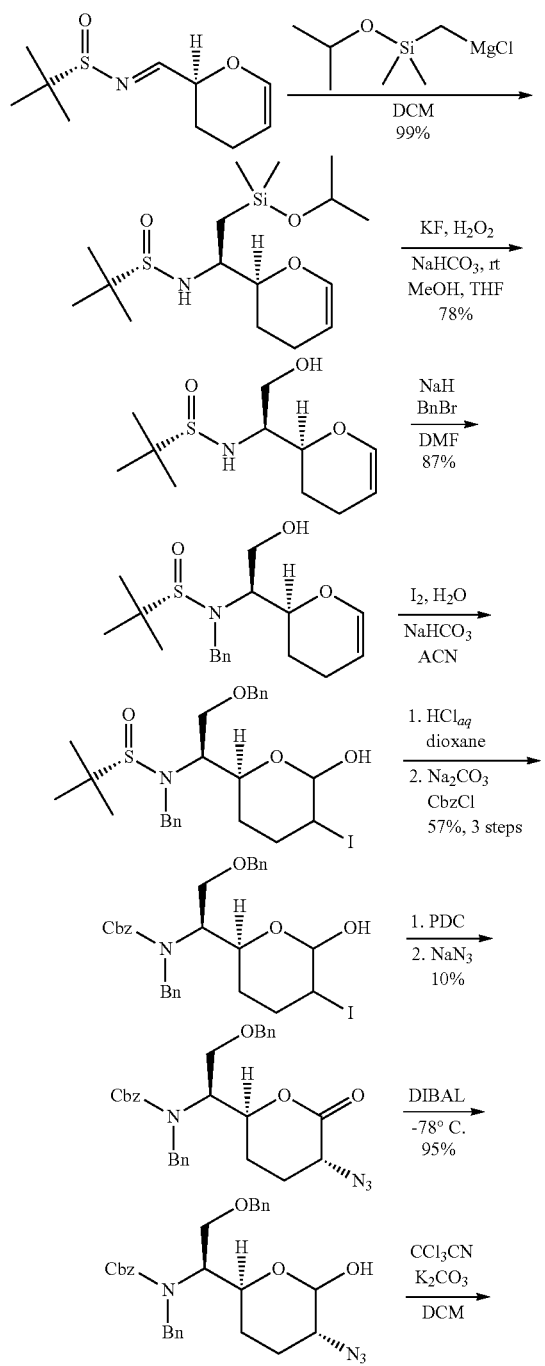

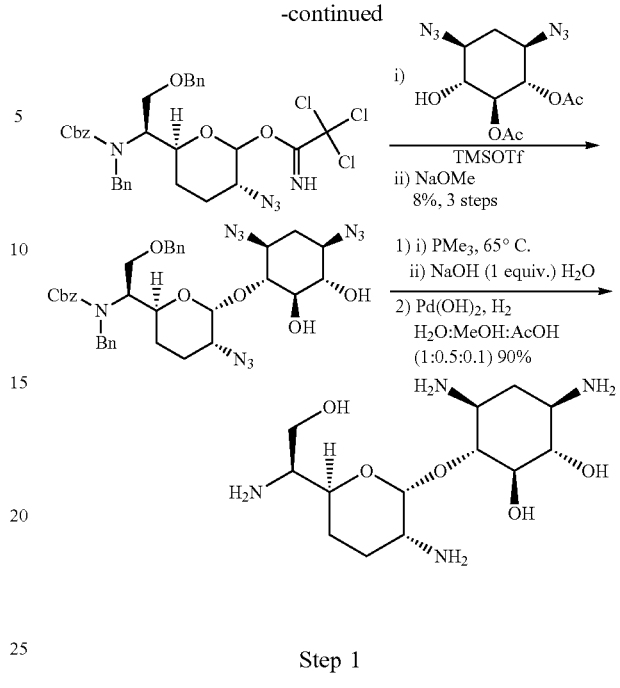

Step 1

(S)—N-[(1R)-1-[(2S)-3,4-dihydro-2H-pyran-2-yl]-2-[isopropoxy(dimethyl)silyl]ethyl]-2-methyl-propane-2-sulfinamide

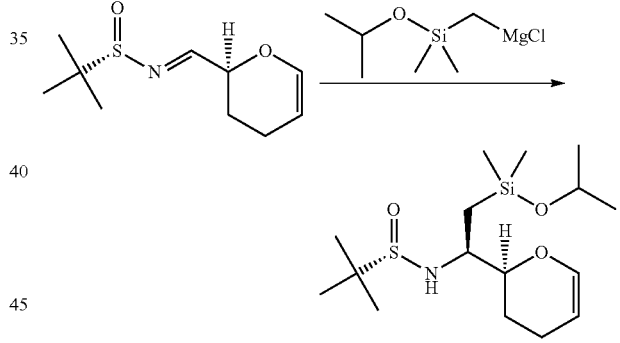

A suspension of magnesium filings (4.85 g, 199 mmol) in dry THF (125 mL) was heated at 65° C. with high agitation under an atmosphere of nitrogen. 1,2-Dibromoethane (0.52 mL, 6 mmol) was then added over 1 min, followed by slow addition of chloromethyl dimethylisopropoxysilane (25 g, 150 mmol) over 15 min. The mixture was stirred at 65° C. for 90 min, then cooled to room temperature to give a 1 M solution of Chloro-[[isopropoxy(dimethyl)silyl]methyl] in THF.

Chloro-[[isopropoxy(dimethyl)silyl]methyl]magnesium (1M in THF, 86 mL, 86 mmol) was added dropwise to a solution of (NE,S)—N-[[(2S)-3,4-dihydro-2H-pyran-2-yl]methylene]-2-methyl-propane-2-sulfinamide (9.30 g, 43.2 mmol) in DCM (500 mL) at −78° C. The mixture was stirred at −78° C. for 3 h, then warmed to room temperature. A saturated solution of NaHCO$_3$ (400 mL) was added and the separated aqueous layer was extracted with DCM (3×). The combined organic layers were washed with brine, then dried (MgSO$_4$) and concentrated under reduced pressure to afford the title compound (15 g, 99%), which was used in the next step without further purification. MS (ESI) [M+Na]+ 370.4.

Step 2

(S)—N-[(1S)-1-[(2S)-3,4-dihydro-2H-pyran-2-yl]-2-hydroxy-ethyl]-2-methyl-propane-2-sulfinamide

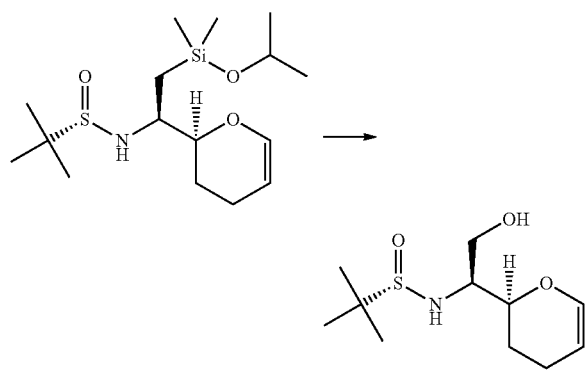

To a solution of (S)—N-[(1R)-1-[(2S)-3,4-dihydro-2H-pyran-2-yl]-2-[isopropoxy(dimethyl)silyl]ethyl]-2-methyl-propane-2-sulfinamide (15.0 g, 43.2 mmol) in a mixture of THF (600 mL) and MeOH (600 mL), was added KF (2.88 g, 49.6 mmol) and NaHCO$_3$ (4.35 g, 51.8 mmol). The mixture was cooled to 5° C. and a solution of H$_2$O$_2$ (7.42 mL 30 wt % H$_2$O$_2$; 86.3 mmol) was added dropwise. The reaction mixture was warmed room temperature and was stirred for 16 h. The mixture was quenched with saturated Na$_2$S$_2$O$_3$ (~250 mL) and diluted with saturated NaHCO$_3$ (~100 mL). The aqueous layer was extracted with EtOAc (2.5 L). The organic phase was dried (MgSO$_4$), filtered and concentrated under reduced pressure. The crude oil was diluted with ether (1.5 L) and washed with brine (500 mL). The organic layer was dried (Na$_2$SO$_4$), filtered and concentrated under reduced pressure to afford the title compound (8.31 g, 78%). MS (ESI) [M+H]+ 248.3.

Step 3

(S)—N-benzyl-N-[(1S)-2-benzyloxy-1-[(2S)-3,4-dihydro-2H-pyran-2-yl]ethyl]-2-methyl-propane-2-sulfinamide

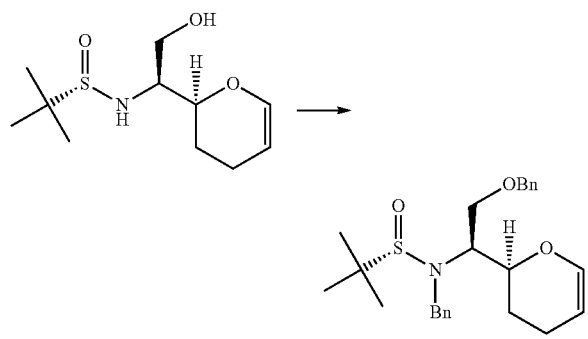

NaH (60%, 1.15 g, 28.9 mmol) was added to a mixture of BnBr (4.90 mL, 41.2 mmol) and (S)—N-[(1S)-1-[(2S)-3,4-dihydro-2H-pyran-2-yl]-2-hydroxy-ethyl]-2-methyl-propane-2-sulfinamide (3.40 g, 13.7 mmol) in DMF (100 mL) at 0° C. The reaction mixture was stirred at 0° C. for 1 h, then brine (500 mL) was added. The separated aqueous layer was extracted with EtOAc (3×150 mL). The combined organic layers were dried (Na$_2$SO$_4$), filtered and concentrated under reduced pressure. The material was purified by flash chromatography (120 g, dry loading) using a gradient of 5-45% EtOAc in hexane as eluent to provide the title compound (5.11 g, 87%). MS (ESI) [M+Na]+ 450.4.

Step 4

Benzyl N-benzyl-N-[(1S)-2-benzyloxy-1-[(2S)-6-hydroxy-5-iodo-tetrahydropyran-2-yl]ethyl]carbamate

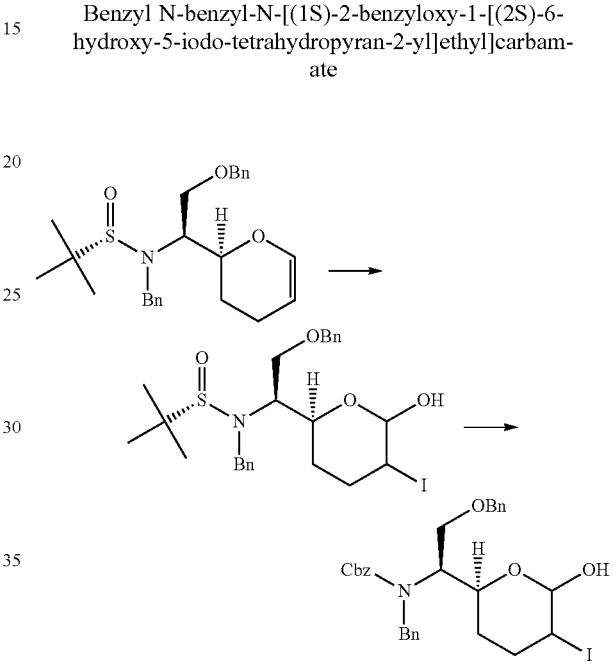

I$_2$ (3.34 g, 13.1 mmol) was added to a mixture of (R)—N-benzyl-N-[(1S)-2-benzyloxy-1-[(2S)-3,4-dihydro-2H-pyran-2-yl]ethyl]-2-methyl-propane-2-sulfinamide (5.11 g, 12.0 mmol) and NaHCO$_3$ (3.01 g, 35.9 mmol) in a mixture ACN (100 mL) and water (100 mL) at 0° C. The reaction mixture was stirred at 0° C. for 45 min, then a saturated aqueous solution of Na$_2$S$_2$O$_3$ (200 mL) was added. The aqueous layer was extracted with EtOAc (3×150 mL). The combined organic layer was washed with brine (500 mL), then dried (Na$_2$SO$_4$), filtered and concentrated under reduced pressure to afford (S)—N-benzyl-N-((1S)-2-(benzyloxy)-1-((2S)-6-hydroxy-5-iodotetrahydro-2H-pyran-2-yl)ethyl)-2-methylpropane-2-sulfinamide.

To the above material (S)—N-benzyl-N-((1S)-2-(benzyloxy)-1-((2S)-6-hydroxy-5-iodotetrahydro-2H-pyran-2-yl)ethyl)-2-methylpropane-2-sulfinamide was taken in dioxane (50 mL), was added aqueous solution of 1 N HCl (17.9 mL, 17.9 mmol) dropwise and the reaction mixture was stirred at room temperature for 30 min. Na$_2$CO$_3$ (7.60 g, 71.7 mmol) was then added and the mixture was stirred for 10 min. CbzCl (3.41 mL, 23.9 mmol) was added dropwise and the reaction mixture was stirred at room temperature for 2 h. The mixture was diluted with water (100 mL) and the separated aqueous layer was extracted with EtOAc (3×100 mL). The combined organic layers were washed with brine, then dried (Na$_2$SO$_4$), filtered and concentrated under reduced pressure. The material was purified by flash chromatography (120 g, dry loading) using a gradient of 0-50% EtOAc in hexane as eluent to provide the title compound (4.10 g, 57% over 3 steps). MS (ESI) [M+Na]$^+$ 624.3.

Step 5

Benzyl N-[(1S)-1-[(2S,5R)-5-azido-6-oxo-tetrahydropyran-2-yl]-2-benzyloxy-ethyl]-N-benzyl-carbamate

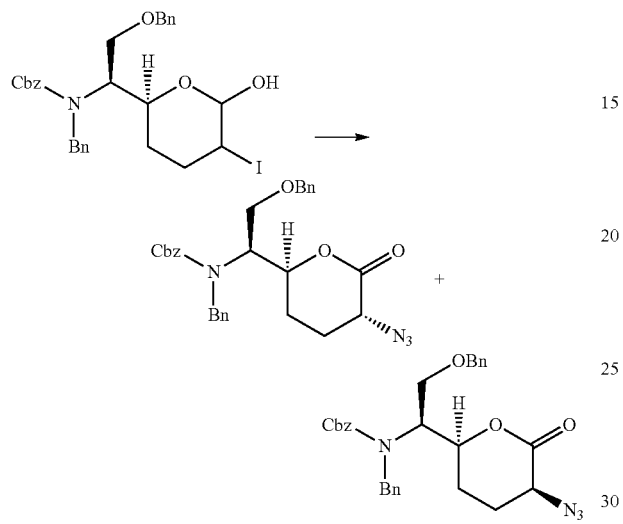

To a solution of benzyl N-benzyl-N-[(1S)-2-benzyloxy-1-[(2S)-6-hydroxy-5-iodo-tetrahydropyran-2-yl]ethyl]carbamate (4.10 g, 6.82 mmol) in DCM (200 mL), was added 4 Å molecular sieves (2.00 g), and then PDC (11.5 g, 30.7 mmol) and the suspension was stirred at room temperature for 18 h. The mixture was filtered on a silica pad, rinsed with EtOAc and concentrated under reduced pressure.

To the above material in DMF (30 mL) at 0° C., was added NaN$_3$ (0.49 g, 7.50 mmol) and the reaction mixture was stirred for 1 h at room temperature. The mixture was diluted with brine (250 mL) and the separated aqueous layer was extracted with Et$_2$O. The combined organic layers were dried (Na$_2$SO$_4$), filtered and concentrated under reduced pressure. The material was purified by flash chromatography (40 g, dry loading) using a gradient of 0-50% EtOAc in hexane as eluent to provide the title compound (first eluting, 350 mg, 10%) along with benzyl ((S)-1-((2S,5S)-5-azido-6-oxotetrahydro-2H-pyran-2-yl)-2-(benzyloxy)ethyl)(benzyl)carbamate (second eluting, 335 mg). MS (ESI) [M+H]$^+$ 515.4.

Step 6

Benzyl N-[(1S)-1-[(2S,5R)-5-azido-6-hydroxy-tetrahydropyran-2-yl]-2-benzyloxy-ethyl]-N-benzyl-carbamate

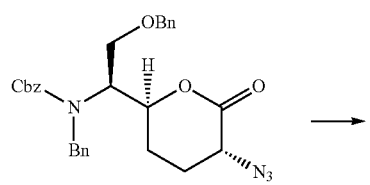

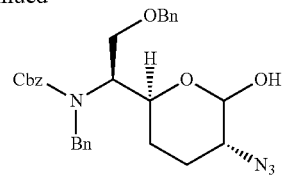

DIBAL-H (1 M in toluene, 1.36 mL, 1.36 mmol) was added dropwise to a solution of benzyl N-[(1S)-1-[(2S,5R)-5-azido-6-oxo-tetrahydropyran-2-yl]-2-benzyloxy-ethyl]-N-benzyl-carbamate (350 mg, 0.68 mmol) in DCM (20 mL) at −78° C. After 1 h at −78° C., EtOH (1 mL) was added dropwise and the mixture was poured into a saturated aqueous solution of Rochelle's salt (300 mL). The mixture was vigorously stirred for 1 h and the separated aqueous layer was extracted with DCM (2×75 mL). The combined organic layers were washed with brine, then dried (Na$_2$SO$_4$), filtered and concentrated under reduced pressure. The material was purified by flash chromatography (40 g, dry loading) using a gradient of 5-40% EtOAc in hexane to provide the title compound (334 mg, 95%) as an oil. MS (ESI) [M+Na]$^+$ 539.3.

Step 7

Benzyl N-[(1S)-1-[(2S,5R,6R)-5-azido-6-[(1R,2R,3S,4R,6S)-4,6-diazido-2,3-dihydroxy-cyclohexoxy]tetrahydropyran-2-yl]-2-benzyloxy-ethyl]-N-benzyl-carbamate

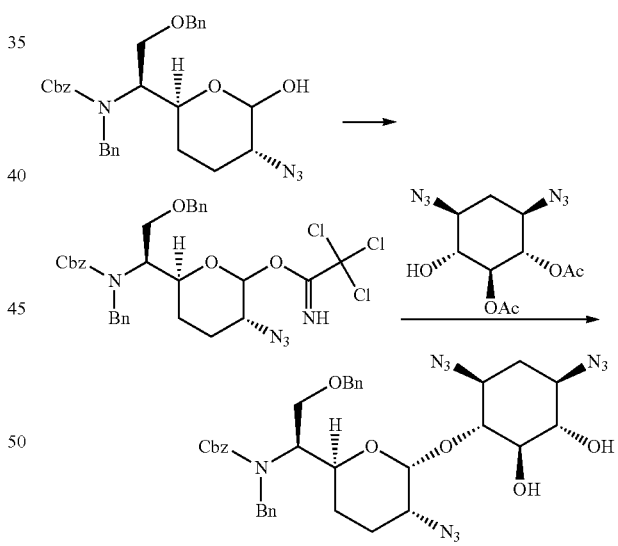

CCl$_3$CN (0.45 mL, 4.50 mmol) was added dropwise to a suspension of benzyl N-[(1S)-1-[(2S,5R)-5-azido-6-hydroxy-tetrahydropyran-2-yl]-2-benzyloxy-ethyl]-N-benzyl-carbamate (334 mg, 0.65 mmol) and K$_2$CO$_3$ (544 mg, 3.94 mmol) in dry DCM (10 mL) at room temperature. The mixture was stirred at room temperature for 18 h, then filtered on Celite and rinsed with DCM. The filtrate was concentrated under reduced pressure to afford (3R,6S)-3-azido-6-((S)-1-(benzyl((benzyloxy)carbonyl)amino)-2-(benzyloxy)ethyl)tetrahydro-2H-pyran-2-yl 2,2,2-trichloroacetimidate, which was used in the next step without further purification.

To a solution of above material in anhydrous DCM (10 mL), [(1S,2S,3R,4S,6R)-2-acetoxy-4,6-diazido-3-hydroxy-cyclohexyl]acetate (168 mg, 0.56 mmol) was added followed activated molecular sieve and the reaction mixture was stirred for 2 h. The mixture was cooled to −78° C., and then BF$_3$·Et$_2$O (0.22 mL, 1.74 mmol) was added dropwise and the reaction mixture was stirred for 1.5 h. The mixture was warmed to 0° C. and stirred for 1 h. The mixture was then diluted with saturated aqueous solution of NaHCO$_3$ (50 mL) and the separated aqueous layer was extracted with DCM (2×30 mL). The combined organic layers were washed with brine, then dried (Na$_2$SO$_4$), filtered and concentrated under reduced pressure. The material was purified by column chromatography on silica gel (40 g) using a gradient of 0-30% EtOAc in hexane as eluent to afford the bis acetate intermediate. MS (ESI) [M+Na]$^+$ 819.5.

To a solution of above material in MeOH (10 mL), NaOMe (4.62 M in MeOH, 0.56 mL, 2.59 mmol) was added and the reaction mixture was stirred at room temperature for 2 h. The mixture was concentrated under reduced pressure and the residue was diluted in DCM and saturated NH$_4$Cl (100 mL). The separated aqueous layer was extracted with DCM (2×30 mL). The combined organic layers were washed with brine, then dried (Na$_2$SO$_4$), filtered and concentrated under reduced pressure. The material was purified by preparative HPLC (BEH 30×150 mm C18 ACN/AmForm 73-80%) to afford to afford the title compound (first eluting, 31 mg) along with P2 (second eluting, 70.9 mg). MS (ESI) [M+Na]$^+$ 735.4.

Step 8

(1S,2R,3R,4S,6R)-4,6-diamino-3-[(2R,3R,6S)-3-amino-6-[(1S)-1-amino-2-hydroxy-ethyl]tetrahydro-pyran-2-yl]oxy-cyclohexane-1,2-diol; acetic acid

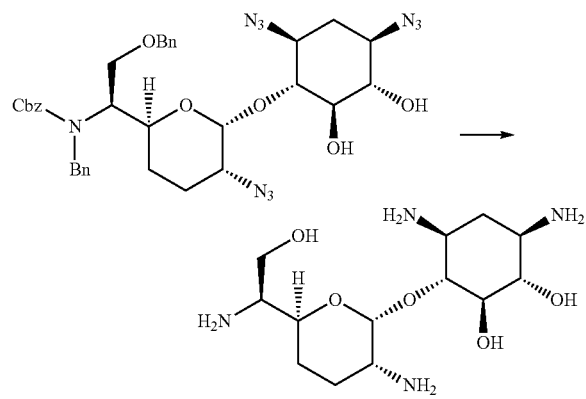

To a solution of benzyl N-[(1S)-1-[(2S,5R,6R)-5-azido-6-[(1R,2R,3S,4R,6S)-4,6-diazido-2,3-dihydroxy-cyclohexoxy]tetrahydropyran-2-yl]-2-benzyloxy-ethyl]-N-benzyl-carbamate (25 mg, 0.035 mmol) in tetrahydrofuran (1 mL), was added trimethyl phosphine (0.21 mL 1.0 M tetrahydrofuran solution, 0.21 mmol) at room temperature and the reaction mixture was heated to 65° C. for 30 min. The mixture was diluted 0.1 M aq. sodium hydroxide (0.42 mL, 0.042 mmol) and the mixture was stirred for 5 h. The mixture was cooled to room temperature and stirred overnight. The volatiles were concentrated under reduced pressure and the material was purified with reverse phase chromatography on C18 using 10-100% AcCN in H$_2$O (ammonium formate:Formic acid 1:1. 0.1%) to amine. MS (ESI) [M+Na]$^+$ 657.5.

To a solution of above material in a mixture of water: MeOH:AcOH (1:0.5:0.1, 5 mL), was added palladium(II) hydroxide (20 wt % loading on carbon, 24.6 mg, 0.018 mmol). The suspension was hydrogenated under hydrogen atmosphere for 16 h. The mixture was filtered and the filtrated was concentrated under reduced pressure and then lyophilized to afford the title compound (18.4 mg, 90%) as a salt. $^1$H NMR (500 MHz, MeOD) δ 5.85 (d, J=3.0 Hz, 1H), 4.20-4.11 (m, 1H), 3.78 (dd, J=11.9, 4.2 Hz, 1H), 3.75-3.64 (m, 2H), 3.52 (t, J=9.1 Hz, 1H), 3.39 (t, J=9.3 Hz, 1H), 3.37-3.33 (m, 1H), 3.15 (dt, J=9.5, 8.6 Hz, 2H), 3.06 (t, J=9.2 Hz, 1H), 2.30 (d, J=12.5 Hz, 1H), 2.09-2.02 (m, 1H), 1.72 (dd, J=25.0, 12.7 Hz, 1H), 1.62-1.48 (m, 1H). 2H missing (in the 1.9 ppm peak together with acetic acid according to HSQC). MS (ESI) [M+H]$^+$ 321.2.

Example 41

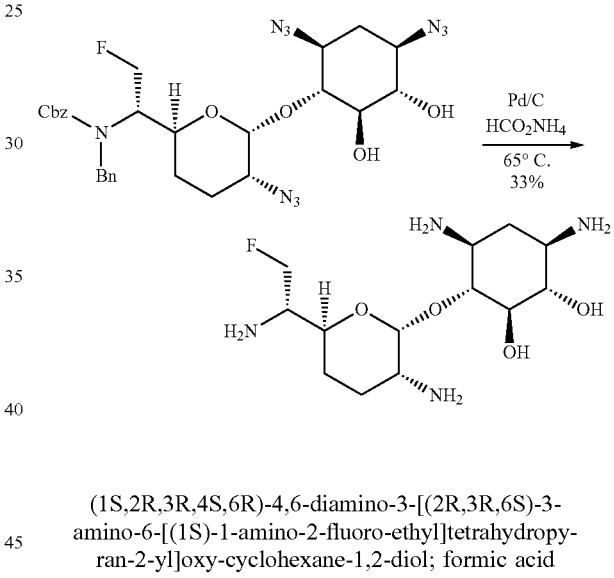

(1S,2R,3R,4S,6R)-4,6-diamino-3-[(2R,3R,6S)-3-amino-6-[(1S)-1-amino-2-fluoro-ethyl]tetrahydropyran-2-yl]oxy-cyclohexane-1,2-diol; formic acid To a mixture of benzyl N-[(1S)-1-[(2S,5R,6R)-5-azido-6-[(1R,2R,3S,4R,6S)-4,6-diazido-2,3-dihydroxy-cyclohexoxy]tetrahydropyran-2-yl]-2-fluoro-ethyl]-N-benzyl-carbamate (see Example 23 for synthesis, 10 mg, 0.016 mmol) and 10% Pd/C (5.1 mg, 0.0048 mmol) was added anhydrous MeOH (1 mL). Nitrogen was bubbled for 5 min, then ammonium formate (9.1 mg, 0.14 mmol) was added and the mixture was heated at 63° C. for 6 h. The mixture was cooled to room temperature and then filtered through a nylon filter (45 μm) and the volatiles were evaporated under reduced pressure then lyophilized (1 drop of formic acid in water) to provide the title compound (2.7 mg, 33%) as formate salt. $^1$H NMR (500 MHz, MeOD) δ 8.21 (s, 4H), 5.85 (d, J=3.5 Hz, 1H), 4.82-4.68 (m, 2H), 4.38 (d, J=12.3 Hz, 1H), 3.93 (t, J=9.6 Hz, 1H), 3.74-3.67 (m, 1H), 3.60 (t, J=9.2 Hz, 1H), 3.46-3.39 (m, 3H), 3.20 (ddd, J=11.0, 10.0, 3.5 Hz, 1H), 2.39 (dt, J=12.4, 4.1 Hz, 1H), 2.22-2.12 (m, 1H), 2.06-1.96 (m, 1H), 1.94-1.83 (m, 2H), 1.74-1.64 (m, 1H). MS (ESI) [M+H]$^+$ 323.2.

Example 42

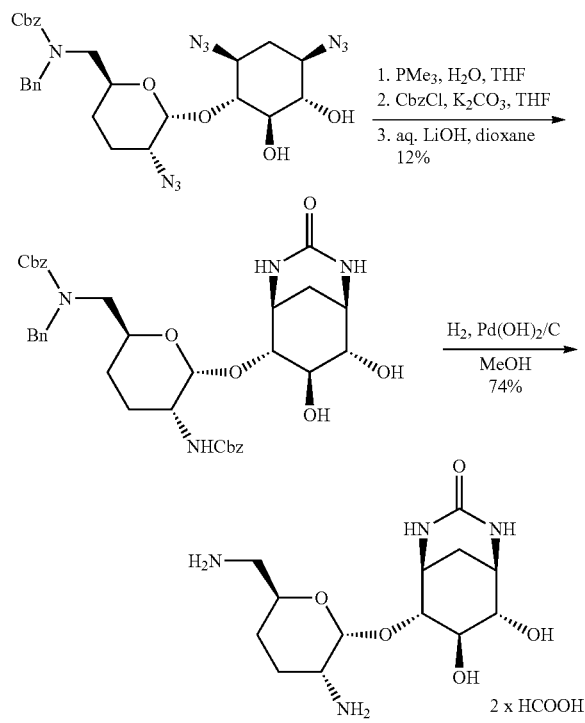

Step 1

Benzyl N-benzyl-N-[[(2S,5R,6R)-5-(benzyloxycarbonylamino)-6-[[(1R,5S,6R,7R,8S)-7,8-dihydroxy-3-oxo-2,4-diazabicyclo[3.3.1]nonan-6-yl]oxy]tetrahydropyran-2-yl]methyl]carbamate

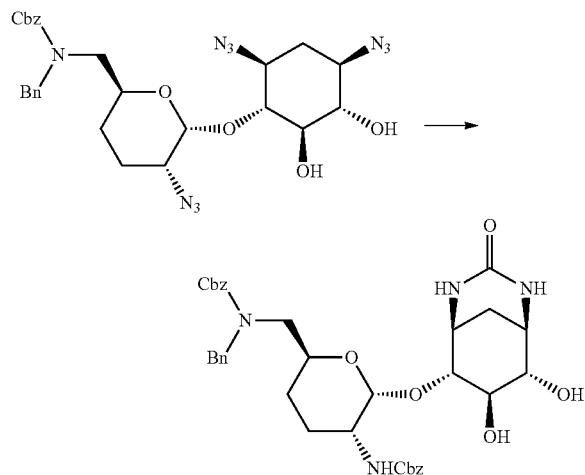

PMe$_3$ (1.0 M in THF, 1.14 mL, 1.14 mmol) was added to a solution of benzyl N-[[(2S,5R,6R)-5-azido-6-[(1R,2R,3S,4R,6S)-4,6-diazido-2,3-dihydroxy-cyclohexoxy]tetrahydropyran-2-yl]methyl]-N-benzyl-carbamate (see Example 11 for synthesis, 150 mg, 253 μmol) and water (150 μL, 8.33 mmol) in THF (6.0 mL) under N$_2$ at ambient temperature. The reaction was warmed to 40° C. under a refluxing condenser. After 18 h, the solution was cooled to room temperature and K$_2$CO$_3$ (315 mg, 2.28 mmol) was added followed by water (1.5 mL). After another 30 min, CbzCl (162 μL, 1.14 mmol) was added dropwise and the reaction mixture was stirred at for 2 h. The volatiles were evaporated under reduced pressure and the material was purified by silica gel chromatography (12 g cartridge) with using a gradient of EtOAc and hexane (30-80%) as eluent then 30% MeOH in DCM to produce benzyl N-benzyl-N-[[(2S,5R,6R)-5-(benzyloxycarbonylamino)-6-[(1R,2R,3S,4R,6S)-4,6-bis(benzyloxycarbonylamino)-2,3-dihydroxy-cyclohexoxy]tetrahydropyran-2-yl]methyl]carbamate (282 mg).

LiOH·H$_2$O (70 mg, 1.68 mmol) was added to a suspension of benzyl N-benzyl-N-[[(2S,5R,6R)-5-(benzyloxycarbonylamino)-6-[(1R,2R,3S,4R,6S)-4,6-bis(benzyloxycarbonylamino)-2,3-dihydroxy-cyclohexoxy]tetrahydropyran-2-yl]methyl]carbamate (220 mg, 240 μmol) in a mixture dioxane and H$_2$O (2.25 mL 2:1) in a microwave tube. The tube was sealed and the reaction mixture was warmed to 50° C. for 18 h. The mixture was filtered through silica gel (4.0 g) and eluted with a mixture of MeOH in DCM (80.0 mL, 4:1). To the filtrate was added HOAc (150 μL) and the mixture was concentrated under reduced pressure. The material was purified by preparative HPLC (BEH 30×150 mm C18 ACN/AmForm 40-60%) to provide the title compound (20 mg, 12% over 3 steps) as a solid. MS (ESI) [M+H]$^+$ 675.3.

Step 2

(1R,5S,6R,7R,8S)-6-[(2R,3R,6S)-3-amino-6-(aminomethyl)tetrahydropyran-2-yl]oxy-7,8-dihydroxy-2,4-diazabicyclo[3.3.1]nonan-3-one: formic acid

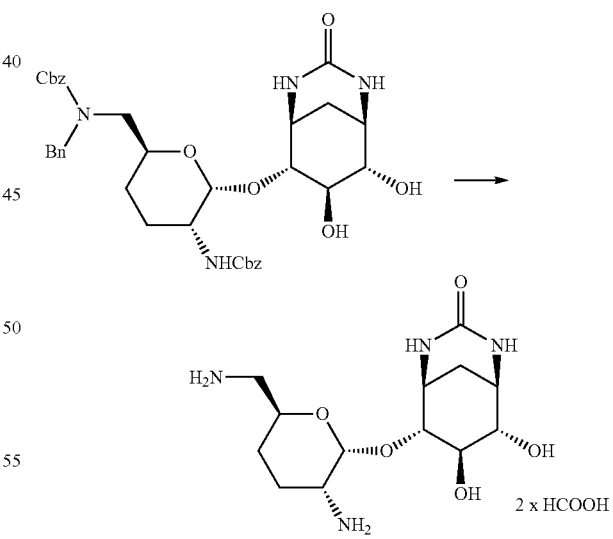

Pd(OH)$_2$/C (10 wt %, 25 mg, 18 μmol) was added to a solution of benzyl N-benzyl-N-[[(2S,5R,6R)-5-(benzyloxycarbonylamino)-6-[[(1R,5S,6R,7R,8S)-7,8-dihydroxy-3-oxo-2,4-diazabicyclo[3.3.1]nonan-6-yl]oxy]tetrahydropyran-2-yl]methyl]carbamate (20 mg, 30 μmol) in MeOH (1.0 mL) under N$_2$ at ambient temperature. H$_2$ was bubbled through the suspension for 15 min and the mixture was stirred under hydrogen atmosphere for 18 h. The mixture was filtered through a frit (0.45 m diameter) and the filtrate was concentrated under reduced pressure. The material was purified by preparative HPLC (BEH 30×150 mm ACN/AmForm 10% ISO) to provide the title compound (bis-formate, 9.0 mg, 74%). $^1$H NMR (500 MHz, MeOD) δ 8.57 (s, 2H), 5.21 (s, 1H), 4.05 (t, J=9.8 Hz, 1H), 3.98-3.86 (m, 3H), 3.68 (s, 1H), 3.50 (s, 1H), 3.37 (s, 1H), 3.13 (d, J=12.7 Hz, 1H), 2.99-2.88 (m, 1H), 2.60 (d, J=13.1 Hz, 1H), 1.98-1.89 (m, 2H), 1.85 (d, J=12.5 Hz, 1H), 1.66 (d, J=13.1 Hz, 1H), 1.59-1.47 (m, 1H). MS ESI [M+H]$^+$ 317.2.

Example 43

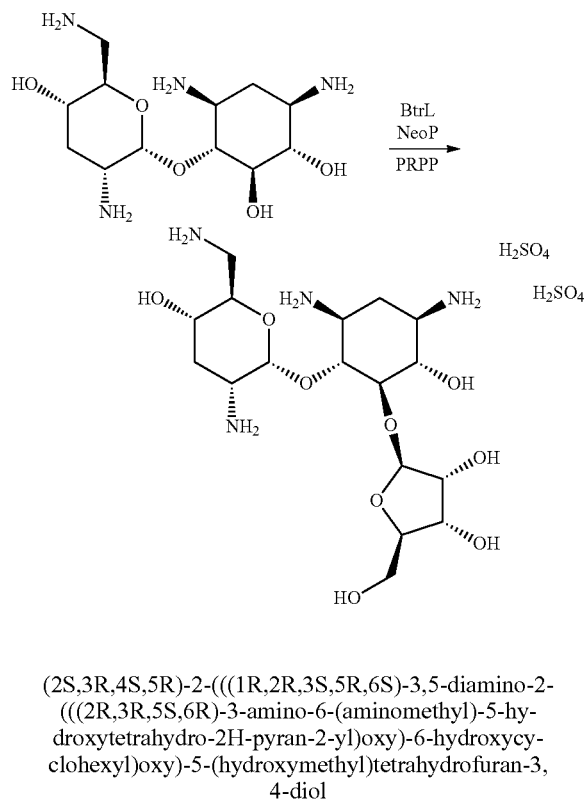

(2S,3R,4S,5R)-2-(((1R,2R,3S,5R,6S)-3,5-diamino-2-(((2R,3R,5S,6R)-3-amino-6-(aminomethyl)-5-hydroxytetrahydro-2H-pyran-2-yl)oxy)-6-hydroxycyclohexyl)oxy)-5-(hydroxymethyl)tetrahydrofuran-3,4-diol BtrL is prepared as a cell free extract (CFE), flash frozen in liquid nitrogen, and stored in 50 mM HEPES buffer (pH 8.0) at −80° C. NeoP is purified, flash frozen in liquid nitrogen, and stored in 20 mM Tris buffer (pH 7.5), supplemented with 200 mM KCl at −80° C. 5-phospho-D-ribose 1-diphosphate pentasodium salt (PRPP) is purchased from Sigma-Aldrich®. Ribosylation reaction conditions are as follows: 50% v/v BtrL CFE, nebramine (30.6 mg, 0.10 mmol, 10 mM final concentration), 10 mM PRPP (final concentration), 1 mM MgCl$_2$, 50 mM HEPES buffer (pH 7.5) (final concentration), 10% glycerol (final) and 10% v/v purified NeoP. The reaction is incubated at 30° C. with rotation for 16 hours (not exceeding 24 hours) to allow for successful installation of the ribose to the nebramine substrate. The reaction is then heat inactivated at 98° C. for 2 minutes to allow protein precipitation to occur. To remove the precipitated protein, the reaction is then spun at 12,000 rpm for 30 minutes. The supernatant is then purified by ion exchange with Amberlyst CG50 resin to separate and concentrate the target aminoglycoside molecule from contaminating neutral and cationic molecules. The aminoglycoside molecule is eluted with 3% NH$_4$OH$_4$ and fractions containing the desired product are lyophilized. The lyophilized aminoglycoside is then further purified by preparative HPLC. The product was dissolved in water, two equivalents of sulfuric acid was added and the solution was lyophilized to give the sulfate salt (5.1 mg, 0.0080 mmol, 8.0%). LCMS m/z ES$^+$ [M+H]$^+$: 439.2

Example 44

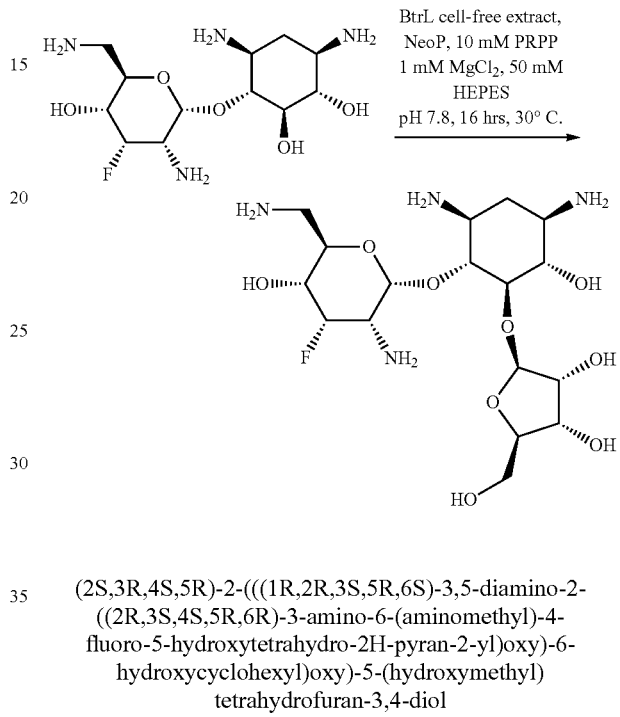

(2S,3R,4S,5R)-2-(((1R,2R,3S,5R,6S)-3,5-diamino-2-((2R,3S,4S,5R,6R)-3-amino-6-(aminomethyl)-4-fluoro-5-hydroxytetrahydro-2H-pyran-2-yl)oxy)-6-hydroxycyclohexyl)oxy)-5-(hydroxymethyl)tetrahydrofuran-3,4-diol 310 μL of buffer mix (250 mM HEPES, 5 mM MgCl$_2$, 50% glycerol) was combined with 775 μL of cell-free extract from BL-21 E. coli expressing BtrL and 155 μL of 100 mM PRPP (in H$_2$O) and 155 μL of NeoP (5 mg/mL) in a 2 mL Eppendorf tube. Next, 155 μL of (1S,2R,3R,4S,6R)-4,6-diamino-3-(((2R,3S,4S,5R,6R)-3-amino-6-(aminomethyl)-4-fluoro-5-hydroxytetrahydro-2H-pyran-2-yl)oxy)cyclohexane-1,2-diol (100 mM in H$_2$O) was added and the reaction incubated at 30° C. for 16 hours. The reaction was then heated at 95° C. for 10 minutes and centrifuged at 12,000 rpm to removed solids. The supernatant was applied to 1 g of Amberlyst CG50 ion exchange resin (pre-equilibrated with 20 mL H$_2$O). The loaded resin was washed with 12 mL of H$_2$O and the aminoglycoside was eluted with 3×1 mL portions of 3% NH$_4$OH. The combined elutions were lyophilized to yield a white solid that contained product and remaining starting material. The solids were taken up in concentrated NH$_4$OH, loaded onto a C18 column, and eluted with a gradient of 0-30% acetonitrile in 0.1 M NH$_4$OH to yield 0.4 mg of (2S,3R,4S,5R)-2-(((1R,2R,3S,5R,6S)-3,5-diamino-2-(((2R,3S,4S,5R,6R)-3-amino-6-(aminomethyl)-4-fluoro-5-hydroxytetrahydro-2H-pyran-2-yl)oxy)-6-hydroxycyclohexyl)oxy)-5-(hydroxymethyl)tetrahydrofuran-3,4-diol. LCMS: expected [M+1H]$^+$=457.2, found 457.2.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the disclosure have been described herein for purposes of illustration, various modifications may be made without deviating from the spirit and scope of the disclosure. Accordingly, the disclosure is not limited except as by the appended claims.

What is claimed is:
1. A process for preparing a compound of formula ABC-1':

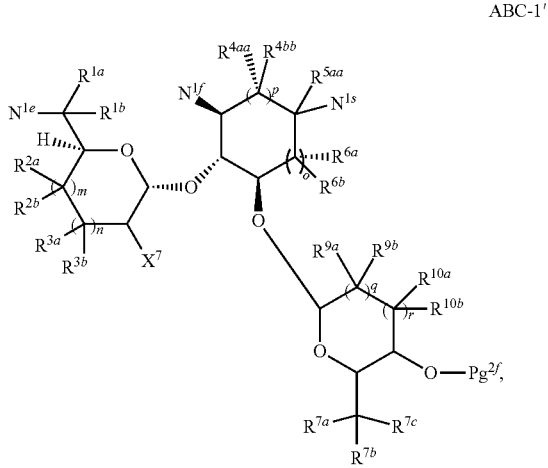

ABC-1' or a salt thereof,
wherein:
- $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, $NR^{14}R^{15}$, —$N_3$, and —$OR^{16}$, and wherein each $R^{12}$, $R^{13}$, $R^{14}$, $R^{15}$ and $R^{16}$ is independently H or alkyl; or
- $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$ and —$OR^{16}$;
- $R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, —$OR^{30}$, —$NR^{31}R^{32}$, —$SR^{33}$, and —$SO_2R^{34}$;
  - wherein each $R^{30}$, $R^{31}$, $R^{32}$, $R^{33}$ and $R^{34}$ is independently H or alkyl substituted with one or more substituents independently selected from the group consisting of halogen, cyano, $NR^{14}R^{15}$ and —$OR^{16}$; or
- $R^{2a}$ and $R^{2b}$ form an oxo or imino group substituted with $C_1$-$C_6$ alkyl;
- $R^{3a}$ and $R^{3b}$ form an oxo or imino group substituted with $C_1$-$C_6$ alkyl;
- $R^{4aa}$ and $R^{4bb}$ are, independently H, —OH, —$OR^{40}$, —$NR^{41}R^{42}$, or halogen;
  - wherein each $R^{40}$, $R^{41}$, and $R^{42}$ are independently H, alkyl, —$CONH_2$, or —$COCH_3$; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;
- $R^{5aa}$ is H, —CN, —$CONH_2$ or $C_1$-$C_3$alkyl, wherein the alkyl is unsubstituted or substituted with one or more substituents selected from the group consisting of —OH, —OC(O)$CH_3$, —$NH_2$, —CN, —$CONH_2$, and halogen;
- $R^{6a}$ and $R^{6b}$ are, independently H, halogen, $NH_2$, —OH, $C_1$-$C_3$alkoxy, —OC(O)$CH_3$, or -$OPg^{2m}$; wherein $Pg^{2m}$ is a hydroxyl protecting group;
- $N^{1s}$ is $N_3$ or —$NR^{8a}R^{8b}$;
- $R^8$ is H, $C_1$-$C_6$ alkyl, an amino protecting group, or

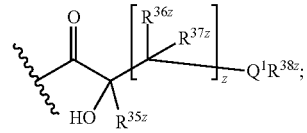

wherein
$Q^1$ is NH, O, or S;
z is an integer from 0 to 4,
$R^{35z}$ is H or $C_1$-$C_3$ alkyl;
each $R^{36z}$ and $R^{37z}$ is independently selected from the group consisting of H, alkyl, halogen, and —OH, and
$R^{38z}$ is H, alkyl, or —C(=NH)$NR^{39z}R^{40z}$ wherein $R^{39z}$ and $R^{40z}$ are independently H or $C_1$-$C_3$ alkyl; or
$R^{35z}$ and $R^{38z}$, together with the atoms to which they are attached, form a heterocycloalkyl group comprising at least one N;
$R^{8b}$ is H or $C_1$-$C_3$alkyl;
$N^{1e}$ is —OH, protected hydroxyl group, —$NHPg^{1e}$ or $N_3$, wherein $Pg^{1e}$ is an amino protecting group;
$N^{1f}$ is —$NHPg^{1f}$ or $N_3$, wherein $Pg^{1f}$ is an amino protecting group;
$X^7$ is H, —$NH_2$, —$N_3$, protected amino group, —OH, protected hydroxyl group, or halogen;
m is zero, 1, or 2;
n is zero, 1, or 2;
wherein m+n is 1, 2 or 3;
is zero, 1, or 2;
p is zero, 1, or 2;
wherein o+p is 1, 2 or 3;
$R^{7a}$, $R^{7b}$, and $R^{7c}$ are independently H, $NH_2$, OH, —$OR^{71}$ or -$OPg^{2r}$;

wherein $R^{71}$ is alkyl; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;

wherein $Pg^{2r}$ is a hydroxyl protecting group;

$R^{9a}$ and $R^{9b}$ are independently H, OH, or —$OR^{91}$, wherein $R^{91}$ is alkyl, alkenyl, or alkynyl; wherein the alkyl, alkenyl, and alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$R^{10a}$ and $R^{10b}$ are independently H, OH, or —$OR^{101}$, wherein $R^{101}$ is alkyl, alkenyl, or alkynyl; wherein the alkyl, alkenyl, or alkynyl is unsubstituted or substituted with one or more substituents selected from the group consisting of —$CONH_2$, —OH, —$NH_2$, —$COCH_3$, aryl, substituted aryl, heteroaryl, and substituted heteroaryl;

$Pg^{2f}$ is a hydroxyl protecting group;

q is zero, 1, or 2;

r is zero, 1, or 2; and wherein q+r is 1, 2 or 3;

the process comprising:

(a) contacting a compound of formula A-9':

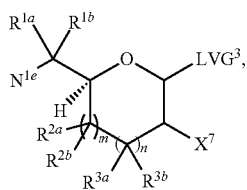

A-9' wherein $LVG^3$ is a leaving group, with a compound of formula B-12:

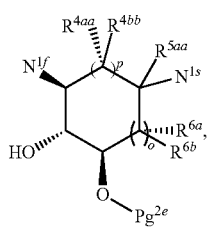

B-12' to yield a compound of formula AB-1'

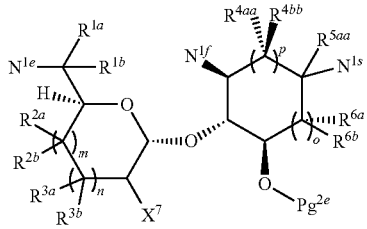

AB-1' where $Pg^2e$ is a hydroxyl protecting group;

(b) selectively deprotecting the compound of formula AB-1' by removing the $Pg^2e$ group to yield a compound of formula AB-3':

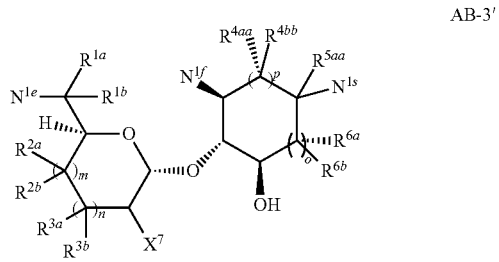

AB-3' or a salt thereof, and (c) contacting the compound of formula AB-3' with a compound of formula C-1,

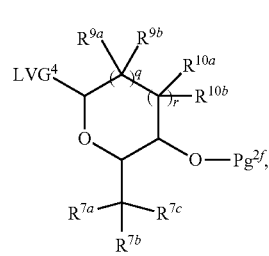

C-1 or a salt thereof, where $LVG^4$ is a leaving group, to yield the compound of formula ABC-1' or salt thereof.

2. The process of claim 1, further comprising after step (c):

(d) if amino protecting groups and hydroxyl protecting groups are present, removing the amino protecting groups and hydroxyl protecting groups to yield a compound of formula ABC'',

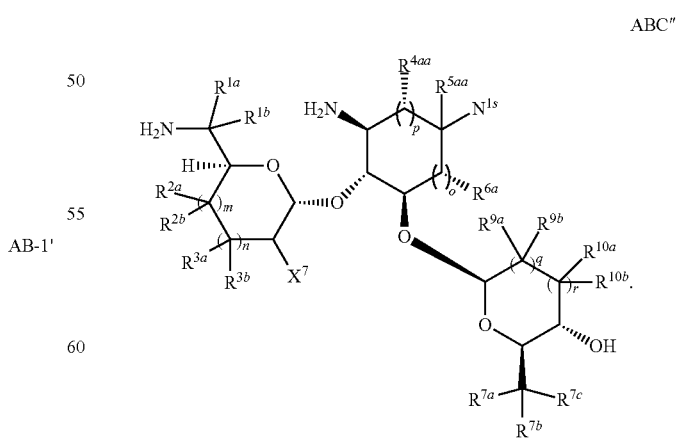

ABC''

3. A process for preparing a compound of formula ABCD-1:

ABCD-1'

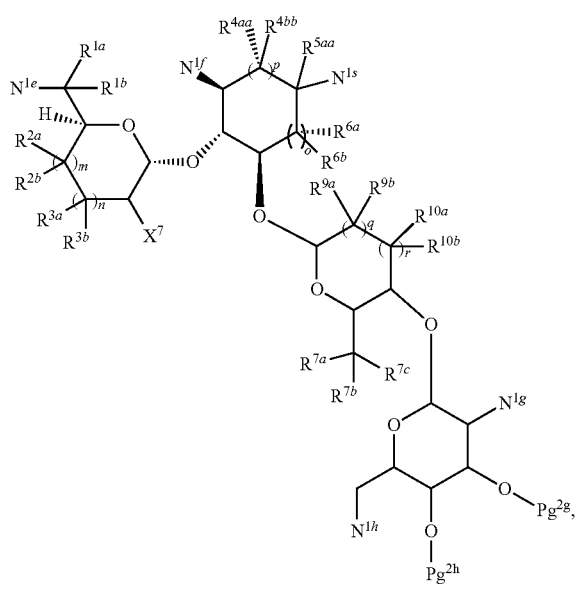

or a salt thereof,
wherein:
  $R^{1a}$ and $R^{1b}$ are independently selected from the group consisting of H, $C_1$-$C_{12}$ alkyl, $C_1$-$C_6$ cycloalkyl, aryl, and heteroaryl, wherein the alkyl, cycloalkyl, aryl, or heteroaryl is unsubstituted or substituted with one or more substituents independently selected from the group consisting of halogen, cyano, alkyl, aryl, heteroaryl, —$SR^{12}$, —$SO_2R^{13}$, —$OSF_2NR^{14}R^{15}$, —$NR^{14}R^{15}$, —$N_3$, and —$OR^{16}$, and
  wherein each $R^{12}$, $R^{13}$, $R^{14}$, $R^{15}$ and $R^{16}$ is independently H or alkyl; or
  $R^{1a}$ and $R^{1b}$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, alkyl, aryl, heteroaryl, —$SR^{22}$, —$SO_2R^{23}$, —$NR^{24}R^{25}$, and —$OR^{26}$, and
  wherein each $R^{22}$, $R^{23}$, $R^{24}$, $R^{25}$, and $R^{26}$ is independently H or alkyl, wherein the alkyl is unsubstituted or substituted with one or more substituents independently selected from the group consisting of halogen, cyano, $NR^{14}R^{15}$ and —$OR^{16}$;
  $R^{2a}$, $R^{2b}$, $R^{3a}$ and $R^{3b}$ are independently selected from the group consisting of H, —$OR^{27}$, —$NR^{28}R^{29}$, halogen, $C_1$-$C_4$ cycloalkyl, and $C_1$-$C_6$ alkyl, wherein each $R^{27}$, $R^{28}$, and $R^{29}$ is independently H, alkyl, amino protecting group, or hydroxyl protecting group; wherein the $C_1$-$C_6$ alkyl or alkyl is unsubstituted or substituted with one or more substituents selected from the group consisting of aryl, halogen, —$OR^{30}$, —$NR^{31}R^{32}$, —$SR^{33}$, and —$SO_2R^{34}$;
  wherein each $R^{30}$, $R^{31}$, $R^{32}$, $R^{33}$ and $R^{34}$ is independently H or alkyl substituted with one or more substituents independently selected from the group consisting of halogen, cyano, $NR^{14}R^{15}$ and —$OR^{16}$; or
  $R^{2a}$ and $R^{2b}$ form an oxo or imino group substituted with $C_1$-$C_6$ alkyl;

$R^{3a}$ and $R^{3b}$ form an oxo or imino group substituted with $C_1$-$C_6$ alkyl;
$R^{4aa}$ and $R^{4bb}$ are, independently, H, —OH, —$OR^{40}$, —$NR^{41}R^{42}$, or halogen;
  wherein each $R^{40}$, $R^{41}$, and $R^{42}$ are independently H, alkyl, —$CONH_2$, or —$COCH_3$; wherein the alkyl is unsubstituted or substituted with one or more substituents selected from the group consisting of —$CONH_2$, —OH, —$NH_2$, —$COCH_3$, aryl, substituted aryl, heteroaryl, halogen, and substituted heteroaryl;
$R^{5aa}$ is H, —CN, —$CONH_2$ or $C_1$-$C_3$ alkyl, wherein the alkyl is unsubstituted or substituted with one or more substituents selected from the group consisting of —OH, —$OC(O)CH_3$, —$NH_2$, —CN, —$CONH_2$, and halogen;
$R^{6a}$ and $R^{6b}$ are, independently H, halogen, $NH_2$, —OH, $C_1$-$C_3$alkoxy, —$OC(O)CH_3$, or -$OPg^{2m}$;
  wherein $Pg^{2m}$ is a hydroxyl protecting group;
$N^{1s}$ is $N_3$ or —$NR^{8a}R^{8b}$;
$R^{8a}$ is H, $C_1$-$C_6$ alkyl, an amino protecting group, or

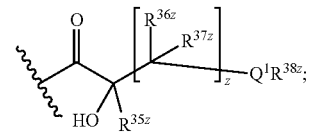

wherein
$Q^1$ is NH, O, or S;
z is an integer from 0 to 4, 35z
$R^{35z}$ is H or $C_1$-$C_3$ alkyl; H
each $R^{36z}$ and $R^{37z}$ is independently selected from the group consisting of H, alkyl, halogen, and —OH, and
$R^{38z}$ is H, alkyl, or —C(=NH)$NR^{39z}R^{40z}$ wherein $R^{39z}$ and $R^{40z}$ are independently H or $C_1$-$C_3$ alkyl; or
$R^{35z}$ and $R^{38z}$, together with the atoms to which they are attached, form a heterocycloalkyl group comprising at least one N;
$R^{8b}$ is H or $C_1$-$C_3$alkyl;
$N^{1e}$ is —OH, protected hydroxyl group, —$NHPg^{1e}$ or $N_3$, wherein $Pg^{1e}$ is an amino protecting group;
$N^{1f}$ is —$NHPg^{1f}$ or $N_3$, wherein $Pg^{1f}$ is an amino protecting group;
$X^7$ is H, —$NH_2$, —$N_3$, protected amino group, —OH, protected hydroxyl group, or halogen;
m is zero, 1, or 2;
n is zero, 1, or 2;
  wherein m+n is 1, 2 or 3;
o is zero, 1, or 2;
p is zero, 1, or 2;
  wherein o+p is 1, 2 or 3;
$R^{7a}$, $R^{7b}$, and $R^{7c}$ are independently H, $NH_2$, OH, —$OR^{71}$ or -$OPg^{2r}$;
wherein $R^{71}$ is alkyl; wherein the alkyl is unsubstituted or substituted with one or more substituents selected from the group consisting of —CONH$_2$, —OH, —NH$_2$, —COCH$_3$, aryl, substituted aryl, heteroaryl, halogen, and substituted heteroaryl;

wherein Pg$^{2r}$ is a hydroxyl protecting group;

R$^{9a}$ and R$^{9b}$ are independently H, OH, or —OR$^{91}$, wherein R$^{91}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

R$^{10a}$ and R$^{10b}$ are independently H, OH, or —OR$^{101}$, wherein R$^{101}$ is alkyl, alkenyl, or alkynyl; wherein the alkyl, alkenyl, and alkynyl is unsubstituted or substituted with one or more substituents selected from the group consisting of —CONH$_2$, —OH, —NH$_2$, —COCH$_3$, aryl, substituted aryl, heteroaryl, and substituted heteroaryl;

N$^{1g}$ is —NHPg$^{1g}$ or N$_3$, wherein Pg$^{1g}$ is an amino protecting group;

N$^{1h}$ is —NHPg$^{1h}$ or N$_3$, wherein Pg$^{1h}$ is an amino protecting group;

Pg$^{2g}$ is a hydroxyl protecting group;

Pg$^{2h}$ is a hydroxyl protecting group;

q is zero, 1, or 2;

r is zero, 1, or 2;

wherein q+r is 1, 2 or 3;

the process comprising:

(a) contacting a compound of formula A-9':

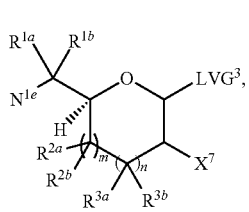

A-9' wherein LVG$^3$ is a leaving group,
with a compound of formula B-12:

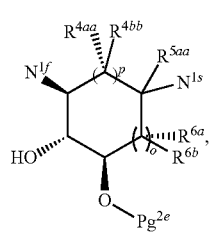

B-12' where Pg$^2$e is a hydroxyl protecting group, to yield a compound of formula AB-1':

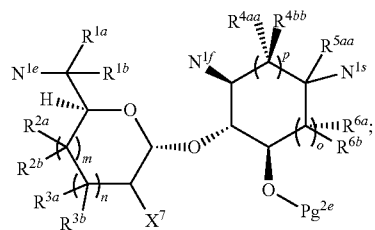

AB-1'

(b) selectively deprotecting the compound of formula AB-1' by removing the Pg$^{2e}$ moiety to yield a compound of formula AB-3':

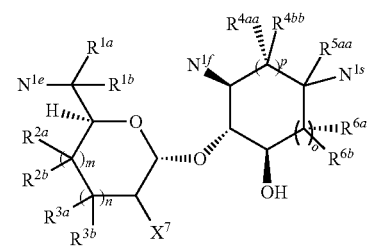

AB-3' or a salt thereof;

(c) contacting the compound of formula AB-3' with a compound of formula CD-1,

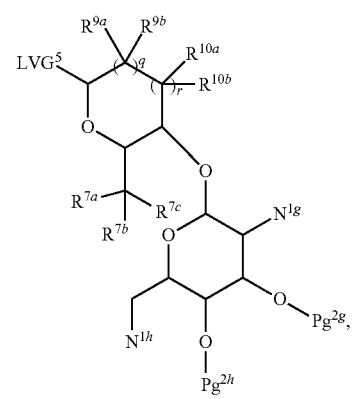

CD-1 or a salt thereof, where LVG$^5$ is a leaving group;
to yield the compound of formula ABCD-1', or a salt thereof.

4. The process of claim 3, further comprising after step (c):

(d) if amino protecting groups and hydroxyl protecting groups are present, removing the amino protecting groups and hydroxyl protecting groups to yield a compound of formula ABCD-2', or a salt, solvate, enantiomer, or diastereomer thereof, 573
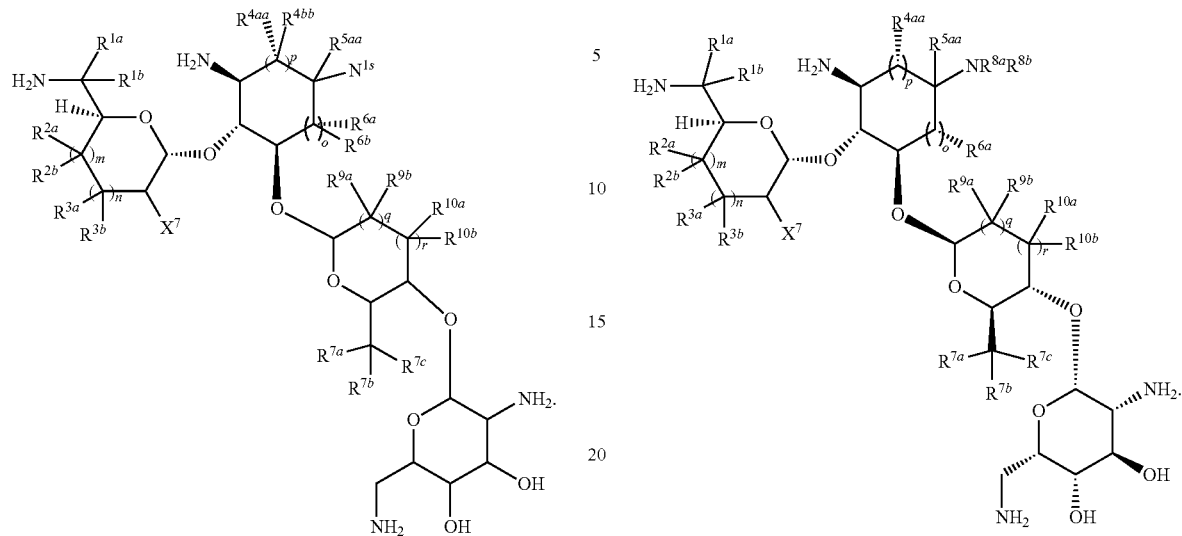
5. The process of claim 4, wherein the stereochemistry in the ABCD-2' ring is as indicated in formula ABCD":
* * * * *